US012527746B2

(12) United States Patent
Green et al.

(10) Patent No.: US 12,527,746 B2
(45) **Date of Patent: *Jan. 20, 2026**

(54) PEPTIDE/PARTICLE DELIVERY SYSTEMS

(71) Applicant: The Johns Hopkins University, Baltimore, MD (US)

(72) Inventors: Jordan Jamieson Green, Nottingham, MD (US); Aleksander S. Popel, Lutherville, MD (US); Joel Chaim Sunshine, Pikesville, MD (US); Ron B. Shmueli, Baltimore, MD (US); Stephany Yi Tzeng, Baltimroe, MD (US); Kristen Lynn Kozielski, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/149,583

(22) Filed: Jan. 14, 2021

(65) Prior Publication Data

US 2021/0220287 A1 Jul. 22, 2021

Related U.S. Application Data

(63) Continuation of application No. 16/860,773, filed on Apr. 28, 2020, now abandoned, which is a continuation of application No. 15/645,337, filed on Jul. 10, 2017, now Pat. No. 10,786,463, which is a continuation of application No. 13/272,042, filed on Oct. 12, 2011, now Pat. No. 9,717,694, which is a continuation-in-part of application No. PCT/US2010/035127, filed on May 17, 2010.

(60) Provisional application No. 61/542,995, filed on Oct. 4, 2011, provisional application No. 61/543,046, filed on Oct. 4, 2011, provisional application No. 61/392,224, filed on Oct. 12, 2010, provisional application No. 61/178,611, filed on May 15, 2009.

(51) Int. Cl.

| | |
|---|---|
| ***A61K 9/50*** | (2006.01) |
| ***A61K 9/00*** | (2006.01) |
| ***A61K 9/06*** | (2006.01) |
| ***A61K 9/19*** | (2006.01) |
| ***A61K 9/51*** | (2006.01) |
| ***A61K 31/7105*** | (2006.01) |
| ***A61K 31/711*** | (2006.01) |
| ***A61K 31/713*** | (2006.01) |
| ***A61K 38/39*** | (2006.01) |
| ***A61K 47/34*** | (2017.01) |
| ***B82Y 5/00*** | (2011.01) |
| ***C12N 15/11*** | (2006.01) |
| ***C12N 15/88*** | (2006.01) |

(52) U.S. Cl.

CPC .......... *A61K 9/5026* (2013.01); *A61K 9/0019* (2013.01); *A61K 9/06* (2013.01); *A61K 9/19* (2013.01); *A61K 9/5146* (2013.01); *A61K 31/7105* (2013.01); *A61K 31/711* (2013.01); *A61K 31/713* (2013.01); *A61K 38/39* (2013.01); *A61K 47/34* (2013.01); *B82Y 5/00* (2013.01); *C12N 15/111* (2013.01); *C12N 15/88* (2013.01); *C12N 2310/14* (2013.01); *C12N 2320/32* (2013.01); *Y10T 428/2982* (2015.01)

(58) Field of Classification Search

None

See application file for complete search history.

(56) References Cited

U.S. PATENT DOCUMENTS

| | | | | |
|---|---|---|---|---|
| 6,998,115 | B2 | 2/2006 | Langer et al. | |
| 7,427,394 | B2 | 9/2008 | Anderson et al. | |
| 8,992,991 | B2 * | 3/2015 | Green | C07C 323/25 424/490 |
| 9,717,694 | B2 * | 8/2017 | Green | A61K 38/39 |
| 9,884,118 | B2 * | 2/2018 | Green | A61P 35/00 |
| 10,786,463 | B2 | 9/2020 | Green et al. | |
| 2005/0265961 | A1 | 12/2005 | Langer et al. | |
| 2010/0036084 | A1 | 2/2010 | Langer et al. | |
| 2018/0028455 | A1 | 2/2018 | Green et al. | |

FOREIGN PATENT DOCUMENTS

| | | | |
|---|---|---|---|
| WO | WO2007033215 | A2 | 3/2007 |
| WO | WO2008085828 | A2 | 6/2009 |
| WO | WO 2010/132879 | * | 11/2010 |
| WO | WO2010132879 | A2 | 11/2010 |

OTHER PUBLICATIONS

Harris et al. ('Tissue-specific gene delivery via nanoparticle coating' Biomaterials v31 2010 pp. 998-1006) (Year: 2010).*
Lee et al. ('Gold, poly(beta-amino ester) nanoparticles for small interfering RNA delivery' Nano Letters v9(6) 2009 pp. 2402-2406) (Year: 2009).*
Chiang, et al., Molecular basis of metastasis. N Engl J Med 2008; 359(26):2814-23.
Gupta, et al., Cancer metastasis: building a framework. Cell 2006; 127( 4):679-95.
Sawyers, Cancer: mixing cocktails. Nature 2007; 449(7165):993-6.
Dorrell, et al., Combination angiostatic therapy completely inhibits ocular and tumor angiogenesis. Proc Natl Acad Sci USA 2007; 104(3):967-72.

(Continued)

*Primary Examiner* — Ronald T Niebauer
(74) *Attorney, Agent, or Firm* — Casimir Jones, SC; Jeffrey W. Childers

(57) ABSTRACT

Polymeric nanoparticles, microparticles, and gels for delivering cargo, e.g., a therapeutic agent, such as a peptide, to a target, e.g., a cell, and their use for treating diseases, including angiogenesis-dependent diseases, such as age-related macular degeneration and cancer, are disclosed. Methods for formulating, stabilizing, and administering single peptides or combinations of peptides via polymeric particle and gel delivery systems also are disclosed.

6 Claims, 56 Drawing Sheets

Specification includes a Sequence Listing.

(56) References Cited

OTHER PUBLICATIONS

Farokhzad, Nanotechnology for drug delivery: the perfect partnership. Expert Opin Drug Deliv 2008; 5(9):927-9.
Putnam, Polymers for gene delivery across length scales. Nat Mater 2006; 5(6):439-51.
Brigger, et al., Nanoparticles in cancer therapy and diagnosis. Adv Drug Deliv Rev 2002; 54(5):631-51.
Green, et al., Biodegradable polymeric vectors for gene delivery to human endothelial cells. Bioconjug Chem 2006; 17:1162-9.
Green, et al., Electrostatic ligand coatings of nanoparticles enable ligand-specific gene delivery to human primary cells. Nano Lett 2007; 7( 4):874-9.
Harris, et al., Tissue-specific gene delivery via nanoparticle coating. Biomaterials 2010; 31(5):998-1006.
Green, et al., Combinatorial modification of degradable polymers enables transfection of human cells comparable to adenovirus. Adv Mater 2007; 19(19):2836-42.
Lee, et al., Gold, poly(beta-amino ester) nanoparticles for small interfering RNA delivery. Nano Lett 2009; 9(6): 2402-2406.
Reichert, Development trends for peptide therapeutics. Tufts Center for the Study of Drug Development 2008.
Rosca, et al., Anti-angiogenic peptides for cancer therapeutics. Curr Phann Biotechnol 12(8):1101-1116 (2011).
Lucas, et al., Multiple forms of angiostatin induce apoptosis in endothelial cells. Blood 1998; 92(12): 4730-41.
Green, et al., A combinatorial polymer library approach yields insight into nonviral gene delivery. Ace Chem Res 2008; 41(6):749-59.
Shmueli, et al., Electrostatic surface modifications to improve gene delivery. Expert Opin Drug Deliv 2010; 7 4):535-50.
Zhang, et al., Nanoparticulate systems for growth factor delivery. Phann Res 2009; 26(7):1561-80.
Jain, The manufacturing techniques of various drug loaded biodegradable poly(lactide-co-glycolide) (PLGA) devices. 3iomaterials 2000; 21(23):2475-90.
Little, et al., Poly-beta amino ester-containing microparticles enhance the activity of nonviral genetic vaccines. Proc Natl Acad Sci USA 2004; 101(26):9534-9.
Koskimaki, et al., Pentastatin-1, a collagen IV derived 20-mer peptide, suppresses tumor growth in a small cell lung lancer xenograft model. BMC Cancer 2010; 10:29.
Koskimaki, et al., Peptides derived from type IV collagen, CXC chemokines, and thrombospondin-1 domain-.containing proteins inhibit neovascularization and suppress tumor growth in MDA-MB-231 breast cancer xenografts. Neoplasia 2009; 11(12):1285-91.
Oquendo, et al., CD36 directly mediates cytoadherence of Plasmodium falciparum parasitized erythrocytes. Cell 58: 35-101, 1989.
Han, et al., CD47, a ligand for the macrophage fusion receptor, participates in macrophage multinucleation. J. Biol. Them. 275: 37984-37992, 2000.
Trentin, et al., The chemokine receptor CXCR3 is expressed on malignant B cells and mediates chemotaxis. J. Clin. invest. 104: 115-121, 1999.
Pearson WR, "Using the FASTA program to search protein and DNA sequence Databases", Methods in Molecular Biology, (1994) 24: 307-331.
Smith, et al., Comparison of biosequences. Adv. Appl. Math., 2: 482, 1981.
Needleman, et al., A general method applicable to the search for similarities in the amino acid sequence of two proteins. J. Mal. Biol., 48: 443, 1970.
Pearson, et al., Improved tools for biological sequence comparison. Proc. Natl. Acad. Sci. USA, 8: 2444, 1988.
Higgins, et al., CLUSTAL: a package for performing multiple sequence alignment on a microcomputer. Gene, 73: 237-244, 1988.
Corpet, et al., Multiple sequence alignment with hierarchical clustering. Nucleic Acids Research, 16:10881-10890, 1988.
Altschul, et al., Gapped BLAST and PSI-BLAST: a new generation of protein database search programs. Nucleic Acids Res, 2:3389-3402, 1997.
Gombotz et al."Biodegradable polymers for protein and peptide drug delivery" Bioconjugate Chem v6 1995 pp. 332-351).
Shukla et al."Antimicrobial peptide delivery from degradable polymer thin films" Bioengineering conference, 2009 EEE 35th annual Northeast total of 3 pages).
Meyers, et al., Optimal alignments in linear space. Computer Applic. Biosci., 4: 11-17, 1988.
Wootton, et al., Statistics of local complexity in amino acid sequences and sequence databases. Comput. Chem.,36 17:149-163, 1993.
Claverie, et al., Information enhancement methods for large scale sequence analysis. Comput. Chem., 17:191-1, 1993.
Lee, et al., supporting information (retrieved from https://pubs.acs.org/doi/suppl/10.1021/n19009793/suppl_file/nl9009793_si_001.pdf on Apr. 1, 2019, 8 pages) (Year: 2019).
Murata et al. ('Role of prostaglandin D2 receptor DP as a suppressor of tumor hyperpermeability and angiogenesis in vivo' PNAS Dec. 16, 2008 v105(50) pp. 20009-20014) (Year: 2008).
Griffin et al. ('Natural nanoparticles: a particular matter inspired by nature' Antioxidants 2018 v7(3) pp. 1-21) (Year: 2018).

* cited by examiner

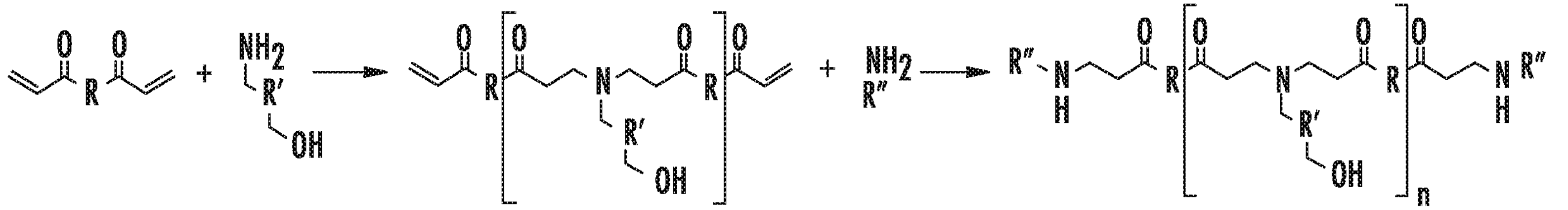

EIELVEEEPPF (Serpin, DEAH box-derived)
MW: 1330, pI: 2.9, Average Hydrophilicty: 0.7

B3
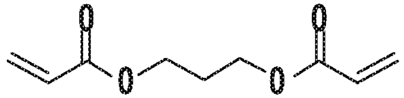
1,3-propanediol diacrylatepropane-1,3-diyl diacrylate

B6
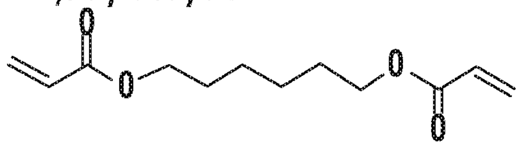
1,6-hexanediol diacrylatehexane-1,6-diyl diacrylate

BH1
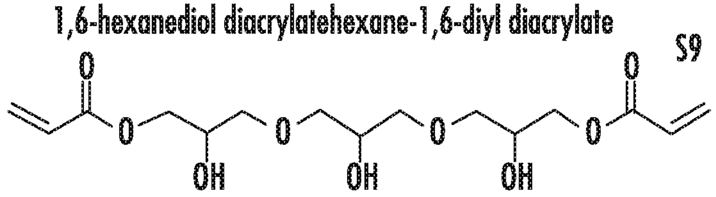
glycerol 1,3-diglycerolate diacrylate

S3
3-amino-1-propanol

S4
4-amino-1-butanol

S9
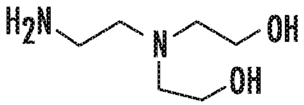
2,2′-((2-aminoethyl)azanediyl)diethanol

E1
propane-1, 3-diamine

E6
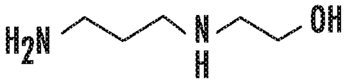
2-((3-aminopropyl)amino)ethanol

E8
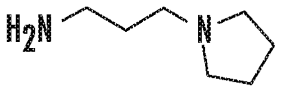
1-(3-aminopropyl)pyrrolidine

E15
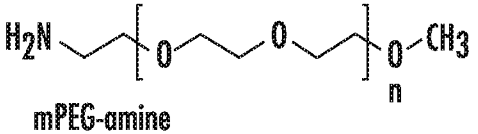
mPEG-amine

FIG. 4A

NGRKACLNPASPIVKKIIEKMLNS (CXC chemokine-derived)
MW: 2625, pI: 10.5, Average Hydrophilicity: 0.2

B5

1,5-pentanediol diacrylatepentane-1,5-diyl diacrylate

S5

5-amino-1-pentanol

E6

2-((3-aminopropyl)amino)ethanol

BP1 di(ethylene glycol) diacrylate

S7

3-aminopropane-1,2-diol

E15 mPEG-amine

BL2 ethoxylated bisphenol A diacrylate

E16 oligo(glutamic acid)

LLRISLLLIESWLE (Somatotropin-derived)
MW: 1698, pI: 4.3, Average Hydrophilicity: -0.6

BP4

(hexane-1,6-diylbis(oxy))bis(ethane-2,1-diyl) diacrylate

BSS

N,N′-bis(acrylyl)cystamine

BP5 polycaprolactone diacrylate

S10 piperazine

E11

N-(3-aminopropyl)-imidazole

S12

1-(3-aminopropyl)-4-methylpiperazine

S14

4,4′-trimethylenedipiperidine

E15 mPEG-amine

LRRFSTMPFMF-Abu-NINNV-Abu-NF (Collagen IV-derived / Pentastatin)
MW: 2419, pI: 12.4, Average Hydrophilicity: -0.7

BL1 trimethylolpropane benzoate diacrylate

S5

5-amino-1-pentanol

S14

4,4'-trimethylenedipiperidine

E8

1-(3-aminopropyl)pyrrolidine

E10 cystamine

BL2 ethoxylated bisphenol A diacrylate

E15 mPEG-amine

DEAH BOX POLY8 - 336 NPs

| AVG. (nm) → | MEAN | MODE | SD | REL. # |
|---|---|---|---|---|
| DEAH8 | - | - | - | 1 |
| 336 | - | 49±7 | - | ~6x |
| 336/DEAH8 5:1 wt/wt | 119±11 | 105±21 | 34±1 | ~29x (~5x) |

DEAH BOX POLY8 - 648 NPs

| AVG. (nm) → | MEAN | MODE | SD | REL. # |
|---|---|---|---|---|
| DEAH8 | - | - | - | 1 |
| 648 | - | - | - | 1 |
| 648/DEAH8 5:1 wt/wt | 100±24 | 98±33 | 35±11 | ~35x |

| AVG. (nm) → | MEAN | MODE | SD | REL. # |
|---|---|---|---|---|
| WISP | - | - | - | 1 |
| L141 | 81±18 | 72±22 | 38±9 | ~25x |
| L141/WISP 1:1 wt/wt | 88±7 | 80±9 | 35±6 | ~25x |

| NUMBER MEAN (nm) | CHEMOKINOSTATIN | PENTASTATIN |
|---|---|---|
| 556 POLYMERIC PARTICLE, 10w/w IN DMEM | 90.71 | 234 |
| L258 POLYMERIC PARTICLE, 10w/w IN DMEM | 242.9 | 155.5 |

| | $M_N$ | $M_W$ | PDI |
|---|---|---|---|
| BR6-S4-Ac | 2640 | 8375 | 3.17 |
| BR6-S4-E7 | 2534 | 5073 | 2.00 |

FIG. 23

DNA DELIVERY TO BCSCs: DsRed

TRANSFECTION (RED) IS ALSO EFFECTIVE IN GB-DERIVED CELLS POSITIVE FOR NESTIN (BLUE), A PROGENITOR MARKER

SEQUENCE LISTING

```
<160> NUMBER OF SEQ ID NOS: 2497

<210> SEQ ID NO 1
<211> LENGTH: 11
<212> TYPE: PRT
<213> ORGANISM: Homo sapiens

<400> SEQUENCE: 1

Trp Ser Gln Cys Ser Lys Thr Cys Gly Thr Gly
1               5                   10


<210> SEQ ID NO 2
<211> LENGTH: 11
<212> TYPE: PRT
<213> ORGANISM: Homo sapiens

<400> SEQUENCE: 2

Trp Gly Glu Cys Thr Arg Asp Cys Gly Gly Gly
1               5                   10


<210> SEQ ID NO 3
<211> LENGTH: 11
<212> TYPE: PRT
<213> ORGANISM: Homo sapiens

<400> SEQUENCE: 3

Trp Ser Val Cys Ser Ser Thr Cys Gly Glu Gly
1               5                   10


<210> SEQ ID NO 4
<211> LENGTH: 11
<212> TYPE: PRT
<213> ORGANISM: Homo sapiens

<400> SEQUENCE: 4

Trp Ser Leu Cys Ser Ser Thr Cys Gly Arg Gly
1               5                   10


<210> SEQ ID NO 5
<211> LENGTH: 11
<212> TYPE: PRT
<213> ORGANISM: Homo sapiens

<400> SEQUENCE: 5

Trp Ser Ala Cys Ser Ala Ser Cys Ser Gln Gly
1               5                   10


<210> SEQ ID NO 6
<211> LENGTH: 11
<212> TYPE: PRT
```

<213> ORGANISM: Homo sapiens

<400> SEQUENCE: 6

Trp Gly Ser Cys Ser Val Thr Cys Gly Ala Gly
1 5 10

<210> SEQ ID NO 7
<211> LENGTH: 11
<212> TYPE: PRT
<213> ORGANISM: Homo sapiens

<400> SEQUENCE: 7

Trp Ser Glu Cys Ser Val Thr Cys Gly Glu Gly
1 5 10

<210> SEQ ID NO 8
<211> LENGTH: 11
<212> TYPE: PRT
<213> ORGANISM: Homo sapiens

<400> SEQUENCE: 8

Trp Ser Val Cys Ser Leu Thr Cys Gly Gln Gly
1 5 10

<210> SEQ ID NO 9
<211> LENGTH: 11
<212> TYPE: PRT
<213> ORGANISM: Homo sapiens

<400> SEQUENCE: 9

Trp Ser Leu Cys Ser Arg Ser Cys Gly Arg Gly
1 5 10

<210> SEQ ID NO 10
<211> LENGTH: 11
<212> TYPE: PRT
<213> ORGANISM: Homo sapiens

<400> SEQUENCE: 10

Trp Gly Pro Cys Ser Thr Ser Cys Ala Asn Gly
1 5 10

<210> SEQ ID NO 11
<211> LENGTH: 11
<212> TYPE: PRT
<213> ORGANISM: Homo sapiens

<400> SEQUENCE: 11

Trp Ser Leu Cys Ser Lys Thr Cys Asp Thr Gly
1 5 10

<210> SEQ ID NO 12
<211> LENGTH: 11
<212> TYPE: PRT
<213> ORGANISM: Homo sapiens

<400> SEQUENCE: 12

Trp Ser Thr Cys Ser Val Thr Cys Gly Gln Gly
1 5 10

<210> SEQ ID NO 13
<211> LENGTH: 11
<212> TYPE: PRT
<213> ORGANISM: Homo sapiens

<400> SEQUENCE: 13

Trp Ser Leu Cys Ser Phe Thr Cys Gly Arg Gly
1 5 10

<210> SEQ ID NO 14
<211> LENGTH: 11
<212> TYPE: PRT
<213> ORGANISM: Homo sapiens

<400> SEQUENCE: 14

Trp Ser Gln Cys Ser Val Thr Cys Ser Asn Gly
1 5 10

<210> SEQ ID NO 15
<211> LENGTH: 11
<212> TYPE: PRT
<213> ORGANISM: Homo sapiens

<400> SEQUENCE: 15

Trp Ser Gly Cys Ser Lys Ser Cys Asp Gly Gly
1 5 10

<210> SEQ ID NO 16
<211> LENGTH: 11
<212> TYPE: PRT
<213> ORGANISM: Homo sapiens

<400> SEQUENCE: 16

Trp Gly Asp Cys Ser Arg Thr Cys Gly Gly Gly
1 5 10

<210> SEQ ID NO 17
<211> LENGTH: 11
<212> TYPE: PRT
<213> ORGANISM: Homo sapiens

<400> SEQUENCE: 17

Trp Gly Pro Cys Ser Thr Thr Cys Gly Leu Gly
1 5 10

<210> SEQ ID NO 18
<211> LENGTH: 11
<212> TYPE: PRT
<213> ORGANISM: Homo sapiens

<400> SEQUENCE: 18

Trp Ser Val Cys Asn Ser Arg Cys Gly Arg Gly
1 5 10

<210> SEQ ID NO 19
<211> LENGTH: 11
<212> TYPE: PRT
<213> ORGANISM: Homo sapiens

<400> SEQUENCE: 19

Trp Ser Pro Cys Ser Thr Ser Cys Gly Leu Gly
1 5 10

<210> SEQ ID NO 20
<211> LENGTH: 11
<212> TYPE: PRT
<213> ORGANISM: Homo sapiens

<400> SEQUENCE: 20

Trp Thr Pro Cys Ser Arg Thr Cys Gly Met Gly
1 5 10

<210> SEQ ID NO 21
<211> LENGTH: 11
<212> TYPE: PRT
<213> ORGANISM: Homo sapiens

<400> SEQUENCE: 21

Trp Ser Pro Cys Ser Lys Pro Cys Gly Gly Gly
1 5 10

<210> SEQ ID NO 22
<211> LENGTH: 11
<212> TYPE: PRT
<213> ORGANISM: Homo sapiens

<400> SEQUENCE: 22

Trp Ser Gln Cys Ser Val Thr Cys Gly Asn Gly
1 5 10

<210> SEQ ID NO 23
<211> LENGTH: 11
<212> TYPE: PRT
<213> ORGANISM: Homo sapiens

<400> SEQUENCE: 23

Trp Thr Ser Cys Ser Thr Ser Cys Gly Asn Gly
1 5 10

<210> SEQ ID NO 24
<211> LENGTH: 11
<212> TYPE: PRT
<213> ORGANISM: Homo sapiens

<400> SEQUENCE: 24

Trp Ser Ser Cys Ser Val Thr Cys Gly Asp Gly
1 5 10

<210> SEQ ID NO 25
<211> LENGTH: 11
<212> TYPE: PRT
<213> ORGANISM: Homo sapiens

<400> SEQUENCE: 25

Trp Asp Ile Cys Ser Val Thr Cys Gly Gly Gly
1 5 10

<210> SEQ ID NO 26
<211> LENGTH: 11
<212> TYPE: PRT
<213> ORGANISM: Homo sapiens

<400> SEQUENCE: 26

Trp Thr Ser Cys Ser Lys Thr Cys Asn Ser Gly
1 5 10

<210> SEQ ID NO 27
<211> LENGTH: 11
<212> TYPE: PRT
<213> ORGANISM: Homo sapiens

<400> SEQUENCE: 27

Trp Gln Arg Cys Pro Ile Asn Cys Leu Leu Gly
1 5 10

<210> SEQ ID NO 28
<211> LENGTH: 11
<212> TYPE: PRT
<213> ORGANISM: Homo sapiens

<400> SEQUENCE: 28

Trp Arg Asp Cys Ser Arg Pro Cys Pro Pro Gly
1               5                   10

<210> SEQ ID NO 29
<211> LENGTH: 11
<212> TYPE: PRT
<213> ORGANISM: Homo sapiens

<400> SEQUENCE: 29

Trp Ala Pro Cys Ser Val Thr Cys Ser Glu Gly
1               5                   10

<210> SEQ ID NO 30
<211> LENGTH: 11
<212> TYPE: PRT
<213> ORGANISM: Homo sapiens

<400> SEQUENCE: 30

Trp Glu Pro Cys Ser Val Thr Cys Ser Lys Gly
1               5                   10

<210> SEQ ID NO 31
<211> LENGTH: 11
<212> TYPE: PRT
<213> ORGANISM: Homo sapiens

<400> SEQUENCE: 31

Trp Thr Pro Cys Ser Ala Ser Cys His Gly Gly
1               5                   10

<210> SEQ ID NO 32
<211> LENGTH: 11
<212> TYPE: PRT
<213> ORGANISM: Homo sapiens

<400> SEQUENCE: 32

Trp Ser Ala Cys Ser Lys Thr Cys Gly Met Gly
1               5                   10

<210> SEQ ID NO 33
<211> LENGTH: 11
<212> TYPE: PRT
<213> ORGANISM: Homo sapiens

<400> SEQUENCE: 33

Trp Thr Gln Cys Ser Val Thr Cys Gly Ser Gly
1               5                   10

<210> SEQ ID NO 34
<211> LENGTH: 11
<212> TYPE: PRT
<213> ORGANISM: Homo sapiens

<400> SEQUENCE: 34

Trp Ser Ser Cys Ser Val Thr Cys Gly Val Gly
1               5                   10

<210> SEQ ID NO 35
<211> LENGTH: 11
<212> TYPE: PRT
<213> ORGANISM: Homo sapiens

<400> SEQUENCE: 35

Trp Ser Ala Cys Thr Val Thr Cys Ala Gly Gly
1               5                   10

<210> SEQ ID NO 36
<211> LENGTH: 11
<212> TYPE: PRT
<213> ORGANISM: Homo sapiens

<400> SEQUENCE: 36

Trp Thr Ala Cys Ser Lys Ser Cys Gly Met Gly
1               5                   10

<210> SEQ ID NO 37
<211> LENGTH: 11
<212> TYPE: PRT
<213> ORGANISM: Homo sapiens

<400> SEQUENCE: 37

Trp Glu Glu Cys Lys Gln Arg Cys Pro Pro Gly
1               5                   10

<210> SEQ ID NO 38
<211> LENGTH: 11
<212> TYPE: PRT
<213> ORGANISM: Homo sapiens

<400> SEQUENCE: 38

Trp Ser His Cys Ser Arg Thr Cys Gly Ala Gly
1               5                   10

<210> SEQ ID NO 39
<211> LENGTH: 11
<212> TYPE: PRT
<213> ORGANISM: Homo sapiens

<400> SEQUENCE: 39

Trp Thr Glu Cys Ser Val Thr Cys Gly Thr Gly
1               5                   10

<210> SEQ ID NO 40
<211> LENGTH: 11
<212> TYPE: PRT
<213> ORGANISM: Homo sapiens

<400> SEQUENCE: 40

Trp Ser Glu Cys Ser Val Ser Cys Gly Gly Gly
1               5                   10

<210> SEQ ID NO 41
<211> LENGTH: 11
<212> TYPE: PRT
<213> ORGANISM: Homo sapiens

<400> SEQUENCE: 41

Trp Ser Glu Cys Ser Thr Thr Cys Gly Leu Gly
1               5                   10

<210> SEQ ID NO 42
<211> LENGTH: 11

<212> TYPE: PRT
<213> ORGANISM: Homo sapiens

<400> SEQUENCE: 42

Trp Ser Lys Cys Ser Arg Asn Cys Ser Gly Gly
1 5 10

<210> SEQ ID NO 43
<211> LENGTH: 11
<212> TYPE: PRT
<213> ORGANISM: Homo sapiens

<400> SEQUENCE: 43

Trp Ser Gln Cys Ser Arg Ser Cys Gly Gly Gly
1 5 10

<210> SEQ ID NO 44
<211> LENGTH: 11
<212> TYPE: PRT
<213> ORGANISM: Homo sapiens

<400> SEQUENCE: 44

Trp Asp Leu Cys Ser Thr Ser Cys Gly Gly Gly
1 5 10

<210> SEQ ID NO 45
<211> LENGTH: 11
<212> TYPE: PRT
<213> ORGANISM: Homo sapiens

<400> SEQUENCE: 45

Trp Ser Gln Cys Ser Arg Ser Cys Gly Gly Gly
1 5 10

<210> SEQ ID NO 46
<211> LENGTH: 11
<212> TYPE: PRT
<213> ORGANISM: Homo sapiens

<400> SEQUENCE: 46

Trp Ser Glu Cys Leu Val Thr Cys Gly Lys Gly
1 5 10

<210> SEQ ID NO 47
<211> LENGTH: 11
<212> TYPE: PRT
<213> ORGANISM: Homo sapiens

<400> SEQUENCE: 47

Trp Gly Pro Cys Thr Thr Thr Cys Gly His Gly
1 5 10

<210> SEQ ID NO 48
<211> LENGTH: 11
<212> TYPE: PRT
<213> ORGANISM: Homo sapiens

<400> SEQUENCE: 48

Trp Thr Pro Cys Ser Val Ser Cys Gly Arg Gly
1 5 10

<210> SEQ ID NO 49
<211> LENGTH: 11
<212> TYPE: PRT
<213> ORGANISM: Homo sapiens

<400> SEQUENCE: 49

Trp Ser Pro Cys Ser Ala Ser Cys Gly His Gly
1               5                   10

<210> SEQ ID NO 50
<211> LENGTH: 11
<212> TYPE: PRT
<213> ORGANISM: Homo sapiens

<400> SEQUENCE: 50

Trp Gly Ser Cys Ser Ser Ser Cys Ser Gly Gly
1               5                   10

<210> SEQ ID NO 51
<211> LENGTH: 11
<212> TYPE: PRT
<213> ORGANISM: Homo sapiens

<400> SEQUENCE: 51

Trp Gly Glu Cys Ser Gln Thr Cys Gly Gly Gly
1               5                   10

<210> SEQ ID NO 52
<211> LENGTH: 11
<212> TYPE: PRT
<213> ORGANISM: Homo sapiens

<400> SEQUENCE: 52

Trp Thr Ser Cys Ser Ala Ser Cys Gly Lys Gly
1               5                   10

<210> SEQ ID NO 53
<211> LENGTH: 11
<212> TYPE: PRT
<213> ORGANISM: Homo sapiens

<400> SEQUENCE: 53

Trp Asn Glu Cys Ser Val Thr Cys Gly Ser Gly
1               5                   10

<210> SEQ ID NO 54
<211> LENGTH: 11
<212> TYPE: PRT
<213> ORGANISM: Homo sapiens

<400> SEQUENCE: 54

Trp Ser Lys Cys Ser Val Thr Cys Gly Ile Gly
1               5                   10

<210> SEQ ID NO 55
<211> LENGTH: 11
<212> TYPE: PRT
<213> ORGANISM: Homo sapiens

<400> SEQUENCE: 55

Trp Ser Asp Cys Ser Arg Thr Cys Gly Gly Gly
1               5                   10

<210> SEQ ID NO 56
<211> LENGTH: 11
<212> TYPE: PRT
<213> ORGANISM: Homo sapiens

<400> SEQUENCE: 56

Trp Thr Ala Cys Ser Val Ser Cys Gly Gly Gly
1 5 10

<210> SEQ ID NO 57
<211> LENGTH: 11
<212> TYPE: PRT
<213> ORGANISM: Homo sapiens

<400> SEQUENCE: 57

Trp Ser Gln Cys Thr Val Thr Cys Gly Arg Gly
1 5 10

<210> SEQ ID NO 58
<211> LENGTH: 11
<212> TYPE: PRT
<213> ORGANISM: Homo sapiens

<400> SEQUENCE: 58

Trp Ser Ala Cys Ser Thr Thr Cys Gly Pro Gly
1 5 10

<210> SEQ ID NO 59
<211> LENGTH: 11
<212> TYPE: PRT
<213> ORGANISM: Homo sapiens

<400> SEQUENCE: 59

Trp Gly Pro Cys Ser Ala Thr Cys Gly Val Gly
1 5 10

<210> SEQ ID NO 60
<211> LENGTH: 11
<212> TYPE: PRT
<213> ORGANISM: Homo sapiens

<400> SEQUENCE: 60

Trp Gln Gln Cys Ser Arg Thr Cys Gly Gly Gly
1 5 10

<210> SEQ ID NO 61
<211> LENGTH: 11
<212> TYPE: PRT
<213> ORGANISM: Homo sapiens

<400> SEQUENCE: 61

Trp Ser Lys Cys Ser Val Ser Cys Gly Val Gly
1 5 10

<210> SEQ ID NO 62
<211> LENGTH: 11
<212> TYPE: PRT
<213> ORGANISM: Homo sapiens

<400> SEQUENCE: 62

Trp Ser Gln Cys Ser Val Ser Cys Gly Glu Gly
1 5 10

<210> SEQ ID NO 63
<211> LENGTH: 11
<212> TYPE: PRT
<213> ORGANISM: Homo sapiens

<400> SEQUENCE: 63

Trp Lys Pro Cys Thr Ala Ala Cys Gly Arg Gly
1               5                   10

<210> SEQ ID NO 64
<211> LENGTH: 11
<212> TYPE: PRT
<213> ORGANISM: Homo sapiens

<400> SEQUENCE: 64

Trp Ser Pro Cys Ser Thr Thr Cys Gly Ile Gly
1               5                   10

<210> SEQ ID NO 65
<211> LENGTH: 11
<212> TYPE: PRT
<213> ORGANISM: Homo sapiens

<400> SEQUENCE: 65

Trp Glu Arg Cys Thr Ala Gln Cys Gly Gly Gly
1               5                   10

<210> SEQ ID NO 66
<211> LENGTH: 11
<212> TYPE: PRT
<213> ORGANISM: Homo sapiens

<400> SEQUENCE: 66

Trp Ser Gln Cys Ser Arg Asp Cys Ser Arg Gly
1               5                   10

<210> SEQ ID NO 67
<211> LENGTH: 11
<212> TYPE: PRT
<213> ORGANISM: Homo sapiens

<400> SEQUENCE: 67

Trp Thr Lys Cys Ser Ala Thr Cys Gly Gly Gly
1               5                   10

<210> SEQ ID NO 68
<211> LENGTH: 11
<212> TYPE: PRT
<213> ORGANISM: Homo sapiens

<400> SEQUENCE: 68

Trp Ser Ala Cys Thr Arg Ser Cys Gly Gly Gly
1               5                   10

<210> SEQ ID NO 69
<211> LENGTH: 11
<212> TYPE: PRT
<213> ORGANISM: Homo sapiens

<400> SEQUENCE: 69

Trp Cys Cys Cys Cys Phe Pro Cys Cys Arg Gly
1               5                   10

<210> SEQ ID NO 70
<211> LENGTH: 11
<212> TYPE: PRT
<213> ORGANISM: Homo sapiens

<400> SEQUENCE: 70

Trp Ser Ala Cys Asn Val Arg Cys Gly Arg Gly
1 5 10

<210> SEQ ID NO 71
<211> LENGTH: 11
<212> TYPE: PRT
<213> ORGANISM: Homo sapiens

<400> SEQUENCE: 71

Trp Ala Ser Cys Ser Gln Pro Cys Gly Val Gly
1 5 10

<210> SEQ ID NO 72
<211> LENGTH: 11
<212> TYPE: PRT
<213> ORGANISM: Homo sapiens

<400> SEQUENCE: 72

Trp Thr Ser Cys Ser Arg Ser Cys Gly Pro Gly
1 5 10

<210> SEQ ID NO 73
<211> LENGTH: 11
<212> TYPE: PRT
<213> ORGANISM: Homo sapiens

<400> SEQUENCE: 73

Trp Ser Gln Cys Ser Val Arg Cys Gly Arg Gly
1 5 10

<210> SEQ ID NO 74
<211> LENGTH: 11
<212> TYPE: PRT
<213> ORGANISM: Homo sapiens

<400> SEQUENCE: 74

Trp Gly Glu Cys Ser Ser Glu Cys Gly Ser Gly
1 5 10

<210> SEQ ID NO 75
<211> LENGTH: 11
<212> TYPE: PRT
<213> ORGANISM: Homo sapiens

<400> SEQUENCE: 75

Trp Ser Pro Cys Ser Arg Ser Cys Gln Gly Gly
1 5 10

<210> SEQ ID NO 76
<211> LENGTH: 11
<212> TYPE: PRT
<213> ORGANISM: Homo sapiens

<400> SEQUENCE: 76

Trp Thr Arg Cys Ser Ser Ser Cys Gly Arg Gly
1 5 10

<210> SEQ ID NO 77
<211> LENGTH: 11
<212> TYPE: PRT
<213> ORGANISM: Homo sapiens

<400> SEQUENCE: 77

Trp Met Glu Cys Ser Val Ser Cys Gly Asp Gly
1               5                   10

<210> SEQ ID NO 78
<211> LENGTH: 11
<212> TYPE: PRT
<213> ORGANISM: Homo sapiens

<400> SEQUENCE: 78

Trp Thr Ala Cys Ser Arg Ser Cys Gly Gly Gly
1               5                   10

<210> SEQ ID NO 79
<211> LENGTH: 11
<212> TYPE: PRT
<213> ORGANISM: Homo sapiens

<400> SEQUENCE: 79

Trp Ser Glu Cys Ser Arg Thr Cys Gly Glu Gly
1               5                   10

<210> SEQ ID NO 80
<211> LENGTH: 11
<212> TYPE: PRT
<213> ORGANISM: Homo sapiens

<400> SEQUENCE: 80

Trp Gly Pro Cys Ser Gly Ser Cys Gly Gln Gly
1               5                   10

<210> SEQ ID NO 81
<211> LENGTH: 11
<212> TYPE: PRT
<213> ORGANISM: Homo sapiens

<400> SEQUENCE: 81

Trp Glu Arg Cys Asn Thr Thr Cys Gly Arg Gly
1               5                   10

<210> SEQ ID NO 82
<211> LENGTH: 11
<212> TYPE: PRT
<213> ORGANISM: Homo sapiens

<400> SEQUENCE: 82

Trp Ser Glu Cys Thr Lys Thr Cys Gly Val Gly
1               5                   10

<210> SEQ ID NO 83
<211> LENGTH: 11
<212> TYPE: PRT
<213> ORGANISM: Homo sapiens

<400> SEQUENCE: 83

Trp Gly Pro Cys Ser Gly Ser Cys Gly Pro Gly
1               5                   10

<210> SEQ ID NO 84
<211> LENGTH: 11
<212> TYPE: PRT
<213> ORGANISM: Homo sapiens

<400> SEQUENCE: 84

Trp Ser Pro Cys Ser Asn Arg Cys Gly Arg Gly
1 5 10

<210> SEQ ID NO 85
<211> LENGTH: 11
<212> TYPE: PRT
<213> ORGANISM: Homo sapiens

<400> SEQUENCE: 85

Trp Ser Glu Cys Ser Arg Thr Cys Gly Gly Gly
1 5 10

<210> SEQ ID NO 86
<211> LENGTH: 11
<212> TYPE: PRT
<213> ORGANISM: Homo sapiens

<400> SEQUENCE: 86

Trp Thr Ala Cys Ser Ser Ser Cys Gly Gly Gly
1 5 10

<210> SEQ ID NO 87
<211> LENGTH: 11
<212> TYPE: PRT
<213> ORGANISM: Homo sapiens

<400> SEQUENCE: 87

Trp Ser Pro Cys Thr Val Thr Cys Gly Gln Gly
1 5 10

<210> SEQ ID NO 88
<211> LENGTH: 11
<212> TYPE: PRT
<213> ORGANISM: Homo sapiens

<400> SEQUENCE: 88

Trp Ser Met Cys Ser Arg Thr Cys Gly Thr Gly
1 5 10

<210> SEQ ID NO 89
<211> LENGTH: 11
<212> TYPE: PRT
<213> ORGANISM: Homo sapiens

<400> SEQUENCE: 89

Trp Glu Gly Cys Ser Val Gln Cys Gly Gly Gly
1 5 10

<210> SEQ ID NO 90
<211> LENGTH: 11
<212> TYPE: PRT
<213> ORGANISM: Homo sapiens

<400> SEQUENCE: 90

Trp Ser Pro Cys Ser Ala Thr Cys Glu Lys Gly
1 5 10

<210> SEQ ID NO 91
<211> LENGTH: 11
<212> TYPE: PRT
<213> ORGANISM: Homo sapiens

<400> SEQUENCE: 91

Trp Ser Gln Cys Ser Ala Ser Cys Gly Lys Gly
1 5 10

<210> SEQ ID NO 92
<211> LENGTH: 11
<212> TYPE: PRT
<213> ORGANISM: Homo sapiens

<400> SEQUENCE: 92

Trp Ser Thr Cys Ser Ser Thr Cys Gly Lys Gly
1 5 10

<210> SEQ ID NO 93
<211> LENGTH: 11
<212> TYPE: PRT
<213> ORGANISM: Homo sapiens

<400> SEQUENCE: 93

Trp Ser Pro Cys Ser Arg Thr Cys Gly Gly Gly
1 5 10

<210> SEQ ID NO 94
<211> LENGTH: 11
<212> TYPE: PRT
<213> ORGANISM: Homo sapiens

<400> SEQUENCE: 94

Trp Ser Ala Cys Ser Arg Thr Cys Gly Gly Gly
1 5 10

<210> SEQ ID NO 95
<211> LENGTH: 11
<212> TYPE: PRT
<213> ORGANISM: Homo sapiens

<400> SEQUENCE: 95

Trp Ala Glu Cys Ser His Thr Cys Gly Lys Gly
1 5 10

<210> SEQ ID NO 96
<211> LENGTH: 11
<212> TYPE: PRT
<213> ORGANISM: Homo sapiens

<400> SEQUENCE: 96

Trp Ser Gln Cys Ser Val Thr Cys Glu Arg Gly
1 5 10

<210> SEQ ID NO 97
<211> LENGTH: 11
<212> TYPE: PRT
<213> ORGANISM: Homo sapiens

<400> SEQUENCE: 97

Trp Ser Gln Cys Thr Ala Ser Cys Gly Gly Gly
1 5 10

<210> SEQ ID NO 98
<211> LENGTH: 11
<212> TYPE: PRT
<213> ORGANISM: Homo sapiens

<400> SEQUENCE: 98

Trp Gly Pro Cys Ser Ala Ser Cys Gly Ser Gly
1 5 10

<210> SEQ ID NO 99
<211> LENGTH: 11
<212> TYPE: PRT
<213> ORGANISM: Homo sapiens

<400> SEQUENCE: 99

Trp Ser Pro Cys Ser Lys Ser Cys Gly Arg Gly
1 5 10

<210> SEQ ID NO 100
<211> LENGTH: 11
<212> TYPE: PRT
<213> ORGANISM: Homo sapiens

<400> SEQUENCE: 100

Trp Ser Pro Cys Ser Arg Thr Cys Ser Ala Gly
1 5 10

<210> SEQ ID NO 101
<211> LENGTH: 11
<212> TYPE: PRT
<213> ORGANISM: Homo sapiens

<400> SEQUENCE: 101

Trp Glu Asp Cys Asp Ala Thr Cys Gly Gly Gly
1 5 10

<210> SEQ ID NO 102
<211> LENGTH: 11
<212> TYPE: PRT
<213> ORGANISM: Homo sapiens

<400> SEQUENCE: 102

Trp Thr Pro Cys Ser Arg Thr Cys Gly Lys Gly
1 5 10

<210> SEQ ID NO 103
<211> LENGTH: 11
<212> TYPE: PRT
<213> ORGANISM: Homo sapiens

<400> SEQUENCE: 103

Trp Ser Lys Cys Ser Ile Thr Cys Gly Lys Gly
1 5 10

<210> SEQ ID NO 104
<211> LENGTH: 11
<212> TYPE: PRT
<213> ORGANISM: Homo sapiens

<400> SEQUENCE: 104

Trp Ser Glu Cys Ser Arg Thr Cys Gly Gly Gly
1 5 10

<210> SEQ ID NO 105
<211> LENGTH: 11
<212> TYPE: PRT
<213> ORGANISM: Homo sapiens

<400> SEQUENCE: 105

Trp Ser Thr Cys Ser Lys Ala Cys Ala Gly Gly
1 5 10

<210> SEQ ID NO 106
<211> LENGTH: 11
<212> TYPE: PRT
<213> ORGANISM: Homo sapiens

<400> SEQUENCE: 106

Trp Ser Gln Cys Ser Lys Thr Cys Gly Arg Gly
1 5 10

<210> SEQ ID NO 107
<211> LENGTH: 11
<212> TYPE: PRT
<213> ORGANISM: Homo sapiens

<400> SEQUENCE: 107

Trp Ser Glu Cys Ser Ala Thr Cys Gly Leu Gly
1 5 10

<210> SEQ ID NO 108
<211> LENGTH: 11
<212> TYPE: PRT
<213> ORGANISM: Homo sapiens

<400> SEQUENCE: 108

Trp Gln Gln Cys Thr Val Thr Cys Gly Gly Gly
1 5 10

<210> SEQ ID NO 109
<211> LENGTH: 11
<212> TYPE: PRT
<213> ORGANISM: Homo sapiens

<400> SEQUENCE: 109

Trp Ala Pro Cys Ser Lys Ala Cys Gly Gly Gly
1 5 10

<210> SEQ ID NO 110
<211> LENGTH: 11
<212> TYPE: PRT
<213> ORGANISM: Homo sapiens

<400> SEQUENCE: 110

Trp Ser Gln Cys Ser Ala Thr Cys Gly Glu Gly
1 5 10

<210> SEQ ID NO 111
<211> LENGTH: 11
<212> TYPE: PRT
<213> ORGANISM: Homo sapiens

<400> SEQUENCE: 111

Trp Ala Arg Cys Glu Asp Gly Cys Ile Arg Gly
1 5 10

<210> SEQ ID NO 112
<211> LENGTH: 11
<212> TYPE: PRT
<213> ORGANISM: Homo sapiens

<400> SEQUENCE: 112

Trp Arg Ala Cys Ser Val Thr Cys Gly Lys Gly
1               5                   10

<210> SEQ ID NO 113
<211> LENGTH: 11
<212> TYPE: PRT
<213> ORGANISM: Homo sapiens

<400> SEQUENCE: 113

Trp Glu Glu Cys Thr Arg Ser Cys Gly Arg Gly
1               5                   10

<210> SEQ ID NO 114
<211> LENGTH: 11
<212> TYPE: PRT
<213> ORGANISM: Homo sapiens

<400> SEQUENCE: 114

Trp Gly Thr Cys Ser Glu Ser Cys Gly Lys Gly
1               5                   10

<210> SEQ ID NO 115
<211> LENGTH: 11
<212> TYPE: PRT
<213> ORGANISM: Homo sapiens

<400> SEQUENCE: 115

Trp Ser Ala Cys Ser Val Ser Cys Gly Gly Gly
1               5                   10

<210> SEQ ID NO 116
<211> LENGTH: 11
<212> TYPE: PRT
<213> ORGANISM: Homo sapiens

<400> SEQUENCE: 116

Trp Gly Thr Cys Ser Arg Thr Cys Asn Gly Gly
1               5                   10

<210> SEQ ID NO 117
<211> LENGTH: 11
<212> TYPE: PRT
<213> ORGANISM: Homo sapiens

<400> SEQUENCE: 117

Trp Ser Gln Cys Ser Ala Ser Cys Gly Gly Gly
1               5                   10

<210> SEQ ID NO 118
<211> LENGTH: 11
<212> TYPE: PRT
<213> ORGANISM: Homo sapiens

<400> SEQUENCE: 118

Trp Leu Ser Cys Gly Ser Leu Cys Leu Leu Gly
1               5                   10

<210> SEQ ID NO 119
<211> LENGTH: 11
<212> TYPE: PRT
<213> ORGANISM: Homo sapiens

<400> SEQUENCE: 119

Trp Gly Arg Cys Thr Gly Asp Cys Gly Pro Gly
1               5                   10

<210> SEQ ID NO 120
<211> LENGTH: 11
<212> TYPE: PRT
<213> ORGANISM: Homo sapiens

<400> SEQUENCE: 120

Trp Ser Pro Cys Ser Lys Thr Cys Arg Ser Gly
1               5                   10

<210> SEQ ID NO 121
<211> LENGTH: 11
<212> TYPE: PRT
<213> ORGANISM: Homo sapiens

<400> SEQUENCE: 121

Trp Thr Pro Cys Pro Arg Met Cys Gln Ala Gly
1               5                   10

<210> SEQ ID NO 122
<211> LENGTH: 11
<212> TYPE: PRT
<213> ORGANISM: Homo sapiens

<400> SEQUENCE: 122

Trp Gly Ser Cys Ser Ser Ser Cys Gly Ile Gly
1               5                   10

<210> SEQ ID NO 123
<211> LENGTH: 11
<212> TYPE: PRT
<213> ORGANISM: Homo sapiens

<400> SEQUENCE: 123

Trp Thr Glu Cys Ser Gln Thr Cys Gly His Gly
1               5                   10

<210> SEQ ID NO 124
<211> LENGTH: 11
<212> TYPE: PRT
<213> ORGANISM: Homo sapiens

<400> SEQUENCE: 124

Trp Ser Thr Cys Glu Leu Thr Cys Ile Asp Gly
1               5                   10

<210> SEQ ID NO 125
<211> LENGTH: 11
<212> TYPE: PRT
<213> ORGANISM: Homo sapiens

<400> SEQUENCE: 125

Trp Gly Asp Cys Ser Arg Thr Cys Gly Gly Gly
1               5                   10

<210> SEQ ID NO 126
<211> LENGTH: 11
<212> TYPE: PRT
<213> ORGANISM: Homo sapiens

<400> SEQUENCE: 126

Trp Thr Lys Cys Ser Ala Gln Cys Ala Gly Gly
1 5 10

<210> SEQ ID NO 127
<211> LENGTH: 11
<212> TYPE: PRT
<213> ORGANISM: Homo sapiens

<400> SEQUENCE: 127

Trp Ser Leu Cys Ser Arg Ser Cys Asp Ala Gly
1 5 10

<210> SEQ ID NO 128
<211> LENGTH: 11
<212> TYPE: PRT
<213> ORGANISM: Homo sapiens

<400> SEQUENCE: 128

Trp Ser Glu Cys Thr Pro Ser Cys Gly Pro Gly
1 5 10

<210> SEQ ID NO 129
<211> LENGTH: 11
<212> TYPE: PRT
<213> ORGANISM: Homo sapiens

<400> SEQUENCE: 129

Trp Gly Glu Cys Ser Ala Gln Cys Gly Val Gly
1 5 10

<210> SEQ ID NO 130
<211> LENGTH: 11
<212> TYPE: PRT
<213> ORGANISM: Homo sapiens

<400> SEQUENCE: 130

Trp Ser Pro Cys Ser Ile Ser Cys Gly Met Gly
1 5 10

<210> SEQ ID NO 131
<211> LENGTH: 11
<212> TYPE: PRT
<213> ORGANISM: Homo sapiens

<400> SEQUENCE: 131

Trp Asp Glu Cys Ser Ala Thr Cys Gly Met Gly
1 5 10

<210> SEQ ID NO 132
<211> LENGTH: 11
<212> TYPE: PRT
<213> ORGANISM: Homo sapiens

<400> SEQUENCE: 132

Trp Ser Asp Cys Ser Val Thr Cys Gly Lys Gly
1 5 10

<210> SEQ ID NO 133
<211> LENGTH: 11
<212> TYPE: PRT
<213> ORGANISM: Homo sapiens

<400> SEQUENCE: 133

Trp Ser Glu Cys Asn Lys Ser Cys Gly Lys Gly
1 5 10

<210> SEQ ID NO 134
<211> LENGTH: 11
<212> TYPE: PRT
<213> ORGANISM: Homo sapiens

<400> SEQUENCE: 134

Trp Ser Glu Cys Thr Lys Leu Cys Gly Gly Gly
1 5 10

<210> SEQ ID NO 135
<211> LENGTH: 11
<212> TYPE: PRT
<213> ORGANISM: Homo sapiens

<400> SEQUENCE: 135

Trp Ser Gln Cys Ser Ala Thr Cys Gly Asp Gly
1 5 10

<210> SEQ ID NO 136
<211> LENGTH: 11
<212> TYPE: PRT
<213> ORGANISM: Homo sapiens

<400> SEQUENCE: 136

Trp Ala Leu Cys Ser Thr Ser Cys Gly Ile Gly
1 5 10

<210> SEQ ID NO 137
<211> LENGTH: 11
<212> TYPE: PRT
<213> ORGANISM: Homo sapiens

<400> SEQUENCE: 137

Trp Ser Lys Cys Ser Ser Asn Cys Gly Gly Gly
1 5 10

<210> SEQ ID NO 138
<211> LENGTH: 11
<212> TYPE: PRT
<213> ORGANISM: Homo sapiens

<400> SEQUENCE: 138

Trp Ser Ser Cys Ser Arg Asp Cys Glu Leu Gly
1 5 10

<210> SEQ ID NO 139
<211> LENGTH: 11
<212> TYPE: PRT
<213> ORGANISM: Homo sapiens

<400> SEQUENCE: 139

Trp Ser Pro Cys Ser Ala Ser Cys Gly Gly Gly
1 5 10

<210> SEQ ID NO 140
<211> LENGTH: 11
<212> TYPE: PRT
<213> ORGANISM: Homo sapiens

<400> SEQUENCE: 140

Trp Thr Glu Cys Ser Lys Ser Cys Asp Gly Gly
1 5 10

<210> SEQ ID NO 141
<211> LENGTH: 11
<212> TYPE: PRT
<213> ORGANISM: Homo sapiens

<400> SEQUENCE: 141

Trp Ser Glu Cys Leu Val Thr Cys Gly Lys Gly
1 5 10

<210> SEQ ID NO 142
<211> LENGTH: 11
<212> TYPE: PRT
<213> ORGANISM: Homo sapiens

<400> SEQUENCE: 142

Trp Val Gln Cys Ser Val Thr Cys Gly Gln Gly
1 5 10

<210> SEQ ID NO 143
<211> LENGTH: 11
<212> TYPE: PRT
<213> ORGANISM: Homo sapiens

<400> SEQUENCE: 143

Trp Thr Pro Cys Ser Ala Thr Cys Gly Lys Gly
1 5 10

<210> SEQ ID NO 144
<211> LENGTH: 11
<212> TYPE: PRT
<213> ORGANISM: Homo sapiens

<400> SEQUENCE: 144

Trp Ser Ser Cys Ser Val Thr Cys Gly Gln Gly
1 5 10

<210> SEQ ID NO 145
<211> LENGTH: 11
<212> TYPE: PRT
<213> ORGANISM: Homo sapiens

<400> SEQUENCE: 145

Trp Gly Ala Cys Ser Ser Thr Cys Ala Gly Gly
1 5 10

<210> SEQ ID NO 146
<211> LENGTH: 11
<212> TYPE: PRT
<213> ORGANISM: Homo sapiens

<400> SEQUENCE: 146

Trp Gly Glu Cys Thr Lys Leu Cys Gly Gly Gly
1 5 10

<210> SEQ ID NO 147
<211> LENGTH: 11
<212> TYPE: PRT
<213> ORGANISM: Homo sapiens

<400> SEQUENCE: 147

Trp Ser Ser Cys Ser Val Ser Cys Gly Arg Gly
1               5                   10

<210> SEQ ID NO 148
<211> LENGTH: 11
<212> TYPE: PRT
<213> ORGANISM: Homo sapiens

<400> SEQUENCE: 148

Trp Ser Gln Cys Ser Val Ser Cys Gly Arg Gly
1               5                   10

<210> SEQ ID NO 149
<211> LENGTH: 11
<212> TYPE: PRT
<213> ORGANISM: Homo sapiens

<400> SEQUENCE: 149

Trp Gln Glu Cys Thr Lys Thr Cys Gly Glu Gly
1               5                   10

<210> SEQ ID NO 150
<211> LENGTH: 11
<212> TYPE: PRT
<213> ORGANISM: Homo sapiens

<400> SEQUENCE: 150

Trp Ser Glu Cys Ser Val Thr Cys Gly Lys Gly
1               5                   10

<210> SEQ ID NO 151
<211> LENGTH: 11
<212> TYPE: PRT
<213> ORGANISM: Homo sapiens

<400> SEQUENCE: 151

Trp Gly Ser Cys Ser Val Ser Cys Gly Val Gly
1               5                   10

<210> SEQ ID NO 152
<211> LENGTH: 11
<212> TYPE: PRT
<213> ORGANISM: Homo sapiens

<400> SEQUENCE: 152

Trp Gly Asp Cys Ser Arg Thr Cys Gly Gly Gly
1               5                   10

<210> SEQ ID NO 153
<211> LENGTH: 11
<212> TYPE: PRT
<213> ORGANISM: Homo sapiens

<400> SEQUENCE: 153

Trp Gly Glu Cys Ser Lys Ser Cys Glu Leu Gly
1               5                   10

<210> SEQ ID NO 154
<211> LENGTH: 11
<212> TYPE: PRT
<213> ORGANISM: Homo sapiens

<400> SEQUENCE: 154

Trp Ser Ser Cys Ser Lys Thr Cys Gly Lys Gly
1 5 10

<210> SEQ ID NO 155
<211> LENGTH: 11
<212> TYPE: PRT
<213> ORGANISM: Homo sapiens

<400> SEQUENCE: 155

Trp Ser Ile Cys Ser Arg Ser Cys Gly Met Gly
1 5 10

<210> SEQ ID NO 156
<211> LENGTH: 11
<212> TYPE: PRT
<213> ORGANISM: Homo sapiens

<400> SEQUENCE: 156

Trp Thr Lys Cys Thr Val Thr Cys Gly Arg Gly
1 5 10

<210> SEQ ID NO 157
<211> LENGTH: 11
<212> TYPE: PRT
<213> ORGANISM: Homo sapiens

<400> SEQUENCE: 157

Trp Gly Glu Cys Ser Arg Thr Cys Gly Gly Gly
1 5 10

<210> SEQ ID NO 158
<211> LENGTH: 11
<212> TYPE: PRT
<213> ORGANISM: Homo sapiens

<400> SEQUENCE: 158

Trp Ser Glu Cys Ser Ala Thr Cys Ala Gly Gly
1 5 10

<210> SEQ ID NO 159
<211> LENGTH: 11
<212> TYPE: PRT
<213> ORGANISM: Homo sapiens

<400> SEQUENCE: 159

Trp Gly Gln Cys Ser Arg Ser Cys Gly Gly Gly
1 5 10

<210> SEQ ID NO 160
<211> LENGTH: 11
<212> TYPE: PRT
<213> ORGANISM: Homo sapiens

<400> SEQUENCE: 160

Trp Leu Ala Cys Ser Arg Thr Cys Asp Thr Gly
1 5 10

<210> SEQ ID NO 161
<211> LENGTH: 11
<212> TYPE: PRT
<213> ORGANISM: Homo sapiens

<400> SEQUENCE: 161

Trp Gly Glu Cys Ser Arg Thr Cys Gly Gly Gly
1 5 10

<210> SEQ ID NO 162
<211> LENGTH: 11
<212> TYPE: PRT
<213> ORGANISM: Homo sapiens

<400> SEQUENCE: 162

Trp Ser Glu Cys Ser Ser Thr Cys Gly Ala Gly
1 5 10

<210> SEQ ID NO 163
<211> LENGTH: 11
<212> TYPE: PRT
<213> ORGANISM: Homo sapiens

<400> SEQUENCE: 163

Trp Ser Glu Cys Ser Lys Thr Cys Gly Ser Gly
1 5 10

<210> SEQ ID NO 164
<211> LENGTH: 11
<212> TYPE: PRT
<213> ORGANISM: Homo sapiens

<400> SEQUENCE: 164

Trp Thr Ser Cys Pro Ser Ser Cys Lys Glu Gly
1 5 10

<210> SEQ ID NO 165
<211> LENGTH: 11
<212> TYPE: PRT
<213> ORGANISM: Homo sapiens

<400> SEQUENCE: 165

Trp Ser Arg Cys Ser Lys Ser Cys Gly Ser Gly
1 5 10

<210> SEQ ID NO 166
<211> LENGTH: 11
<212> TYPE: PRT
<213> ORGANISM: Homo sapiens

<400> SEQUENCE: 166

Trp Ser Leu Cys Gln Leu Thr Cys Val Asn Gly
1 5 10

<210> SEQ ID NO 167
<211> LENGTH: 6
<212> TYPE: PRT
<213> ORGANISM: Homo sapiens

<400> SEQUENCE: 167

Gly Lys Thr Thr Cys Leu
1 5

<210> SEQ ID NO 168
<211> LENGTH: 6
<212> TYPE: PRT
<213> ORGANISM: Homo sapiens

<400> SEQUENCE: 168

Gly Ala Asn Leu Cys Leu
1 5

<210> SEQ ID NO 169
<211> LENGTH: 6
<212> TYPE: PRT
<213> ORGANISM: Homo sapiens

<400> SEQUENCE: 169

Gly Glu Ala Gln Cys Leu
1 5

<210> SEQ ID NO 170
<211> LENGTH: 6
<212> TYPE: PRT
<213> ORGANISM: Homo sapiens

<400> SEQUENCE: 170

Gly Ala Thr Thr Cys Leu
1 5

<210> SEQ ID NO 171
<211> LENGTH: 6
<212> TYPE: PRT
<213> ORGANISM: Homo sapiens

<400> SEQUENCE: 171

Gly Ile Arg Ser Cys Leu
1 5

<210> SEQ ID NO 172
<211> LENGTH: 6
<212> TYPE: PRT
<213> ORGANISM: Homo sapiens

<400> SEQUENCE: 172

Gly His Arg Ile Cys Leu
1 5

<210> SEQ ID NO 173
<211> LENGTH: 6
<212> TYPE: PRT
<213> ORGANISM: Homo sapiens

<400> SEQUENCE: 173

Gly Glu Ala Val Cys Leu
1 5

<210> SEQ ID NO 174
<211> LENGTH: 6
<212> TYPE: PRT
<213> ORGANISM: Homo sapiens

<400> SEQUENCE: 174

Gly Asp His Pro Cys Leu
1 5

<210> SEQ ID NO 175
<211> LENGTH: 6
<212> TYPE: PRT
<213> ORGANISM: Homo sapiens

<400> SEQUENCE: 175

Gly Phe Val Gly Cys Leu
1               5

<210> SEQ ID NO 176
<211> LENGTH: 6
<212> TYPE: PRT
<213> ORGANISM: Homo sapiens

<400> SEQUENCE: 176

Gly Cys Val Cys Cys Leu
1               5

<210> SEQ ID NO 177
<211> LENGTH: 6
<212> TYPE: PRT
<213> ORGANISM: Homo sapiens

<400> SEQUENCE: 177

Gly Leu His Arg Cys Leu
1               5

<210> SEQ ID NO 178
<211> LENGTH: 6
<212> TYPE: PRT
<213> ORGANISM: Homo sapiens

<400> SEQUENCE: 178

Gly Leu Val Leu Cys Leu
1               5

<210> SEQ ID NO 179
<211> LENGTH: 6
<212> TYPE: PRT
<213> ORGANISM: Homo sapiens

<400> SEQUENCE: 179

Gly Cys Val Cys Cys Leu
1               5

<210> SEQ ID NO 180
<211> LENGTH: 6
<212> TYPE: PRT
<213> ORGANISM: Homo sapiens

<400> SEQUENCE: 180

Gly Pro Glu Asn Cys Leu
1               5

<210> SEQ ID NO 181
<211> LENGTH: 6
<212> TYPE: PRT
<213> ORGANISM: Homo sapiens

<400> SEQUENCE: 181

Gly Thr Pro Leu Cys Leu
1               5

<210> SEQ ID NO 182
<211> LENGTH: 6
<212> TYPE: PRT
<213> ORGANISM: Homo sapiens

<400> SEQUENCE: 182

Gly Thr Ile Tyr Cys Leu
1               5

<210> SEQ ID NO 183
<211> LENGTH: 6
<212> TYPE: PRT
<213> ORGANISM: Homo sapiens

<400> SEQUENCE: 183

Gly His His Val Cys Leu
1               5

<210> SEQ ID NO 184
<211> LENGTH: 6
<212> TYPE: PRT
<213> ORGANISM: Homo sapiens

<400> SEQUENCE: 184

Gly Leu Ile Thr Cys Leu
1               5

<210> SEQ ID NO 185
<211> LENGTH: 6
<212> TYPE: PRT
<213> ORGANISM: Homo sapiens

<400> SEQUENCE: 185

Gly Asn Lys Thr Cys Leu
1               5

<210> SEQ ID NO 186
<211> LENGTH: 6
<212> TYPE: PRT
<213> ORGANISM: Homo sapiens

<400> SEQUENCE: 186

Gly Leu Gln Ala Cys Leu
1               5

<210> SEQ ID NO 187
<211> LENGTH: 6
<212> TYPE: PRT
<213> ORGANISM: Homo sapiens

<400> SEQUENCE: 187

Gly Arg Asp Arg Cys Leu
1               5

<210> SEQ ID NO 188
<211> LENGTH: 6
<212> TYPE: PRT
<213> ORGANISM: Homo sapiens

<400> SEQUENCE: 188

Gly Phe Val Gly Cys Leu
1               5

<210> SEQ ID NO 189
<211> LENGTH: 6
<212> TYPE: PRT
<213> ORGANISM: Homo sapiens

<400> SEQUENCE: 189

Gly Asp Val Phe Cys Leu
1               5

<210> SEQ ID NO 190
<211> LENGTH: 6
<212> TYPE: PRT
<213> ORGANISM: Homo sapiens

<400> SEQUENCE: 190

Gly Ser Pro Val Cys Leu
1               5

<210> SEQ ID NO 191
<211> LENGTH: 6
<212> TYPE: PRT
<213> ORGANISM: Homo sapiens

<400> SEQUENCE: 191

Gly Ala Ile Tyr Cys Leu
1               5

<210> SEQ ID NO 192
<211> LENGTH: 6
<212> TYPE: PRT
<213> ORGANISM: Homo sapiens

<400> SEQUENCE: 192

Gly Ala Trp Leu Cys Leu
1               5

<210> SEQ ID NO 193
<211> LENGTH: 6
<212> TYPE: PRT
<213> ORGANISM: Homo sapiens

<400> SEQUENCE: 193

Gly Ser His Glu Cys Leu
1               5

<210> SEQ ID NO 194
<211> LENGTH: 6
<212> TYPE: PRT
<213> ORGANISM: Homo sapiens

<400> SEQUENCE: 194

Gly Ala Gly Leu Cys Leu
1               5

<210> SEQ ID NO 195
<211> LENGTH: 6
<212> TYPE: PRT
<213> ORGANISM: Homo sapiens

<400> SEQUENCE: 195

Gly Arg Asp Asp Cys Leu
1               5

<210> SEQ ID NO 196
<211> LENGTH: 6
<212> TYPE: PRT
<213> ORGANISM: Homo sapiens

<400> SEQUENCE: 196

Gly Thr Asn Ser Cys Leu
1 5

<210> SEQ ID NO 197
<211> LENGTH: 6
<212> TYPE: PRT
<213> ORGANISM: Homo sapiens

<400> SEQUENCE: 197

Gly Cys Asp Gly Cys Leu
1 5

<210> SEQ ID NO 198
<211> LENGTH: 6
<212> TYPE: PRT
<213> ORGANISM: Homo sapiens

<400> SEQUENCE: 198

Gly Leu Val Thr Cys Leu
1 5

<210> SEQ ID NO 199
<211> LENGTH: 6
<212> TYPE: PRT
<213> ORGANISM: Homo sapiens

<400> SEQUENCE: 199

Gly Pro Ser Tyr Cys Leu
1 5

<210> SEQ ID NO 200
<211> LENGTH: 6
<212> TYPE: PRT
<213> ORGANISM: Homo sapiens

<400> SEQUENCE: 200

Gly Asn Leu Glu Cys Leu
1 5

<210> SEQ ID NO 201
<211> LENGTH: 6
<212> TYPE: PRT
<213> ORGANISM: Homo sapiens

<400> SEQUENCE: 201

Gly His Arg Leu Cys Leu
1 5

<210> SEQ ID NO 202
<211> LENGTH: 6
<212> TYPE: PRT
<213> ORGANISM: Homo sapiens

<400> SEQUENCE: 202

Gly His Ser Glu Cys Leu
1 5

<210> SEQ ID NO 203
<211> LENGTH: 6
<212> TYPE: PRT
<213> ORGANISM: Homo sapiens

<400> SEQUENCE: 203

Gly Asn Gly Phe Cys Leu
1               5

<210> SEQ ID NO 204
<211> LENGTH: 6
<212> TYPE: PRT
<213> ORGANISM: Homo sapiens

<400> SEQUENCE: 204

Gly Lys Pro Met Cys Leu
1               5

<210> SEQ ID NO 205
<211> LENGTH: 6
<212> TYPE: PRT
<213> ORGANISM: Homo sapiens

<400> SEQUENCE: 205

Gly Phe Glu Asp Cys Leu
1               5

<210> SEQ ID NO 206
<211> LENGTH: 6
<212> TYPE: PRT
<213> ORGANISM: Homo sapiens

<400> SEQUENCE: 206

Gly Arg Thr Gln Cys Leu
1               5

<210> SEQ ID NO 207
<211> LENGTH: 6
<212> TYPE: PRT
<213> ORGANISM: Homo sapiens

<400> SEQUENCE: 207

Gly Trp Pro His Cys Leu
1               5

<210> SEQ ID NO 208
<211> LENGTH: 6
<212> TYPE: PRT
<213> ORGANISM: Homo sapiens

<400> SEQUENCE: 208

Gly Pro Ala Leu Cys Leu
1               5

<210> SEQ ID NO 209
<211> LENGTH: 6
<212> TYPE: PRT
<213> ORGANISM: Homo sapiens

<400> SEQUENCE: 209

Gly Cys Tyr Phe Cys Leu
1               5

<210> SEQ ID NO 210
<211> LENGTH: 6
<212> TYPE: PRT
<213> ORGANISM: Homo sapiens

<400> SEQUENCE: 210

Gly Arg Tyr Tyr Cys Leu
1 5

<210> SEQ ID NO 211
<211> LENGTH: 6
<212> TYPE: PRT
<213> ORGANISM: Homo sapiens

<400> SEQUENCE: 211

Gly Ser Leu Leu Cys Leu
1 5

<210> SEQ ID NO 212
<211> LENGTH: 6
<212> TYPE: PRT
<213> ORGANISM: Homo sapiens

<400> SEQUENCE: 212

Gly Lys Ile Val Cys Leu
1 5

<210> SEQ ID NO 213
<211> LENGTH: 6
<212> TYPE: PRT
<213> ORGANISM: Homo sapiens

<400> SEQUENCE: 213

Gly Lys Asp Phe Cys Leu
1 5

<210> SEQ ID NO 214
<211> LENGTH: 6
<212> TYPE: PRT
<213> ORGANISM: Homo sapiens

<400> SEQUENCE: 214

Gly Met Ile Met Cys Leu
1 5

<210> SEQ ID NO 215
<211> LENGTH: 6
<212> TYPE: PRT
<213> ORGANISM: Homo sapiens

<400> SEQUENCE: 215

Gly Phe Gly Glu Cys Leu
1 5

<210> SEQ ID NO 216
<211> LENGTH: 6
<212> TYPE: PRT
<213> ORGANISM: Homo sapiens

<400> SEQUENCE: 216

Gly Met Gly Val Cys Leu
1 5

<210> SEQ ID NO 217
<211> LENGTH: 6
<212> TYPE: PRT
<213> ORGANISM: Homo sapiens

<400> SEQUENCE: 217

Gly Leu Phe Gly Cys Leu
1               5

<210> SEQ ID NO 218
<211> LENGTH: 6
<212> TYPE: PRT
<213> ORGANISM: Homo sapiens

<400> SEQUENCE: 218

Gly Cys Gly Pro Cys Leu
1               5

<210> SEQ ID NO 219
<211> LENGTH: 6
<212> TYPE: PRT
<213> ORGANISM: Homo sapiens

<400> SEQUENCE: 219

Gly Phe Asp Asn Cys Leu
1               5

<210> SEQ ID NO 220
<211> LENGTH: 6
<212> TYPE: PRT
<213> ORGANISM: Homo sapiens

<400> SEQUENCE: 220

Gly Leu Gly Val Cys Leu
1               5

<210> SEQ ID NO 221
<211> LENGTH: 6
<212> TYPE: PRT
<213> ORGANISM: Homo sapiens

<400> SEQUENCE: 221

Gly Ser Gly Phe Cys Leu
1               5

<210> SEQ ID NO 222
<211> LENGTH: 6
<212> TYPE: PRT
<213> ORGANISM: Homo sapiens

<400> SEQUENCE: 222

Gly Thr Cys Met Cys Leu
1               5

<210> SEQ ID NO 223
<211> LENGTH: 6
<212> TYPE: PRT
<213> ORGANISM: Homo sapiens

<400> SEQUENCE: 223

Gly Leu Thr Pro Cys Leu
1               5

<210> SEQ ID NO 224
<211> LENGTH: 6
<212> TYPE: PRT
<213> ORGANISM: Homo sapiens

<400> SEQUENCE: 224

Gly Gln Leu Glu Cys Leu
1 5

<210> SEQ ID NO 225
<211> LENGTH: 6
<212> TYPE: PRT
<213> ORGANISM: Homo sapiens

<400> SEQUENCE: 225

Gly Val Ala Leu Cys Leu
1 5

<210> SEQ ID NO 226
<211> LENGTH: 6
<212> TYPE: PRT
<213> ORGANISM: Homo sapiens

<400> SEQUENCE: 226

Gly Val Ile Glu Cys Leu
1 5

<210> SEQ ID NO 227
<211> LENGTH: 6
<212> TYPE: PRT
<213> ORGANISM: Homo sapiens

<400> SEQUENCE: 227

Gly Asn Thr Ser Cys Leu
1 5

<210> SEQ ID NO 228
<211> LENGTH: 6
<212> TYPE: PRT
<213> ORGANISM: Homo sapiens

<400> SEQUENCE: 228

Gly Asn Ser Glu Cys Leu
1 5

<210> SEQ ID NO 229
<211> LENGTH: 6
<212> TYPE: PRT
<213> ORGANISM: Homo sapiens

<400> SEQUENCE: 229

Gly Ser Cys Leu Cys Leu
1 5

<210> SEQ ID NO 230
<211> LENGTH: 6
<212> TYPE: PRT
<213> ORGANISM: Homo sapiens

<400> SEQUENCE: 230

Gly Gly Ile Glu Cys Leu
1 5

<210> SEQ ID NO 231
<211> LENGTH: 6
<212> TYPE: PRT
<213> ORGANISM: Homo sapiens

<400> SEQUENCE: 231

Gly Glu Lys Val Cys Leu
1               5

<210> SEQ ID NO 232
<211> LENGTH: 6
<212> TYPE: PRT
<213> ORGANISM: Homo sapiens

<400> SEQUENCE: 232

Gly Asp Val Val Cys Leu
1               5

<210> SEQ ID NO 233
<211> LENGTH: 6
<212> TYPE: PRT
<213> ORGANISM: Homo sapiens

<400> SEQUENCE: 233

Gly Glu His Ile Cys Leu
1               5

<210> SEQ ID NO 234
<211> LENGTH: 6
<212> TYPE: PRT
<213> ORGANISM: Homo sapiens

<400> SEQUENCE: 234

Gly Glu Arg Arg Cys Leu
1               5

<210> SEQ ID NO 235
<211> LENGTH: 6
<212> TYPE: PRT
<213> ORGANISM: Homo sapiens

<400> SEQUENCE: 235

Gly Pro Ser Gly Cys Leu
1               5

<210> SEQ ID NO 236
<211> LENGTH: 6
<212> TYPE: PRT
<213> ORGANISM: Homo sapiens

<400> SEQUENCE: 236

Gly Tyr Arg Lys Cys Leu
1               5

<210> SEQ ID NO 237
<211> LENGTH: 6
<212> TYPE: PRT
<213> ORGANISM: Homo sapiens

<400> SEQUENCE: 237

Gly Met Ile Tyr Cys Leu
1               5

<210> SEQ ID NO 238
<211> LENGTH: 6
<212> TYPE: PRT
<213> ORGANISM: Homo sapiens

<400> SEQUENCE: 238

Gly Leu Leu Cys Cys Leu
1 5

<210> SEQ ID NO 239
<211> LENGTH: 6
<212> TYPE: PRT
<213> ORGANISM: Homo sapiens

<400> SEQUENCE: 239

Gly Gln Lys Thr Cys Leu
1 5

<210> SEQ ID NO 240
<211> LENGTH: 6
<212> TYPE: PRT
<213> ORGANISM: Homo sapiens

<400> SEQUENCE: 240

Gly Lys Glu Lys Cys Leu
1 5

<210> SEQ ID NO 241
<211> LENGTH: 6
<212> TYPE: PRT
<213> ORGANISM: Homo sapiens

<400> SEQUENCE: 241

Gly Ile Phe Leu Cys Leu
1 5

<210> SEQ ID NO 242
<211> LENGTH: 6
<212> TYPE: PRT
<213> ORGANISM: Homo sapiens

<400> SEQUENCE: 242

Gly Cys Tyr Phe Cys Leu
1 5

<210> SEQ ID NO 243
<211> LENGTH: 6
<212> TYPE: PRT
<213> ORGANISM: Homo sapiens

<400> SEQUENCE: 243

Gly Pro Val Met Cys Leu
1 5

<210> SEQ ID NO 244
<211> LENGTH: 6
<212> TYPE: PRT
<213> ORGANISM: Homo sapiens

<400> SEQUENCE: 244

Gly Leu Thr Pro Cys Leu
1 5

<210> SEQ ID NO 245
<211> LENGTH: 6
<212> TYPE: PRT
<213> ORGANISM: Homo sapiens

<400> SEQUENCE: 245

Gly Arg Arg Asp Cys Leu
1 5

<210> SEQ ID NO 246
<211> LENGTH: 6
<212> TYPE: PRT
<213> ORGANISM: Homo sapiens

<400> SEQUENCE: 246

Gly Gly Gly Ala Cys Leu
1 5

<210> SEQ ID NO 247
<211> LENGTH: 6
<212> TYPE: PRT
<213> ORGANISM: Homo sapiens

<400> SEQUENCE: 247

Gly Gly Gly Ser Cys Leu
1 5

<210> SEQ ID NO 248
<211> LENGTH: 6
<212> TYPE: PRT
<213> ORGANISM: Homo sapiens

<400> SEQUENCE: 248

Gly Glu Pro Tyr Cys Leu
1 5

<210> SEQ ID NO 249
<211> LENGTH: 6
<212> TYPE: PRT
<213> ORGANISM: Homo sapiens

<400> SEQUENCE: 249

Gly Ala Cys Leu Cys Leu
1 5

<210> SEQ ID NO 250
<211> LENGTH: 6
<212> TYPE: PRT
<213> ORGANISM: Homo sapiens

<400> SEQUENCE: 250

Gly Ala Gln Pro Cys Leu
1 5

<210> SEQ ID NO 251
<211> LENGTH: 6
<212> TYPE: PRT
<213> ORGANISM: Homo sapiens

<400> SEQUENCE: 251

Gly Tyr Gly His Cys Leu
1 5

<210> SEQ ID NO 252
<211> LENGTH: 6
<212> TYPE: PRT
<213> ORGANISM: Homo sapiens

<400> SEQUENCE: 252

Gly Met Gly Pro Cys Leu
1               5

<210> SEQ ID NO 253
<211> LENGTH: 6
<212> TYPE: PRT
<213> ORGANISM: Homo sapiens

<400> SEQUENCE: 253

Gly Cys His Gly Cys Leu
1               5

<210> SEQ ID NO 254
<211> LENGTH: 6
<212> TYPE: PRT
<213> ORGANISM: Homo sapiens

<400> SEQUENCE: 254

Gly Glu Gly Thr Cys Leu
1               5

<210> SEQ ID NO 255
<211> LENGTH: 6
<212> TYPE: PRT
<213> ORGANISM: Homo sapiens

<400> SEQUENCE: 255

Gly Phe Pro Arg Cys Leu
1               5

<210> SEQ ID NO 256
<211> LENGTH: 6
<212> TYPE: PRT
<213> ORGANISM: Homo sapiens

<400> SEQUENCE: 256

Gly Leu Asn Gln Cys Leu
1               5

<210> SEQ ID NO 257
<211> LENGTH: 6
<212> TYPE: PRT
<213> ORGANISM: Homo sapiens

<400> SEQUENCE: 257

Gly Arg Arg Arg Cys Leu
1               5

<210> SEQ ID NO 258
<211> LENGTH: 6
<212> TYPE: PRT
<213> ORGANISM: Homo sapiens

<400> SEQUENCE: 258

Gly Ile Glu Asp Cys Leu
1               5

<210> SEQ ID NO 259
<211> LENGTH: 6
<212> TYPE: PRT
<213> ORGANISM: Homo sapiens

<400> SEQUENCE: 259

Gly Asp Gly Tyr Cys Leu
1               5

<210> SEQ ID NO 260
<211> LENGTH: 6
<212> TYPE: PRT
<213> ORGANISM: Homo sapiens

<400> SEQUENCE: 260

Gly Phe Val Gly Cys Leu
1               5

<210> SEQ ID NO 261
<211> LENGTH: 6
<212> TYPE: PRT
<213> ORGANISM: Homo sapiens

<400> SEQUENCE: 261

Gly Gln Gly Leu Cys Leu
1               5

<210> SEQ ID NO 262
<211> LENGTH: 6
<212> TYPE: PRT
<213> ORGANISM: Homo sapiens

<400> SEQUENCE: 262

Gly Gln Leu Cys Cys Leu
1               5

<210> SEQ ID NO 263
<211> LENGTH: 6
<212> TYPE: PRT
<213> ORGANISM: Homo sapiens

<400> SEQUENCE: 263

Gly Ala Val Leu Cys Leu
1               5

<210> SEQ ID NO 264
<211> LENGTH: 6
<212> TYPE: PRT
<213> ORGANISM: Homo sapiens

<400> SEQUENCE: 264

Gly Gln Tyr Gln Cys Leu
1               5

<210> SEQ ID NO 265
<211> LENGTH: 6
<212> TYPE: PRT
<213> ORGANISM: Homo sapiens

<400> SEQUENCE: 265

Gly Phe Gly Val Cys Leu
1               5

<210> SEQ ID NO 266
<211> LENGTH: 6
<212> TYPE: PRT
<213> ORGANISM: Homo sapiens

<400> SEQUENCE: 266

Gly Gly Pro Ala Cys Leu
1               5

<210> SEQ ID NO 267
<211> LENGTH: 6
<212> TYPE: PRT
<213> ORGANISM: Homo sapiens

<400> SEQUENCE: 267

Gly Cys Ala Val Cys Leu
1               5

<210> SEQ ID NO 268
<211> LENGTH: 6
<212> TYPE: PRT
<213> ORGANISM: Homo sapiens

<400> SEQUENCE: 268

Gly Cys Thr Val Cys Leu
1               5

<210> SEQ ID NO 269
<211> LENGTH: 6
<212> TYPE: PRT
<213> ORGANISM: Homo sapiens

<400> SEQUENCE: 269

Gly Val Phe Ile Cys Leu
1               5

<210> SEQ ID NO 270
<211> LENGTH: 6
<212> TYPE: PRT
<213> ORGANISM: Homo sapiens

<400> SEQUENCE: 270

Gly Ala Leu Gln Cys Leu
1               5

<210> SEQ ID NO 271
<211> LENGTH: 6
<212> TYPE: PRT
<213> ORGANISM: Homo sapiens

<400> SEQUENCE: 271

Gly Lys Asp Gly Cys Leu
1               5

<210> SEQ ID NO 272
<211> LENGTH: 6
<212> TYPE: PRT
<213> ORGANISM: Homo sapiens

<400> SEQUENCE: 272

Gly Gln Met Glu Cys Leu
1               5

<210> SEQ ID NO 273
<211> LENGTH: 6
<212> TYPE: PRT
<213> ORGANISM: Homo sapiens

<400> SEQUENCE: 273

Gly Ala Lys Asp Cys Leu
1               5

<210> SEQ ID NO 274
<211> LENGTH: 6
<212> TYPE: PRT
<213> ORGANISM: Homo sapiens

<400> SEQUENCE: 274

Gly His Ile Val Cys Leu
1               5

<210> SEQ ID NO 275
<211> LENGTH: 6
<212> TYPE: PRT
<213> ORGANISM: Homo sapiens

<400> SEQUENCE: 275

Gly Ser Gly Thr Cys Leu
1               5

<210> SEQ ID NO 276
<211> LENGTH: 6
<212> TYPE: PRT
<213> ORGANISM: Homo sapiens

<400> SEQUENCE: 276

Gly Ala His Phe Cys Leu
1               5

<210> SEQ ID NO 277
<211> LENGTH: 6
<212> TYPE: PRT
<213> ORGANISM: Homo sapiens

<400> SEQUENCE: 277

Gly Pro Gln Glu Cys Leu
1               5

<210> SEQ ID NO 278
<211> LENGTH: 6
<212> TYPE: PRT
<213> ORGANISM: Homo sapiens

<400> SEQUENCE: 278

Gly Val Asp Gly Cys Leu
1               5

<210> SEQ ID NO 279
<211> LENGTH: 6
<212> TYPE: PRT
<213> ORGANISM: Homo sapiens

<400> SEQUENCE: 279

Gly Cys Leu Cys Cys Leu
1               5

<210> SEQ ID NO 280
<211> LENGTH: 6
<212> TYPE: PRT
<213> ORGANISM: Homo sapiens

<400> SEQUENCE: 280

Gly Phe Leu Gly Cys Leu
1               5

<210> SEQ ID NO 281
<211> LENGTH: 6
<212> TYPE: PRT
<213> ORGANISM: Homo sapiens

<400> SEQUENCE: 281

Gly Ala Thr Glu Cys Leu
1               5

<210> SEQ ID NO 282
<211> LENGTH: 6
<212> TYPE: PRT
<213> ORGANISM: Homo sapiens

<400> SEQUENCE: 282

Gly Leu Gly Ser Cys Leu
1               5

<210> SEQ ID NO 283
<211> LENGTH: 6
<212> TYPE: PRT
<213> ORGANISM: Homo sapiens

<400> SEQUENCE: 283

Gly Arg Ser Trp Cys Leu
1               5

<210> SEQ ID NO 284
<211> LENGTH: 6
<212> TYPE: PRT
<213> ORGANISM: Homo sapiens

<400> SEQUENCE: 284

Gly Ser Arg Leu Cys Leu
1               5

<210> SEQ ID NO 285
<211> LENGTH: 6
<212> TYPE: PRT
<213> ORGANISM: Homo sapiens

<400> SEQUENCE: 285

Gly Asn Leu Thr Cys Leu
1               5

<210> SEQ ID NO 286
<211> LENGTH: 6
<212> TYPE: PRT
<213> ORGANISM: Homo sapiens

<400> SEQUENCE: 286

Gly Lys Thr Thr Cys Leu
1               5

<210> SEQ ID NO 287
<211> LENGTH: 6
<212> TYPE: PRT
<213> ORGANISM: Homo sapiens

<400> SEQUENCE: 287

Gly Leu Pro Pro Cys Leu
1 5

<210> SEQ ID NO 288
<211> LENGTH: 6
<212> TYPE: PRT
<213> ORGANISM: Homo sapiens

<400> SEQUENCE: 288

Gly His Tyr Gln Cys Leu
1 5

<210> SEQ ID NO 289
<211> LENGTH: 6
<212> TYPE: PRT
<213> ORGANISM: Homo sapiens

<400> SEQUENCE: 289

Gly Ser Tyr Ile Cys Leu
1 5

<210> SEQ ID NO 290
<211> LENGTH: 6
<212> TYPE: PRT
<213> ORGANISM: Homo sapiens

<400> SEQUENCE: 290

Gly Met Tyr Gln Cys Leu
1 5

<210> SEQ ID NO 291
<211> LENGTH: 6
<212> TYPE: PRT
<213> ORGANISM: Homo sapiens

<400> SEQUENCE: 291

Gly Gln Gly Arg Cys Leu
1 5

<210> SEQ ID NO 292
<211> LENGTH: 6
<212> TYPE: PRT
<213> ORGANISM: Homo sapiens

<400> SEQUENCE: 292

Gly Glu Tyr Phe Cys Leu
1 5

<210> SEQ ID NO 293
<211> LENGTH: 6
<212> TYPE: PRT
<213> ORGANISM: Homo sapiens

<400> SEQUENCE: 293

Gly Gln Gln His Cys Leu
1 5

<210> SEQ ID NO 294
<211> LENGTH: 6
<212> TYPE: PRT
<213> ORGANISM: Homo sapiens

<400> SEQUENCE: 294

Gly Pro Ser Pro Cys Leu
1 5

<210> SEQ ID NO 295
<211> LENGTH: 6
<212> TYPE: PRT
<213> ORGANISM: Homo sapiens

<400> SEQUENCE: 295

Gly Val Gln Ile Cys Leu
1 5

<210> SEQ ID NO 296
<211> LENGTH: 6
<212> TYPE: PRT
<213> ORGANISM: Homo sapiens

<400> SEQUENCE: 296

Gly Ile Glu Ser Cys Leu
1 5

<210> SEQ ID NO 297
<211> LENGTH: 6
<212> TYPE: PRT
<213> ORGANISM: Homo sapiens

<400> SEQUENCE: 297

Gly Phe Val Asp Cys Leu
1 5

<210> SEQ ID NO 298
<211> LENGTH: 6
<212> TYPE: PRT
<213> ORGANISM: Homo sapiens

<400> SEQUENCE: 298

Gly Lys Ile Asn Cys Leu
1 5

<210> SEQ ID NO 299
<211> LENGTH: 6
<212> TYPE: PRT
<213> ORGANISM: Homo sapiens

<400> SEQUENCE: 299

Gly Met Leu Leu Cys Leu
1 5

<210> SEQ ID NO 300
<211> LENGTH: 6
<212> TYPE: PRT
<213> ORGANISM: Homo sapiens

<400> SEQUENCE: 300

Gly Thr Gln Val Cys Leu
1 5

<210> SEQ ID NO 301
<211> LENGTH: 6
<212> TYPE: PRT
<213> ORGANISM: Homo sapiens

<400> SEQUENCE: 301

Gly Ala Glu Ala Cys Leu
1               5

<210> SEQ ID NO 302
<211> LENGTH: 6
<212> TYPE: PRT
<213> ORGANISM: Homo sapiens

<400> SEQUENCE: 302

Gly Leu Ala Ser Cys Leu
1               5

<210> SEQ ID NO 303
<211> LENGTH: 6
<212> TYPE: PRT
<213> ORGANISM: Homo sapiens

<400> SEQUENCE: 303

Gly Phe Lys Val Cys Leu
1               5

<210> SEQ ID NO 304
<211> LENGTH: 6
<212> TYPE: PRT
<213> ORGANISM: Homo sapiens

<400> SEQUENCE: 304

Gly Leu Arg Asn Cys Leu
1               5

<210> SEQ ID NO 305
<211> LENGTH: 6
<212> TYPE: PRT
<213> ORGANISM: Homo sapiens

<400> SEQUENCE: 305

Gly Asp His Glu Cys Leu
1               5

<210> SEQ ID NO 306
<211> LENGTH: 6
<212> TYPE: PRT
<213> ORGANISM: Homo sapiens

<400> SEQUENCE: 306

Gly Cys Gln Met Cys Leu
1               5

<210> SEQ ID NO 307
<211> LENGTH: 6
<212> TYPE: PRT
<213> ORGANISM: Homo sapiens

<400> SEQUENCE: 307

Gly Leu Asn Val Cys Leu
1               5

<210> SEQ ID NO 308
<211> LENGTH: 6
<212> TYPE: PRT
<213> ORGANISM: Homo sapiens

<400> SEQUENCE: 308

Gly Tyr Arg Trp Cys Leu
1               5

<210> SEQ ID NO 309
<211> LENGTH: 6
<212> TYPE: PRT
<213> ORGANISM: Homo sapiens

<400> SEQUENCE: 309

Gly Ala Leu Val Cys Leu
1               5

<210> SEQ ID NO 310
<211> LENGTH: 6
<212> TYPE: PRT
<213> ORGANISM: Homo sapiens

<400> SEQUENCE: 310

Gly Thr Pro Leu Cys Leu
1               5

<210> SEQ ID NO 311
<211> LENGTH: 6
<212> TYPE: PRT
<213> ORGANISM: Homo sapiens

<400> SEQUENCE: 311

Gly Leu Leu Gly Cys Leu
1               5

<210> SEQ ID NO 312
<211> LENGTH: 6
<212> TYPE: PRT
<213> ORGANISM: Homo sapiens

<400> SEQUENCE: 312

Gly Tyr Ser Leu Cys Leu
1               5

<210> SEQ ID NO 313
<211> LENGTH: 6
<212> TYPE: PRT
<213> ORGANISM: Homo sapiens

<400> SEQUENCE: 313

Gly Val Pro Leu Cys Leu
1               5

<210> SEQ ID NO 314
<211> LENGTH: 6
<212> TYPE: PRT
<213> ORGANISM: Homo sapiens

<400> SEQUENCE: 314

Gly Gln Gly Arg Cys Leu
1               5

<210> SEQ ID NO 315
<211> LENGTH: 6
<212> TYPE: PRT
<213> ORGANISM: Homo sapiens

<400> SEQUENCE: 315

Gly Phe Val Trp Cys Leu
1 5

<210> SEQ ID NO 316
<211> LENGTH: 6
<212> TYPE: PRT
<213> ORGANISM: Homo sapiens

<400> SEQUENCE: 316

Gly Ile Leu Leu Cys Leu
1 5

<210> SEQ ID NO 317
<211> LENGTH: 6
<212> TYPE: PRT
<213> ORGANISM: Homo sapiens

<400> SEQUENCE: 317

Gly Val Leu Gly Cys Leu
1 5

<210> SEQ ID NO 318
<211> LENGTH: 6
<212> TYPE: PRT
<213> ORGANISM: Homo sapiens

<400> SEQUENCE: 318

Gly Asn Leu Ala Cys Leu
1 5

<210> SEQ ID NO 319
<211> LENGTH: 6
<212> TYPE: PRT
<213> ORGANISM: Homo sapiens

<400> SEQUENCE: 319

Gly Arg Phe Arg Cys Leu
1 5

<210> SEQ ID NO 320
<211> LENGTH: 6
<212> TYPE: PRT
<213> ORGANISM: Homo sapiens

<400> SEQUENCE: 320

Gly Thr Leu Leu Cys Leu
1 5

<210> SEQ ID NO 321
<211> LENGTH: 6
<212> TYPE: PRT
<213> ORGANISM: Homo sapiens

<400> SEQUENCE: 321

Gly Asn Glu Leu Cys Leu
1 5

<210> SEQ ID NO 322
<211> LENGTH: 6
<212> TYPE: PRT
<213> ORGANISM: Homo sapiens

<400> SEQUENCE: 322

Gly Ile Thr Arg Cys Leu
1               5

<210> SEQ ID NO 323
<211> LENGTH: 6
<212> TYPE: PRT
<213> ORGANISM: Homo sapiens

<400> SEQUENCE: 323

Gly Tyr Gly Ala Cys Leu
1               5

<210> SEQ ID NO 324
<211> LENGTH: 6
<212> TYPE: PRT
<213> ORGANISM: Homo sapiens

<400> SEQUENCE: 324

Gly Leu Val His Cys Leu
1               5

<210> SEQ ID NO 325
<211> LENGTH: 6
<212> TYPE: PRT
<213> ORGANISM: Homo sapiens

<400> SEQUENCE: 325

Gly Glu Tyr Gln Cys Leu
1               5

<210> SEQ ID NO 326
<211> LENGTH: 6
<212> TYPE: PRT
<213> ORGANISM: Homo sapiens

<400> SEQUENCE: 326

Gly Ser Thr His Cys Leu
1               5

<210> SEQ ID NO 327
<211> LENGTH: 6
<212> TYPE: PRT
<213> ORGANISM: Homo sapiens

<400> SEQUENCE: 327

Gly Ala Leu His Cys Leu
1               5

<210> SEQ ID NO 328
<211> LENGTH: 6
<212> TYPE: PRT
<213> ORGANISM: Homo sapiens

<400> SEQUENCE: 328

Gly Gly Lys His Cys Leu
1               5

<210> SEQ ID NO 329
<211> LENGTH: 6
<212> TYPE: PRT
<213> ORGANISM: Homo sapiens

<400> SEQUENCE: 329

Gly Gln Glu His Cys Leu
1               5

<210> SEQ ID NO 330
<211> LENGTH: 6
<212> TYPE: PRT
<213> ORGANISM: Homo sapiens

<400> SEQUENCE: 330

Gly Leu Asn Gln Cys Leu
1               5

<210> SEQ ID NO 331
<211> LENGTH: 6
<212> TYPE: PRT
<213> ORGANISM: Homo sapiens

<400> SEQUENCE: 331

Gly Lys Thr Lys Cys Leu
1               5

<210> SEQ ID NO 332
<211> LENGTH: 6
<212> TYPE: PRT
<213> ORGANISM: Homo sapiens

<400> SEQUENCE: 332

Gly Thr Gly Cys Cys Leu
1               5

<210> SEQ ID NO 333
<211> LENGTH: 6
<212> TYPE: PRT
<213> ORGANISM: Homo sapiens

<400> SEQUENCE: 333

Gly Pro Glu Glu Cys Leu
1               5

<210> SEQ ID NO 334
<211> LENGTH: 6
<212> TYPE: PRT
<213> ORGANISM: Homo sapiens

<400> SEQUENCE: 334

Gly Gly Pro Phe Cys Leu
1               5

<210> SEQ ID NO 335
<211> LENGTH: 6
<212> TYPE: PRT
<213> ORGANISM: Homo sapiens

<400> SEQUENCE: 335

Gly Gly Tyr Leu Cys Leu
1               5

<210> SEQ ID NO 336
<211> LENGTH: 6
<212> TYPE: PRT
<213> ORGANISM: Homo sapiens

<400> SEQUENCE: 336

Gly Pro Gly Asp Cys Leu
1 5

<210> SEQ ID NO 337
<211> LENGTH: 6
<212> TYPE: PRT
<213> ORGANISM: Homo sapiens

<400> SEQUENCE: 337

Gly Ala Pro Asn Cys Leu
1 5

<210> SEQ ID NO 338
<211> LENGTH: 6
<212> TYPE: PRT
<213> ORGANISM: Homo sapiens

<400> SEQUENCE: 338

Gly Ala Cys Gly Cys Leu
1 5

<210> SEQ ID NO 339
<211> LENGTH: 6
<212> TYPE: PRT
<213> ORGANISM: Homo sapiens

<400> SEQUENCE: 339

Gly Val Arg Leu Cys Leu
1 5

<210> SEQ ID NO 340
<211> LENGTH: 6
<212> TYPE: PRT
<213> ORGANISM: Homo sapiens

<400> SEQUENCE: 340

Gly Ile Asn Val Cys Leu
1 5

<210> SEQ ID NO 341
<211> LENGTH: 6
<212> TYPE: PRT
<213> ORGANISM: Homo sapiens

<400> SEQUENCE: 341

Gly Pro Leu Val Cys Leu
1 5

<210> SEQ ID NO 342
<211> LENGTH: 6
<212> TYPE: PRT
<213> ORGANISM: Homo sapiens

<400> SEQUENCE: 342

Gly Ala Lys Lys Cys Leu
1 5

<210> SEQ ID NO 343
<211> LENGTH: 6
<212> TYPE: PRT
<213> ORGANISM: Homo sapiens

<400> SEQUENCE: 343

Gly Thr Asn Glu Cys Leu
1               5

<210> SEQ ID NO 344
<211> LENGTH: 6
<212> TYPE: PRT
<213> ORGANISM: Homo sapiens

<400> SEQUENCE: 344

Gly Ala Asp Pro Cys Leu
1               5

<210> SEQ ID NO 345
<211> LENGTH: 6
<212> TYPE: PRT
<213> ORGANISM: Homo sapiens

<400> SEQUENCE: 345

Gly Glu Val Thr Cys Leu
1               5

<210> SEQ ID NO 346
<211> LENGTH: 6
<212> TYPE: PRT
<213> ORGANISM: Homo sapiens

<400> SEQUENCE: 346

Gly Ser Arg Arg Cys Leu
1               5

<210> SEQ ID NO 347
<211> LENGTH: 6
<212> TYPE: PRT
<213> ORGANISM: Homo sapiens

<400> SEQUENCE: 347

Gly Met Trp Gln Cys Leu
1               5

<210> SEQ ID NO 348
<211> LENGTH: 6
<212> TYPE: PRT
<213> ORGANISM: Homo sapiens

<400> SEQUENCE: 348

Gly Phe Tyr Trp Cys Leu
1               5

<210> SEQ ID NO 349
<211> LENGTH: 6
<212> TYPE: PRT
<213> ORGANISM: Homo sapiens

<400> SEQUENCE: 349

Gly Arg Lys Ile Cys Leu
1               5

<210> SEQ ID NO 350
<211> LENGTH: 6
<212> TYPE: PRT
<213> ORGANISM: Homo sapiens

<400> SEQUENCE: 350

Gly Asp Leu Gln Cys Leu
1               5

<210> SEQ ID NO 351
<211> LENGTH: 6
<212> TYPE: PRT
<213> ORGANISM: Homo sapiens

<400> SEQUENCE: 351

Gly Arg Lys Ile Cys Leu
1               5

<210> SEQ ID NO 352
<211> LENGTH: 6
<212> TYPE: PRT
<213> ORGANISM: Homo sapiens

<400> SEQUENCE: 352

Gly Glu Lys Arg Cys Leu
1               5

<210> SEQ ID NO 353
<211> LENGTH: 6
<212> TYPE: PRT
<213> ORGANISM: Homo sapiens

<400> SEQUENCE: 353

Gly Ala Phe Lys Cys Leu
1               5

<210> SEQ ID NO 354
<211> LENGTH: 6
<212> TYPE: PRT
<213> ORGANISM: Homo sapiens

<400> SEQUENCE: 354

Gly Ala Phe Arg Cys Leu
1               5

<210> SEQ ID NO 355
<211> LENGTH: 6
<212> TYPE: PRT
<213> ORGANISM: Homo sapiens

<400> SEQUENCE: 355

Gly Ala Phe Lys Cys Leu
1               5

<210> SEQ ID NO 356
<211> LENGTH: 6
<212> TYPE: PRT
<213> ORGANISM: Homo sapiens

<400> SEQUENCE: 356

Gly Ala Phe Arg Cys Leu
1               5

<210> SEQ ID NO 357
<211> LENGTH: 6
<212> TYPE: PRT
<213> ORGANISM: Homo sapiens

<400> SEQUENCE: 357

Gly Thr Tyr Leu Cys Leu
1               5

<210> SEQ ID NO 358
<211> LENGTH: 6
<212> TYPE: PRT
<213> ORGANISM: Homo sapiens

<400> SEQUENCE: 358

Gly Val Thr Thr Cys Leu
1               5

<210> SEQ ID NO 359
<211> LENGTH: 6
<212> TYPE: PRT
<213> ORGANISM: Homo sapiens

<400> SEQUENCE: 359

Gly Val Val Phe Cys Leu
1               5

<210> SEQ ID NO 360
<211> LENGTH: 6
<212> TYPE: PRT
<213> ORGANISM: Homo sapiens

<400> SEQUENCE: 360

Gly Val Arg Gln Cys Leu
1               5

<210> SEQ ID NO 361
<211> LENGTH: 6
<212> TYPE: PRT
<213> ORGANISM: Homo sapiens

<400> SEQUENCE: 361

Gly Leu Gly Asp Cys Leu
1               5

<210> SEQ ID NO 362
<211> LENGTH: 6
<212> TYPE: PRT
<213> ORGANISM: Homo sapiens

<400> SEQUENCE: 362

Gly Ile Gln Ser Cys Leu
1               5

<210> SEQ ID NO 363
<211> LENGTH: 6
<212> TYPE: PRT
<213> ORGANISM: Homo sapiens

<400> SEQUENCE: 363

Gly Ala Ser Gly Cys Leu
1               5

<210> SEQ ID NO 364
<211> LENGTH: 6
<212> TYPE: PRT
<213> ORGANISM: Homo sapiens

<400> SEQUENCE: 364

Gly Val Ala Gln Cys Leu
1               5

<210> SEQ ID NO 365
<211> LENGTH: 6
<212> TYPE: PRT
<213> ORGANISM: Homo sapiens

<400> SEQUENCE: 365

Gly Gly Phe Gln Cys Leu
1               5

<210> SEQ ID NO 366
<211> LENGTH: 6
<212> TYPE: PRT
<213> ORGANISM: Homo sapiens

<400> SEQUENCE: 366

Gly Lys Thr Leu Cys Leu
1               5

<210> SEQ ID NO 367
<211> LENGTH: 6
<212> TYPE: PRT
<213> ORGANISM: Homo sapiens

<400> SEQUENCE: 367

Gly Asp Gln Asp Cys Leu
1               5

<210> SEQ ID NO 368
<211> LENGTH: 6
<212> TYPE: PRT
<213> ORGANISM: Homo sapiens

<400> SEQUENCE: 368

Gly Val Thr Thr Cys Leu
1               5

<210> SEQ ID NO 369
<211> LENGTH: 6
<212> TYPE: PRT
<213> ORGANISM: Homo sapiens

<400> SEQUENCE: 369

Gly Gly Glu Ala Cys Leu
1               5

<210> SEQ ID NO 370
<211> LENGTH: 6
<212> TYPE: PRT
<213> ORGANISM: Homo sapiens

<400> SEQUENCE: 370

Gly His Ser Cys Cys Leu
1               5

<210> SEQ ID NO 371
<211> LENGTH: 6
<212> TYPE: PRT
<213> ORGANISM: Homo sapiens

<400> SEQUENCE: 371

Gly Gln Cys Leu Cys Leu
1               5

<210> SEQ ID NO 372
<211> LENGTH: 6
<212> TYPE: PRT
<213> ORGANISM: Homo sapiens

<400> SEQUENCE: 372

Gly Ile Cys Gln Cys Leu
1               5

<210> SEQ ID NO 373
<211> LENGTH: 6
<212> TYPE: PRT
<213> ORGANISM: Homo sapiens

<400> SEQUENCE: 373

Gly Glu Pro Cys Cys Leu
1               5

<210> SEQ ID NO 374
<211> LENGTH: 6
<212> TYPE: PRT
<213> ORGANISM: Homo sapiens

<400> SEQUENCE: 374

Gly Leu Ala Pro Cys Leu
1               5

<210> SEQ ID NO 375
<211> LENGTH: 6
<212> TYPE: PRT
<213> ORGANISM: Homo sapiens

<400> SEQUENCE: 375

Gly Ser Asp Asp Cys Leu
1               5

<210> SEQ ID NO 376
<211> LENGTH: 6
<212> TYPE: PRT
<213> ORGANISM: Homo sapiens

<400> SEQUENCE: 376

Gly Ala Thr Asp Cys Leu
1               5

<210> SEQ ID NO 377
<211> LENGTH: 6
<212> TYPE: PRT
<213> ORGANISM: Homo sapiens

<400> SEQUENCE: 377

Gly Ala Phe Arg Cys Leu
1               5

<210> SEQ ID NO 378
<211> LENGTH: 6
<212> TYPE: PRT
<213> ORGANISM: Homo sapiens

<400> SEQUENCE: 378

Gly Ala Phe Arg Cys Leu
1 5

<210> SEQ ID NO 379
<211> LENGTH: 6
<212> TYPE: PRT
<213> ORGANISM: Homo sapiens

<400> SEQUENCE: 379

Gly Ala Arg Val Cys Leu
1 5

<210> SEQ ID NO 380
<211> LENGTH: 6
<212> TYPE: PRT
<213> ORGANISM: Homo sapiens

<400> SEQUENCE: 380

Gly Ser Gly Pro Cys Leu
1 5

<210> SEQ ID NO 381
<211> LENGTH: 6
<212> TYPE: PRT
<213> ORGANISM: Homo sapiens

<400> SEQUENCE: 381

Gly Leu Gln Gly Cys Leu
1 5

<210> SEQ ID NO 382
<211> LENGTH: 6
<212> TYPE: PRT
<213> ORGANISM: Homo sapiens

<400> SEQUENCE: 382

Gly Asp Val Ile Cys Leu
1 5

<210> SEQ ID NO 383
<211> LENGTH: 6
<212> TYPE: PRT
<213> ORGANISM: Homo sapiens

<400> SEQUENCE: 383

Gly His Lys Asn Cys Leu
1 5

<210> SEQ ID NO 384
<211> LENGTH: 6
<212> TYPE: PRT
<213> ORGANISM: Homo sapiens

<400> SEQUENCE: 384

Gly Trp Asp Ser Cys Leu
1 5

<210> SEQ ID NO 385
<211> LENGTH: 6
<212> TYPE: PRT
<213> ORGANISM: Homo sapiens

<400> SEQUENCE: 385

Gly Arg Lys Ala Cys Leu
1 5

<210> SEQ ID NO 386
<211> LENGTH: 6
<212> TYPE: PRT
<213> ORGANISM: Homo sapiens

<400> SEQUENCE: 386

Gly Pro His Ala Cys Leu
1 5

<210> SEQ ID NO 387
<211> LENGTH: 6
<212> TYPE: PRT
<213> ORGANISM: Homo sapiens

<400> SEQUENCE: 387

Gly Pro Glu Ser Cys Leu
1 5

<210> SEQ ID NO 388
<211> LENGTH: 6
<212> TYPE: PRT
<213> ORGANISM: Homo sapiens

<400> SEQUENCE: 388

Gly Cys Gln Ile Cys Leu
1 5

<210> SEQ ID NO 389
<211> LENGTH: 6
<212> TYPE: PRT
<213> ORGANISM: Homo sapiens

<400> SEQUENCE: 389

Gly Arg Glu Leu Cys Leu
1 5

<210> SEQ ID NO 390
<211> LENGTH: 6
<212> TYPE: PRT
<213> ORGANISM: Homo sapiens

<400> SEQUENCE: 390

Gly Arg Arg Ala Cys Leu
1 5

<210> SEQ ID NO 391
<211> LENGTH: 6
<212> TYPE: PRT
<213> ORGANISM: Homo sapiens

<400> SEQUENCE: 391

Gly Pro Ser Trp Cys Leu
1 5

<210> SEQ ID NO 392
<211> LENGTH: 6
<212> TYPE: PRT
<213> ORGANISM: Homo sapiens

<400> SEQUENCE: 392

Gly Asp Leu Gln Cys Leu
1 5

<210> SEQ ID NO 393
<211> LENGTH: 6
<212> TYPE: PRT
<213> ORGANISM: Homo sapiens

<400> SEQUENCE: 393

Gly Arg Lys Ile Cys Leu
1 5

<210> SEQ ID NO 394
<211> LENGTH: 6
<212> TYPE: PRT
<213> ORGANISM: Homo sapiens

<400> SEQUENCE: 394

Gly Val Val His Cys Leu
1 5

<210> SEQ ID NO 395
<211> LENGTH: 6
<212> TYPE: PRT
<213> ORGANISM: Homo sapiens

<400> SEQUENCE: 395

Gly Gln Cys Glu Cys Leu
1 5

<210> SEQ ID NO 396
<211> LENGTH: 6
<212> TYPE: PRT
<213> ORGANISM: Homo sapiens

<400> SEQUENCE: 396

Gly Glu Tyr Thr Cys Leu
1 5

<210> SEQ ID NO 397
<211> LENGTH: 6
<212> TYPE: PRT
<213> ORGANISM: Homo sapiens

<400> SEQUENCE: 397

Gly Thr Ala Ala Cys Leu
1 5

<210> SEQ ID NO 398
<211> LENGTH: 6
<212> TYPE: PRT
<213> ORGANISM: Homo sapiens

<400> SEQUENCE: 398

Gly Leu Gly Asp Cys Leu
1 5

<210> SEQ ID NO 399
<211> LENGTH: 6
<212> TYPE: PRT
<213> ORGANISM: Homo sapiens

<400> SEQUENCE: 399

Gly Asn Asp Thr Cys Leu
1               5

<210> SEQ ID NO 400
<211> LENGTH: 6
<212> TYPE: PRT
<213> ORGANISM: Homo sapiens

<400> SEQUENCE: 400

Gly Val Phe Val Cys Leu
1               5

<210> SEQ ID NO 401
<211> LENGTH: 6
<212> TYPE: PRT
<213> ORGANISM: Homo sapiens

<400> SEQUENCE: 401

Gly Ile Gly Leu Cys Leu
1               5

<210> SEQ ID NO 402
<211> LENGTH: 6
<212> TYPE: PRT
<213> ORGANISM: Homo sapiens

<400> SEQUENCE: 402

Gly Pro Thr His Cys Leu
1               5

<210> SEQ ID NO 403
<211> LENGTH: 6
<212> TYPE: PRT
<213> ORGANISM: Homo sapiens

<400> SEQUENCE: 403

Gly Glu Val Ser Cys Leu
1               5

<210> SEQ ID NO 404
<211> LENGTH: 6
<212> TYPE: PRT
<213> ORGANISM: Homo sapiens

<400> SEQUENCE: 404

Gly Val Gly Leu Cys Leu
1               5

<210> SEQ ID NO 405
<211> LENGTH: 6
<212> TYPE: PRT
<213> ORGANISM: Homo sapiens

<400> SEQUENCE: 405

Gly Asp Val Lys Cys Leu
1               5

<210> SEQ ID NO 406
<211> LENGTH: 6
<212> TYPE: PRT
<213> ORGANISM: Homo sapiens

<400> SEQUENCE: 406

Gly Gly Gly Thr Cys Leu
1               5

<210> SEQ ID NO 407
<211> LENGTH: 6
<212> TYPE: PRT
<213> ORGANISM: Homo sapiens

<400> SEQUENCE: 407

Gly Pro Val Gly Cys Leu
1               5

<210> SEQ ID NO 408
<211> LENGTH: 6
<212> TYPE: PRT
<213> ORGANISM: Homo sapiens

<400> SEQUENCE: 408

Gly Leu Ser Asp Cys Leu
1               5

<210> SEQ ID NO 409
<211> LENGTH: 6
<212> TYPE: PRT
<213> ORGANISM: Homo sapiens

<400> SEQUENCE: 409

Gly Asn Tyr Thr Cys Leu
1               5

<210> SEQ ID NO 410
<211> LENGTH: 6
<212> TYPE: PRT
<213> ORGANISM: Homo sapiens

<400> SEQUENCE: 410

Gly Met Arg Gln Cys Leu
1               5

<210> SEQ ID NO 411
<211> LENGTH: 6
<212> TYPE: PRT
<213> ORGANISM: Homo sapiens

<400> SEQUENCE: 411

Gly Ala Arg Cys Cys Leu
1               5

<210> SEQ ID NO 412
<211> LENGTH: 6
<212> TYPE: PRT
<213> ORGANISM: Homo sapiens

<400> SEQUENCE: 412

Gly Asn Met Ile Cys Leu
1               5

<210> SEQ ID NO 413
<211> LENGTH: 6
<212> TYPE: PRT
<213> ORGANISM: Homo sapiens

<400> SEQUENCE: 413

Gly His Val Ile Cys Leu
1               5

<210> SEQ ID NO 414
<211> LENGTH: 6
<212> TYPE: PRT
<213> ORGANISM: Homo sapiens

<400> SEQUENCE: 414

Gly Tyr Met Asn Cys Leu
1               5

<210> SEQ ID NO 415
<211> LENGTH: 6
<212> TYPE: PRT
<213> ORGANISM: Homo sapiens

<400> SEQUENCE: 415

Gly Phe Asn Gln Cys Leu
1               5

<210> SEQ ID NO 416
<211> LENGTH: 6
<212> TYPE: PRT
<213> ORGANISM: Homo sapiens

<400> SEQUENCE: 416

Gly Asn Ser Val Cys Leu
1               5

<210> SEQ ID NO 417
<211> LENGTH: 6
<212> TYPE: PRT
<213> ORGANISM: Homo sapiens

<400> SEQUENCE: 417

Gly Cys Gly Cys Cys Leu
1               5

<210> SEQ ID NO 418
<211> LENGTH: 6
<212> TYPE: PRT
<213> ORGANISM: Homo sapiens

<400> SEQUENCE: 418

Gly Gly Lys Met Cys Leu
1               5

<210> SEQ ID NO 419
<211> LENGTH: 6
<212> TYPE: PRT
<213> ORGANISM: Homo sapiens

<400> SEQUENCE: 419

Gly Glu Asn Glu Cys Leu
1               5

<210> SEQ ID NO 420
<211> LENGTH: 6
<212> TYPE: PRT
<213> ORGANISM: Homo sapiens

<400> SEQUENCE: 420

Gly Gly Ala Lys Cys Leu
1               5

<210> SEQ ID NO 421
<211> LENGTH: 6
<212> TYPE: PRT
<213> ORGANISM: Homo sapiens

<400> SEQUENCE: 421

Gly Met Arg Gln Cys Leu
1               5

<210> SEQ ID NO 422
<211> LENGTH: 6
<212> TYPE: PRT
<213> ORGANISM: Homo sapiens

<400> SEQUENCE: 422

Gly Tyr Arg Lys Cys Leu
1               5

<210> SEQ ID NO 423
<211> LENGTH: 6
<212> TYPE: PRT
<213> ORGANISM: Homo sapiens

<400> SEQUENCE: 423

Gly Asp Asn Gly Cys Leu
1               5

<210> SEQ ID NO 424
<211> LENGTH: 6
<212> TYPE: PRT
<213> ORGANISM: Homo sapiens

<400> SEQUENCE: 424

Gly Asp Glu Asp Cys Leu
1               5

<210> SEQ ID NO 425
<211> LENGTH: 6
<212> TYPE: PRT
<213> ORGANISM: Homo sapiens

<400> SEQUENCE: 425

Gly Gln Lys Ala Cys Leu
1               5

<210> SEQ ID NO 426
<211> LENGTH: 6
<212> TYPE: PRT
<213> ORGANISM: Homo sapiens

<400> SEQUENCE: 426

Gly Lys Lys Ala Cys Leu
1               5

<210> SEQ ID NO 427
<211> LENGTH: 6
<212> TYPE: PRT
<213> ORGANISM: Homo sapiens

<400> SEQUENCE: 427

Gly Gly Lys Lys Cys Leu
1               5

<210> SEQ ID NO 428
<211> LENGTH: 6
<212> TYPE: PRT
<213> ORGANISM: Homo sapiens

<400> SEQUENCE: 428

Gly Tyr Gln Gln Cys Leu
1               5

<210> SEQ ID NO 429
<211> LENGTH: 6
<212> TYPE: PRT
<213> ORGANISM: Homo sapiens

<400> SEQUENCE: 429

Gly Leu Gly Ser Cys Leu
1               5

<210> SEQ ID NO 430
<211> LENGTH: 6
<212> TYPE: PRT
<213> ORGANISM: Homo sapiens

<400> SEQUENCE: 430

Gly Gly Leu Gln Cys Leu
1               5

<210> SEQ ID NO 431
<211> LENGTH: 6
<212> TYPE: PRT
<213> ORGANISM: Homo sapiens

<400> SEQUENCE: 431

Gly Thr Gly His Cys Leu
1               5

<210> SEQ ID NO 432
<211> LENGTH: 6
<212> TYPE: PRT
<213> ORGANISM: Homo sapiens

<400> SEQUENCE: 432

Gly Asp Pro Gly Cys Leu
1               5

<210> SEQ ID NO 433
<211> LENGTH: 6
<212> TYPE: PRT
<213> ORGANISM: Homo sapiens

<400> SEQUENCE: 433

Gly Lys Arg Ile Cys Leu
1               5

<210> SEQ ID NO 434
<211> LENGTH: 6
<212> TYPE: PRT
<213> ORGANISM: Homo sapiens

<400> SEQUENCE: 434

Gly Val Tyr Ala Cys Leu
1               5

<210> SEQ ID NO 435
<211> LENGTH: 6
<212> TYPE: PRT
<213> ORGANISM: Homo sapiens

<400> SEQUENCE: 435

Gly Val Val His Cys Leu
1               5

<210> SEQ ID NO 436
<211> LENGTH: 6
<212> TYPE: PRT
<213> ORGANISM: Homo sapiens

<400> SEQUENCE: 436

Gly Asp Ser Asp Cys Leu
1               5

<210> SEQ ID NO 437
<211> LENGTH: 6
<212> TYPE: PRT
<213> ORGANISM: Homo sapiens

<400> SEQUENCE: 437

Gly Asp Gly Asn Cys Leu
1               5

<210> SEQ ID NO 438
<211> LENGTH: 6
<212> TYPE: PRT
<213> ORGANISM: Homo sapiens

<400> SEQUENCE: 438

Gly Arg Phe Ile Cys Leu
1               5

<210> SEQ ID NO 439
<211> LENGTH: 6
<212> TYPE: PRT
<213> ORGANISM: Homo sapiens

<400> SEQUENCE: 439

Gly Glu Tyr Thr Cys Leu
1               5

<210> SEQ ID NO 440
<211> LENGTH: 6
<212> TYPE: PRT
<213> ORGANISM: Homo sapiens

<400> SEQUENCE: 440

Gly Pro Ser Arg Cys Leu
1               5

<210> SEQ ID NO 441
<211> LENGTH: 6
<212> TYPE: PRT
<213> ORGANISM: Homo sapiens

<400> SEQUENCE: 441

Gly Pro Gly Gln Cys Leu
1               5

<210> SEQ ID NO 442
<211> LENGTH: 6
<212> TYPE: PRT
<213> ORGANISM: Homo sapiens

<400> SEQUENCE: 442

Gly Trp Gly Leu Cys Leu
1               5

<210> SEQ ID NO 443
<211> LENGTH: 6
<212> TYPE: PRT
<213> ORGANISM: Homo sapiens

<400> SEQUENCE: 443

Gly Ser Phe Arg Cys Leu
1               5

<210> SEQ ID NO 444
<211> LENGTH: 6
<212> TYPE: PRT
<213> ORGANISM: Homo sapiens

<400> SEQUENCE: 444

Gly Ser Tyr Lys Cys Leu
1               5

<210> SEQ ID NO 445
<211> LENGTH: 6
<212> TYPE: PRT
<213> ORGANISM: Homo sapiens

<400> SEQUENCE: 445

Gly Arg Gly Gln Cys Leu
1               5

<210> SEQ ID NO 446
<211> LENGTH: 6
<212> TYPE: PRT
<213> ORGANISM: Homo sapiens

<400> SEQUENCE: 446

Gly Gly Ile Asn Cys Leu
1               5

<210> SEQ ID NO 447
<211> LENGTH: 6
<212> TYPE: PRT
<213> ORGANISM: Homo sapiens

<400> SEQUENCE: 447

Gly Tyr Arg Lys Cys Leu
1               5

<210> SEQ ID NO 448
<211> LENGTH: 6
<212> TYPE: PRT
<213> ORGANISM: Homo sapiens

<400> SEQUENCE: 448

Gly Tyr Arg Lys Cys Leu
1 5

<210> SEQ ID NO 449
<211> LENGTH: 6
<212> TYPE: PRT
<213> ORGANISM: Homo sapiens

<400> SEQUENCE: 449

Gly Val Val Thr Cys Leu
1 5

<210> SEQ ID NO 450
<211> LENGTH: 6
<212> TYPE: PRT
<213> ORGANISM: Homo sapiens

<400> SEQUENCE: 450

Gly Arg Tyr Leu Cys Leu
1 5

<210> SEQ ID NO 451
<211> LENGTH: 6
<212> TYPE: PRT
<213> ORGANISM: Homo sapiens

<400> SEQUENCE: 451

Gly Thr Tyr Thr Cys Leu
1 5

<210> SEQ ID NO 452
<211> LENGTH: 6
<212> TYPE: PRT
<213> ORGANISM: Homo sapiens

<400> SEQUENCE: 452

Gly Glu Tyr Thr Cys Leu
1 5

<210> SEQ ID NO 453
<211> LENGTH: 6
<212> TYPE: PRT
<213> ORGANISM: Homo sapiens

<400> SEQUENCE: 453

Gly Glu Tyr Thr Cys Leu
1 5

<210> SEQ ID NO 454
<211> LENGTH: 6
<212> TYPE: PRT
<213> ORGANISM: Homo sapiens

<400> SEQUENCE: 454

Gly Asn Pro Ile Cys Leu
1 5

<210> SEQ ID NO 455
<211> LENGTH: 6
<212> TYPE: PRT
<213> ORGANISM: Homo sapiens

<400> SEQUENCE: 455

Gly Phe Ser Ile Cys Leu
1               5

<210> SEQ ID NO 456
<211> LENGTH: 6
<212> TYPE: PRT
<213> ORGANISM: Homo sapiens

<400> SEQUENCE: 456

Gly Ile His Asn Cys Leu
1               5

<210> SEQ ID NO 457
<211> LENGTH: 6
<212> TYPE: PRT
<213> ORGANISM: Homo sapiens

<400> SEQUENCE: 457

Gly Gly Phe Arg Cys Leu
1               5

<210> SEQ ID NO 458
<211> LENGTH: 6
<212> TYPE: PRT
<213> ORGANISM: Homo sapiens

<400> SEQUENCE: 458

Gly Met Gly His Cys Leu
1               5

<210> SEQ ID NO 459
<211> LENGTH: 6
<212> TYPE: PRT
<213> ORGANISM: Homo sapiens

<400> SEQUENCE: 459

Gly Gln Ser Glu Cys Leu
1               5

<210> SEQ ID NO 460
<211> LENGTH: 6
<212> TYPE: PRT
<213> ORGANISM: Homo sapiens

<400> SEQUENCE: 460

Gly Gly Ile Tyr Cys Leu
1               5

<210> SEQ ID NO 461
<211> LENGTH: 6
<212> TYPE: PRT
<213> ORGANISM: Homo sapiens

<400> SEQUENCE: 461

Gly Pro Arg Ser Cys Leu
1               5

<210> SEQ ID NO 462
<211> LENGTH: 6
<212> TYPE: PRT
<213> ORGANISM: Homo sapiens

<400> SEQUENCE: 462

Gly Arg Gly Arg Cys Leu
1               5

<210> SEQ ID NO 463
<211> LENGTH: 6
<212> TYPE: PRT
<213> ORGANISM: Homo sapiens

<400> SEQUENCE: 463

Gly Arg Gly Val Cys Leu
1               5

<210> SEQ ID NO 464
<211> LENGTH: 6
<212> TYPE: PRT
<213> ORGANISM: Homo sapiens

<400> SEQUENCE: 464

Gly Ala Gly Cys Cys Leu
1               5

<210> SEQ ID NO 465
<211> LENGTH: 6
<212> TYPE: PRT
<213> ORGANISM: Homo sapiens

<400> SEQUENCE: 465

Gly Arg Arg Leu Cys Leu
1               5

<210> SEQ ID NO 466
<211> LENGTH: 6
<212> TYPE: PRT
<213> ORGANISM: Homo sapiens

<400> SEQUENCE: 466

Gly Thr Tyr Arg Cys Leu
1               5

<210> SEQ ID NO 467
<211> LENGTH: 6
<212> TYPE: PRT
<213> ORGANISM: Homo sapiens

<400> SEQUENCE: 467

Gly Ile Ala Ala Cys Leu
1               5

<210> SEQ ID NO 468
<211> LENGTH: 6
<212> TYPE: PRT
<213> ORGANISM: Homo sapiens

<400> SEQUENCE: 468

Gly Gly Glu Thr Cys Leu
1               5

<210> SEQ ID NO 469
<211> LENGTH: 6
<212> TYPE: PRT
<213> ORGANISM: Homo sapiens

<400> SEQUENCE: 469

Gly Gly Ile Tyr Cys Leu
1 5

<210> SEQ ID NO 470
<211> LENGTH: 6
<212> TYPE: PRT
<213> ORGANISM: Homo sapiens

<400> SEQUENCE: 470

Gly Leu Glu Glu Cys Leu
1 5

<210> SEQ ID NO 471
<211> LENGTH: 6
<212> TYPE: PRT
<213> ORGANISM: Homo sapiens

<400> SEQUENCE: 471

Gly Arg Trp Asn Cys Leu
1 5

<210> SEQ ID NO 472
<211> LENGTH: 6
<212> TYPE: PRT
<213> ORGANISM: Homo sapiens

<400> SEQUENCE: 472

Gly Ser Lys Phe Cys Leu
1 5

<210> SEQ ID NO 473
<211> LENGTH: 6
<212> TYPE: PRT
<213> ORGANISM: Homo sapiens

<400> SEQUENCE: 473

Gly Thr Arg Ser Cys Leu
1 5

<210> SEQ ID NO 474
<211> LENGTH: 6
<212> TYPE: PRT
<213> ORGANISM: Homo sapiens

<400> SEQUENCE: 474

Gly Ala Thr Glu Cys Leu
1 5

<210> SEQ ID NO 475
<211> LENGTH: 6
<212> TYPE: PRT
<213> ORGANISM: Homo sapiens

<400> SEQUENCE: 475

Gly Lys Leu Pro Cys Leu
1 5

<210> SEQ ID NO 476
<211> LENGTH: 6
<212> TYPE: PRT
<213> ORGANISM: Homo sapiens

<400> SEQUENCE: 476

Gly Gln Val Ala Cys Leu
1               5

<210> SEQ ID NO 477
<211> LENGTH: 6
<212> TYPE: PRT
<213> ORGANISM: Homo sapiens

<400> SEQUENCE: 477

Gly Ser Glu Leu Cys Leu
1               5

<210> SEQ ID NO 478
<211> LENGTH: 6
<212> TYPE: PRT
<213> ORGANISM: Homo sapiens

<400> SEQUENCE: 478

Gly Met Phe Pro Cys Leu
1               5

<210> SEQ ID NO 479
<211> LENGTH: 6
<212> TYPE: PRT
<213> ORGANISM: Homo sapiens

<400> SEQUENCE: 479

Gly Met Pro Gly Cys Leu
1               5

<210> SEQ ID NO 480
<211> LENGTH: 6
<212> TYPE: PRT
<213> ORGANISM: Homo sapiens

<400> SEQUENCE: 480

Gly Gln Tyr Gln Cys Leu
1               5

<210> SEQ ID NO 481
<211> LENGTH: 6
<212> TYPE: PRT
<213> ORGANISM: Homo sapiens

<400> SEQUENCE: 481

Gly Glu Lys Ile Cys Leu
1               5

<210> SEQ ID NO 482
<211> LENGTH: 6
<212> TYPE: PRT
<213> ORGANISM: Homo sapiens

<400> SEQUENCE: 482

Gly Lys Arg Cys Cys Leu
1               5

<210> SEQ ID NO 483
<211> LENGTH: 6
<212> TYPE: PRT
<213> ORGANISM: Homo sapiens

<400> SEQUENCE: 483

Gly Thr Val Lys Cys Leu
1               5

<210> SEQ ID NO 484
<211> LENGTH: 6
<212> TYPE: PRT
<213> ORGANISM: Homo sapiens

<400> SEQUENCE: 484

Gly Glu Tyr Arg Cys Leu
1               5

<210> SEQ ID NO 485
<211> LENGTH: 6
<212> TYPE: PRT
<213> ORGANISM: Homo sapiens

<400> SEQUENCE: 485

Gly Arg Tyr Phe Cys Leu
1               5

<210> SEQ ID NO 486
<211> LENGTH: 6
<212> TYPE: PRT
<213> ORGANISM: Homo sapiens

<400> SEQUENCE: 486

Gly Ile Arg Thr Cys Leu
1               5

<210> SEQ ID NO 487
<211> LENGTH: 6
<212> TYPE: PRT
<213> ORGANISM: Homo sapiens

<400> SEQUENCE: 487

Gly Thr Tyr Gln Cys Leu
1               5

<210> SEQ ID NO 488
<211> LENGTH: 6
<212> TYPE: PRT
<213> ORGANISM: Homo sapiens

<400> SEQUENCE: 488

Gly Ala Lys Tyr Cys Leu
1               5

<210> SEQ ID NO 489
<211> LENGTH: 6
<212> TYPE: PRT
<213> ORGANISM: Homo sapiens

<400> SEQUENCE: 489

Gly Leu Val Ile Cys Leu
1               5

<210> SEQ ID NO 490
<211> LENGTH: 6
<212> TYPE: PRT
<213> ORGANISM: Homo sapiens

<400> SEQUENCE: 490

Gly Asn Cys Ser Cys Leu
1 5

<210> SEQ ID NO 491
<211> LENGTH: 6
<212> TYPE: PRT
<213> ORGANISM: Homo sapiens

<400> SEQUENCE: 491

Gly Pro Ala Val Cys Leu
1 5

<210> SEQ ID NO 492
<211> LENGTH: 6
<212> TYPE: PRT
<213> ORGANISM: Homo sapiens

<400> SEQUENCE: 492

Gly Tyr Val Gly Cys Leu
1 5

<210> SEQ ID NO 493
<211> LENGTH: 6
<212> TYPE: PRT
<213> ORGANISM: Homo sapiens

<400> SEQUENCE: 493

Gly Tyr Arg Glu Cys Leu
1 5

<210> SEQ ID NO 494
<211> LENGTH: 6
<212> TYPE: PRT
<213> ORGANISM: Homo sapiens

<400> SEQUENCE: 494

Gly Ser Leu Asn Cys Leu
1 5

<210> SEQ ID NO 495
<211> LENGTH: 6
<212> TYPE: PRT
<213> ORGANISM: Homo sapiens

<400> SEQUENCE: 495

Gly Ala Glu Asn Cys Leu
1 5

<210> SEQ ID NO 496
<211> LENGTH: 6
<212> TYPE: PRT
<213> ORGANISM: Homo sapiens

<400> SEQUENCE: 496

Gly Arg Ala Val Cys Leu
1 5

<210> SEQ ID NO 497
<211> LENGTH: 6
<212> TYPE: PRT
<213> ORGANISM: Homo sapiens

<400> SEQUENCE: 497

Gly Arg Pro Leu Cys Leu
1               5

<210> SEQ ID NO 498
<211> LENGTH: 6
<212> TYPE: PRT
<213> ORGANISM: Homo sapiens

<400> SEQUENCE: 498

Gly Val Ala Ser Cys Leu
1               5

<210> SEQ ID NO 499
<211> LENGTH: 6
<212> TYPE: PRT
<213> ORGANISM: Homo sapiens

<400> SEQUENCE: 499

Gly Gln Ala Met Cys Leu
1               5

<210> SEQ ID NO 500
<211> LENGTH: 6
<212> TYPE: PRT
<213> ORGANISM: Homo sapiens

<400> SEQUENCE: 500

Gly Gln Ala Met Cys Leu
1               5

<210> SEQ ID NO 501
<211> LENGTH: 6
<212> TYPE: PRT
<213> ORGANISM: Homo sapiens

<400> SEQUENCE: 501

Gly Tyr Arg Lys Cys Leu
1               5

<210> SEQ ID NO 502
<211> LENGTH: 6
<212> TYPE: PRT
<213> ORGANISM: Homo sapiens

<400> SEQUENCE: 502

Gly Tyr Arg Lys Cys Leu
1               5

<210> SEQ ID NO 503
<211> LENGTH: 6
<212> TYPE: PRT
<213> ORGANISM: Homo sapiens

<400> SEQUENCE: 503

Gly Glu Tyr Arg Cys Leu
1               5

<210> SEQ ID NO 504
<211> LENGTH: 6
<212> TYPE: PRT
<213> ORGANISM: Homo sapiens

<400> SEQUENCE: 504

Gly Ser Tyr Arg Cys Leu
1               5

<210> SEQ ID NO 505
<211> LENGTH: 6
<212> TYPE: PRT
<213> ORGANISM: Homo sapiens

<400> SEQUENCE: 505

Gly Asn Gly Gln Cys Leu
1               5

<210> SEQ ID NO 506
<211> LENGTH: 6
<212> TYPE: PRT
<213> ORGANISM: Homo sapiens

<400> SEQUENCE: 506

Gly Ser Phe Tyr Cys Leu
1               5

<210> SEQ ID NO 507
<211> LENGTH: 6
<212> TYPE: PRT
<213> ORGANISM: Homo sapiens

<400> SEQUENCE: 507

Gly Ser Phe Lys Cys Leu
1               5

<210> SEQ ID NO 508
<211> LENGTH: 6
<212> TYPE: PRT
<213> ORGANISM: Homo sapiens

<400> SEQUENCE: 508

Gly Glu Tyr Arg Cys Leu
1               5

<210> SEQ ID NO 509
<211> LENGTH: 6
<212> TYPE: PRT
<213> ORGANISM: Homo sapiens

<400> SEQUENCE: 509

Gly Ser Tyr Asn Cys Leu
1               5

<210> SEQ ID NO 510
<211> LENGTH: 6
<212> TYPE: PRT
<213> ORGANISM: Homo sapiens

<400> SEQUENCE: 510

Gly Ser Phe Lys Cys Leu
1               5

<210> SEQ ID NO 511
<211> LENGTH: 6
<212> TYPE: PRT
<213> ORGANISM: Homo sapiens

<400> SEQUENCE: 511

Gly Gly Phe Gln Cys Leu
1               5

<210> SEQ ID NO 512
<211> LENGTH: 6
<212> TYPE: PRT
<213> ORGANISM: Homo sapiens

<400> SEQUENCE: 512

Gly Leu Thr Phe Cys Leu
1               5

<210> SEQ ID NO 513
<211> LENGTH: 6
<212> TYPE: PRT
<213> ORGANISM: Homo sapiens

<400> SEQUENCE: 513

Gly Ala Ala Leu Cys Leu
1               5

<210> SEQ ID NO 514
<211> LENGTH: 6
<212> TYPE: PRT
<213> ORGANISM: Homo sapiens

<400> SEQUENCE: 514

Gly Asp Tyr Val Cys Leu
1               5

<210> SEQ ID NO 515
<211> LENGTH: 6
<212> TYPE: PRT
<213> ORGANISM: Homo sapiens

<400> SEQUENCE: 515

Gly Tyr Arg Lys Cys Leu
1               5

<210> SEQ ID NO 516
<211> LENGTH: 6
<212> TYPE: PRT
<213> ORGANISM: Homo sapiens

<400> SEQUENCE: 516

Gly Asn Ile Ser Cys Leu
1               5

<210> SEQ ID NO 517
<211> LENGTH: 6
<212> TYPE: PRT
<213> ORGANISM: Homo sapiens

<400> SEQUENCE: 517

Gly Leu Leu Val Cys Leu
1               5

<210> SEQ ID NO 518
<211> LENGTH: 6
<212> TYPE: PRT
<213> ORGANISM: Homo sapiens

<400> SEQUENCE: 518

Gly Ser Arg Phe Cys Leu
1               5

<210> SEQ ID NO 519
<211> LENGTH: 6
<212> TYPE: PRT
<213> ORGANISM: Homo sapiens

<400> SEQUENCE: 519

Gly Leu Val Val Cys Leu
1               5

<210> SEQ ID NO 520
<211> LENGTH: 6
<212> TYPE: PRT
<213> ORGANISM: Homo sapiens

<400> SEQUENCE: 520

Gly Tyr Ile Leu Cys Leu
1               5

<210> SEQ ID NO 521
<211> LENGTH: 6
<212> TYPE: PRT
<213> ORGANISM: Homo sapiens

<400> SEQUENCE: 521

Gly Arg Val Lys Cys Leu
1               5

<210> SEQ ID NO 522
<211> LENGTH: 6
<212> TYPE: PRT
<213> ORGANISM: Homo sapiens

<400> SEQUENCE: 522

Gly Arg Val Lys Cys Leu
1               5

<210> SEQ ID NO 523
<211> LENGTH: 6
<212> TYPE: PRT
<213> ORGANISM: Homo sapiens

<400> SEQUENCE: 523

Gly Gln Cys Trp Cys Leu
1               5

<210> SEQ ID NO 524
<211> LENGTH: 6
<212> TYPE: PRT
<213> ORGANISM: Homo sapiens

<400> SEQUENCE: 524

Gly Arg Pro Pro Cys Leu
1               5

<210> SEQ ID NO 525
<211> LENGTH: 6
<212> TYPE: PRT
<213> ORGANISM: Homo sapiens

<400> SEQUENCE: 525

Gly Phe Pro Pro Cys Leu
1               5

<210> SEQ ID NO 526
<211> LENGTH: 6
<212> TYPE: PRT
<213> ORGANISM: Homo sapiens

<400> SEQUENCE: 526

Gly Cys Tyr Met Cys Leu
1               5

<210> SEQ ID NO 527
<211> LENGTH: 6
<212> TYPE: PRT
<213> ORGANISM: Homo sapiens

<400> SEQUENCE: 527

Gly Gln Ser Ala Cys Leu
1               5

<210> SEQ ID NO 528
<211> LENGTH: 6
<212> TYPE: PRT
<213> ORGANISM: Homo sapiens

<400> SEQUENCE: 528

Gly Arg Met Arg Cys Leu
1               5

<210> SEQ ID NO 529
<211> LENGTH: 6
<212> TYPE: PRT
<213> ORGANISM: Homo sapiens

<400> SEQUENCE: 529

Gly Gln Val Lys Cys Leu
1               5

<210> SEQ ID NO 530
<211> LENGTH: 6
<212> TYPE: PRT
<213> ORGANISM: Homo sapiens

<400> SEQUENCE: 530

Gly Lys Glu Ile Cys Leu
1               5

<210> SEQ ID NO 531
<211> LENGTH: 6
<212> TYPE: PRT
<213> ORGANISM: Homo sapiens

<400> SEQUENCE: 531

Gly Leu Val Ala Cys Leu
1               5

<210> SEQ ID NO 532
<211> LENGTH: 6
<212> TYPE: PRT
<213> ORGANISM: Homo sapiens

<400> SEQUENCE: 532

Gly Asp Val Pro Cys Leu
1 5

<210> SEQ ID NO 533
<211> LENGTH: 6
<212> TYPE: PRT
<213> ORGANISM: Homo sapiens

<400> SEQUENCE: 533

Gly Val Phe Asp Cys Leu
1 5

<210> SEQ ID NO 534
<211> LENGTH: 6
<212> TYPE: PRT
<213> ORGANISM: Homo sapiens

<400> SEQUENCE: 534

Gly Leu Ile Tyr Cys Leu
1 5

<210> SEQ ID NO 535
<211> LENGTH: 6
<212> TYPE: PRT
<213> ORGANISM: Homo sapiens

<400> SEQUENCE: 535

Gly Leu Phe Glu Cys Leu
1 5

<210> SEQ ID NO 536
<211> LENGTH: 6
<212> TYPE: PRT
<213> ORGANISM: Homo sapiens

<400> SEQUENCE: 536

Gly Ser Leu Arg Cys Leu
1 5

<210> SEQ ID NO 537
<211> LENGTH: 6
<212> TYPE: PRT
<213> ORGANISM: Homo sapiens

<400> SEQUENCE: 537

Gly Thr Ser Ile Cys Leu
1 5

<210> SEQ ID NO 538
<211> LENGTH: 6
<212> TYPE: PRT
<213> ORGANISM: Homo sapiens

<400> SEQUENCE: 538

Gly Ile Trp Gln Cys Leu
1 5

<210> SEQ ID NO 539
<211> LENGTH: 6
<212> TYPE: PRT
<213> ORGANISM: Homo sapiens

<400> SEQUENCE: 539

Gly Gly Lys Leu Cys Leu
1 5

<210> SEQ ID NO 540
<211> LENGTH: 6
<212> TYPE: PRT
<213> ORGANISM: Homo sapiens

<400> SEQUENCE: 540

Gly His Ile Tyr Cys Leu
1 5

<210> SEQ ID NO 541
<211> LENGTH: 6
<212> TYPE: PRT
<213> ORGANISM: Homo sapiens

<400> SEQUENCE: 541

Gly Glu Leu Tyr Cys Leu
1 5

<210> SEQ ID NO 542
<211> LENGTH: 6
<212> TYPE: PRT
<213> ORGANISM: Homo sapiens

<400> SEQUENCE: 542

Gly Thr Gln Phe Cys Leu
1 5

<210> SEQ ID NO 543
<211> LENGTH: 6
<212> TYPE: PRT
<213> ORGANISM: Homo sapiens

<400> SEQUENCE: 543

Gly Cys Ala Arg Cys Leu
1 5

<210> SEQ ID NO 544
<211> LENGTH: 6
<212> TYPE: PRT
<213> ORGANISM: Homo sapiens

<400> SEQUENCE: 544

Gly Cys Ser Cys Cys Leu
1 5

<210> SEQ ID NO 545
<211> LENGTH: 6
<212> TYPE: PRT
<213> ORGANISM: Homo sapiens

<400> SEQUENCE: 545

Gly Gly Gly Gly Cys Leu
1 5

<210> SEQ ID NO 546
<211> LENGTH: 6
<212> TYPE: PRT
<213> ORGANISM: Homo sapiens

<400> SEQUENCE: 546

Gly Leu Val Asn Cys Leu
1               5

<210> SEQ ID NO 547
<211> LENGTH: 6
<212> TYPE: PRT
<213> ORGANISM: Homo sapiens

<400> SEQUENCE: 547

Gly Lys Ile Thr Cys Leu
1               5

<210> SEQ ID NO 548
<211> LENGTH: 6
<212> TYPE: PRT
<213> ORGANISM: Homo sapiens

<400> SEQUENCE: 548

Gly Pro Cys Ser Cys Leu
1               5

<210> SEQ ID NO 549
<211> LENGTH: 6
<212> TYPE: PRT
<213> ORGANISM: Homo sapiens

<400> SEQUENCE: 549

Gly Trp Arg Gly Cys Leu
1               5

<210> SEQ ID NO 550
<211> LENGTH: 6
<212> TYPE: PRT
<213> ORGANISM: Homo sapiens

<400> SEQUENCE: 550

Gly Glu Thr Pro Cys Leu
1               5

<210> SEQ ID NO 551
<211> LENGTH: 6
<212> TYPE: PRT
<213> ORGANISM: Homo sapiens

<400> SEQUENCE: 551

Gly Gly Glu Leu Cys Leu
1               5

<210> SEQ ID NO 552
<211> LENGTH: 6
<212> TYPE: PRT
<213> ORGANISM: Homo sapiens

<400> SEQUENCE: 552

Gly Leu Leu Ile Cys Leu
1               5

<210> SEQ ID NO 553
<211> LENGTH: 6
<212> TYPE: PRT
<213> ORGANISM: Homo sapiens

<400> SEQUENCE: 553

Gly Gln Asp Thr Cys Leu
1               5

<210> SEQ ID NO 554
<211> LENGTH: 6
<212> TYPE: PRT
<213> ORGANISM: Homo sapiens

<400> SEQUENCE: 554

Gly Pro Glu Asn Cys Leu
1               5

<210> SEQ ID NO 555
<211> LENGTH: 6
<212> TYPE: PRT
<213> ORGANISM: Homo sapiens

<400> SEQUENCE: 555

Gly Ser Asp Cys Cys Leu
1               5

<210> SEQ ID NO 556
<211> LENGTH: 6
<212> TYPE: PRT
<213> ORGANISM: Homo sapiens

<400> SEQUENCE: 556

Gly Ser Val Leu Cys Leu
1               5

<210> SEQ ID NO 557
<211> LENGTH: 6
<212> TYPE: PRT
<213> ORGANISM: Homo sapiens

<400> SEQUENCE: 557

Gly Lys Arg Ala Cys Leu
1               5

<210> SEQ ID NO 558
<211> LENGTH: 6
<212> TYPE: PRT
<213> ORGANISM: Homo sapiens

<400> SEQUENCE: 558

Gly Phe Phe Thr Cys Leu
1               5

<210> SEQ ID NO 559
<211> LENGTH: 6
<212> TYPE: PRT
<213> ORGANISM: Homo sapiens

<400> SEQUENCE: 559

Gly Ala Asn Leu Cys Leu
1               5

<210> SEQ ID NO 560
<211> LENGTH: 6
<212> TYPE: PRT
<213> ORGANISM: Homo sapiens

<400> SEQUENCE: 560

Gly Thr Thr Leu Cys Leu
1 5

<210> SEQ ID NO 561
<211> LENGTH: 6
<212> TYPE: PRT
<213> ORGANISM: Homo sapiens

<400> SEQUENCE: 561

Gly Ala Ala Ala Cys Leu
1 5

<210> SEQ ID NO 562
<211> LENGTH: 6
<212> TYPE: PRT
<213> ORGANISM: Homo sapiens

<400> SEQUENCE: 562

Gly Leu Arg Gln Cys Leu
1 5

<210> SEQ ID NO 563
<211> LENGTH: 6
<212> TYPE: PRT
<213> ORGANISM: Homo sapiens

<400> SEQUENCE: 563

Gly Ala Ala Ala Cys Leu
1 5

<210> SEQ ID NO 564
<211> LENGTH: 6
<212> TYPE: PRT
<213> ORGANISM: Homo sapiens

<400> SEQUENCE: 564

Gly Leu Arg Gln Cys Leu
1 5

<210> SEQ ID NO 565
<211> LENGTH: 6
<212> TYPE: PRT
<213> ORGANISM: Homo sapiens

<400> SEQUENCE: 565

Gly Ala Ala Ala Cys Leu
1 5

<210> SEQ ID NO 566
<211> LENGTH: 6
<212> TYPE: PRT
<213> ORGANISM: Homo sapiens

<400> SEQUENCE: 566

Gly Leu Arg Gln Cys Leu
1 5

<210> SEQ ID NO 567
<211> LENGTH: 6
<212> TYPE: PRT
<213> ORGANISM: Homo sapiens

<400> SEQUENCE: 567

Gly His Gln Gln Cys Leu
1               5

<210> SEQ ID NO 568
<211> LENGTH: 6
<212> TYPE: PRT
<213> ORGANISM: Homo sapiens

<400> SEQUENCE: 568

Gly His Gln Gln Cys Leu
1               5

<210> SEQ ID NO 569
<211> LENGTH: 6
<212> TYPE: PRT
<213> ORGANISM: Homo sapiens

<400> SEQUENCE: 569

Gly Glu Gly Lys Cys Leu
1               5

<210> SEQ ID NO 570
<211> LENGTH: 6
<212> TYPE: PRT
<213> ORGANISM: Homo sapiens

<400> SEQUENCE: 570

Gly Cys Leu Asp Cys Leu
1               5

<210> SEQ ID NO 571
<211> LENGTH: 6
<212> TYPE: PRT
<213> ORGANISM: Homo sapiens

<400> SEQUENCE: 571

Gly Leu Val Glu Cys Leu
1               5

<210> SEQ ID NO 572
<211> LENGTH: 6
<212> TYPE: PRT
<213> ORGANISM: Homo sapiens

<400> SEQUENCE: 572

Gly Thr Lys Asp Cys Leu
1               5

<210> SEQ ID NO 573
<211> LENGTH: 6
<212> TYPE: PRT
<213> ORGANISM: Homo sapiens

<400> SEQUENCE: 573

Gly Leu Asn Gln Cys Leu
1               5

<210> SEQ ID NO 574
<211> LENGTH: 6
<212> TYPE: PRT
<213> ORGANISM: Homo sapiens

<400> SEQUENCE: 574

Gly Asp Asn Gly Cys Leu
1               5

<210> SEQ ID NO 575
<211> LENGTH: 6
<212> TYPE: PRT
<213> ORGANISM: Homo sapiens

<400> SEQUENCE: 575

Gly Arg Arg Ser Cys Leu
1               5

<210> SEQ ID NO 576
<211> LENGTH: 6
<212> TYPE: PRT
<213> ORGANISM: Homo sapiens

<400> SEQUENCE: 576

Gly Ala Phe Ala Cys Leu
1               5

<210> SEQ ID NO 577
<211> LENGTH: 6
<212> TYPE: PRT
<213> ORGANISM: Homo sapiens

<400> SEQUENCE: 577

Gly Lys Thr Lys Cys Leu
1               5

<210> SEQ ID NO 578
<211> LENGTH: 6
<212> TYPE: PRT
<213> ORGANISM: Homo sapiens

<400> SEQUENCE: 578

Gly Lys Arg Leu Cys Leu
1               5

<210> SEQ ID NO 579
<211> LENGTH: 6
<212> TYPE: PRT
<213> ORGANISM: Homo sapiens

<400> SEQUENCE: 579

Gly Lys Thr Arg Cys Leu
1               5

<210> SEQ ID NO 580
<211> LENGTH: 6
<212> TYPE: PRT
<213> ORGANISM: Homo sapiens

<400> SEQUENCE: 580

Gly Ile Trp Thr Cys Leu
1               5

<210> SEQ ID NO 581
<211> LENGTH: 6
<212> TYPE: PRT
<213> ORGANISM: Homo sapiens

<400> SEQUENCE: 581

Gly Lys Asp Trp Cys Leu
1 5

<210> SEQ ID NO 582
<211> LENGTH: 6
<212> TYPE: PRT
<213> ORGANISM: Homo sapiens

<400> SEQUENCE: 582

Gly Ile Ile Tyr Cys Leu
1 5

<210> SEQ ID NO 583
<211> LENGTH: 6
<212> TYPE: PRT
<213> ORGANISM: Homo sapiens

<400> SEQUENCE: 583

Gly Met Ala Asn Cys Leu
1 5

<210> SEQ ID NO 584
<211> LENGTH: 6
<212> TYPE: PRT
<213> ORGANISM: Homo sapiens

<400> SEQUENCE: 584

Gly Ile Leu Arg Cys Leu
1 5

<210> SEQ ID NO 585
<211> LENGTH: 6
<212> TYPE: PRT
<213> ORGANISM: Homo sapiens

<400> SEQUENCE: 585

Gly Glu Gly Pro Cys Leu
1 5

<210> SEQ ID NO 586
<211> LENGTH: 6
<212> TYPE: PRT
<213> ORGANISM: Homo sapiens

<400> SEQUENCE: 586

Gly Ala Trp Leu Cys Leu
1 5

<210> SEQ ID NO 587
<211> LENGTH: 6
<212> TYPE: PRT
<213> ORGANISM: Homo sapiens

<400> SEQUENCE: 587

Gly Pro Ile Glu Cys Leu
1 5

<210> SEQ ID NO 588
<211> LENGTH: 6
<212> TYPE: PRT
<213> ORGANISM: Homo sapiens

<400> SEQUENCE: 588

Gly Cys Asp Arg Cys Leu
1 5

<210> SEQ ID NO 589
<211> LENGTH: 6
<212> TYPE: PRT
<213> ORGANISM: Homo sapiens

<400> SEQUENCE: 589

Gly Gln Cys Pro Cys Leu
1 5

<210> SEQ ID NO 590
<211> LENGTH: 6
<212> TYPE: PRT
<213> ORGANISM: Homo sapiens

<400> SEQUENCE: 590

Gly Val Pro Gly Cys Leu
1 5

<210> SEQ ID NO 591
<211> LENGTH: 6
<212> TYPE: PRT
<213> ORGANISM: Homo sapiens

<400> SEQUENCE: 591

Gly Ser Ser Asp Cys Leu
1 5

<210> SEQ ID NO 592
<211> LENGTH: 6
<212> TYPE: PRT
<213> ORGANISM: Homo sapiens

<400> SEQUENCE: 592

Gly Phe Leu Lys Cys Leu
1 5

<210> SEQ ID NO 593
<211> LENGTH: 6
<212> TYPE: PRT
<213> ORGANISM: Homo sapiens

<400> SEQUENCE: 593

Gly Ser Ser Gln Cys Leu
1 5

<210> SEQ ID NO 594
<211> LENGTH: 6
<212> TYPE: PRT
<213> ORGANISM: Homo sapiens

<400> SEQUENCE: 594

Gly Leu Leu Leu Cys Leu
1 5

<210> SEQ ID NO 595
<211> LENGTH: 6
<212> TYPE: PRT
<213> ORGANISM: Homo sapiens

<400> SEQUENCE: 595

Gly Trp Gly Phe Cys Leu
1 5

<210> SEQ ID NO 596
<211> LENGTH: 6
<212> TYPE: PRT
<213> ORGANISM: Homo sapiens

<400> SEQUENCE: 596

Gly Ser Cys Gly Cys Leu
1 5

<210> SEQ ID NO 597
<211> LENGTH: 6
<212> TYPE: PRT
<213> ORGANISM: Homo sapiens

<400> SEQUENCE: 597

Gly Phe Pro Ala Cys Leu
1 5

<210> SEQ ID NO 598
<211> LENGTH: 6
<212> TYPE: PRT
<213> ORGANISM: Homo sapiens

<400> SEQUENCE: 598

Gly Leu Gln Trp Cys Leu
1 5

<210> SEQ ID NO 599
<211> LENGTH: 6
<212> TYPE: PRT
<213> ORGANISM: Homo sapiens

<400> SEQUENCE: 599

Gly Tyr Gly Glu Cys Leu
1 5

<210> SEQ ID NO 600
<211> LENGTH: 6
<212> TYPE: PRT
<213> ORGANISM: Homo sapiens

<400> SEQUENCE: 600

Gly Thr Ala Pro Cys Leu
1 5

<210> SEQ ID NO 601
<211> LENGTH: 6
<212> TYPE: PRT
<213> ORGANISM: Homo sapiens

<400> SEQUENCE: 601

Gly Ser Arg Val Cys Leu
1 5

<210> SEQ ID NO 602
<211> LENGTH: 6
<212> TYPE: PRT
<213> ORGANISM: Homo sapiens

<400> SEQUENCE: 602

Gly Ser Arg Val Cys Leu
1 5

<210> SEQ ID NO 603
<211> LENGTH: 6
<212> TYPE: PRT
<213> ORGANISM: Homo sapiens

<400> SEQUENCE: 603

Gly Ser Arg Val Cys Leu
1 5

<210> SEQ ID NO 604
<211> LENGTH: 6
<212> TYPE: PRT
<213> ORGANISM: Homo sapiens

<400> SEQUENCE: 604

Gly Thr Phe Ser Cys Leu
1 5

<210> SEQ ID NO 605
<211> LENGTH: 6
<212> TYPE: PRT
<213> ORGANISM: Homo sapiens

<400> SEQUENCE: 605

Gly Trp Lys Thr Cys Leu
1 5

<210> SEQ ID NO 606
<211> LENGTH: 6
<212> TYPE: PRT
<213> ORGANISM: Homo sapiens

<400> SEQUENCE: 606

Gly Asn Ala Ser Cys Leu
1 5

<210> SEQ ID NO 607
<211> LENGTH: 6
<212> TYPE: PRT
<213> ORGANISM: Homo sapiens

<400> SEQUENCE: 607

Gly Ala Gly Ile Cys Leu
1 5

<210> SEQ ID NO 608
<211> LENGTH: 6
<212> TYPE: PRT
<213> ORGANISM: Homo sapiens

<400> SEQUENCE: 608

Gly Glu Ser Val Cys Leu
1 5

<210> SEQ ID NO 609
<211> LENGTH: 6
<212> TYPE: PRT
<213> ORGANISM: Homo sapiens

<400> SEQUENCE: 609

Gly Val Leu Ala Cys Leu
1               5

<210> SEQ ID NO 610
<211> LENGTH: 6
<212> TYPE: PRT
<213> ORGANISM: Homo sapiens

<400> SEQUENCE: 610

Gly Gln Ile Phe Cys Leu
1               5

<210> SEQ ID NO 611
<211> LENGTH: 6
<212> TYPE: PRT
<213> ORGANISM: Homo sapiens

<400> SEQUENCE: 611

Gly Gln Ile Phe Cys Leu
1               5

<210> SEQ ID NO 612
<211> LENGTH: 6
<212> TYPE: PRT
<213> ORGANISM: Homo sapiens

<400> SEQUENCE: 612

Gly Val Thr Thr Cys Leu
1               5

<210> SEQ ID NO 613
<211> LENGTH: 6
<212> TYPE: PRT
<213> ORGANISM: Homo sapiens

<400> SEQUENCE: 613

Gly Lys Val Ser Cys Leu
1               5

<210> SEQ ID NO 614
<211> LENGTH: 6
<212> TYPE: PRT
<213> ORGANISM: Homo sapiens

<400> SEQUENCE: 614

Gly Ser Asp Gln Cys Leu
1               5

<210> SEQ ID NO 615
<211> LENGTH: 6
<212> TYPE: PRT
<213> ORGANISM: Homo sapiens

<400> SEQUENCE: 615

Gly Pro Leu Leu Cys Leu
1               5

<210> SEQ ID NO 616
<211> LENGTH: 6
<212> TYPE: PRT
<213> ORGANISM: Homo sapiens

<400> SEQUENCE: 616

Gly Gln Asp His Cys Leu
1 5

<210> SEQ ID NO 617
<211> LENGTH: 6
<212> TYPE: PRT
<213> ORGANISM: Homo sapiens

<400> SEQUENCE: 617

Gly Asp Glu Asp Cys Leu
1 5

<210> SEQ ID NO 618
<211> LENGTH: 6
<212> TYPE: PRT
<213> ORGANISM: Homo sapiens

<400> SEQUENCE: 618

Gly Phe Ser Gly Cys Leu
1 5

<210> SEQ ID NO 619
<211> LENGTH: 6
<212> TYPE: PRT
<213> ORGANISM: Homo sapiens

<400> SEQUENCE: 619

Gly Leu Leu Phe Cys Leu
1 5

<210> SEQ ID NO 620
<211> LENGTH: 6
<212> TYPE: PRT
<213> ORGANISM: Homo sapiens

<400> SEQUENCE: 620

Gly Pro Arg Pro Cys Leu
1 5

<210> SEQ ID NO 621
<211> LENGTH: 6
<212> TYPE: PRT
<213> ORGANISM: Homo sapiens

<400> SEQUENCE: 621

Gly His Gly Asp Cys Leu
1 5

<210> SEQ ID NO 622
<211> LENGTH: 6
<212> TYPE: PRT
<213> ORGANISM: Homo sapiens

<400> SEQUENCE: 622

Gly Val Ala Ala Cys Leu
1 5

<210> SEQ ID NO 623
<211> LENGTH: 6
<212> TYPE: PRT
<213> ORGANISM: Homo sapiens

<400> SEQUENCE: 623

Gly Gln Gln Thr Cys Leu
1               5

<210> SEQ ID NO 624
<211> LENGTH: 6
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Any amino acid

<400> SEQUENCE: 624

Gly Pro Gln Gly Cys Xaa
1               5

<210> SEQ ID NO 625
<211> LENGTH: 6
<212> TYPE: PRT
<213> ORGANISM: Homo sapiens

<400> SEQUENCE: 625

Gly Lys Gln Val Cys Leu
1               5

<210> SEQ ID NO 626
<211> LENGTH: 6
<212> TYPE: PRT
<213> ORGANISM: Homo sapiens

<400> SEQUENCE: 626

Gly Leu Gln Gly Cys Leu
1               5

<210> SEQ ID NO 627
<211> LENGTH: 6
<212> TYPE: PRT
<213> ORGANISM: Homo sapiens

<400> SEQUENCE: 627

Gly Leu Gly Arg Cys Leu
1               5

<210> SEQ ID NO 628
<211> LENGTH: 6
<212> TYPE: PRT
<213> ORGANISM: Homo sapiens

<400> SEQUENCE: 628

Gly Cys Pro Arg Cys Leu
1               5

<210> SEQ ID NO 629
<211> LENGTH: 6
<212> TYPE: PRT
<213> ORGANISM: Homo sapiens

<400> SEQUENCE: 629

Gly Ser Phe Arg Cys Leu
1               5

<210> SEQ ID NO 630
<211> LENGTH: 6

-continued

<212> TYPE: PRT
<213> ORGANISM: Homo sapiens

<400> SEQUENCE: 630

Gly Asp Asp Pro Cys Leu
1               5

<210> SEQ ID NO 631
<211> LENGTH: 6
<212> TYPE: PRT
<213> ORGANISM: Homo sapiens

<400> SEQUENCE: 631

Gly Thr Tyr Val Cys Leu
1               5

<210> SEQ ID NO 632
<211> LENGTH: 6
<212> TYPE: PRT
<213> ORGANISM: Homo sapiens

<400> SEQUENCE: 632

Gly Ala Asn Ile Cys Leu
1               5

<210> SEQ ID NO 633
<211> LENGTH: 6
<212> TYPE: PRT
<213> ORGANISM: Homo sapiens

<400> SEQUENCE: 633

Gly His Pro Asp Cys Leu
1               5

<210> SEQ ID NO 634
<211> LENGTH: 6
<212> TYPE: PRT
<213> ORGANISM: Homo sapiens

<400> SEQUENCE: 634

Gly Ser Ala Asp Cys Leu
1               5

<210> SEQ ID NO 635
<211> LENGTH: 6
<212> TYPE: PRT
<213> ORGANISM: Homo sapiens

<400> SEQUENCE: 635

Gly Pro Lys Ile Cys Leu
1               5

<210> SEQ ID NO 636
<211> LENGTH: 6
<212> TYPE: PRT
<213> ORGANISM: Homo sapiens

<400> SEQUENCE: 636

Gly Asp Thr Val Cys Leu
1               5

<210> SEQ ID NO 637
<211> LENGTH: 6
<212> TYPE: PRT
<213> ORGANISM: Homo sapiens

<400> SEQUENCE: 637

Gly Lys Glu Ile Cys Leu
1               5

<210> SEQ ID NO 638
<211> LENGTH: 6
<212> TYPE: PRT
<213> ORGANISM: Homo sapiens

<400> SEQUENCE: 638

Gly Leu Gly Asn Cys Leu
1               5

<210> SEQ ID NO 639
<211> LENGTH: 6
<212> TYPE: PRT
<213> ORGANISM: Homo sapiens

<400> SEQUENCE: 639

Gly Met Val His Cys Leu
1               5

<210> SEQ ID NO 640
<211> LENGTH: 6
<212> TYPE: PRT
<213> ORGANISM: Homo sapiens

<400> SEQUENCE: 640

Gly Pro Ala Pro Cys Leu
1               5

<210> SEQ ID NO 641
<211> LENGTH: 6
<212> TYPE: PRT
<213> ORGANISM: Homo sapiens

<400> SEQUENCE: 641

Gly Val Tyr Gln Cys Leu
1               5

<210> SEQ ID NO 642
<211> LENGTH: 6
<212> TYPE: PRT
<213> ORGANISM: Homo sapiens

<400> SEQUENCE: 642

Gly Asn Tyr Ser Cys Leu
1               5

<210> SEQ ID NO 643
<211> LENGTH: 6
<212> TYPE: PRT
<213> ORGANISM: Homo sapiens

<400> SEQUENCE: 643

Gly Val Arg Ala Cys Leu
1               5

<210> SEQ ID NO 644
<211> LENGTH: 6
<212> TYPE: PRT
<213> ORGANISM: Homo sapiens

<400> SEQUENCE: 644

Gly Ser Ile Thr Cys Leu
1               5

<210> SEQ ID NO 645
<211> LENGTH: 6
<212> TYPE: PRT
<213> ORGANISM: Homo sapiens

<400> SEQUENCE: 645

Gly Leu Asn Gln Cys Leu
1               5

<210> SEQ ID NO 646
<211> LENGTH: 6
<212> TYPE: PRT
<213> ORGANISM: Homo sapiens

<400> SEQUENCE: 646

Gly Met Ile Ser Cys Leu
1               5

<210> SEQ ID NO 647
<211> LENGTH: 6
<212> TYPE: PRT
<213> ORGANISM: Homo sapiens

<400> SEQUENCE: 647

Gly Leu Asn Gln Cys Leu
1               5

<210> SEQ ID NO 648
<211> LENGTH: 6
<212> TYPE: PRT
<213> ORGANISM: Homo sapiens

<400> SEQUENCE: 648

Gly Leu Asn Gln Cys Leu
1               5

<210> SEQ ID NO 649
<211> LENGTH: 6
<212> TYPE: PRT
<213> ORGANISM: Homo sapiens

<400> SEQUENCE: 649

Gly Leu Asn Gln Cys Leu
1               5

<210> SEQ ID NO 650
<211> LENGTH: 6
<212> TYPE: PRT
<213> ORGANISM: Homo sapiens

<400> SEQUENCE: 650

Gly Gly Phe Thr Cys Leu
1               5

<210> SEQ ID NO 651
<211> LENGTH: 6
<212> TYPE: PRT
<213> ORGANISM: Homo sapiens

<400> SEQUENCE: 651

Gly Glu Arg Ile Cys Leu
1               5

<210> SEQ ID NO 652
<211> LENGTH: 6
<212> TYPE: PRT
<213> ORGANISM: Homo sapiens

<400> SEQUENCE: 652

Gly Lys Thr Phe Cys Leu
1               5

<210> SEQ ID NO 653
<211> LENGTH: 6
<212> TYPE: PRT
<213> ORGANISM: Homo sapiens

<400> SEQUENCE: 653

Gly Lys Thr Phe Cys Leu
1               5

<210> SEQ ID NO 654
<211> LENGTH: 6
<212> TYPE: PRT
<213> ORGANISM: Homo sapiens

<400> SEQUENCE: 654

Gly Val Gln Thr Cys Leu
1               5

<210> SEQ ID NO 655
<211> LENGTH: 6
<212> TYPE: PRT
<213> ORGANISM: Homo sapiens

<400> SEQUENCE: 655

Gly Ser Asn Ser Cys Leu
1               5

<210> SEQ ID NO 656
<211> LENGTH: 6
<212> TYPE: PRT
<213> ORGANISM: Homo sapiens

<400> SEQUENCE: 656

Gly Asp Asn Asp Cys Leu
1               5

<210> SEQ ID NO 657
<211> LENGTH: 6
<212> TYPE: PRT
<213> ORGANISM: Homo sapiens

<400> SEQUENCE: 657

Gly Ser Tyr Lys Cys Leu
1               5

<210> SEQ ID NO 658
<211> LENGTH: 6
<212> TYPE: PRT
<213> ORGANISM: Homo sapiens

<400> SEQUENCE: 658

Gly Pro Cys Pro Cys Leu
1               5

<210> SEQ ID NO 659
<211> LENGTH: 6
<212> TYPE: PRT
<213> ORGANISM: Homo sapiens

<400> SEQUENCE: 659

Gly Ile Val Leu Cys Leu
1               5

<210> SEQ ID NO 660
<211> LENGTH: 6
<212> TYPE: PRT
<213> ORGANISM: Homo sapiens

<400> SEQUENCE: 660

Gly Ser Asn Leu Cys Leu
1               5

<210> SEQ ID NO 661
<211> LENGTH: 6
<212> TYPE: PRT
<213> ORGANISM: Homo sapiens

<400> SEQUENCE: 661

Gly Asp Gly Pro Cys Leu
1               5

<210> SEQ ID NO 662
<211> LENGTH: 6
<212> TYPE: PRT
<213> ORGANISM: Homo sapiens

<400> SEQUENCE: 662

Gly Gly Tyr Leu Cys Leu
1               5

<210> SEQ ID NO 663
<211> LENGTH: 6
<212> TYPE: PRT
<213> ORGANISM: Homo sapiens

<400> SEQUENCE: 663

Gly Phe Pro Glu Cys Leu
1               5

<210> SEQ ID NO 664
<211> LENGTH: 6
<212> TYPE: PRT
<213> ORGANISM: Homo sapiens

<400> SEQUENCE: 664

Gly Glu Pro Thr Cys Leu
1               5

<210> SEQ ID NO 665
<211> LENGTH: 6
<212> TYPE: PRT
<213> ORGANISM: Homo sapiens

<400> SEQUENCE: 665

Gly Leu Phe Gly Cys Leu
1               5

<210> SEQ ID NO 666
<211> LENGTH: 6
<212> TYPE: PRT
<213> ORGANISM: Homo sapiens

<400> SEQUENCE: 666

Gly Ile Tyr Tyr Cys Leu
1               5

<210> SEQ ID NO 667
<211> LENGTH: 6
<212> TYPE: PRT
<213> ORGANISM: Homo sapiens

<400> SEQUENCE: 667

Gly Cys Thr Leu Cys Leu
1               5

<210> SEQ ID NO 668
<211> LENGTH: 6
<212> TYPE: PRT
<213> ORGANISM: Homo sapiens

<400> SEQUENCE: 668

Gly Tyr Lys Met Cys Leu
1               5

<210> SEQ ID NO 669
<211> LENGTH: 6
<212> TYPE: PRT
<213> ORGANISM: Homo sapiens

<400> SEQUENCE: 669

Gly Asp Phe Ser Cys Leu
1               5

<210> SEQ ID NO 670
<211> LENGTH: 6
<212> TYPE: PRT
<213> ORGANISM: Homo sapiens

<400> SEQUENCE: 670

Gly Tyr Lys Leu Cys Leu
1               5

<210> SEQ ID NO 671
<211> LENGTH: 6
<212> TYPE: PRT
<213> ORGANISM: Homo sapiens

<400> SEQUENCE: 671

Gly Leu Arg Pro Cys Leu
1               5

<210> SEQ ID NO 672
<211> LENGTH: 6
<212> TYPE: PRT
<213> ORGANISM: Homo sapiens

<400> SEQUENCE: 672

Gly Glu Arg Glu Cys Leu
1               5

<210> SEQ ID NO 673
<211> LENGTH: 6
<212> TYPE: PRT
<213> ORGANISM: Homo sapiens

<400> SEQUENCE: 673

Gly Tyr Asn Arg Cys Leu
1               5

<210> SEQ ID NO 674
<211> LENGTH: 6
<212> TYPE: PRT
<213> ORGANISM: Homo sapiens

<400> SEQUENCE: 674

Gly Asp Asp Gln Cys Leu
1               5

<210> SEQ ID NO 675
<211> LENGTH: 6
<212> TYPE: PRT
<213> ORGANISM: Homo sapiens

<400> SEQUENCE: 675

Gly Ile Asn Arg Cys Leu
1               5

<210> SEQ ID NO 676
<211> LENGTH: 6
<212> TYPE: PRT
<213> ORGANISM: Homo sapiens

<400> SEQUENCE: 676

Gly Gly His Cys Cys Leu
1               5

<210> SEQ ID NO 677
<211> LENGTH: 6
<212> TYPE: PRT
<213> ORGANISM: Homo sapiens

<400> SEQUENCE: 677

Gly Tyr Leu Asp Cys Leu
1               5

<210> SEQ ID NO 678
<211> LENGTH: 6
<212> TYPE: PRT
<213> ORGANISM: Homo sapiens

<400> SEQUENCE: 678

Gly Ile Phe Ser Cys Leu
1               5

<210> SEQ ID NO 679
<211> LENGTH: 6
<212> TYPE: PRT
<213> ORGANISM: Homo sapiens

<400> SEQUENCE: 679

Gly Leu Glu Arg Cys Leu
1               5

<210> SEQ ID NO 680
<211> LENGTH: 6
<212> TYPE: PRT
<213> ORGANISM: Homo sapiens

<400> SEQUENCE: 680

Gly Gly Ala Gly Cys Leu
1               5

<210> SEQ ID NO 681
<211> LENGTH: 6
<212> TYPE: PRT
<213> ORGANISM: Homo sapiens

<400> SEQUENCE: 681

Gly Cys Met Ile Cys Leu
1               5

<210> SEQ ID NO 682
<211> LENGTH: 6
<212> TYPE: PRT
<213> ORGANISM: Homo sapiens

<400> SEQUENCE: 682

Gly Leu Phe Ser Cys Leu
1               5

<210> SEQ ID NO 683
<211> LENGTH: 6
<212> TYPE: PRT
<213> ORGANISM: Homo sapiens

<400> SEQUENCE: 683

Gly Leu Pro Arg Cys Leu
1               5

<210> SEQ ID NO 684
<211> LENGTH: 6
<212> TYPE: PRT
<213> ORGANISM: Homo sapiens

<400> SEQUENCE: 684

Gly Met Gly Ser Cys Leu
1               5

<210> SEQ ID NO 685
<211> LENGTH: 6
<212> TYPE: PRT
<213> ORGANISM: Homo sapiens

<400> SEQUENCE: 685

Gly Gly Leu Lys Cys Leu
1               5

<210> SEQ ID NO 686
<211> LENGTH: 6
<212> TYPE: PRT
<213> ORGANISM: Homo sapiens

<400> SEQUENCE: 686

Gly Asp Arg Phe Cys Leu
1 5

<210> SEQ ID NO 687
<211> LENGTH: 6
<212> TYPE: PRT
<213> ORGANISM: Homo sapiens

<400> SEQUENCE: 687

Gly Pro Pro Pro Cys Leu
1 5

<210> SEQ ID NO 688
<211> LENGTH: 6
<212> TYPE: PRT
<213> ORGANISM: Homo sapiens

<400> SEQUENCE: 688

Gly Gly Met Pro Cys Leu
1 5

<210> SEQ ID NO 689
<211> LENGTH: 6
<212> TYPE: PRT
<213> ORGANISM: Homo sapiens

<400> SEQUENCE: 689

Gly Gly Asp Ile Cys Leu
1 5

<210> SEQ ID NO 690
<211> LENGTH: 6
<212> TYPE: PRT
<213> ORGANISM: Homo sapiens

<400> SEQUENCE: 690

Gly Glu Val Phe Cys Leu
1 5

<210> SEQ ID NO 691
<211> LENGTH: 6
<212> TYPE: PRT
<213> ORGANISM: Homo sapiens

<400> SEQUENCE: 691

Gly His His Cys Cys Leu
1 5

<210> SEQ ID NO 692
<211> LENGTH: 6
<212> TYPE: PRT
<213> ORGANISM: Homo sapiens

<400> SEQUENCE: 692

Gly Leu Pro His Cys Leu
1 5

<210> SEQ ID NO 693
<211> LENGTH: 6
<212> TYPE: PRT
<213> ORGANISM: Homo sapiens

<400> SEQUENCE: 693

Gly Gly Leu Tyr Cys Leu
1 5

<210> SEQ ID NO 694
<211> LENGTH: 6
<212> TYPE: PRT
<213> ORGANISM: Homo sapiens

<400> SEQUENCE: 694

Gly Arg Cys Leu Cys Leu
1 5

<210> SEQ ID NO 695
<211> LENGTH: 6
<212> TYPE: PRT
<213> ORGANISM: Homo sapiens

<400> SEQUENCE: 695

Gly Gln Phe Asn Cys Leu
1 5

<210> SEQ ID NO 696
<211> LENGTH: 6
<212> TYPE: PRT
<213> ORGANISM: Homo sapiens

<400> SEQUENCE: 696

Gly Asn Leu Lys Cys Leu
1 5

<210> SEQ ID NO 697
<211> LENGTH: 6
<212> TYPE: PRT
<213> ORGANISM: Homo sapiens

<400> SEQUENCE: 697

Gly Arg Arg Asp Cys Leu
1 5

<210> SEQ ID NO 698
<211> LENGTH: 6
<212> TYPE: PRT
<213> ORGANISM: Homo sapiens

<400> SEQUENCE: 698

Gly Val Asn Ile Cys Leu
1 5

<210> SEQ ID NO 699
<211> LENGTH: 6
<212> TYPE: PRT
<213> ORGANISM: Homo sapiens

<400> SEQUENCE: 699

Gly Val Thr Thr Cys Leu
1 5

<210> SEQ ID NO 700
<211> LENGTH: 6
<212> TYPE: PRT
<213> ORGANISM: Homo sapiens

<400> SEQUENCE: 700

Gly Ile Glu Ile Cys Leu
1               5

<210> SEQ ID NO 701
<211> LENGTH: 6
<212> TYPE: PRT
<213> ORGANISM: Homo sapiens

<400> SEQUENCE: 701

Gly Val Ile Gly Cys Leu
1               5

<210> SEQ ID NO 702
<211> LENGTH: 6
<212> TYPE: PRT
<213> ORGANISM: Homo sapiens

<400> SEQUENCE: 702

Gly Asn Arg Ser Cys Leu
1               5

<210> SEQ ID NO 703
<211> LENGTH: 6
<212> TYPE: PRT
<213> ORGANISM: Homo sapiens

<400> SEQUENCE: 703

Gly Leu Asn Glu Cys Leu
1               5

<210> SEQ ID NO 704
<211> LENGTH: 6
<212> TYPE: PRT
<213> ORGANISM: Homo sapiens

<400> SEQUENCE: 704

Gly Thr Arg Ala Cys Leu
1               5

<210> SEQ ID NO 705
<211> LENGTH: 6
<212> TYPE: PRT
<213> ORGANISM: Homo sapiens

<400> SEQUENCE: 705

Gly Glu Leu Thr Cys Leu
1               5

<210> SEQ ID NO 706
<211> LENGTH: 6
<212> TYPE: PRT
<213> ORGANISM: Homo sapiens

<400> SEQUENCE: 706

Gly Leu Gly Ala Cys Leu
1               5

<210> SEQ ID NO 707
<211> LENGTH: 6
<212> TYPE: PRT
<213> ORGANISM: Homo sapiens

<400> SEQUENCE: 707

Gly Asp Pro His Cys Leu
1 5

<210> SEQ ID NO 708
<211> LENGTH: 6
<212> TYPE: PRT
<213> ORGANISM: Homo sapiens

<400> SEQUENCE: 708

Gly Ser Leu Pro Cys Leu
1 5

<210> SEQ ID NO 709
<211> LENGTH: 6
<212> TYPE: PRT
<213> ORGANISM: Homo sapiens

<400> SEQUENCE: 709

Gly Asn Phe Phe Cys Leu
1 5

<210> SEQ ID NO 710
<211> LENGTH: 6
<212> TYPE: PRT
<213> ORGANISM: Homo sapiens

<400> SEQUENCE: 710

Gly Ser Tyr Ser Cys Leu
1 5

<210> SEQ ID NO 711
<211> LENGTH: 6
<212> TYPE: PRT
<213> ORGANISM: Homo sapiens

<400> SEQUENCE: 711

Gly Glu Arg Pro Cys Leu
1 5

<210> SEQ ID NO 712
<211> LENGTH: 6
<212> TYPE: PRT
<213> ORGANISM: Homo sapiens

<400> SEQUENCE: 712

Gly Gln Pro Leu Cys Leu
1 5

<210> SEQ ID NO 713
<211> LENGTH: 6
<212> TYPE: PRT
<213> ORGANISM: Homo sapiens

<400> SEQUENCE: 713

Gly Ile Leu Pro Cys Leu
1 5

<210> SEQ ID NO 714
<211> LENGTH: 6
<212> TYPE: PRT
<213> ORGANISM: Homo sapiens

<400> SEQUENCE: 714

Gly Arg Gly Gln Cys Leu
1               5

<210> SEQ ID NO 715
<211> LENGTH: 6
<212> TYPE: PRT
<213> ORGANISM: Homo sapiens

<400> SEQUENCE: 715

Gly Gln Ser Leu Cys Leu
1               5

<210> SEQ ID NO 716
<211> LENGTH: 6
<212> TYPE: PRT
<213> ORGANISM: Homo sapiens

<400> SEQUENCE: 716

Gly Thr Phe Leu Cys Leu
1               5

<210> SEQ ID NO 717
<211> LENGTH: 6
<212> TYPE: PRT
<213> ORGANISM: Homo sapiens

<400> SEQUENCE: 717

Gly Leu Asn Gln Cys Leu
1               5

<210> SEQ ID NO 718
<211> LENGTH: 6
<212> TYPE: PRT
<213> ORGANISM: Homo sapiens

<400> SEQUENCE: 718

Gly Val Leu Ser Cys Leu
1               5

<210> SEQ ID NO 719
<211> LENGTH: 6
<212> TYPE: PRT
<213> ORGANISM: Homo sapiens

<400> SEQUENCE: 719

Gly Leu Ala Asp Cys Leu
1               5

<210> SEQ ID NO 720
<211> LENGTH: 6
<212> TYPE: PRT
<213> ORGANISM: Homo sapiens

<400> SEQUENCE: 720

Gly Gly Ala Glu Cys Leu
1               5

<210> SEQ ID NO 721
<211> LENGTH: 6
<212> TYPE: PRT
<213> ORGANISM: Homo sapiens

<400> SEQUENCE: 721

Gly Asp Ser Asn Cys Leu
1               5

<210> SEQ ID NO 722
<211> LENGTH: 6
<212> TYPE: PRT
<213> ORGANISM: Homo sapiens

<400> SEQUENCE: 722

Gly Ile Ile Val Cys Leu
1               5

<210> SEQ ID NO 723
<211> LENGTH: 6
<212> TYPE: PRT
<213> ORGANISM: Homo sapiens

<400> SEQUENCE: 723

Gly Ser Phe Arg Cys Leu
1               5

<210> SEQ ID NO 724
<211> LENGTH: 6
<212> TYPE: PRT
<213> ORGANISM: Homo sapiens

<400> SEQUENCE: 724

Gly Ser Tyr Lys Cys Leu
1               5

<210> SEQ ID NO 725
<211> LENGTH: 6
<212> TYPE: PRT
<213> ORGANISM: Homo sapiens

<400> SEQUENCE: 725

Gly Ser Tyr Thr Cys Leu
1               5

<210> SEQ ID NO 726
<211> LENGTH: 6
<212> TYPE: PRT
<213> ORGANISM: Homo sapiens

<400> SEQUENCE: 726

Gly Ser Tyr Gln Cys Leu
1               5

<210> SEQ ID NO 727
<211> LENGTH: 6
<212> TYPE: PRT
<213> ORGANISM: Homo sapiens

<400> SEQUENCE: 727

Gly Ser Phe Phe Cys Leu
1               5

<210> SEQ ID NO 728
<211> LENGTH: 6
<212> TYPE: PRT
<213> ORGANISM: Homo sapiens

<400> SEQUENCE: 728

Gly Ser Phe Asn Cys Leu
1               5

<210> SEQ ID NO 729
<211> LENGTH: 6
<212> TYPE: PRT
<213> ORGANISM: Homo sapiens

<400> SEQUENCE: 729

Gly Ser Phe Arg Cys Leu
1               5

<210> SEQ ID NO 730
<211> LENGTH: 6
<212> TYPE: PRT
<213> ORGANISM: Homo sapiens

<400> SEQUENCE: 730

Gly Ser Phe Leu Cys Leu
1               5

<210> SEQ ID NO 731
<211> LENGTH: 6
<212> TYPE: PRT
<213> ORGANISM: Homo sapiens

<400> SEQUENCE: 731

Gly Ala Leu Gly Cys Leu
1               5

<210> SEQ ID NO 732
<211> LENGTH: 6
<212> TYPE: PRT
<213> ORGANISM: Homo sapiens

<400> SEQUENCE: 732

Gly Phe Ala Leu Cys Leu
1               5

<210> SEQ ID NO 733
<211> LENGTH: 6
<212> TYPE: PRT
<213> ORGANISM: Homo sapiens

<400> SEQUENCE: 733

Gly Cys Ala Val Cys Leu
1               5

<210> SEQ ID NO 734
<211> LENGTH: 6
<212> TYPE: PRT
<213> ORGANISM: Homo sapiens

<400> SEQUENCE: 734

Gly Ser Gly Ala Cys Leu
1               5

<210> SEQ ID NO 735
<211> LENGTH: 6
<212> TYPE: PRT
<213> ORGANISM: Homo sapiens

<400> SEQUENCE: 735

Gly Pro Ser Pro Cys Leu
1 5

<210> SEQ ID NO 736
<211> LENGTH: 6
<212> TYPE: PRT
<213> ORGANISM: Homo sapiens

<400> SEQUENCE: 736

Gly Thr Ile Gln Cys Leu
1 5

<210> SEQ ID NO 737
<211> LENGTH: 6
<212> TYPE: PRT
<213> ORGANISM: Homo sapiens

<400> SEQUENCE: 737

Gly Asn Trp His Cys Leu
1 5

<210> SEQ ID NO 738
<211> LENGTH: 6
<212> TYPE: PRT
<213> ORGANISM: Homo sapiens

<400> SEQUENCE: 738

Gly Arg Phe Thr Cys Leu
1 5

<210> SEQ ID NO 739
<211> LENGTH: 6
<212> TYPE: PRT
<213> ORGANISM: Homo sapiens

<400> SEQUENCE: 739

Gly Phe Asn Thr Cys Leu
1 5

<210> SEQ ID NO 740
<211> LENGTH: 6
<212> TYPE: PRT
<213> ORGANISM: Homo sapiens

<400> SEQUENCE: 740

Gly Thr Cys Thr Cys Leu
1 5

<210> SEQ ID NO 741
<211> LENGTH: 6
<212> TYPE: PRT
<213> ORGANISM: Homo sapiens

<400> SEQUENCE: 741

Gly Gly Ser Asn Cys Leu
1 5

<210> SEQ ID NO 742
<211> LENGTH: 6
<212> TYPE: PRT
<213> ORGANISM: Homo sapiens

<400> SEQUENCE: 742

Gly Lys Val Ser Cys Leu
1               5

<210> SEQ ID NO 743
<211> LENGTH: 6
<212> TYPE: PRT
<213> ORGANISM: Homo sapiens

<400> SEQUENCE: 743

Gly Pro Ala His Cys Leu
1               5

<210> SEQ ID NO 744
<211> LENGTH: 6
<212> TYPE: PRT
<213> ORGANISM: Homo sapiens

<400> SEQUENCE: 744

Gly Pro Asp Gln Cys Leu
1               5

<210> SEQ ID NO 745
<211> LENGTH: 6
<212> TYPE: PRT
<213> ORGANISM: Homo sapiens

<400> SEQUENCE: 745

Gly Val Val Arg Cys Leu
1               5

<210> SEQ ID NO 746
<211> LENGTH: 6
<212> TYPE: PRT
<213> ORGANISM: Homo sapiens

<400> SEQUENCE: 746

Gly Met Gln Ile Cys Leu
1               5

<210> SEQ ID NO 747
<211> LENGTH: 6
<212> TYPE: PRT
<213> ORGANISM: Homo sapiens

<400> SEQUENCE: 747

Gly His Asp Glu Cys Leu
1               5

<210> SEQ ID NO 748
<211> LENGTH: 6
<212> TYPE: PRT
<213> ORGANISM: Homo sapiens

<400> SEQUENCE: 748

Gly Leu Arg Thr Cys Leu
1               5

<210> SEQ ID NO 749
<211> LENGTH: 6
<212> TYPE: PRT
<213> ORGANISM: Homo sapiens

<400> SEQUENCE: 749

Gly Asn Pro Glu Cys Leu
1               5

<210> SEQ ID NO 750
<211> LENGTH: 6
<212> TYPE: PRT
<213> ORGANISM: Homo sapiens

<400> SEQUENCE: 750

Gly Leu Ile Tyr Cys Leu
1               5

<210> SEQ ID NO 751
<211> LENGTH: 6
<212> TYPE: PRT
<213> ORGANISM: Homo sapiens

<400> SEQUENCE: 751

Gly Leu Cys Gln Cys Leu
1               5

<210> SEQ ID NO 752
<211> LENGTH: 6
<212> TYPE: PRT
<213> ORGANISM: Homo sapiens

<400> SEQUENCE: 752

Gly Ser Gly Pro Cys Leu
1               5

<210> SEQ ID NO 753
<211> LENGTH: 6
<212> TYPE: PRT
<213> ORGANISM: Homo sapiens

<400> SEQUENCE: 753

Gly Phe Val Val Cys Leu
1               5

<210> SEQ ID NO 754
<211> LENGTH: 6
<212> TYPE: PRT
<213> ORGANISM: Homo sapiens

<400> SEQUENCE: 754

Gly Pro Gly Arg Cys Leu
1               5

<210> SEQ ID NO 755
<211> LENGTH: 6
<212> TYPE: PRT
<213> ORGANISM: Homo sapiens

<400> SEQUENCE: 755

Gly Val Tyr Thr Cys Leu
1               5

<210> SEQ ID NO 756
<211> LENGTH: 6
<212> TYPE: PRT
<213> ORGANISM: Homo sapiens

<400> SEQUENCE: 756

Gly Thr Tyr Thr Cys Leu
1 5

<210> SEQ ID NO 757
<211> LENGTH: 6
<212> TYPE: PRT
<213> ORGANISM: Homo sapiens

<400> SEQUENCE: 757

Gly Gln Ala Met Cys Leu
1 5

<210> SEQ ID NO 758
<211> LENGTH: 6
<212> TYPE: PRT
<213> ORGANISM: Homo sapiens

<400> SEQUENCE: 758

Gly Ser Tyr His Cys Leu
1 5

<210> SEQ ID NO 759
<211> LENGTH: 6
<212> TYPE: PRT
<213> ORGANISM: Homo sapiens

<400> SEQUENCE: 759

Gly Glu Ser Val Cys Leu
1 5

<210> SEQ ID NO 760
<211> LENGTH: 6
<212> TYPE: PRT
<213> ORGANISM: Homo sapiens

<400> SEQUENCE: 760

Gly Phe Val Gly Cys Leu
1 5

<210> SEQ ID NO 761
<211> LENGTH: 6
<212> TYPE: PRT
<213> ORGANISM: Homo sapiens

<400> SEQUENCE: 761

Gly Leu Pro Thr Cys Leu
1 5

<210> SEQ ID NO 762
<211> LENGTH: 6
<212> TYPE: PRT
<213> ORGANISM: Homo sapiens

<400> SEQUENCE: 762

Gly Leu Met Phe Cys Leu
1 5

<210> SEQ ID NO 763
<211> LENGTH: 6
<212> TYPE: PRT
<213> ORGANISM: Homo sapiens

<400> SEQUENCE: 763

Gly His Asn His Cys Leu
1               5

<210> SEQ ID NO 764
<211> LENGTH: 6
<212> TYPE: PRT
<213> ORGANISM: Homo sapiens

<400> SEQUENCE: 764

Gly Val Ser Ser Cys Leu
1               5

<210> SEQ ID NO 765
<211> LENGTH: 6
<212> TYPE: PRT
<213> ORGANISM: Homo sapiens

<400> SEQUENCE: 765

Gly Thr His Cys Cys Leu
1               5

<210> SEQ ID NO 766
<211> LENGTH: 6
<212> TYPE: PRT
<213> ORGANISM: Homo sapiens

<400> SEQUENCE: 766

Gly Thr His Arg Cys Leu
1               5

<210> SEQ ID NO 767
<211> LENGTH: 6
<212> TYPE: PRT
<213> ORGANISM: Homo sapiens

<400> SEQUENCE: 767

Gly Ala Glu His Cys Leu
1               5

<210> SEQ ID NO 768
<211> LENGTH: 6
<212> TYPE: PRT
<213> ORGANISM: Homo sapiens

<400> SEQUENCE: 768

Gly Gln Leu Asn Cys Leu
1               5

<210> SEQ ID NO 769
<211> LENGTH: 6
<212> TYPE: PRT
<213> ORGANISM: Homo sapiens

<400> SEQUENCE: 769

Gly Gly Arg Leu Cys Leu
1               5

<210> SEQ ID NO 770
<211> LENGTH: 6
<212> TYPE: PRT
<213> ORGANISM: Homo sapiens

<400> SEQUENCE: 770

Gly Cys Ala Asp Cys Leu
1               5

<210> SEQ ID NO 771
<211> LENGTH: 6
<212> TYPE: PRT
<213> ORGANISM: Homo sapiens

<400> SEQUENCE: 771

Gly His Leu His Cys Leu
1               5

<210> SEQ ID NO 772
<211> LENGTH: 6
<212> TYPE: PRT
<213> ORGANISM: Homo sapiens

<400> SEQUENCE: 772

Gly Glu Phe Ser Cys Leu
1               5

<210> SEQ ID NO 773
<211> LENGTH: 6
<212> TYPE: PRT
<213> ORGANISM: Homo sapiens

<400> SEQUENCE: 773

Gly Arg Phe Arg Cys Leu
1               5

<210> SEQ ID NO 774
<211> LENGTH: 6
<212> TYPE: PRT
<213> ORGANISM: Homo sapiens

<400> SEQUENCE: 774

Gly Ile Glu Asp Cys Leu
1               5

<210> SEQ ID NO 775
<211> LENGTH: 6
<212> TYPE: PRT
<213> ORGANISM: Homo sapiens

<400> SEQUENCE: 775

Gly Tyr Tyr Gln Cys Leu
1               5

<210> SEQ ID NO 776
<211> LENGTH: 6
<212> TYPE: PRT
<213> ORGANISM: Homo sapiens

<400> SEQUENCE: 776

Gly Val Ile Tyr Cys Leu
1               5

<210> SEQ ID NO 777
<211> LENGTH: 6
<212> TYPE: PRT
<213> ORGANISM: Homo sapiens

<400> SEQUENCE: 777

Gly Thr Cys Ser Cys Leu
1               5

<210> SEQ ID NO 778
<211> LENGTH: 6
<212> TYPE: PRT
<213> ORGANISM: Homo sapiens

<400> SEQUENCE: 778

Gly Phe Leu Gly Cys Leu
1               5

<210> SEQ ID NO 779
<211> LENGTH: 6
<212> TYPE: PRT
<213> ORGANISM: Homo sapiens

<400> SEQUENCE: 779

Gly Thr Tyr Thr Cys Leu
1               5

<210> SEQ ID NO 780
<211> LENGTH: 6
<212> TYPE: PRT
<213> ORGANISM: Homo sapiens

<400> SEQUENCE: 780

Gly Arg Phe Leu Cys Leu
1               5

<210> SEQ ID NO 781
<211> LENGTH: 6
<212> TYPE: PRT
<213> ORGANISM: Homo sapiens

<400> SEQUENCE: 781

Gly Ser Phe Arg Cys Leu
1               5

<210> SEQ ID NO 782
<211> LENGTH: 6
<212> TYPE: PRT
<213> ORGANISM: Homo sapiens

<400> SEQUENCE: 782

Gly Lys Val Ser Cys Leu
1               5

<210> SEQ ID NO 783
<211> LENGTH: 6
<212> TYPE: PRT
<213> ORGANISM: Homo sapiens

<400> SEQUENCE: 783

Gly Lys Ser Lys Cys Leu
1               5

<210> SEQ ID NO 784
<211> LENGTH: 6
<212> TYPE: PRT
<213> ORGANISM: Homo sapiens

<400> SEQUENCE: 784

Gly Leu Lys Gln Cys Leu
1               5

<210> SEQ ID NO 785
<211> LENGTH: 6
<212> TYPE: PRT
<213> ORGANISM: Homo sapiens

<400> SEQUENCE: 785

Gly Val Arg Asn Cys Leu
1               5

<210> SEQ ID NO 786
<211> LENGTH: 6
<212> TYPE: PRT
<213> ORGANISM: Homo sapiens

<400> SEQUENCE: 786

Gly Thr Ser Gly Cys Leu
1               5

<210> SEQ ID NO 787
<211> LENGTH: 6
<212> TYPE: PRT
<213> ORGANISM: Homo sapiens

<400> SEQUENCE: 787

Gly Cys Cys Val Cys Leu
1               5

<210> SEQ ID NO 788
<211> LENGTH: 6
<212> TYPE: PRT
<213> ORGANISM: Homo sapiens

<400> SEQUENCE: 788

Gly Lys Asp Trp Cys Leu
1               5

<210> SEQ ID NO 789
<211> LENGTH: 6
<212> TYPE: PRT
<213> ORGANISM: Homo sapiens

<400> SEQUENCE: 789

Gly Ala Thr Ala Cys Leu
1               5

<210> SEQ ID NO 790
<211> LENGTH: 6
<212> TYPE: PRT
<213> ORGANISM: Homo sapiens

<400> SEQUENCE: 790

Gly Ser Ile Lys Cys Leu
1               5

<210> SEQ ID NO 791
<211> LENGTH: 6
<212> TYPE: PRT
<213> ORGANISM: Homo sapiens

<400> SEQUENCE: 791

Gly Asp Gly Asn Cys Leu
1               5

<210> SEQ ID NO 792
<211> LENGTH: 6
<212> TYPE: PRT
<213> ORGANISM: Homo sapiens

<400> SEQUENCE: 792

Gly Arg Arg Pro Cys Leu
1               5

<210> SEQ ID NO 793
<211> LENGTH: 6
<212> TYPE: PRT
<213> ORGANISM: Homo sapiens

<400> SEQUENCE: 793

Gly Gly Gly Cys Cys Leu
1               5

<210> SEQ ID NO 794
<211> LENGTH: 6
<212> TYPE: PRT
<213> ORGANISM: Homo sapiens

<400> SEQUENCE: 794

Gly Gly Gly Cys Cys Leu
1               5

<210> SEQ ID NO 795
<211> LENGTH: 6
<212> TYPE: PRT
<213> ORGANISM: Homo sapiens

<400> SEQUENCE: 795

Gly Gly Gly Cys Cys Leu
1               5

<210> SEQ ID NO 796
<211> LENGTH: 6
<212> TYPE: PRT
<213> ORGANISM: Homo sapiens

<400> SEQUENCE: 796

Gly Gly Gly Cys Cys Leu
1               5

<210> SEQ ID NO 797
<211> LENGTH: 6
<212> TYPE: PRT
<213> ORGANISM: Homo sapiens

<400> SEQUENCE: 797

Gly Gly Gly Cys Cys Leu
1               5

<210> SEQ ID NO 798
<211> LENGTH: 6
<212> TYPE: PRT
<213> ORGANISM: Homo sapiens

<400> SEQUENCE: 798

Gly Gly Gly Cys Cys Leu
1 5

<210> SEQ ID NO 799
<211> LENGTH: 6
<212> TYPE: PRT
<213> ORGANISM: Homo sapiens

<400> SEQUENCE: 799

Gly Gly Gly Cys Cys Leu
1 5

<210> SEQ ID NO 800
<211> LENGTH: 6
<212> TYPE: PRT
<213> ORGANISM: Homo sapiens

<400> SEQUENCE: 800

Gly Gly Gly Cys Cys Leu
1 5

<210> SEQ ID NO 801
<211> LENGTH: 6
<212> TYPE: PRT
<213> ORGANISM: Homo sapiens

<400> SEQUENCE: 801

Gly Gly Gly Cys Cys Leu
1 5

<210> SEQ ID NO 802
<211> LENGTH: 6
<212> TYPE: PRT
<213> ORGANISM: Homo sapiens

<400> SEQUENCE: 802

Gly Gly Gly Cys Cys Leu
1 5

<210> SEQ ID NO 803
<211> LENGTH: 6
<212> TYPE: PRT
<213> ORGANISM: Homo sapiens

<400> SEQUENCE: 803

Gly Gly Asn Gly Cys Leu
1 5

<210> SEQ ID NO 804
<211> LENGTH: 6
<212> TYPE: PRT
<213> ORGANISM: Homo sapiens

<400> SEQUENCE: 804

Gly Asn Glu Cys Cys Leu
1 5

<210> SEQ ID NO 805
<211> LENGTH: 6
<212> TYPE: PRT
<213> ORGANISM: Homo sapiens

<400> SEQUENCE: 805

Gly Ser Leu Gly Cys Leu
1 5

<210> SEQ ID NO 806
<211> LENGTH: 6
<212> TYPE: PRT
<213> ORGANISM: Homo sapiens

<400> SEQUENCE: 806

Gly Asp Arg Tyr Cys Leu
1 5

<210> SEQ ID NO 807
<211> LENGTH: 6
<212> TYPE: PRT
<213> ORGANISM: Homo sapiens

<400> SEQUENCE: 807

Gly Val Gln Trp Cys Leu
1 5

<210> SEQ ID NO 808
<211> LENGTH: 6
<212> TYPE: PRT
<213> ORGANISM: Homo sapiens

<400> SEQUENCE: 808

Gly Val Tyr Arg Cys Leu
1 5

<210> SEQ ID NO 809
<211> LENGTH: 6
<212> TYPE: PRT
<213> ORGANISM: Homo sapiens

<400> SEQUENCE: 809

Gly Val Tyr Thr Cys Leu
1 5

<210> SEQ ID NO 810
<211> LENGTH: 6
<212> TYPE: PRT
<213> ORGANISM: Homo sapiens

<400> SEQUENCE: 810

Gly Ala Leu Thr Cys Leu
1 5

<210> SEQ ID NO 811
<211> LENGTH: 6
<212> TYPE: PRT
<213> ORGANISM: Homo sapiens

<400> SEQUENCE: 811

Gly Pro Ser Pro Cys Leu
1 5

<210> SEQ ID NO 812
<211> LENGTH: 6
<212> TYPE: PRT
<213> ORGANISM: Homo sapiens

<400> SEQUENCE: 812

Gly Ala Ser Ala Cys Leu
1 5

<210> SEQ ID NO 813
<211> LENGTH: 6
<212> TYPE: PRT
<213> ORGANISM: Homo sapiens

<400> SEQUENCE: 813

Gly Pro Lys Gln Cys Leu
1 5

<210> SEQ ID NO 814
<211> LENGTH: 6
<212> TYPE: PRT
<213> ORGANISM: Homo sapiens

<400> SEQUENCE: 814

Gly Thr Gly Gly Cys Leu
1 5

<210> SEQ ID NO 815
<211> LENGTH: 6
<212> TYPE: PRT
<213> ORGANISM: Homo sapiens

<400> SEQUENCE: 815

Gly Gly Ser Leu Cys Leu
1 5

<210> SEQ ID NO 816
<211> LENGTH: 6
<212> TYPE: PRT
<213> ORGANISM: Homo sapiens

<400> SEQUENCE: 816

Gly Thr Tyr Ser Cys Leu
1 5

<210> SEQ ID NO 817
<211> LENGTH: 6
<212> TYPE: PRT
<213> ORGANISM: Homo sapiens

<400> SEQUENCE: 817

Gly Thr Tyr Ser Cys Leu
1 5

<210> SEQ ID NO 818
<211> LENGTH: 6
<212> TYPE: PRT
<213> ORGANISM: Homo sapiens

<400> SEQUENCE: 818

Gly Leu Ser Val Cys Leu
1 5

<210> SEQ ID NO 819
<211> LENGTH: 6
<212> TYPE: PRT
<213> ORGANISM: Homo sapiens

<400> SEQUENCE: 819

Gly Ala Glu His Cys Leu
1 5

<210> SEQ ID NO 820
<211> LENGTH: 6
<212> TYPE: PRT
<213> ORGANISM: Homo sapiens

<400> SEQUENCE: 820

Gly Lys Gly Arg Cys Leu
1 5

<210> SEQ ID NO 821
<211> LENGTH: 6
<212> TYPE: PRT
<213> ORGANISM: Homo sapiens

<400> SEQUENCE: 821

Gly Phe Tyr Lys Cys Leu
1 5

<210> SEQ ID NO 822
<211> LENGTH: 6
<212> TYPE: PRT
<213> ORGANISM: Homo sapiens

<400> SEQUENCE: 822

Gly Asn Leu Phe Cys Leu
1 5

<210> SEQ ID NO 823
<211> LENGTH: 6
<212> TYPE: PRT
<213> ORGANISM: Homo sapiens

<400> SEQUENCE: 823

Gly Asp Gly Asn Cys Leu
1 5

<210> SEQ ID NO 824
<211> LENGTH: 6
<212> TYPE: PRT
<213> ORGANISM: Homo sapiens

<400> SEQUENCE: 824

Gly Leu Val Leu Cys Leu
1 5

<210> SEQ ID NO 825
<211> LENGTH: 6
<212> TYPE: PRT
<213> ORGANISM: Homo sapiens

<400> SEQUENCE: 825

Gly Thr Gly Arg Cys Leu
1 5

<210> SEQ ID NO 826
<211> LENGTH: 6
<212> TYPE: PRT
<213> ORGANISM: Homo sapiens

<400> SEQUENCE: 826

Gly Leu Val Leu Cys Leu
1               5

<210> SEQ ID NO 827
<211> LENGTH: 6
<212> TYPE: PRT
<213> ORGANISM: Homo sapiens

<400> SEQUENCE: 827

Gly Leu Tyr Arg Cys Leu
1               5

<210> SEQ ID NO 828
<211> LENGTH: 6
<212> TYPE: PRT
<213> ORGANISM: Homo sapiens

<400> SEQUENCE: 828

Gly Arg Ser Ser Cys Leu
1               5

<210> SEQ ID NO 829
<211> LENGTH: 6
<212> TYPE: PRT
<213> ORGANISM: Homo sapiens

<400> SEQUENCE: 829

Gly Asn Ala Arg Cys Leu
1               5

<210> SEQ ID NO 830
<211> LENGTH: 6
<212> TYPE: PRT
<213> ORGANISM: Homo sapiens

<400> SEQUENCE: 830

Gly Ile Gly Gln Cys Leu
1               5

<210> SEQ ID NO 831
<211> LENGTH: 6
<212> TYPE: PRT
<213> ORGANISM: Homo sapiens

<400> SEQUENCE: 831

Gly Asn Ile Gln Cys Leu
1               5

<210> SEQ ID NO 832
<211> LENGTH: 6
<212> TYPE: PRT
<213> ORGANISM: Homo sapiens

<400> SEQUENCE: 832

Gly Tyr Ala Leu Cys Leu
1               5

<210> SEQ ID NO 833
<211> LENGTH: 6
<212> TYPE: PRT
<213> ORGANISM: Homo sapiens

<400> SEQUENCE: 833

Gly Gln Asp Phe Cys Leu
1 5

<210> SEQ ID NO 834
<211> LENGTH: 6
<212> TYPE: PRT
<213> ORGANISM: Homo sapiens

<400> SEQUENCE: 834

Gly Val Gly Gln Cys Leu
1 5

<210> SEQ ID NO 835
<211> LENGTH: 6
<212> TYPE: PRT
<213> ORGANISM: Homo sapiens

<400> SEQUENCE: 835

Gly Gly Asp Ala Cys Leu
1 5

<210> SEQ ID NO 836
<211> LENGTH: 6
<212> TYPE: PRT
<213> ORGANISM: Homo sapiens

<400> SEQUENCE: 836

Gly Pro Val Trp Cys Leu
1 5

<210> SEQ ID NO 837
<211> LENGTH: 6
<212> TYPE: PRT
<213> ORGANISM: Homo sapiens

<400> SEQUENCE: 837

Gly Leu Glu Asp Cys Leu
1 5

<210> SEQ ID NO 838
<211> LENGTH: 6
<212> TYPE: PRT
<213> ORGANISM: Homo sapiens

<400> SEQUENCE: 838

Gly Thr Glu Ile Cys Leu
1 5

<210> SEQ ID NO 839
<211> LENGTH: 6
<212> TYPE: PRT
<213> ORGANISM: Homo sapiens

<400> SEQUENCE: 839

Gly Ser Ser Gly Cys Leu
1 5

<210> SEQ ID NO 840
<211> LENGTH: 6
<212> TYPE: PRT
<213> ORGANISM: Homo sapiens

<400> SEQUENCE: 840

Gly Gly Cys Cys Cys Leu
1 5

<210> SEQ ID NO 841
<211> LENGTH: 6
<212> TYPE: PRT
<213> ORGANISM: Homo sapiens

<400> SEQUENCE: 841

Gly Ala Ala Leu Cys Leu
1 5

<210> SEQ ID NO 842
<211> LENGTH: 6
<212> TYPE: PRT
<213> ORGANISM: Homo sapiens

<400> SEQUENCE: 842

Gly Asn Cys Val Cys Leu
1 5

<210> SEQ ID NO 843
<211> LENGTH: 6
<212> TYPE: PRT
<213> ORGANISM: Homo sapiens

<400> SEQUENCE: 843

Gly Asp Gly Cys Cys Leu
1 5

<210> SEQ ID NO 844
<211> LENGTH: 6
<212> TYPE: PRT
<213> ORGANISM: Homo sapiens

<400> SEQUENCE: 844

Gly Ile Leu Ser Cys Leu
1 5

<210> SEQ ID NO 845
<211> LENGTH: 6
<212> TYPE: PRT
<213> ORGANISM: Homo sapiens

<400> SEQUENCE: 845

Gly Met Trp Ser Cys Leu
1 5

<210> SEQ ID NO 846
<211> LENGTH: 6
<212> TYPE: PRT
<213> ORGANISM: Homo sapiens

<400> SEQUENCE: 846

Gly Leu Tyr Arg Cys Leu
1 5

<210> SEQ ID NO 847
<211> LENGTH: 6
<212> TYPE: PRT
<213> ORGANISM: Homo sapiens

<400> SEQUENCE: 847

Gly Ala Arg Ser Cys Leu
1 5

<210> SEQ ID NO 848
<211> LENGTH: 6
<212> TYPE: PRT
<213> ORGANISM: Homo sapiens

<400> SEQUENCE: 848

Gly Asn Gly Leu Cys Leu
1 5

<210> SEQ ID NO 849
<211> LENGTH: 6
<212> TYPE: PRT
<213> ORGANISM: Homo sapiens

<400> SEQUENCE: 849

Gly His Val Val Cys Leu
1 5

<210> SEQ ID NO 850
<211> LENGTH: 6
<212> TYPE: PRT
<213> ORGANISM: Homo sapiens

<400> SEQUENCE: 850

Gly Arg Arg His Cys Leu
1 5

<210> SEQ ID NO 851
<211> LENGTH: 6
<212> TYPE: PRT
<213> ORGANISM: Homo sapiens

<400> SEQUENCE: 851

Gly Asp Cys Glu Cys Leu
1 5

<210> SEQ ID NO 852
<211> LENGTH: 6
<212> TYPE: PRT
<213> ORGANISM: Homo sapiens

<400> SEQUENCE: 852

Gly Leu Met Tyr Cys Leu
1 5

<210> SEQ ID NO 853
<211> LENGTH: 6
<212> TYPE: PRT
<213> ORGANISM: Homo sapiens

<400> SEQUENCE: 853

Gly Ala Arg Gln Cys Leu
1 5

<210> SEQ ID NO 854
<211> LENGTH: 6
<212> TYPE: PRT
<213> ORGANISM: Homo sapiens

<400> SEQUENCE: 854

Gly Gly Ser Pro Cys Leu
1 5

<210> SEQ ID NO 855
<211> LENGTH: 6
<212> TYPE: PRT
<213> ORGANISM: Homo sapiens

<400> SEQUENCE: 855

Gly Leu Ser Thr Cys Leu
1 5

<210> SEQ ID NO 856
<211> LENGTH: 6
<212> TYPE: PRT
<213> ORGANISM: Homo sapiens

<400> SEQUENCE: 856

Gly Ile Leu Lys Cys Leu
1 5

<210> SEQ ID NO 857
<211> LENGTH: 6
<212> TYPE: PRT
<213> ORGANISM: Homo sapiens

<400> SEQUENCE: 857

Gly Ala Glu Val Cys Leu
1 5

<210> SEQ ID NO 858
<211> LENGTH: 6
<212> TYPE: PRT
<213> ORGANISM: Homo sapiens

<400> SEQUENCE: 858

Gly Gly His Ser Cys Leu
1 5

<210> SEQ ID NO 859
<211> LENGTH: 6
<212> TYPE: PRT
<213> ORGANISM: Homo sapiens

<400> SEQUENCE: 859

Gly Ser Arg Asn Cys Leu
1 5

<210> SEQ ID NO 860
<211> LENGTH: 6
<212> TYPE: PRT
<213> ORGANISM: Homo sapiens

<400> SEQUENCE: 860

Gly Gln Ala Leu Cys Leu
1 5

<210> SEQ ID NO 861
<211> LENGTH: 6
<212> TYPE: PRT
<213> ORGANISM: Homo sapiens

<400> SEQUENCE: 861

Gly Ser Phe Ser Cys Leu
1 5

<210> SEQ ID NO 862
<211> LENGTH: 6
<212> TYPE: PRT
<213> ORGANISM: Homo sapiens

<400> SEQUENCE: 862

Gly Gly His Arg Cys Leu
1 5

<210> SEQ ID NO 863
<211> LENGTH: 6
<212> TYPE: PRT
<213> ORGANISM: Homo sapiens

<400> SEQUENCE: 863

Gly Ser Tyr Met Cys Leu
1 5

<210> SEQ ID NO 864
<211> LENGTH: 6
<212> TYPE: PRT
<213> ORGANISM: Homo sapiens

<400> SEQUENCE: 864

Gly Ser Tyr Asn Cys Leu
1 5

<210> SEQ ID NO 865
<211> LENGTH: 6
<212> TYPE: PRT
<213> ORGANISM: Homo sapiens

<400> SEQUENCE: 865

Gly Ser Phe His Cys Leu
1 5

<210> SEQ ID NO 866
<211> LENGTH: 6
<212> TYPE: PRT
<213> ORGANISM: Homo sapiens

<400> SEQUENCE: 866

Gly Ser Phe Gln Cys Leu
1 5

<210> SEQ ID NO 867
<211> LENGTH: 6
<212> TYPE: PRT
<213> ORGANISM: Homo sapiens

<400> SEQUENCE: 867

Gly Glu Trp Leu Cys Leu
1 5

<210> SEQ ID NO 868
<211> LENGTH: 6
<212> TYPE: PRT
<213> ORGANISM: Homo sapiens

<400> SEQUENCE: 868

Gly Arg Arg Gln Cys Leu
1               5

<210> SEQ ID NO 869
<211> LENGTH: 6
<212> TYPE: PRT
<213> ORGANISM: Homo sapiens

<400> SEQUENCE: 869

Gly Lys Glu Tyr Cys Leu
1               5

<210> SEQ ID NO 870
<211> LENGTH: 6
<212> TYPE: PRT
<213> ORGANISM: Homo sapiens

<400> SEQUENCE: 870

Gly Ile Thr Asp Cys Leu
1               5

<210> SEQ ID NO 871
<211> LENGTH: 6
<212> TYPE: PRT
<213> ORGANISM: Homo sapiens

<400> SEQUENCE: 871

Gly Phe Gly Val Cys Leu
1               5

<210> SEQ ID NO 872
<211> LENGTH: 6
<212> TYPE: PRT
<213> ORGANISM: Homo sapiens

<400> SEQUENCE: 872

Gly Arg Leu Leu Cys Leu
1               5

<210> SEQ ID NO 873
<211> LENGTH: 6
<212> TYPE: PRT
<213> ORGANISM: Homo sapiens

<400> SEQUENCE: 873

Gly Thr Val Pro Cys Leu
1               5

<210> SEQ ID NO 874
<211> LENGTH: 6
<212> TYPE: PRT
<213> ORGANISM: Homo sapiens

<400> SEQUENCE: 874

Gly Lys Leu Gly Cys Leu
1               5

<210> SEQ ID NO 875
<211> LENGTH: 6
<212> TYPE: PRT
<213> ORGANISM: Homo sapiens

<400> SEQUENCE: 875

Gly Ala Cys Ser Cys Leu
1               5

<210> SEQ ID NO 876
<211> LENGTH: 6
<212> TYPE: PRT
<213> ORGANISM: Homo sapiens

<400> SEQUENCE: 876

Gly Ala Pro Leu Cys Leu
1               5

<210> SEQ ID NO 877
<211> LENGTH: 6
<212> TYPE: PRT
<213> ORGANISM: Homo sapiens

<400> SEQUENCE: 877

Gly Gly Ser Asn Cys Leu
1               5

<210> SEQ ID NO 878
<211> LENGTH: 6
<212> TYPE: PRT
<213> ORGANISM: Homo sapiens

<400> SEQUENCE: 878

Gly Glu Lys Lys Cys Leu
1               5

<210> SEQ ID NO 879
<211> LENGTH: 6
<212> TYPE: PRT
<213> ORGANISM: Homo sapiens

<400> SEQUENCE: 879

Gly Arg Gln Thr Cys Leu
1               5

<210> SEQ ID NO 880
<211> LENGTH: 6
<212> TYPE: PRT
<213> ORGANISM: Homo sapiens

<400> SEQUENCE: 880

Gly Gly Val Glu Cys Leu
1               5

<210> SEQ ID NO 881
<211> LENGTH: 6
<212> TYPE: PRT
<213> ORGANISM: Homo sapiens

<400> SEQUENCE: 881

Gly Ser Ala Asp Cys Leu
1               5

<210> SEQ ID NO 882
<211> LENGTH: 6
<212> TYPE: PRT
<213> ORGANISM: Homo sapiens

<400> SEQUENCE: 882

Gly Ile Cys Leu Cys Leu
1 5

<210> SEQ ID NO 883
<211> LENGTH: 6
<212> TYPE: PRT
<213> ORGANISM: Homo sapiens

<400> SEQUENCE: 883

Gly Pro Val Met Cys Leu
1 5

<210> SEQ ID NO 884
<211> LENGTH: 6
<212> TYPE: PRT
<213> ORGANISM: Homo sapiens

<400> SEQUENCE: 884

Gly Cys Leu Ala Cys Leu
1 5

<210> SEQ ID NO 885
<211> LENGTH: 6
<212> TYPE: PRT
<213> ORGANISM: Homo sapiens

<400> SEQUENCE: 885

Gly Ala Glu Arg Cys Leu
1 5

<210> SEQ ID NO 886
<211> LENGTH: 6
<212> TYPE: PRT
<213> ORGANISM: Homo sapiens

<400> SEQUENCE: 886

Gly Ser Leu Glu Cys Leu
1 5

<210> SEQ ID NO 887
<211> LENGTH: 6
<212> TYPE: PRT
<213> ORGANISM: Homo sapiens

<400> SEQUENCE: 887

Gly Pro Gly Pro Cys Leu
1 5

<210> SEQ ID NO 888
<211> LENGTH: 6
<212> TYPE: PRT
<213> ORGANISM: Homo sapiens

<400> SEQUENCE: 888

Gly Cys Gly Trp Cys Leu
1 5

<210> SEQ ID NO 889
<211> LENGTH: 6
<212> TYPE: PRT
<213> ORGANISM: Homo sapiens

<400> SEQUENCE: 889

Gly Ser Glu Leu Cys Leu
1               5

<210> SEQ ID NO 890
<211> LENGTH: 6
<212> TYPE: PRT
<213> ORGANISM: Homo sapiens

<400> SEQUENCE: 890

Gly Ser Asn Gly Cys Leu
1               5

<210> SEQ ID NO 891
<211> LENGTH: 6
<212> TYPE: PRT
<213> ORGANISM: Homo sapiens

<400> SEQUENCE: 891

Gly Arg Ala Ala Cys Leu
1               5

<210> SEQ ID NO 892
<211> LENGTH: 6
<212> TYPE: PRT
<213> ORGANISM: Homo sapiens

<400> SEQUENCE: 892

Gly His Ala Ser Cys Leu
1               5

<210> SEQ ID NO 893
<211> LENGTH: 6
<212> TYPE: PRT
<213> ORGANISM: Homo sapiens

<400> SEQUENCE: 893

Gly Val Leu Asp Cys Leu
1               5

<210> SEQ ID NO 894
<211> LENGTH: 6
<212> TYPE: PRT
<213> ORGANISM: Homo sapiens

<400> SEQUENCE: 894

Gly Ala Pro Pro Cys Leu
1               5

<210> SEQ ID NO 895
<211> LENGTH: 6
<212> TYPE: PRT
<213> ORGANISM: Homo sapiens

<400> SEQUENCE: 895

Gly Gly Glu Leu Cys Leu
1               5

<210> SEQ ID NO 896
<211> LENGTH: 6
<212> TYPE: PRT
<213> ORGANISM: Homo sapiens

<400> SEQUENCE: 896

Gly Lys Glu His Cys Leu
1               5

<210> SEQ ID NO 897
<211> LENGTH: 6
<212> TYPE: PRT
<213> ORGANISM: Homo sapiens

<400> SEQUENCE: 897

Gly Val Val Leu Cys Leu
1               5

<210> SEQ ID NO 898
<211> LENGTH: 6
<212> TYPE: PRT
<213> ORGANISM: Homo sapiens

<400> SEQUENCE: 898

Gly Trp Leu Cys Cys Leu
1               5

<210> SEQ ID NO 899
<211> LENGTH: 6
<212> TYPE: PRT
<213> ORGANISM: Homo sapiens

<400> SEQUENCE: 899

Gly Gly Arg Gly Cys Leu
1               5

<210> SEQ ID NO 900
<211> LENGTH: 6
<212> TYPE: PRT
<213> ORGANISM: Homo sapiens

<400> SEQUENCE: 900

Gly Pro Pro Phe Cys Leu
1               5

<210> SEQ ID NO 901
<211> LENGTH: 6
<212> TYPE: PRT
<213> ORGANISM: Homo sapiens

<400> SEQUENCE: 901

Gly Ser Phe Lys Cys Leu
1               5

<210> SEQ ID NO 902
<211> LENGTH: 6
<212> TYPE: PRT
<213> ORGANISM: Homo sapiens

<400> SEQUENCE: 902

Gly Cys Met Leu Cys Leu
1               5

<210> SEQ ID NO 903
<211> LENGTH: 6
<212> TYPE: PRT
<213> ORGANISM: Homo sapiens

<400> SEQUENCE: 903

Gly Val Asp Thr Cys Leu
1 5

<210> SEQ ID NO 904
<211> LENGTH: 6
<212> TYPE: PRT
<213> ORGANISM: Homo sapiens

<400> SEQUENCE: 904

Gly Asn Pro Asn Cys Leu
1 5

<210> SEQ ID NO 905
<211> LENGTH: 6
<212> TYPE: PRT
<213> ORGANISM: Homo sapiens

<400> SEQUENCE: 905

Gly Leu Pro Val Cys Leu
1 5

<210> SEQ ID NO 906
<211> LENGTH: 6
<212> TYPE: PRT
<213> ORGANISM: Homo sapiens

<400> SEQUENCE: 906

Gly Ala Ile Leu Cys Leu
1 5

<210> SEQ ID NO 907
<211> LENGTH: 6
<212> TYPE: PRT
<213> ORGANISM: Homo sapiens

<400> SEQUENCE: 907

Gly Leu Asn Gln Cys Leu
1 5

<210> SEQ ID NO 908
<211> LENGTH: 6
<212> TYPE: PRT
<213> ORGANISM: Homo sapiens

<400> SEQUENCE: 908

Gly Thr Phe Lys Cys Leu
1 5

<210> SEQ ID NO 909
<211> LENGTH: 6
<212> TYPE: PRT
<213> ORGANISM: Homo sapiens

<400> SEQUENCE: 909

Gly Ala Ser Asp Cys Leu
1 5

<210> SEQ ID NO 910
<211> LENGTH: 6
<212> TYPE: PRT
<213> ORGANISM: Homo sapiens

<400> SEQUENCE: 910

Gly Tyr Arg Ser Cys Leu
1 5

<210> SEQ ID NO 911
<211> LENGTH: 6
<212> TYPE: PRT
<213> ORGANISM: Homo sapiens

<400> SEQUENCE: 911

Gly Leu Phe Val Cys Leu
1 5

<210> SEQ ID NO 912
<211> LENGTH: 6
<212> TYPE: PRT
<213> ORGANISM: Homo sapiens

<400> SEQUENCE: 912

Gly Gly Val Cys Cys Leu
1 5

<210> SEQ ID NO 913
<211> LENGTH: 6
<212> TYPE: PRT
<213> ORGANISM: Homo sapiens

<400> SEQUENCE: 913

Gly Pro Gly Leu Cys Leu
1 5

<210> SEQ ID NO 914
<211> LENGTH: 6
<212> TYPE: PRT
<213> ORGANISM: Homo sapiens

<400> SEQUENCE: 914

Gly Thr Asp Val Cys Leu
1 5

<210> SEQ ID NO 915
<211> LENGTH: 6
<212> TYPE: PRT
<213> ORGANISM: Homo sapiens

<400> SEQUENCE: 915

Gly Leu Pro Val Cys Leu
1 5

<210> SEQ ID NO 916
<211> LENGTH: 6
<212> TYPE: PRT
<213> ORGANISM: Homo sapiens

<400> SEQUENCE: 916

Gly Trp Leu Leu Cys Leu
1 5

<210> SEQ ID NO 917
<211> LENGTH: 6
<212> TYPE: PRT
<213> ORGANISM: Homo sapiens

<400> SEQUENCE: 917

Gly Leu Ala Ser Cys Leu
1 5

<210> SEQ ID NO 918
<211> LENGTH: 6
<212> TYPE: PRT
<213> ORGANISM: Homo sapiens

<400> SEQUENCE: 918

Gly Gln Pro Asp Cys Leu
1 5

<210> SEQ ID NO 919
<211> LENGTH: 6
<212> TYPE: PRT
<213> ORGANISM: Homo sapiens

<400> SEQUENCE: 919

Gly Cys Gly Ser Cys Leu
1 5

<210> SEQ ID NO 920
<211> LENGTH: 6
<212> TYPE: PRT
<213> ORGANISM: Homo sapiens

<400> SEQUENCE: 920

Gly Cys Gln Lys Cys Leu
1 5

<210> SEQ ID NO 921
<211> LENGTH: 6
<212> TYPE: PRT
<213> ORGANISM: Homo sapiens

<400> SEQUENCE: 921

Gly Tyr Lys Lys Cys Leu
1 5

<210> SEQ ID NO 922
<211> LENGTH: 6
<212> TYPE: PRT
<213> ORGANISM: Homo sapiens

<400> SEQUENCE: 922

Gly Gln Arg Ala Cys Leu
1 5

<210> SEQ ID NO 923
<211> LENGTH: 6
<212> TYPE: PRT
<213> ORGANISM: Homo sapiens

<400> SEQUENCE: 923

Gly Ser Val Ala Cys Leu
1 5

<210> SEQ ID NO 924
<211> LENGTH: 6
<212> TYPE: PRT
<213> ORGANISM: Homo sapiens

<400> SEQUENCE: 924

Gly Ser Lys Arg Cys Leu
1 5

<210> SEQ ID NO 925
<211> LENGTH: 6
<212> TYPE: PRT
<213> ORGANISM: Homo sapiens

<400> SEQUENCE: 925

Gly Met Tyr Gln Cys Leu
1 5

<210> SEQ ID NO 926
<211> LENGTH: 6
<212> TYPE: PRT
<213> ORGANISM: Homo sapiens

<400> SEQUENCE: 926

Gly Ser Phe Gln Cys Leu
1 5

<210> SEQ ID NO 927
<211> LENGTH: 6
<212> TYPE: PRT
<213> ORGANISM: Homo sapiens

<400> SEQUENCE: 927

Gly Ser Phe Gln Cys Leu
1 5

<210> SEQ ID NO 928
<211> LENGTH: 6
<212> TYPE: PRT
<213> ORGANISM: Homo sapiens

<400> SEQUENCE: 928

Gly Gln Thr Pro Cys Leu
1 5

<210> SEQ ID NO 929
<211> LENGTH: 6
<212> TYPE: PRT
<213> ORGANISM: Homo sapiens

<400> SEQUENCE: 929

Gly Ser Leu Pro Cys Leu
1 5

<210> SEQ ID NO 930
<211> LENGTH: 6
<212> TYPE: PRT
<213> ORGANISM: Homo sapiens

<400> SEQUENCE: 930

Gly Thr Leu Tyr Cys Leu
1 5

<210> SEQ ID NO 931
<211> LENGTH: 6
<212> TYPE: PRT
<213> ORGANISM: Homo sapiens

<400> SEQUENCE: 931

Gly Val Phe Tyr Cys Leu
1               5

<210> SEQ ID NO 932
<211> LENGTH: 6
<212> TYPE: PRT
<213> ORGANISM: Homo sapiens

<400> SEQUENCE: 932

Gly Val Tyr Gln Cys Leu
1               5

<210> SEQ ID NO 933
<211> LENGTH: 6
<212> TYPE: PRT
<213> ORGANISM: Homo sapiens

<400> SEQUENCE: 933

Gly Asn Leu Val Cys Leu
1               5

<210> SEQ ID NO 934
<211> LENGTH: 6
<212> TYPE: PRT
<213> ORGANISM: Homo sapiens

<400> SEQUENCE: 934

Gly Gly Ser Leu Cys Leu
1               5

<210> SEQ ID NO 935
<211> LENGTH: 6
<212> TYPE: PRT
<213> ORGANISM: Homo sapiens

<400> SEQUENCE: 935

Gly Gly Ser Phe Cys Leu
1               5

<210> SEQ ID NO 936
<211> LENGTH: 6
<212> TYPE: PRT
<213> ORGANISM: Homo sapiens

<400> SEQUENCE: 936

Gly Glu Thr Pro Cys Leu
1               5

<210> SEQ ID NO 937
<211> LENGTH: 6
<212> TYPE: PRT
<213> ORGANISM: Homo sapiens

<400> SEQUENCE: 937

Gly Lys Leu Leu Cys Leu
1               5

<210> SEQ ID NO 938
<211> LENGTH: 6
<212> TYPE: PRT
<213> ORGANISM: Homo sapiens

<400> SEQUENCE: 938

Gly Thr Phe Gly Cys Leu
1 5

<210> SEQ ID NO 939
<211> LENGTH: 6
<212> TYPE: PRT
<213> ORGANISM: Homo sapiens

<400> SEQUENCE: 939

Gly Leu Ala Arg Cys Leu
1 5

<210> SEQ ID NO 940
<211> LENGTH: 6
<212> TYPE: PRT
<213> ORGANISM: Homo sapiens

<400> SEQUENCE: 940

Gly Arg Phe Arg Cys Leu
1 5

<210> SEQ ID NO 941
<211> LENGTH: 6
<212> TYPE: PRT
<213> ORGANISM: Homo sapiens

<400> SEQUENCE: 941

Gly Gln Glu Ala Cys Leu
1 5

<210> SEQ ID NO 942
<211> LENGTH: 6
<212> TYPE: PRT
<213> ORGANISM: Homo sapiens

<400> SEQUENCE: 942

Gly Ala Ile Ser Cys Leu
1 5

<210> SEQ ID NO 943
<211> LENGTH: 6
<212> TYPE: PRT
<213> ORGANISM: Homo sapiens

<400> SEQUENCE: 943

Gly Asp Pro Pro Cys Leu
1 5

<210> SEQ ID NO 944
<211> LENGTH: 6
<212> TYPE: PRT
<213> ORGANISM: Homo sapiens

<400> SEQUENCE: 944

Gly Ala Gln Gln Cys Leu
1 5

<210> SEQ ID NO 945
<211> LENGTH: 6
<212> TYPE: PRT
<213> ORGANISM: Homo sapiens

<400> SEQUENCE: 945

Gly Leu Thr Glu Cys Leu
1 5

<210> SEQ ID NO 946
<211> LENGTH: 6
<212> TYPE: PRT
<213> ORGANISM: Homo sapiens

<400> SEQUENCE: 946

Gly Leu Trp Asp Cys Leu
1 5

<210> SEQ ID NO 947
<211> LENGTH: 6
<212> TYPE: PRT
<213> ORGANISM: Homo sapiens

<400> SEQUENCE: 947

Gly Glu Phe Ser Cys Leu
1 5

<210> SEQ ID NO 948
<211> LENGTH: 6
<212> TYPE: PRT
<213> ORGANISM: Homo sapiens

<400> SEQUENCE: 948

Gly Ala Val Lys Cys Leu
1 5

<210> SEQ ID NO 949
<211> LENGTH: 6
<212> TYPE: PRT
<213> ORGANISM: Homo sapiens

<400> SEQUENCE: 949

Gly Ser Tyr Arg Cys Leu
1 5

<210> SEQ ID NO 950
<211> LENGTH: 6
<212> TYPE: PRT
<213> ORGANISM: Homo sapiens

<400> SEQUENCE: 950

Gly Met Tyr Ile Cys Leu
1 5

<210> SEQ ID NO 951
<211> LENGTH: 6
<212> TYPE: PRT
<213> ORGANISM: Homo sapiens

<400> SEQUENCE: 951

Gly Asp Thr Leu Cys Leu
1 5

<210> SEQ ID NO 952
<211> LENGTH: 6
<212> TYPE: PRT
<213> ORGANISM: Homo sapiens

<400> SEQUENCE: 952

Gly Leu Leu Ser Cys Leu
1 5

<210> SEQ ID NO 953
<211> LENGTH: 6
<212> TYPE: PRT
<213> ORGANISM: Homo sapiens

<400> SEQUENCE: 953

Gly Cys Val Asn Cys Leu
1 5

<210> SEQ ID NO 954
<211> LENGTH: 6
<212> TYPE: PRT
<213> ORGANISM: Homo sapiens

<400> SEQUENCE: 954

Gly Leu Gly Phe Cys Leu
1 5

<210> SEQ ID NO 955
<211> LENGTH: 6
<212> TYPE: PRT
<213> ORGANISM: Homo sapiens

<400> SEQUENCE: 955

Gly Asp Val Lys Cys Leu
1 5

<210> SEQ ID NO 956
<211> LENGTH: 6
<212> TYPE: PRT
<213> ORGANISM: Homo sapiens

<400> SEQUENCE: 956

Gly Gly Leu Val Cys Leu
1 5

<210> SEQ ID NO 957
<211> LENGTH: 6
<212> TYPE: PRT
<213> ORGANISM: Homo sapiens

<400> SEQUENCE: 957

Gly Ile Trp Ile Cys Leu
1 5

<210> SEQ ID NO 958
<211> LENGTH: 6
<212> TYPE: PRT
<213> ORGANISM: Homo sapiens

<400> SEQUENCE: 958

Gly Arg Ser Leu Cys Leu
1 5

<210> SEQ ID NO 959
<211> LENGTH: 6
<212> TYPE: PRT
<213> ORGANISM: Homo sapiens

<400> SEQUENCE: 959

Gly Pro Phe Ser Cys Leu
1 5

<210> SEQ ID NO 960
<211> LENGTH: 6
<212> TYPE: PRT
<213> ORGANISM: Homo sapiens

<400> SEQUENCE: 960

Gly Ile Tyr Ile Cys Leu
1 5

<210> SEQ ID NO 961
<211> LENGTH: 6
<212> TYPE: PRT
<213> ORGANISM: Homo sapiens

<400> SEQUENCE: 961

Gly Arg Ala Arg Cys Leu
1 5

<210> SEQ ID NO 962
<211> LENGTH: 6
<212> TYPE: PRT
<213> ORGANISM: Homo sapiens

<400> SEQUENCE: 962

Gly Ser Cys Thr Cys Leu
1 5

<210> SEQ ID NO 963
<211> LENGTH: 6
<212> TYPE: PRT
<213> ORGANISM: Homo sapiens

<400> SEQUENCE: 963

Gly Arg Asp Glu Cys Leu
1 5

<210> SEQ ID NO 964
<211> LENGTH: 6
<212> TYPE: PRT
<213> ORGANISM: Homo sapiens

<400> SEQUENCE: 964

Gly His Arg Gln Cys Leu
1 5

<210> SEQ ID NO 965
<211> LENGTH: 6
<212> TYPE: PRT
<213> ORGANISM: Homo sapiens

<400> SEQUENCE: 965

Gly His Thr Leu Cys Leu
1 5

<210> SEQ ID NO 966
<211> LENGTH: 6
<212> TYPE: PRT
<213> ORGANISM: Homo sapiens

<400> SEQUENCE: 966

Gly Lys Ile Gly Cys Leu
1 5

<210> SEQ ID NO 967
<211> LENGTH: 6
<212> TYPE: PRT
<213> ORGANISM: Homo sapiens

<400> SEQUENCE: 967

Gly Ser Leu Asp Cys Leu
1 5

<210> SEQ ID NO 968
<211> LENGTH: 6
<212> TYPE: PRT
<213> ORGANISM: Homo sapiens

<400> SEQUENCE: 968

Gly Arg Leu Gly Cys Leu
1 5

<210> SEQ ID NO 969
<211> LENGTH: 6
<212> TYPE: PRT
<213> ORGANISM: Homo sapiens

<400> SEQUENCE: 969

Gly His Ile Glu Cys Leu
1 5

<210> SEQ ID NO 970
<211> LENGTH: 6
<212> TYPE: PRT
<213> ORGANISM: Homo sapiens

<400> SEQUENCE: 970

Gly Ala Asp Ile Cys Leu
1 5

<210> SEQ ID NO 971
<211> LENGTH: 6
<212> TYPE: PRT
<213> ORGANISM: Homo sapiens

<400> SEQUENCE: 971

Gly Asn Val Glu Cys Leu
1 5

<210> SEQ ID NO 972
<211> LENGTH: 6
<212> TYPE: PRT
<213> ORGANISM: Homo sapiens

<400> SEQUENCE: 972

Gly Cys Glu Asp Cys Leu
1 5

<210> SEQ ID NO 973
<211> LENGTH: 6
<212> TYPE: PRT
<213> ORGANISM: Homo sapiens

<400> SEQUENCE: 973

Gly His Glu Asp Cys Leu
1 5

<210> SEQ ID NO 974
<211> LENGTH: 6
<212> TYPE: PRT
<213> ORGANISM: Homo sapiens

<400> SEQUENCE: 974

Gly Tyr Glu Asp Cys Leu
1 5

<210> SEQ ID NO 975
<211> LENGTH: 6
<212> TYPE: PRT
<213> ORGANISM: Homo sapiens

<400> SEQUENCE: 975

Gly Met Leu Phe Cys Leu
1 5

<210> SEQ ID NO 976
<211> LENGTH: 6
<212> TYPE: PRT
<213> ORGANISM: Homo sapiens

<400> SEQUENCE: 976

Gly Thr Ile Leu Cys Leu
1 5

<210> SEQ ID NO 977
<211> LENGTH: 6
<212> TYPE: PRT
<213> ORGANISM: Homo sapiens

<400> SEQUENCE: 977

Gly Thr Asn Gln Cys Leu
1 5

<210> SEQ ID NO 978
<211> LENGTH: 6
<212> TYPE: PRT
<213> ORGANISM: Homo sapiens

<400> SEQUENCE: 978

Gly Ser Gly Thr Cys Leu
1 5

<210> SEQ ID NO 979
<211> LENGTH: 6
<212> TYPE: PRT
<213> ORGANISM: Homo sapiens

<400> SEQUENCE: 979

Gly Cys Ala Gly Cys Leu
1 5

<210> SEQ ID NO 980
<211> LENGTH: 6
<212> TYPE: PRT
<213> ORGANISM: Homo sapiens

<400> SEQUENCE: 980

Gly Leu Lys Cys Cys Leu
1               5

<210> SEQ ID NO 981
<211> LENGTH: 6
<212> TYPE: PRT
<213> ORGANISM: Homo sapiens

<400> SEQUENCE: 981

Gly Glu Asp His Cys Leu
1               5

<210> SEQ ID NO 982
<211> LENGTH: 6
<212> TYPE: PRT
<213> ORGANISM: Homo sapiens

<400> SEQUENCE: 982

Gly Gly Leu Ile Cys Leu
1               5

<210> SEQ ID NO 983
<211> LENGTH: 6
<212> TYPE: PRT
<213> ORGANISM: Homo sapiens

<400> SEQUENCE: 983

Gly Ser Ala Ala Cys Leu
1               5

<210> SEQ ID NO 984
<211> LENGTH: 6
<212> TYPE: PRT
<213> ORGANISM: Homo sapiens

<400> SEQUENCE: 984

Gly Pro Glu Asn Cys Leu
1               5

<210> SEQ ID NO 985
<211> LENGTH: 6
<212> TYPE: PRT
<213> ORGANISM: Homo sapiens

<400> SEQUENCE: 985

Gly Val Thr Ala Cys Leu
1               5

<210> SEQ ID NO 986
<211> LENGTH: 6
<212> TYPE: PRT
<213> ORGANISM: Homo sapiens

<400> SEQUENCE: 986

Gly Thr Ser Glu Cys Leu
1               5

<210> SEQ ID NO 987
<211> LENGTH: 6
<212> TYPE: PRT
<213> ORGANISM: Homo sapiens

<400> SEQUENCE: 987

Gly Leu Glu Asn Cys Leu
1 5

<210> SEQ ID NO 988
<211> LENGTH: 6
<212> TYPE: PRT
<213> ORGANISM: Homo sapiens

<400> SEQUENCE: 988

Gly Thr Thr Glu Cys Leu
1 5

<210> SEQ ID NO 989
<211> LENGTH: 6
<212> TYPE: PRT
<213> ORGANISM: Homo sapiens

<400> SEQUENCE: 989

Gly Tyr Thr Val Cys Leu
1 5

<210> SEQ ID NO 990
<211> LENGTH: 6
<212> TYPE: PRT
<213> ORGANISM: Homo sapiens

<400> SEQUENCE: 990

Gly Tyr Ile Val Cys Leu
1 5

<210> SEQ ID NO 991
<211> LENGTH: 6
<212> TYPE: PRT
<213> ORGANISM: Homo sapiens

<400> SEQUENCE: 991

Gly Phe Asp Glu Cys Leu
1 5

<210> SEQ ID NO 992
<211> LENGTH: 6
<212> TYPE: PRT
<213> ORGANISM: Homo sapiens

<400> SEQUENCE: 992

Gly Leu Ser Glu Cys Leu
1 5

<210> SEQ ID NO 993
<211> LENGTH: 6
<212> TYPE: PRT
<213> ORGANISM: Homo sapiens

<400> SEQUENCE: 993

Gly Leu Asp Ala Cys Leu
1 5

<210> SEQ ID NO 994
<211> LENGTH: 6
<212> TYPE: PRT
<213> ORGANISM: Homo sapiens

<400> SEQUENCE: 994

Gly Leu Asp Asn Cys Leu
1               5

<210> SEQ ID NO 995
<211> LENGTH: 6
<212> TYPE: PRT
<213> ORGANISM: Homo sapiens

<400> SEQUENCE: 995

Gly Ser Thr Glu Cys Leu
1               5

<210> SEQ ID NO 996
<211> LENGTH: 6
<212> TYPE: PRT
<213> ORGANISM: Homo sapiens

<400> SEQUENCE: 996

Gly Ser Thr Glu Cys Leu
1               5

<210> SEQ ID NO 997
<211> LENGTH: 6
<212> TYPE: PRT
<213> ORGANISM: Homo sapiens

<400> SEQUENCE: 997

Gly Tyr Gly Ser Cys Leu
1               5

<210> SEQ ID NO 998
<211> LENGTH: 6
<212> TYPE: PRT
<213> ORGANISM: Homo sapiens

<400> SEQUENCE: 998

Gly His Ser Glu Cys Leu
1               5

<210> SEQ ID NO 999
<211> LENGTH: 6
<212> TYPE: PRT
<213> ORGANISM: Homo sapiens

<400> SEQUENCE: 999

Gly Tyr Gly Ser Cys Leu
1               5

<210> SEQ ID NO 1000
<211> LENGTH: 6
<212> TYPE: PRT
<213> ORGANISM: Homo sapiens

<400> SEQUENCE: 1000

Gly Ala Glu Cys Cys Leu
1               5

<210> SEQ ID NO 1001
<211> LENGTH: 6
<212> TYPE: PRT
<213> ORGANISM: Homo sapiens

<400> SEQUENCE: 1001

Gly Thr Glu Ala Cys Leu
1               5

<210> SEQ ID NO 1002
<211> LENGTH: 6
<212> TYPE: PRT
<213> ORGANISM: Homo sapiens

<400> SEQUENCE: 1002

Gly Gly Thr Glu Cys Leu
1               5

<210> SEQ ID NO 1003
<211> LENGTH: 6
<212> TYPE: PRT
<213> ORGANISM: Homo sapiens

<400> SEQUENCE: 1003

Gly Asn Leu Ser Cys Leu
1               5

<210> SEQ ID NO 1004
<211> LENGTH: 6
<212> TYPE: PRT
<213> ORGANISM: Homo sapiens

<400> SEQUENCE: 1004

Gly Ser Asp His Cys Leu
1               5

<210> SEQ ID NO 1005
<211> LENGTH: 6
<212> TYPE: PRT
<213> ORGANISM: Homo sapiens

<400> SEQUENCE: 1005

Gly Asn Ile Pro Cys Leu
1               5

<210> SEQ ID NO 1006
<211> LENGTH: 6
<212> TYPE: PRT
<213> ORGANISM: Homo sapiens

<400> SEQUENCE: 1006

Gly Phe Lys Ser Cys Leu
1               5

<210> SEQ ID NO 1007
<211> LENGTH: 6
<212> TYPE: PRT
<213> ORGANISM: Homo sapiens

<400> SEQUENCE: 1007

Gly Leu Ala Leu Cys Leu
1               5

<210> SEQ ID NO 1008
<211> LENGTH: 6
<212> TYPE: PRT
<213> ORGANISM: Homo sapiens

<400> SEQUENCE: 1008

Gly Ser Arg Ser Cys Leu
1 5

<210> SEQ ID NO 1009
<211> LENGTH: 6
<212> TYPE: PRT
<213> ORGANISM: Homo sapiens

<400> SEQUENCE: 1009

Gly Lys Pro Tyr Cys Leu
1 5

<210> SEQ ID NO 1010
<211> LENGTH: 6
<212> TYPE: PRT
<213> ORGANISM: Homo sapiens

<400> SEQUENCE: 1010

Gly Pro Ala Glu Cys Leu
1 5

<210> SEQ ID NO 1011
<211> LENGTH: 6
<212> TYPE: PRT
<213> ORGANISM: Homo sapiens

<400> SEQUENCE: 1011

Gly Met Arg Leu Cys Leu
1 5

<210> SEQ ID NO 1012
<211> LENGTH: 6
<212> TYPE: PRT
<213> ORGANISM: Homo sapiens

<400> SEQUENCE: 1012

Gly Ser Pro Pro Cys Leu
1 5

<210> SEQ ID NO 1013
<211> LENGTH: 6
<212> TYPE: PRT
<213> ORGANISM: Homo sapiens

<400> SEQUENCE: 1013

Gly Val Gly Asn Cys Leu
1 5

<210> SEQ ID NO 1014
<211> LENGTH: 6
<212> TYPE: PRT
<213> ORGANISM: Homo sapiens

<400> SEQUENCE: 1014

Gly Met Tyr Arg Cys Leu
1 5

<210> SEQ ID NO 1015
<211> LENGTH: 6
<212> TYPE: PRT
<213> ORGANISM: Homo sapiens

<400> SEQUENCE: 1015

Gly Leu Tyr Ser Cys Leu
1 5

<210> SEQ ID NO 1016
<211> LENGTH: 6
<212> TYPE: PRT
<213> ORGANISM: Homo sapiens

<400> SEQUENCE: 1016

Gly Ile Ala Phe Cys Leu
1 5

<210> SEQ ID NO 1017
<211> LENGTH: 6
<212> TYPE: PRT
<213> ORGANISM: Homo sapiens

<400> SEQUENCE: 1017

Gly Ile Ala Phe Cys Leu
1 5

<210> SEQ ID NO 1018
<211> LENGTH: 6
<212> TYPE: PRT
<213> ORGANISM: Homo sapiens

<400> SEQUENCE: 1018

Gly Asn Leu Cys Cys Leu
1 5

<210> SEQ ID NO 1019
<211> LENGTH: 6
<212> TYPE: PRT
<213> ORGANISM: Homo sapiens

<400> SEQUENCE: 1019

Gly Thr His Gly Cys Leu
1 5

<210> SEQ ID NO 1020
<211> LENGTH: 6
<212> TYPE: PRT
<213> ORGANISM: Homo sapiens

<400> SEQUENCE: 1020

Gly Ala Ala Asp Cys Leu
1 5

<210> SEQ ID NO 1021
<211> LENGTH: 6
<212> TYPE: PRT
<213> ORGANISM: Homo sapiens

<400> SEQUENCE: 1021

Gly Asp Ala Thr Cys Leu
1 5

<210> SEQ ID NO 1022
<211> LENGTH: 6
<212> TYPE: PRT
<213> ORGANISM: Homo sapiens

<400> SEQUENCE: 1022

Gly Gly Arg Arg Cys Leu
1               5

<210> SEQ ID NO 1023
<211> LENGTH: 6
<212> TYPE: PRT
<213> ORGANISM: Homo sapiens

<400> SEQUENCE: 1023

Gly Lys Asp Asp Cys Leu
1               5

<210> SEQ ID NO 1024
<211> LENGTH: 6
<212> TYPE: PRT
<213> ORGANISM: Homo sapiens

<400> SEQUENCE: 1024

Gly Val Lys Asp Cys Leu
1               5

<210> SEQ ID NO 1025
<211> LENGTH: 6
<212> TYPE: PRT
<213> ORGANISM: Homo sapiens

<400> SEQUENCE: 1025

Gly Ser Gly Pro Cys Leu
1               5

<210> SEQ ID NO 1026
<211> LENGTH: 6
<212> TYPE: PRT
<213> ORGANISM: Homo sapiens

<400> SEQUENCE: 1026

Gly Tyr Trp Ser Cys Leu
1               5

<210> SEQ ID NO 1027
<211> LENGTH: 6
<212> TYPE: PRT
<213> ORGANISM: Homo sapiens

<400> SEQUENCE: 1027

Gly Val Arg Leu Cys Leu
1               5

<210> SEQ ID NO 1028
<211> LENGTH: 6
<212> TYPE: PRT
<213> ORGANISM: Homo sapiens

<400> SEQUENCE: 1028

Gly Val Glu Met Cys Leu
1               5

<210> SEQ ID NO 1029
<211> LENGTH: 6
<212> TYPE: PRT
<213> ORGANISM: Homo sapiens

<400> SEQUENCE: 1029

Gly Glu Ala Leu Cys Leu
1               5

<210> SEQ ID NO 1030
<211> LENGTH: 6
<212> TYPE: PRT
<213> ORGANISM: Homo sapiens

<400> SEQUENCE: 1030

Gly Glu Leu Val Cys Leu
1               5

<210> SEQ ID NO 1031
<211> LENGTH: 6
<212> TYPE: PRT
<213> ORGANISM: Homo sapiens

<400> SEQUENCE: 1031

Gly His Phe Tyr Cys Leu
1               5

<210> SEQ ID NO 1032
<211> LENGTH: 6
<212> TYPE: PRT
<213> ORGANISM: Homo sapiens

<400> SEQUENCE: 1032

Gly Asp Gly Asn Cys Leu
1               5

<210> SEQ ID NO 1033
<211> LENGTH: 6
<212> TYPE: PRT
<213> ORGANISM: Homo sapiens

<400> SEQUENCE: 1033

Gly His Gly Asp Cys Leu
1               5

<210> SEQ ID NO 1034
<211> LENGTH: 6
<212> TYPE: PRT
<213> ORGANISM: Homo sapiens

<400> SEQUENCE: 1034

Gly Val Lys Gly Cys Leu
1               5

<210> SEQ ID NO 1035
<211> LENGTH: 6
<212> TYPE: PRT
<213> ORGANISM: Homo sapiens

<400> SEQUENCE: 1035

Gly Asp Val Leu Cys Leu
1               5

<210> SEQ ID NO 1036
<211> LENGTH: 6
<212> TYPE: PRT
<213> ORGANISM: Homo sapiens

<400> SEQUENCE: 1036

Gly Phe Leu Ile Cys Leu
1 5

<210> SEQ ID NO 1037
<211> LENGTH: 6
<212> TYPE: PRT
<213> ORGANISM: Homo sapiens

<400> SEQUENCE: 1037

Gly Thr Ser Ala Cys Leu
1 5

<210> SEQ ID NO 1038
<211> LENGTH: 6
<212> TYPE: PRT
<213> ORGANISM: Homo sapiens

<400> SEQUENCE: 1038

Gly Phe Cys Pro Cys Leu
1 5

<210> SEQ ID NO 1039
<211> LENGTH: 6
<212> TYPE: PRT
<213> ORGANISM: Homo sapiens

<400> SEQUENCE: 1039

Gly His Pro Ser Cys Leu
1 5

<210> SEQ ID NO 1040
<211> LENGTH: 6
<212> TYPE: PRT
<213> ORGANISM: Homo sapiens

<400> SEQUENCE: 1040

Gly Gly Trp Ala Cys Leu
1 5

<210> SEQ ID NO 1041
<211> LENGTH: 6
<212> TYPE: PRT
<213> ORGANISM: Homo sapiens

<400> SEQUENCE: 1041

Gly Asn Gly Ile Cys Leu
1 5

<210> SEQ ID NO 1042
<211> LENGTH: 6
<212> TYPE: PRT
<213> ORGANISM: Homo sapiens

<400> SEQUENCE: 1042

Gly Ser Gly Gln Cys Leu
1 5

<210> SEQ ID NO 1043
<211> LENGTH: 6
<212> TYPE: PRT
<213> ORGANISM: Homo sapiens

<400> SEQUENCE: 1043

Gly His His Glu Cys Leu
1               5

<210> SEQ ID NO 1044
<211> LENGTH: 6
<212> TYPE: PRT
<213> ORGANISM: Homo sapiens

<400> SEQUENCE: 1044

Gly Gly Ser Arg Cys Leu
1               5

<210> SEQ ID NO 1045
<211> LENGTH: 6
<212> TYPE: PRT
<213> ORGANISM: Homo sapiens

<400> SEQUENCE: 1045

Gly Leu Asp Asp Cys Leu
1               5

<210> SEQ ID NO 1046
<211> LENGTH: 6
<212> TYPE: PRT
<213> ORGANISM: Homo sapiens

<400> SEQUENCE: 1046

Gly Leu Ile Thr Cys Leu
1               5

<210> SEQ ID NO 1047
<211> LENGTH: 6
<212> TYPE: PRT
<213> ORGANISM: Homo sapiens

<400> SEQUENCE: 1047

Gly His Leu Ser Cys Leu
1               5

<210> SEQ ID NO 1048
<211> LENGTH: 6
<212> TYPE: PRT
<213> ORGANISM: Homo sapiens

<400> SEQUENCE: 1048

Gly Tyr Gln Thr Cys Leu
1               5

<210> SEQ ID NO 1049
<211> LENGTH: 6
<212> TYPE: PRT
<213> ORGANISM: Homo sapiens

<400> SEQUENCE: 1049

Gly Gly Arg Pro Cys Leu
1               5

<210> SEQ ID NO 1050
<211> LENGTH: 6
<212> TYPE: PRT
<213> ORGANISM: Homo sapiens

<400> SEQUENCE: 1050

Gly His Pro Ser Cys Leu
1               5

<210> SEQ ID NO 1051
<211> LENGTH: 6
<212> TYPE: PRT
<213> ORGANISM: Homo sapiens

<400> SEQUENCE: 1051

Gly Ser Val Leu Cys Leu
1               5

<210> SEQ ID NO 1052
<211> LENGTH: 6
<212> TYPE: PRT
<213> ORGANISM: Homo sapiens

<400> SEQUENCE: 1052

Gly Asn Arg Lys Cys Leu
1               5

<210> SEQ ID NO 1053
<211> LENGTH: 6
<212> TYPE: PRT
<213> ORGANISM: Homo sapiens

<400> SEQUENCE: 1053

Gly Tyr Asn Arg Cys Leu
1               5

<210> SEQ ID NO 1054
<211> LENGTH: 6
<212> TYPE: PRT
<213> ORGANISM: Homo sapiens

<400> SEQUENCE: 1054

Gly Lys Tyr Thr Cys Leu
1               5

<210> SEQ ID NO 1055
<211> LENGTH: 6
<212> TYPE: PRT
<213> ORGANISM: Homo sapiens

<400> SEQUENCE: 1055

Gly Ser Ala Val Cys Leu
1               5

<210> SEQ ID NO 1056
<211> LENGTH: 6
<212> TYPE: PRT
<213> ORGANISM: Homo sapiens

<400> SEQUENCE: 1056

Gly Asp Tyr Ser Cys Leu
1               5

<210> SEQ ID NO 1057
<211> LENGTH: 6
<212> TYPE: PRT
<213> ORGANISM: Homo sapiens

<400> SEQUENCE: 1057

Gly Ala Gln Asp Cys Leu
1               5

<210> SEQ ID NO 1058
<211> LENGTH: 6
<212> TYPE: PRT
<213> ORGANISM: Homo sapiens

<400> SEQUENCE: 1058

Gly Thr Asn Val Cys Leu
1               5

<210> SEQ ID NO 1059
<211> LENGTH: 6
<212> TYPE: PRT
<213> ORGANISM: Homo sapiens

<400> SEQUENCE: 1059

Gly Pro Arg Leu Cys Leu
1               5

<210> SEQ ID NO 1060
<211> LENGTH: 6
<212> TYPE: PRT
<213> ORGANISM: Homo sapiens

<400> SEQUENCE: 1060

Gly Phe Lys Asn Cys Leu
1               5

<210> SEQ ID NO 1061
<211> LENGTH: 6
<212> TYPE: PRT
<213> ORGANISM: Homo sapiens

<400> SEQUENCE: 1061

Gly Ile Gln Ser Cys Leu
1               5

<210> SEQ ID NO 1062
<211> LENGTH: 6
<212> TYPE: PRT
<213> ORGANISM: Homo sapiens

<400> SEQUENCE: 1062

Gly Ser Ile Thr Cys Leu
1               5

<210> SEQ ID NO 1063
<211> LENGTH: 6
<212> TYPE: PRT
<213> ORGANISM: Homo sapiens

<400> SEQUENCE: 1063

Gly Pro Lys Ile Cys Leu
1               5

<210> SEQ ID NO 1064
<211> LENGTH: 6
<212> TYPE: PRT
<213> ORGANISM: Homo sapiens

<400> SEQUENCE: 1064

Gly Glu Pro Pro Cys Leu
1               5

<210> SEQ ID NO 1065
<211> LENGTH: 6
<212> TYPE: PRT
<213> ORGANISM: Homo sapiens

<400> SEQUENCE: 1065

Gly Ser Glu Leu Cys Leu
1               5

<210> SEQ ID NO 1066
<211> LENGTH: 6
<212> TYPE: PRT
<213> ORGANISM: Homo sapiens

<400> SEQUENCE: 1066

Gly Thr Val Ala Cys Leu
1               5

<210> SEQ ID NO 1067
<211> LENGTH: 6
<212> TYPE: PRT
<213> ORGANISM: Homo sapiens

<400> SEQUENCE: 1067

Gly Arg Glu Cys Cys Leu
1               5

<210> SEQ ID NO 1068
<211> LENGTH: 6
<212> TYPE: PRT
<213> ORGANISM: Homo sapiens

<400> SEQUENCE: 1068

Gly Phe Val Glu Cys Leu
1               5

<210> SEQ ID NO 1069
<211> LENGTH: 6
<212> TYPE: PRT
<213> ORGANISM: Homo sapiens

<400> SEQUENCE: 1069

Gly Thr Asp Gly Cys Leu
1               5

<210> SEQ ID NO 1070
<211> LENGTH: 6
<212> TYPE: PRT
<213> ORGANISM: Homo sapiens

<400> SEQUENCE: 1070

Gly Pro Ser Thr Cys Leu
1               5

<210> SEQ ID NO 1071
<211> LENGTH: 6
<212> TYPE: PRT
<213> ORGANISM: Homo sapiens

<400> SEQUENCE: 1071

Gly Ala Ala Ile Cys Leu
1               5

<210> SEQ ID NO 1072
<211> LENGTH: 6
<212> TYPE: PRT
<213> ORGANISM: Homo sapiens

<400> SEQUENCE: 1072

Gly Gln Arg Gln Cys Leu
1               5

<210> SEQ ID NO 1073
<211> LENGTH: 6
<212> TYPE: PRT
<213> ORGANISM: Homo sapiens

<400> SEQUENCE: 1073

Gly His Pro Ser Cys Leu
1               5

<210> SEQ ID NO 1074
<211> LENGTH: 6
<212> TYPE: PRT
<213> ORGANISM: Homo sapiens

<400> SEQUENCE: 1074

Gly Pro Lys Asp Cys Leu
1               5

<210> SEQ ID NO 1075
<211> LENGTH: 6
<212> TYPE: PRT
<213> ORGANISM: Homo sapiens

<400> SEQUENCE: 1075

Gly His Pro Ser Cys Leu
1               5

<210> SEQ ID NO 1076
<211> LENGTH: 6
<212> TYPE: PRT
<213> ORGANISM: Homo sapiens

<400> SEQUENCE: 1076

Gly His Pro Ser Cys Leu
1               5

<210> SEQ ID NO 1077
<211> LENGTH: 6
<212> TYPE: PRT
<213> ORGANISM: Homo sapiens

<400> SEQUENCE: 1077

Gly Gly Phe Asp Cys Leu
1               5

<210> SEQ ID NO 1078
<211> LENGTH: 6
<212> TYPE: PRT
<213> ORGANISM: Homo sapiens

<400> SEQUENCE: 1078

Gly Val Tyr Gln Cys Leu
1               5

<210> SEQ ID NO 1079
<211> LENGTH: 6
<212> TYPE: PRT
<213> ORGANISM: Homo sapiens

<400> SEQUENCE: 1079

Gly Asp Glu Ile Cys Leu
1               5

<210> SEQ ID NO 1080
<211> LENGTH: 6
<212> TYPE: PRT
<213> ORGANISM: Homo sapiens

<400> SEQUENCE: 1080

Gly Arg Leu Gly Cys Leu
1               5

<210> SEQ ID NO 1081
<211> LENGTH: 6
<212> TYPE: PRT
<213> ORGANISM: Homo sapiens

<400> SEQUENCE: 1081

Gly Leu Ile Tyr Cys Leu
1               5

<210> SEQ ID NO 1082
<211> LENGTH: 6
<212> TYPE: PRT
<213> ORGANISM: Homo sapiens

<400> SEQUENCE: 1082

Gly Pro Phe Gly Cys Leu
1               5

<210> SEQ ID NO 1083
<211> LENGTH: 6
<212> TYPE: PRT
<213> ORGANISM: Homo sapiens

<400> SEQUENCE: 1083

Gly Leu His Ala Cys Leu
1               5

<210> SEQ ID NO 1084
<211> LENGTH: 6
<212> TYPE: PRT
<213> ORGANISM: Homo sapiens

<400> SEQUENCE: 1084

Gly Lys Gly Val Cys Leu
1               5

<210> SEQ ID NO 1085
<211> LENGTH: 6
<212> TYPE: PRT
<213> ORGANISM: Homo sapiens

<400> SEQUENCE: 1085

Gly Leu Ser Lys Cys Leu
1 5

<210> SEQ ID NO 1086
<211> LENGTH: 6
<212> TYPE: PRT
<213> ORGANISM: Homo sapiens

<400> SEQUENCE: 1086

Gly Thr Val Ala Cys Leu
1 5

<210> SEQ ID NO 1087
<211> LENGTH: 6
<212> TYPE: PRT
<213> ORGANISM: Homo sapiens

<400> SEQUENCE: 1087

Gly Asn Ser Thr Cys Leu
1 5

<210> SEQ ID NO 1088
<211> LENGTH: 6
<212> TYPE: PRT
<213> ORGANISM: Homo sapiens

<400> SEQUENCE: 1088

Gly Ala Phe Val Cys Leu
1 5

<210> SEQ ID NO 1089
<211> LENGTH: 6
<212> TYPE: PRT
<213> ORGANISM: Homo sapiens

<400> SEQUENCE: 1089

Gly Thr Tyr Arg Cys Leu
1 5

<210> SEQ ID NO 1090
<211> LENGTH: 6
<212> TYPE: PRT
<213> ORGANISM: Homo sapiens

<400> SEQUENCE: 1090

Gly Ala Val Leu Cys Leu
1 5

<210> SEQ ID NO 1091
<211> LENGTH: 6
<212> TYPE: PRT
<213> ORGANISM: Homo sapiens

<400> SEQUENCE: 1091

Gly Ala Leu Val Cys Leu
1 5

<210> SEQ ID NO 1092
<211> LENGTH: 6
<212> TYPE: PRT
<213> ORGANISM: Homo sapiens

<400> SEQUENCE: 1092

Gly Thr Val Leu Cys Leu
1 5

<210> SEQ ID NO 1093
<211> LENGTH: 6
<212> TYPE: PRT
<213> ORGANISM: Homo sapiens

<400> SEQUENCE: 1093

Gly Lys Leu Cys Cys Leu
1 5

<210> SEQ ID NO 1094
<211> LENGTH: 6
<212> TYPE: PRT
<213> ORGANISM: Homo sapiens

<400> SEQUENCE: 1094

Gly Leu Tyr Leu Cys Leu
1 5

<210> SEQ ID NO 1095
<211> LENGTH: 6
<212> TYPE: PRT
<213> ORGANISM: Homo sapiens

<400> SEQUENCE: 1095

Gly Leu Glu Thr Cys Leu
1 5

<210> SEQ ID NO 1096
<211> LENGTH: 6
<212> TYPE: PRT
<213> ORGANISM: Homo sapiens

<400> SEQUENCE: 1096

Gly Cys Leu Ser Cys Leu
1 5

<210> SEQ ID NO 1097
<211> LENGTH: 6
<212> TYPE: PRT
<213> ORGANISM: Homo sapiens

<400> SEQUENCE: 1097

Gly Val Gly Asp Cys Leu
1 5

<210> SEQ ID NO 1098
<211> LENGTH: 6
<212> TYPE: PRT
<213> ORGANISM: Homo sapiens

<400> SEQUENCE: 1098

Gly His Gln Leu Cys Leu
1 5

<210> SEQ ID NO 1099
<211> LENGTH: 6
<212> TYPE: PRT
<213> ORGANISM: Homo sapiens

<400> SEQUENCE: 1099

Gly Thr Gly Asp Cys Leu
1 5

<210> SEQ ID NO 1100
<211> LENGTH: 6
<212> TYPE: PRT
<213> ORGANISM: Homo sapiens

<400> SEQUENCE: 1100

Gly Ala Ala Lys Cys Leu
1 5

<210> SEQ ID NO 1101
<211> LENGTH: 6
<212> TYPE: PRT
<213> ORGANISM: Homo sapiens

<400> SEQUENCE: 1101

Gly Cys Tyr Gly Cys Leu
1 5

<210> SEQ ID NO 1102
<211> LENGTH: 6
<212> TYPE: PRT
<213> ORGANISM: Homo sapiens

<400> SEQUENCE: 1102

Gly Tyr Phe Leu Cys Leu
1 5

<210> SEQ ID NO 1103
<211> LENGTH: 6
<212> TYPE: PRT
<213> ORGANISM: Homo sapiens

<400> SEQUENCE: 1103

Gly Arg Arg Ala Cys Leu
1 5

<210> SEQ ID NO 1104
<211> LENGTH: 6
<212> TYPE: PRT
<213> ORGANISM: Homo sapiens

<400> SEQUENCE: 1104

Gly Ser Gln Ala Cys Leu
1 5

<210> SEQ ID NO 1105
<211> LENGTH: 6
<212> TYPE: PRT
<213> ORGANISM: Homo sapiens

<400> SEQUENCE: 1105

Gly Thr Thr Cys Cys Leu
1 5

<210> SEQ ID NO 1106
<211> LENGTH: 6
<212> TYPE: PRT
<213> ORGANISM: Homo sapiens

<400> SEQUENCE: 1106

Gly Leu Asn Gln Cys Leu
1 5

<210> SEQ ID NO 1107
<211> LENGTH: 6
<212> TYPE: PRT
<213> ORGANISM: Homo sapiens

<400> SEQUENCE: 1107

Gly Val Leu Leu Cys Leu
1 5

<210> SEQ ID NO 1108
<211> LENGTH: 6
<212> TYPE: PRT
<213> ORGANISM: Homo sapiens

<400> SEQUENCE: 1108

Gly Thr Tyr Arg Cys Leu
1 5

<210> SEQ ID NO 1109
<211> LENGTH: 6
<212> TYPE: PRT
<213> ORGANISM: Homo sapiens

<400> SEQUENCE: 1109

Gly Ala Val Glu Cys Leu
1 5

<210> SEQ ID NO 1110
<211> LENGTH: 6
<212> TYPE: PRT
<213> ORGANISM: Homo sapiens

<400> SEQUENCE: 1110

Gly Thr Ala Ala Cys Leu
1 5

<210> SEQ ID NO 1111
<211> LENGTH: 6
<212> TYPE: PRT
<213> ORGANISM: Homo sapiens

<400> SEQUENCE: 1111

Gly Val Ser Leu Cys Leu
1 5

<210> SEQ ID NO 1112
<211> LENGTH: 6
<212> TYPE: PRT
<213> ORGANISM: Homo sapiens

<400> SEQUENCE: 1112

Gly Leu Lys Val Cys Leu
1 5

<210> SEQ ID NO 1113
<211> LENGTH: 6
<212> TYPE: PRT
<213> ORGANISM: Homo sapiens

<400> SEQUENCE: 1113

Gly Asp Gly His Cys Leu
1 5

<210> SEQ ID NO 1114
<211> LENGTH: 6
<212> TYPE: PRT
<213> ORGANISM: Homo sapiens

<400> SEQUENCE: 1114

Gly Glu Pro Phe Cys Leu
1 5

<210> SEQ ID NO 1115
<211> LENGTH: 6
<212> TYPE: PRT
<213> ORGANISM: Homo sapiens

<400> SEQUENCE: 1115

Gly Leu Glu Val Cys Leu
1 5

<210> SEQ ID NO 1116
<211> LENGTH: 6
<212> TYPE: PRT
<213> ORGANISM: Homo sapiens

<400> SEQUENCE: 1116

Gly Arg Gly Ile Cys Leu
1 5

<210> SEQ ID NO 1117
<211> LENGTH: 6
<212> TYPE: PRT
<213> ORGANISM: Homo sapiens

<400> SEQUENCE: 1117

Gly Gln Ala Arg Cys Leu
1 5

<210> SEQ ID NO 1118
<211> LENGTH: 6
<212> TYPE: PRT
<213> ORGANISM: Homo sapiens

<400> SEQUENCE: 1118

Gly Ile Trp Phe Cys Leu
1 5

<210> SEQ ID NO 1119
<211> LENGTH: 6
<212> TYPE: PRT
<213> ORGANISM: Homo sapiens

<400> SEQUENCE: 1119

Gly Lys Tyr Arg Cys Leu
1 5

<210> SEQ ID NO 1120
<211> LENGTH: 6
<212> TYPE: PRT
<213> ORGANISM: Homo sapiens

<400> SEQUENCE: 1120

Gly Gln Ser Leu Cys Leu
1 5

<210> SEQ ID NO 1121
<211> LENGTH: 6
<212> TYPE: PRT
<213> ORGANISM: Homo sapiens

<400> SEQUENCE: 1121

Gly His Asn Phe Cys Leu
1 5

<210> SEQ ID NO 1122
<211> LENGTH: 6
<212> TYPE: PRT
<213> ORGANISM: Homo sapiens

<400> SEQUENCE: 1122

Gly Glu Pro Arg Cys Leu
1 5

<210> SEQ ID NO 1123
<211> LENGTH: 6
<212> TYPE: PRT
<213> ORGANISM: Homo sapiens

<400> SEQUENCE: 1123

Gly Cys Val His Cys Leu
1 5

<210> SEQ ID NO 1124
<211> LENGTH: 6
<212> TYPE: PRT
<213> ORGANISM: Homo sapiens

<400> SEQUENCE: 1124

Gly Gln Pro Glu Cys Leu
1 5

<210> SEQ ID NO 1125
<211> LENGTH: 6
<212> TYPE: PRT
<213> ORGANISM: Homo sapiens

<400> SEQUENCE: 1125

Gly Lys Tyr Lys Cys Leu
1 5

<210> SEQ ID NO 1126
<211> LENGTH: 6
<212> TYPE: PRT
<213> ORGANISM: Homo sapiens

<400> SEQUENCE: 1126

Gly Thr Gln Leu Cys Leu
1 5

<210> SEQ ID NO 1127
<211> LENGTH: 6
<212> TYPE: PRT
<213> ORGANISM: Homo sapiens

<400> SEQUENCE: 1127

Gly Gly Lys Pro Cys Leu
1               5

<210> SEQ ID NO 1128
<211> LENGTH: 6
<212> TYPE: PRT
<213> ORGANISM: Homo sapiens

<400> SEQUENCE: 1128

Gly Lys Thr Phe Cys Leu
1               5

<210> SEQ ID NO 1129
<211> LENGTH: 6
<212> TYPE: PRT
<213> ORGANISM: Homo sapiens

<400> SEQUENCE: 1129

Gly Asn Tyr Tyr Cys Leu
1               5

<210> SEQ ID NO 1130
<211> LENGTH: 6
<212> TYPE: PRT
<213> ORGANISM: Homo sapiens

<400> SEQUENCE: 1130

Gly Ala Glu His Cys Leu
1               5

<210> SEQ ID NO 1131
<211> LENGTH: 6
<212> TYPE: PRT
<213> ORGANISM: Homo sapiens

<400> SEQUENCE: 1131

Gly Cys Gly Gln Cys Leu
1               5

<210> SEQ ID NO 1132
<211> LENGTH: 6
<212> TYPE: PRT
<213> ORGANISM: Homo sapiens

<400> SEQUENCE: 1132

Gly Ser Tyr Arg Cys Leu
1               5

<210> SEQ ID NO 1133
<211> LENGTH: 6
<212> TYPE: PRT
<213> ORGANISM: Homo sapiens

<400> SEQUENCE: 1133

Gly Ala Val Pro Cys Leu
1               5

<210> SEQ ID NO 1134
<211> LENGTH: 6
<212> TYPE: PRT
<213> ORGANISM: Homo sapiens

<400> SEQUENCE: 1134

Gly Ala Cys Ser Cys Leu
1               5

<210> SEQ ID NO 1135
<211> LENGTH: 6
<212> TYPE: PRT
<213> ORGANISM: Homo sapiens

<400> SEQUENCE: 1135

Gly Asn Val Thr Cys Leu
1               5

<210> SEQ ID NO 1136
<211> LENGTH: 6
<212> TYPE: PRT
<213> ORGANISM: Homo sapiens

<400> SEQUENCE: 1136

Gly Gln Val Gly Cys Leu
1               5

<210> SEQ ID NO 1137
<211> LENGTH: 6
<212> TYPE: PRT
<213> ORGANISM: Homo sapiens

<400> SEQUENCE: 1137

Gly His Leu Asp Cys Leu
1               5

<210> SEQ ID NO 1138
<211> LENGTH: 6
<212> TYPE: PRT
<213> ORGANISM: Homo sapiens

<400> SEQUENCE: 1138

Gly Ala Ala Phe Cys Leu
1               5

<210> SEQ ID NO 1139
<211> LENGTH: 6
<212> TYPE: PRT
<213> ORGANISM: Homo sapiens

<400> SEQUENCE: 1139

Gly Met Glu Glu Cys Leu
1               5

<210> SEQ ID NO 1140
<211> LENGTH: 6
<212> TYPE: PRT
<213> ORGANISM: Homo sapiens

<400> SEQUENCE: 1140

Gly Pro Thr His Cys Leu
1               5

<210> SEQ ID NO 1141
<211> LENGTH: 6
<212> TYPE: PRT
<213> ORGANISM: Homo sapiens

<400> SEQUENCE: 1141

Gly Tyr Phe Ser Cys Leu
1 5

<210> SEQ ID NO 1142
<211> LENGTH: 6
<212> TYPE: PRT
<213> ORGANISM: Homo sapiens

<400> SEQUENCE: 1142

Gly Leu Phe Val Cys Leu
1 5

<210> SEQ ID NO 1143
<211> LENGTH: 6
<212> TYPE: PRT
<213> ORGANISM: Homo sapiens

<400> SEQUENCE: 1143

Gly Thr Val Ala Cys Leu
1 5

<210> SEQ ID NO 1144
<211> LENGTH: 6
<212> TYPE: PRT
<213> ORGANISM: Homo sapiens

<400> SEQUENCE: 1144

Gly Ile Tyr Gly Cys Leu
1 5

<210> SEQ ID NO 1145
<211> LENGTH: 6
<212> TYPE: PRT
<213> ORGANISM: Homo sapiens

<400> SEQUENCE: 1145

Gly Arg Tyr Thr Cys Leu
1 5

<210> SEQ ID NO 1146
<211> LENGTH: 6
<212> TYPE: PRT
<213> ORGANISM: Homo sapiens

<400> SEQUENCE: 1146

Gly Arg Tyr Thr Cys Leu
1 5

<210> SEQ ID NO 1147
<211> LENGTH: 6
<212> TYPE: PRT
<213> ORGANISM: Homo sapiens

<400> SEQUENCE: 1147

Gly Gly Ala Pro Cys Leu
1 5

<210> SEQ ID NO 1148
<211> LENGTH: 6
<212> TYPE: PRT
<213> ORGANISM: Homo sapiens

<400> SEQUENCE: 1148

Gly Lys Arg Val Cys Leu
1               5

<210> SEQ ID NO 1149
<211> LENGTH: 6
<212> TYPE: PRT
<213> ORGANISM: Homo sapiens

<400> SEQUENCE: 1149

Gly Cys Val Ser Cys Leu
1               5

<210> SEQ ID NO 1150
<211> LENGTH: 6
<212> TYPE: PRT
<213> ORGANISM: Homo sapiens

<400> SEQUENCE: 1150

Gly Gln Thr Met Cys Leu
1               5

<210> SEQ ID NO 1151
<211> LENGTH: 6
<212> TYPE: PRT
<213> ORGANISM: Homo sapiens

<400> SEQUENCE: 1151

Gly Ser Phe Gln Cys Leu
1               5

<210> SEQ ID NO 1152
<211> LENGTH: 6
<212> TYPE: PRT
<213> ORGANISM: Homo sapiens

<400> SEQUENCE: 1152

Gly Ser Phe Ser Cys Leu
1               5

<210> SEQ ID NO 1153
<211> LENGTH: 6
<212> TYPE: PRT
<213> ORGANISM: Homo sapiens

<400> SEQUENCE: 1153

Gly Ser Thr Leu Cys Leu
1               5

<210> SEQ ID NO 1154
<211> LENGTH: 6
<212> TYPE: PRT
<213> ORGANISM: Homo sapiens

<400> SEQUENCE: 1154

Gly Ser Phe Asn Cys Leu
1               5

<210> SEQ ID NO 1155
<211> LENGTH: 6
<212> TYPE: PRT
<213> ORGANISM: Homo sapiens

<400> SEQUENCE: 1155

Gly Ala Phe Phe Cys Leu
1 5

<210> SEQ ID NO 1156
<211> LENGTH: 6
<212> TYPE: PRT
<213> ORGANISM: Homo sapiens

<400> SEQUENCE: 1156

Gly Thr Phe Ser Cys Leu
1 5

<210> SEQ ID NO 1157
<211> LENGTH: 6
<212> TYPE: PRT
<213> ORGANISM: Homo sapiens

<400> SEQUENCE: 1157

Gly Gly Pro Asp Cys Leu
1 5

<210> SEQ ID NO 1158
<211> LENGTH: 6
<212> TYPE: PRT
<213> ORGANISM: Homo sapiens

<400> SEQUENCE: 1158

Gly Gly Gly Ala Cys Leu
1 5

<210> SEQ ID NO 1159
<211> LENGTH: 6
<212> TYPE: PRT
<213> ORGANISM: Homo sapiens

<400> SEQUENCE: 1159

Gly His Ala Val Cys Leu
1 5

<210> SEQ ID NO 1160
<211> LENGTH: 6
<212> TYPE: PRT
<213> ORGANISM: Homo sapiens

<400> SEQUENCE: 1160

Gly Leu Leu Ile Cys Leu
1 5

<210> SEQ ID NO 1161
<211> LENGTH: 6
<212> TYPE: PRT
<213> ORGANISM: Homo sapiens

<400> SEQUENCE: 1161

Gly Ala Arg Gly Cys Leu
1 5

<210> SEQ ID NO 1162
<211> LENGTH: 6
<212> TYPE: PRT
<213> ORGANISM: Homo sapiens

<400> SEQUENCE: 1162

Gly Lys Thr Ala Cys Leu
1 5

<210> SEQ ID NO 1163
<211> LENGTH: 6
<212> TYPE: PRT
<213> ORGANISM: Homo sapiens

<400> SEQUENCE: 1163

Gly Gln Phe Lys Cys Leu
1 5

<210> SEQ ID NO 1164
<211> LENGTH: 6
<212> TYPE: PRT
<213> ORGANISM: Homo sapiens

<400> SEQUENCE: 1164

Gly Gln Leu Lys Cys Leu
1 5

<210> SEQ ID NO 1165
<211> LENGTH: 6
<212> TYPE: PRT
<213> ORGANISM: Homo sapiens

<400> SEQUENCE: 1165

Gly Leu Lys Gln Cys Leu
1 5

<210> SEQ ID NO 1166
<211> LENGTH: 6
<212> TYPE: PRT
<213> ORGANISM: Homo sapiens

<400> SEQUENCE: 1166

Gly Val Thr Thr Cys Leu
1 5

<210> SEQ ID NO 1167
<211> LENGTH: 6
<212> TYPE: PRT
<213> ORGANISM: Homo sapiens

<400> SEQUENCE: 1167

Gly Leu Leu Ser Cys Leu
1 5

<210> SEQ ID NO 1168
<211> LENGTH: 6
<212> TYPE: PRT
<213> ORGANISM: Homo sapiens

<400> SEQUENCE: 1168

Gly Pro Phe Ala Cys Leu
1 5

<210> SEQ ID NO 1169
<211> LENGTH: 6
<212> TYPE: PRT
<213> ORGANISM: Homo sapiens

<400> SEQUENCE: 1169

Gly Ala Arg Leu Cys Leu
1 5

<210> SEQ ID NO 1170
<211> LENGTH: 6
<212> TYPE: PRT
<213> ORGANISM: Homo sapiens

<400> SEQUENCE: 1170

Gly Ile Ser Ala Cys Leu
1 5

<210> SEQ ID NO 1171
<211> LENGTH: 6
<212> TYPE: PRT
<213> ORGANISM: Homo sapiens

<400> SEQUENCE: 1171

Gly Ser Val Ser Cys Leu
1 5

<210> SEQ ID NO 1172
<211> LENGTH: 6
<212> TYPE: PRT
<213> ORGANISM: Homo sapiens

<400> SEQUENCE: 1172

Gly Leu Leu Asn Cys Leu
1 5

<210> SEQ ID NO 1173
<211> LENGTH: 6
<212> TYPE: PRT
<213> ORGANISM: Homo sapiens

<400> SEQUENCE: 1173

Gly Pro Ser Ser Cys Leu
1 5

<210> SEQ ID NO 1174
<211> LENGTH: 6
<212> TYPE: PRT
<213> ORGANISM: Homo sapiens

<400> SEQUENCE: 1174

Gly Met Phe Thr Cys Leu
1 5

<210> SEQ ID NO 1175
<211> LENGTH: 6
<212> TYPE: PRT
<213> ORGANISM: Homo sapiens

<400> SEQUENCE: 1175

Gly Pro Leu Val Cys Leu
1 5

<210> SEQ ID NO 1176
<211> LENGTH: 6
<212> TYPE: PRT
<213> ORGANISM: Homo sapiens

<400> SEQUENCE: 1176

Gly Ala Ser Cys Cys Leu
1               5

<210> SEQ ID NO 1177
<211> LENGTH: 6
<212> TYPE: PRT
<213> ORGANISM: Homo sapiens

<400> SEQUENCE: 1177

Gly Leu Ser Ala Cys Leu
1               5

<210> SEQ ID NO 1178
<211> LENGTH: 6
<212> TYPE: PRT
<213> ORGANISM: Homo sapiens

<400> SEQUENCE: 1178

Gly Arg Ser Ala Cys Leu
1               5

<210> SEQ ID NO 1179
<211> LENGTH: 6
<212> TYPE: PRT
<213> ORGANISM: Homo sapiens

<400> SEQUENCE: 1179

Gly Pro Ala Pro Cys Leu
1               5

<210> SEQ ID NO 1180
<211> LENGTH: 6
<212> TYPE: PRT
<213> ORGANISM: Homo sapiens

<400> SEQUENCE: 1180

Gly Ala Lys Thr Cys Leu
1               5

<210> SEQ ID NO 1181
<211> LENGTH: 6
<212> TYPE: PRT
<213> ORGANISM: Homo sapiens

<400> SEQUENCE: 1181

Gly Val Asn Ile Cys Leu
1               5

<210> SEQ ID NO 1182
<211> LENGTH: 6
<212> TYPE: PRT
<213> ORGANISM: Homo sapiens

<400> SEQUENCE: 1182

Gly Phe Ser His Cys Leu
1               5

<210> SEQ ID NO 1183
<211> LENGTH: 6
<212> TYPE: PRT
<213> ORGANISM: Homo sapiens

<400> SEQUENCE: 1183

Gly Ile Lys Lys Cys Leu
1 5

<210> SEQ ID NO 1184
<211> LENGTH: 6
<212> TYPE: PRT
<213> ORGANISM: Homo sapiens

<400> SEQUENCE: 1184

Gly Ser Asp Glu Cys Leu
1 5

<210> SEQ ID NO 1185
<211> LENGTH: 6
<212> TYPE: PRT
<213> ORGANISM: Homo sapiens

<400> SEQUENCE: 1185

Gly Asp Pro Val Cys Leu
1 5

<210> SEQ ID NO 1186
<211> LENGTH: 6
<212> TYPE: PRT
<213> ORGANISM: Homo sapiens

<400> SEQUENCE: 1186

Gly Tyr Pro Ser Cys Leu
1 5

<210> SEQ ID NO 1187
<211> LENGTH: 6
<212> TYPE: PRT
<213> ORGANISM: Homo sapiens

<400> SEQUENCE: 1187

Gly Pro Val Thr Cys Leu
1 5

<210> SEQ ID NO 1188
<211> LENGTH: 6
<212> TYPE: PRT
<213> ORGANISM: Homo sapiens

<400> SEQUENCE: 1188

Gly Gly Lys Asp Cys Leu
1 5

<210> SEQ ID NO 1189
<211> LENGTH: 6
<212> TYPE: PRT
<213> ORGANISM: Homo sapiens

<400> SEQUENCE: 1189

Gly Glu Val Arg Cys Leu
1 5

<210> SEQ ID NO 1190
<211> LENGTH: 6
<212> TYPE: PRT
<213> ORGANISM: Homo sapiens

<400> SEQUENCE: 1190

Gly Gln Leu Gln Cys Leu
1               5

<210> SEQ ID NO 1191
<211> LENGTH: 6
<212> TYPE: PRT
<213> ORGANISM: Homo sapiens

<400> SEQUENCE: 1191

Gly Val Thr Thr Cys Leu
1               5

<210> SEQ ID NO 1192
<211> LENGTH: 6
<212> TYPE: PRT
<213> ORGANISM: Homo sapiens

<400> SEQUENCE: 1192

Gly Leu Ala Val Cys Leu
1               5

<210> SEQ ID NO 1193
<211> LENGTH: 6
<212> TYPE: PRT
<213> ORGANISM: Homo sapiens

<400> SEQUENCE: 1193

Gly Phe Leu Arg Cys Leu
1               5

<210> SEQ ID NO 1194
<211> LENGTH: 6
<212> TYPE: PRT
<213> ORGANISM: Homo sapiens

<400> SEQUENCE: 1194

Gly Lys Lys His Cys Leu
1               5

<210> SEQ ID NO 1195
<211> LENGTH: 6
<212> TYPE: PRT
<213> ORGANISM: Homo sapiens

<400> SEQUENCE: 1195

Gly Thr Ser Tyr Cys Leu
1               5

<210> SEQ ID NO 1196
<211> LENGTH: 6
<212> TYPE: PRT
<213> ORGANISM: Homo sapiens

<400> SEQUENCE: 1196

Gly Cys Asp Val Cys Leu
1               5

<210> SEQ ID NO 1197
<211> LENGTH: 6
<212> TYPE: PRT
<213> ORGANISM: Homo sapiens

<400> SEQUENCE: 1197

Gly Pro Pro Cys Cys Leu
1 5

<210> SEQ ID NO 1198
<211> LENGTH: 6
<212> TYPE: PRT
<213> ORGANISM: Homo sapiens

<400> SEQUENCE: 1198

Gly Thr His Pro Cys Leu
1 5

<210> SEQ ID NO 1199
<211> LENGTH: 6
<212> TYPE: PRT
<213> ORGANISM: Homo sapiens

<400> SEQUENCE: 1199

Gly Phe Lys Lys Cys Leu
1 5

<210> SEQ ID NO 1200
<211> LENGTH: 6
<212> TYPE: PRT
<213> ORGANISM: Homo sapiens

<400> SEQUENCE: 1200

Gly Gly Asn Gly Cys Leu
1 5

<210> SEQ ID NO 1201
<211> LENGTH: 6
<212> TYPE: PRT
<213> ORGANISM: Homo sapiens

<400> SEQUENCE: 1201

Gly Cys Arg Ile Cys Leu
1 5

<210> SEQ ID NO 1202
<211> LENGTH: 6
<212> TYPE: PRT
<213> ORGANISM: Homo sapiens

<400> SEQUENCE: 1202

Gly Phe Leu Arg Cys Leu
1 5

<210> SEQ ID NO 1203
<211> LENGTH: 6
<212> TYPE: PRT
<213> ORGANISM: Homo sapiens

<400> SEQUENCE: 1203

Gly Glu Lys Lys Cys Leu
1 5

<210> SEQ ID NO 1204
<211> LENGTH: 6
<212> TYPE: PRT
<213> ORGANISM: Homo sapiens

<400> SEQUENCE: 1204

Gly Gly His Ile Cys Leu
1               5

<210> SEQ ID NO 1205
<211> LENGTH: 6
<212> TYPE: PRT
<213> ORGANISM: Homo sapiens

<400> SEQUENCE: 1205

Gly Cys Thr Trp Cys Leu
1               5

<210> SEQ ID NO 1206
<211> LENGTH: 6
<212> TYPE: PRT
<213> ORGANISM: Homo sapiens

<400> SEQUENCE: 1206

Gly Ile Gly Lys Cys Leu
1               5

<210> SEQ ID NO 1207
<211> LENGTH: 6
<212> TYPE: PRT
<213> ORGANISM: Homo sapiens

<400> SEQUENCE: 1207

Gly Met Pro Met Cys Leu
1               5

<210> SEQ ID NO 1208
<211> LENGTH: 6
<212> TYPE: PRT
<213> ORGANISM: Homo sapiens

<400> SEQUENCE: 1208

Gly Phe Arg Glu Cys Leu
1               5

<210> SEQ ID NO 1209
<211> LENGTH: 6
<212> TYPE: PRT
<213> ORGANISM: Homo sapiens

<400> SEQUENCE: 1209

Gly Gln Asp Thr Cys Leu
1               5

<210> SEQ ID NO 1210
<211> LENGTH: 6
<212> TYPE: PRT
<213> ORGANISM: Homo sapiens

<400> SEQUENCE: 1210

Gly Phe Ser Leu Cys Leu
1               5

<210> SEQ ID NO 1211
<211> LENGTH: 6
<212> TYPE: PRT
<213> ORGANISM: Homo sapiens

<400> SEQUENCE: 1211

Gly Ser Trp Thr Cys Leu
1 5

<210> SEQ ID NO 1212
<211> LENGTH: 6
<212> TYPE: PRT
<213> ORGANISM: Homo sapiens

<400> SEQUENCE: 1212

Gly Ser Val Ser Cys Leu
1 5

<210> SEQ ID NO 1213
<211> LENGTH: 6
<212> TYPE: PRT
<213> ORGANISM: Homo sapiens

<400> SEQUENCE: 1213

Gly Gly Gly Ala Cys Leu
1 5

<210> SEQ ID NO 1214
<211> LENGTH: 6
<212> TYPE: PRT
<213> ORGANISM: Homo sapiens

<400> SEQUENCE: 1214

Gly Phe Gln Gly Cys Leu
1 5

<210> SEQ ID NO 1215
<211> LENGTH: 6
<212> TYPE: PRT
<213> ORGANISM: Homo sapiens

<400> SEQUENCE: 1215

Gly Phe Thr Gly Cys Leu
1 5

<210> SEQ ID NO 1216
<211> LENGTH: 6
<212> TYPE: PRT
<213> ORGANISM: Homo sapiens

<400> SEQUENCE: 1216

Gly Arg Leu Arg Cys Leu
1 5

<210> SEQ ID NO 1217
<211> LENGTH: 6
<212> TYPE: PRT
<213> ORGANISM: Homo sapiens

<400> SEQUENCE: 1217

Gly Arg Arg Ala Cys Leu
1 5

<210> SEQ ID NO 1218
<211> LENGTH: 6
<212> TYPE: PRT
<213> ORGANISM: Homo sapiens

<400> SEQUENCE: 1218

Gly Asn Leu Glu Cys Leu
1 5

<210> SEQ ID NO 1219
<211> LENGTH: 6
<212> TYPE: PRT
<213> ORGANISM: Homo sapiens

<400> SEQUENCE: 1219

Gly His Ala Leu Cys Leu
1 5

<210> SEQ ID NO 1220
<211> LENGTH: 6
<212> TYPE: PRT
<213> ORGANISM: Homo sapiens

<400> SEQUENCE: 1220

Gly Ser Pro Tyr Cys Leu
1 5

<210> SEQ ID NO 1221
<211> LENGTH: 6
<212> TYPE: PRT
<213> ORGANISM: Homo sapiens

<400> SEQUENCE: 1221

Gly Arg Ala Gln Cys Leu
1 5

<210> SEQ ID NO 1222
<211> LENGTH: 6
<212> TYPE: PRT
<213> ORGANISM: Homo sapiens

<400> SEQUENCE: 1222

Gly His Asn Phe Cys Leu
1 5

<210> SEQ ID NO 1223
<211> LENGTH: 6
<212> TYPE: PRT
<213> ORGANISM: Homo sapiens

<400> SEQUENCE: 1223

Gly Met Tyr His Cys Leu
1 5

<210> SEQ ID NO 1224
<211> LENGTH: 6
<212> TYPE: PRT
<213> ORGANISM: Homo sapiens

<400> SEQUENCE: 1224

Gly Thr Cys Met Cys Leu
1 5

<210> SEQ ID NO 1225
<211> LENGTH: 6
<212> TYPE: PRT
<213> ORGANISM: Homo sapiens

<400> SEQUENCE: 1225

Gly Phe Thr Gly Cys Leu
1 5

<210> SEQ ID NO 1226
<211> LENGTH: 6
<212> TYPE: PRT
<213> ORGANISM: Homo sapiens

<400> SEQUENCE: 1226

Gly Ser Ser Glu Cys Leu
1 5

<210> SEQ ID NO 1227
<211> LENGTH: 6
<212> TYPE: PRT
<213> ORGANISM: Homo sapiens

<400> SEQUENCE: 1227

Gly Ser Thr Glu Cys Leu
1 5

<210> SEQ ID NO 1228
<211> LENGTH: 6
<212> TYPE: PRT
<213> ORGANISM: Homo sapiens

<400> SEQUENCE: 1228

Gly Ala Leu His Cys Leu
1 5

<210> SEQ ID NO 1229
<211> LENGTH: 6
<212> TYPE: PRT
<213> ORGANISM: Homo sapiens

<400> SEQUENCE: 1229

Gly Leu Glu Cys Cys Leu
1 5

<210> SEQ ID NO 1230
<211> LENGTH: 6
<212> TYPE: PRT
<213> ORGANISM: Homo sapiens

<400> SEQUENCE: 1230

Gly Gly Gly Met Cys Leu
1 5

<210> SEQ ID NO 1231
<211> LENGTH: 6
<212> TYPE: PRT
<213> ORGANISM: Homo sapiens

<400> SEQUENCE: 1231

Gly Pro Gly Ser Cys Leu
1 5

<210> SEQ ID NO 1232
<211> LENGTH: 6
<212> TYPE: PRT
<213> ORGANISM: Homo sapiens

<400> SEQUENCE: 1232

Gly Arg Phe Pro Cys Leu
1 5

<210> SEQ ID NO 1233
<211> LENGTH: 6
<212> TYPE: PRT
<213> ORGANISM: Homo sapiens

<400> SEQUENCE: 1233

Gly Lys Ile Arg Cys Leu
1 5

<210> SEQ ID NO 1234
<211> LENGTH: 6
<212> TYPE: PRT
<213> ORGANISM: Homo sapiens

<400> SEQUENCE: 1234

Gly Asp Gln Ile Cys Leu
1 5

<210> SEQ ID NO 1235
<211> LENGTH: 6
<212> TYPE: PRT
<213> ORGANISM: Homo sapiens

<400> SEQUENCE: 1235

Gly Phe Gly Gln Cys Leu
1 5

<210> SEQ ID NO 1236
<211> LENGTH: 6
<212> TYPE: PRT
<213> ORGANISM: Homo sapiens

<400> SEQUENCE: 1236

Gly Asp Leu Thr Cys Leu
1 5

<210> SEQ ID NO 1237
<211> LENGTH: 6
<212> TYPE: PRT
<213> ORGANISM: Homo sapiens

<400> SEQUENCE: 1237

Gly Gln Cys Ala Cys Leu
1 5

<210> SEQ ID NO 1238
<211> LENGTH: 6
<212> TYPE: PRT
<213> ORGANISM: Homo sapiens

<400> SEQUENCE: 1238

Gly Gly Pro Ala Cys Leu
1 5

<210> SEQ ID NO 1239
<211> LENGTH: 6
<212> TYPE: PRT
<213> ORGANISM: Homo sapiens

<400> SEQUENCE: 1239

Gly Leu Ile Leu Cys Leu
1               5

<210> SEQ ID NO 1240
<211> LENGTH: 6
<212> TYPE: PRT
<213> ORGANISM: Homo sapiens

<400> SEQUENCE: 1240

Gly Met Ile Asp Cys Leu
1               5

<210> SEQ ID NO 1241
<211> LENGTH: 6
<212> TYPE: PRT
<213> ORGANISM: Homo sapiens

<400> SEQUENCE: 1241

Gly Leu Arg Arg Cys Leu
1               5

<210> SEQ ID NO 1242
<211> LENGTH: 6
<212> TYPE: PRT
<213> ORGANISM: Homo sapiens

<400> SEQUENCE: 1242

Gly Arg Tyr Cys Cys Leu
1               5

<210> SEQ ID NO 1243
<211> LENGTH: 6
<212> TYPE: PRT
<213> ORGANISM: Homo sapiens

<400> SEQUENCE: 1243

Gly Leu Asn Lys Cys Leu
1               5

<210> SEQ ID NO 1244
<211> LENGTH: 6
<212> TYPE: PRT
<213> ORGANISM: Homo sapiens

<400> SEQUENCE: 1244

Gly Gln Ala Leu Cys Leu
1               5

<210> SEQ ID NO 1245
<211> LENGTH: 6
<212> TYPE: PRT
<213> ORGANISM: Homo sapiens

<400> SEQUENCE: 1245

Gly Leu Asp Pro Cys Leu
1               5

<210> SEQ ID NO 1246
<211> LENGTH: 6
<212> TYPE: PRT
<213> ORGANISM: Homo sapiens

<400> SEQUENCE: 1246

Gly Ala Glu Ala Cys Leu
1 5

<210> SEQ ID NO 1247
<211> LENGTH: 6
<212> TYPE: PRT
<213> ORGANISM: Homo sapiens

<400> SEQUENCE: 1247

Gly Leu Arg Arg Cys Leu
1 5

<210> SEQ ID NO 1248
<211> LENGTH: 6
<212> TYPE: PRT
<213> ORGANISM: Homo sapiens

<400> SEQUENCE: 1248

Gly Phe Pro Glu Cys Leu
1 5

<210> SEQ ID NO 1249
<211> LENGTH: 6
<212> TYPE: PRT
<213> ORGANISM: Homo sapiens

<400> SEQUENCE: 1249

Gly Ile Leu His Cys Leu
1 5

<210> SEQ ID NO 1250
<211> LENGTH: 6
<212> TYPE: PRT
<213> ORGANISM: Homo sapiens

<400> SEQUENCE: 1250

Gly Glu Ser Glu Cys Leu
1 5

<210> SEQ ID NO 1251
<211> LENGTH: 6
<212> TYPE: PRT
<213> ORGANISM: Homo sapiens

<400> SEQUENCE: 1251

Gly Glu Ser Ile Cys Leu
1 5

<210> SEQ ID NO 1252
<211> LENGTH: 6
<212> TYPE: PRT
<213> ORGANISM: Homo sapiens

<400> SEQUENCE: 1252

Gly Lys Gly Val Cys Leu
1 5

<210> SEQ ID NO 1253
<211> LENGTH: 6
<212> TYPE: PRT
<213> ORGANISM: Homo sapiens

<400> SEQUENCE: 1253

Gly Met Ser Leu Cys Leu
1               5

<210> SEQ ID NO 1254
<211> LENGTH: 6
<212> TYPE: PRT
<213> ORGANISM: Homo sapiens

<400> SEQUENCE: 1254

Gly Glu Gly Asn Cys Leu
1               5

<210> SEQ ID NO 1255
<211> LENGTH: 6
<212> TYPE: PRT
<213> ORGANISM: Homo sapiens

<400> SEQUENCE: 1255

Gly Leu Gly Leu Cys Leu
1               5

<210> SEQ ID NO 1256
<211> LENGTH: 6
<212> TYPE: PRT
<213> ORGANISM: Homo sapiens

<400> SEQUENCE: 1256

Gly Gly Lys Tyr Cys Leu
1               5

<210> SEQ ID NO 1257
<211> LENGTH: 6
<212> TYPE: PRT
<213> ORGANISM: Homo sapiens

<400> SEQUENCE: 1257

Gly Cys Ser Ser Cys Leu
1               5

<210> SEQ ID NO 1258
<211> LENGTH: 6
<212> TYPE: PRT
<213> ORGANISM: Homo sapiens

<400> SEQUENCE: 1258

Gly Lys Thr Lys Cys Leu
1               5

<210> SEQ ID NO 1259
<211> LENGTH: 6
<212> TYPE: PRT
<213> ORGANISM: Homo sapiens

<400> SEQUENCE: 1259

Gly Leu Pro Leu Cys Leu
1               5

<210> SEQ ID NO 1260
<211> LENGTH: 6
<212> TYPE: PRT
<213> ORGANISM: Homo sapiens

<400> SEQUENCE: 1260

Gly Phe Asp Ser Cys Leu
1 5

<210> SEQ ID NO 1261
<211> LENGTH: 6
<212> TYPE: PRT
<213> ORGANISM: Homo sapiens

<400> SEQUENCE: 1261

Gly Cys Phe Val Cys Leu
1 5

<210> SEQ ID NO 1262
<211> LENGTH: 6
<212> TYPE: PRT
<213> ORGANISM: Homo sapiens

<400> SEQUENCE: 1262

Gly Phe Arg Cys Cys Leu
1 5

<210> SEQ ID NO 1263
<211> LENGTH: 6
<212> TYPE: PRT
<213> ORGANISM: Homo sapiens

<400> SEQUENCE: 1263

Gly Ile Ser Leu Cys Leu
1 5

<210> SEQ ID NO 1264
<211> LENGTH: 6
<212> TYPE: PRT
<213> ORGANISM: Homo sapiens

<400> SEQUENCE: 1264

Gly Ile Leu Gln Cys Leu
1 5

<210> SEQ ID NO 1265
<211> LENGTH: 6
<212> TYPE: PRT
<213> ORGANISM: Homo sapiens

<400> SEQUENCE: 1265

Gly His Ala Val Cys Leu
1 5

<210> SEQ ID NO 1266
<211> LENGTH: 6
<212> TYPE: PRT
<213> ORGANISM: Homo sapiens

<400> SEQUENCE: 1266

Gly Leu Tyr Cys Cys Leu
1 5

<210> SEQ ID NO 1267
<211> LENGTH: 6
<212> TYPE: PRT
<213> ORGANISM: Homo sapiens

<400> SEQUENCE: 1267

Gly Pro Asp Ala Cys Leu
1 5

<210> SEQ ID NO 1268
<211> LENGTH: 6
<212> TYPE: PRT
<213> ORGANISM: Homo sapiens

<400> SEQUENCE: 1268

Gly Tyr Ala Met Cys Leu
1 5

<210> SEQ ID NO 1269
<211> LENGTH: 6
<212> TYPE: PRT
<213> ORGANISM: Homo sapiens

<400> SEQUENCE: 1269

Gly Ala Gly Ile Cys Leu
1 5

<210> SEQ ID NO 1270
<211> LENGTH: 6
<212> TYPE: PRT
<213> ORGANISM: Homo sapiens

<400> SEQUENCE: 1270

Gly Val Arg Met Cys Leu
1 5

<210> SEQ ID NO 1271
<211> LENGTH: 6
<212> TYPE: PRT
<213> ORGANISM: Homo sapiens

<400> SEQUENCE: 1271

Gly Cys Tyr Tyr Cys Leu
1 5

<210> SEQ ID NO 1272
<211> LENGTH: 6
<212> TYPE: PRT
<213> ORGANISM: Homo sapiens

<400> SEQUENCE: 1272

Gly Pro Leu Phe Cys Leu
1 5

<210> SEQ ID NO 1273
<211> LENGTH: 6
<212> TYPE: PRT
<213> ORGANISM: Homo sapiens

<400> SEQUENCE: 1273

Gly Ala Ala Glu Cys Leu
1 5

<210> SEQ ID NO 1274
<211> LENGTH: 6
<212> TYPE: PRT
<213> ORGANISM: Homo sapiens

<400> SEQUENCE: 1274

Gly Tyr Arg Lys Cys Leu
1 5

<210> SEQ ID NO 1275
<211> LENGTH: 6
<212> TYPE: PRT
<213> ORGANISM: Homo sapiens

<400> SEQUENCE: 1275

Gly Tyr Arg Lys Cys Leu
1 5

<210> SEQ ID NO 1276
<211> LENGTH: 6
<212> TYPE: PRT
<213> ORGANISM: Homo sapiens

<400> SEQUENCE: 1276

Gly Tyr Arg Lys Cys Leu
1 5

<210> SEQ ID NO 1277
<211> LENGTH: 6
<212> TYPE: PRT
<213> ORGANISM: Homo sapiens

<400> SEQUENCE: 1277

Gly Val Leu Gly Cys Leu
1 5

<210> SEQ ID NO 1278
<211> LENGTH: 6
<212> TYPE: PRT
<213> ORGANISM: Homo sapiens

<400> SEQUENCE: 1278

Gly Ser Lys Tyr Cys Leu
1 5

<210> SEQ ID NO 1279
<211> LENGTH: 6
<212> TYPE: PRT
<213> ORGANISM: Homo sapiens

<400> SEQUENCE: 1279

Gly Leu Met Thr Cys Leu
1 5

<210> SEQ ID NO 1280
<211> LENGTH: 6
<212> TYPE: PRT
<213> ORGANISM: Homo sapiens

<400> SEQUENCE: 1280

Gly Lys Leu Ser Cys Leu
1 5

<210> SEQ ID NO 1281
<211> LENGTH: 6
<212> TYPE: PRT
<213> ORGANISM: Homo sapiens

<400> SEQUENCE: 1281

Gly Leu Gly Ala Cys Leu
1               5

<210> SEQ ID NO 1282
<211> LENGTH: 6
<212> TYPE: PRT
<213> ORGANISM: Homo sapiens

<400> SEQUENCE: 1282

Gly Phe His Glu Cys Leu
1               5

<210> SEQ ID NO 1283
<211> LENGTH: 6
<212> TYPE: PRT
<213> ORGANISM: Homo sapiens

<400> SEQUENCE: 1283

Gly Ala Thr Asn Cys Leu
1               5

<210> SEQ ID NO 1284
<211> LENGTH: 6
<212> TYPE: PRT
<213> ORGANISM: Homo sapiens

<400> SEQUENCE: 1284

Gly Gly Arg Arg Cys Leu
1               5

<210> SEQ ID NO 1285
<211> LENGTH: 6
<212> TYPE: PRT
<213> ORGANISM: Homo sapiens

<400> SEQUENCE: 1285

Gly Lys Gln Pro Cys Leu
1               5

<210> SEQ ID NO 1286
<211> LENGTH: 6
<212> TYPE: PRT
<213> ORGANISM: Homo sapiens

<400> SEQUENCE: 1286

Gly Ser Pro Tyr Cys Leu
1               5

<210> SEQ ID NO 1287
<211> LENGTH: 6
<212> TYPE: PRT
<213> ORGANISM: Homo sapiens

<400> SEQUENCE: 1287

Gly Gly Tyr Thr Cys Leu
1               5

<210> SEQ ID NO 1288
<211> LENGTH: 6
<212> TYPE: PRT
<213> ORGANISM: Homo sapiens

<400> SEQUENCE: 1288

Gly Phe Arg Gly Cys Leu
1               5

<210> SEQ ID NO 1289
<211> LENGTH: 6
<212> TYPE: PRT
<213> ORGANISM: Homo sapiens

<400> SEQUENCE: 1289

Gly Ser Pro Thr Cys Leu
1               5

<210> SEQ ID NO 1290
<211> LENGTH: 6
<212> TYPE: PRT
<213> ORGANISM: Homo sapiens

<400> SEQUENCE: 1290

Gly Val Val Ala Cys Leu
1               5

<210> SEQ ID NO 1291
<211> LENGTH: 6
<212> TYPE: PRT
<213> ORGANISM: Homo sapiens

<400> SEQUENCE: 1291

Gly Ala Gly Ser Cys Leu
1               5

<210> SEQ ID NO 1292
<211> LENGTH: 6
<212> TYPE: PRT
<213> ORGANISM: Homo sapiens

<400> SEQUENCE: 1292

Gly Ala Asp Cys Cys Leu
1               5

<210> SEQ ID NO 1293
<211> LENGTH: 6
<212> TYPE: PRT
<213> ORGANISM: Homo sapiens

<400> SEQUENCE: 1293

Gly Lys Tyr Pro Cys Leu
1               5

<210> SEQ ID NO 1294
<211> LENGTH: 6
<212> TYPE: PRT
<213> ORGANISM: Homo sapiens

<400> SEQUENCE: 1294

Gly Ser Gly Gly Cys Leu
1               5

<210> SEQ ID NO 1295
<211> LENGTH: 6
<212> TYPE: PRT
<213> ORGANISM: Homo sapiens

<400> SEQUENCE: 1295

Gly Phe Ser Asp Cys Leu
1 5

<210> SEQ ID NO 1296
<211> LENGTH: 6
<212> TYPE: PRT
<213> ORGANISM: Homo sapiens

<400> SEQUENCE: 1296

Gly Ile Phe Ile Cys Leu
1 5

<210> SEQ ID NO 1297
<211> LENGTH: 6
<212> TYPE: PRT
<213> ORGANISM: Homo sapiens

<400> SEQUENCE: 1297

Gly Trp Asp Pro Cys Leu
1 5

<210> SEQ ID NO 1298
<211> LENGTH: 6
<212> TYPE: PRT
<213> ORGANISM: Homo sapiens

<400> SEQUENCE: 1298

Gly Leu Gly Leu Cys Leu
1 5

<210> SEQ ID NO 1299
<211> LENGTH: 6
<212> TYPE: PRT
<213> ORGANISM: Homo sapiens

<400> SEQUENCE: 1299

Gly Ser Pro Thr Cys Leu
1 5

<210> SEQ ID NO 1300
<211> LENGTH: 6
<212> TYPE: PRT
<213> ORGANISM: Homo sapiens

<400> SEQUENCE: 1300

Gly Thr Gly Lys Cys Leu
1 5

<210> SEQ ID NO 1301
<211> LENGTH: 6
<212> TYPE: PRT
<213> ORGANISM: Homo sapiens

<400> SEQUENCE: 1301

Gly Trp Trp Lys Cys Leu
1 5

<210> SEQ ID NO 1302
<211> LENGTH: 6
<212> TYPE: PRT
<213> ORGANISM: Homo sapiens

<400> SEQUENCE: 1302

Gly Glu Gly Ser Cys Leu
1 5

<210> SEQ ID NO 1303
<211> LENGTH: 6
<212> TYPE: PRT
<213> ORGANISM: Homo sapiens

<400> SEQUENCE: 1303

Gly Phe Ala Leu Cys Leu
1 5

<210> SEQ ID NO 1304
<211> LENGTH: 6
<212> TYPE: PRT
<213> ORGANISM: Homo sapiens

<400> SEQUENCE: 1304

Gly Ile Phe Tyr Cys Leu
1 5

<210> SEQ ID NO 1305
<211> LENGTH: 6
<212> TYPE: PRT
<213> ORGANISM: Homo sapiens

<400> SEQUENCE: 1305

Gly Leu Pro Glu Cys Leu
1 5

<210> SEQ ID NO 1306
<211> LENGTH: 6
<212> TYPE: PRT
<213> ORGANISM: Homo sapiens

<400> SEQUENCE: 1306

Gly Ala Asn Pro Cys Leu
1 5

<210> SEQ ID NO 1307
<211> LENGTH: 6
<212> TYPE: PRT
<213> ORGANISM: Homo sapiens

<400> SEQUENCE: 1307

Gly Asn Leu Ser Cys Leu
1 5

<210> SEQ ID NO 1308
<211> LENGTH: 6
<212> TYPE: PRT
<213> ORGANISM: Homo sapiens

<400> SEQUENCE: 1308

Gly Val Arg Thr Cys Leu
1 5

<210> SEQ ID NO 1309
<211> LENGTH: 6
<212> TYPE: PRT
<213> ORGANISM: Homo sapiens

<400> SEQUENCE: 1309

Gly Trp Leu Pro Cys Leu
1 5

<210> SEQ ID NO 1310
<211> LENGTH: 6
<212> TYPE: PRT
<213> ORGANISM: Homo sapiens

<400> SEQUENCE: 1310

Gly Asn Tyr Thr Cys Leu
1 5

<210> SEQ ID NO 1311
<211> LENGTH: 6
<212> TYPE: PRT
<213> ORGANISM: Homo sapiens

<400> SEQUENCE: 1311

Gly Ser Arg Asp Cys Leu
1 5

<210> SEQ ID NO 1312
<211> LENGTH: 6
<212> TYPE: PRT
<213> ORGANISM: Homo sapiens

<400> SEQUENCE: 1312

Gly Ser Ala Pro Cys Leu
1 5

<210> SEQ ID NO 1313
<211> LENGTH: 6
<212> TYPE: PRT
<213> ORGANISM: Homo sapiens

<400> SEQUENCE: 1313

Gly Ser Tyr Arg Cys Leu
1 5

<210> SEQ ID NO 1314
<211> LENGTH: 6
<212> TYPE: PRT
<213> ORGANISM: Homo sapiens

<400> SEQUENCE: 1314

Gly Phe Pro Glu Cys Leu
1 5

<210> SEQ ID NO 1315
<211> LENGTH: 6
<212> TYPE: PRT
<213> ORGANISM: Homo sapiens

<400> SEQUENCE: 1315

Gly Ile Ser Leu Cys Leu
1 5

<210> SEQ ID NO 1316
<211> LENGTH: 6
<212> TYPE: PRT
<213> ORGANISM: Homo sapiens

<400> SEQUENCE: 1316

Gly Glu Glu Leu Cys Leu
1               5

<210> SEQ ID NO 1317
<211> LENGTH: 6
<212> TYPE: PRT
<213> ORGANISM: Homo sapiens

<400> SEQUENCE: 1317

Gly Ser Asp Asp Cys Leu
1               5

<210> SEQ ID NO 1318
<211> LENGTH: 6
<212> TYPE: PRT
<213> ORGANISM: Homo sapiens

<400> SEQUENCE: 1318

Gly Ile Ile Gln Cys Leu
1               5

<210> SEQ ID NO 1319
<211> LENGTH: 6
<212> TYPE: PRT
<213> ORGANISM: Homo sapiens

<400> SEQUENCE: 1319

Gly Ala Thr Arg Cys Leu
1               5

<210> SEQ ID NO 1320
<211> LENGTH: 6
<212> TYPE: PRT
<213> ORGANISM: Homo sapiens

<400> SEQUENCE: 1320

Gly Leu Cys Lys Cys Leu
1               5

<210> SEQ ID NO 1321
<211> LENGTH: 6
<212> TYPE: PRT
<213> ORGANISM: Homo sapiens

<400> SEQUENCE: 1321

Gly Leu Val Asp Cys Leu
1               5

<210> SEQ ID NO 1322
<211> LENGTH: 6
<212> TYPE: PRT
<213> ORGANISM: Homo sapiens

<400> SEQUENCE: 1322

Gly Arg Gly Asp Cys Leu
1               5

<210> SEQ ID NO 1323
<211> LENGTH: 6
<212> TYPE: PRT
<213> ORGANISM: Homo sapiens

<400> SEQUENCE: 1323

Gly Leu Ala Phe Cys Leu
1 5

<210> SEQ ID NO 1324
<211> LENGTH: 6
<212> TYPE: PRT
<213> ORGANISM: Homo sapiens

<400> SEQUENCE: 1324

Gly Tyr Ala Ala Cys Leu
1 5

<210> SEQ ID NO 1325
<211> LENGTH: 6
<212> TYPE: PRT
<213> ORGANISM: Homo sapiens

<400> SEQUENCE: 1325

Gly Gln Leu Ala Cys Leu
1 5

<210> SEQ ID NO 1326
<211> LENGTH: 6
<212> TYPE: PRT
<213> ORGANISM: Homo sapiens

<400> SEQUENCE: 1326

Gly Gly Leu Arg Cys Leu
1 5

<210> SEQ ID NO 1327
<211> LENGTH: 6
<212> TYPE: PRT
<213> ORGANISM: Homo sapiens

<400> SEQUENCE: 1327

Gly Lys Asp Lys Cys Leu
1 5

<210> SEQ ID NO 1328
<211> LENGTH: 6
<212> TYPE: PRT
<213> ORGANISM: Homo sapiens

<400> SEQUENCE: 1328

Gly Phe Gly Arg Cys Leu
1 5

<210> SEQ ID NO 1329
<211> LENGTH: 6
<212> TYPE: PRT
<213> ORGANISM: Homo sapiens

<400> SEQUENCE: 1329

Gly Thr Ile Thr Cys Leu
1 5

<210> SEQ ID NO 1330
<211> LENGTH: 6
<212> TYPE: PRT
<213> ORGANISM: Homo sapiens

<400> SEQUENCE: 1330

Gly Arg Gly Gln Cys Leu
1 5

<210> SEQ ID NO 1331
<211> LENGTH: 6
<212> TYPE: PRT
<213> ORGANISM: Homo sapiens

<400> SEQUENCE: 1331

Gly Asp Asp Leu Cys Leu
1 5

<210> SEQ ID NO 1332
<211> LENGTH: 6
<212> TYPE: PRT
<213> ORGANISM: Homo sapiens

<400> SEQUENCE: 1332

Gly Asn Val Ile Cys Leu
1 5

<210> SEQ ID NO 1333
<211> LENGTH: 6
<212> TYPE: PRT
<213> ORGANISM: Homo sapiens

<400> SEQUENCE: 1333

Gly Ile Val Leu Cys Leu
1 5

<210> SEQ ID NO 1334
<211> LENGTH: 6
<212> TYPE: PRT
<213> ORGANISM: Homo sapiens

<400> SEQUENCE: 1334

Gly Lys Leu Glu Cys Leu
1 5

<210> SEQ ID NO 1335
<211> LENGTH: 6
<212> TYPE: PRT
<213> ORGANISM: Homo sapiens

<400> SEQUENCE: 1335

Gly His Pro Gln Cys Leu
1 5

<210> SEQ ID NO 1336
<211> LENGTH: 6
<212> TYPE: PRT
<213> ORGANISM: Homo sapiens

<400> SEQUENCE: 1336

Gly Leu Phe Ala Cys Leu
1 5

<210> SEQ ID NO 1337
<211> LENGTH: 6
<212> TYPE: PRT
<213> ORGANISM: Homo sapiens

<400> SEQUENCE: 1337

Gly Ile Arg Thr Cys Leu
1               5

<210> SEQ ID NO 1338
<211> LENGTH: 6
<212> TYPE: PRT
<213> ORGANISM: Homo sapiens

<400> SEQUENCE: 1338

Gly His Gly Thr Cys Leu
1               5

<210> SEQ ID NO 1339
<211> LENGTH: 6
<212> TYPE: PRT
<213> ORGANISM: Homo sapiens

<400> SEQUENCE: 1339

Gly Asp Gly Ser Cys Leu
1               5

<210> SEQ ID NO 1340
<211> LENGTH: 6
<212> TYPE: PRT
<213> ORGANISM: Homo sapiens

<400> SEQUENCE: 1340

Gly Asn Gly Ala Cys Leu
1               5

<210> SEQ ID NO 1341
<211> LENGTH: 6
<212> TYPE: PRT
<213> ORGANISM: Homo sapiens

<400> SEQUENCE: 1341

Gly Ser Ser Arg Cys Leu
1               5

<210> SEQ ID NO 1342
<211> LENGTH: 6
<212> TYPE: PRT
<213> ORGANISM: Homo sapiens

<400> SEQUENCE: 1342

Gly Ser Gly Gln Cys Leu
1               5

<210> SEQ ID NO 1343
<211> LENGTH: 6
<212> TYPE: PRT
<213> ORGANISM: Homo sapiens

<400> SEQUENCE: 1343

Gly Phe His Leu Cys Leu
1               5

<210> SEQ ID NO 1344
<211> LENGTH: 6
<212> TYPE: PRT
<213> ORGANISM: Homo sapiens

<400> SEQUENCE: 1344

Gly Leu Tyr Leu Cys Leu
1 5

<210> SEQ ID NO 1345
<211> LENGTH: 6
<212> TYPE: PRT
<213> ORGANISM: Homo sapiens

<400> SEQUENCE: 1345

Gly Trp Ser Phe Cys Leu
1 5

<210> SEQ ID NO 1346
<211> LENGTH: 6
<212> TYPE: PRT
<213> ORGANISM: Homo sapiens

<400> SEQUENCE: 1346

Gly Gln Thr Met Cys Leu
1 5

<210> SEQ ID NO 1347
<211> LENGTH: 6
<212> TYPE: PRT
<213> ORGANISM: Homo sapiens

<400> SEQUENCE: 1347

Gly Thr Gly Ser Cys Leu
1 5

<210> SEQ ID NO 1348
<211> LENGTH: 6
<212> TYPE: PRT
<213> ORGANISM: Homo sapiens

<400> SEQUENCE: 1348

Gly Arg Gln Gly Cys Leu
1 5

<210> SEQ ID NO 1349
<211> LENGTH: 6
<212> TYPE: PRT
<213> ORGANISM: Homo sapiens

<400> SEQUENCE: 1349

Gly Glu Cys Arg Cys Leu
1 5

<210> SEQ ID NO 1350
<211> LENGTH: 6
<212> TYPE: PRT
<213> ORGANISM: Homo sapiens

<400> SEQUENCE: 1350

Gly Arg Pro Ile Cys Leu
1 5

<210> SEQ ID NO 1351
<211> LENGTH: 6
<212> TYPE: PRT
<213> ORGANISM: Homo sapiens

<400> SEQUENCE: 1351

Gly Ser Asp Ser Cys Leu
1 5

<210> SEQ ID NO 1352
<211> LENGTH: 6
<212> TYPE: PRT
<213> ORGANISM: Homo sapiens

<400> SEQUENCE: 1352

Gly Phe Glu Gly Cys Leu
1 5

<210> SEQ ID NO 1353
<211> LENGTH: 6
<212> TYPE: PRT
<213> ORGANISM: Homo sapiens

<400> SEQUENCE: 1353

Gly Gly Gly Pro Cys Leu
1 5

<210> SEQ ID NO 1354
<211> LENGTH: 6
<212> TYPE: PRT
<213> ORGANISM: Homo sapiens

<400> SEQUENCE: 1354

Gly Val Leu Tyr Cys Leu
1 5

<210> SEQ ID NO 1355
<211> LENGTH: 6
<212> TYPE: PRT
<213> ORGANISM: Homo sapiens

<400> SEQUENCE: 1355

Gly Lys Glu Gln Cys Leu
1 5

<210> SEQ ID NO 1356
<211> LENGTH: 6
<212> TYPE: PRT
<213> ORGANISM: Homo sapiens

<400> SEQUENCE: 1356

Gly Lys Thr Leu Cys Leu
1 5

<210> SEQ ID NO 1357
<211> LENGTH: 6
<212> TYPE: PRT
<213> ORGANISM: Homo sapiens

<400> SEQUENCE: 1357

Gly Arg Ser Leu Cys Leu
1 5

<210> SEQ ID NO 1358
<211> LENGTH: 6
<212> TYPE: PRT
<213> ORGANISM: Homo sapiens

<400> SEQUENCE: 1358

Gly Leu Ala Leu Cys Leu
1               5

<210> SEQ ID NO 1359
<211> LENGTH: 6
<212> TYPE: PRT
<213> ORGANISM: Homo sapiens

<400> SEQUENCE: 1359

Gly Lys Asp Leu Cys Leu
1               5

<210> SEQ ID NO 1360
<211> LENGTH: 6
<212> TYPE: PRT
<213> ORGANISM: Homo sapiens

<400> SEQUENCE: 1360

Gly Trp Ala Ser Cys Leu
1               5

<210> SEQ ID NO 1361
<211> LENGTH: 6
<212> TYPE: PRT
<213> ORGANISM: Homo sapiens

<400> SEQUENCE: 1361

Gly Asp Asp Asp Cys Leu
1               5

<210> SEQ ID NO 1362
<211> LENGTH: 6
<212> TYPE: PRT
<213> ORGANISM: Homo sapiens

<400> SEQUENCE: 1362

Gly Thr Tyr Lys Cys Leu
1               5

<210> SEQ ID NO 1363
<211> LENGTH: 6
<212> TYPE: PRT
<213> ORGANISM: Homo sapiens

<400> SEQUENCE: 1363

Gly Ala Val Ala Cys Leu
1               5

<210> SEQ ID NO 1364
<211> LENGTH: 6
<212> TYPE: PRT
<213> ORGANISM: Homo sapiens

<400> SEQUENCE: 1364

Gly Gly Gly Ala Cys Leu
1               5

<210> SEQ ID NO 1365
<211> LENGTH: 6
<212> TYPE: PRT
<213> ORGANISM: Homo sapiens

<400> SEQUENCE: 1365

Gly His Val Glu Cys Leu
1 5

<210> SEQ ID NO 1366
<211> LENGTH: 6
<212> TYPE: PRT
<213> ORGANISM: Homo sapiens

<400> SEQUENCE: 1366

Gly Leu Ser Lys Cys Leu
1 5

<210> SEQ ID NO 1367
<211> LENGTH: 6
<212> TYPE: PRT
<213> ORGANISM: Homo sapiens

<400> SEQUENCE: 1367

Gly Lys Asn Lys Cys Leu
1 5

<210> SEQ ID NO 1368
<211> LENGTH: 6
<212> TYPE: PRT
<213> ORGANISM: Homo sapiens

<400> SEQUENCE: 1368

Gly Val His Trp Cys Leu
1 5

<210> SEQ ID NO 1369
<211> LENGTH: 6
<212> TYPE: PRT
<213> ORGANISM: Homo sapiens

<400> SEQUENCE: 1369

Gly Arg Glu Cys Cys Leu
1 5

<210> SEQ ID NO 1370
<211> LENGTH: 6
<212> TYPE: PRT
<213> ORGANISM: Homo sapiens

<400> SEQUENCE: 1370

Gly Asn Gln Asn Cys Leu
1 5

<210> SEQ ID NO 1371
<211> LENGTH: 6
<212> TYPE: PRT
<213> ORGANISM: Homo sapiens

<400> SEQUENCE: 1371

Gly Leu Asn Gln Cys Leu
1 5

<210> SEQ ID NO 1372
<211> LENGTH: 6
<212> TYPE: PRT
<213> ORGANISM: Homo sapiens

<400> SEQUENCE: 1372

Gly Arg Ser Ser Cys Leu
1               5

<210> SEQ ID NO 1373
<211> LENGTH: 6
<212> TYPE: PRT
<213> ORGANISM: Homo sapiens

<400> SEQUENCE: 1373

Gly Thr Asn Gly Cys Leu
1               5

<210> SEQ ID NO 1374
<211> LENGTH: 6
<212> TYPE: PRT
<213> ORGANISM: Homo sapiens

<400> SEQUENCE: 1374

Gly Ser Glu Thr Cys Leu
1               5

<210> SEQ ID NO 1375
<211> LENGTH: 6
<212> TYPE: PRT
<213> ORGANISM: Homo sapiens

<400> SEQUENCE: 1375

Gly Gly Leu Asp Cys Leu
1               5

<210> SEQ ID NO 1376
<211> LENGTH: 6
<212> TYPE: PRT
<213> ORGANISM: Homo sapiens

<400> SEQUENCE: 1376

Gly Glu Asp Ile Cys Leu
1               5

<210> SEQ ID NO 1377
<211> LENGTH: 6
<212> TYPE: PRT
<213> ORGANISM: Homo sapiens

<400> SEQUENCE: 1377

Gly Leu Gly Gly Cys Leu
1               5

<210> SEQ ID NO 1378
<211> LENGTH: 6
<212> TYPE: PRT
<213> ORGANISM: Homo sapiens

<400> SEQUENCE: 1378

Gly Leu Leu Ser Cys Leu
1               5

<210> SEQ ID NO 1379
<211> LENGTH: 6
<212> TYPE: PRT
<213> ORGANISM: Homo sapiens

<400> SEQUENCE: 1379

Gly Glu Arg Lys Cys Leu
1               5

<210> SEQ ID NO 1380
<211> LENGTH: 6
<212> TYPE: PRT
<213> ORGANISM: Homo sapiens

<400> SEQUENCE: 1380

Gly Gln Leu Phe Cys Leu
1               5

<210> SEQ ID NO 1381
<211> LENGTH: 6
<212> TYPE: PRT
<213> ORGANISM: Homo sapiens

<400> SEQUENCE: 1381

Gly Leu Glu Gly Cys Leu
1               5

<210> SEQ ID NO 1382
<211> LENGTH: 6
<212> TYPE: PRT
<213> ORGANISM: Homo sapiens

<400> SEQUENCE: 1382

Gly Val Ala Ser Cys Leu
1               5

<210> SEQ ID NO 1383
<211> LENGTH: 6
<212> TYPE: PRT
<213> ORGANISM: Homo sapiens

<400> SEQUENCE: 1383

Gly Met Trp Ser Cys Leu
1               5

<210> SEQ ID NO 1384
<211> LENGTH: 6
<212> TYPE: PRT
<213> ORGANISM: Homo sapiens

<400> SEQUENCE: 1384

Gly Tyr Gly Glu Cys Leu
1               5

<210> SEQ ID NO 1385
<211> LENGTH: 6
<212> TYPE: PRT
<213> ORGANISM: Homo sapiens

<400> SEQUENCE: 1385

Gly Glu Ala Asp Cys Leu
1               5

<210> SEQ ID NO 1386
<211> LENGTH: 6
<212> TYPE: PRT
<213> ORGANISM: Homo sapiens

<400> SEQUENCE: 1386

Gly Pro Gly Gly Cys Leu
1               5

<210> SEQ ID NO 1387
<211> LENGTH: 6
<212> TYPE: PRT
<213> ORGANISM: Homo sapiens

<400> SEQUENCE: 1387

Gly Asn Ile Gly Cys Leu
1               5

<210> SEQ ID NO 1388
<211> LENGTH: 6
<212> TYPE: PRT
<213> ORGANISM: Homo sapiens

<400> SEQUENCE: 1388

Gly Phe Gln Gly Cys Leu
1               5

<210> SEQ ID NO 1389
<211> LENGTH: 6
<212> TYPE: PRT
<213> ORGANISM: Homo sapiens

<400> SEQUENCE: 1389

Gly Met Leu Ala Cys Leu
1               5

<210> SEQ ID NO 1390
<211> LENGTH: 6
<212> TYPE: PRT
<213> ORGANISM: Homo sapiens

<400> SEQUENCE: 1390

Gly Ile Val Glu Cys Leu
1               5

<210> SEQ ID NO 1391
<211> LENGTH: 6
<212> TYPE: PRT
<213> ORGANISM: Homo sapiens

<400> SEQUENCE: 1391

Gly Leu Gln Gly Cys Leu
1               5

<210> SEQ ID NO 1392
<211> LENGTH: 6
<212> TYPE: PRT
<213> ORGANISM: Homo sapiens

<400> SEQUENCE: 1392

Gly Thr Met Gln Cys Leu
1               5

<210> SEQ ID NO 1393
<211> LENGTH: 6
<212> TYPE: PRT
<213> ORGANISM: Homo sapiens

<400> SEQUENCE: 1393

Gly Asp Gln Arg Cys Leu
1               5

<210> SEQ ID NO 1394
<211> LENGTH: 6
<212> TYPE: PRT
<213> ORGANISM: Homo sapiens

<400> SEQUENCE: 1394

Gly Val Arg Arg Cys Leu
1               5

<210> SEQ ID NO 1395
<211> LENGTH: 6
<212> TYPE: PRT
<213> ORGANISM: Homo sapiens

<400> SEQUENCE: 1395

Gly Thr Tyr Leu Cys Leu
1               5

<210> SEQ ID NO 1396
<211> LENGTH: 6
<212> TYPE: PRT
<213> ORGANISM: Homo sapiens

<400> SEQUENCE: 1396

Gly Gly Ser Gln Cys Leu
1               5

<210> SEQ ID NO 1397
<211> LENGTH: 6
<212> TYPE: PRT
<213> ORGANISM: Homo sapiens

<400> SEQUENCE: 1397

Gly Leu Pro Thr Cys Leu
1               5

<210> SEQ ID NO 1398
<211> LENGTH: 6
<212> TYPE: PRT
<213> ORGANISM: Homo sapiens

<400> SEQUENCE: 1398

Gly Phe Arg Glu Cys Leu
1               5

<210> SEQ ID NO 1399
<211> LENGTH: 6
<212> TYPE: PRT
<213> ORGANISM: Homo sapiens

<400> SEQUENCE: 1399

Gly Gln Val Gln Cys Leu
1               5

<210> SEQ ID NO 1400
<211> LENGTH: 6
<212> TYPE: PRT
<213> ORGANISM: Homo sapiens

<400> SEQUENCE: 1400

Gly Thr Phe Phe Cys Leu
1 5

<210> SEQ ID NO 1401
<211> LENGTH: 6
<212> TYPE: PRT
<213> ORGANISM: Homo sapiens

<400> SEQUENCE: 1401

Gly Phe Leu Gly Cys Leu
1 5

<210> SEQ ID NO 1402
<211> LENGTH: 6
<212> TYPE: PRT
<213> ORGANISM: Homo sapiens

<400> SEQUENCE: 1402

Gly Asn Pro Lys Cys Leu
1 5

<210> SEQ ID NO 1403
<211> LENGTH: 6
<212> TYPE: PRT
<213> ORGANISM: Homo sapiens

<400> SEQUENCE: 1403

Gly Ser Leu Thr Cys Leu
1 5

<210> SEQ ID NO 1404
<211> LENGTH: 6
<212> TYPE: PRT
<213> ORGANISM: Homo sapiens

<400> SEQUENCE: 1404

Gly Asn Pro Lys Cys Leu
1 5

<210> SEQ ID NO 1405
<211> LENGTH: 6
<212> TYPE: PRT
<213> ORGANISM: Homo sapiens

<400> SEQUENCE: 1405

Gly Asn Leu Ser Cys Leu
1 5

<210> SEQ ID NO 1406
<211> LENGTH: 6
<212> TYPE: PRT
<213> ORGANISM: Homo sapiens

<400> SEQUENCE: 1406

Gly Lys Gly Val Cys Leu
1 5

<210> SEQ ID NO 1407
<211> LENGTH: 6
<212> TYPE: PRT
<213> ORGANISM: Homo sapiens

<400> SEQUENCE: 1407

Gly Pro Leu Ala Cys Leu
1               5

<210> SEQ ID NO 1408
<211> LENGTH: 6
<212> TYPE: PRT
<213> ORGANISM: Homo sapiens

<400> SEQUENCE: 1408

Gly Leu Asn Leu Cys Leu
1               5

<210> SEQ ID NO 1409
<211> LENGTH: 6
<212> TYPE: PRT
<213> ORGANISM: Homo sapiens

<400> SEQUENCE: 1409

Gly Phe Thr Gly Cys Leu
1               5

<210> SEQ ID NO 1410
<211> LENGTH: 6
<212> TYPE: PRT
<213> ORGANISM: Homo sapiens

<400> SEQUENCE: 1410

Gly Leu Arg Arg Cys Leu
1               5

<210> SEQ ID NO 1411
<211> LENGTH: 6
<212> TYPE: PRT
<213> ORGANISM: Homo sapiens

<400> SEQUENCE: 1411

Gly His Gly Glu Cys Leu
1               5

<210> SEQ ID NO 1412
<211> LENGTH: 6
<212> TYPE: PRT
<213> ORGANISM: Homo sapiens

<400> SEQUENCE: 1412

Gly Met Ser Ile Cys Leu
1               5

<210> SEQ ID NO 1413
<211> LENGTH: 6
<212> TYPE: PRT
<213> ORGANISM: Homo sapiens

<400> SEQUENCE: 1413

Gly Cys Thr Trp Cys Leu
1               5

<210> SEQ ID NO 1414
<211> LENGTH: 6
<212> TYPE: PRT
<213> ORGANISM: Homo sapiens

<400> SEQUENCE: 1414

Gly Cys Cys Ser Cys Leu
1               5

<210> SEQ ID NO 1415
<211> LENGTH: 6
<212> TYPE: PRT
<213> ORGANISM: Homo sapiens

<400> SEQUENCE: 1415

Gly Lys Ser Phe Cys Leu
1               5

<210> SEQ ID NO 1416
<211> LENGTH: 6
<212> TYPE: PRT
<213> ORGANISM: Homo sapiens

<400> SEQUENCE: 1416

Gly Met Gln Trp Cys Leu
1               5

<210> SEQ ID NO 1417
<211> LENGTH: 6
<212> TYPE: PRT
<213> ORGANISM: Homo sapiens

<400> SEQUENCE: 1417

Gly Pro Glu Glu Cys Leu
1               5

<210> SEQ ID NO 1418
<211> LENGTH: 6
<212> TYPE: PRT
<213> ORGANISM: Homo sapiens

<400> SEQUENCE: 1418

Gly Glu His Phe Cys Leu
1               5

<210> SEQ ID NO 1419
<211> LENGTH: 6
<212> TYPE: PRT
<213> ORGANISM: Homo sapiens

<400> SEQUENCE: 1419

Gly Gln Tyr Arg Cys Leu
1               5

<210> SEQ ID NO 1420
<211> LENGTH: 6
<212> TYPE: PRT
<213> ORGANISM: Homo sapiens

<400> SEQUENCE: 1420

Gly Trp Ala Ser Cys Leu
1               5

<210> SEQ ID NO 1421
<211> LENGTH: 6
<212> TYPE: PRT
<213> ORGANISM: Homo sapiens

<400> SEQUENCE: 1421

Gly Lys Ser Phe Cys Leu
1 5

<210> SEQ ID NO 1422
<211> LENGTH: 6
<212> TYPE: PRT
<213> ORGANISM: Homo sapiens

<400> SEQUENCE: 1422

Gly Lys Ser Phe Cys Leu
1 5

<210> SEQ ID NO 1423
<211> LENGTH: 6
<212> TYPE: PRT
<213> ORGANISM: Homo sapiens

<400> SEQUENCE: 1423

Gly Trp Ala Ser Cys Leu
1 5

<210> SEQ ID NO 1424
<211> LENGTH: 6
<212> TYPE: PRT
<213> ORGANISM: Homo sapiens

<400> SEQUENCE: 1424

Gly Trp Ala Ser Cys Leu
1 5

<210> SEQ ID NO 1425
<211> LENGTH: 6
<212> TYPE: PRT
<213> ORGANISM: Homo sapiens

<400> SEQUENCE: 1425

Gly Leu Lys Tyr Cys Leu
1 5

<210> SEQ ID NO 1426
<211> LENGTH: 6
<212> TYPE: PRT
<213> ORGANISM: Homo sapiens

<400> SEQUENCE: 1426

Gly Ser Val Leu Cys Leu
1 5

<210> SEQ ID NO 1427
<211> LENGTH: 6
<212> TYPE: PRT
<213> ORGANISM: Homo sapiens

<400> SEQUENCE: 1427

Gly Trp Gly Leu Cys Leu
1 5

<210> SEQ ID NO 1428
<211> LENGTH: 6
<212> TYPE: PRT
<213> ORGANISM: Homo sapiens

<400> SEQUENCE: 1428

Gly Gly Lys Tyr Cys Leu
1 5

<210> SEQ ID NO 1429
<211> LENGTH: 6
<212> TYPE: PRT
<213> ORGANISM: Homo sapiens

<400> SEQUENCE: 1429

Gly Lys Gly His Cys Leu
1 5

<210> SEQ ID NO 1430
<211> LENGTH: 6
<212> TYPE: PRT
<213> ORGANISM: Homo sapiens

<400> SEQUENCE: 1430

Gly Asn Gly Pro Cys Leu
1 5

<210> SEQ ID NO 1431
<211> LENGTH: 6
<212> TYPE: PRT
<213> ORGANISM: Homo sapiens

<400> SEQUENCE: 1431

Gly Asn Glu Ile Cys Leu
1 5

<210> SEQ ID NO 1432
<211> LENGTH: 6
<212> TYPE: PRT
<213> ORGANISM: Homo sapiens

<400> SEQUENCE: 1432

Gly Phe Gln Gly Cys Leu
1 5

<210> SEQ ID NO 1433
<211> LENGTH: 6
<212> TYPE: PRT
<213> ORGANISM: Homo sapiens

<400> SEQUENCE: 1433

Gly Arg Gly Glu Cys Leu
1 5

<210> SEQ ID NO 1434
<211> LENGTH: 6
<212> TYPE: PRT
<213> ORGANISM: Homo sapiens

<400> SEQUENCE: 1434

Gly Thr Val Pro Cys Leu
1 5

<210> SEQ ID NO 1435
<211> LENGTH: 6
<212> TYPE: PRT
<213> ORGANISM: Homo sapiens

<400> SEQUENCE: 1435

Gly Gly Phe Arg Cys Leu
1               5

<210> SEQ ID NO 1436
<211> LENGTH: 6
<212> TYPE: PRT
<213> ORGANISM: Homo sapiens

<400> SEQUENCE: 1436

Gly Ser Asp Glu Cys Leu
1               5

<210> SEQ ID NO 1437
<211> LENGTH: 6
<212> TYPE: PRT
<213> ORGANISM: Homo sapiens

<400> SEQUENCE: 1437

Gly Glu Ala Val Cys Leu
1               5

<210> SEQ ID NO 1438
<211> LENGTH: 6
<212> TYPE: PRT
<213> ORGANISM: Homo sapiens

<400> SEQUENCE: 1438

Gly Gln Thr Cys Cys Leu
1               5

<210> SEQ ID NO 1439
<211> LENGTH: 6
<212> TYPE: PRT
<213> ORGANISM: Homo sapiens

<400> SEQUENCE: 1439

Gly His Gly Asn Cys Leu
1               5

<210> SEQ ID NO 1440
<211> LENGTH: 6
<212> TYPE: PRT
<213> ORGANISM: Homo sapiens

<400> SEQUENCE: 1440

Gly Gln Met Val Cys Leu
1               5

<210> SEQ ID NO 1441
<211> LENGTH: 6
<212> TYPE: PRT
<213> ORGANISM: Homo sapiens

<400> SEQUENCE: 1441

Gly Pro Leu His Cys Leu
1               5

<210> SEQ ID NO 1442
<211> LENGTH: 6
<212> TYPE: PRT
<213> ORGANISM: Homo sapiens

<400> SEQUENCE: 1442

Gly His Gly Asp Cys Leu
1 5

<210> SEQ ID NO 1443
<211> LENGTH: 6
<212> TYPE: PRT
<213> ORGANISM: Homo sapiens

<400> SEQUENCE: 1443

Gly Gly Arg Tyr Cys Leu
1 5

<210> SEQ ID NO 1444
<211> LENGTH: 6
<212> TYPE: PRT
<213> ORGANISM: Homo sapiens

<400> SEQUENCE: 1444

Gly Met Ser Leu Cys Leu
1 5

<210> SEQ ID NO 1445
<211> LENGTH: 6
<212> TYPE: PRT
<213> ORGANISM: Homo sapiens

<400> SEQUENCE: 1445

Gly Ser Pro Val Cys Leu
1 5

<210> SEQ ID NO 1446
<211> LENGTH: 6
<212> TYPE: PRT
<213> ORGANISM: Homo sapiens

<400> SEQUENCE: 1446

Gly Ile His Glu Cys Leu
1 5

<210> SEQ ID NO 1447
<211> LENGTH: 6
<212> TYPE: PRT
<213> ORGANISM: Homo sapiens

<400> SEQUENCE: 1447

Gly Gly Ser Arg Cys Leu
1 5

<210> SEQ ID NO 1448
<211> LENGTH: 6
<212> TYPE: PRT
<213> ORGANISM: Homo sapiens

<400> SEQUENCE: 1448

Gly Leu Phe Gly Cys Leu
1 5

<210> SEQ ID NO 1449
<211> LENGTH: 6
<212> TYPE: PRT
<213> ORGANISM: Homo sapiens

<400> SEQUENCE: 1449

Gly Met Tyr Gln Cys Leu
1               5

<210> SEQ ID NO 1450
<211> LENGTH: 6
<212> TYPE: PRT
<213> ORGANISM: Homo sapiens

<400> SEQUENCE: 1450

Gly Gln Ala Met Cys Leu
1               5

<210> SEQ ID NO 1451
<211> LENGTH: 6
<212> TYPE: PRT
<213> ORGANISM: Homo sapiens

<400> SEQUENCE: 1451

Gly Trp Lys Pro Cys Leu
1               5

<210> SEQ ID NO 1452
<211> LENGTH: 6
<212> TYPE: PRT
<213> ORGANISM: Homo sapiens

<400> SEQUENCE: 1452

Gly Val Thr Arg Cys Leu
1               5

<210> SEQ ID NO 1453
<211> LENGTH: 6
<212> TYPE: PRT
<213> ORGANISM: Homo sapiens

<400> SEQUENCE: 1453

Gly Lys Ala Gln Cys Leu
1               5

<210> SEQ ID NO 1454
<211> LENGTH: 6
<212> TYPE: PRT
<213> ORGANISM: Homo sapiens

<400> SEQUENCE: 1454

Gly Ala Pro Arg Cys Leu
1               5

<210> SEQ ID NO 1455
<211> LENGTH: 6
<212> TYPE: PRT
<213> ORGANISM: Homo sapiens

<400> SEQUENCE: 1455

Gly Ser Val Leu Cys Leu
1               5

<210> SEQ ID NO 1456
<211> LENGTH: 6
<212> TYPE: PRT
<213> ORGANISM: Homo sapiens

<400> SEQUENCE: 1456

Gly Ile Val Thr Cys Leu
1 5

<210> SEQ ID NO 1457
<211> LENGTH: 6
<212> TYPE: PRT
<213> ORGANISM: Homo sapiens

<400> SEQUENCE: 1457

Gly Ser Gln Arg Cys Leu
1 5

<210> SEQ ID NO 1458
<211> LENGTH: 6
<212> TYPE: PRT
<213> ORGANISM: Homo sapiens

<400> SEQUENCE: 1458

Gly Ile Leu Gly Cys Leu
1 5

<210> SEQ ID NO 1459
<211> LENGTH: 6
<212> TYPE: PRT
<213> ORGANISM: Homo sapiens

<400> SEQUENCE: 1459

Gly Lys Met Ser Cys Leu
1 5

<210> SEQ ID NO 1460
<211> LENGTH: 6
<212> TYPE: PRT
<213> ORGANISM: Homo sapiens

<400> SEQUENCE: 1460

Gly Leu Asn Gln Cys Leu
1 5

<210> SEQ ID NO 1461
<211> LENGTH: 6
<212> TYPE: PRT
<213> ORGANISM: Homo sapiens

<400> SEQUENCE: 1461

Gly Phe Ile Val Cys Leu
1 5

<210> SEQ ID NO 1462
<211> LENGTH: 6
<212> TYPE: PRT
<213> ORGANISM: Homo sapiens

<400> SEQUENCE: 1462

Gly Lys Lys Ile Cys Leu
1 5

<210> SEQ ID NO 1463
<211> LENGTH: 6
<212> TYPE: PRT
<213> ORGANISM: Homo sapiens

<400> SEQUENCE: 1463

Gly Glu Cys Leu Cys Leu
1 5

<210> SEQ ID NO 1464
<211> LENGTH: 6
<212> TYPE: PRT
<213> ORGANISM: Homo sapiens

<400> SEQUENCE: 1464

Gly Gly Lys Ile Cys Leu
1 5

<210> SEQ ID NO 1465
<211> LENGTH: 6
<212> TYPE: PRT
<213> ORGANISM: Homo sapiens

<400> SEQUENCE: 1465

Gly Asp Leu Ile Cys Leu
1 5

<210> SEQ ID NO 1466
<211> LENGTH: 6
<212> TYPE: PRT
<213> ORGANISM: Homo sapiens

<400> SEQUENCE: 1466

Gly Ser Val Glu Cys Leu
1 5

<210> SEQ ID NO 1467
<211> LENGTH: 6
<212> TYPE: PRT
<213> ORGANISM: Homo sapiens

<400> SEQUENCE: 1467

Gly Pro Gly His Cys Leu
1 5

<210> SEQ ID NO 1468
<211> LENGTH: 6
<212> TYPE: PRT
<213> ORGANISM: Homo sapiens

<400> SEQUENCE: 1468

Gly Gln His Ser Cys Leu
1 5

<210> SEQ ID NO 1469
<211> LENGTH: 6
<212> TYPE: PRT
<213> ORGANISM: Homo sapiens

<400> SEQUENCE: 1469

Gly Lys Asp Asp Cys Leu
1 5

<210> SEQ ID NO 1470
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Any amino acid

<400> SEQUENCE: 1470

Xaa Arg Asn Val Cys Leu
1 5

<210> SEQ ID NO 1471
<211> LENGTH: 6
<212> TYPE: PRT
<213> ORGANISM: Homo sapiens

<400> SEQUENCE: 1471

Gly Thr Ala Thr Cys Leu
1 5

<210> SEQ ID NO 1472
<211> LENGTH: 6
<212> TYPE: PRT
<213> ORGANISM: Homo sapiens

<400> SEQUENCE: 1472

Gly Phe Gln Gly Cys Leu
1 5

<210> SEQ ID NO 1473
<211> LENGTH: 6
<212> TYPE: PRT
<213> ORGANISM: Homo sapiens

<400> SEQUENCE: 1473

Gly Val Pro His Cys Leu
1 5

<210> SEQ ID NO 1474
<211> LENGTH: 6
<212> TYPE: PRT
<213> ORGANISM: Homo sapiens

<400> SEQUENCE: 1474

Gly His Tyr Pro Cys Leu
1 5

<210> SEQ ID NO 1475
<211> LENGTH: 6
<212> TYPE: PRT
<213> ORGANISM: Homo sapiens

<400> SEQUENCE: 1475

Gly Glu Gln Pro Cys Leu
1 5

<210> SEQ ID NO 1476
<211> LENGTH: 6
<212> TYPE: PRT
<213> ORGANISM: Homo sapiens

<400> SEQUENCE: 1476

Gly Leu Cys Ile Cys Leu
1 5

<210> SEQ ID NO 1477
<211> LENGTH: 6
<212> TYPE: PRT
<213> ORGANISM: Homo sapiens

<400> SEQUENCE: 1477

Gly Asn Ile Asp Cys Leu
1 5

<210> SEQ ID NO 1478
<211> LENGTH: 6
<212> TYPE: PRT
<213> ORGANISM: Homo sapiens

<400> SEQUENCE: 1478

Gly His Val Glu Cys Leu
1 5

<210> SEQ ID NO 1479
<211> LENGTH: 6
<212> TYPE: PRT
<213> ORGANISM: Homo sapiens

<400> SEQUENCE: 1479

Gly His Glu Asp Cys Leu
1 5

<210> SEQ ID NO 1480
<211> LENGTH: 6
<212> TYPE: PRT
<213> ORGANISM: Homo sapiens

<400> SEQUENCE: 1480

Gly Thr Cys Ala Cys Leu
1 5

<210> SEQ ID NO 1481
<211> LENGTH: 6
<212> TYPE: PRT
<213> ORGANISM: Homo sapiens

<400> SEQUENCE: 1481

Gly Phe Arg Glu Cys Leu
1 5

<210> SEQ ID NO 1482
<211> LENGTH: 6
<212> TYPE: PRT
<213> ORGANISM: Homo sapiens

<400> SEQUENCE: 1482

Gly Val Glu Ile Cys Leu
1 5

<210> SEQ ID NO 1483
<211> LENGTH: 6
<212> TYPE: PRT
<213> ORGANISM: Homo sapiens

<400> SEQUENCE: 1483

Gly Asp Gln Arg Cys Leu
1 5

<210> SEQ ID NO 1484
<211> LENGTH: 6
<212> TYPE: PRT
<213> ORGANISM: Homo sapiens

<400> SEQUENCE: 1484

Gly Val Val Ser Cys Leu
1               5

<210> SEQ ID NO 1485
<211> LENGTH: 6
<212> TYPE: PRT
<213> ORGANISM: Homo sapiens

<400> SEQUENCE: 1485

Gly Ser Asn Pro Cys Leu
1               5

<210> SEQ ID NO 1486
<211> LENGTH: 6
<212> TYPE: PRT
<213> ORGANISM: Homo sapiens

<400> SEQUENCE: 1486

Gly Ser Val Gln Cys Leu
1               5

<210> SEQ ID NO 1487
<211> LENGTH: 6
<212> TYPE: PRT
<213> ORGANISM: Homo sapiens

<400> SEQUENCE: 1487

Gly Val Pro Lys Cys Leu
1               5

<210> SEQ ID NO 1488
<211> LENGTH: 6
<212> TYPE: PRT
<213> ORGANISM: Homo sapiens

<400> SEQUENCE: 1488

Gly Leu Asp Ser Cys Leu
1               5

<210> SEQ ID NO 1489
<211> LENGTH: 6
<212> TYPE: PRT
<213> ORGANISM: Homo sapiens

<400> SEQUENCE: 1489

Gly Ala Gly Phe Cys Leu
1               5

<210> SEQ ID NO 1490
<211> LENGTH: 6
<212> TYPE: PRT
<213> ORGANISM: Homo sapiens

<400> SEQUENCE: 1490

Gly Gly Arg Ser Cys Leu
1               5

<210> SEQ ID NO 1491
<211> LENGTH: 6
<212> TYPE: PRT
<213> ORGANISM: Homo sapiens

<400> SEQUENCE: 1491

Gly Met Ser Leu Cys Leu
1               5

<210> SEQ ID NO 1492
<211> LENGTH: 6
<212> TYPE: PRT
<213> ORGANISM: Homo sapiens

<400> SEQUENCE: 1492

Gly His Ala Glu Cys Leu
1               5

<210> SEQ ID NO 1493
<211> LENGTH: 6
<212> TYPE: PRT
<213> ORGANISM: Homo sapiens

<400> SEQUENCE: 1493

Gly Pro Glu Ser Cys Leu
1               5

<210> SEQ ID NO 1494
<211> LENGTH: 6
<212> TYPE: PRT
<213> ORGANISM: Homo sapiens

<400> SEQUENCE: 1494

Gly Gln Cys Ser Cys Leu
1               5

<210> SEQ ID NO 1495
<211> LENGTH: 6
<212> TYPE: PRT
<213> ORGANISM: Homo sapiens

<400> SEQUENCE: 1495

Gly Ala Ile Phe Cys Leu
1               5

<210> SEQ ID NO 1496
<211> LENGTH: 6
<212> TYPE: PRT
<213> ORGANISM: Homo sapiens

<400> SEQUENCE: 1496

Gly Gln Gly Val Cys Leu
1               5

<210> SEQ ID NO 1497
<211> LENGTH: 6
<212> TYPE: PRT
<213> ORGANISM: Homo sapiens

<400> SEQUENCE: 1497

Gly Gln Cys Gly Cys Leu
1               5

<210> SEQ ID NO 1498
<211> LENGTH: 6
<212> TYPE: PRT
<213> ORGANISM: Homo sapiens

<400> SEQUENCE: 1498

Gly Gln Gly Val Cys Leu
1 5

<210> SEQ ID NO 1499
<211> LENGTH: 6
<212> TYPE: PRT
<213> ORGANISM: Homo sapiens

<400> SEQUENCE: 1499

Gly Gln Cys Gly Cys Leu
1 5

<210> SEQ ID NO 1500
<211> LENGTH: 6
<212> TYPE: PRT
<213> ORGANISM: Homo sapiens

<400> SEQUENCE: 1500

Gly Gln Gly Val Cys Leu
1 5

<210> SEQ ID NO 1501
<211> LENGTH: 6
<212> TYPE: PRT
<213> ORGANISM: Homo sapiens

<400> SEQUENCE: 1501

Gly Gln Cys Gly Cys Leu
1 5

<210> SEQ ID NO 1502
<211> LENGTH: 6
<212> TYPE: PRT
<213> ORGANISM: Homo sapiens

<400> SEQUENCE: 1502

Gly Cys Gly Arg Cys Leu
1 5

<210> SEQ ID NO 1503
<211> LENGTH: 6
<212> TYPE: PRT
<213> ORGANISM: Homo sapiens

<400> SEQUENCE: 1503

Gly Cys Pro Val Cys Leu
1 5

<210> SEQ ID NO 1504
<211> LENGTH: 7
<212> TYPE: PRT
<213> ORGANISM: Homo sapiens

<400> SEQUENCE: 1504

Cys Asn Asn Ser Ala Val Cys
1 5

<210> SEQ ID NO 1505
<211> LENGTH: 7
<212> TYPE: PRT
<213> ORGANISM: Homo sapiens

<400> SEQUENCE: 1505

Cys Asn Ser Asp Val Val Cys
1 5

<210> SEQ ID NO 1506
<211> LENGTH: 7
<212> TYPE: PRT
<213> ORGANISM: Homo sapiens

<400> SEQUENCE: 1506

Cys Asn Val Trp Arg Val Cys
1 5

<210> SEQ ID NO 1507
<211> LENGTH: 7
<212> TYPE: PRT
<213> ORGANISM: Homo sapiens

<400> SEQUENCE: 1507

Cys Asn Ile Asn Asn Val Cys
1 5

<210> SEQ ID NO 1508
<211> LENGTH: 7
<212> TYPE: PRT
<213> ORGANISM: Homo sapiens

<400> SEQUENCE: 1508

Cys Asn Pro Gly Asp Val Cys
1 5

<210> SEQ ID NO 1509
<211> LENGTH: 7
<212> TYPE: PRT
<213> ORGANISM: Homo sapiens

<400> SEQUENCE: 1509

Cys Asn Gln Thr Ser Val Cys
1 5

<210> SEQ ID NO 1510
<211> LENGTH: 7
<212> TYPE: PRT
<213> ORGANISM: Homo sapiens

<400> SEQUENCE: 1510

Cys Asn Val His Gly Val Cys
1 5

<210> SEQ ID NO 1511
<211> LENGTH: 7
<212> TYPE: PRT
<213> ORGANISM: Homo sapiens

<400> SEQUENCE: 1511

Cys Asn Ile Asn Asn Val Cys
1 5

<210> SEQ ID NO 1512
<211> LENGTH: 7
<212> TYPE: PRT
<213> ORGANISM: Homo sapiens

<400> SEQUENCE: 1512

Cys Asn Ile His Gln Val Cys
1               5

<210> SEQ ID NO 1513
<211> LENGTH: 7
<212> TYPE: PRT
<213> ORGANISM: Homo sapiens

<400> SEQUENCE: 1513

Cys Asn Cys Cys Leu Val Cys
1               5

<210> SEQ ID NO 1514
<211> LENGTH: 7
<212> TYPE: PRT
<213> ORGANISM: Homo sapiens

<400> SEQUENCE: 1514

Cys Asn Val Asn Asp Val Cys
1               5

<210> SEQ ID NO 1515
<211> LENGTH: 7
<212> TYPE: PRT
<213> ORGANISM: Homo sapiens

<400> SEQUENCE: 1515

Cys Asn Asn Val Gln Val Cys
1               5

<210> SEQ ID NO 1516
<211> LENGTH: 7
<212> TYPE: PRT
<213> ORGANISM: Homo sapiens

<400> SEQUENCE: 1516

Cys Asn Arg Tyr Pro Val Cys
1               5

<210> SEQ ID NO 1517
<211> LENGTH: 7
<212> TYPE: PRT
<213> ORGANISM: Homo sapiens

<400> SEQUENCE: 1517

Cys Asn Ile Asn Glu Val Cys
1               5

<210> SEQ ID NO 1518
<211> LENGTH: 7
<212> TYPE: PRT
<213> ORGANISM: Homo sapiens

<400> SEQUENCE: 1518

Cys Asn Asn Arg Gly Val Cys
1               5

<210> SEQ ID NO 1519
<211> LENGTH: 7
<212> TYPE: PRT
<213> ORGANISM: Homo sapiens

<400> SEQUENCE: 1519

Cys Asn Arg Asn Glu Val Cys
1               5

<210> SEQ ID NO 1520
<211> LENGTH: 7
<212> TYPE: PRT
<213> ORGANISM: Homo sapiens

<400> SEQUENCE: 1520

Cys Asn Asp Arg Gly Val Cys
1               5

<210> SEQ ID NO 1521
<211> LENGTH: 7
<212> TYPE: PRT
<213> ORGANISM: Homo sapiens

<400> SEQUENCE: 1521

Cys Asn Gln Leu Asp Val Cys
1               5

<210> SEQ ID NO 1522
<211> LENGTH: 7
<212> TYPE: PRT
<213> ORGANISM: Homo sapiens

<400> SEQUENCE: 1522

Cys Asn Asp Met Pro Val Cys
1               5

<210> SEQ ID NO 1523
<211> LENGTH: 7
<212> TYPE: PRT
<213> ORGANISM: Homo sapiens

<400> SEQUENCE: 1523

Cys Asn Gly His Gly Val Cys
1               5

<210> SEQ ID NO 1524
<211> LENGTH: 7
<212> TYPE: PRT
<213> ORGANISM: Homo sapiens

<400> SEQUENCE: 1524

Cys Asn Leu Leu Val Val Cys
1               5

<210> SEQ ID NO 1525
<211> LENGTH: 7
<212> TYPE: PRT
<213> ORGANISM: Homo sapiens

<400> SEQUENCE: 1525

Cys Asn Gln Val Leu Val Cys
1               5

<210> SEQ ID NO 1526
<211> LENGTH: 7
<212> TYPE: PRT
<213> ORGANISM: Homo sapiens

<400> SEQUENCE: 1526

Cys Asn Asp Pro Met Val Cys
1               5

<210> SEQ ID NO 1527
<211> LENGTH: 7
<212> TYPE: PRT
<213> ORGANISM: Homo sapiens

<400> SEQUENCE: 1527

Cys Asn Thr Arg Gly Val Cys
1               5

<210> SEQ ID NO 1528
<211> LENGTH: 5
<212> TYPE: PRT
<213> ORGANISM: Homo sapiens

<400> SEQUENCE: 1528

Pro Phe Ser Thr Cys
1               5

<210> SEQ ID NO 1529
<211> LENGTH: 5
<212> TYPE: PRT
<213> ORGANISM: Homo sapiens

<400> SEQUENCE: 1529

Pro Phe Asp Leu Cys
1               5

<210> SEQ ID NO 1530
<211> LENGTH: 5
<212> TYPE: PRT
<213> ORGANISM: Homo sapiens

<400> SEQUENCE: 1530

Pro Phe Gln Leu Cys
1               5

<210> SEQ ID NO 1531
<211> LENGTH: 5
<212> TYPE: PRT
<213> ORGANISM: Homo sapiens

<400> SEQUENCE: 1531

Pro Phe Pro Asn Cys
1               5

<210> SEQ ID NO 1532
<211> LENGTH: 5
<212> TYPE: PRT
<213> ORGANISM: Homo sapiens

<400> SEQUENCE: 1532

Pro Phe Cys Leu Cys
1               5

<210> SEQ ID NO 1533
<211> LENGTH: 5
<212> TYPE: PRT
<213> ORGANISM: Homo sapiens

<400> SEQUENCE: 1533

Pro Phe Gly Gln Cys
1 5

<210> SEQ ID NO 1534
<211> LENGTH: 5
<212> TYPE: PRT
<213> ORGANISM: Homo sapiens

<400> SEQUENCE: 1534

Pro Phe Lys Asp Cys
1 5

<210> SEQ ID NO 1535
<211> LENGTH: 5
<212> TYPE: PRT
<213> ORGANISM: Homo sapiens

<400> SEQUENCE: 1535

Pro Phe Ile Leu Cys
1 5

<210> SEQ ID NO 1536
<211> LENGTH: 5
<212> TYPE: PRT
<213> ORGANISM: Homo sapiens

<400> SEQUENCE: 1536

Pro Phe Ser Glu Cys
1 5

<210> SEQ ID NO 1537
<211> LENGTH: 5
<212> TYPE: PRT
<213> ORGANISM: Homo sapiens

<400> SEQUENCE: 1537

Pro Phe Leu Cys Cys
1 5

<210> SEQ ID NO 1538
<211> LENGTH: 5
<212> TYPE: PRT
<213> ORGANISM: Homo sapiens

<400> SEQUENCE: 1538

Pro Phe Tyr Asp Cys
1 5

<210> SEQ ID NO 1539
<211> LENGTH: 5
<212> TYPE: PRT
<213> ORGANISM: Homo sapiens

<400> SEQUENCE: 1539

Pro Phe Thr Leu Cys
1 5

<210> SEQ ID NO 1540
<211> LENGTH: 5
<212> TYPE: PRT
<213> ORGANISM: Homo sapiens

<400> SEQUENCE: 1540

Pro Phe Leu Pro Cys
1 5

<210> SEQ ID NO 1541
<211> LENGTH: 5
<212> TYPE: PRT
<213> ORGANISM: Homo sapiens

<400> SEQUENCE: 1541

Pro Phe Ile Leu Cys
1 5

<210> SEQ ID NO 1542
<211> LENGTH: 5
<212> TYPE: PRT
<213> ORGANISM: Homo sapiens

<400> SEQUENCE: 1542

Pro Phe Ser Ser Cys
1 5

<210> SEQ ID NO 1543
<211> LENGTH: 5
<212> TYPE: PRT
<213> ORGANISM: Homo sapiens

<400> SEQUENCE: 1543

Pro Phe Ala Ala Cys
1 5

<210> SEQ ID NO 1544
<211> LENGTH: 5
<212> TYPE: PRT
<213> ORGANISM: Homo sapiens

<400> SEQUENCE: 1544

Pro Phe Leu Arg Cys
1 5

<210> SEQ ID NO 1545
<211> LENGTH: 5
<212> TYPE: PRT
<213> ORGANISM: Homo sapiens

<400> SEQUENCE: 1545

Pro Phe Val Gly Cys
1 5

<210> SEQ ID NO 1546
<211> LENGTH: 5
<212> TYPE: PRT
<213> ORGANISM: Homo sapiens

<400> SEQUENCE: 1546

Pro Phe Gln Asn Cys
1 5

<210> SEQ ID NO 1547
<211> LENGTH: 5
<212> TYPE: PRT
<213> ORGANISM: Homo sapiens

<400> SEQUENCE: 1547

Pro Phe Pro Gly Cys
1               5

<210> SEQ ID NO 1548
<211> LENGTH: 5
<212> TYPE: PRT
<213> ORGANISM: Homo sapiens

<400> SEQUENCE: 1548

Pro Phe Thr Ala Cys
1               5

<210> SEQ ID NO 1549
<211> LENGTH: 5
<212> TYPE: PRT
<213> ORGANISM: Homo sapiens

<400> SEQUENCE: 1549

Pro Phe Ser Ile Cys
1               5

<210> SEQ ID NO 1550
<211> LENGTH: 5
<212> TYPE: PRT
<213> ORGANISM: Homo sapiens

<400> SEQUENCE: 1550

Pro Phe Lys Leu Cys
1               5

<210> SEQ ID NO 1551
<211> LENGTH: 5
<212> TYPE: PRT
<213> ORGANISM: Homo sapiens

<400> SEQUENCE: 1551

Pro Phe Asp Asn Cys
1               5

<210> SEQ ID NO 1552
<211> LENGTH: 5
<212> TYPE: PRT
<213> ORGANISM: Homo sapiens

<400> SEQUENCE: 1552

Pro Phe Glu Ser Cys
1               5

<210> SEQ ID NO 1553
<211> LENGTH: 5
<212> TYPE: PRT
<213> ORGANISM: Homo sapiens

<400> SEQUENCE: 1553

Pro Phe Arg His Cys
1               5

<210> SEQ ID NO 1554
<211> LENGTH: 5
<212> TYPE: PRT
<213> ORGANISM: Homo sapiens

<400> SEQUENCE: 1554

Pro Phe Tyr Thr Cys
1 5

<210> SEQ ID NO 1555
<211> LENGTH: 5
<212> TYPE: PRT
<213> ORGANISM: Homo sapiens

<400> SEQUENCE: 1555

Pro Phe Leu Tyr Cys
1 5

<210> SEQ ID NO 1556
<211> LENGTH: 5
<212> TYPE: PRT
<213> ORGANISM: Homo sapiens

<400> SEQUENCE: 1556

Pro Phe Lys Pro Cys
1 5

<210> SEQ ID NO 1557
<211> LENGTH: 5
<212> TYPE: PRT
<213> ORGANISM: Homo sapiens

<400> SEQUENCE: 1557

Pro Phe Phe Leu Cys
1 5

<210> SEQ ID NO 1558
<211> LENGTH: 5
<212> TYPE: PRT
<213> ORGANISM: Homo sapiens

<400> SEQUENCE: 1558

Pro Phe Tyr Gln Cys
1 5

<210> SEQ ID NO 1559
<211> LENGTH: 5
<212> TYPE: PRT
<213> ORGANISM: Homo sapiens

<400> SEQUENCE: 1559

Pro Phe Ile His Cys
1 5

<210> SEQ ID NO 1560
<211> LENGTH: 5
<212> TYPE: PRT
<213> ORGANISM: Homo sapiens

<400> SEQUENCE: 1560

Pro Phe Gly Gln Cys
1 5

<210> SEQ ID NO 1561
<211> LENGTH: 5
<212> TYPE: PRT
<213> ORGANISM: Homo sapiens

<400> SEQUENCE: 1561

Pro Phe Ala Ile Cys
1 5

<210> SEQ ID NO 1562
<211> LENGTH: 5
<212> TYPE: PRT
<213> ORGANISM: Homo sapiens

<400> SEQUENCE: 1562

Pro Phe Gln Ser Cys
1 5

<210> SEQ ID NO 1563
<211> LENGTH: 5
<212> TYPE: PRT
<213> ORGANISM: Homo sapiens

<400> SEQUENCE: 1563

Pro Phe Ile Tyr Cys
1 5

<210> SEQ ID NO 1564
<211> LENGTH: 5
<212> TYPE: PRT
<213> ORGANISM: Homo sapiens

<400> SEQUENCE: 1564

Pro Phe Tyr Asp Cys
1 5

<210> SEQ ID NO 1565
<211> LENGTH: 5
<212> TYPE: PRT
<213> ORGANISM: Homo sapiens

<400> SEQUENCE: 1565

Pro Phe Gly Cys Cys
1 5

<210> SEQ ID NO 1566
<211> LENGTH: 5
<212> TYPE: PRT
<213> ORGANISM: Homo sapiens

<400> SEQUENCE: 1566

Pro Phe Pro Gly Cys
1 5

<210> SEQ ID NO 1567
<211> LENGTH: 5
<212> TYPE: PRT
<213> ORGANISM: Homo sapiens

<400> SEQUENCE: 1567

Pro Phe Gly Ser Cys
1 5

<210> SEQ ID NO 1568
<211> LENGTH: 5
<212> TYPE: PRT
<213> ORGANISM: Homo sapiens

<400> SEQUENCE: 1568

Pro Phe Ser Arg Cys
1               5

<210> SEQ ID NO 1569
<211> LENGTH: 5
<212> TYPE: PRT
<213> ORGANISM: Homo sapiens

<400> SEQUENCE: 1569

Pro Phe Lys Asp Cys
1               5

<210> SEQ ID NO 1570
<211> LENGTH: 5
<212> TYPE: PRT
<213> ORGANISM: Homo sapiens

<400> SEQUENCE: 1570

Pro Phe Asp Thr Cys
1               5

<210> SEQ ID NO 1571
<211> LENGTH: 5
<212> TYPE: PRT
<213> ORGANISM: Homo sapiens

<400> SEQUENCE: 1571

Pro Phe Gly Glu Cys
1               5

<210> SEQ ID NO 1572
<211> LENGTH: 5
<212> TYPE: PRT
<213> ORGANISM: Homo sapiens

<400> SEQUENCE: 1572

Pro Phe Leu Phe Cys
1               5

<210> SEQ ID NO 1573
<211> LENGTH: 5
<212> TYPE: PRT
<213> ORGANISM: Homo sapiens

<400> SEQUENCE: 1573

Pro Phe Ile Glu Cys
1               5

<210> SEQ ID NO 1574
<211> LENGTH: 5
<212> TYPE: PRT
<213> ORGANISM: Homo sapiens

<400> SEQUENCE: 1574

Pro Phe Pro Thr Cys
1               5

<210> SEQ ID NO 1575
<211> LENGTH: 5
<212> TYPE: PRT
<213> ORGANISM: Homo sapiens

<400> SEQUENCE: 1575

Pro Phe Leu Tyr Cys
1               5

<210> SEQ ID NO 1576
<211> LENGTH: 5
<212> TYPE: PRT
<213> ORGANISM: Homo sapiens

<400> SEQUENCE: 1576

Pro Phe Ile Glu Cys
1               5

<210> SEQ ID NO 1577
<211> LENGTH: 5
<212> TYPE: PRT
<213> ORGANISM: Homo sapiens

<400> SEQUENCE: 1577

Pro Phe Val Gln Cys
1               5

<210> SEQ ID NO 1578
<211> LENGTH: 5
<212> TYPE: PRT
<213> ORGANISM: Homo sapiens

<400> SEQUENCE: 1578

Pro Phe Gly Thr Cys
1               5

<210> SEQ ID NO 1579
<211> LENGTH: 5
<212> TYPE: PRT
<213> ORGANISM: Homo sapiens

<400> SEQUENCE: 1579

Pro Phe Leu Ser Cys
1               5

<210> SEQ ID NO 1580
<211> LENGTH: 5
<212> TYPE: PRT
<213> ORGANISM: Homo sapiens

<400> SEQUENCE: 1580

Pro Phe Leu Ser Cys
1               5

<210> SEQ ID NO 1581
<211> LENGTH: 5
<212> TYPE: PRT
<213> ORGANISM: Homo sapiens

<400> SEQUENCE: 1581

Pro Phe Arg Asn Cys
1               5

<210> SEQ ID NO 1582
<211> LENGTH: 5
<212> TYPE: PRT
<213> ORGANISM: Homo sapiens

<400> SEQUENCE: 1582

Pro Phe Tyr Cys Cys
1 5

<210> SEQ ID NO 1583
<211> LENGTH: 5
<212> TYPE: PRT
<213> ORGANISM: Homo sapiens

<400> SEQUENCE: 1583

Pro Phe Cys Glu Cys
1 5

<210> SEQ ID NO 1584
<211> LENGTH: 5
<212> TYPE: PRT
<213> ORGANISM: Homo sapiens

<400> SEQUENCE: 1584

Pro Phe Tyr Ser Cys
1 5

<210> SEQ ID NO 1585
<211> LENGTH: 5
<212> TYPE: PRT
<213> ORGANISM: Homo sapiens

<400> SEQUENCE: 1585

Pro Phe Pro Ile Cys
1 5

<210> SEQ ID NO 1586
<211> LENGTH: 5
<212> TYPE: PRT
<213> ORGANISM: Homo sapiens

<400> SEQUENCE: 1586

Pro Phe Leu Leu Cys
1 5

<210> SEQ ID NO 1587
<211> LENGTH: 5
<212> TYPE: PRT
<213> ORGANISM: Homo sapiens

<400> SEQUENCE: 1587

Pro Phe Tyr His Cys
1 5

<210> SEQ ID NO 1588
<211> LENGTH: 5
<212> TYPE: PRT
<213> ORGANISM: Homo sapiens

<400> SEQUENCE: 1588

Pro Phe Phe Thr Cys
1 5

<210> SEQ ID NO 1589
<211> LENGTH: 5
<212> TYPE: PRT
<213> ORGANISM: Homo sapiens

<400> SEQUENCE: 1589

Pro Phe Leu Pro Cys
1 5

<210> SEQ ID NO 1590
<211> LENGTH: 5
<212> TYPE: PRT
<213> ORGANISM: Homo sapiens

<400> SEQUENCE: 1590

Pro Phe Ser Arg Cys
1 5

<210> SEQ ID NO 1591
<211> LENGTH: 5
<212> TYPE: PRT
<213> ORGANISM: Homo sapiens

<400> SEQUENCE: 1591

Pro Phe Cys Arg Cys
1 5

<210> SEQ ID NO 1592
<211> LENGTH: 5
<212> TYPE: PRT
<213> ORGANISM: Homo sapiens

<400> SEQUENCE: 1592

Pro Phe Ser Cys Cys
1 5

<210> SEQ ID NO 1593
<211> LENGTH: 5
<212> TYPE: PRT
<213> ORGANISM: Homo sapiens

<400> SEQUENCE: 1593

Pro Phe Glu Gly Cys
1 5

<210> SEQ ID NO 1594
<211> LENGTH: 5
<212> TYPE: PRT
<213> ORGANISM: Homo sapiens

<400> SEQUENCE: 1594

Pro Phe Arg Gly Cys
1 5

<210> SEQ ID NO 1595
<211> LENGTH: 5
<212> TYPE: PRT
<213> ORGANISM: Homo sapiens

<400> SEQUENCE: 1595

Pro Phe Gln Leu Cys
1 5

<210> SEQ ID NO 1596
<211> LENGTH: 5
<212> TYPE: PRT
<213> ORGANISM: Homo sapiens

<400> SEQUENCE: 1596

Pro Phe Ile Val Cys
1 5

<210> SEQ ID NO 1597
<211> LENGTH: 5
<212> TYPE: PRT
<213> ORGANISM: Homo sapiens

<400> SEQUENCE: 1597

Pro Phe Asp Gly Cys
1 5

<210> SEQ ID NO 1598
<211> LENGTH: 5
<212> TYPE: PRT
<213> ORGANISM: Homo sapiens

<400> SEQUENCE: 1598

Pro Phe Val Gln Cys
1 5

<210> SEQ ID NO 1599
<211> LENGTH: 5
<212> TYPE: PRT
<213> ORGANISM: Homo sapiens

<400> SEQUENCE: 1599

Pro Phe Phe Phe Cys
1 5

<210> SEQ ID NO 1600
<211> LENGTH: 5
<212> TYPE: PRT
<213> ORGANISM: Homo sapiens

<400> SEQUENCE: 1600

Pro Phe Asp Tyr Cys
1 5

<210> SEQ ID NO 1601
<211> LENGTH: 5
<212> TYPE: PRT
<213> ORGANISM: Homo sapiens

<400> SEQUENCE: 1601

Pro Phe Phe Lys Cys
1 5

<210> SEQ ID NO 1602
<211> LENGTH: 5
<212> TYPE: PRT
<213> ORGANISM: Homo sapiens

<400> SEQUENCE: 1602

Pro Phe Met Phe Cys
1 5

<210> SEQ ID NO 1603
<211> LENGTH: 5
<212> TYPE: PRT
<213> ORGANISM: Homo sapiens

<400> SEQUENCE: 1603

Pro Phe Ile Glu Cys
1               5

<210> SEQ ID NO 1604
<211> LENGTH: 5
<212> TYPE: PRT
<213> ORGANISM: Homo sapiens

<400> SEQUENCE: 1604

Pro Phe Glu His Cys
1               5

<210> SEQ ID NO 1605
<211> LENGTH: 5
<212> TYPE: PRT
<213> ORGANISM: Homo sapiens

<400> SEQUENCE: 1605

Pro Phe His Leu Cys
1               5

<210> SEQ ID NO 1606
<211> LENGTH: 5
<212> TYPE: PRT
<213> ORGANISM: Homo sapiens

<400> SEQUENCE: 1606

Pro Phe Glu His Cys
1               5

<210> SEQ ID NO 1607
<211> LENGTH: 5
<212> TYPE: PRT
<213> ORGANISM: Homo sapiens

<400> SEQUENCE: 1607

Pro Phe Ile Val Cys
1               5

<210> SEQ ID NO 1608
<211> LENGTH: 5
<212> TYPE: PRT
<213> ORGANISM: Homo sapiens

<400> SEQUENCE: 1608

Pro Phe Tyr Val Cys
1               5

<210> SEQ ID NO 1609
<211> LENGTH: 5
<212> TYPE: PRT
<213> ORGANISM: Homo sapiens

<400> SEQUENCE: 1609

Pro Phe Glu Gly Cys
1               5

<210> SEQ ID NO 1610
<211> LENGTH: 5
<212> TYPE: PRT
<213> ORGANISM: Homo sapiens

<400> SEQUENCE: 1610

Pro Phe Asp Asn Cys
1 5

<210> SEQ ID NO 1611
<211> LENGTH: 5
<212> TYPE: PRT
<213> ORGANISM: Homo sapiens

<400> SEQUENCE: 1611

Pro Phe Leu Lys Cys
1 5

<210> SEQ ID NO 1612
<211> LENGTH: 5
<212> TYPE: PRT
<213> ORGANISM: Homo sapiens

<400> SEQUENCE: 1612

Pro Phe Ser Asn Cys
1 5

<210> SEQ ID NO 1613
<211> LENGTH: 5
<212> TYPE: PRT
<213> ORGANISM: Homo sapiens

<400> SEQUENCE: 1613

Pro Phe Leu Asp Cys
1 5

<210> SEQ ID NO 1614
<211> LENGTH: 5
<212> TYPE: PRT
<213> ORGANISM: Homo sapiens

<400> SEQUENCE: 1614

Pro Phe Pro Val Cys
1 5

<210> SEQ ID NO 1615
<211> LENGTH: 5
<212> TYPE: PRT
<213> ORGANISM: Homo sapiens

<400> SEQUENCE: 1615

Pro Phe Ser Ser Cys
1 5

<210> SEQ ID NO 1616
<211> LENGTH: 5
<212> TYPE: PRT
<213> ORGANISM: Homo sapiens

<400> SEQUENCE: 1616

Pro Phe Tyr Arg Cys
1 5

<210> SEQ ID NO 1617
<211> LENGTH: 5
<212> TYPE: PRT
<213> ORGANISM: Homo sapiens

<400> SEQUENCE: 1617

Pro Phe Glu Asn Cys
1               5

<210> SEQ ID NO 1618
<211> LENGTH: 5
<212> TYPE: PRT
<213> ORGANISM: Homo sapiens

<400> SEQUENCE: 1618

Pro Phe Pro Ser Cys
1               5

<210> SEQ ID NO 1619
<211> LENGTH: 5
<212> TYPE: PRT
<213> ORGANISM: Homo sapiens

<400> SEQUENCE: 1619

Pro Phe Leu Glu Cys
1               5

<210> SEQ ID NO 1620
<211> LENGTH: 5
<212> TYPE: PRT
<213> ORGANISM: Homo sapiens

<400> SEQUENCE: 1620

Pro Phe Leu Tyr Cys
1               5

<210> SEQ ID NO 1621
<211> LENGTH: 5
<212> TYPE: PRT
<213> ORGANISM: Homo sapiens

<400> SEQUENCE: 1621

Pro Phe Val Leu Cys
1               5

<210> SEQ ID NO 1622
<211> LENGTH: 5
<212> TYPE: PRT
<213> ORGANISM: Homo sapiens

<400> SEQUENCE: 1622

Pro Phe Lys Gly Cys
1               5

<210> SEQ ID NO 1623
<211> LENGTH: 5
<212> TYPE: PRT
<213> ORGANISM: Homo sapiens

<400> SEQUENCE: 1623

Pro Phe Pro Phe Cys
1               5

<210> SEQ ID NO 1624
<211> LENGTH: 5
<212> TYPE: PRT
<213> ORGANISM: Homo sapiens

<400> SEQUENCE: 1624

Pro Phe Cys Ser Cys
1               5

<210> SEQ ID NO 1625
<211> LENGTH: 5
<212> TYPE: PRT
<213> ORGANISM: Homo sapiens

<400> SEQUENCE: 1625

Pro Phe Pro Leu Cys
1               5

<210> SEQ ID NO 1626
<211> LENGTH: 5
<212> TYPE: PRT
<213> ORGANISM: Homo sapiens

<400> SEQUENCE: 1626

Pro Phe Glu Cys Cys
1               5

<210> SEQ ID NO 1627
<211> LENGTH: 5
<212> TYPE: PRT
<213> ORGANISM: Homo sapiens

<400> SEQUENCE: 1627

Pro Phe Glu Gly Cys
1               5

<210> SEQ ID NO 1628
<211> LENGTH: 5
<212> TYPE: PRT
<213> ORGANISM: Homo sapiens

<400> SEQUENCE: 1628

Pro Phe Ala Tyr Cys
1               5

<210> SEQ ID NO 1629
<211> LENGTH: 5
<212> TYPE: PRT
<213> ORGANISM: Homo sapiens

<400> SEQUENCE: 1629

Pro Phe Leu Glu Cys
1               5

<210> SEQ ID NO 1630
<211> LENGTH: 5
<212> TYPE: PRT
<213> ORGANISM: Homo sapiens

<400> SEQUENCE: 1630

Pro Phe Asp Ile Cys
1               5

<210> SEQ ID NO 1631
<211> LENGTH: 5
<212> TYPE: PRT
<213> ORGANISM: Homo sapiens

<400> SEQUENCE: 1631

Pro Phe Asp Glu Cys
1 5

<210> SEQ ID NO 1632
<211> LENGTH: 5
<212> TYPE: PRT
<213> ORGANISM: Homo sapiens

<400> SEQUENCE: 1632

Pro Phe Cys Leu Cys
1 5

<210> SEQ ID NO 1633
<211> LENGTH: 5
<212> TYPE: PRT
<213> ORGANISM: Homo sapiens

<400> SEQUENCE: 1633

Pro Phe Ile Trp Cys
1 5

<210> SEQ ID NO 1634
<211> LENGTH: 5
<212> TYPE: PRT
<213> ORGANISM: Homo sapiens

<400> SEQUENCE: 1634

Pro Phe Leu Val Cys
1 5

<210> SEQ ID NO 1635
<211> LENGTH: 5
<212> TYPE: PRT
<213> ORGANISM: Homo sapiens

<400> SEQUENCE: 1635

Pro Phe Ser Cys Cys
1 5

<210> SEQ ID NO 1636
<211> LENGTH: 5
<212> TYPE: PRT
<213> ORGANISM: Homo sapiens

<400> SEQUENCE: 1636

Pro Phe Val Gly Cys
1 5

<210> SEQ ID NO 1637
<211> LENGTH: 5
<212> TYPE: PRT
<213> ORGANISM: Homo sapiens

<400> SEQUENCE: 1637

Pro Phe Val Ser Cys
1 5

<210> SEQ ID NO 1638
<211> LENGTH: 5
<212> TYPE: PRT
<213> ORGANISM: Homo sapiens

<400> SEQUENCE: 1638

Pro Phe Asp Gly Cys
1               5

<210> SEQ ID NO 1639
<211> LENGTH: 5
<212> TYPE: PRT
<213> ORGANISM: Homo sapiens

<400> SEQUENCE: 1639

Pro Phe Lys Met Cys
1               5

<210> SEQ ID NO 1640
<211> LENGTH: 5
<212> TYPE: PRT
<213> ORGANISM: Homo sapiens

<400> SEQUENCE: 1640

Pro Phe Leu Phe Cys
1               5

<210> SEQ ID NO 1641
<211> LENGTH: 5
<212> TYPE: PRT
<213> ORGANISM: Homo sapiens

<400> SEQUENCE: 1641

Pro Phe Leu Glu Cys
1               5

<210> SEQ ID NO 1642
<211> LENGTH: 5
<212> TYPE: PRT
<213> ORGANISM: Homo sapiens

<400> SEQUENCE: 1642

Pro Phe Gly Arg Cys
1               5

<210> SEQ ID NO 1643
<211> LENGTH: 5
<212> TYPE: PRT
<213> ORGANISM: Homo sapiens

<400> SEQUENCE: 1643

Pro Phe Gly Leu Cys
1               5

<210> SEQ ID NO 1644
<211> LENGTH: 5
<212> TYPE: PRT
<213> ORGANISM: Homo sapiens

<400> SEQUENCE: 1644

Pro Phe Tyr Trp Cys
1               5

<210> SEQ ID NO 1645
<211> LENGTH: 5
<212> TYPE: PRT
<213> ORGANISM: Homo sapiens

<400> SEQUENCE: 1645

Pro Phe Ser Cys Cys
1 5

<210> SEQ ID NO 1646
<211> LENGTH: 5
<212> TYPE: PRT
<213> ORGANISM: Homo sapiens

<400> SEQUENCE: 1646

Pro Phe Ala Trp Cys
1 5

<210> SEQ ID NO 1647
<211> LENGTH: 5
<212> TYPE: PRT
<213> ORGANISM: Homo sapiens

<400> SEQUENCE: 1647

Pro Phe Tyr Gln Cys
1 5

<210> SEQ ID NO 1648
<211> LENGTH: 5
<212> TYPE: PRT
<213> ORGANISM: Homo sapiens

<400> SEQUENCE: 1648

Pro Phe Thr Ser Cys
1 5

<210> SEQ ID NO 1649
<211> LENGTH: 5
<212> TYPE: PRT
<213> ORGANISM: Homo sapiens

<400> SEQUENCE: 1649

Pro Phe Arg Asn Cys
1 5

<210> SEQ ID NO 1650
<211> LENGTH: 5
<212> TYPE: PRT
<213> ORGANISM: Homo sapiens

<400> SEQUENCE: 1650

Pro Phe Pro Cys Cys
1 5

<210> SEQ ID NO 1651
<211> LENGTH: 5
<212> TYPE: PRT
<213> ORGANISM: Homo sapiens

<400> SEQUENCE: 1651

Pro Phe Gln Tyr Cys
1 5

<210> SEQ ID NO 1652
<211> LENGTH: 5
<212> TYPE: PRT
<213> ORGANISM: Homo sapiens

<400> SEQUENCE: 1652

Pro Phe Cys Arg Cys
1 5

<210> SEQ ID NO 1653
<211> LENGTH: 5
<212> TYPE: PRT
<213> ORGANISM: Homo sapiens

<400> SEQUENCE: 1653

Pro Phe Tyr Arg Cys
1 5

<210> SEQ ID NO 1654
<211> LENGTH: 5
<212> TYPE: PRT
<213> ORGANISM: Homo sapiens

<400> SEQUENCE: 1654

Pro Phe Asp His Cys
1 5

<210> SEQ ID NO 1655
<211> LENGTH: 5
<212> TYPE: PRT
<213> ORGANISM: Homo sapiens

<400> SEQUENCE: 1655

Pro Phe Gln Ser Cys
1 5

<210> SEQ ID NO 1656
<211> LENGTH: 5
<212> TYPE: PRT
<213> ORGANISM: Homo sapiens

<400> SEQUENCE: 1656

Pro Phe Gly Thr Cys
1 5

<210> SEQ ID NO 1657
<211> LENGTH: 5
<212> TYPE: PRT
<213> ORGANISM: Homo sapiens

<400> SEQUENCE: 1657

Pro Phe Val Asn Cys
1 5

<210> SEQ ID NO 1658
<211> LENGTH: 5
<212> TYPE: PRT
<213> ORGANISM: Homo sapiens

<400> SEQUENCE: 1658

Pro Phe Ile Tyr Cys
1 5

<210> SEQ ID NO 1659
<211> LENGTH: 5
<212> TYPE: PRT
<213> ORGANISM: Homo sapiens

<400> SEQUENCE: 1659

Pro Phe Ile Glu Cys
1 5

<210> SEQ ID NO 1660
<211> LENGTH: 5
<212> TYPE: PRT
<213> ORGANISM: Homo sapiens

<400> SEQUENCE: 1660

Pro Phe Pro Thr Cys
1 5

<210> SEQ ID NO 1661
<211> LENGTH: 5
<212> TYPE: PRT
<213> ORGANISM: Homo sapiens

<400> SEQUENCE: 1661

Pro Phe His Ile Cys
1 5

<210> SEQ ID NO 1662
<211> LENGTH: 5
<212> TYPE: PRT
<213> ORGANISM: Homo sapiens

<400> SEQUENCE: 1662

Pro Phe Thr Asp Cys
1 5

<210> SEQ ID NO 1663
<211> LENGTH: 5
<212> TYPE: PRT
<213> ORGANISM: Homo sapiens

<400> SEQUENCE: 1663

Pro Phe Gly Ala Cys
1 5

<210> SEQ ID NO 1664
<211> LENGTH: 5
<212> TYPE: PRT
<213> ORGANISM: Homo sapiens

<400> SEQUENCE: 1664

Pro Phe Arg Asp Cys
1 5

<210> SEQ ID NO 1665
<211> LENGTH: 5
<212> TYPE: PRT
<213> ORGANISM: Homo sapiens

<400> SEQUENCE: 1665

Pro Phe His Ser Cys
1 5

<210> SEQ ID NO 1666
<211> LENGTH: 5
<212> TYPE: PRT
<213> ORGANISM: Homo sapiens

<400> SEQUENCE: 1666

Pro Phe Ser Leu Cys
1               5

<210> SEQ ID NO 1667
<211> LENGTH: 5
<212> TYPE: PRT
<213> ORGANISM: Homo sapiens

<400> SEQUENCE: 1667

Pro Phe Leu Gln Cys
1               5

<210> SEQ ID NO 1668
<211> LENGTH: 5
<212> TYPE: PRT
<213> ORGANISM: Homo sapiens

<400> SEQUENCE: 1668

Pro Phe Pro Gly Cys
1               5

<210> SEQ ID NO 1669
<211> LENGTH: 5
<212> TYPE: PRT
<213> ORGANISM: Homo sapiens

<400> SEQUENCE: 1669

Pro Phe Thr Gly Cys
1               5

<210> SEQ ID NO 1670
<211> LENGTH: 5
<212> TYPE: PRT
<213> ORGANISM: Homo sapiens

<400> SEQUENCE: 1670

Pro Phe Asp Glu Cys
1               5

<210> SEQ ID NO 1671
<211> LENGTH: 5
<212> TYPE: PRT
<213> ORGANISM: Homo sapiens

<400> SEQUENCE: 1671

Pro Phe Ser Thr Cys
1               5

<210> SEQ ID NO 1672
<211> LENGTH: 5
<212> TYPE: PRT
<213> ORGANISM: Homo sapiens

<400> SEQUENCE: 1672

Pro Phe Phe Asp Cys
1               5

<210> SEQ ID NO 1673
<211> LENGTH: 5
<212> TYPE: PRT
<213> ORGANISM: Homo sapiens

<400> SEQUENCE: 1673

Pro Phe Asp Thr Cys
1               5

<210> SEQ ID NO 1674
<211> LENGTH: 5
<212> TYPE: PRT
<213> ORGANISM: Homo sapiens

<400> SEQUENCE: 1674

Pro Phe Ser Thr Cys
1               5

<210> SEQ ID NO 1675
<211> LENGTH: 5
<212> TYPE: PRT
<213> ORGANISM: Homo sapiens

<400> SEQUENCE: 1675

Pro Phe Leu Ala Cys
1               5

<210> SEQ ID NO 1676
<211> LENGTH: 5
<212> TYPE: PRT
<213> ORGANISM: Homo sapiens

<400> SEQUENCE: 1676

Pro Phe Ala Asn Cys
1               5

<210> SEQ ID NO 1677
<211> LENGTH: 5
<212> TYPE: PRT
<213> ORGANISM: Homo sapiens

<400> SEQUENCE: 1677

Pro Phe Ile Arg Cys
1               5

<210> SEQ ID NO 1678
<211> LENGTH: 5
<212> TYPE: PRT
<213> ORGANISM: Homo sapiens

<400> SEQUENCE: 1678

Pro Phe Pro Val Cys
1               5

<210> SEQ ID NO 1679
<211> LENGTH: 5
<212> TYPE: PRT
<213> ORGANISM: Homo sapiens

<400> SEQUENCE: 1679

Pro Phe Arg Gly Cys
1               5

<210> SEQ ID NO 1680
<211> LENGTH: 5
<212> TYPE: PRT
<213> ORGANISM: Homo sapiens

<400> SEQUENCE: 1680

Pro Phe Phe Pro Cys
1 5

<210> SEQ ID NO 1681
<211> LENGTH: 5
<212> TYPE: PRT
<213> ORGANISM: Homo sapiens

<400> SEQUENCE: 1681

Pro Phe Leu Ala Cys
1 5

<210> SEQ ID NO 1682
<211> LENGTH: 5
<212> TYPE: PRT
<213> ORGANISM: Homo sapiens

<400> SEQUENCE: 1682

Pro Phe His Gly Cys
1 5

<210> SEQ ID NO 1683
<211> LENGTH: 5
<212> TYPE: PRT
<213> ORGANISM: Homo sapiens

<400> SEQUENCE: 1683

Pro Phe Tyr Asn Cys
1 5

<210> SEQ ID NO 1684
<211> LENGTH: 5
<212> TYPE: PRT
<213> ORGANISM: Homo sapiens

<400> SEQUENCE: 1684

Pro Phe Gln Ala Cys
1 5

<210> SEQ ID NO 1685
<211> LENGTH: 5
<212> TYPE: PRT
<213> ORGANISM: Homo sapiens

<400> SEQUENCE: 1685

Pro Phe Leu Glu Cys
1 5

<210> SEQ ID NO 1686
<211> LENGTH: 5
<212> TYPE: PRT
<213> ORGANISM: Homo sapiens

<400> SEQUENCE: 1686

Pro Phe Ala Ser Cys
1 5

<210> SEQ ID NO 1687
<211> LENGTH: 5
<212> TYPE: PRT
<213> ORGANISM: Homo sapiens

<400> SEQUENCE: 1687

Pro Phe Ser Ala Cys
1               5

<210> SEQ ID NO 1688
<211> LENGTH: 5
<212> TYPE: PRT
<213> ORGANISM: Homo sapiens

<400> SEQUENCE: 1688

Pro Phe Ser Ala Cys
1               5

<210> SEQ ID NO 1689
<211> LENGTH: 5
<212> TYPE: PRT
<213> ORGANISM: Homo sapiens

<400> SEQUENCE: 1689

Pro Phe Thr Ala Cys
1               5

<210> SEQ ID NO 1690
<211> LENGTH: 5
<212> TYPE: PRT
<213> ORGANISM: Homo sapiens

<400> SEQUENCE: 1690

Pro Phe Ser Gly Cys
1               5

<210> SEQ ID NO 1691
<211> LENGTH: 5
<212> TYPE: PRT
<213> ORGANISM: Homo sapiens

<400> SEQUENCE: 1691

Pro Phe Thr Met Cys
1               5

<210> SEQ ID NO 1692
<211> LENGTH: 5
<212> TYPE: PRT
<213> ORGANISM: Homo sapiens

<400> SEQUENCE: 1692

Pro Phe Phe Asp Cys
1               5

<210> SEQ ID NO 1693
<211> LENGTH: 5
<212> TYPE: PRT
<213> ORGANISM: Homo sapiens

<400> SEQUENCE: 1693

Pro Phe Arg Asn Cys
1               5

<210> SEQ ID NO 1694
<211> LENGTH: 5
<212> TYPE: PRT
<213> ORGANISM: Homo sapiens

<400> SEQUENCE: 1694

Pro Phe Leu Cys Cys
1 5

<210> SEQ ID NO 1695
<211> LENGTH: 5
<212> TYPE: PRT
<213> ORGANISM: Homo sapiens

<400> SEQUENCE: 1695

Pro Phe Thr Phe Cys
1 5

<210> SEQ ID NO 1696
<211> LENGTH: 5
<212> TYPE: PRT
<213> ORGANISM: Homo sapiens

<400> SEQUENCE: 1696

Pro Phe Ile Ile Cys
1 5

<210> SEQ ID NO 1697
<211> LENGTH: 5
<212> TYPE: PRT
<213> ORGANISM: Homo sapiens

<400> SEQUENCE: 1697

Pro Phe Ala Cys Cys
1 5

<210> SEQ ID NO 1698
<211> LENGTH: 5
<212> TYPE: PRT
<213> ORGANISM: Homo sapiens

<400> SEQUENCE: 1698

Pro Phe Leu Cys Cys
1 5

<210> SEQ ID NO 1699
<211> LENGTH: 5
<212> TYPE: PRT
<213> ORGANISM: Homo sapiens

<400> SEQUENCE: 1699

Pro Phe Ser Arg Cys
1 5

<210> SEQ ID NO 1700
<211> LENGTH: 5
<212> TYPE: PRT
<213> ORGANISM: Homo sapiens

<400> SEQUENCE: 1700

Pro Phe Ile Met Cys
1 5

<210> SEQ ID NO 1701
<211> LENGTH: 5
<212> TYPE: PRT
<213> ORGANISM: Homo sapiens

<400> SEQUENCE: 1701

Pro Phe Gly Asn Cys
1               5

<210> SEQ ID NO 1702
<211> LENGTH: 5
<212> TYPE: PRT
<213> ORGANISM: Homo sapiens

<400> SEQUENCE: 1702

Pro Phe Cys Ala Cys
1               5

<210> SEQ ID NO 1703
<211> LENGTH: 5
<212> TYPE: PRT
<213> ORGANISM: Homo sapiens

<400> SEQUENCE: 1703

Pro Phe Leu Lys Cys
1               5

<210> SEQ ID NO 1704
<211> LENGTH: 5
<212> TYPE: PRT
<213> ORGANISM: Homo sapiens

<400> SEQUENCE: 1704

Pro Phe Phe Leu Cys
1               5

<210> SEQ ID NO 1705
<211> LENGTH: 5
<212> TYPE: PRT
<213> ORGANISM: Homo sapiens

<400> SEQUENCE: 1705

Pro Phe Pro Gln Cys
1               5

<210> SEQ ID NO 1706
<211> LENGTH: 5
<212> TYPE: PRT
<213> ORGANISM: Homo sapiens

<400> SEQUENCE: 1706

Pro Phe Pro Leu Cys
1               5

<210> SEQ ID NO 1707
<211> LENGTH: 5
<212> TYPE: PRT
<213> ORGANISM: Homo sapiens

<400> SEQUENCE: 1707

Pro Phe Thr Thr Cys
1               5

<210> SEQ ID NO 1708
<211> LENGTH: 5
<212> TYPE: PRT
<213> ORGANISM: Homo sapiens

<400> SEQUENCE: 1708

Pro Phe Pro Ala Cys
1               5

<210> SEQ ID NO 1709
<211> LENGTH: 5
<212> TYPE: PRT
<213> ORGANISM: Homo sapiens

<400> SEQUENCE: 1709

Pro Phe Gln Asp Cys
1               5

<210> SEQ ID NO 1710
<211> LENGTH: 5
<212> TYPE: PRT
<213> ORGANISM: Homo sapiens

<400> SEQUENCE: 1710

Pro Phe Thr Thr Cys
1               5

<210> SEQ ID NO 1711
<211> LENGTH: 5
<212> TYPE: PRT
<213> ORGANISM: Homo sapiens

<400> SEQUENCE: 1711

Pro Phe Asp Asp Cys
1               5

<210> SEQ ID NO 1712
<211> LENGTH: 5
<212> TYPE: PRT
<213> ORGANISM: Homo sapiens

<400> SEQUENCE: 1712

Pro Phe Thr Pro Cys
1               5

<210> SEQ ID NO 1713
<211> LENGTH: 5
<212> TYPE: PRT
<213> ORGANISM: Homo sapiens

<400> SEQUENCE: 1713

Pro Phe Gly Ser Cys
1               5

<210> SEQ ID NO 1714
<211> LENGTH: 5
<212> TYPE: PRT
<213> ORGANISM: Homo sapiens

<400> SEQUENCE: 1714

Pro Phe His Ile Cys
1               5

<210> SEQ ID NO 1715
<211> LENGTH: 5
<212> TYPE: PRT
<213> ORGANISM: Homo sapiens

<400> SEQUENCE: 1715

Pro Phe Pro Ala Cys
1 5

<210> SEQ ID NO 1716
<211> LENGTH: 5
<212> TYPE: PRT
<213> ORGANISM: Homo sapiens

<400> SEQUENCE: 1716

Pro Phe Gly Ser Cys
1 5

<210> SEQ ID NO 1717
<211> LENGTH: 5
<212> TYPE: PRT
<213> ORGANISM: Homo sapiens

<400> SEQUENCE: 1717

Pro Phe Ala Lys Cys
1 5

<210> SEQ ID NO 1718
<211> LENGTH: 5
<212> TYPE: PRT
<213> ORGANISM: Homo sapiens

<400> SEQUENCE: 1718

Pro Phe Tyr Asn Cys
1 5

<210> SEQ ID NO 1719
<211> LENGTH: 5
<212> TYPE: PRT
<213> ORGANISM: Homo sapiens

<400> SEQUENCE: 1719

Pro Phe Gly Ser Cys
1 5

<210> SEQ ID NO 1720
<211> LENGTH: 5
<212> TYPE: PRT
<213> ORGANISM: Homo sapiens

<400> SEQUENCE: 1720

Pro Phe Pro Gly Cys
1 5

<210> SEQ ID NO 1721
<211> LENGTH: 5
<212> TYPE: PRT
<213> ORGANISM: Homo sapiens

<400> SEQUENCE: 1721

Pro Phe Gln Gly Cys
1 5

<210> SEQ ID NO 1722
<211> LENGTH: 5
<212> TYPE: PRT
<213> ORGANISM: Homo sapiens

<400> SEQUENCE: 1722

Pro Phe Ser Cys Cys
1 5

<210> SEQ ID NO 1723
<211> LENGTH: 5
<212> TYPE: PRT
<213> ORGANISM: Homo sapiens

<400> SEQUENCE: 1723

Pro Phe Gly Gly Cys
1 5

<210> SEQ ID NO 1724
<211> LENGTH: 5
<212> TYPE: PRT
<213> ORGANISM: Homo sapiens

<400> SEQUENCE: 1724

Pro Phe Gly Gly Cys
1 5

<210> SEQ ID NO 1725
<211> LENGTH: 5
<212> TYPE: PRT
<213> ORGANISM: Homo sapiens

<400> SEQUENCE: 1725

Pro Phe Pro Phe Cys
1 5

<210> SEQ ID NO 1726
<211> LENGTH: 5
<212> TYPE: PRT
<213> ORGANISM: Homo sapiens

<400> SEQUENCE: 1726

Pro Phe Tyr Gly Cys
1 5

<210> SEQ ID NO 1727
<211> LENGTH: 5
<212> TYPE: PRT
<213> ORGANISM: Homo sapiens

<400> SEQUENCE: 1727

Pro Phe His Ala Cys
1 5

<210> SEQ ID NO 1728
<211> LENGTH: 5
<212> TYPE: PRT
<213> ORGANISM: Homo sapiens

<400> SEQUENCE: 1728

Pro Phe Asn Thr Cys
1 5

<210> SEQ ID NO 1729
<211> LENGTH: 5
<212> TYPE: PRT
<213> ORGANISM: Homo sapiens

<400> SEQUENCE: 1729

Pro Phe Leu Arg Cys
1 5

<210> SEQ ID NO 1730
<211> LENGTH: 5
<212> TYPE: PRT
<213> ORGANISM: Homo sapiens

<400> SEQUENCE: 1730

Pro Phe Gln Cys Cys
1 5

<210> SEQ ID NO 1731
<211> LENGTH: 5
<212> TYPE: PRT
<213> ORGANISM: Homo sapiens

<400> SEQUENCE: 1731

Pro Phe Ile Leu Cys
1 5

<210> SEQ ID NO 1732
<211> LENGTH: 5
<212> TYPE: PRT
<213> ORGANISM: Homo sapiens

<400> SEQUENCE: 1732

Pro Phe Glu Leu Cys
1 5

<210> SEQ ID NO 1733
<211> LENGTH: 5
<212> TYPE: PRT
<213> ORGANISM: Homo sapiens

<400> SEQUENCE: 1733

Pro Phe Gly Lys Cys
1 5

<210> SEQ ID NO 1734
<211> LENGTH: 5
<212> TYPE: PRT
<213> ORGANISM: Homo sapiens

<400> SEQUENCE: 1734

Pro Phe Pro Gly Cys
1 5

<210> SEQ ID NO 1735
<211> LENGTH: 5
<212> TYPE: PRT
<213> ORGANISM: Homo sapiens

<400> SEQUENCE: 1735

Pro Phe Ser His Cys
1 5

<210> SEQ ID NO 1736
<211> LENGTH: 5
<212> TYPE: PRT
<213> ORGANISM: Homo sapiens

<400> SEQUENCE: 1736

Pro Phe Leu Ser Cys
1 5

<210> SEQ ID NO 1737
<211> LENGTH: 5
<212> TYPE: PRT
<213> ORGANISM: Homo sapiens

<400> SEQUENCE: 1737

Pro Phe Pro Gln Cys
1 5

<210> SEQ ID NO 1738
<211> LENGTH: 5
<212> TYPE: PRT
<213> ORGANISM: Homo sapiens

<400> SEQUENCE: 1738

Pro Phe Cys Arg Cys
1 5

<210> SEQ ID NO 1739
<211> LENGTH: 5
<212> TYPE: PRT
<213> ORGANISM: Homo sapiens

<400> SEQUENCE: 1739

Pro Phe Cys His Cys
1 5

<210> SEQ ID NO 1740
<211> LENGTH: 5
<212> TYPE: PRT
<213> ORGANISM: Homo sapiens

<400> SEQUENCE: 1740

Pro Phe Pro Cys Cys
1 5

<210> SEQ ID NO 1741
<211> LENGTH: 5
<212> TYPE: PRT
<213> ORGANISM: Homo sapiens

<400> SEQUENCE: 1741

Pro Phe Ala Val Cys
1 5

<210> SEQ ID NO 1742
<211> LENGTH: 5
<212> TYPE: PRT
<213> ORGANISM: Homo sapiens

<400> SEQUENCE: 1742

Pro Phe Pro Ile Cys
1 5

<210> SEQ ID NO 1743
<211> LENGTH: 5
<212> TYPE: PRT
<213> ORGANISM: Homo sapiens

<400> SEQUENCE: 1743

Pro Phe His Asn Cys
1 5

<210> SEQ ID NO 1744
<211> LENGTH: 5
<212> TYPE: PRT
<213> ORGANISM: Homo sapiens

<400> SEQUENCE: 1744

Pro Phe Gln Val Cys
1 5

<210> SEQ ID NO 1745
<211> LENGTH: 5
<212> TYPE: PRT
<213> ORGANISM: Homo sapiens

<400> SEQUENCE: 1745

Pro Phe Val Asp Cys
1 5

<210> SEQ ID NO 1746
<211> LENGTH: 5
<212> TYPE: PRT
<213> ORGANISM: Homo sapiens

<400> SEQUENCE: 1746

Pro Phe Leu Gln Cys
1 5

<210> SEQ ID NO 1747
<211> LENGTH: 5
<212> TYPE: PRT
<213> ORGANISM: Homo sapiens

<400> SEQUENCE: 1747

Pro Phe Ser Ala Cys
1 5

<210> SEQ ID NO 1748
<211> LENGTH: 5
<212> TYPE: PRT
<213> ORGANISM: Homo sapiens

<400> SEQUENCE: 1748

Pro Phe Gly Gln Cys
1 5

<210> SEQ ID NO 1749
<211> LENGTH: 5
<212> TYPE: PRT
<213> ORGANISM: Homo sapiens

<400> SEQUENCE: 1749

Pro Phe Tyr His Cys
1 5

<210> SEQ ID NO 1750
<211> LENGTH: 5
<212> TYPE: PRT
<213> ORGANISM: Homo sapiens

<400> SEQUENCE: 1750

Pro Phe Ser Cys Cys
1 5

<210> SEQ ID NO 1751
<211> LENGTH: 5
<212> TYPE: PRT
<213> ORGANISM: Homo sapiens

<400> SEQUENCE: 1751

Pro Phe Trp Gly Cys
1 5

<210> SEQ ID NO 1752
<211> LENGTH: 5
<212> TYPE: PRT
<213> ORGANISM: Homo sapiens

<400> SEQUENCE: 1752

Pro Phe His Leu Cys
1 5

<210> SEQ ID NO 1753
<211> LENGTH: 5
<212> TYPE: PRT
<213> ORGANISM: Homo sapiens

<400> SEQUENCE: 1753

Pro Phe Glu Asp Cys
1 5

<210> SEQ ID NO 1754
<211> LENGTH: 5
<212> TYPE: PRT
<213> ORGANISM: Homo sapiens

<400> SEQUENCE: 1754

Pro Phe Thr Gln Cys
1 5

<210> SEQ ID NO 1755
<211> LENGTH: 5
<212> TYPE: PRT
<213> ORGANISM: Homo sapiens

<400> SEQUENCE: 1755

Pro Phe Pro Arg Cys
1 5

<210> SEQ ID NO 1756
<211> LENGTH: 5
<212> TYPE: PRT
<213> ORGANISM: Homo sapiens

<400> SEQUENCE: 1756

Pro Phe Ser Thr Cys
1 5

<210> SEQ ID NO 1757
<211> LENGTH: 5
<212> TYPE: PRT
<213> ORGANISM: Homo sapiens

<400> SEQUENCE: 1757

Pro Phe Ala Ser Cys
1 5

<210> SEQ ID NO 1758
<211> LENGTH: 5
<212> TYPE: PRT
<213> ORGANISM: Homo sapiens

<400> SEQUENCE: 1758

Pro Phe Phe Ile Cys
1 5

<210> SEQ ID NO 1759
<211> LENGTH: 5
<212> TYPE: PRT
<213> ORGANISM: Homo sapiens

<400> SEQUENCE: 1759

Pro Phe Glu Lys Cys
1 5

<210> SEQ ID NO 1760
<211> LENGTH: 5
<212> TYPE: PRT
<213> ORGANISM: Homo sapiens

<400> SEQUENCE: 1760

Pro Phe Ser Ile Cys
1 5

<210> SEQ ID NO 1761
<211> LENGTH: 5
<212> TYPE: PRT
<213> ORGANISM: Homo sapiens

<400> SEQUENCE: 1761

Pro Phe Pro Gly Cys
1 5

<210> SEQ ID NO 1762
<211> LENGTH: 5
<212> TYPE: PRT
<213> ORGANISM: Homo sapiens

<400> SEQUENCE: 1762

Pro Phe Pro Val Cys
1 5

<210> SEQ ID NO 1763
<211> LENGTH: 5
<212> TYPE: PRT
<213> ORGANISM: Homo sapiens

<400> SEQUENCE: 1763

Pro Phe Asp Leu Cys
1 5

<210> SEQ ID NO 1764
<211> LENGTH: 5
<212> TYPE: PRT
<213> ORGANISM: Homo sapiens

<400> SEQUENCE: 1764

Pro Phe His His Cys
1 5

<210> SEQ ID NO 1765
<211> LENGTH: 5
<212> TYPE: PRT
<213> ORGANISM: Homo sapiens

<400> SEQUENCE: 1765

Pro Phe Arg Arg Cys
1 5

<210> SEQ ID NO 1766
<211> LENGTH: 5
<212> TYPE: PRT
<213> ORGANISM: Homo sapiens

<400> SEQUENCE: 1766

Pro Phe Trp Ile Cys
1 5

<210> SEQ ID NO 1767
<211> LENGTH: 5
<212> TYPE: PRT
<213> ORGANISM: Homo sapiens

<400> SEQUENCE: 1767

Pro Phe Gln Val Cys
1 5

<210> SEQ ID NO 1768
<211> LENGTH: 5
<212> TYPE: PRT
<213> ORGANISM: Homo sapiens

<400> SEQUENCE: 1768

Pro Phe Cys Leu Cys
1 5

<210> SEQ ID NO 1769
<211> LENGTH: 5
<212> TYPE: PRT
<213> ORGANISM: Homo sapiens

<400> SEQUENCE: 1769

Pro Phe Pro Asp Cys
1 5

<210> SEQ ID NO 1770
<211> LENGTH: 5
<212> TYPE: PRT
<213> ORGANISM: Homo sapiens

<400> SEQUENCE: 1770

Pro Phe Gln Leu Cys
1 5

<210> SEQ ID NO 1771
<211> LENGTH: 5
<212> TYPE: PRT
<213> ORGANISM: Homo sapiens

<400> SEQUENCE: 1771

Pro Phe Arg Pro Cys
1               5

<210> SEQ ID NO 1772
<211> LENGTH: 5
<212> TYPE: PRT
<213> ORGANISM: Homo sapiens

<400> SEQUENCE: 1772

Pro Phe Ala Val Cys
1               5

<210> SEQ ID NO 1773
<211> LENGTH: 5
<212> TYPE: PRT
<213> ORGANISM: Homo sapiens

<400> SEQUENCE: 1773

Pro Phe Ser Tyr Cys
1               5

<210> SEQ ID NO 1774
<211> LENGTH: 5
<212> TYPE: PRT
<213> ORGANISM: Homo sapiens

<400> SEQUENCE: 1774

Pro Phe Phe Leu Cys
1               5

<210> SEQ ID NO 1775
<211> LENGTH: 5
<212> TYPE: PRT
<213> ORGANISM: Homo sapiens

<400> SEQUENCE: 1775

Pro Phe Tyr Glu Cys
1               5

<210> SEQ ID NO 1776
<211> LENGTH: 5
<212> TYPE: PRT
<213> ORGANISM: Homo sapiens

<400> SEQUENCE: 1776

Pro Phe Pro Ala Cys
1               5

<210> SEQ ID NO 1777
<211> LENGTH: 5
<212> TYPE: PRT
<213> ORGANISM: Homo sapiens

<400> SEQUENCE: 1777

Pro Phe His Ala Cys
1               5

<210> SEQ ID NO 1778
<211> LENGTH: 5
<212> TYPE: PRT
<213> ORGANISM: Homo sapiens

<400> SEQUENCE: 1778

Pro Phe Gln Ile Cys
1 5

<210> SEQ ID NO 1779
<211> LENGTH: 5
<212> TYPE: PRT
<213> ORGANISM: Homo sapiens

<400> SEQUENCE: 1779

Pro Phe Pro Asn Cys
1 5

<210> SEQ ID NO 1780
<211> LENGTH: 5
<212> TYPE: PRT
<213> ORGANISM: Homo sapiens

<400> SEQUENCE: 1780

Pro Phe Glu Lys Cys
1 5

<210> SEQ ID NO 1781
<211> LENGTH: 5
<212> TYPE: PRT
<213> ORGANISM: Homo sapiens

<400> SEQUENCE: 1781

Pro Phe Leu Asn Cys
1 5

<210> SEQ ID NO 1782
<211> LENGTH: 5
<212> TYPE: PRT
<213> ORGANISM: Homo sapiens

<400> SEQUENCE: 1782

Pro Phe Gln Asp Cys
1 5

<210> SEQ ID NO 1783
<211> LENGTH: 5
<212> TYPE: PRT
<213> ORGANISM: Homo sapiens

<400> SEQUENCE: 1783

Pro Phe Tyr Asn Cys
1 5

<210> SEQ ID NO 1784
<211> LENGTH: 5
<212> TYPE: PRT
<213> ORGANISM: Homo sapiens

<400> SEQUENCE: 1784

Pro Phe Gln Trp Cys
1 5

<210> SEQ ID NO 1785
<211> LENGTH: 5
<212> TYPE: PRT
<213> ORGANISM: Homo sapiens

<400> SEQUENCE: 1785

Pro Phe Arg Gln Cys
1 5

<210> SEQ ID NO 1786
<211> LENGTH: 5
<212> TYPE: PRT
<213> ORGANISM: Homo sapiens

<400> SEQUENCE: 1786

Pro Phe Asp Ala Cys
1 5

<210> SEQ ID NO 1787
<211> LENGTH: 5
<212> TYPE: PRT
<213> ORGANISM: Homo sapiens

<400> SEQUENCE: 1787

Pro Phe Asp Thr Cys
1 5

<210> SEQ ID NO 1788
<211> LENGTH: 5
<212> TYPE: PRT
<213> ORGANISM: Homo sapiens

<400> SEQUENCE: 1788

Pro Phe Asp Ala Cys
1 5

<210> SEQ ID NO 1789
<211> LENGTH: 5
<212> TYPE: PRT
<213> ORGANISM: Homo sapiens

<400> SEQUENCE: 1789

Pro Phe Lys Pro Cys
1 5

<210> SEQ ID NO 1790
<211> LENGTH: 5
<212> TYPE: PRT
<213> ORGANISM: Homo sapiens

<400> SEQUENCE: 1790

Pro Phe Asp Ile Cys
1 5

<210> SEQ ID NO 1791
<211> LENGTH: 5
<212> TYPE: PRT
<213> ORGANISM: Homo sapiens

<400> SEQUENCE: 1791

Pro Phe Leu Val Cys
1 5

<210> SEQ ID NO 1792
<211> LENGTH: 5
<212> TYPE: PRT
<213> ORGANISM: Homo sapiens

<400> SEQUENCE: 1792

Pro Phe Gln Ala Cys
1 5

<210> SEQ ID NO 1793
<211> LENGTH: 5
<212> TYPE: PRT
<213> ORGANISM: Homo sapiens

<400> SEQUENCE: 1793

Pro Phe Gln Asp Cys
1 5

<210> SEQ ID NO 1794
<211> LENGTH: 5
<212> TYPE: PRT
<213> ORGANISM: Homo sapiens

<400> SEQUENCE: 1794

Pro Phe Glu Val Cys
1 5

<210> SEQ ID NO 1795
<211> LENGTH: 5
<212> TYPE: PRT
<213> ORGANISM: Homo sapiens

<400> SEQUENCE: 1795

Pro Phe Ile Tyr Cys
1 5

<210> SEQ ID NO 1796
<211> LENGTH: 5
<212> TYPE: PRT
<213> ORGANISM: Homo sapiens

<400> SEQUENCE: 1796

Pro Phe Asp Pro Cys
1 5

<210> SEQ ID NO 1797
<211> LENGTH: 5
<212> TYPE: PRT
<213> ORGANISM: Homo sapiens

<400> SEQUENCE: 1797

Pro Phe Ile Leu Cys
1 5

<210> SEQ ID NO 1798
<211> LENGTH: 5
<212> TYPE: PRT
<213> ORGANISM: Homo sapiens

<400> SEQUENCE: 1798

Pro Phe Cys Val Cys
1 5

<210> SEQ ID NO 1799
<211> LENGTH: 5
<212> TYPE: PRT
<213> ORGANISM: Homo sapiens

<400> SEQUENCE: 1799

Pro Phe Ser Asp Cys
1               5

<210> SEQ ID NO 1800
<211> LENGTH: 5
<212> TYPE: PRT
<213> ORGANISM: Homo sapiens

<400> SEQUENCE: 1800

Pro Phe Pro Val Cys
1               5

<210> SEQ ID NO 1801
<211> LENGTH: 5
<212> TYPE: PRT
<213> ORGANISM: Homo sapiens

<400> SEQUENCE: 1801

Pro Phe Phe Asp Cys
1               5

<210> SEQ ID NO 1802
<211> LENGTH: 5
<212> TYPE: PRT
<213> ORGANISM: Homo sapiens

<400> SEQUENCE: 1802

Pro Phe Gly Thr Cys
1               5

<210> SEQ ID NO 1803
<211> LENGTH: 5
<212> TYPE: PRT
<213> ORGANISM: Homo sapiens

<400> SEQUENCE: 1803

Pro Phe Ala Phe Cys
1               5

<210> SEQ ID NO 1804
<211> LENGTH: 5
<212> TYPE: PRT
<213> ORGANISM: Homo sapiens

<400> SEQUENCE: 1804

Pro Phe Arg Pro Cys
1               5

<210> SEQ ID NO 1805
<211> LENGTH: 5
<212> TYPE: PRT
<213> ORGANISM: Homo sapiens

<400> SEQUENCE: 1805

Pro Phe Val Thr Cys
1               5

<210> SEQ ID NO 1806
<211> LENGTH: 5
<212> TYPE: PRT
<213> ORGANISM: Homo sapiens

<400> SEQUENCE: 1806

Pro Phe Arg Val Cys
1 5

<210> SEQ ID NO 1807
<211> LENGTH: 5
<212> TYPE: PRT
<213> ORGANISM: Homo sapiens

<400> SEQUENCE: 1807

Pro Phe Ser His Cys
1 5

<210> SEQ ID NO 1808
<211> LENGTH: 5
<212> TYPE: PRT
<213> ORGANISM: Homo sapiens

<400> SEQUENCE: 1808

Pro Phe Ser Ser Cys
1 5

<210> SEQ ID NO 1809
<211> LENGTH: 5
<212> TYPE: PRT
<213> ORGANISM: Homo sapiens

<400> SEQUENCE: 1809

Pro Phe Pro Thr Cys
1 5

<210> SEQ ID NO 1810
<211> LENGTH: 5
<212> TYPE: PRT
<213> ORGANISM: Homo sapiens

<400> SEQUENCE: 1810

Pro Phe Pro Asn Cys
1 5

<210> SEQ ID NO 1811
<211> LENGTH: 5
<212> TYPE: PRT
<213> ORGANISM: Homo sapiens

<400> SEQUENCE: 1811

Pro Phe Gly Leu Cys
1 5

<210> SEQ ID NO 1812
<211> LENGTH: 5
<212> TYPE: PRT
<213> ORGANISM: Homo sapiens

<400> SEQUENCE: 1812

Pro Phe Cys Arg Cys
1 5

<210> SEQ ID NO 1813
<211> LENGTH: 5
<212> TYPE: PRT
<213> ORGANISM: Homo sapiens

<400> SEQUENCE: 1813

Pro Phe Phe Arg Cys
1               5

<210> SEQ ID NO 1814
<211> LENGTH: 5
<212> TYPE: PRT
<213> ORGANISM: Homo sapiens

<400> SEQUENCE: 1814

Pro Phe Phe Arg Cys
1               5

<210> SEQ ID NO 1815
<211> LENGTH: 5
<212> TYPE: PRT
<213> ORGANISM: Homo sapiens

<400> SEQUENCE: 1815

Pro Phe Thr Gly Cys
1               5

<210> SEQ ID NO 1816
<211> LENGTH: 5
<212> TYPE: PRT
<213> ORGANISM: Homo sapiens

<400> SEQUENCE: 1816

Pro Phe Pro Ser Cys
1               5

<210> SEQ ID NO 1817
<211> LENGTH: 5
<212> TYPE: PRT
<213> ORGANISM: Homo sapiens

<400> SEQUENCE: 1817

Pro Phe Tyr Thr Cys
1               5

<210> SEQ ID NO 1818
<211> LENGTH: 5
<212> TYPE: PRT
<213> ORGANISM: Homo sapiens

<400> SEQUENCE: 1818

Pro Phe Arg Leu Cys
1               5

<210> SEQ ID NO 1819
<211> LENGTH: 5
<212> TYPE: PRT
<213> ORGANISM: Homo sapiens

<400> SEQUENCE: 1819

Pro Phe Glu Thr Cys
1               5

<210> SEQ ID NO 1820
<211> LENGTH: 5
<212> TYPE: PRT
<213> ORGANISM: Homo sapiens

<400> SEQUENCE: 1820

Pro Phe Ser Gln Cys
1 5

<210> SEQ ID NO 1821
<211> LENGTH: 5
<212> TYPE: PRT
<213> ORGANISM: Homo sapiens

<400> SEQUENCE: 1821

Pro Phe Ala Ala Cys
1 5

<210> SEQ ID NO 1822
<211> LENGTH: 5
<212> TYPE: PRT
<213> ORGANISM: Homo sapiens

<400> SEQUENCE: 1822

Pro Phe Trp Ile Cys
1 5

<210> SEQ ID NO 1823
<211> LENGTH: 5
<212> TYPE: PRT
<213> ORGANISM: Homo sapiens

<400> SEQUENCE: 1823

Pro Phe Ser Arg Cys
1 5

<210> SEQ ID NO 1824
<211> LENGTH: 5
<212> TYPE: PRT
<213> ORGANISM: Homo sapiens

<400> SEQUENCE: 1824

Pro Phe Gln Asp Cys
1 5

<210> SEQ ID NO 1825
<211> LENGTH: 5
<212> TYPE: PRT
<213> ORGANISM: Homo sapiens

<400> SEQUENCE: 1825

Pro Phe Gln Leu Cys
1 5

<210> SEQ ID NO 1826
<211> LENGTH: 5
<212> TYPE: PRT
<213> ORGANISM: Homo sapiens

<400> SEQUENCE: 1826

Pro Phe Ala Tyr Cys
1 5

<210> SEQ ID NO 1827
<211> LENGTH: 5
<212> TYPE: PRT
<213> ORGANISM: Homo sapiens

<400> SEQUENCE: 1827

Pro Phe Ser Gln Cys
1               5

<210> SEQ ID NO 1828
<211> LENGTH: 5
<212> TYPE: PRT
<213> ORGANISM: Homo sapiens

<400> SEQUENCE: 1828

Pro Phe Ala Val Cys
1               5

<210> SEQ ID NO 1829
<211> LENGTH: 5
<212> TYPE: PRT
<213> ORGANISM: Homo sapiens

<400> SEQUENCE: 1829

Pro Phe Arg Glu Cys
1               5

<210> SEQ ID NO 1830
<211> LENGTH: 5
<212> TYPE: PRT
<213> ORGANISM: Homo sapiens

<400> SEQUENCE: 1830

Pro Phe Thr Thr Cys
1               5

<210> SEQ ID NO 1831
<211> LENGTH: 5
<212> TYPE: PRT
<213> ORGANISM: Homo sapiens

<400> SEQUENCE: 1831

Pro Phe Thr Thr Cys
1               5

<210> SEQ ID NO 1832
<211> LENGTH: 5
<212> TYPE: PRT
<213> ORGANISM: Homo sapiens

<400> SEQUENCE: 1832

Pro Phe Thr Thr Cys
1               5

<210> SEQ ID NO 1833
<211> LENGTH: 5
<212> TYPE: PRT
<213> ORGANISM: Homo sapiens

<400> SEQUENCE: 1833

Pro Phe Ala Thr Cys
1               5

<210> SEQ ID NO 1834
<211> LENGTH: 12
<212> TYPE: PRT
<213> ORGANISM: Homo sapiens

<400> SEQUENCE: 1834

Leu Val Gly Tyr Leu Leu Gly Ser Ala Ser Leu Leu
1 5 10

<210> SEQ ID NO 1835
<211> LENGTH: 12
<212> TYPE: PRT
<213> ORGANISM: Homo sapiens

<400> SEQUENCE: 1835

Leu Cys Glu Glu Leu Leu Ser Arg Thr Ser Ser Leu
1 5 10

<210> SEQ ID NO 1836
<211> LENGTH: 12
<212> TYPE: PRT
<213> ORGANISM: Homo sapiens

<400> SEQUENCE: 1836

Leu Ala Thr Val Leu Leu Val Phe Val Ser Thr Leu
1 5 10

<210> SEQ ID NO 1837
<211> LENGTH: 12
<212> TYPE: PRT
<213> ORGANISM: Homo sapiens

<400> SEQUENCE: 1837

Leu Leu Leu Pro Leu Leu Leu Ala Val Ser Gly Leu
1 5 10

<210> SEQ ID NO 1838
<211> LENGTH: 12
<212> TYPE: PRT
<213> ORGANISM: Homo sapiens

<400> SEQUENCE: 1838

Leu Met Leu Leu Leu Leu Leu Pro Pro Ser Pro Leu
1 5 10

<210> SEQ ID NO 1839
<211> LENGTH: 12
<212> TYPE: PRT
<213> ORGANISM: Homo sapiens

<400> SEQUENCE: 1839

Leu Phe Asp Thr Leu Leu Glu Glu Tyr Ser Val Leu
1 5 10

<210> SEQ ID NO 1840
<211> LENGTH: 12
<212> TYPE: PRT
<213> ORGANISM: Homo sapiens

<400> SEQUENCE: 1840

Leu Val Met Lys Leu Leu Ser Gly Gly Ser Val Leu
1 5 10

<210> SEQ ID NO 1841
<211> LENGTH: 12
<212> TYPE: PRT
<213> ORGANISM: Homo sapiens

<400> SEQUENCE: 1841

Leu Arg Ile Ser Leu Leu Leu Ile Gln Ser Trp Leu
1 5 10

<210> SEQ ID NO 1842
<211> LENGTH: 12
<212> TYPE: PRT
<213> ORGANISM: Homo sapiens

<400> SEQUENCE: 1842

Leu Arg Ile Ser Leu Leu Leu Ile Gln Ser Trp Leu
1 5 10

<210> SEQ ID NO 1843
<211> LENGTH: 12
<212> TYPE: PRT
<213> ORGANISM: Homo sapiens

<400> SEQUENCE: 1843

Leu Arg Ile Ser Leu Leu Leu Ile Glu Ser Trp Leu
1 5 10

<210> SEQ ID NO 1844
<211> LENGTH: 12
<212> TYPE: PRT
<213> ORGANISM: Homo sapiens

<400> SEQUENCE: 1844

Leu Pro Ala Asn Leu Leu Gln Gly Ala Ser Lys Leu
1 5 10

<210> SEQ ID NO 1845
<211> LENGTH: 12
<212> TYPE: PRT
<213> ORGANISM: Homo sapiens

<400> SEQUENCE: 1845

Leu Asn Val Ser Leu Leu Leu Thr Leu Ser Ile Leu
1 5 10

<210> SEQ ID NO 1846
<211> LENGTH: 12
<212> TYPE: PRT
<213> ORGANISM: Homo sapiens

<400> SEQUENCE: 1846

Leu Val Cys Ala Leu Leu Trp Ala Leu Ser Cys Leu
1 5 10

<210> SEQ ID NO 1847
<211> LENGTH: 12
<212> TYPE: PRT
<213> ORGANISM: Homo sapiens

<400> SEQUENCE: 1847

Leu Asn Gly Ile Leu Leu His Leu Glu Ser Glu Leu
1 5 10

<210> SEQ ID NO 1848
<211> LENGTH: 12
<212> TYPE: PRT
<213> ORGANISM: Homo sapiens

<400> SEQUENCE: 1848

Leu Leu Leu Leu Leu Leu Leu Leu Pro Ser Pro Leu
1 5 10

<210> SEQ ID NO 1849
<211> LENGTH: 12
<212> TYPE: PRT
<213> ORGANISM: Homo sapiens

<400> SEQUENCE: 1849

Leu Thr Asn Asp Leu Leu His Asn Leu Ser Gly Leu
1 5 10

<210> SEQ ID NO 1850
<211> LENGTH: 12
<212> TYPE: PRT
<213> ORGANISM: Homo sapiens

<400> SEQUENCE: 1850

Leu Val Gly Ala Leu Leu Met Gly Phe Ser Lys Leu
1 5 10

<210> SEQ ID NO 1851
<211> LENGTH: 12
<212> TYPE: PRT
<213> ORGANISM: Homo sapiens

<400> SEQUENCE: 1851

Leu Ser Phe Leu Leu Leu Leu Phe Phe Ser His Leu
1 5 10

<210> SEQ ID NO 1852
<211> LENGTH: 12
<212> TYPE: PRT
<213> ORGANISM: Homo sapiens

<400> SEQUENCE: 1852

Leu Cys Pro Gly Leu Leu His Pro Ser Ser Arg Leu
1 5 10

<210> SEQ ID NO 1853
<211> LENGTH: 12
<212> TYPE: PRT
<213> ORGANISM: Homo sapiens

<400> SEQUENCE: 1853

Leu Leu Lys Ala Leu Leu Glu Ile Ala Ser Cys Leu
1 5 10

<210> SEQ ID NO 1854
<211> LENGTH: 12
<212> TYPE: PRT
<213> ORGANISM: Homo sapiens

<400> SEQUENCE: 1854

Leu Pro Ala Trp Leu Leu Glu Lys Glu Ser Ile Leu
1 5 10

<210> SEQ ID NO 1855
<211> LENGTH: 12
<212> TYPE: PRT
<213> ORGANISM: Homo sapiens

<400> SEQUENCE: 1855

Leu Val Arg Asp Leu Leu Glu Val Thr Ser Gly Leu
1 5 10

<210> SEQ ID NO 1856
<211> LENGTH: 12
<212> TYPE: PRT
<213> ORGANISM: Homo sapiens

<400> SEQUENCE: 1856

Leu Val Arg Gly Leu Leu Ala Lys Lys Ser Lys Leu
1 5 10

<210> SEQ ID NO 1857
<211> LENGTH: 12
<212> TYPE: PRT
<213> ORGANISM: Homo sapiens

<400> SEQUENCE: 1857

Leu Ile Leu Gly Leu Leu Leu Cys Phe Ser Val Leu
1 5 10

<210> SEQ ID NO 1858
<211> LENGTH: 12
<212> TYPE: PRT
<213> ORGANISM: Homo sapiens

<400> SEQUENCE: 1858

Leu Cys Ser Gly Leu Leu Phe Pro Val Ser Cys Leu
1 5 10

<210> SEQ ID NO 1859
<211> LENGTH: 12
<212> TYPE: PRT
<213> ORGANISM: Homo sapiens

<400> SEQUENCE: 1859

Leu Ser Ile Leu Leu Leu Leu Ser Cys Ser Val Leu
1 5 10

<210> SEQ ID NO 1860
<211> LENGTH: 12
<212> TYPE: PRT
<213> ORGANISM: Homo sapiens

<400> SEQUENCE: 1860

Leu Ala Ser Leu Leu Leu Ile Cys Lys Ser Ser Leu
1 5 10

<210> SEQ ID NO 1861
<211> LENGTH: 12
<212> TYPE: PRT
<213> ORGANISM: Homo sapiens

<400> SEQUENCE: 1861

Leu Leu Ala Ser Leu Leu Ser Pro Gly Ser Val Leu
1 5 10

<210> SEQ ID NO 1862
<211> LENGTH: 12
<212> TYPE: PRT
<213> ORGANISM: Homo sapiens

<400> SEQUENCE: 1862

Leu Pro Pro Arg Leu Leu Ala Arg Pro Ser Leu Leu
1 5 10

<210> SEQ ID NO 1863
<211> LENGTH: 12
<212> TYPE: PRT
<213> ORGANISM: Homo sapiens

<400> SEQUENCE: 1863

Leu Glu Asp Met Leu Leu Thr Thr Leu Ser Gly Leu
1 5 10

<210> SEQ ID NO 1864
<211> LENGTH: 12
<212> TYPE: PRT
<213> ORGANISM: Homo sapiens

<400> SEQUENCE: 1864

Leu Leu Glu Tyr Leu Leu Tyr Phe Leu Ser Phe Leu
1 5 10

<210> SEQ ID NO 1865
<211> LENGTH: 12
<212> TYPE: PRT
<213> ORGANISM: Homo sapiens

<400> SEQUENCE: 1865

Leu Asn Ser Lys Leu Leu Asp Ile Arg Ser Tyr Leu
1 5 10

<210> SEQ ID NO 1866
<211> LENGTH: 12
<212> TYPE: PRT
<213> ORGANISM: Homo sapiens

<400> SEQUENCE: 1866

Leu Ile Ser Phe Leu Leu Ser Leu Ile Ser Leu Leu
1 5 10

<210> SEQ ID NO 1867
<211> LENGTH: 12
<212> TYPE: PRT
<213> ORGANISM: Homo sapiens

<400> SEQUENCE: 1867

Leu Ile Pro Leu Leu Leu Gln Leu Thr Ser Arg Leu
1 5 10

<210> SEQ ID NO 1868
<211> LENGTH: 12
<212> TYPE: PRT
<213> ORGANISM: Homo sapiens

<400> SEQUENCE: 1868

Leu Asp Val Gly Leu Leu Ala Asn Leu Ser Ala Leu
1 5 10

<210> SEQ ID NO 1869
<211> LENGTH: 12
<212> TYPE: PRT
<213> ORGANISM: Homo sapiens

<400> SEQUENCE: 1869

Leu Gln Asp Glu Leu Leu Glu Val Val Ser Glu Leu
1 5 10

<210> SEQ ID NO 1870
<211> LENGTH: 12
<212> TYPE: PRT
<213> ORGANISM: Homo sapiens

<400> SEQUENCE: 1870

Leu Ala Ile Val Leu Leu Val Thr Ile Ser Leu Leu
1 5 10

<210> SEQ ID NO 1871
<211> LENGTH: 12
<212> TYPE: PRT
<213> ORGANISM: Homo sapiens

<400> SEQUENCE: 1871

Leu Cys Gly Ala Leu Leu Cys Ala Pro Ser Leu Leu
1 5 10

<210> SEQ ID NO 1872
<211> LENGTH: 12
<212> TYPE: PRT
<213> ORGANISM: Homo sapiens

<400> SEQUENCE: 1872

Leu Val Ile Val Leu Leu Gly Phe Lys Ser Phe Leu
1 5 10

<210> SEQ ID NO 1873
<211> LENGTH: 12
<212> TYPE: PRT
<213> ORGANISM: Homo sapiens

<400> SEQUENCE: 1873

Leu Gly Ala Ser Leu Leu Ala Ala Ser Ser Ser Leu
1 5 10

<210> SEQ ID NO 1874
<211> LENGTH: 12
<212> TYPE: PRT
<213> ORGANISM: Homo sapiens

<400> SEQUENCE: 1874

Leu Val Ala Gly Leu Leu Leu Trp Ala Ser Leu Leu
1 5 10

<210> SEQ ID NO 1875
<211> LENGTH: 12
<212> TYPE: PRT
<213> ORGANISM: Homo sapiens

<400> SEQUENCE: 1875

Leu Asn Gly Ile Leu Leu Gln Leu Ile Ser Cys Leu
1 5 10

<210> SEQ ID NO 1876
<211> LENGTH: 12
<212> TYPE: PRT
<213> ORGANISM: Homo sapiens

<400> SEQUENCE: 1876

Leu Leu Leu Leu Leu Leu Ser Ile His Ser Ala Leu
1               5                   10

<210> SEQ ID NO 1877
<211> LENGTH: 12
<212> TYPE: PRT
<213> ORGANISM: Homo sapiens

<400> SEQUENCE: 1877

Leu Leu Arg Ser Leu Leu Gly Met Leu Ser Asp Leu
1               5                   10

<210> SEQ ID NO 1878
<211> LENGTH: 12
<212> TYPE: PRT
<213> ORGANISM: Homo sapiens

<400> SEQUENCE: 1878

Leu Leu Arg Ser Leu Leu Ser Met Leu Ser Asp Leu
1               5                   10

<210> SEQ ID NO 1879
<211> LENGTH: 12
<212> TYPE: PRT
<213> ORGANISM: Homo sapiens

<400> SEQUENCE: 1879

Leu His Ile Ser Leu Leu Leu Ile Glu Ser Arg Leu
1               5                   10

<210> SEQ ID NO 1880
<211> LENGTH: 12
<212> TYPE: PRT
<213> ORGANISM: Homo sapiens

<400> SEQUENCE: 1880

Leu Leu Val Leu Leu Leu Val Ala Leu Ser Ala Leu
1               5                   10

<210> SEQ ID NO 1881
<211> LENGTH: 12
<212> TYPE: PRT
<213> ORGANISM: Homo sapiens

<400> SEQUENCE: 1881

Leu Ile Pro Leu Leu Leu Gln Leu Thr Ser Arg Leu
1               5                   10

<210> SEQ ID NO 1882
<211> LENGTH: 12
<212> TYPE: PRT
<213> ORGANISM: Homo sapiens

<400> SEQUENCE: 1882

Leu Ile Leu Asn Leu Leu Phe Leu Leu Ser Trp Leu
1               5                   10

<210> SEQ ID NO 1883
<211> LENGTH: 12
<212> TYPE: PRT
<213> ORGANISM: Homo sapiens

<400> SEQUENCE: 1883

Leu Ala Cys Asp Leu Leu Pro Cys Asn Ser Asp Leu
1               5                   10

<210> SEQ ID NO 1884
<211> LENGTH: 12
<212> TYPE: PRT
<213> ORGANISM: Homo sapiens

<400> SEQUENCE: 1884

Leu Ala Thr Asp Leu Leu Ser Thr Trp Ser Val Leu
1               5                   10

<210> SEQ ID NO 1885
<211> LENGTH: 12
<212> TYPE: PRT
<213> ORGANISM: Homo sapiens

<400> SEQUENCE: 1885

Leu Leu Tyr Glu Leu Leu Gln Tyr Glu Ser Ser Leu
1               5                   10

<210> SEQ ID NO 1886
<211> LENGTH: 12
<212> TYPE: PRT
<213> ORGANISM: Homo sapiens

<400> SEQUENCE: 1886

Leu Asn Arg Ala Leu Leu Met Thr Phe Ser Leu Leu
1               5                   10

<210> SEQ ID NO 1887
<211> LENGTH: 12
<212> TYPE: PRT
<213> ORGANISM: Homo sapiens

<400> SEQUENCE: 1887

Leu Ile Pro Leu Leu Leu Gln Leu Thr Ser Arg Leu
1               5                   10

<210> SEQ ID NO 1888
<211> LENGTH: 12
<212> TYPE: PRT
<213> ORGANISM: Homo sapiens

<400> SEQUENCE: 1888

Leu Pro Gln Leu Leu Leu Arg Met Ile Ser Ala Leu
1               5                   10

<210> SEQ ID NO 1889
<211> LENGTH: 12
<212> TYPE: PRT
<213> ORGANISM: Homo sapiens

<400> SEQUENCE: 1889

Leu Ser Lys Asn Leu Leu Ala Gln Ile Ser Ala Leu
1               5                   10

<210> SEQ ID NO 1890
<211> LENGTH: 12
<212> TYPE: PRT
<213> ORGANISM: Homo sapiens

<400> SEQUENCE: 1890

Leu Ser Gln Asp Leu Leu Glu Asp Asn Ser His Leu
1 5 10

<210> SEQ ID NO 1891
<211> LENGTH: 12
<212> TYPE: PRT
<213> ORGANISM: Homo sapiens

<400> SEQUENCE: 1891

Leu Arg Glu Ala Leu Leu Ser Ser Arg Ser His Leu
1 5 10

<210> SEQ ID NO 1892
<211> LENGTH: 12
<212> TYPE: PRT
<213> ORGANISM: Homo sapiens

<400> SEQUENCE: 1892

Leu Ile Pro Ala Leu Leu Glu Ser Leu Ser Val Leu
1 5 10

<210> SEQ ID NO 1893
<211> LENGTH: 12
<212> TYPE: PRT
<213> ORGANISM: Homo sapiens

<400> SEQUENCE: 1893

Leu Val Ile Val Leu Leu Gly Phe Arg Ser Leu Leu
1 5 10

<210> SEQ ID NO 1894
<211> LENGTH: 12
<212> TYPE: PRT
<213> ORGANISM: Homo sapiens

<400> SEQUENCE: 1894

Leu Trp Asp Asp Leu Leu Ser Val Leu Ser Ser Leu
1 5 10

<210> SEQ ID NO 1895
<211> LENGTH: 12
<212> TYPE: PRT
<213> ORGANISM: Homo sapiens

<400> SEQUENCE: 1895

Leu Val Pro Trp Leu Leu Leu Gly Ala Ser Trp Leu
1 5 10

<210> SEQ ID NO 1896
<211> LENGTH: 12
<212> TYPE: PRT
<213> ORGANISM: Homo sapiens

<400> SEQUENCE: 1896

Leu Ala Val Leu Leu Leu Ser Leu Pro Ser Pro Leu
1 5 10

<210> SEQ ID NO 1897
<211> LENGTH: 12
<212> TYPE: PRT
<213> ORGANISM: Homo sapiens

<400> SEQUENCE: 1897

Leu His Asn Ser Leu Leu Gln Arg Lys Ser Lys Leu
1 5 10

<210> SEQ ID NO 1898
<211> LENGTH: 12
<212> TYPE: PRT
<213> ORGANISM: Homo sapiens

<400> SEQUENCE: 1898

Leu Phe Pro Ile Leu Leu Cys Glu Ile Ser Thr Leu
1 5 10

<210> SEQ ID NO 1899
<211> LENGTH: 12
<212> TYPE: PRT
<213> ORGANISM: Homo sapiens

<400> SEQUENCE: 1899

Leu Phe Gly Thr Leu Leu Tyr Phe Asp Ser Val Leu
1 5 10

<210> SEQ ID NO 1900
<211> LENGTH: 12
<212> TYPE: PRT
<213> ORGANISM: Homo sapiens

<400> SEQUENCE: 1900

Leu Arg Val Glu Leu Leu Ser Ala Ser Ser Leu Leu
1 5 10

<210> SEQ ID NO 1901
<211> LENGTH: 12
<212> TYPE: PRT
<213> ORGANISM: Homo sapiens

<400> SEQUENCE: 1901

Leu Arg Ile Ala Leu Leu Tyr Ser His Ser Glu Leu
1 5 10

<210> SEQ ID NO 1902
<211> LENGTH: 12
<212> TYPE: PRT
<213> ORGANISM: Homo sapiens

<400> SEQUENCE: 1902

Leu Gln Glu Gly Leu Leu Gln Leu Asp Ser Ile Leu
1 5 10

<210> SEQ ID NO 1903
<211> LENGTH: 12
<212> TYPE: PRT
<213> ORGANISM: Homo sapiens

<400> SEQUENCE: 1903

Leu Val Ile Val Leu Leu Gly Phe Arg Ser Leu Leu
1 5 10

<210> SEQ ID NO 1904
<211> LENGTH: 12
<212> TYPE: PRT
<213> ORGANISM: Homo sapiens

<400> SEQUENCE: 1904

Leu Leu Asn Phe Leu Leu Pro Val Phe Ser Pro Leu
1 5 10

<210> SEQ ID NO 1905
<211> LENGTH: 12
<212> TYPE: PRT
<213> ORGANISM: Homo sapiens

<400> SEQUENCE: 1905

Leu Glu Lys Lys Leu Leu His His Leu Ser Asp Leu
1 5 10

<210> SEQ ID NO 1906
<211> LENGTH: 12
<212> TYPE: PRT
<213> ORGANISM: Homo sapiens

<400> SEQUENCE: 1906

Leu Leu Asn Ser Leu Leu Asp Ile Val Ser Ser Leu
1 5 10

<210> SEQ ID NO 1907
<211> LENGTH: 12
<212> TYPE: PRT
<213> ORGANISM: Homo sapiens

<400> SEQUENCE: 1907

Leu Leu Gln Ser Leu Leu Leu Ser Leu Ser Glu Leu
1 5 10

<210> SEQ ID NO 1908
<211> LENGTH: 12
<212> TYPE: PRT
<213> ORGANISM: Homo sapiens

<400> SEQUENCE: 1908

Leu Phe Phe Pro Leu Leu Pro Gln Tyr Ser Lys Leu
1 5 10

<210> SEQ ID NO 1909
<211> LENGTH: 12
<212> TYPE: PRT
<213> ORGANISM: Homo sapiens

<400> SEQUENCE: 1909

Leu Ala Trp Ser Leu Leu Leu Leu Ser Ser Ala Leu
1 5 10

<210> SEQ ID NO 1910
<211> LENGTH: 12
<212> TYPE: PRT
<213> ORGANISM: Homo sapiens

<400> SEQUENCE: 1910

Leu Glu Ser Asp Leu Leu Ile Glu Glu Ser Val Leu
1 5 10

<210> SEQ ID NO 1911
<211> LENGTH: 12
<212> TYPE: PRT
<213> ORGANISM: Homo sapiens

<400> SEQUENCE: 1911

Leu Arg Leu Leu Leu Leu Glu Ser Val Ser Gly Leu
1 5 10

<210> SEQ ID NO 1912
<211> LENGTH: 12
<212> TYPE: PRT
<213> ORGANISM: Homo sapiens

<400> SEQUENCE: 1912

Leu Phe Thr Leu Leu Leu Gln His Arg Ser Gln Leu
1 5 10

<210> SEQ ID NO 1913
<211> LENGTH: 12
<212> TYPE: PRT
<213> ORGANISM: Homo sapiens

<400> SEQUENCE: 1913

Leu Phe Glu Asp Leu Leu Arg Gln Met Ser Asp Leu
1 5 10

<210> SEQ ID NO 1914
<211> LENGTH: 12
<212> TYPE: PRT
<213> ORGANISM: Homo sapiens

<400> SEQUENCE: 1914

Leu Ala Gly Ser Leu Leu Lys Glu Leu Ser Pro Leu
1 5 10

<210> SEQ ID NO 1915
<211> LENGTH: 12
<212> TYPE: PRT
<213> ORGANISM: Homo sapiens

<400> SEQUENCE: 1915

Leu Leu Pro Cys Leu Leu Gly Val Gly Ser Trp Leu
1 5 10

<210> SEQ ID NO 1916
<211> LENGTH: 12
<212> TYPE: PRT
<213> ORGANISM: Homo sapiens

<400> SEQUENCE: 1916

Leu Ser Lys Ser Leu Leu Leu Val Pro Ser Ala Leu
1 5 10

<210> SEQ ID NO 1917
<211> LENGTH: 12
<212> TYPE: PRT
<213> ORGANISM: Homo sapiens

<400> SEQUENCE: 1917

Leu Thr Gln Pro Leu Leu Gly Glu Gln Ser Leu Leu
1 5 10

<210> SEQ ID NO 1918
<211> LENGTH: 12
<212> TYPE: PRT
<213> ORGANISM: Homo sapiens

<400> SEQUENCE: 1918

Leu Cys Gln His Leu Leu Ser Gly Gly Ser Gly Leu
1 5 10

<210> SEQ ID NO 1919
<211> LENGTH: 12
<212> TYPE: PRT
<213> ORGANISM: Homo sapiens

<400> SEQUENCE: 1919

Leu Pro Glu Phe Leu Leu Leu Gly Phe Ser Asp Leu
1 5 10

<210> SEQ ID NO 1920
<211> LENGTH: 12
<212> TYPE: PRT
<213> ORGANISM: Homo sapiens

<400> SEQUENCE: 1920

Leu Leu Gly Ala Leu Leu Ala Val Gly Ser Gln Leu
1 5 10

<210> SEQ ID NO 1921
<211> LENGTH: 12
<212> TYPE: PRT
<213> ORGANISM: Homo sapiens

<400> SEQUENCE: 1921

Leu Arg Ile Gln Leu Leu His Lys Leu Ser Phe Leu
1 5 10

<210> SEQ ID NO 1922
<211> LENGTH: 12
<212> TYPE: PRT
<213> ORGANISM: Homo sapiens

<400> SEQUENCE: 1922

Leu Glu Gly Gln Leu Leu Glu Thr Ile Ser Gln Leu
1 5 10

<210> SEQ ID NO 1923
<211> LENGTH: 12
<212> TYPE: PRT
<213> ORGANISM: Homo sapiens

<400> SEQUENCE: 1923

Leu Val Phe Leu Leu Leu Phe Leu Gln Ser Phe Leu
1 5 10

<210> SEQ ID NO 1924
<211> LENGTH: 12
<212> TYPE: PRT
<213> ORGANISM: Homo sapiens

<400> SEQUENCE: 1924

Leu Leu Ala His Leu Leu Gln Ser Lys Ser Glu Leu
1 5 10

<210> SEQ ID NO 1925
<211> LENGTH: 12
<212> TYPE: PRT
<213> ORGANISM: Homo sapiens

<400> SEQUENCE: 1925

Leu Glu Glu Gln Leu Leu Gln Glu Leu Ser Ser Leu
1 5 10

<210> SEQ ID NO 1926
<211> LENGTH: 12
<212> TYPE: PRT
<213> ORGANISM: Homo sapiens

<400> SEQUENCE: 1926

Leu Gly Met Ile Leu Leu Ile Ala Val Ser Pro Leu
1 5 10

<210> SEQ ID NO 1927
<211> LENGTH: 12
<212> TYPE: PRT
<213> ORGANISM: Homo sapiens

<400> SEQUENCE: 1927

Leu Phe Ala Leu Leu Leu Met Ser Ile Ser Cys Leu
1 5 10

<210> SEQ ID NO 1928
<211> LENGTH: 12
<212> TYPE: PRT
<213> ORGANISM: Homo sapiens

<400> SEQUENCE: 1928

Leu Arg Ile Leu Leu Leu Met Lys Pro Ser Val Leu
1 5 10

<210> SEQ ID NO 1929
<211> LENGTH: 12
<212> TYPE: PRT
<213> ORGANISM: Homo sapiens

<400> SEQUENCE: 1929

Leu Pro Val Leu Leu Leu Gly Arg Ser Ser Glu Leu
1 5 10

<210> SEQ ID NO 1930
<211> LENGTH: 12
<212> TYPE: PRT
<213> ORGANISM: Homo sapiens

<400> SEQUENCE: 1930

Leu Leu Leu Val Leu Leu Gly Gly Phe Ser Leu Leu
1 5 10

<210> SEQ ID NO 1931
<211> LENGTH: 12
<212> TYPE: PRT
<213> ORGANISM: Homo sapiens

<400> SEQUENCE: 1931

Leu Gln Thr Ile Leu Leu Cys Cys Pro Ser Ala Leu
1 5 10

<210> SEQ ID NO 1932
<211> LENGTH: 12
<212> TYPE: PRT
<213> ORGANISM: Homo sapiens

<400> SEQUENCE: 1932

Leu Gly Ala Ser Leu Leu Gly Asp Leu Ser Ser Leu
1 5 10

<210> SEQ ID NO 1933
<211> LENGTH: 12
<212> TYPE: PRT
<213> ORGANISM: Homo sapiens

<400> SEQUENCE: 1933

Leu Thr Phe Leu Leu Leu Val Leu Gly Ser Leu Leu
1 5 10

<210> SEQ ID NO 1934
<211> LENGTH: 12
<212> TYPE: PRT
<213> ORGANISM: Homo sapiens

<400> SEQUENCE: 1934

Leu Ala Lys Leu Leu Leu Thr Cys Cys Ser Ala Leu
1 5 10

<210> SEQ ID NO 1935
<211> LENGTH: 12
<212> TYPE: PRT
<213> ORGANISM: Homo sapiens

<400> SEQUENCE: 1935

Leu Met Asn Arg Leu Leu Arg Thr Val Ser Met Leu
1 5 10

<210> SEQ ID NO 1936
<211> LENGTH: 12
<212> TYPE: PRT
<213> ORGANISM: Homo sapiens

<400> SEQUENCE: 1936

Leu Leu Asp Lys Leu Leu Glu Thr Pro Ser Thr Leu
1 5 10

<210> SEQ ID NO 1937
<211> LENGTH: 12
<212> TYPE: PRT
<213> ORGANISM: Homo sapiens

<400> SEQUENCE: 1937

Leu Lys Gly Arg Leu Leu Leu Ala Glu Ser Gly Leu
1 5 10

<210> SEQ ID NO 1938
<211> LENGTH: 12
<212> TYPE: PRT
<213> ORGANISM: Homo sapiens

<400> SEQUENCE: 1938

Leu Val Val Ala Leu Leu Val Gly Leu Ser Trp Leu
1 5 10

<210> SEQ ID NO 1939
<211> LENGTH: 12
<212> TYPE: PRT
<213> ORGANISM: Homo sapiens

<400> SEQUENCE: 1939

Leu Ser Ser Asp Leu Leu Phe Ile Ile Ser Glu Leu
1 5 10

<210> SEQ ID NO 1940
<211> LENGTH: 12
<212> TYPE: PRT
<213> ORGANISM: Homo sapiens

<400> SEQUENCE: 1940

Leu Pro Arg Ala Leu Leu Ser Ser Leu Ser Gly Leu
1 5 10

<210> SEQ ID NO 1941
<211> LENGTH: 12
<212> TYPE: PRT
<213> ORGANISM: Homo sapiens

<400> SEQUENCE: 1941

Leu Ile Pro Gly Leu Leu Leu Trp Gln Ser Trp Leu
1 5 10

<210> SEQ ID NO 1942
<211> LENGTH: 12
<212> TYPE: PRT
<213> ORGANISM: Homo sapiens

<400> SEQUENCE: 1942

Leu Cys Leu Met Leu Leu Leu Ala Gly Ser Cys Leu
1 5 10

<210> SEQ ID NO 1943
<211> LENGTH: 12
<212> TYPE: PRT
<213> ORGANISM: Homo sapiens

<400> SEQUENCE: 1943

Leu Leu Phe Asp Leu Leu Ala Ser Ser Ser Ala Leu
1 5 10

<210> SEQ ID NO 1944
<211> LENGTH: 12
<212> TYPE: PRT
<213> ORGANISM: Homo sapiens

<400> SEQUENCE: 1944

Leu Asp Lys Lys Leu Leu His Met Glu Ser Gln Leu
1 5 10

<210> SEQ ID NO 1945
<211> LENGTH: 12
<212> TYPE: PRT
<213> ORGANISM: Homo sapiens

<400> SEQUENCE: 1945

Leu Gly Lys Phe Leu Leu Lys Val Asp Ser Lys Leu
1 5 10

<210> SEQ ID NO 1946
<211> LENGTH: 12
<212> TYPE: PRT
<213> ORGANISM: Homo sapiens

<400> SEQUENCE: 1946

Leu Leu Gln Arg Leu Leu Lys Ser Asn Ser His Leu
1 5 10

<210> SEQ ID NO 1947
<211> LENGTH: 12
<212> TYPE: PRT
<213> ORGANISM: Homo sapiens

<400> SEQUENCE: 1947

Leu Pro Gln Thr Leu Leu Ser His Pro Ser Tyr Leu
1 5 10

<210> SEQ ID NO 1948
<211> LENGTH: 12
<212> TYPE: PRT
<213> ORGANISM: Homo sapiens

<400> SEQUENCE: 1948

Leu Trp Gly Gly Leu Leu Arg Leu Gly Ser Leu Leu
1 5 10

<210> SEQ ID NO 1949
<211> LENGTH: 12
<212> TYPE: PRT
<213> ORGANISM: Homo sapiens

<400> SEQUENCE: 1949

Leu Leu Lys Ala Leu Leu Asp Asn Met Ser Phe Leu
1 5 10

<210> SEQ ID NO 1950
<211> LENGTH: 12
<212> TYPE: PRT
<213> ORGANISM: Homo sapiens

<400> SEQUENCE: 1950

Leu Gly Leu Asp Leu Leu Leu Asn Cys Ser Leu Leu
1 5 10

<210> SEQ ID NO 1951
<211> LENGTH: 12
<212> TYPE: PRT
<213> ORGANISM: Homo sapiens

<400> SEQUENCE: 1951

Leu Gly Ala Leu Leu Leu Leu Ala Leu Ser Ala Leu
1 5 10

<210> SEQ ID NO 1952
<211> LENGTH: 12
<212> TYPE: PRT
<213> ORGANISM: Homo sapiens

<400> SEQUENCE: 1952

Leu Ser Lys Val Leu Leu Ser Ile Cys Ser Leu Leu
1 5 10

<210> SEQ ID NO 1953
<211> LENGTH: 12
<212> TYPE: PRT
<213> ORGANISM: Homo sapiens

<400> SEQUENCE: 1953

Leu Arg Ile Asp Leu Leu Gln Ala Phe Ser Gln Leu
1               5                   10

<210> SEQ ID NO 1954
<211> LENGTH: 12
<212> TYPE: PRT
<213> ORGANISM: Homo sapiens

<400> SEQUENCE: 1954

Leu Thr Asn Phe Leu Leu Asn Gly Arg Ser Val Leu
1               5                   10

<210> SEQ ID NO 1955
<211> LENGTH: 12
<212> TYPE: PRT
<213> ORGANISM: Homo sapiens

<400> SEQUENCE: 1955

Leu Pro Thr Gln Leu Leu Phe Leu Leu Ser Val Leu
1               5                   10

<210> SEQ ID NO 1956
<211> LENGTH: 12
<212> TYPE: PRT
<213> ORGANISM: Homo sapiens

<400> SEQUENCE: 1956

Leu Arg Gln Leu Leu Leu Glu Ser Gln Ser Gln Leu
1               5                   10

<210> SEQ ID NO 1957
<211> LENGTH: 12
<212> TYPE: PRT
<213> ORGANISM: Homo sapiens

<400> SEQUENCE: 1957

Leu Leu Asn Ala Leu Leu Val Glu Leu Ser Leu Leu
1               5                   10

<210> SEQ ID NO 1958
<211> LENGTH: 12
<212> TYPE: PRT
<213> ORGANISM: Homo sapiens

<400> SEQUENCE: 1958

Leu Pro Leu Thr Leu Leu Val Cys Cys Ser Ala Leu
1               5                   10

<210> SEQ ID NO 1959
<211> LENGTH: 12
<212> TYPE: PRT
<213> ORGANISM: Homo sapiens

<400> SEQUENCE: 1959

Leu Arg Glu Pro Leu Leu Arg Arg Leu Ser Glu Leu
1               5                   10

<210> SEQ ID NO 1960
<211> LENGTH: 12
<212> TYPE: PRT
<213> ORGANISM: Homo sapiens

<400> SEQUENCE: 1960

Leu Val Met Lys Leu Leu Ser Gly Gly Ser Met Leu
1 5 10

<210> SEQ ID NO 1961
<211> LENGTH: 12
<212> TYPE: PRT
<213> ORGANISM: Homo sapiens

<400> SEQUENCE: 1961

Leu Leu Leu Leu Leu Leu Val Gly Ala Ser Leu Leu
1 5 10

<210> SEQ ID NO 1962
<211> LENGTH: 12
<212> TYPE: PRT
<213> ORGANISM: Homo sapiens

<400> SEQUENCE: 1962

Leu Gly His Met Leu Leu Gly Ile Ser Ser Thr Leu
1 5 10

<210> SEQ ID NO 1963
<211> LENGTH: 12
<212> TYPE: PRT
<213> ORGANISM: Homo sapiens

<400> SEQUENCE: 1963

Leu Cys Gly Ala Leu Leu Phe Phe Ser Ser Leu Leu
1 5 10

<210> SEQ ID NO 1964
<211> LENGTH: 12
<212> TYPE: PRT
<213> ORGANISM: Homo sapiens

<400> SEQUENCE: 1964

Leu Gly Ala Ser Leu Leu Thr Gln Ala Ser Thr Leu
1 5 10

<210> SEQ ID NO 1965
<211> LENGTH: 12
<212> TYPE: PRT
<213> ORGANISM: Homo sapiens

<400> SEQUENCE: 1965

Leu Thr Gly Arg Leu Leu Asp Pro Ser Ser Pro Leu
1 5 10

<210> SEQ ID NO 1966
<211> LENGTH: 12
<212> TYPE: PRT
<213> ORGANISM: Homo sapiens

<400> SEQUENCE: 1966

Leu Ser Gly Lys Leu Leu Lys Gly Ala Ser Lys Leu
1 5 10

<210> SEQ ID NO 1967
<211> LENGTH: 12
<212> TYPE: PRT
<213> ORGANISM: Homo sapiens

<400> SEQUENCE: 1967

Leu Leu Thr Thr Leu Leu Gly Thr Ala Ser Pro Leu
1               5                   10

<210> SEQ ID NO 1968
<211> LENGTH: 12
<212> TYPE: PRT
<213> ORGANISM: Homo sapiens

<400> SEQUENCE: 1968

Leu Pro Ser Ala Leu Leu Phe Ala Ala Ser Ile Leu
1               5                   10

<210> SEQ ID NO 1969
<211> LENGTH: 12
<212> TYPE: PRT
<213> ORGANISM: Homo sapiens

<400> SEQUENCE: 1969

Leu Pro Phe Leu Leu Leu Gly Thr Val Ser Ala Leu
1               5                   10

<210> SEQ ID NO 1970
<211> LENGTH: 12
<212> TYPE: PRT
<213> ORGANISM: Homo sapiens

<400> SEQUENCE: 1970

Leu Asn Gly Ile Leu Leu Gln Leu Ile Ser Cys Leu
1               5                   10

<210> SEQ ID NO 1971
<211> LENGTH: 12
<212> TYPE: PRT
<213> ORGANISM: Homo sapiens

<400> SEQUENCE: 1971

Leu Gln Asn Ala Leu Leu Leu Ser Asp Ser Ser Leu
1               5                   10

<210> SEQ ID NO 1972
<211> LENGTH: 12
<212> TYPE: PRT
<213> ORGANISM: Homo sapiens

<400> SEQUENCE: 1972

Leu Ile Val Ala Leu Leu Phe Ile Leu Ser Trp Leu
1               5                   10

<210> SEQ ID NO 1973
<211> LENGTH: 8
<212> TYPE: PRT
<213> ORGANISM: Homo sapiens

<400> SEQUENCE: 1973

Leu Gly Leu Glu Glu Arg Pro Glu
1               5

<210> SEQ ID NO 1974
<211> LENGTH: 8
<212> TYPE: PRT
<213> ORGANISM: Homo sapiens

<400> SEQUENCE: 1974

Leu Cys Pro Glu Glu Glu Pro Asp
1               5

<210> SEQ ID NO 1975
<211> LENGTH: 8
<212> TYPE: PRT
<213> ORGANISM: Homo sapiens

<400> SEQUENCE: 1975

Leu Lys Ser Glu Glu Ile Pro Lys
1               5

<210> SEQ ID NO 1976
<211> LENGTH: 8
<212> TYPE: PRT
<213> ORGANISM: Homo sapiens

<400> SEQUENCE: 1976

Leu Asp Glu Glu Glu Thr Pro Tyr
1               5

<210> SEQ ID NO 1977
<211> LENGTH: 8
<212> TYPE: PRT
<213> ORGANISM: Homo sapiens

<400> SEQUENCE: 1977

Leu Gly Pro Glu Glu Arg Pro Pro
1               5

<210> SEQ ID NO 1978
<211> LENGTH: 8
<212> TYPE: PRT
<213> ORGANISM: Homo sapiens

<400> SEQUENCE: 1978

Leu Ser Gln Glu Glu Asn Pro Arg
1               5

<210> SEQ ID NO 1979
<211> LENGTH: 8
<212> TYPE: PRT
<213> ORGANISM: Homo sapiens

<400> SEQUENCE: 1979

Leu Gly Asn Glu Glu Gly Pro Glu
1               5

<210> SEQ ID NO 1980
<211> LENGTH: 8
<212> TYPE: PRT
<213> ORGANISM: Homo sapiens

<400> SEQUENCE: 1980

Leu Ser Ser Glu Glu Pro Pro Thr
1               5

<210> SEQ ID NO 1981
<211> LENGTH: 8
<212> TYPE: PRT
<213> ORGANISM: Homo sapiens

<400> SEQUENCE: 1981

Leu Gln Leu Glu Glu Ala Pro Glu
1               5

<210> SEQ ID NO 1982
<211> LENGTH: 8
<212> TYPE: PRT
<213> ORGANISM: Homo sapiens

<400> SEQUENCE: 1982

Leu Phe Arg Glu Glu Leu Pro Ala
1               5

<210> SEQ ID NO 1983
<211> LENGTH: 8
<212> TYPE: PRT
<213> ORGANISM: Homo sapiens

<400> SEQUENCE: 1983

Leu Gln Leu Glu Glu Leu Pro Arg
1               5

<210> SEQ ID NO 1984
<211> LENGTH: 8
<212> TYPE: PRT
<213> ORGANISM: Homo sapiens

<400> SEQUENCE: 1984

Leu Lys Glu Glu Glu Glu Pro Met
1               5

<210> SEQ ID NO 1985
<211> LENGTH: 8
<212> TYPE: PRT
<213> ORGANISM: Homo sapiens

<400> SEQUENCE: 1985

Leu Pro Pro Glu Glu Pro Pro Asn
1               5

<210> SEQ ID NO 1986
<211> LENGTH: 8
<212> TYPE: PRT
<213> ORGANISM: Homo sapiens

<400> SEQUENCE: 1986

Leu Tyr Glu Glu Glu Thr Pro Lys
1               5

<210> SEQ ID NO 1987
<211> LENGTH: 8
<212> TYPE: PRT
<213> ORGANISM: Homo sapiens

<400> SEQUENCE: 1987

Leu Glu Ala Glu Glu Lys Pro Leu
1               5

<210> SEQ ID NO 1988
<211> LENGTH: 8
<212> TYPE: PRT
<213> ORGANISM: Homo sapiens

<400> SEQUENCE: 1988

Leu Asn Met Glu Glu Pro Pro Val
1 5

<210> SEQ ID NO 1989
<211> LENGTH: 8
<212> TYPE: PRT
<213> ORGANISM: Homo sapiens

<400> SEQUENCE: 1989

Leu Glu Asp Glu Glu Pro Pro Ala
1 5

<210> SEQ ID NO 1990
<211> LENGTH: 8
<212> TYPE: PRT
<213> ORGANISM: Homo sapiens

<400> SEQUENCE: 1990

Leu Glu Arg Glu Glu Lys Pro Ser
1 5

<210> SEQ ID NO 1991
<211> LENGTH: 8
<212> TYPE: PRT
<213> ORGANISM: Homo sapiens

<400> SEQUENCE: 1991

Leu Glu Glu Glu Glu Glu Pro Ser
1 5

<210> SEQ ID NO 1992
<211> LENGTH: 8
<212> TYPE: PRT
<213> ORGANISM: Homo sapiens

<400> SEQUENCE: 1992

Leu Phe Ser Glu Glu Thr Pro Val
1 5

<210> SEQ ID NO 1993
<211> LENGTH: 8
<212> TYPE: PRT
<213> ORGANISM: Homo sapiens

<400> SEQUENCE: 1993

Leu Asp Asn Glu Glu Lys Pro Pro
1 5

<210> SEQ ID NO 1994
<211> LENGTH: 8
<212> TYPE: PRT
<213> ORGANISM: Homo sapiens

<400> SEQUENCE: 1994

Leu Gln Leu Glu Glu Asn Pro Trp
1 5

<210> SEQ ID NO 1995
<211> LENGTH: 8
<212> TYPE: PRT
<213> ORGANISM: Homo sapiens

<400> SEQUENCE: 1995

Leu Glu Ala Glu Glu Glu Pro Val
1               5

<210> SEQ ID NO 1996
<211> LENGTH: 8
<212> TYPE: PRT
<213> ORGANISM: Homo sapiens

<400> SEQUENCE: 1996

Leu Lys Asn Glu Glu Val Pro Val
1               5

<210> SEQ ID NO 1997
<211> LENGTH: 8
<212> TYPE: PRT
<213> ORGANISM: Homo sapiens

<400> SEQUENCE: 1997

Leu Gln Leu Glu Glu Asn Pro Trp
1               5

<210> SEQ ID NO 1998
<211> LENGTH: 8
<212> TYPE: PRT
<213> ORGANISM: Homo sapiens

<400> SEQUENCE: 1998

Leu Asn Gly Glu Glu Cys Pro Pro
1               5

<210> SEQ ID NO 1999
<211> LENGTH: 8
<212> TYPE: PRT
<213> ORGANISM: Homo sapiens

<400> SEQUENCE: 1999

Leu Ala Gly Glu Glu Ser Pro Gln
1               5

<210> SEQ ID NO 2000
<211> LENGTH: 8
<212> TYPE: PRT
<213> ORGANISM: Homo sapiens

<400> SEQUENCE: 2000

Leu Lys Ile Glu Glu Pro Pro Ser
1               5

<210> SEQ ID NO 2001
<211> LENGTH: 8
<212> TYPE: PRT
<213> ORGANISM: Homo sapiens

<400> SEQUENCE: 2001

Leu Glu Asp Glu Glu Glu Pro Lys
1               5

<210> SEQ ID NO 2002
<211> LENGTH: 8
<212> TYPE: PRT
<213> ORGANISM: Homo sapiens

<400> SEQUENCE: 2002

Leu His Cys Glu Glu Cys Pro Pro
1               5

<210> SEQ ID NO 2003
<211> LENGTH: 8
<212> TYPE: PRT
<213> ORGANISM: Homo sapiens

<400> SEQUENCE: 2003

Leu His Ser Glu Glu Val Pro Leu
1               5

<210> SEQ ID NO 2004
<211> LENGTH: 8
<212> TYPE: PRT
<213> ORGANISM: Homo sapiens

<400> SEQUENCE: 2004

Leu Gln Val Glu Glu Asp Pro Val
1               5

<210> SEQ ID NO 2005
<211> LENGTH: 8
<212> TYPE: PRT
<213> ORGANISM: Homo sapiens

<400> SEQUENCE: 2005

Leu Tyr Ala Glu Glu Lys Pro Cys
1               5

<210> SEQ ID NO 2006
<211> LENGTH: 8
<212> TYPE: PRT
<213> ORGANISM: Homo sapiens

<400> SEQUENCE: 2006

Leu Leu Asn Glu Glu Asn Pro Ser
1               5

<210> SEQ ID NO 2007
<211> LENGTH: 8
<212> TYPE: PRT
<213> ORGANISM: Homo sapiens

<400> SEQUENCE: 2007

Leu Lys Lys Glu Glu Cys Pro Ala
1               5

<210> SEQ ID NO 2008
<211> LENGTH: 8
<212> TYPE: PRT
<213> ORGANISM: Homo sapiens

<400> SEQUENCE: 2008

Leu Ser Glu Glu Glu Thr Pro Leu
1               5

<210> SEQ ID NO 2009
<211> LENGTH: 8
<212> TYPE: PRT
<213> ORGANISM: Homo sapiens

<400> SEQUENCE: 2009

Leu Pro Ser Glu Glu Ala Pro Thr
1               5

<210> SEQ ID NO 2010
<211> LENGTH: 8
<212> TYPE: PRT
<213> ORGANISM: Homo sapiens

<400> SEQUENCE: 2010

Leu Asp Pro Glu Glu Arg Pro Thr
1               5

<210> SEQ ID NO 2011
<211> LENGTH: 8
<212> TYPE: PRT
<213> ORGANISM: Homo sapiens

<400> SEQUENCE: 2011

Leu Val Val Glu Glu Ala Pro Pro
1               5

<210> SEQ ID NO 2012
<211> LENGTH: 8
<212> TYPE: PRT
<213> ORGANISM: Homo sapiens

<400> SEQUENCE: 2012

Leu Leu Val Glu Glu Leu Pro Leu
1               5

<210> SEQ ID NO 2013
<211> LENGTH: 8
<212> TYPE: PRT
<213> ORGANISM: Homo sapiens

<400> SEQUENCE: 2013

Leu Gln Val Glu Glu Glu Pro Val
1               5

<210> SEQ ID NO 2014
<211> LENGTH: 8
<212> TYPE: PRT
<213> ORGANISM: Homo sapiens

<400> SEQUENCE: 2014

Leu Lys Gly Glu Glu Glu Pro Leu
1               5

<210> SEQ ID NO 2015
<211> LENGTH: 8
<212> TYPE: PRT
<213> ORGANISM: Homo sapiens

<400> SEQUENCE: 2015

Leu Glu Val Glu Glu Cys Pro Ala
1               5

<210> SEQ ID NO 2016
<211> LENGTH: 8
<212> TYPE: PRT
<213> ORGANISM: Homo sapiens

<400> SEQUENCE: 2016

Leu Gly Thr Glu Glu Phe Pro Leu
1               5

<210> SEQ ID NO 2017
<211> LENGTH: 8
<212> TYPE: PRT
<213> ORGANISM: Homo sapiens

<400> SEQUENCE: 2017

Leu Pro Pro Glu Glu Pro Pro Thr
1               5

<210> SEQ ID NO 2018
<211> LENGTH: 8
<212> TYPE: PRT
<213> ORGANISM: Homo sapiens

<400> SEQUENCE: 2018

Leu Pro Pro Glu Glu Pro Pro Met
1               5

<210> SEQ ID NO 2019
<211> LENGTH: 8
<212> TYPE: PRT
<213> ORGANISM: Homo sapiens

<400> SEQUENCE: 2019

Leu Pro Pro Glu Glu Pro Pro Glu
1               5

<210> SEQ ID NO 2020
<211> LENGTH: 8
<212> TYPE: PRT
<213> ORGANISM: Homo sapiens

<400> SEQUENCE: 2020

Leu Pro Ser Glu Glu Gly Pro Gly
1               5

<210> SEQ ID NO 2021
<211> LENGTH: 8
<212> TYPE: PRT
<213> ORGANISM: Homo sapiens

<400> SEQUENCE: 2021

Leu Pro Arg Glu Glu Gly Pro Tyr
1               5

<210> SEQ ID NO 2022
<211> LENGTH: 8
<212> TYPE: PRT
<213> ORGANISM: Homo sapiens

<400> SEQUENCE: 2022

Leu Glu Pro Glu Glu Pro Pro Thr
1               5

<210> SEQ ID NO 2023
<211> LENGTH: 8
<212> TYPE: PRT
<213> ORGANISM: Homo sapiens

<400> SEQUENCE: 2023

Leu Arg Glu Glu Glu Arg Pro Leu
1               5

<210> SEQ ID NO 2024
<211> LENGTH: 8
<212> TYPE: PRT
<213> ORGANISM: Homo sapiens

<400> SEQUENCE: 2024

Leu Val Ser Glu Glu Ser Pro Ser
1               5

<210> SEQ ID NO 2025
<211> LENGTH: 8
<212> TYPE: PRT
<213> ORGANISM: Homo sapiens

<400> SEQUENCE: 2025

Leu Asp Pro Glu Glu Arg Pro Lys
1               5

<210> SEQ ID NO 2026
<211> LENGTH: 8
<212> TYPE: PRT
<213> ORGANISM: Homo sapiens

<400> SEQUENCE: 2026

Leu Val Glu Glu Glu Asp Pro Phe
1               5

<210> SEQ ID NO 2027
<211> LENGTH: 8
<212> TYPE: PRT
<213> ORGANISM: Homo sapiens

<400> SEQUENCE: 2027

Leu Asp Ser Glu Glu Arg Pro Glu
1               5

<210> SEQ ID NO 2028
<211> LENGTH: 8
<212> TYPE: PRT
<213> ORGANISM: Homo sapiens

<400> SEQUENCE: 2028

Leu Tyr Glu Glu Glu Ser Pro Ser
1               5

<210> SEQ ID NO 2029
<211> LENGTH: 8
<212> TYPE: PRT
<213> ORGANISM: Homo sapiens

<400> SEQUENCE: 2029

Leu Arg Phe Glu Glu Ala Pro Asp
1               5

<210> SEQ ID NO 2030
<211> LENGTH: 8
<212> TYPE: PRT
<213> ORGANISM: Homo sapiens

<400> SEQUENCE: 2030

Leu Thr Phe Glu Glu Val Pro Tyr
1               5

<210> SEQ ID NO 2031
<211> LENGTH: 8
<212> TYPE: PRT
<213> ORGANISM: Homo sapiens

<400> SEQUENCE: 2031

Leu Gly Ala Glu Glu Asn Pro Leu
1               5

<210> SEQ ID NO 2032
<211> LENGTH: 8
<212> TYPE: PRT
<213> ORGANISM: Homo sapiens

<400> SEQUENCE: 2032

Leu Thr Val Glu Glu Leu Pro Ala
1               5

<210> SEQ ID NO 2033
<211> LENGTH: 8
<212> TYPE: PRT
<213> ORGANISM: Homo sapiens

<400> SEQUENCE: 2033

Leu Phe Lys Glu Glu Asn Pro Tyr
1               5

<210> SEQ ID NO 2034
<211> LENGTH: 8
<212> TYPE: PRT
<213> ORGANISM: Homo sapiens

<400> SEQUENCE: 2034

Leu Leu Thr Glu Glu Ser Pro Ser
1               5

<210> SEQ ID NO 2035
<211> LENGTH: 8
<212> TYPE: PRT
<213> ORGANISM: Homo sapiens

<400> SEQUENCE: 2035

Leu Asp Arg Glu Glu Lys Pro Val
1               5

<210> SEQ ID NO 2036
<211> LENGTH: 8
<212> TYPE: PRT
<213> ORGANISM: Homo sapiens

<400> SEQUENCE: 2036

Leu Asp Arg Glu Glu Lys Pro Phe
1               5

<210> SEQ ID NO 2037
<211> LENGTH: 8
<212> TYPE: PRT
<213> ORGANISM: Homo sapiens

<400> SEQUENCE: 2037

Leu Leu Gln Glu Glu Met Pro Arg
1               5

<210> SEQ ID NO 2038
<211> LENGTH: 8
<212> TYPE: PRT
<213> ORGANISM: Homo sapiens

<400> SEQUENCE: 2038

Leu Leu Pro Glu Glu Asp Pro Glu
1               5

<210> SEQ ID NO 2039
<211> LENGTH: 8
<212> TYPE: PRT
<213> ORGANISM: Homo sapiens

<400> SEQUENCE: 2039

Leu Arg Lys Glu Glu Asp Pro Lys
1               5

<210> SEQ ID NO 2040
<211> LENGTH: 8
<212> TYPE: PRT
<213> ORGANISM: Homo sapiens

<400> SEQUENCE: 2040

Leu Val Glu Glu Glu Arg Pro Ser
1               5

<210> SEQ ID NO 2041
<211> LENGTH: 8
<212> TYPE: PRT
<213> ORGANISM: Homo sapiens

<400> SEQUENCE: 2041

Leu Pro Ala Glu Glu Pro Pro Ala
1               5

<210> SEQ ID NO 2042
<211> LENGTH: 8
<212> TYPE: PRT
<213> ORGANISM: Homo sapiens

<400> SEQUENCE: 2042

Leu Tyr Pro Glu Glu Ile Pro Ser
1               5

<210> SEQ ID NO 2043
<211> LENGTH: 8
<212> TYPE: PRT
<213> ORGANISM: Homo sapiens

<400> SEQUENCE: 2043

Leu Arg His Glu Glu Gln Pro Ala
1               5

<210> SEQ ID NO 2044
<211> LENGTH: 8
<212> TYPE: PRT
<213> ORGANISM: Homo sapiens

<400> SEQUENCE: 2044

Leu Met Lys Glu Glu Ser Pro Val
1 5

<210> SEQ ID NO 2045
<211> LENGTH: 8
<212> TYPE: PRT
<213> ORGANISM: Homo sapiens

<400> SEQUENCE: 2045

Leu Pro Thr Glu Glu Pro Pro Glu
1 5

<210> SEQ ID NO 2046
<211> LENGTH: 8
<212> TYPE: PRT
<213> ORGANISM: Homo sapiens

<400> SEQUENCE: 2046

Leu Thr Ala Glu Glu Thr Pro Leu
1 5

<210> SEQ ID NO 2047
<211> LENGTH: 8
<212> TYPE: PRT
<213> ORGANISM: Homo sapiens

<400> SEQUENCE: 2047

Leu Pro Gly Glu Glu Tyr Pro Leu
1 5

<210> SEQ ID NO 2048
<211> LENGTH: 8
<212> TYPE: PRT
<213> ORGANISM: Homo sapiens

<400> SEQUENCE: 2048

Leu Glu Gln Glu Glu Asn Pro Gly
1 5

<210> SEQ ID NO 2049
<211> LENGTH: 8
<212> TYPE: PRT
<213> ORGANISM: Homo sapiens

<400> SEQUENCE: 2049

Leu Glu Lys Glu Glu Leu Pro Arg
1 5

<210> SEQ ID NO 2050
<211> LENGTH: 8
<212> TYPE: PRT
<213> ORGANISM: Homo sapiens

<400> SEQUENCE: 2050

Leu Asp Arg Glu Glu Thr Pro Trp
1 5

<210> SEQ ID NO 2051
<211> LENGTH: 8
<212> TYPE: PRT
<213> ORGANISM: Homo sapiens

<400> SEQUENCE: 2051

Leu Met Ala Glu Glu Asn Pro Pro
1               5

<210> SEQ ID NO 2052
<211> LENGTH: 8
<212> TYPE: PRT
<213> ORGANISM: Homo sapiens

<400> SEQUENCE: 2052

Leu Asp Arg Glu Glu Thr Pro Phe
1               5

<210> SEQ ID NO 2053
<211> LENGTH: 8
<212> TYPE: PRT
<213> ORGANISM: Homo sapiens

<400> SEQUENCE: 2053

Leu Trp Ser Glu Glu Thr Pro Ala
1               5

<210> SEQ ID NO 2054
<211> LENGTH: 8
<212> TYPE: PRT
<213> ORGANISM: Homo sapiens

<400> SEQUENCE: 2054

Leu Pro His Glu Glu Glu Pro Ser
1               5

<210> SEQ ID NO 2055
<211> LENGTH: 8
<212> TYPE: PRT
<213> ORGANISM: Homo sapiens

<400> SEQUENCE: 2055

Leu Pro Glu Glu Glu Ala Pro Arg
1               5

<210> SEQ ID NO 2056
<211> LENGTH: 8
<212> TYPE: PRT
<213> ORGANISM: Homo sapiens

<400> SEQUENCE: 2056

Leu Lys Lys Glu Glu Lys Pro Leu
1               5

<210> SEQ ID NO 2057
<211> LENGTH: 8
<212> TYPE: PRT
<213> ORGANISM: Homo sapiens

<400> SEQUENCE: 2057

Leu Ser Lys Glu Glu Phe Pro Asp
1               5

<210> SEQ ID NO 2058
<211> LENGTH: 8
<212> TYPE: PRT
<213> ORGANISM: Homo sapiens

<400> SEQUENCE: 2058

Leu Val Glu Glu Glu Pro Pro Phe
1               5

<210> SEQ ID NO 2059
<211> LENGTH: 8
<212> TYPE: PRT
<213> ORGANISM: Homo sapiens

<400> SEQUENCE: 2059

Leu Ala Ala Glu Glu Asn Pro Ser
1               5

<210> SEQ ID NO 2060
<211> LENGTH: 8
<212> TYPE: PRT
<213> ORGANISM: Homo sapiens

<400> SEQUENCE: 2060

Leu Ser Pro Glu Glu Thr Pro Ala
1               5

<210> SEQ ID NO 2061
<211> LENGTH: 8
<212> TYPE: PRT
<213> ORGANISM: Homo sapiens

<400> SEQUENCE: 2061

Leu Thr Val Glu Glu Thr Pro Arg
1               5

<210> SEQ ID NO 2062
<211> LENGTH: 8
<212> TYPE: PRT
<213> ORGANISM: Homo sapiens

<400> SEQUENCE: 2062

Leu Ser Ala Glu Glu Ile Pro Glu
1               5

<210> SEQ ID NO 2063
<211> LENGTH: 8
<212> TYPE: PRT
<213> ORGANISM: Homo sapiens

<400> SEQUENCE: 2063

Leu Gly Val Glu Glu Glu Pro Phe
1               5

<210> SEQ ID NO 2064
<211> LENGTH: 8
<212> TYPE: PRT
<213> ORGANISM: Homo sapiens

<400> SEQUENCE: 2064

Leu Ala Ser Glu Glu Gln Pro Pro
1               5

<210> SEQ ID NO 2065
<211> LENGTH: 8
<212> TYPE: PRT
<213> ORGANISM: Homo sapiens

<400> SEQUENCE: 2065

Leu Ile Met Glu Glu Arg Pro Asn
1 5

<210> SEQ ID NO 2066
<211> LENGTH: 8
<212> TYPE: PRT
<213> ORGANISM: Homo sapiens

<400> SEQUENCE: 2066

Leu Asn Arg Glu Glu Ala Pro Thr
1 5

<210> SEQ ID NO 2067
<211> LENGTH: 8
<212> TYPE: PRT
<213> ORGANISM: Homo sapiens

<400> SEQUENCE: 2067

Leu Cys Thr Glu Glu Gly Pro Leu
1 5

<210> SEQ ID NO 2068
<211> LENGTH: 8
<212> TYPE: PRT
<213> ORGANISM: Homo sapiens

<400> SEQUENCE: 2068

Leu Arg Val Glu Glu Arg Pro Glu
1 5

<210> SEQ ID NO 2069
<211> LENGTH: 8
<212> TYPE: PRT
<213> ORGANISM: Homo sapiens

<400> SEQUENCE: 2069

Leu Tyr Ser Glu Glu Gln Pro Gln
1 5

<210> SEQ ID NO 2070
<211> LENGTH: 8
<212> TYPE: PRT
<213> ORGANISM: Homo sapiens

<400> SEQUENCE: 2070

Leu Pro Glu Glu Glu Thr Pro Glu
1 5

<210> SEQ ID NO 2071
<211> LENGTH: 8
<212> TYPE: PRT
<213> ORGANISM: Homo sapiens

<400> SEQUENCE: 2071

Leu Glu Gln Glu Glu Glu Pro Trp
1 5

<210> SEQ ID NO 2072
<211> LENGTH: 8
<212> TYPE: PRT
<213> ORGANISM: Homo sapiens

<400> SEQUENCE: 2072

Leu Leu His Glu Glu Ser Pro Leu
1 5

<210> SEQ ID NO 2073
<211> LENGTH: 8
<212> TYPE: PRT
<213> ORGANISM: Homo sapiens

<400> SEQUENCE: 2073

Leu Val Ile Glu Glu Cys Pro Leu
1 5

<210> SEQ ID NO 2074
<211> LENGTH: 8
<212> TYPE: PRT
<213> ORGANISM: Homo sapiens

<400> SEQUENCE: 2074

Leu Ile Gln Glu Glu Asp Pro Ser
1 5

<210> SEQ ID NO 2075
<211> LENGTH: 8
<212> TYPE: PRT
<213> ORGANISM: Homo sapiens

<400> SEQUENCE: 2075

Leu Arg Ala Glu Glu Pro Pro Thr
1 5

<210> SEQ ID NO 2076
<211> LENGTH: 8
<212> TYPE: PRT
<213> ORGANISM: Homo sapiens

<400> SEQUENCE: 2076

Leu Glu Ala Glu Glu Pro Pro Asp
1 5

<210> SEQ ID NO 2077
<211> LENGTH: 8
<212> TYPE: PRT
<213> ORGANISM: Homo sapiens

<400> SEQUENCE: 2077

Leu Asp Gln Glu Glu Ala Pro Lys
1 5

<210> SEQ ID NO 2078
<211> LENGTH: 8
<212> TYPE: PRT
<213> ORGANISM: Homo sapiens

<400> SEQUENCE: 2078

Leu Ser Ala Glu Glu Ser Pro Glu
1 5

<210> SEQ ID NO 2079
<211> LENGTH: 8
<212> TYPE: PRT
<213> ORGANISM: Homo sapiens

<400> SEQUENCE: 2079

Leu Glu Leu Glu Glu Ala Pro Glu
1               5

<210> SEQ ID NO 2080
<211> LENGTH: 8
<212> TYPE: PRT
<213> ORGANISM: Homo sapiens

<400> SEQUENCE: 2080

Leu Arg Cys Glu Glu Ala Pro Ser
1               5

<210> SEQ ID NO 2081
<211> LENGTH: 8
<212> TYPE: PRT
<213> ORGANISM: Homo sapiens

<400> SEQUENCE: 2081

Leu Leu Pro Glu Glu Ala Pro Arg
1               5

<210> SEQ ID NO 2082
<211> LENGTH: 8
<212> TYPE: PRT
<213> ORGANISM: Homo sapiens

<400> SEQUENCE: 2082

Leu Pro Ala Glu Glu Thr Pro Ile
1               5

<210> SEQ ID NO 2083
<211> LENGTH: 8
<212> TYPE: PRT
<213> ORGANISM: Homo sapiens

<400> SEQUENCE: 2083

Leu Leu Thr Glu Glu Phe Pro Ile
1               5

<210> SEQ ID NO 2084
<211> LENGTH: 8
<212> TYPE: PRT
<213> ORGANISM: Homo sapiens

<400> SEQUENCE: 2084

Leu Gln Gln Glu Glu Pro Pro Ile
1               5

<210> SEQ ID NO 2085
<211> LENGTH: 8
<212> TYPE: PRT
<213> ORGANISM: Homo sapiens

<400> SEQUENCE: 2085

Leu Leu Ala Glu Glu Tyr Pro Met
1               5

<210> SEQ ID NO 2086
<211> LENGTH: 8
<212> TYPE: PRT
<213> ORGANISM: Homo sapiens

<400> SEQUENCE: 2086

Leu Glu Gln Glu Glu Glu Pro Trp
1               5

<210> SEQ ID NO 2087
<211> LENGTH: 8
<212> TYPE: PRT
<213> ORGANISM: Homo sapiens

<400> SEQUENCE: 2087

Leu Ile Lys Glu Glu Gln Pro Pro
1               5

<210> SEQ ID NO 2088
<211> LENGTH: 8
<212> TYPE: PRT
<213> ORGANISM: Homo sapiens

<400> SEQUENCE: 2088

Leu Thr Gly Glu Glu Ile Pro Phe
1               5

<210> SEQ ID NO 2089
<211> LENGTH: 8
<212> TYPE: PRT
<213> ORGANISM: Homo sapiens

<400> SEQUENCE: 2089

Leu Glu Ser Glu Glu Thr Pro Asn
1               5

<210> SEQ ID NO 2090
<211> LENGTH: 8
<212> TYPE: PRT
<213> ORGANISM: Homo sapiens

<400> SEQUENCE: 2090

Leu Arg Thr Glu Glu Lys Pro Pro
1               5

<210> SEQ ID NO 2091
<211> LENGTH: 8
<212> TYPE: PRT
<213> ORGANISM: Homo sapiens

<400> SEQUENCE: 2091

Leu Lys Lys Glu Glu Arg Pro Thr
1               5

<210> SEQ ID NO 2092
<211> LENGTH: 8
<212> TYPE: PRT
<213> ORGANISM: Homo sapiens

<400> SEQUENCE: 2092

Leu Asp Asp Glu Glu Gln Pro Thr
1               5

<210> SEQ ID NO 2093
<211> LENGTH: 8
<212> TYPE: PRT
<213> ORGANISM: Homo sapiens

<400> SEQUENCE: 2093

Leu Gly Ala Glu Glu Thr Pro Pro
1               5

<210> SEQ ID NO 2094
<211> LENGTH: 8
<212> TYPE: PRT
<213> ORGANISM: Homo sapiens

<400> SEQUENCE: 2094

Leu Pro Ala Glu Glu Thr Pro Val
1               5

<210> SEQ ID NO 2095
<211> LENGTH: 8
<212> TYPE: PRT
<213> ORGANISM: Homo sapiens

<400> SEQUENCE: 2095

Leu Tyr Gln Glu Glu Asn Pro Ala
1               5

<210> SEQ ID NO 2096
<211> LENGTH: 8
<212> TYPE: PRT
<213> ORGANISM: Homo sapiens

<400> SEQUENCE: 2096

Leu Glu Asp Glu Glu Ile Pro Val
1               5

<210> SEQ ID NO 2097
<211> LENGTH: 8
<212> TYPE: PRT
<213> ORGANISM: Homo sapiens

<400> SEQUENCE: 2097

Leu Thr Arg Glu Glu Leu Pro Lys
1               5

<210> SEQ ID NO 2098
<211> LENGTH: 8
<212> TYPE: PRT
<213> ORGANISM: Homo sapiens

<400> SEQUENCE: 2098

Leu His Thr Glu Glu Ala Pro Ala
1               5

<210> SEQ ID NO 2099
<211> LENGTH: 8
<212> TYPE: PRT
<213> ORGANISM: Homo sapiens

<400> SEQUENCE: 2099

Leu Val Pro Glu Glu Leu Pro Pro
1               5

<210> SEQ ID NO 2100
<211> LENGTH: 8
<212> TYPE: PRT
<213> ORGANISM: Homo sapiens

<400> SEQUENCE: 2100

Leu Ile Leu Glu Glu Thr Pro Glu
1               5

<210> SEQ ID NO 2101
<211> LENGTH: 8
<212> TYPE: PRT
<213> ORGANISM: Homo sapiens

<400> SEQUENCE: 2101

Leu Asn Gln Glu Glu Leu Pro Pro
1               5

<210> SEQ ID NO 2102
<211> LENGTH: 8
<212> TYPE: PRT
<213> ORGANISM: Homo sapiens

<400> SEQUENCE: 2102

Leu Asp Glu Glu Glu Ser Pro Arg
1               5

<210> SEQ ID NO 2103
<211> LENGTH: 8
<212> TYPE: PRT
<213> ORGANISM: Homo sapiens

<400> SEQUENCE: 2103

Leu Pro Val Glu Glu Gln Pro Lys
1               5

<210> SEQ ID NO 2104
<211> LENGTH: 8
<212> TYPE: PRT
<213> ORGANISM: Homo sapiens

<400> SEQUENCE: 2104

Leu Val Ala Glu Glu Ser Pro Glu
1               5

<210> SEQ ID NO 2105
<211> LENGTH: 8
<212> TYPE: PRT
<213> ORGANISM: Homo sapiens

<400> SEQUENCE: 2105

Leu Gly Lys Glu Glu Gln Pro Gln
1               5

<210> SEQ ID NO 2106
<211> LENGTH: 8
<212> TYPE: PRT
<213> ORGANISM: Homo sapiens

<400> SEQUENCE: 2106

Leu Ser Pro Glu Glu Leu Pro Glu
1               5

<210> SEQ ID NO 2107
<211> LENGTH: 8
<212> TYPE: PRT
<213> ORGANISM: Homo sapiens

<400> SEQUENCE: 2107

Leu Pro Lys Glu Glu Asn Pro Arg
1 5

<210> SEQ ID NO 2108
<211> LENGTH: 8
<212> TYPE: PRT
<213> ORGANISM: Homo sapiens

<400> SEQUENCE: 2108

Leu Arg Lys Glu Glu Arg Pro Gly
1 5

<210> SEQ ID NO 2109
<211> LENGTH: 8
<212> TYPE: PRT
<213> ORGANISM: Homo sapiens

<400> SEQUENCE: 2109

Leu Thr Ser Glu Glu Glu Pro Gln
1 5

<210> SEQ ID NO 2110
<211> LENGTH: 8
<212> TYPE: PRT
<213> ORGANISM: Homo sapiens

<400> SEQUENCE: 2110

Leu Leu Gly Glu Glu Val Pro Arg
1 5

<210> SEQ ID NO 2111
<211> LENGTH: 8
<212> TYPE: PRT
<213> ORGANISM: Homo sapiens

<400> SEQUENCE: 2111

Leu Ser Ser Glu Glu Leu Pro Gln
1 5

<210> SEQ ID NO 2112
<211> LENGTH: 8
<212> TYPE: PRT
<213> ORGANISM: Homo sapiens

<400> SEQUENCE: 2112

Leu Ser Lys Glu Glu Pro Pro Gly
1 5

<210> SEQ ID NO 2113
<211> LENGTH: 8
<212> TYPE: PRT
<213> ORGANISM: Homo sapiens

<400> SEQUENCE: 2113

Leu Glu Gln Glu Glu Ala Pro Trp
1 5

<210> SEQ ID NO 2114
<211> LENGTH: 8
<212> TYPE: PRT
<213> ORGANISM: Homo sapiens

<400> SEQUENCE: 2114

Leu Arg Ala Glu Glu Asn Pro Met
1               5

<210> SEQ ID NO 2115
<211> LENGTH: 8
<212> TYPE: PRT
<213> ORGANISM: Homo sapiens

<400> SEQUENCE: 2115

Leu His Arg Glu Glu Gly Pro Ala
1               5

<210> SEQ ID NO 2116
<211> LENGTH: 8
<212> TYPE: PRT
<213> ORGANISM: Homo sapiens

<400> SEQUENCE: 2116

Leu Pro Gln Glu Glu Gln Pro Leu
1               5

<210> SEQ ID NO 2117
<211> LENGTH: 8
<212> TYPE: PRT
<213> ORGANISM: Homo sapiens

<400> SEQUENCE: 2117

Leu Glu Lys Glu Glu Pro Pro Leu
1               5

<210> SEQ ID NO 2118
<211> LENGTH: 8
<212> TYPE: PRT
<213> ORGANISM: Homo sapiens

<400> SEQUENCE: 2118

Leu Ala Glu Glu Glu Leu Pro Thr
1               5

<210> SEQ ID NO 2119
<211> LENGTH: 8
<212> TYPE: PRT
<213> ORGANISM: Homo sapiens

<400> SEQUENCE: 2119

Leu Asn Ser Glu Glu Leu Pro Asp
1               5

<210> SEQ ID NO 2120
<211> LENGTH: 8
<212> TYPE: PRT
<213> ORGANISM: Homo sapiens

<400> SEQUENCE: 2120

Leu Ala Cys Glu Glu Ala Pro Gly
1               5

<210> SEQ ID NO 2121
<211> LENGTH: 8
<212> TYPE: PRT
<213> ORGANISM: Homo sapiens

<400> SEQUENCE: 2121

Leu Cys Ser Glu Glu Pro Pro Arg
1               5

<210> SEQ ID NO 2122
<211> LENGTH: 8
<212> TYPE: PRT
<213> ORGANISM: Homo sapiens

<400> SEQUENCE: 2122

Leu Asp Leu Glu Glu Asp Pro Tyr
1               5

<210> SEQ ID NO 2123
<211> LENGTH: 8
<212> TYPE: PRT
<213> ORGANISM: Homo sapiens

<400> SEQUENCE: 2123

Leu Glu Arg Glu Glu Lys Pro Glu
1               5

<210> SEQ ID NO 2124
<211> LENGTH: 8
<212> TYPE: PRT
<213> ORGANISM: Homo sapiens

<400> SEQUENCE: 2124

Leu Ser Gln Glu Glu Asn Pro Glu
1               5

<210> SEQ ID NO 2125
<211> LENGTH: 8
<212> TYPE: PRT
<213> ORGANISM: Homo sapiens

<400> SEQUENCE: 2125

Leu Leu Pro Glu Glu Phe Pro Gly
1               5

<210> SEQ ID NO 2126
<211> LENGTH: 8
<212> TYPE: PRT
<213> ORGANISM: Homo sapiens

<400> SEQUENCE: 2126

Leu Met Lys Glu Glu Ser Pro Val
1               5

<210> SEQ ID NO 2127
<211> LENGTH: 8
<212> TYPE: PRT
<213> ORGANISM: Homo sapiens

<400> SEQUENCE: 2127

Leu Met Lys Glu Glu Ser Pro Val
1               5

<210> SEQ ID NO 2128
<211> LENGTH: 8
<212> TYPE: PRT
<213> ORGANISM: Homo sapiens

<400> SEQUENCE: 2128

Leu Met Lys Glu Glu Ser Pro Val
1 5

<210> SEQ ID NO 2129
<211> LENGTH: 8
<212> TYPE: PRT
<213> ORGANISM: Homo sapiens

<400> SEQUENCE: 2129

Leu Met Lys Glu Glu Ser Pro Val
1 5

<210> SEQ ID NO 2130
<211> LENGTH: 8
<212> TYPE: PRT
<213> ORGANISM: Homo sapiens

<400> SEQUENCE: 2130

Leu Gly Gln Glu Glu Pro Pro Leu
1 5

<210> SEQ ID NO 2131
<211> LENGTH: 8
<212> TYPE: PRT
<213> ORGANISM: Homo sapiens

<400> SEQUENCE: 2131

Leu Gln Asp Glu Glu Cys Pro Leu
1 5

<210> SEQ ID NO 2132
<211> LENGTH: 8
<212> TYPE: PRT
<213> ORGANISM: Homo sapiens

<400> SEQUENCE: 2132

Leu Thr Tyr Glu Glu Lys Pro Pro
1 5

<210> SEQ ID NO 2133
<211> LENGTH: 8
<212> TYPE: PRT
<213> ORGANISM: Homo sapiens

<400> SEQUENCE: 2133

Leu Leu Pro Glu Glu Thr Pro Ala
1 5

<210> SEQ ID NO 2134
<211> LENGTH: 8
<212> TYPE: PRT
<213> ORGANISM: Homo sapiens

<400> SEQUENCE: 2134

Leu Val Gly Glu Glu Phe Pro Glu
1 5

<210> SEQ ID NO 2135
<211> LENGTH: 8
<212> TYPE: PRT
<213> ORGANISM: Homo sapiens

<400> SEQUENCE: 2135

Leu Val Ser Glu Glu Phe Pro Glu
1               5

<210> SEQ ID NO 2136
<211> LENGTH: 8
<212> TYPE: PRT
<213> ORGANISM: Homo sapiens

<400> SEQUENCE: 2136

Leu Val Thr Glu Glu Leu Pro Arg
1               5

<210> SEQ ID NO 2137
<211> LENGTH: 8
<212> TYPE: PRT
<213> ORGANISM: Homo sapiens

<400> SEQUENCE: 2137

Leu His Thr Glu Glu Lys Pro Tyr
1               5

<210> SEQ ID NO 2138
<211> LENGTH: 8
<212> TYPE: PRT
<213> ORGANISM: Homo sapiens

<400> SEQUENCE: 2138

Leu Phe Asp Glu Glu Phe Pro Gly
1               5

<210> SEQ ID NO 2139
<211> LENGTH: 8
<212> TYPE: PRT
<213> ORGANISM: Homo sapiens

<400> SEQUENCE: 2139

Leu Leu Glu Glu Glu Ile Pro Ser
1               5

<210> SEQ ID NO 2140
<211> LENGTH: 8
<212> TYPE: PRT
<213> ORGANISM: Homo sapiens

<400> SEQUENCE: 2140

Leu Leu Gln Glu Glu Glu Pro Leu
1               5

<210> SEQ ID NO 2141
<211> LENGTH: 8
<212> TYPE: PRT
<213> ORGANISM: Homo sapiens

<400> SEQUENCE: 2141

Leu Leu Val Glu Glu Ser Pro Glu
1               5

<210> SEQ ID NO 2142
<211> LENGTH: 8
<212> TYPE: PRT
<213> ORGANISM: Homo sapiens

<400> SEQUENCE: 2142

Leu Ser Phe Glu Glu Lys Pro Val
1               5

<210> SEQ ID NO 2143
<211> LENGTH: 8
<212> TYPE: PRT
<213> ORGANISM: Homo sapiens

<400> SEQUENCE: 2143

Leu Ala Thr Glu Glu Asp Pro Lys
1               5

<210> SEQ ID NO 2144
<211> LENGTH: 8
<212> TYPE: PRT
<213> ORGANISM: Homo sapiens

<400> SEQUENCE: 2144

Leu Lys Ala Glu Glu Trp Pro Trp
1               5

<210> SEQ ID NO 2145
<211> LENGTH: 8
<212> TYPE: PRT
<213> ORGANISM: Homo sapiens

<400> SEQUENCE: 2145

Leu Ile Ser Glu Glu Gln Pro Ala
1               5

<210> SEQ ID NO 2146
<211> LENGTH: 8
<212> TYPE: PRT
<213> ORGANISM: Homo sapiens

<400> SEQUENCE: 2146

Leu Arg Phe Glu Glu Val Pro Asp
1               5

<210> SEQ ID NO 2147
<211> LENGTH: 8
<212> TYPE: PRT
<213> ORGANISM: Homo sapiens

<400> SEQUENCE: 2147

Leu Arg Gly Glu Glu Lys Pro Ala
1               5

<210> SEQ ID NO 2148
<211> LENGTH: 8
<212> TYPE: PRT
<213> ORGANISM: Homo sapiens

<400> SEQUENCE: 2148

Leu Arg Met Glu Glu Thr Pro Thr
1               5

<210> SEQ ID NO 2149
<211> LENGTH: 8
<212> TYPE: PRT
<213> ORGANISM: Homo sapiens

<400> SEQUENCE: 2149

Leu Leu Arg Glu Glu Glu Pro Glu
1               5

<210> SEQ ID NO 2150
<211> LENGTH: 8
<212> TYPE: PRT
<213> ORGANISM: Homo sapiens

<400> SEQUENCE: 2150

Leu Asp Ala Glu Glu Leu Pro Pro
1               5

<210> SEQ ID NO 2151
<211> LENGTH: 8
<212> TYPE: PRT
<213> ORGANISM: Homo sapiens

<400> SEQUENCE: 2151

Leu Leu Leu Glu Glu Gln Pro Leu
1               5

<210> SEQ ID NO 2152
<211> LENGTH: 8
<212> TYPE: PRT
<213> ORGANISM: Homo sapiens

<400> SEQUENCE: 2152

Leu Val Lys Glu Glu Pro Pro Glu
1               5

<210> SEQ ID NO 2153
<211> LENGTH: 8
<212> TYPE: PRT
<213> ORGANISM: Homo sapiens

<400> SEQUENCE: 2153

Leu Gly Glu Glu Glu Pro Pro Ala
1               5

<210> SEQ ID NO 2154
<211> LENGTH: 8
<212> TYPE: PRT
<213> ORGANISM: Homo sapiens

<400> SEQUENCE: 2154

Leu Pro Leu Glu Glu Thr Pro Asp
1               5

<210> SEQ ID NO 2155
<211> LENGTH: 8
<212> TYPE: PRT
<213> ORGANISM: Homo sapiens

<400> SEQUENCE: 2155

Leu Asp Lys Glu Glu Ser Pro Ala
1               5

<210> SEQ ID NO 2156
<211> LENGTH: 8
<212> TYPE: PRT
<213> ORGANISM: Homo sapiens

<400> SEQUENCE: 2156

Leu Trp Leu Glu Glu Gly Pro Arg
1               5

<210> SEQ ID NO 2157
<211> LENGTH: 8
<212> TYPE: PRT
<213> ORGANISM: Homo sapiens

<400> SEQUENCE: 2157

Leu Tyr Ser Glu Glu Asp Pro Asn
1               5

<210> SEQ ID NO 2158
<211> LENGTH: 8
<212> TYPE: PRT
<213> ORGANISM: Homo sapiens

<400> SEQUENCE: 2158

Leu Ser Ala Glu Glu Ser Pro Gly
1               5

<210> SEQ ID NO 2159
<211> LENGTH: 8
<212> TYPE: PRT
<213> ORGANISM: Homo sapiens

<400> SEQUENCE: 2159

Leu Ser Pro Glu Glu Gly Pro Pro
1               5

<210> SEQ ID NO 2160
<211> LENGTH: 8
<212> TYPE: PRT
<213> ORGANISM: Homo sapiens

<400> SEQUENCE: 2160

Leu Arg Gly Glu Glu His Pro Thr
1               5

<210> SEQ ID NO 2161
<211> LENGTH: 8
<212> TYPE: PRT
<213> ORGANISM: Homo sapiens

<400> SEQUENCE: 2161

Leu Ser Leu Glu Glu Cys Pro Trp
1               5

<210> SEQ ID NO 2162
<211> LENGTH: 8
<212> TYPE: PRT
<213> ORGANISM: Homo sapiens

<400> SEQUENCE: 2162

Leu Tyr Thr Glu Glu Arg Pro Arg
1               5

<210> SEQ ID NO 2163
<211> LENGTH: 8
<212> TYPE: PRT
<213> ORGANISM: Homo sapiens

<400> SEQUENCE: 2163

Leu Val Glu Glu Glu Glu Pro Met
1               5

<210> SEQ ID NO 2164
<211> LENGTH: 8
<212> TYPE: PRT
<213> ORGANISM: Homo sapiens

<400> SEQUENCE: 2164

Leu Gly Gln Glu Glu Arg Pro Pro
1               5

<210> SEQ ID NO 2165
<211> LENGTH: 8
<212> TYPE: PRT
<213> ORGANISM: Homo sapiens

<400> SEQUENCE: 2165

Leu Val Val Glu Glu Leu Pro Val
1               5

<210> SEQ ID NO 2166
<211> LENGTH: 8
<212> TYPE: PRT
<213> ORGANISM: Homo sapiens

<400> SEQUENCE: 2166

Leu Phe Val Glu Glu Ile Pro Val
1               5

<210> SEQ ID NO 2167
<211> LENGTH: 8
<212> TYPE: PRT
<213> ORGANISM: Homo sapiens

<400> SEQUENCE: 2167

Leu Gln Arg Glu Glu Thr Pro Ser
1               5

<210> SEQ ID NO 2168
<211> LENGTH: 8
<212> TYPE: PRT
<213> ORGANISM: Homo sapiens

<400> SEQUENCE: 2168

Leu His Glu Glu Glu Leu Pro Asp
1               5

<210> SEQ ID NO 2169
<211> LENGTH: 8
<212> TYPE: PRT
<213> ORGANISM: Homo sapiens

<400> SEQUENCE: 2169

Leu Ala Cys Glu Glu Leu Pro Val
1               5

<210> SEQ ID NO 2170
<211> LENGTH: 8
<212> TYPE: PRT
<213> ORGANISM: Homo sapiens

<400> SEQUENCE: 2170

Leu Leu Ser Glu Glu Asp Pro Phe
1 5

<210> SEQ ID NO 2171
<211> LENGTH: 8
<212> TYPE: PRT
<213> ORGANISM: Homo sapiens

<400> SEQUENCE: 2171

Leu Glu Pro Glu Glu Pro Pro Gly
1 5

<210> SEQ ID NO 2172
<211> LENGTH: 8
<212> TYPE: PRT
<213> ORGANISM: Homo sapiens

<400> SEQUENCE: 2172

Leu Cys Pro Glu Glu Glu Pro Asp
1 5

<210> SEQ ID NO 2173
<211> LENGTH: 8
<212> TYPE: PRT
<213> ORGANISM: Homo sapiens

<400> SEQUENCE: 2173

Leu Val Lys Glu Glu Gly Pro Arg
1 5

<210> SEQ ID NO 2174
<211> LENGTH: 8
<212> TYPE: PRT
<213> ORGANISM: Homo sapiens

<400> SEQUENCE: 2174

Leu Arg Lys Glu Glu Ile Pro Val
1 5

<210> SEQ ID NO 2175
<211> LENGTH: 8
<212> TYPE: PRT
<213> ORGANISM: Homo sapiens

<400> SEQUENCE: 2175

Leu His Pro Glu Glu Phe Pro His
1 5

<210> SEQ ID NO 2176
<211> LENGTH: 8
<212> TYPE: PRT
<213> ORGANISM: Homo sapiens

<400> SEQUENCE: 2176

Leu Gln Ala Glu Glu Ala Pro Glu
1 5

<210> SEQ ID NO 2177
<211> LENGTH: 8
<212> TYPE: PRT
<213> ORGANISM: Homo sapiens

<400> SEQUENCE: 2177

Leu Ser Leu Glu Glu Gln Pro Leu
1 5

<210> SEQ ID NO 2178
<211> LENGTH: 8
<212> TYPE: PRT
<213> ORGANISM: Homo sapiens

<400> SEQUENCE: 2178

Leu Ser Glu Glu Glu Lys Pro Asp
1 5

<210> SEQ ID NO 2179
<211> LENGTH: 8
<212> TYPE: PRT
<213> ORGANISM: Homo sapiens

<400> SEQUENCE: 2179

Leu His Pro Glu Glu Asp Pro Glu
1 5

<210> SEQ ID NO 2180
<211> LENGTH: 8
<212> TYPE: PRT
<213> ORGANISM: Homo sapiens

<400> SEQUENCE: 2180

Leu Leu Glu Glu Glu Asp Pro Trp
1 5

<210> SEQ ID NO 2181
<211> LENGTH: 8
<212> TYPE: PRT
<213> ORGANISM: Homo sapiens

<400> SEQUENCE: 2181

Leu Met Ala Glu Glu Gly Pro Trp
1 5

<210> SEQ ID NO 2182
<211> LENGTH: 8
<212> TYPE: PRT
<213> ORGANISM: Homo sapiens

<400> SEQUENCE: 2182

Leu Trp Ser Glu Glu Gln Pro Ala
1 5

<210> SEQ ID NO 2183
<211> LENGTH: 8
<212> TYPE: PRT
<213> ORGANISM: Homo sapiens

<400> SEQUENCE: 2183

Leu Leu Glu Glu Glu Ala Pro Asp
1 5

<210> SEQ ID NO 2184
<211> LENGTH: 8
<212> TYPE: PRT
<213> ORGANISM: Homo sapiens

<400> SEQUENCE: 2184

Leu Lys Pro Glu Glu Leu Pro Ser
1 5

<210> SEQ ID NO 2185
<211> LENGTH: 8
<212> TYPE: PRT
<213> ORGANISM: Homo sapiens

<400> SEQUENCE: 2185

Leu Tyr Arg Glu Glu Gly Pro Pro
1 5

<210> SEQ ID NO 2186
<211> LENGTH: 8
<212> TYPE: PRT
<213> ORGANISM: Homo sapiens

<400> SEQUENCE: 2186

Leu Asp His Glu Glu Glu Pro Gln
1 5

<210> SEQ ID NO 2187
<211> LENGTH: 8
<212> TYPE: PRT
<213> ORGANISM: Homo sapiens

<400> SEQUENCE: 2187

Leu Thr Thr Glu Glu Lys Pro Arg
1 5

<210> SEQ ID NO 2188
<211> LENGTH: 8
<212> TYPE: PRT
<213> ORGANISM: Homo sapiens

<400> SEQUENCE: 2188

Leu Glu Gln Glu Glu Glu Pro Arg
1 5

<210> SEQ ID NO 2189
<211> LENGTH: 8
<212> TYPE: PRT
<213> ORGANISM: Homo sapiens

<400> SEQUENCE: 2189

Leu His Ala Glu Glu Ala Pro Ser
1 5

<210> SEQ ID NO 2190
<211> LENGTH: 8
<212> TYPE: PRT
<213> ORGANISM: Homo sapiens

<400> SEQUENCE: 2190

Leu Val Phe Glu Glu Asn Pro Phe
1 5

<210> SEQ ID NO 2191
<211> LENGTH: 8
<212> TYPE: PRT
<213> ORGANISM: Homo sapiens

<400> SEQUENCE: 2191

Leu Leu Leu Glu Glu Glu Pro Thr
1 5

<210> SEQ ID NO 2192
<211> LENGTH: 8
<212> TYPE: PRT
<213> ORGANISM: Homo sapiens

<400> SEQUENCE: 2192

Leu Ser Glu Glu Glu Asp Pro Ala
1 5

<210> SEQ ID NO 2193
<211> LENGTH: 8
<212> TYPE: PRT
<213> ORGANISM: Homo sapiens

<400> SEQUENCE: 2193

Leu Asp Ser Glu Glu Val Pro Glu
1 5

<210> SEQ ID NO 2194
<211> LENGTH: 8
<212> TYPE: PRT
<213> ORGANISM: Homo sapiens

<400> SEQUENCE: 2194

Leu His Arg Glu Glu Arg Pro Asn
1 5

<210> SEQ ID NO 2195
<211> LENGTH: 8
<212> TYPE: PRT
<213> ORGANISM: Homo sapiens

<400> SEQUENCE: 2195

Leu Gln Leu Glu Glu Phe Pro Met
1 5

<210> SEQ ID NO 2196
<211> LENGTH: 8
<212> TYPE: PRT
<213> ORGANISM: Homo sapiens

<400> SEQUENCE: 2196

Leu Thr Tyr Glu Glu Leu Pro Gly
1 5

<210> SEQ ID NO 2197
<211> LENGTH: 8
<212> TYPE: PRT
<213> ORGANISM: Homo sapiens

<400> SEQUENCE: 2197

Leu Glu Pro Glu Glu Ser Pro Gly
1 5

<210> SEQ ID NO 2198
<211> LENGTH: 8
<212> TYPE: PRT
<213> ORGANISM: Homo sapiens

<400> SEQUENCE: 2198

Leu His Glu Glu Glu Pro Pro Gln
1               5

<210> SEQ ID NO 2199
<211> LENGTH: 8
<212> TYPE: PRT
<213> ORGANISM: Homo sapiens

<400> SEQUENCE: 2199

Leu Asn Glu Glu Glu Pro Pro Gly
1               5

<210> SEQ ID NO 2200
<211> LENGTH: 8
<212> TYPE: PRT
<213> ORGANISM: Homo sapiens

<400> SEQUENCE: 2200

Leu Thr His Glu Glu Met Pro Gln
1               5

<210> SEQ ID NO 2201
<211> LENGTH: 8
<212> TYPE: PRT
<213> ORGANISM: Homo sapiens

<400> SEQUENCE: 2201

Leu Asp Arg Glu Glu Thr Pro Asn
1               5

<210> SEQ ID NO 2202
<211> LENGTH: 8
<212> TYPE: PRT
<213> ORGANISM: Homo sapiens

<400> SEQUENCE: 2202

Leu Asp Arg Glu Glu Thr Pro Asn
1               5

<210> SEQ ID NO 2203
<211> LENGTH: 8
<212> TYPE: PRT
<213> ORGANISM: Homo sapiens

<400> SEQUENCE: 2203

Leu Arg Pro Glu Glu Ala Pro Gly
1               5

<210> SEQ ID NO 2204
<211> LENGTH: 8
<212> TYPE: PRT
<213> ORGANISM: Homo sapiens

<400> SEQUENCE: 2204

Leu Ile Thr Glu Glu Gly Pro Asn
1               5

<210> SEQ ID NO 2205
<211> LENGTH: 8
<212> TYPE: PRT
<213> ORGANISM: Homo sapiens

<400> SEQUENCE: 2205

Leu Gly Gly Glu Glu Pro Pro Gly
1               5

<210> SEQ ID NO 2206
<211> LENGTH: 8
<212> TYPE: PRT
<213> ORGANISM: Homo sapiens

<400> SEQUENCE: 2206

Leu Asp Gly Glu Glu Ile Pro Val
1               5

<210> SEQ ID NO 2207
<211> LENGTH: 8
<212> TYPE: PRT
<213> ORGANISM: Homo sapiens

<400> SEQUENCE: 2207

Leu Arg Leu Glu Glu Gly Pro Pro
1               5

<210> SEQ ID NO 2208
<211> LENGTH: 8
<212> TYPE: PRT
<213> ORGANISM: Homo sapiens

<400> SEQUENCE: 2208

Leu Ser His Glu Glu His Pro His
1               5

<210> SEQ ID NO 2209
<211> LENGTH: 8
<212> TYPE: PRT
<213> ORGANISM: Homo sapiens

<400> SEQUENCE: 2209

Leu Phe Pro Glu Glu Pro Pro Pro
1               5

<210> SEQ ID NO 2210
<211> LENGTH: 8
<212> TYPE: PRT
<213> ORGANISM: Homo sapiens

<400> SEQUENCE: 2210

Leu Val Gln Glu Glu Arg Pro His
1               5

<210> SEQ ID NO 2211
<211> LENGTH: 8
<212> TYPE: PRT
<213> ORGANISM: Homo sapiens

<400> SEQUENCE: 2211

Leu Ala Thr Glu Glu Pro Pro Pro
1               5

<210> SEQ ID NO 2212
<211> LENGTH: 8
<212> TYPE: PRT
<213> ORGANISM: Homo sapiens

<400> SEQUENCE: 2212

Leu Asn Lys Glu Glu Leu Pro Val
1               5

<210> SEQ ID NO 2213
<211> LENGTH: 8
<212> TYPE: PRT
<213> ORGANISM: Homo sapiens

<400> SEQUENCE: 2213

Leu Ala Asn Glu Glu Lys Pro Ala
1               5

<210> SEQ ID NO 2214
<211> LENGTH: 8
<212> TYPE: PRT
<213> ORGANISM: Homo sapiens

<400> SEQUENCE: 2214

Leu Ala Pro Glu Glu Val Pro Leu
1               5

<210> SEQ ID NO 2215
<211> LENGTH: 8
<212> TYPE: PRT
<213> ORGANISM: Homo sapiens

<400> SEQUENCE: 2215

Leu Cys Ser Glu Glu Ser Pro Glu
1               5

<210> SEQ ID NO 2216
<211> LENGTH: 8
<212> TYPE: PRT
<213> ORGANISM: Homo sapiens

<400> SEQUENCE: 2216

Leu Ile Val Glu Glu Cys Pro Ser
1               5

<210> SEQ ID NO 2217
<211> LENGTH: 8
<212> TYPE: PRT
<213> ORGANISM: Homo sapiens

<400> SEQUENCE: 2217

Leu Phe Ser Glu Glu Thr Pro Gly
1               5

<210> SEQ ID NO 2218
<211> LENGTH: 8
<212> TYPE: PRT
<213> ORGANISM: Homo sapiens

<400> SEQUENCE: 2218

Leu Asn Arg Glu Glu Ile Pro Val
1               5

<210> SEQ ID NO 2219
<211> LENGTH: 8
<212> TYPE: PRT
<213> ORGANISM: Homo sapiens

<400> SEQUENCE: 2219

Leu Glu Asp Glu Glu Leu Pro Ala
1               5

<210> SEQ ID NO 2220
<211> LENGTH: 8
<212> TYPE: PRT
<213> ORGANISM: Homo sapiens

<400> SEQUENCE: 2220

Leu Gly Ser Glu Glu Arg Pro Phe
1               5

<210> SEQ ID NO 2221
<211> LENGTH: 8
<212> TYPE: PRT
<213> ORGANISM: Homo sapiens

<400> SEQUENCE: 2221

Leu Cys Pro Glu Glu Pro Pro Val
1               5

<210> SEQ ID NO 2222
<211> LENGTH: 8
<212> TYPE: PRT
<213> ORGANISM: Homo sapiens

<400> SEQUENCE: 2222

Leu Asp Arg Glu Glu Glu Pro Gln
1               5

<210> SEQ ID NO 2223
<211> LENGTH: 8
<212> TYPE: PRT
<213> ORGANISM: Homo sapiens

<400> SEQUENCE: 2223

Leu Arg Thr Glu Glu Thr Pro Met
1               5

<210> SEQ ID NO 2224
<211> LENGTH: 8
<212> TYPE: PRT
<213> ORGANISM: Homo sapiens

<400> SEQUENCE: 2224

Leu His Ser Glu Glu Gly Pro Ala
1               5

<210> SEQ ID NO 2225
<211> LENGTH: 8
<212> TYPE: PRT
<213> ORGANISM: Homo sapiens

<400> SEQUENCE: 2225

Leu Ile Gly Glu Glu Trp Pro Ser
1               5

<210> SEQ ID NO 2226
<211> LENGTH: 8
<212> TYPE: PRT
<213> ORGANISM: Homo sapiens

<400> SEQUENCE: 2226

Leu Gly Met Glu Glu Arg Pro Tyr
1               5

<210> SEQ ID NO 2227
<211> LENGTH: 8
<212> TYPE: PRT
<213> ORGANISM: Homo sapiens

<400> SEQUENCE: 2227

Leu Leu Glu Glu Glu Ile Pro Gly
1               5

<210> SEQ ID NO 2228
<211> LENGTH: 8
<212> TYPE: PRT
<213> ORGANISM: Homo sapiens

<400> SEQUENCE: 2228

Leu Leu Ala Glu Glu Thr Pro Pro
1               5

<210> SEQ ID NO 2229
<211> LENGTH: 8
<212> TYPE: PRT
<213> ORGANISM: Homo sapiens

<400> SEQUENCE: 2229

Leu Ala Gln Glu Glu Ala Pro Gly
1               5

<210> SEQ ID NO 2230
<211> LENGTH: 8
<212> TYPE: PRT
<213> ORGANISM: Homo sapiens

<400> SEQUENCE: 2230

Leu Asp Tyr Glu Glu Ser Pro Val
1               5

<210> SEQ ID NO 2231
<211> LENGTH: 8
<212> TYPE: PRT
<213> ORGANISM: Homo sapiens

<400> SEQUENCE: 2231

Leu Glu Val Glu Glu Glu Pro Val
1               5

<210> SEQ ID NO 2232
<211> LENGTH: 8
<212> TYPE: PRT
<213> ORGANISM: Homo sapiens

<400> SEQUENCE: 2232

Leu Ala Ser Glu Glu Pro Pro Asp
1               5

<210> SEQ ID NO 2233
<211> LENGTH: 8
<212> TYPE: PRT
<213> ORGANISM: Homo sapiens

<400> SEQUENCE: 2233

Leu Lys Glu Glu Glu Cys Pro Ala
1 5

<210> SEQ ID NO 2234
<211> LENGTH: 8
<212> TYPE: PRT
<213> ORGANISM: Homo sapiens

<400> SEQUENCE: 2234

Leu Leu Phe Glu Glu Ser Pro Ser
1 5

<210> SEQ ID NO 2235
<211> LENGTH: 8
<212> TYPE: PRT
<213> ORGANISM: Homo sapiens

<400> SEQUENCE: 2235

Leu Ser Lys Glu Glu Leu Pro Gln
1 5

<210> SEQ ID NO 2236
<211> LENGTH: 8
<212> TYPE: PRT
<213> ORGANISM: Homo sapiens

<400> SEQUENCE: 2236

Leu Leu Ser Glu Glu Thr Pro Ser
1 5

<210> SEQ ID NO 2237
<211> LENGTH: 8
<212> TYPE: PRT
<213> ORGANISM: Homo sapiens

<400> SEQUENCE: 2237

Leu Arg Leu Glu Glu Gly Pro Pro
1 5

<210> SEQ ID NO 2238
<211> LENGTH: 8
<212> TYPE: PRT
<213> ORGANISM: Homo sapiens

<400> SEQUENCE: 2238

Leu Ser Ala Glu Glu Ile Pro Ser
1 5

<210> SEQ ID NO 2239
<211> LENGTH: 8
<212> TYPE: PRT
<213> ORGANISM: Homo sapiens

<400> SEQUENCE: 2239

Leu Leu Lys Glu Glu Phe Pro Ala
1 5

<210> SEQ ID NO 2240
<211> LENGTH: 8
<212> TYPE: PRT
<213> ORGANISM: Homo sapiens

<400> SEQUENCE: 2240

Leu Pro Ala Glu Glu Val Pro Leu
1               5

<210> SEQ ID NO 2241
<211> LENGTH: 8
<212> TYPE: PRT
<213> ORGANISM: Homo sapiens

<400> SEQUENCE: 2241

Leu Ser Ser Glu Glu Ser Pro Arg
1               5

<210> SEQ ID NO 2242
<211> LENGTH: 8
<212> TYPE: PRT
<213> ORGANISM: Homo sapiens

<400> SEQUENCE: 2242

Leu Arg Gly Glu Glu Glu Pro Arg
1               5

<210> SEQ ID NO 2243
<211> LENGTH: 8
<212> TYPE: PRT
<213> ORGANISM: Homo sapiens

<400> SEQUENCE: 2243

Leu Gly Gln Glu Glu Leu Pro Ser
1               5

<210> SEQ ID NO 2244
<211> LENGTH: 8
<212> TYPE: PRT
<213> ORGANISM: Homo sapiens

<400> SEQUENCE: 2244

Leu Val Thr Glu Glu Thr Pro Ser
1               5

<210> SEQ ID NO 2245
<211> LENGTH: 8
<212> TYPE: PRT
<213> ORGANISM: Homo sapiens

<400> SEQUENCE: 2245

Leu Asp Arg Glu Glu Thr Pro Glu
1               5

<210> SEQ ID NO 2246
<211> LENGTH: 8
<212> TYPE: PRT
<213> ORGANISM: Homo sapiens

<400> SEQUENCE: 2246

Leu Asp Arg Glu Glu Ala Pro Ala
1               5

<210> SEQ ID NO 2247
<211> LENGTH: 8
<212> TYPE: PRT
<213> ORGANISM: Homo sapiens

<400> SEQUENCE: 2247

Leu Asp Arg Glu Glu Ala Pro Glu
1               5

<210> SEQ ID NO 2248
<211> LENGTH: 8
<212> TYPE: PRT
<213> ORGANISM: Homo sapiens

<400> SEQUENCE: 2248

Leu Gly Pro Glu Glu Leu Pro Gly
1               5

<210> SEQ ID NO 2249
<211> LENGTH: 8
<212> TYPE: PRT
<213> ORGANISM: Homo sapiens

<400> SEQUENCE: 2249

Leu Arg Leu Glu Glu Gly Pro Pro
1               5

<210> SEQ ID NO 2250
<211> LENGTH: 8
<212> TYPE: PRT
<213> ORGANISM: Homo sapiens

<400> SEQUENCE: 2250

Leu Leu Pro Glu Glu His Pro Ser
1               5

<210> SEQ ID NO 2251
<211> LENGTH: 8
<212> TYPE: PRT
<213> ORGANISM: Homo sapiens

<400> SEQUENCE: 2251

Leu Ala Thr Glu Glu Glu Pro Pro
1               5

<210> SEQ ID NO 2252
<211> LENGTH: 8
<212> TYPE: PRT
<213> ORGANISM: Homo sapiens

<400> SEQUENCE: 2252

Leu Arg Lys Glu Glu Asp Pro Arg
1               5

<210> SEQ ID NO 2253
<211> LENGTH: 8
<212> TYPE: PRT
<213> ORGANISM: Homo sapiens

<400> SEQUENCE: 2253

Leu Glu Glu Glu Glu Leu Pro Glu
1               5

<210> SEQ ID NO 2254
<211> LENGTH: 8
<212> TYPE: PRT
<213> ORGANISM: Homo sapiens

<400> SEQUENCE: 2254

Leu Asn Thr Glu Glu Val Pro Asp
1               5

<210> SEQ ID NO 2255
<211> LENGTH: 8
<212> TYPE: PRT
<213> ORGANISM: Homo sapiens

<400> SEQUENCE: 2255

Leu Leu Gly Glu Glu Leu Pro Pro
1               5

<210> SEQ ID NO 2256
<211> LENGTH: 8
<212> TYPE: PRT
<213> ORGANISM: Homo sapiens

<400> SEQUENCE: 2256

Leu Arg Asn Glu Glu Ala Pro Gln
1               5

<210> SEQ ID NO 2257
<211> LENGTH: 8
<212> TYPE: PRT
<213> ORGANISM: Homo sapiens

<400> SEQUENCE: 2257

Leu Ser Phe Glu Glu Ser Pro Gln
1               5

<210> SEQ ID NO 2258
<211> LENGTH: 8
<212> TYPE: PRT
<213> ORGANISM: Homo sapiens

<400> SEQUENCE: 2258

Leu Ala Tyr Glu Glu Arg Pro Arg
1               5

<210> SEQ ID NO 2259
<211> LENGTH: 8
<212> TYPE: PRT
<213> ORGANISM: Homo sapiens

<400> SEQUENCE: 2259

Leu Glu Leu Glu Glu Pro Pro Gln
1               5

<210> SEQ ID NO 2260
<211> LENGTH: 8
<212> TYPE: PRT
<213> ORGANISM: Homo sapiens

<400> SEQUENCE: 2260

Leu Leu Asn Glu Glu Leu Pro Asn
1               5

<210> SEQ ID NO 2261
<211> LENGTH: 8
<212> TYPE: PRT
<213> ORGANISM: Homo sapiens

<400> SEQUENCE: 2261

Leu Pro Ser Glu Glu Asp Pro Ala
1               5

<210> SEQ ID NO 2262
<211> LENGTH: 8
<212> TYPE: PRT
<213> ORGANISM: Homo sapiens

<400> SEQUENCE: 2262

Leu Ser Glu Glu Glu Gln Pro Lys
1               5

<210> SEQ ID NO 2263
<211> LENGTH: 8
<212> TYPE: PRT
<213> ORGANISM: Homo sapiens

<400> SEQUENCE: 2263

Leu Glu Asn Glu Glu Leu Pro Lys
1               5

<210> SEQ ID NO 2264
<211> LENGTH: 8
<212> TYPE: PRT
<213> ORGANISM: Homo sapiens

<400> SEQUENCE: 2264

Leu Val Met Glu Glu Ala Pro Glu
1               5

<210> SEQ ID NO 2265
<211> LENGTH: 8
<212> TYPE: PRT
<213> ORGANISM: Homo sapiens

<400> SEQUENCE: 2265

Leu Ser Glu Glu Glu Leu Pro Ala
1               5

<210> SEQ ID NO 2266
<211> LENGTH: 8
<212> TYPE: PRT
<213> ORGANISM: Homo sapiens

<400> SEQUENCE: 2266

Leu Ala Ser Glu Glu Leu Pro Ser
1               5

<210> SEQ ID NO 2267
<211> LENGTH: 8
<212> TYPE: PRT
<213> ORGANISM: Homo sapiens

<400> SEQUENCE: 2267

Leu Ser Glu Glu Glu Leu Pro Tyr
1               5

<210> SEQ ID NO 2268
<211> LENGTH: 8
<212> TYPE: PRT
<213> ORGANISM: Homo sapiens

<400> SEQUENCE: 2268

Leu Ser Phe Glu Glu Asp Pro Arg
1 5

<210> SEQ ID NO 2269
<211> LENGTH: 8
<212> TYPE: PRT
<213> ORGANISM: Homo sapiens

<400> SEQUENCE: 2269

Leu Pro Trp Glu Glu Gly Pro Gly
1 5

<210> SEQ ID NO 2270
<211> LENGTH: 8
<212> TYPE: PRT
<213> ORGANISM: Homo sapiens

<400> SEQUENCE: 2270

Leu Asn Leu Glu Glu Pro Pro Ser
1 5

<210> SEQ ID NO 2271
<211> LENGTH: 8
<212> TYPE: PRT
<213> ORGANISM: Homo sapiens

<400> SEQUENCE: 2271

Leu Asp Arg Glu Glu Ile Pro Glu
1 5

<210> SEQ ID NO 2272
<211> LENGTH: 8
<212> TYPE: PRT
<213> ORGANISM: Homo sapiens

<400> SEQUENCE: 2272

Leu Asp Arg Glu Glu Gln Pro Gln
1 5

<210> SEQ ID NO 2273
<211> LENGTH: 8
<212> TYPE: PRT
<213> ORGANISM: Homo sapiens

<400> SEQUENCE: 2273

Leu Asp Arg Glu Glu Arg Pro Glu
1 5

<210> SEQ ID NO 2274
<211> LENGTH: 8
<212> TYPE: PRT
<213> ORGANISM: Homo sapiens

<400> SEQUENCE: 2274

Leu Asp Arg Glu Glu Gln Pro Glu
1 5

<210> SEQ ID NO 2275
<211> LENGTH: 8
<212> TYPE: PRT
<213> ORGANISM: Homo sapiens

<400> SEQUENCE: 2275

Leu Asp Arg Glu Glu Gln Pro Glu
1               5

<210> SEQ ID NO 2276
<211> LENGTH: 8
<212> TYPE: PRT
<213> ORGANISM: Homo sapiens

<400> SEQUENCE: 2276

Leu Asp Arg Glu Glu Gln Pro Glu
1               5

<210> SEQ ID NO 2277
<211> LENGTH: 8
<212> TYPE: PRT
<213> ORGANISM: Homo sapiens

<400> SEQUENCE: 2277

Leu Asp Tyr Glu Glu Arg Pro Glu
1               5

<210> SEQ ID NO 2278
<211> LENGTH: 8
<212> TYPE: PRT
<213> ORGANISM: Homo sapiens

<400> SEQUENCE: 2278

Leu Asp Tyr Glu Glu Leu Pro Glu
1               5

<210> SEQ ID NO 2279
<211> LENGTH: 8
<212> TYPE: PRT
<213> ORGANISM: Homo sapiens

<400> SEQUENCE: 2279

Leu Asp Arg Glu Glu Gln Pro Glu
1               5

<210> SEQ ID NO 2280
<211> LENGTH: 8
<212> TYPE: PRT
<213> ORGANISM: Homo sapiens

<400> SEQUENCE: 2280

Leu Asp Arg Glu Glu Gln Pro His
1               5

<210> SEQ ID NO 2281
<211> LENGTH: 8
<212> TYPE: PRT
<213> ORGANISM: Homo sapiens

<400> SEQUENCE: 2281

Leu Asp Arg Glu Glu Ile Pro Glu
1               5

<210> SEQ ID NO 2282
<211> LENGTH: 8
<212> TYPE: PRT
<213> ORGANISM: Homo sapiens

<400> SEQUENCE: 2282

Leu Asp Arg Glu Glu Thr Pro Glu
1               5

<210> SEQ ID NO 2283
<211> LENGTH: 8
<212> TYPE: PRT
<213> ORGANISM: Homo sapiens

<400> SEQUENCE: 2283

Leu Asp Arg Glu Glu Asn Pro Gln
1               5

<210> SEQ ID NO 2284
<211> LENGTH: 8
<212> TYPE: PRT
<213> ORGANISM: Homo sapiens

<400> SEQUENCE: 2284

Leu Asp Arg Glu Glu Thr Pro Glu
1               5

<210> SEQ ID NO 2285
<211> LENGTH: 8
<212> TYPE: PRT
<213> ORGANISM: Homo sapiens

<400> SEQUENCE: 2285

Leu Ser Ala Glu Glu Asn Pro Asp
1               5

<210> SEQ ID NO 2286
<211> LENGTH: 8
<212> TYPE: PRT
<213> ORGANISM: Homo sapiens

<400> SEQUENCE: 2286

Leu Thr Phe Glu Glu Val Pro Tyr
1               5

<210> SEQ ID NO 2287
<211> LENGTH: 13
<212> TYPE: PRT
<213> ORGANISM: Homo sapiens

<400> SEQUENCE: 2287

Lys Cys His Gly His Gly Val Cys Asn Ser Asn Lys Asn
1               5                   10

<210> SEQ ID NO 2288
<211> LENGTH: 14
<212> TYPE: PRT
<213> ORGANISM: Homo sapiens

<400> SEQUENCE: 2288

Met Gln Cys His Gly Arg Gly Val Cys Asn Asn Arg Lys Asn
1               5                   10

<210> SEQ ID NO 2289
<211> LENGTH: 19
<212> TYPE: PRT
<213> ORGANISM: Homo sapiens

<400> SEQUENCE: 2289

Gly Pro Trp Gly Asp Cys Ser Arg Thr Cys Gly Gly Gly Val Gln Tyr
1 5 10 15

Thr Met Arg

<210> SEQ ID NO 2290
<211> LENGTH: 17
<212> TYPE: PRT
<213> ORGANISM: Homo sapiens

<400> SEQUENCE: 2290

Gly Pro Trp Ser Gln Cys Ser Val Thr Cys Gly Asn Gly Thr Gln Glu
1 5 10 15

Arg

<210> SEQ ID NO 2291
<211> LENGTH: 17
<212> TYPE: PRT
<213> ORGANISM: Homo sapiens

<400> SEQUENCE: 2291

Gly Pro Trp Ser Glu Cys Ser Val Thr Cys Gly Glu Gly Thr Glu Val
1 5 10 15

Arg

<210> SEQ ID NO 2292
<211> LENGTH: 14
<212> TYPE: PRT
<213> ORGANISM: Homo sapiens

<400> SEQUENCE: 2292

Gly Pro Trp Gly Asp Cys Ser Arg Thr Cys Gly Gly Gly Val
1 5 10

<210> SEQ ID NO 2293
<211> LENGTH: 19
<212> TYPE: PRT
<213> ORGANISM: Homo sapiens

<400> SEQUENCE: 2293

Gly Pro Trp Gly Asp Cys Ser Arg Thr Cys Gly Gly Gly Val Gln Phe
1 5 10 15

Ser Ser Arg

<210> SEQ ID NO 2294
<211> LENGTH: 17
<212> TYPE: PRT
<213> ORGANISM: Homo sapiens

<400> SEQUENCE: 2294

Gly Pro Trp Leu Ala Cys Ser Arg Thr Cys Asp Thr Gly Trp His Thr
1 5 10 15

Arg

<210> SEQ ID NO 2295
<211> LENGTH: 14
<212> TYPE: PRT
<213> ORGANISM: Homo sapiens

<400> SEQUENCE: 2295

Gln Pro Trp Ser Glu Cys Ser Ala Thr Cys Ala Gly Gly Val
1               5                   10

<210> SEQ ID NO 2296
<211> LENGTH: 17
<212> TYPE: PRT
<213> ORGANISM: Homo sapiens

<400> SEQUENCE: 2296

Gln Pro Trp Ser Glu Cys Ser Ala Thr Cys Ala Gly Gly Val Gln Arg
1               5                   10                  15

Gln

<210> SEQ ID NO 2297
<211> LENGTH: 17
<212> TYPE: PRT
<213> ORGANISM: Homo sapiens

<400> SEQUENCE: 2297

Gly Pro Trp Gly Gln Cys Ser Gly Pro Cys Gly Gly Gly Val Gln Arg
1               5                   10                  15

Arg

<210> SEQ ID NO 2298
<211> LENGTH: 14
<212> TYPE: PRT
<213> ORGANISM: Homo sapiens

<400> SEQUENCE: 2298

Gly Pro Trp Thr Lys Cys Thr Val Thr Cys Gly Arg Gly Val
1               5                   10

<210> SEQ ID NO 2299
<211> LENGTH: 14
<212> TYPE: PRT
<213> ORGANISM: Homo sapiens

<400> SEQUENCE: 2299

Gly Pro Trp Gly Glu Cys Ser Arg Thr Cys Gly Gly Gly Val
1               5                   10

<210> SEQ ID NO 2300
<211> LENGTH: 19
<212> TYPE: PRT
<213> ORGANISM: Homo sapiens

<400> SEQUENCE: 2300

Gly Pro Trp Gly Glu Cys Ser Arg Thr Cys Gly Gly Gly Val Gln Phe
1               5                   10                  15

Ser His Arg

<210> SEQ ID NO 2301
<211> LENGTH: 15
<212> TYPE: PRT
<213> ORGANISM: Homo sapiens

<400> SEQUENCE: 2301

Trp Ser Ser Cys Ser Val Thr Cys Gly Gln Gly Arg Ala Thr Arg
1               5                   10                  15

<210> SEQ ID NO 2302
<211> LENGTH: 17
<212> TYPE: PRT
<213> ORGANISM: Homo sapiens

<400> SEQUENCE: 2302

Gly Pro Trp Gly Ala Cys Ser Ser Thr Cys Ala Gly Gly Ser Gln Arg
1 5 10 15

Arg

<210> SEQ ID NO 2303
<211> LENGTH: 19
<212> TYPE: PRT
<213> ORGANISM: Homo sapiens

<400> SEQUENCE: 2303

Ser Pro Phe Gly Thr Cys Ser Arg Thr Cys Gly Gly Gly Ile Lys Thr
1 5 10 15

Ala Ile Arg

<210> SEQ ID NO 2304
<211> LENGTH: 19
<212> TYPE: PRT
<213> ORGANISM: Homo sapiens

<400> SEQUENCE: 2304

Thr Pro Trp Gly Asp Cys Ser Arg Thr Cys Gly Gly Gly Val Ser Ser
1 5 10 15

Ser Ser Arg

<210> SEQ ID NO 2305
<211> LENGTH: 15
<212> TYPE: PRT
<213> ORGANISM: Homo sapiens

<400> SEQUENCE: 2305

Trp Asp Leu Cys Ser Thr Ser Cys Gly Gly Gly Phe Gln Lys Arg
1 5 10 15

<210> SEQ ID NO 2306
<211> LENGTH: 14
<212> TYPE: PRT
<213> ORGANISM: Homo sapiens

<400> SEQUENCE: 2306

Ser Pro Trp Ser His Cys Ser Arg Thr Cys Gly Ala Gly Val
1 5 10

<210> SEQ ID NO 2307
<211> LENGTH: 15
<212> TYPE: PRT
<213> ORGANISM: Homo sapiens

<400> SEQUENCE: 2307

Trp Met Glu Cys Ser Val Ser Cys Gly Asp Gly Ile Gln Arg Arg
1 5 10 15

<210> SEQ ID NO 2308
<211> LENGTH: 15
<212> TYPE: PRT
<213> ORGANISM: Homo sapiens

<400> SEQUENCE: 2308

Trp Ser Gln Cys Ser Ala Thr Cys Gly Glu Gly Ile Gln Gln Arg
1               5                   10                  15

<210> SEQ ID NO 2309
<211> LENGTH: 17
<212> TYPE: PRT
<213> ORGANISM: Homo sapiens

<400> SEQUENCE: 2309

Ser Ala Trp Ser Pro Cys Ser Lys Ser Cys Gly Arg Gly Phe Gln Arg
1               5                   10                  15

Arg

<210> SEQ ID NO 2310
<211> LENGTH: 17
<212> TYPE: PRT
<213> ORGANISM: Homo sapiens

<400> SEQUENCE: 2310

Ser Pro Trp Ser Gln Cys Thr Ala Ser Cys Gly Gly Gly Val Gln Thr
1               5                   10                  15

Arg

<210> SEQ ID NO 2311
<211> LENGTH: 18
<212> TYPE: PRT
<213> ORGANISM: Homo sapiens

<400> SEQUENCE: 2311

Ser Pro Trp Ser Gln Cys Thr Ala Ser Cys Gly Gly Gly Val Gln Thr
1               5                   10                  15

Arg Ser

<210> SEQ ID NO 2312
<211> LENGTH: 16
<212> TYPE: PRT
<213> ORGANISM: Homo sapiens

<400> SEQUENCE: 2312

Pro Trp Gln Gln Cys Thr Val Thr Cys Gly Gly Gly Val Gln Thr Arg
1               5                   10                  15

<210> SEQ ID NO 2313
<211> LENGTH: 17
<212> TYPE: PRT
<213> ORGANISM: Homo sapiens

<400> SEQUENCE: 2313

Pro Trp Gln Gln Cys Thr Val Thr Cys Gly Gly Gly Val Gln Thr Arg
1               5                   10                  15

Ser

<210> SEQ ID NO 2314
<211> LENGTH: 17
<212> TYPE: PRT
<213> ORGANISM: Homo sapiens

<400> SEQUENCE: 2314

Gly Pro Trp Ser Gln Cys Ser Lys Thr Cys Gly Arg Gly Val Arg Lys
1 5 10 15

Arg

<210> SEQ ID NO 2315
<211> LENGTH: 19
<212> TYPE: PRT
<213> ORGANISM: Homo sapiens

<400> SEQUENCE: 2315

Ser Lys Trp Ser Glu Cys Ser Arg Thr Cys Gly Gly Gly Val Lys Phe
1 5 10 15

Gln Glu Arg

<210> SEQ ID NO 2316
<211> LENGTH: 16
<212> TYPE: PRT
<213> ORGANISM: Homo sapiens

<400> SEQUENCE: 2316

Trp Ser Lys Cys Ser Ile Thr Cys Gly Lys Gly Met Gln Ser Arg Val
1 5 10 15

<210> SEQ ID NO 2317
<211> LENGTH: 17
<212> TYPE: PRT
<213> ORGANISM: Homo sapiens

<400> SEQUENCE: 2317

Asn Ser Trp Asn Glu Cys Ser Val Thr Cys Gly Ser Gly Val Gln Gln
1 5 10 15

Arg

<210> SEQ ID NO 2318
<211> LENGTH: 18
<212> TYPE: PRT
<213> ORGANISM: Homo sapiens

<400> SEQUENCE: 2318

Gly Pro Trp Gly Gln Cys Ser Ser Ser Cys Ser Gly Gly Leu Gln His
1 5 10 15

Arg Ala

<210> SEQ ID NO 2319
<211> LENGTH: 15
<212> TYPE: PRT
<213> ORGANISM: Homo sapiens

<400> SEQUENCE: 2319

Trp Ser Lys Cys Ser Val Thr Cys Gly Ile Gly Ile Met Lys Arg
1 5 10 15

<210> SEQ ID NO 2320
<211> LENGTH: 18
<212> TYPE: PRT
<213> ORGANISM: Homo sapiens

<400> SEQUENCE: 2320

Pro Tyr Ser Ser Cys Ser Arg Thr Cys Gly Gly Gly Ile Glu Ser Ala
1 5 10 15

Thr Arg

<210> SEQ ID NO 2321
<211> LENGTH: 19
<212> TYPE: PRT
<213> ORGANISM: Homo sapiens

<400> SEQUENCE: 2321

Ser Pro Trp Ser Val Cys Ser Ser Thr Cys Gly Glu Gly Trp Gln Thr
1 5 10 15

Arg Thr Arg

<210> SEQ ID NO 2322
<211> LENGTH: 19
<212> TYPE: PRT
<213> ORGANISM: Homo sapiens

<400> SEQUENCE: 2322

Ser Pro Trp Ser Val Cys Ser Leu Thr Cys Gly Gln Gly Leu Gln Val
1 5 10 15

Arg Thr Arg

<210> SEQ ID NO 2323
<211> LENGTH: 19
<212> TYPE: PRT
<213> ORGANISM: Homo sapiens

<400> SEQUENCE: 2323

Ser Pro Trp Ser Leu Cys Ser Phe Thr Cys Gly Arg Gly Gln Arg Thr
1 5 10 15

Arg Thr Arg

<210> SEQ ID NO 2324
<211> LENGTH: 19
<212> TYPE: PRT
<213> ORGANISM: Homo sapiens

<400> SEQUENCE: 2324

Thr Gln Trp Thr Ser Cys Ser Lys Thr Cys Asn Ser Gly Thr Gln Ser
1 5 10 15

Arg His Arg

<210> SEQ ID NO 2325
<211> LENGTH: 20
<212> TYPE: PRT
<213> ORGANISM: Homo sapiens

<400> SEQUENCE: 2325

Ser Pro Trp Ser Lys Cys Ser Ala Ala Cys Gly Gln Thr Gly Val Gln
1 5 10 15

Thr Arg Thr Arg
20

<210> SEQ ID NO 2326
<211> LENGTH: 19
<212> TYPE: PRT
<213> ORGANISM: Homo sapiens

<400> SEQUENCE: 2326

Gly Pro Trp Gly Pro Cys Ser Gly Ser Cys Gly Pro Gly Arg Arg Leu
1 5 10 15

Arg Arg Arg

<210> SEQ ID NO 2327
<211> LENGTH: 18
<212> TYPE: PRT
<213> ORGANISM: Homo sapiens

<400> SEQUENCE: 2327

Thr Glu Trp Ser Ala Cys Ser Lys Thr Cys Gly Met Gly Ile Ser Thr
1 5 10 15

Arg Val

<210> SEQ ID NO 2328
<211> LENGTH: 18
<212> TYPE: PRT
<213> ORGANISM: Homo sapiens

<400> SEQUENCE: 2328

Thr Ser Trp Ser Gln Cys Ser Lys Thr Cys Gly Thr Gly Ile Ser Thr
1 5 10 15

Arg Val

<210> SEQ ID NO 2329
<211> LENGTH: 19
<212> TYPE: PRT
<213> ORGANISM: Homo sapiens

<400> SEQUENCE: 2329

Ser Ala Trp Arg Ala Cys Ser Val Thr Cys Gly Lys Gly Ile Gln Lys
1 5 10 15

Arg Ser Arg

<210> SEQ ID NO 2330
<211> LENGTH: 19
<212> TYPE: PRT
<213> ORGANISM: Homo sapiens

<400> SEQUENCE: 2330

Gln Pro Trp Gly Thr Cys Ser Glu Ser Cys Gly Lys Gly Thr Gln Thr
1 5 10 15

Arg Ala Arg

<210> SEQ ID NO 2331
<211> LENGTH: 19
<212> TYPE: PRT
<213> ORGANISM: Homo sapiens

<400> SEQUENCE: 2331

Ala Ser Trp Ser Ala Cys Ser Val Ser Cys Gly Gly Gly Ala Arg Gln
1 5 10 15

Arg Thr Arg

<210> SEQ ID NO 2332
<211> LENGTH: 18
<212> TYPE: PRT
<213> ORGANISM: Homo sapiens

<400> SEQUENCE: 2332

Thr Glu Trp Thr Ala Cys Ser Lys Ser Cys Gly Met Gly Phe Ser Thr
1 5 10 15

Arg Val

<210> SEQ ID NO 2333
<211> LENGTH: 19
<212> TYPE: PRT
<213> ORGANISM: Homo sapiens

<400> SEQUENCE: 2333

Ser Gln Trp Ser Pro Cys Ser Arg Thr Cys Gly Gly Gly Val Ser Phe
1 5 10 15

Arg Glu Arg

<210> SEQ ID NO 2334
<211> LENGTH: 18
<212> TYPE: PRT
<213> ORGANISM: Homo sapiens

<400> SEQUENCE: 2334

Gly Pro Trp Ala Pro Cys Ser Ala Ser Cys Gly Gly Gly Ser Gln Ser
1 5 10 15

Arg Ser

<210> SEQ ID NO 2335
<211> LENGTH: 19
<212> TYPE: PRT
<213> ORGANISM: Homo sapiens

<400> SEQUENCE: 2335

Gly Pro Trp Glu Pro Cys Ser Val Thr Cys Ser Lys Gly Thr Arg Thr
1 5 10 15

Arg Arg Arg

<210> SEQ ID NO 2336
<211> LENGTH: 79
<212> TYPE: PRT
<213> ORGANISM: Homo sapiens

<400> SEQUENCE: 2336

Cys Tyr Asn Ser Thr Gly Val Asp Tyr Arg Gly Thr Val Ser Val Thr
1 5 10 15

Lys Ser Gly Arg Gln Cys Gln Pro Trp Asn Ser Gln Tyr Pro His Thr
20 25 30

His Thr Phe Thr Ala Leu Arg Phe Pro Glu Leu Asn Gly Gly His Ser
35 40 45

Tyr Cys Arg Asn Pro Gly Asn Gln Lys Glu Ala Pro Trp Cys Phe Thr
50 55 60

Leu Asp Glu Asn Phe Lys Ser Asp Leu Cys Asp Ile Pro Ala Cys
65 70 75

<210> SEQ ID NO 2337
<211> LENGTH: 82
<212> TYPE: PRT
<213> ORGANISM: Homo sapiens

<400> SEQUENCE: 2337

Asn His Lys Cys Tyr Asn Ser Thr Gly Val Asp Tyr Arg Gly Thr Val
1 5 10 15

Ser Val Thr Lys Ser Gly Arg Gln Cys Gln Pro Trp Asn Ser Gln Tyr
20 25 30

Pro His Thr His Thr Phe Thr Ala Leu Arg Phe Pro Glu Leu Asn Gly
35 40 45

Gly His Ser Tyr Cys Arg Asn Pro Gly Asn Gln Lys Glu Ala Pro Trp
50 55 60

Cys Phe Thr Leu Asp Glu Asn Phe Lys Ser Asp Leu Cys Asp Ile Pro
65 70 75 80

Ala Cys

<210> SEQ ID NO 2338
<211> LENGTH: 78
<212> TYPE: PRT
<213> ORGANISM: Homo sapiens

<400> SEQUENCE: 2338

His Lys Cys Tyr Asn Ser Thr Gly Val Asp Tyr Arg Gly Thr Val Ser
1 5 10 15

Val Thr Lys Ser Gly Arg Gln Cys Gln Pro Trp Asn Ser Gln Tyr Pro
20 25 30

His Thr His Thr Phe Thr Ala Leu Arg Phe Pro Glu Leu Asn Gly Gly
35 40 45

His Ser Tyr Cys Arg Asn Pro Gly Asn Gln Lys Glu Ala Pro Trp Cys
50 55 60

Phe Thr Leu Asp Glu Asn Phe Lys Ser Asp Leu Cys Asp Ile
65 70 75

<210> SEQ ID NO 2339
<211> LENGTH: 81
<212> TYPE: PRT
<213> ORGANISM: Homo sapiens

<400> SEQUENCE: 2339

His Lys Cys Tyr Asn Ser Thr Gly Val Asp Tyr Arg Gly Thr Val Ser
1 5 10 15

Val Thr Lys Ser Gly Arg Gln Cys Gln Pro Trp Asn Ser Gln Tyr Pro
20 25 30

His Thr His Thr Phe Thr Ala Leu Arg Phe Pro Glu Leu Asn Gly Gly
35 40 45

His Ser Tyr Cys Arg Asn Pro Gly Asn Gln Lys Glu Ala Pro Trp Cys
50 55 60

Phe Thr Leu Asp Glu Asn Phe Lys Ser Asp Leu Cys Asp Ile Pro Ala
65 70 75 80

Cys

<210> SEQ ID NO 2340
<211> LENGTH: 81
<212> TYPE: PRT
<213> ORGANISM: Homo sapiens

<400> SEQUENCE: 2340

Lys Cys Tyr Asn Ser Thr Gly Val Asp Tyr Arg Gly Thr Val Ser Val
1 5 10 15

Thr Lys Ser Gly Arg Gln Cys Gln Pro Trp Asn Ser Gln Tyr Pro His
20 25 30

Thr His Thr Phe Thr Ala Leu Arg Phe Pro Glu Leu Asn Gly Gly His
35 40 45

```
Ser Tyr Cys Arg Asn Pro Gly Asn Gln Lys Glu Ala Pro Trp Cys Phe
    50                  55                  60

Thr Leu Asp Glu Asn Phe Lys Ser Asp Leu Cys Asp Ile Pro Ala Cys
65                  70                  75                  80

Asp


<210> SEQ ID NO 2341
<211> LENGTH: 81
<212> TYPE: PRT
<213> ORGANISM: Homo sapiens

<400> SEQUENCE: 2341

Gln Cys Tyr Asn Gly Ser Gly Met Asp Tyr Arg Gly Thr Ala Ser Thr
1               5                   10                  15

Thr Lys Ser Gly His Gln Cys Gln Pro Trp Ala Leu Gln His Pro His
            20                  25                  30

Ser His His Leu Ser Ser Thr Asp Phe Pro Glu Leu Gly Gly Gly His
        35                  40                  45

Ala Tyr Cys Arg Asn Pro Gly Gly Gln Met Glu Gly Pro Trp Cys Phe
    50                  55                  60

Thr Gln Asn Lys Asn Val Arg Met Glu Leu Cys Asp Val Pro Ser Cys
65                  70                  75                  80

Ser


<210> SEQ ID NO 2342
<211> LENGTH: 78
<212> TYPE: PRT
<213> ORGANISM: Homo sapiens

<400> SEQUENCE: 2342

His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60

Phe Thr Gln Asn Lys Asn Val Arg Met Glu Leu Cys Asp Val
65                  70                  75


<210> SEQ ID NO 2343
<211> LENGTH: 81
<212> TYPE: PRT
<213> ORGANISM: Homo sapiens

<400> SEQUENCE: 2343

His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60
```

Phe Thr Gln Asn Lys Asn Val Arg Met Glu Leu Cys Asp Val Pro Ser
65 70 75 80

Cys

<210> SEQ ID NO 2344
<211> LENGTH: 82
<212> TYPE: PRT
<213> ORGANISM: Homo sapiens

<400> SEQUENCE: 2344

His Gln Cys Tyr Asn Gly Ser Gly Met Asp Tyr Arg Gly Thr Ala Ser
1 5 10 15

Thr Thr Lys Ser Gly His Gln Cys Gln Pro Trp Ala Leu Gln His Pro
20 25 30

His Ser His His Leu Ser Ser Thr Asp Phe Pro Glu Leu Gly Gly Gly
35 40 45

His Ala Tyr Cys Arg Asn Pro Gly Gly Gln Met Glu Gly Pro Trp Cys
50 55 60

Phe Thr Gln Asn Lys Asn Val Arg Met Glu Leu Cys Asp Val Pro Ser
65 70 75 80

Cys Ser

<210> SEQ ID NO 2345
<211> LENGTH: 80
<212> TYPE: PRT
<213> ORGANISM: Homo sapiens

<400> SEQUENCE: 2345

Gln Cys Tyr Asn Gly Ser Gly Met Asp Tyr Arg Gly Thr Ala Ser Thr
1 5 10 15

Thr Lys Ser Gly His Gln Cys Gln Pro Trp Ala Leu Gln His Pro His
20 25 30

Ser His His Leu Ser Ser Thr Asp Phe Pro Glu Leu Gly Gly Gly His
35 40 45

Ala Tyr Cys Arg Asn Pro Gly Gly Gln Met Glu Gly Pro Trp Cys Phe
50 55 60

Thr Gln Asn Lys Asn Val Arg Met Glu Leu Cys Asp Val Pro Ser Cys
65 70 75 80

<210> SEQ ID NO 2346
<211> LENGTH: 19
<212> TYPE: PRT
<213> ORGANISM: Homo sapiens

<400> SEQUENCE: 2346

Gly Pro Trp Glu Arg Cys Thr Ala Gln Cys Gly Gly Gly Ile Gln Ala
1 5 10 15

Arg Arg Arg

<210> SEQ ID NO 2347
<211> LENGTH: 19
<212> TYPE: PRT
<213> ORGANISM: Homo sapiens

<400> SEQUENCE: 2347

Ser Pro Trp Thr Lys Cys Ser Ala Thr Cys Gly Gly Gly His Tyr Met
1 5 10 15

Arg Thr Arg

<210> SEQ ID NO 2348
<211> LENGTH: 19
<212> TYPE: PRT
<213> ORGANISM: Homo sapiens

<400> SEQUENCE: 2348

Thr Ser Trp Ser Pro Cys Ser Ala Ser Cys Gly Gly Gly His Tyr Gln
1 5 10 15

Arg Thr Arg

<210> SEQ ID NO 2349
<211> LENGTH: 19
<212> TYPE: PRT
<213> ORGANISM: Homo sapiens

<400> SEQUENCE: 2349

Gly Pro Trp Glu Asp Cys Ser Val Ser Cys Gly Gly Gly Glu Gln Leu
1 5 10 15

Arg Ser Arg

<210> SEQ ID NO 2350
<211> LENGTH: 19
<212> TYPE: PRT
<213> ORGANISM: Homo sapiens

<400> SEQUENCE: 2350

Gln Pro Trp Ser Gln Cys Ser Ala Thr Cys Gly Asp Gly Val Arg Glu
1 5 10 15

Arg Arg Arg

<210> SEQ ID NO 2351
<211> LENGTH: 19
<212> TYPE: PRT
<213> ORGANISM: Homo sapiens

<400> SEQUENCE: 2351

Ser Pro Trp Ser Pro Cys Ser Gly Asn Cys Ser Thr Gly Lys Gln Gln
1 5 10 15

Arg Thr Arg

<210> SEQ ID NO 2352
<211> LENGTH: 17
<212> TYPE: PRT
<213> ORGANISM: Homo sapiens

<400> SEQUENCE: 2352

Trp Thr Arg Cys Ser Ser Ser Cys Gly Arg Gly Val Ser Val Arg Ser
1 5 10 15

Arg

<210> SEQ ID NO 2353
<211> LENGTH: 19
<212> TYPE: PRT
<213> ORGANISM: Homo sapiens

<400> SEQUENCE: 2353

Ser Pro Trp Ser Ser Cys Ser Val Thr Cys Gly Val Gly Asn Ile Thr
1 5 10 15

Arg Ile Arg

<210> SEQ ID NO 2354
<211> LENGTH: 19
<212> TYPE: PRT
<213> ORGANISM: Homo sapiens

<400> SEQUENCE: 2354

Ser Pro Trp Ser Ala Cys Thr Val Thr Cys Ala Gly Gly Ile Arg Glu
1 5 10 15

Arg Thr Arg

<210> SEQ ID NO 2355
<211> LENGTH: 20
<212> TYPE: PRT
<213> ORGANISM: Homo sapiens

<400> SEQUENCE: 2355

Ser Pro Trp Ser Gln Cys Ser Val Arg Cys Gly Arg Gly Gln Arg Ser
1 5 10 15

Arg Gln Val Arg
20

<210> SEQ ID NO 2356
<211> LENGTH: 19
<212> TYPE: PRT
<213> ORGANISM: Homo sapiens

<400> SEQUENCE: 2356

Thr Glu Trp Ser Val Cys Asn Ser Arg Cys Gly Arg Gly Tyr Gln Lys
1 5 10 15

Arg Thr Arg

<210> SEQ ID NO 2357
<211> LENGTH: 19
<212> TYPE: PRT
<213> ORGANISM: Homo sapiens

<400> SEQUENCE: 2357

Thr Glu Trp Ser Ala Cys Asn Val Arg Cys Gly Arg Gly Trp Gln Lys
1 5 10 15

Arg Ser Arg

<210> SEQ ID NO 2358
<211> LENGTH: 17
<212> TYPE: PRT
<213> ORGANISM: Homo sapiens

<400> SEQUENCE: 2358

Trp Asp Glu Cys Ser Ala Thr Cys Gly Met Gly Met Lys Lys Arg His
1 5 10 15

Arg

<210> SEQ ID NO 2359
<211> LENGTH: 19
<212> TYPE: PRT
<213> ORGANISM: Homo sapiens

<400> SEQUENCE: 2359

Ser Glu Trp Ser Asp Cys Ser Val Thr Cys Gly Lys Gly Met Arg Thr
1 5 10 15

Arg Gln Arg

<210> SEQ ID NO 2360
<211> LENGTH: 18
<212> TYPE: PRT
<213> ORGANISM: Homo sapiens

<400> SEQUENCE: 2360

Ser Pro Trp Ser Pro Cys Ser Thr Ser Cys Gly Leu Gly Val Ser Thr
1 5 10 15

Arg Ile

<210> SEQ ID NO 2361
<211> LENGTH: 18
<212> TYPE: PRT
<213> ORGANISM: Homo sapiens

<400> SEQUENCE: 2361

Thr Ala Trp Gly Pro Cys Ser Thr Thr Cys Gly Leu Gly Met Ala Thr
1 5 10 15

Arg Val

<210> SEQ ID NO 2362
<211> LENGTH: 18
<212> TYPE: PRT
<213> ORGANISM: Homo sapiens

<400> SEQUENCE: 2362

Thr Lys Trp Thr Pro Cys Ser Arg Thr Cys Gly Met Gly Ile Ser Asn
1 5 10 15

Arg Val

<210> SEQ ID NO 2363
<211> LENGTH: 78
<212> TYPE: PRT
<213> ORGANISM: Homo sapiens

<400> SEQUENCE: 2363

Asn Glu Arg Ala His Gly Gln Asp Leu Gly Thr Ala Gly Ser Cys Leu
1 5 10 15

Arg Lys Phe Ser Thr Met Pro Phe Leu Phe Cys Asn Ile Asn Asn Val
20 25 30

Cys Asn Phe Ala Ser Arg Asn Asp Tyr Ser Tyr Trp Leu Ser Thr Pro
35 40 45

Glu Pro Met Pro Met Ser Met Ala Pro Ile Thr Gly Glu Asn Ile Arg
50 55 60

Pro Phe Ile Ser Arg Cys Ala Val Cys Glu Ala Pro Ala Met
65 70 75

<210> SEQ ID NO 2364
<211> LENGTH: 20
<212> TYPE: PRT
<213> ORGANISM: Homo sapiens

<400> SEQUENCE: 2364

Leu Arg Lys Phe Ser Thr Met Pro Phe Leu Phe Cys Asn Ile Asn Asn
1 5 10 15

Val Cys Asn Phe
20

<210> SEQ ID NO 2365
<211> LENGTH: 20

<212> TYPE: PRT
<213> ORGANISM: Homo sapiens

<400> SEQUENCE: 2365

Phe Cys Asn Ile Asn Asn Val Cys Asn Phe Ala Ser Arg Asn Asp Tyr
1               5                   10                  15

Ser Tyr Trp Leu
            20

<210> SEQ ID NO 2366
<211> LENGTH: 19
<212> TYPE: PRT
<213> ORGANISM: Homo sapiens

<400> SEQUENCE: 2366

Ser Ala Pro Phe Ile Glu Cys His Gly Arg Gly Thr Cys Asn Tyr Tyr
1               5                   10                  15

Ala Asn Ala

<210> SEQ ID NO 2367
<211> LENGTH: 77
<212> TYPE: PRT
<213> ORGANISM: Homo sapiens

<400> SEQUENCE: 2367

Gln Glu Lys Ala His Asn Gln Asp Leu Gly Leu Ala Gly Ser Cys Leu
1               5                   10                  15

Ala Arg Phe Ser Thr Met Pro Phe Leu Tyr Cys Asn Pro Gly Asp Val
            20                  25                  30

Cys Tyr Tyr Ala Ser Arg Asn Asp Lys Ser Tyr Trp Leu Ser Thr Thr
        35                  40                  45

Ala Pro Leu Pro Met Met Pro Val Ala Glu Asp Glu Ile Lys Pro Tyr
    50                  55                  60

Ile Ser Arg Cys Ser Val Cys Glu Ala Pro Ala Ile Ala
65                  70                  75

<210> SEQ ID NO 2368
<211> LENGTH: 20
<212> TYPE: PRT
<213> ORGANISM: Homo sapiens

<400> SEQUENCE: 2368

Tyr Cys Asn Pro Gly Asp Val Cys Tyr Tyr Ala Ser Arg Asn Asp Lys
1               5                   10                  15

Ser Tyr Trp Leu
            20

<210> SEQ ID NO 2369
<211> LENGTH: 19
<212> TYPE: PRT
<213> ORGANISM: Homo sapiens

<400> SEQUENCE: 2369

Ala Thr Pro Phe Ile Glu Cys Asn Gly Gly Arg Gly Thr Cys His Tyr
1               5                   10                  15

Tyr Ala Asn

<210> SEQ ID NO 2370
<211> LENGTH: 77
<212> TYPE: PRT
<213> ORGANISM: Homo sapiens

<400> SEQUENCE: 2370

Gln Glu Lys Ala His Asn Gln Asp Leu Gly Leu Ala Gly Ser Cys Leu
1 5 10 15

Pro Val Phe Ser Thr Leu Pro Phe Ala Tyr Cys Asn Ile His Gln Val
20 25 30

Cys His Tyr Ala Gln Arg Asn Asp Arg Ser Tyr Trp Leu Ala Ser Ala
35 40 45

Ala Pro Leu Pro Met Met Pro Leu Ser Glu Glu Ala Ile Arg Pro Tyr
50 55 60

Val Ser Arg Cys Ala Val Cys Glu Ala Pro Ala Gln Ala
65 70 75

<210> SEQ ID NO 2371
<211> LENGTH: 20
<212> TYPE: PRT
<213> ORGANISM: Homo sapiens

<400> SEQUENCE: 2371

Leu Pro Val Phe Ser Thr Leu Pro Phe Ala Tyr Cys Asn Ile His Gln
1 5 10 15

Val Cys His Tyr
20

<210> SEQ ID NO 2372
<211> LENGTH: 20
<212> TYPE: PRT
<213> ORGANISM: Homo sapiens

<400> SEQUENCE: 2372

Tyr Cys Asn Ile His Gln Val Cys His Tyr Ala Gln Arg Asn Asp Arg
1 5 10 15

Ser Tyr Trp Leu
20

<210> SEQ ID NO 2373
<211> LENGTH: 19
<212> TYPE: PRT
<213> ORGANISM: Homo sapiens

<400> SEQUENCE: 2373

Ala Ala Pro Phe Leu Glu Cys Gln Gly Arg Gln Gly Thr Cys His Phe
1 5 10 15

Phe Ala Asn

<210> SEQ ID NO 2374
<211> LENGTH: 78
<212> TYPE: PRT
<213> ORGANISM: Homo sapiens

<400> SEQUENCE: 2374

Asn Lys Arg Ala His Gly Gln Asp Leu Gly Thr Ala Gly Ser Cys Leu
1 5 10 15

Arg Arg Phe Ser Thr Met Pro Phe Met Phe Cys Asn Ile Asn Asn Val
20 25 30

Cys Asn Phe Ala Ser Arg Asn Asp Tyr Ser Tyr Trp Leu Ser Thr Pro
35 40 45

Glu Pro Met Pro Met Ser Met Gln Pro Leu Lys Gly Gln Ser Ile Gln
50 55 60

-continued

Pro Phe Ile Ser Arg Cys Ala Val Cys Glu Ala Pro Ala Val
65 70 75

<210> SEQ ID NO 2375
<211> LENGTH: 20
<212> TYPE: PRT
<213> ORGANISM: Homo sapiens

<400> SEQUENCE: 2375

Leu Arg Arg Phe Ser Thr Met Pro Phe Met Phe Cys Asn Ile Asn Asn
1 5 10 15

Val Cys Asn Phe
20

<210> SEQ ID NO 2376
<211> LENGTH: 20
<212> TYPE: PRT
<213> ORGANISM: Homo sapiens

<400> SEQUENCE: 2376

Phe Cys Asn Ile Asn Asn Val Cys Asn Phe Ala Ser Arg Asn Asp Tyr
1 5 10 15

Ser Tyr Trp Leu
20

<210> SEQ ID NO 2377
<211> LENGTH: 19
<212> TYPE: PRT
<213> ORGANISM: Homo sapiens

<400> SEQUENCE: 2377

Ser Ala Pro Phe Ile Glu Cys His Gly Arg Gly Thr Cys Asn Tyr Tyr
1 5 10 15

Ala Asn Ser

<210> SEQ ID NO 2378
<211> LENGTH: 77
<212> TYPE: PRT
<213> ORGANISM: Homo sapiens

<400> SEQUENCE: 2378

Gln Glu Lys Ala His Asn Gln Asp Leu Gly Phe Ala Gly Ser Cys Leu
1 5 10 15

Pro Arg Phe Ser Thr Met Pro Phe Ile Tyr Cys Asn Ile Asn Glu Val
20 25 30

Cys His Tyr Ala Arg Arg Asn Asp Lys Ser Tyr Trp Leu Ser Thr Thr
35 40 45

Ala Pro Ile Pro Met Met Pro Val Ser Gln Thr Gln Ile Pro Gln Tyr
50 55 60

Ile Ser Arg Cys Ser Val Cys Glu Ala Pro Ser Gln Ala
65 70 75

<210> SEQ ID NO 2379
<211> LENGTH: 20
<212> TYPE: PRT
<213> ORGANISM: Homo sapiens

<400> SEQUENCE: 2379

Tyr Cys Asn Ile Asn Glu Val Cys His Tyr Ala Arg Arg Asn Asp Lys
1 5 10 15

Ser Tyr Trp Leu
20

<210> SEQ ID NO 2380
<211> LENGTH: 19
<212> TYPE: PRT
<213> ORGANISM: Homo sapiens

<400> SEQUENCE: 2380

Ala Thr Pro Phe Ile Glu Cys Ser Gly Ala Arg Gly Thr Cys His Tyr
1 5 10 15

Phe Ala Asn

<210> SEQ ID NO 2381
<211> LENGTH: 23
<212> TYPE: PRT
<213> ORGANISM: Homo sapiens

<400> SEQUENCE: 2381

Asn Gly Lys Glu Ile Cys Leu Asp Pro Glu Ala Pro Phe Leu Lys Lys
1 5 10 15

Val Ile Gln Lys Ile Leu Asp
20

<210> SEQ ID NO 2382
<211> LENGTH: 56
<212> TYPE: PRT
<213> ORGANISM: Homo sapiens

<400> SEQUENCE: 2382

Arg Cys Val Cys Leu Gln Thr Thr Gln Gly Val His Pro Lys Met Ile
1 5 10 15

Ser Asn Leu Gln Val Phe Ala Ile Gly Pro Gln Cys Ser Lys Val Glu
20 25 30

Val Val Ala Ser Leu Lys Asn Gly Lys Glu Ile Cys Leu Asp Pro Glu
35 40 45

Ala Pro Phe Leu Lys Lys Val Ile
50 55

<210> SEQ ID NO 2383
<211> LENGTH: 57
<212> TYPE: PRT
<213> ORGANISM: Homo sapiens

<400> SEQUENCE: 2383

Cys Leu Gln Thr Thr Gln Gly Val His Pro Lys Met Ile Ser Asn Leu
1 5 10 15

Gln Val Phe Ala Ile Gly Pro Gln Cys Ser Lys Val Glu Val Val Ala
20 25 30

Ser Leu Lys Asn Gly Lys Glu Ile Cys Leu Asp Pro Glu Ala Pro Phe
35 40 45

Leu Lys Lys Val Ile Gln Lys Ile Leu
50 55

<210> SEQ ID NO 2384
<211> LENGTH: 24
<212> TYPE: PRT
<213> ORGANISM: Homo sapiens

<400> SEQUENCE: 2384

Asn Gly Lys Gln Val Cys Leu Asp Pro Glu Ala Pro Phe Leu Lys Lys
1               5                   10                  15

Val Ile Gln Lys Ile Leu Asp Ser
            20

<210> SEQ ID NO 2385
<211> LENGTH: 60
<212> TYPE: PRT
<213> ORGANISM: Homo sapiens

<400> SEQUENCE: 2385

Leu Arg Cys Thr Cys Leu Arg Val Thr Leu Arg Val Asn Pro Lys Thr
1               5                   10                  15

Ile Gly Lys Leu Gln Val Phe Pro Ala Gly Pro Gln Cys Ser Lys Val
            20                  25                  30

Glu Val Val Ala Ser Leu Lys Asn Gly Lys Gln Val Cys Leu Asp Pro
        35                  40                  45

Glu Ala Pro Phe Leu Lys Lys Val Ile Gln Lys Ile
    50                  55                  60

<210> SEQ ID NO 2386
<211> LENGTH: 56
<212> TYPE: PRT
<213> ORGANISM: Homo sapiens

<400> SEQUENCE: 2386

Arg Cys Thr Cys Leu Arg Val Thr Leu Arg Val Asn Pro Lys Thr Ile
1               5                   10                  15

Gly Lys Leu Gln Val Phe Pro Ala Gly Pro Gln Cys Ser Lys Val Glu
            20                  25                  30

Val Val Ala Ser Leu Lys Asn Gly Lys Gln Val Cys Leu Asp Pro Glu
        35                  40                  45

Ala Pro Phe Leu Lys Lys Val Ile
    50                  55

<210> SEQ ID NO 2387
<211> LENGTH: 57
<212> TYPE: PRT
<213> ORGANISM: Homo sapiens

<400> SEQUENCE: 2387

Cys Leu Arg Val Thr Leu Arg Val Asn Pro Lys Thr Ile Gly Lys Leu
1               5                   10                  15

Gln Val Phe Pro Ala Gly Pro Gln Cys Ser Lys Val Glu Val Val Ala
            20                  25                  30

Ser Leu Lys Asn Gly Lys Gln Val Cys Leu Asp Pro Glu Ala Pro Phe
        35                  40                  45

Leu Lys Lys Val Ile Gln Lys Ile Leu
    50                  55

<210> SEQ ID NO 2388
<211> LENGTH: 24
<212> TYPE: PRT
<213> ORGANISM: Homo sapiens

<400> SEQUENCE: 2388

Asn Gly Arg Lys Ala Cys Leu Asn Pro Ala Ser Pro Ile Val Lys Lys
1               5                   10                  15

```
Ile Ile Glu Lys Met Leu Asn Ser
            20


<210> SEQ ID NO 2389
<211> LENGTH: 56
<212> TYPE: PRT
<213> ORGANISM: Homo sapiens

<400> SEQUENCE: 2389

Arg Cys Gln Cys Leu Gln Thr Leu Gln Gly Ile His Pro Lys Asn Ile
1               5                   10                  15

Gln Ser Val Asn Val Lys Ser Pro Gly Pro His Cys Ala Gln Thr Glu
            20                  25                  30

Val Ile Ala Thr Leu Lys Asn Gly Arg Lys Ala Cys Leu Asn Pro Ala
        35                  40                  45

Ser Pro Ile Val Lys Lys Ile Ile
    50                  55


<210> SEQ ID NO 2390
<211> LENGTH: 58
<212> TYPE: PRT
<213> ORGANISM: Homo sapiens

<400> SEQUENCE: 2390

Gln Cys Leu Gln Thr Leu Gln Gly Ile His Pro Lys Asn Ile Gln Ser
1               5                   10                  15

Val Asn Val Lys Ser Pro Gly Pro His Cys Ala Gln Thr Glu Val Ile
            20                  25                  30

Ala Thr Leu Lys Asn Gly Arg Lys Ala Cys Leu Asn Pro Ala Ser Pro
        35                  40                  45

Ile Val Lys Lys Ile Ile Glu Lys Met Leu
    50                  55


<210> SEQ ID NO 2391
<211> LENGTH: 56
<212> TYPE: PRT
<213> ORGANISM: Homo sapiens

<400> SEQUENCE: 2391

Arg Cys Gln Cys Leu Gln Thr Leu Gln Gly Ile His Leu Lys Asn Ile
1               5                   10                  15

Gln Ser Val Lys Val Lys Ser Pro Gly Pro His Cys Ala Gln Thr Glu
            20                  25                  30

Val Ile Ala Thr Leu Lys Asn Gly Gln Lys Ala Cys Leu Asn Pro Ala
        35                  40                  45

Ser Pro Met Val Lys Lys Ile Ile
    50                  55


<210> SEQ ID NO 2392
<211> LENGTH: 22
<212> TYPE: PRT
<213> ORGANISM: Homo sapiens

<400> SEQUENCE: 2392

Asn Gly Lys Lys Ala Cys Leu Asn Pro Ala Ser Pro Met Val Gln Lys
1               5                   10                  15

Ile Ile Glu Lys Ile Leu
            20
```

<210> SEQ ID NO 2393
<211> LENGTH: 58
<212> TYPE: PRT
<213> ORGANISM: Homo sapiens

<400> SEQUENCE: 2393

```
Gln Cys Leu Gln Thr Leu Gln Gly Ile His Leu Lys Asn Ile Gln Ser
1               5                   10                  15

Val Asn Val Arg Ser Pro Gly Pro His Cys Ala Gln Thr Glu Val Ile
            20                  25                  30

Ala Thr Leu Lys Asn Gly Lys Lys Ala Cys Leu Asn Pro Ala Ser Pro
        35                  40                  45

Met Val Gln Lys Ile Ile Glu Lys Ile Leu
    50                  55
```

<210> SEQ ID NO 2394
<211> LENGTH: 56
<212> TYPE: PRT
<213> ORGANISM: Homo sapiens

<400> SEQUENCE: 2394

```
Arg Cys Gln Cys Leu Gln Thr Leu Gln Gly Ile His Leu Lys Asn Ile
1               5                   10                  15

Gln Ser Val Asn Val Arg Ser Pro Gly Pro His Cys Ala Gln Thr Glu
            20                  25                  30

Val Ile Ala Thr Leu Lys Asn Gly Lys Lys Ala Cys Leu Asn Pro Ala
        35                  40                  45

Ser Pro Met Val Gln Lys Ile Ile
    50                  55
```

<210> SEQ ID NO 2395
<211> LENGTH: 60
<212> TYPE: PRT
<213> ORGANISM: Homo sapiens

<400> SEQUENCE: 2395

```
Gln Cys Ile Lys Thr Tyr Ser Lys Pro Phe His Pro Lys Phe Ile Lys
1               5                   10                  15

Glu Leu Arg Val Ile Glu Ser Gly Pro His Cys Ala Asn Thr Glu Ile
            20                  25                  30

Ile Val Lys Leu Ser Asp Gly Arg Glu Leu Cys Leu Asp Pro Lys Glu
        35                  40                  45

Asn Trp Val Gln Arg Val Val Glu Lys Phe Leu Lys
    50                  55                  60
```

<210> SEQ ID NO 2396
<211> LENGTH: 23
<212> TYPE: PRT
<213> ORGANISM: Homo sapiens

<400> SEQUENCE: 2396

```
Asp Gly Arg Glu Leu Cys Leu Asp Pro Lys Glu Asn Trp Val Gln Arg
1               5                   10                  15

Val Val Glu Lys Phe Leu Lys
            20
```

<210> SEQ ID NO 2397
<211> LENGTH: 58
<212> TYPE: PRT
<213> ORGANISM: Homo sapiens

<400> SEQUENCE: 2397

Arg Cys Thr Cys Ile Ser Ile Ser Asn Gln Pro Val Asn Pro Arg Ser
1 5 10 15

Leu Glu Lys Leu Glu Ile Ile Pro Ala Ser Gln Phe Cys Pro Arg Val
20 25 30

Glu Ile Ile Ala Thr Met Lys Lys Lys Gly Glu Lys Arg Cys Leu Asn
35 40 45

Pro Glu Ser Lys Ala Ile Lys Asn Leu Leu
50 55

<210> SEQ ID NO 2398
<211> LENGTH: 60
<212> TYPE: PRT
<213> ORGANISM: Homo sapiens

<400> SEQUENCE: 2398

Ser Cys Ile Ser Thr Asn Gln Gly Thr Ile His Leu Gln Ser Leu Lys
1 5 10 15

Asp Leu Lys Gln Phe Ala Pro Ser Pro Ser Cys Glu Lys Ile Glu Ile
20 25 30

Ile Ala Thr Leu Lys Asn Gly Val Gln Thr Cys Leu Asn Pro Asp Ser
35 40 45

Ala Asp Val Lys Glu Leu Ile Lys Lys Trp Glu Lys
50 55 60

<210> SEQ ID NO 2399
<211> LENGTH: 58
<212> TYPE: PRT
<213> ORGANISM: Homo sapiens

<400> SEQUENCE: 2399

Cys Val Lys Thr Thr Ser Gln Val Arg Pro Arg His Ile Thr Ser Leu
1 5 10 15

Glu Val Ile Lys Ala Gly Pro His Cys Pro Thr Ala Gln Leu Ile Ala
20 25 30

Thr Leu Lys Asn Gly Arg Lys Ile Cys Leu Asp Leu Gln Ala Pro Leu
35 40 45

Tyr Lys Lys Ile Ile Lys Lys Leu Leu Glu
50 55

<210> SEQ ID NO 2400
<211> LENGTH: 22
<212> TYPE: PRT
<213> ORGANISM: Homo sapiens

<400> SEQUENCE: 2400

Asp Gly Arg Lys Ile Cys Leu Asp Pro Asp Ala Pro Arg Ile Lys Lys
1 5 10 15

Ile Val Gln Lys Lys Leu
20

<210> SEQ ID NO 2401
<211> LENGTH: 56
<212> TYPE: PRT
<213> ORGANISM: Homo sapiens

<400> SEQUENCE: 2401

Arg Cys Met Cys Ile Lys Thr Thr Ser Gly Ile His Pro Lys Asn Ile
1 5 10 15

```
Gln Ser Leu Glu Val Ile Gly Lys Gly Thr His Cys Asn Gln Val Glu
            20                  25                  30

Val Ile Ala Thr Leu Lys Asp Gly Arg Lys Ile Cys Leu Asp Pro Asp
        35                  40                  45

Ala Pro Arg Ile Lys Lys Ile Val
    50                  55


<210> SEQ ID NO 2402
<211> LENGTH: 58
<212> TYPE: PRT
<213> ORGANISM: Homo sapiens

<400> SEQUENCE: 2402

Met Cys Ile Lys Thr Thr Ser Gly Ile His Pro Lys Asn Ile Gln Ser
1               5                   10                  15

Leu Glu Val Ile Gly Lys Gly Thr His Cys Asn Gln Val Glu Val Ile
            20                  25                  30

Ala Thr Leu Lys Asp Gly Arg Lys Ile Cys Leu Asp Pro Asp Ala Pro
        35                  40                  45

Arg Ile Lys Lys Ile Val Gln Lys Lys Leu
    50                  55


<210> SEQ ID NO 2403
<211> LENGTH: 82
<212> TYPE: PRT
<213> ORGANISM: Homo sapiens

<400> SEQUENCE: 2403

Asp Cys Met Phe Gly Asn Gly Lys Gly Tyr Arg Gly Lys Lys Ala Thr
1               5                   10                  15

Thr Val Thr Gly Thr Pro Cys Gln Glu Trp Ala Ala Gln Glu Pro His
            20                  25                  30

Arg His Ser Thr Phe Ile Pro Gly Thr Asn Lys Trp Ala Gly Leu Glu
        35                  40                  45

Lys Asn Tyr Cys Arg Asn Pro Asp Gly Asp Ile Asn Gly Pro Trp Cys
    50                  55                  60

Tyr Thr Met Asn Pro Arg Lys Leu Phe Asp Tyr Cys Asp Ile Pro Leu
65                  70                  75                  80

Cys Ala


<210> SEQ ID NO 2404
<211> LENGTH: 83
<212> TYPE: PRT
<213> ORGANISM: Homo sapiens

<400> SEQUENCE: 2404

Gln Asp Cys Met Phe Gly Asn Gly Lys Gly Tyr Arg Gly Lys Lys Ala
1               5                   10                  15

Thr Thr Val Thr Gly Thr Pro Cys Gln Glu Trp Ala Ala Gln Glu Pro
            20                  25                  30

His Arg His Ser Thr Phe Ile Pro Gly Thr Asn Lys Trp Ala Gly Leu
        35                  40                  45

Glu Lys Asn Tyr Cys Arg Asn Pro Asp Gly Asp Ile Asn Gly Pro Trp
    50                  55                  60

Cys Tyr Thr Met Asn Pro Arg Lys Leu Phe Asp Tyr Cys Asp Ile Pro
65                  70                  75                  80

Leu Cys Ala
```

<210> SEQ ID NO 2405
<211> LENGTH: 78
<212> TYPE: PRT
<213> ORGANISM: Homo sapiens

<400> SEQUENCE: 2405

Asp Cys Met Phe Gly Asn Gly Lys Gly Tyr Arg Gly Lys Lys Ala Thr
1 5 10 15

Thr Val Thr Gly Thr Pro Cys Gln Glu Trp Ala Ala Gln Glu Pro His
20 25 30

Arg His Ser Thr Phe Ile Pro Gly Thr Asn Lys Trp Ala Gly Leu Glu
35 40 45

Lys Asn Tyr Cys Arg Asn Pro Asp Gly Asp Ile Asn Gly Pro Trp Cys
50 55 60

Tyr Thr Met Asn Pro Arg Lys Leu Phe Asp Tyr Cys Asp Ile
65 70 75

<210> SEQ ID NO 2406
<211> LENGTH: 80
<212> TYPE: PRT
<213> ORGANISM: Homo sapiens

<400> SEQUENCE: 2406

Cys Met Phe Gly Asn Gly Lys Gly Tyr Arg Gly Lys Lys Ala Thr Thr
1 5 10 15

Val Thr Gly Thr Pro Cys Gln Glu Trp Ala Ala Gln Glu Pro His Arg
20 25 30

His Ser Thr Phe Ile Pro Gly Thr Asn Lys Trp Ala Gly Leu Glu Lys
35 40 45

Asn Tyr Cys Arg Asn Pro Asp Gly Asp Ile Asn Gly Pro Trp Cys Tyr
50 55 60

Thr Met Asn Pro Arg Lys Leu Phe Asp Tyr Cys Asp Ile Pro Leu Cys
65 70 75 80

<210> SEQ ID NO 2407
<211> LENGTH: 77
<212> TYPE: PRT
<213> ORGANISM: Homo sapiens

<400> SEQUENCE: 2407

Ser Cys Tyr Asp Gly Arg Gly Leu Ser Tyr Arg Gly Leu Ala Arg Thr
1 5 10 15

Thr Leu Ser Gly Ala Pro Cys Gln Pro Trp Ala Ser Glu Ala Thr Tyr
20 25 30

Arg Asn Val Thr Ala Glu Gln Ala Arg Asn Trp Gly Leu Gly Gly His
35 40 45

Ala Phe Cys Arg Asn Pro Asp Asn Asp Ile Arg Pro Trp Cys Phe Val
50 55 60

Leu Asn Arg Asp Arg Leu Ser Trp Glu Tyr Cys Asp Leu
65 70 75

<210> SEQ ID NO 2408
<211> LENGTH: 82
<212> TYPE: PRT
<213> ORGANISM: Homo sapiens

<400> SEQUENCE: 2408

Lys Ala Ser Cys Tyr Asp Gly Arg Gly Leu Ser Tyr Arg Gly Leu Ala
1 5 10 15

Arg Thr Thr Leu Ser Gly Ala Pro Cys Gln Pro Trp Ala Ser Glu Ala
20 25 30

Thr Tyr Arg Asn Val Thr Ala Glu Gln Ala Arg Asn Trp Gly Leu Gly
35 40 45

Gly His Ala Phe Cys Arg Asn Pro Asp Asn Asp Ile Arg Pro Trp Cys
50 55 60

Phe Val Leu Asn Arg Asp Arg Leu Ser Trp Glu Tyr Cys Asp Leu Ala
65 70 75 80

Gln Cys

<210> SEQ ID NO 2409
<211> LENGTH: 82
<212> TYPE: PRT
<213> ORGANISM: Homo sapiens

<400> SEQUENCE: 2409

Ala Ser Cys Tyr Asp Gly Arg Gly Leu Ser Tyr Arg Gly Leu Ala Arg
1 5 10 15

Thr Thr Leu Ser Gly Ala Pro Cys Gln Pro Trp Ala Ser Glu Ala Thr
20 25 30

Tyr Arg Asn Val Thr Ala Glu Gln Ala Arg Asn Trp Gly Leu Gly Gly
35 40 45

His Ala Phe Cys Arg Asn Pro Asp Asn Asp Ile Arg Pro Trp Cys Phe
50 55 60

Val Leu Asn Arg Asp Arg Leu Ser Trp Glu Tyr Cys Asp Leu Ala Gln
65 70 75 80

Cys Gln

<210> SEQ ID NO 2410
<211> LENGTH: 80
<212> TYPE: PRT
<213> ORGANISM: Homo sapiens

<400> SEQUENCE: 2410

Asn Cys Ile Ile Gly Lys Gly Arg Ser Tyr Lys Gly Thr Val Ser Ile
1 5 10 15

Thr Lys Ser Gly Ile Lys Cys Gln Pro Trp Ser Ser Met Ile Pro His
20 25 30

Glu His Ser Phe Leu Pro Ser Ser Tyr Arg Gly Lys Asp Leu Gln Glu
35 40 45

Asn Tyr Cys Arg Asn Pro Arg Gly Glu Glu Gly Gly Pro Trp Cys Phe
50 55 60

Thr Ser Asn Pro Glu Val Arg Tyr Glu Val Cys Asp Ile Pro Gln Cys
65 70 75 80

<210> SEQ ID NO 2411
<211> LENGTH: 81
<212> TYPE: PRT
<213> ORGANISM: Homo sapiens

<400> SEQUENCE: 2411

Asn Cys Ile Ile Gly Lys Gly Arg Ser Tyr Lys Gly Thr Val Ser Ile
1 5 10 15

Thr Lys Ser Gly Ile Lys Cys Gln Pro Trp Ser Ser Met Ile Pro His
20 25 30

Glu His Ser Phe Leu Pro Ser Ser Tyr Arg Gly Lys Asp Leu Gln Glu
35 40 45

Asn Tyr Cys Arg Asn Pro Arg Gly Glu Glu Gly Gly Pro Trp Cys Phe
    50                  55                  60

Thr Ser Asn Pro Glu Val Arg Tyr Glu Val Cys Asp Ile Pro Gln Cys
65                  70                  75                  80

Ser

<210> SEQ ID NO 2412
<211> LENGTH: 74
<212> TYPE: PRT
<213> ORGANISM: Homo sapiens

<400> SEQUENCE: 2412

Glu Cys Ile Gln Gly Gln Gly Glu Gly Tyr Arg Gly Thr Val Asn Thr
1               5                   10                  15

Ile Trp Asn Gly Ile Pro Cys Gln Arg Trp Asp Ser Gln Tyr Pro His
            20                  25                  30

Glu His Asp Met Thr Pro Glu Asn Phe Lys Cys Lys Asp Leu Arg Glu
        35                  40                  45

Asn Tyr Cys Arg Asn Pro Asp Gly Ser Glu Ser Pro Trp Cys Phe Thr
    50                  55                  60

Thr Asp Pro Asn Ile Arg Val Gly Tyr Cys
65                  70

<210> SEQ ID NO 2413
<211> LENGTH: 80
<212> TYPE: PRT
<213> ORGANISM: Homo sapiens

<400> SEQUENCE: 2413

Glu Cys Met Thr Cys Asn Gly Glu Ser Tyr Arg Gly Leu Met Asp His
1               5                   10                  15

Thr Glu Ser Gly Lys Ile Cys Gln Arg Trp Asp His Gln Thr Pro His
            20                  25                  30

Arg His Lys Phe Leu Pro Glu Arg Tyr Pro Asp Lys Gly Phe Asp Asp
        35                  40                  45

Asn Tyr Cys Arg Asn Pro Asp Gly Gln Pro Arg Pro Trp Cys Tyr Thr
    50                  55                  60

Leu Asp Pro His Thr Arg Trp Glu Tyr Cys Ala Ile Lys Thr Cys Ala
65                  70                  75                  80

<210> SEQ ID NO 2414
<211> LENGTH: 80
<212> TYPE: PRT
<213> ORGANISM: Homo sapiens

<400> SEQUENCE: 2414

Glu Cys Ile Gln Gly Gln Gly Glu Gly Tyr Arg Gly Thr Val Asn Thr
1               5                   10                  15

Ile Trp Asn Gly Ile Pro Cys Gln Arg Trp Asp Ser Gln Tyr Pro His
            20                  25                  30

Glu His Asp Met Thr Pro Glu Asn Phe Lys Cys Lys Asp Leu Arg Glu
        35                  40                  45

Asn Tyr Cys Arg Asn Pro Asp Gly Ser Glu Ser Pro Trp Cys Phe Thr
    50                  55                  60

Thr Asp Pro Asn Ile Arg Val Gly Tyr Cys Ser Gln Ile Pro Asn Cys
65                  70                  75                  80

<210> SEQ ID NO 2415
<211> LENGTH: 86
<212> TYPE: PRT
<213> ORGANISM: Homo sapiens

<400> SEQUENCE: 2415

Asp Asp Cys Tyr Val Gly Asp Gly Tyr Ser Tyr Arg Gly Lys Met Asn
1 5 10 15

Arg Thr Val Asn Gln His Ala Cys Leu Tyr Trp Asn Ser His Leu Leu
20 25 30

Leu Gln Glu Asn Tyr Asn Met Phe Met Glu Asp Ala Glu Thr His Gly
35 40 45

Ile Gly Glu His Asn Phe Cys Arg Asn Pro Asp Ala Asp Glu Lys Pro
50 55 60

Trp Cys Phe Ile Lys Val Thr Asn Asp Lys Val Lys Trp Glu Tyr Cys
65 70 75 80

Asp Val Ser Ala Cys Ser
85

<210> SEQ ID NO 2416
<211> LENGTH: 85
<212> TYPE: PRT
<213> ORGANISM: Homo sapiens

<400> SEQUENCE: 2416

Asp Asp Cys Tyr Val Gly Asp Gly Tyr Ser Tyr Arg Gly Lys Met Asn
1 5 10 15

Arg Thr Val Asn Gln His Ala Cys Leu Tyr Trp Asn Ser His Leu Leu
20 25 30

Leu Gln Glu Asn Tyr Asn Met Phe Met Glu Asp Ala Glu Thr His Gly
35 40 45

Ile Gly Glu His Asn Phe Cys Arg Asn Pro Asp Ala Asp Glu Lys Pro
50 55 60

Trp Cys Phe Ile Lys Val Thr Asn Asp Lys Val Lys Trp Glu Tyr Cys
65 70 75 80

Asp Val Ser Ala Cys
85

<210> SEQ ID NO 2417
<211> LENGTH: 84
<212> TYPE: PRT
<213> ORGANISM: Homo sapiens

<400> SEQUENCE: 2417

Glu Cys Phe Thr Ala Asn Gly Ala Asp Tyr Arg Gly Thr Gln Asn Trp
1 5 10 15

Thr Ala Leu Gln Gly Gly Lys Pro Cys Leu Phe Trp Asn Glu Thr Phe
20 25 30

Gln His Pro Tyr Asn Thr Leu Lys Tyr Pro Asn Gly Glu Gly Gly Leu
35 40 45

Gly Glu His Asn Tyr Cys Arg Asn Pro Asp Gly Asp Val Ser Pro Trp
50 55 60

Cys Tyr Val Ala Glu His Glu Asp Gly Val Tyr Trp Lys Tyr Cys Glu
65 70 75 80

Ile Pro Ala Cys

<210> SEQ ID NO 2418
<211> LENGTH: 85

<212> TYPE: PRT
<213> ORGANISM: Homo sapiens

<400> SEQUENCE: 2418

Glu Cys Phe Thr Ala Asn Gly Ala Asp Tyr Arg Gly Thr Gln Asn Trp
1 5 10 15

Thr Ala Leu Gln Gly Gly Lys Pro Cys Leu Phe Trp Asn Glu Thr Phe
20 25 30

Gln His Pro Tyr Asn Thr Leu Lys Tyr Pro Asn Gly Glu Gly Gly Leu
35 40 45

Gly Glu His Asn Tyr Cys Arg Asn Pro Asp Gly Asp Val Ser Pro Trp
50 55 60

Cys Tyr Val Ala Glu His Glu Asp Gly Val Tyr Trp Lys Tyr Cys Glu
65 70 75 80

Ile Pro Ala Cys Gln
85

<210> SEQ ID NO 2419
<211> LENGTH: 85
<212> TYPE: PRT
<213> ORGANISM: Homo sapiens

<400> SEQUENCE: 2419

Glu Cys Phe Gln Val Asn Gly Ala Asp Tyr Arg Gly His Gln Asn Arg
1 5 10 15

Thr Gly Pro Arg Gly Ala Gly Arg Pro Cys Leu Phe Trp Asp Gln Thr
20 25 30

Gln Gln His Ser Tyr Ser Ser Ala Ser Asp Pro His Gly Arg Trp Gly
35 40 45

Leu Gly Ala His Asn Phe Cys Arg Asn Pro Asp Gly Asp Val Gln Pro
50 55 60

Trp Cys Tyr Val Ala Glu Thr Glu Glu Gly Ile Tyr Trp Arg Tyr Cys
65 70 75 80

Asp Ile Pro Ser Cys
85

<210> SEQ ID NO 2420
<211> LENGTH: 86
<212> TYPE: PRT
<213> ORGANISM: Homo sapiens

<400> SEQUENCE: 2420

Ser Glu Cys Phe Gln Val Asn Gly Ala Asp Tyr Arg Gly His Gln Asn
1 5 10 15

Arg Thr Gly Pro Arg Gly Ala Gly Arg Pro Cys Leu Phe Trp Asp Gln
20 25 30

Thr Gln Gln His Ser Tyr Ser Ser Ala Ser Asp Pro His Gly Arg Trp
35 40 45

Gly Leu Gly Ala His Asn Phe Cys Arg Asn Pro Asp Gly Asp Val Gln
50 55 60

Pro Trp Cys Tyr Val Ala Glu Thr Glu Glu Gly Ile Tyr Trp Arg Tyr
65 70 75 80

Cys Asp Ile Pro Ser Cys
85

<210> SEQ ID NO 2421
<211> LENGTH: 76
<212> TYPE: PRT

<213> ORGANISM: Homo sapiens

<400> SEQUENCE: 2421

Thr Glu Gln Arg Pro Gly Val Gln Glu Cys Tyr His Gly Asn Gly Gln
1 5 10 15

Ser Tyr Arg Gly Thr Tyr Ser Thr Thr Val Thr Gly Arg Thr Cys Gln
20 25 30

Ala Trp Ser Ser Met Thr Pro His Ser His Ser Arg Thr Pro Glu Tyr
35 40 45

Tyr Pro Asn Ala Gly Leu Ile Met Asn Tyr Cys Arg Asn Pro Asp Ala
50 55 60

Val Ala Ala Pro Tyr Cys Tyr Thr Arg Asp Pro Gly
65 70 75

<210> SEQ ID NO 2422
<211> LENGTH: 80
<212> TYPE: PRT
<213> ORGANISM: Homo sapiens

<400> SEQUENCE: 2422

Gln Asp Cys Tyr Tyr His Tyr Gly Gln Ser Tyr Arg Gly Thr Tyr Ser
1 5 10 15

Thr Thr Val Thr Gly Arg Thr Cys Gln Ala Trp Ser Ser Met Thr Pro
20 25 30

His Gln His Ser Arg Thr Pro Glu Asn Tyr Pro Asn Ala Gly Leu Thr
35 40 45

Arg Asn Tyr Cys Arg Asn Pro Asp Ala Glu Ile Arg Pro Trp Cys Tyr
50 55 60

Thr Met Asp Pro Ser Val Arg Trp Glu Tyr Cys Asn Leu Thr Gln Cys
65 70 75 80

<210> SEQ ID NO 2423
<211> LENGTH: 79
<212> TYPE: PRT
<213> ORGANISM: Homo sapiens

<400> SEQUENCE: 2423

Gln Cys Tyr His Gly Asn Gly Gln Ser Tyr Arg Gly Thr Phe Ser Thr
1 5 10 15

Thr Val Thr Gly Arg Thr Cys Gln Ser Trp Ser Ser Met Thr Pro His
20 25 30

Arg His Gln Arg Thr Pro Glu Asn Tyr Pro Asn Asp Gly Leu Thr Met
35 40 45

Asn Tyr Cys Arg Asn Pro Asp Ala Asp Thr Gly Pro Trp Cys Phe Thr
50 55 60

Met Asp Pro Ser Ile Arg Trp Glu Tyr Cys Asn Leu Thr Arg Cys
65 70 75

<210> SEQ ID NO 2424
<211> LENGTH: 84
<212> TYPE: PRT
<213> ORGANISM: Homo sapiens

<400> SEQUENCE: 2424

Glu Gln Asp Cys Met Phe Gly Asn Gly Lys Gly Tyr Arg Gly Lys Lys
1 5 10 15

Ala Thr Thr Val Thr Gly Thr Pro Cys Gln Glu Trp Ala Ala Gln Glu
20 25 30

```
Pro His Arg His Ser Thr Phe Ile Pro Gly Thr Asn Lys Trp Ala Gly
        35                  40                  45

Leu Glu Lys Asn Tyr Cys Arg Asn Pro Asp Gly Asp Ile Asn Gly Pro
    50                  55                  60

Trp Cys Tyr Thr Met Asn Pro Arg Lys Leu Phe Asp Tyr Cys Asp Ile
65                  70                  75                  80

Pro Leu Cys Ala


<210> SEQ ID NO 2425
<211> LENGTH: 81
<212> TYPE: PRT
<213> ORGANISM: Homo sapiens

<400> SEQUENCE: 2425

Glu Ala Ala Cys Val Trp Cys Asn Gly Glu Glu Tyr Arg Gly Ala Val
1               5                   10                  15

Asp Arg Thr Glu Ser Gly Arg Glu Cys Gln Arg Trp Asp Leu Gln His
            20                  25                  30

Pro His Gln His Pro Phe Glu Pro Gly Lys Phe Leu Asp Gln Gly Leu
        35                  40                  45

Asp Asp Asn Tyr Cys Arg Asn Pro Asp Gly Ser Glu Arg Pro Trp Cys
    50                  55                  60

Tyr Thr Thr Asp Pro Gln Ile Glu Arg Glu Phe Cys Asp Leu Pro Arg
65                  70                  75                  80

Cys


<210> SEQ ID NO 2426
<211> LENGTH: 81
<212> TYPE: PRT
<213> ORGANISM: Homo sapiens

<400> SEQUENCE: 2426

Gln Asp Cys Tyr His Gly Ala Gly Glu Gln Tyr Arg Gly Thr Val Ser
1               5                   10                  15

Lys Thr Arg Lys Gly Val Gln Cys Gln Arg Trp Ser Ala Glu Thr Pro
            20                  25                  30

His Lys Pro Gln Phe Thr Phe Thr Ser Glu Pro His Ala Gln Leu Glu
        35                  40                  45

Glu Asn Phe Cys Arg Asn Pro Asp Gly Asp Ser His Gly Pro Trp Cys
    50                  55                  60

Tyr Thr Met Asp Pro Arg Thr Pro Phe Asp Tyr Cys Ala Leu Arg Arg
65                  70                  75                  80

Cys


<210> SEQ ID NO 2427
<211> LENGTH: 82
<212> TYPE: PRT
<213> ORGANISM: Homo sapiens

<400> SEQUENCE: 2427

Gln Asp Cys Tyr His Gly Ala Gly Glu Gln Tyr Arg Gly Thr Val Ser
1               5                   10                  15

Lys Thr Arg Lys Gly Val Gln Cys Gln Arg Trp Ser Ala Glu Thr Pro
            20                  25                  30

His Lys Pro Gln Phe Thr Phe Thr Ser Glu Pro His Ala Gln Leu Glu
        35                  40                  45
```

Glu Asn Phe Cys Arg Asn Pro Asp Gly Asp Ser His Gly Pro Trp Cys
    50                  55                  60

Tyr Thr Met Asp Pro Arg Thr Pro Phe Asp Tyr Cys Ala Leu Arg Arg
65                  70                  75                  80

Cys Ala

<210> SEQ ID NO 2428
<211> LENGTH: 79
<212> TYPE: PRT
<213> ORGANISM: Homo sapiens

<400> SEQUENCE: 2428

Cys Tyr His Gly Ala Gly Glu Gln Tyr Arg Gly Thr Val Ser Lys Thr
1               5                   10                  15

Arg Lys Gly Val Gln Cys Gln Arg Trp Ser Ala Glu Thr Pro His Lys
            20                  25                  30

Pro Gln Phe Thr Phe Thr Ser Glu Pro His Ala Gln Leu Glu Glu Asn
        35                  40                  45

Phe Cys Arg Asn Pro Asp Gly Asp Ser His Gly Pro Trp Cys Tyr Thr
    50                  55                  60

Met Asp Pro Arg Thr Pro Phe Asp Tyr Cys Ala Leu Arg Arg Cys
65                  70                  75

<210> SEQ ID NO 2429
<211> LENGTH: 82
<212> TYPE: PRT
<213> ORGANISM: Homo sapiens

<400> SEQUENCE: 2429

Glu Gly Asn Cys Ala Glu Gly Leu Gly Thr Asn Tyr Arg Gly His Val
1               5                   10                  15

Asn Ile Thr Arg Ser Gly Ile Glu Cys Gln Leu Trp Arg Ser Arg Tyr
            20                  25                  30

Pro His Lys Pro Glu Ile Asn Ser Thr Thr His Pro Gly Ala Asp Leu
        35                  40                  45

Gln Glu Asn Phe Cys Arg Asn Pro Asp Ser Ser Thr Thr Gly Pro Trp
    50                  55                  60

Cys Tyr Thr Thr Asp Pro Thr Val Arg Arg Gln Glu Cys Ser Ile Pro
65                  70                  75                  80

Val Cys

<210> SEQ ID NO 2430
<211> LENGTH: 81
<212> TYPE: PRT
<213> ORGANISM: Homo sapiens

<400> SEQUENCE: 2430

Gly Asn Cys Ala Glu Gly Leu Gly Thr Asn Tyr Arg Gly His Val Asn
1               5                   10                  15

Ile Thr Arg Ser Gly Ile Glu Cys Gln Leu Trp Arg Ser Arg Tyr Pro
            20                  25                  30

His Lys Pro Glu Ile Asn Ser Thr Thr His Pro Gly Ala Asp Leu Gln
        35                  40                  45

Glu Asn Phe Cys Arg Asn Pro Asp Ser Ser Thr Thr Gly Pro Trp Cys
    50                  55                  60

Tyr Thr Thr Asp Pro Thr Val Arg Arg Gln Glu Cys Ser Ile Pro Val
65 70 75 80

Cys

<210> SEQ ID NO 2431
<211> LENGTH: 77
<212> TYPE: PRT
<213> ORGANISM: Homo sapiens

<400> SEQUENCE: 2431

Asn Cys Ala Glu Gly Leu Gly Thr Asn Tyr Arg Gly His Val Asn Ile
1 5 10 15

Thr Arg Ser Gly Ile Glu Cys Gln Leu Trp Arg Ser Arg Tyr Pro His
20 25 30

Lys Pro Glu Ile Asn Ser Thr Thr His Pro Gly Ala Asp Leu Gln Glu
35 40 45

Asn Phe Cys Arg Asn Pro Asp Ser Ser Thr Thr Gly Pro Trp Cys Tyr
50 55 60

Thr Thr Asp Pro Thr Val Arg Arg Gln Glu Cys Ser Ile
65 70 75

<210> SEQ ID NO 2432
<211> LENGTH: 80
<212> TYPE: PRT
<213> ORGANISM: Homo sapiens

<400> SEQUENCE: 2432

Asn Cys Ala Glu Gly Leu Gly Thr Asn Tyr Arg Gly His Val Asn Ile
1 5 10 15

Thr Arg Ser Gly Ile Glu Cys Gln Leu Trp Arg Ser Arg Tyr Pro His
20 25 30

Lys Pro Glu Ile Asn Ser Thr Thr His Pro Gly Ala Asp Leu Gln Glu
35 40 45

Asn Phe Cys Arg Asn Pro Asp Ser Ser Thr Thr Gly Pro Trp Cys Tyr
50 55 60

Thr Thr Asp Pro Thr Val Arg Arg Gln Glu Cys Ser Ile Pro Val Cys
65 70 75 80

<210> SEQ ID NO 2433
<211> LENGTH: 80
<212> TYPE: PRT
<213> ORGANISM: Homo sapiens

<400> SEQUENCE: 2433

Asp Cys Tyr Phe Gly Asn Gly Ser Ala Tyr Arg Gly Thr His Ser Leu
1 5 10 15

Thr Glu Ser Gly Ala Ser Cys Leu Pro Trp Asn Ser Met Ile Leu Ile
20 25 30

Gly Lys Val Tyr Thr Ala Gln Asn Pro Ser Ala Gln Ala Leu Gly Leu
35 40 45

Gly Lys His Asn Tyr Cys Arg Asn Pro Asp Gly Asp Ala Lys Pro Trp
50 55 60

Cys His Val Leu Lys Ser Arg Arg Leu Thr Trp Glu Tyr Cys Asp Val
65 70 75 80

<210> SEQ ID NO 2434
<211> LENGTH: 84
<212> TYPE: PRT

<213> ORGANISM: Homo sapiens

<400> SEQUENCE: 2434

Ser Asp Cys Tyr Phe Gly Asn Gly Ser Ala Tyr Arg Gly Thr His Ser
1 5 10 15

Leu Thr Glu Ser Gly Ala Ser Cys Leu Pro Trp Asn Ser Met Ile Leu
20 25 30

Ile Gly Lys Val Tyr Thr Ala Gln Asn Pro Ser Ala Gln Ala Leu Gly
35 40 45

Leu Gly Lys His Asn Tyr Cys Arg Asn Pro Asp Gly Asp Ala Lys Pro
50 55 60

Trp Cys His Val Leu Lys Ser Arg Arg Leu Thr Trp Glu Tyr Cys Asp
65 70 75 80

Val Pro Ser Cys

<210> SEQ ID NO 2435
<211> LENGTH: 85
<212> TYPE: PRT
<213> ORGANISM: Homo sapiens

<400> SEQUENCE: 2435

Ser Asp Cys Tyr Phe Gly Asn Gly Ser Ala Tyr Arg Gly Thr His Ser
1 5 10 15

Leu Thr Glu Ser Gly Ala Ser Cys Leu Pro Trp Asn Ser Met Ile Leu
20 25 30

Ile Gly Lys Val Tyr Thr Ala Gln Asn Pro Ser Ala Gln Ala Leu Gly
35 40 45

Leu Gly Lys His Asn Tyr Cys Arg Asn Pro Asp Gly Asp Ala Lys Pro
50 55 60

Trp Cys His Val Leu Lys Ser Arg Arg Leu Thr Trp Glu Tyr Cys Asp
65 70 75 80

Val Pro Ser Cys Ser
85

<210> SEQ ID NO 2436
<211> LENGTH: 83
<212> TYPE: PRT
<213> ORGANISM: Homo sapiens

<400> SEQUENCE: 2436

Asp Cys Tyr Phe Gly Asn Gly Ser Ala Tyr Arg Gly Thr His Ser Leu
1 5 10 15

Thr Glu Ser Gly Ala Ser Cys Leu Pro Trp Asn Ser Met Ile Leu Ile
20 25 30

Gly Lys Val Tyr Thr Ala Gln Asn Pro Ser Ala Gln Ala Leu Gly Leu
35 40 45

Gly Lys His Asn Tyr Cys Arg Asn Pro Asp Gly Asp Ala Lys Pro Trp
50 55 60

Cys His Val Leu Lys Ser Arg Arg Leu Thr Trp Glu Tyr Cys Asp Val
65 70 75 80

Pro Ser Cys

<210> SEQ ID NO 2437
<211> LENGTH: 135
<212> TYPE: PRT
<213> ORGANISM: Homo sapiens

<400> SEQUENCE: 2437

Ala Phe Pro Thr Ile Pro Leu Ser Arg Leu Phe Asp Asn Ala Met Leu
1 5 10 15

Arg Ala His Arg Leu His Gln Leu Ala Phe Asp Thr Tyr Gln Glu Phe
20 25 30

Glu Glu Ala Tyr Ile Pro Lys Glu Gln Lys Tyr Ser Phe Leu Gln Asn
35 40 45

Pro Gln Thr Ser Leu Cys Phe Ser Glu Ser Ile Pro Thr Pro Ser Asn
50 55 60

Arg Glu Glu Thr Gln Gln Lys Ser Asn Leu Glu Leu Leu Arg Ile Ser
65 70 75 80

Leu Leu Leu Ile Gln Ser Trp Leu Glu Pro Val Gln Phe Leu Arg Ser
85 90 95

Val Phe Ala Asn Ser Leu Val Tyr Gly Ala Ser Asp Ser Asn Val Tyr
100 105 110

Asp Leu Leu Lys Asp Leu Glu Glu Gly Ile Gln Thr Leu Met Gly Arg
115 120 125

Leu Glu Asp Gly Ser Pro Arg
130 135

<210> SEQ ID NO 2438
<211> LENGTH: 135
<212> TYPE: PRT
<213> ORGANISM: Homo sapiens

<400> SEQUENCE: 2438

Ala Phe Pro Thr Ile Pro Leu Ser Arg Leu Phe Asp Asn Ala Met Leu
1 5 10 15

Arg Ala Arg Arg Leu Tyr Gln Leu Ala Tyr Asp Thr Tyr Gln Glu Phe
20 25 30

Glu Glu Ala Tyr Ile Leu Lys Glu Gln Lys Tyr Ser Phe Leu Gln Asn
35 40 45

Pro Gln Thr Ser Leu Cys Phe Ser Glu Ser Ile Pro Thr Pro Ser Asn
50 55 60

Arg Ala Lys Thr Gln Gln Lys Ser Asn Leu Glu Leu Leu Arg Ile Ser
65 70 75 80

Leu Leu Leu Ile Gln Ser Trp Leu Glu Pro Val Gln Leu Leu Arg Ser
85 90 95

Val Phe Ala Asn Ser Leu Val Tyr Gly Ala Ser Asp Ser Asn Val Tyr
100 105 110

Arg His Leu Lys Asp Leu Glu Glu Gly Ile Gln Thr Leu Met Trp Arg
115 120 125

Leu Glu Asp Gly Ser Pro Arg
130 135

<210> SEQ ID NO 2439
<211> LENGTH: 135
<212> TYPE: PRT
<213> ORGANISM: Homo sapiens

<400> SEQUENCE: 2439

Ala Val Gln Thr Val Pro Leu Ser Arg Leu Phe Asp His Ala Met Leu
1 5 10 15

Gln Ala His Arg Ala His Gln Leu Ala Ile Asp Thr Tyr Gln Glu Phe
20 25 30

```
Glu Glu Thr Tyr Ile Pro Lys Asp Gln Lys Tyr Ser Phe Leu His Asp
        35                  40                  45

Ser Gln Thr Ser Phe Cys Phe Ser Asp Ser Ile Pro Thr Pro Ser Asn
    50                  55                  60

Met Glu Glu Thr Gln Gln Lys Ser Asn Leu Glu Leu Leu Arg Ile Ser
65                  70                  75                  80

Leu Leu Leu Ile Glu Ser Trp Leu Glu Pro Val Arg Phe Leu Arg Ser
                85                  90                  95

Met Phe Ala Asn Asn Leu Val Tyr Asp Thr Ser Asp Ser Asp Asp Tyr
            100                 105                 110

His Leu Leu Lys Asp Leu Glu Glu Gly Ile Gln Thr Leu Met Gly Arg
        115                 120                 125

Leu Glu Asp Gly Ser Arg Arg
    130                 135


<210> SEQ ID NO 2440
<211> LENGTH: 120
<212> TYPE: PRT
<213> ORGANISM: Homo sapiens

<400> SEQUENCE: 2440

Ala Phe Pro Thr Ile Pro Leu Ser Arg Leu Phe Asp Asn Ala Ser Leu
1               5                   10                  15

Arg Ala His Arg Leu His Gln Leu Ala Phe Asp Thr Tyr Gln Glu Phe
            20                  25                  30

Asn Pro Gln Thr Ser Leu Cys Phe Ser Glu Ser Ile Pro Thr Pro Ser
        35                  40                  45

Met Arg Glu Glu Thr Gln Gln Lys Ser Asn Leu Glu Leu Leu Arg Ile
    50                  55                  60

Ser Leu Leu Leu Ile Gln Ser Trp Leu Glu Pro Val Gln Phe Leu Arg
65                  70                  75                  80

Ser Val Phe Ala Asn Ser Leu Val Tyr Gly Ala Ser Asp Ser Asn Val
                85                  90                  95

Tyr Asp Leu Leu Lys Asp Leu Glu Glu Gly Ile Gln Thr Leu Met Gly
            100                 105                 110

Arg Leu Glu Asp Gly Ser Pro Arg
        115                 120


<210> SEQ ID NO 2441
<211> LENGTH: 24
<212> TYPE: PRT
<213> ORGANISM: Homo sapiens

<400> SEQUENCE: 2441

Glu Cys Leu Trp Thr Asp Met Leu Ser Asn Phe Gly Tyr Pro Gly Tyr
1               5                   10                  15

Gln Ser Lys His Tyr Ala Cys Ile
            20


<210> SEQ ID NO 2442
<211> LENGTH: 24
<212> TYPE: PRT
<213> ORGANISM: Homo sapiens

<400> SEQUENCE: 2442

Glu Cys Leu Trp Thr Asp Trp Leu Leu Glu Arg Lys Leu Tyr Gly Tyr
1               5                   10                  15
```

Gln Ala Gln His Tyr Val Cys Met
20

<210> SEQ ID NO 2443
<211> LENGTH: 20
<212> TYPE: PRT
<213> ORGANISM: Homo sapiens

<400> SEQUENCE: 2443

Leu Arg Arg Phe Ser Thr Met Pro Phe Met Phe Cys Asn Ile Asn Asn
1 5 10 15

Val Cys Asn Phe
20

<210> SEQ ID NO 2444
<211> LENGTH: 20
<212> TYPE: PRT
<213> ORGANISM: Homo sapiens

<400> SEQUENCE: 2444

Leu Arg Arg Phe Ser Thr Met Pro Phe Met Phe Gly Asn Ile Asn Asn
1 5 10 15

Val Gly Asn Phe
20

<210> SEQ ID NO 2445
<211> LENGTH: 11
<212> TYPE: PRT
<213> ORGANISM: Homo sapiens

<400> SEQUENCE: 2445

Leu Arg Arg Phe Ser Thr Met Pro Phe Met Phe
1 5 10

<210> SEQ ID NO 2446
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu

<400> SEQUENCE: 2446

Leu Arg Arg Phe Ser Thr Met Pro Phe Met Phe Xaa Asn Ile Asn Val
1 5 10 15

<210> SEQ ID NO 2447
<211> LENGTH: 12
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu

<400> SEQUENCE: 2447

Leu Arg Arg Phe Ser Thr Met Pro Phe Met Phe Xaa
1 5 10

<210> SEQ ID NO 2448
<211> LENGTH: 8
<212> TYPE: PRT
<213> ORGANISM: Homo sapiens

<400> SEQUENCE: 2448

Leu Arg Arg Phe Ser Thr Met Pro
1 5

<210> SEQ ID NO 2449
<211> LENGTH: 8
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Abu

<400> SEQUENCE: 2449

Asn Ile Asn Asn Val Xaa Asn Phe
1 5

<210> SEQ ID NO 2450
<211> LENGTH: 12
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Abu
<220> FEATURE:
<221> NAME/KEY: MOD_RES
<222> LOCATION: (10)..(10)
<223> OTHER INFORMATION: Abu

<400> SEQUENCE: 2450

Phe Met Phe Xaa Asn Ile Asn Asn Val Xaa Asn Phe
1 5 10

<210> SEQ ID NO 2451
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Abu
<220> FEATURE:
<221> NAME/KEY: MOD_RES
<222> LOCATION: (14)..(14)
<223> OTHER INFORMATION: Abu

<400> SEQUENCE: 2451

Ser Thr Met Pro Phe Met Phe Xaa Asn Ile Asn Asn Val Xaa Asn Phe
1 5 10 15

<210> SEQ ID NO 2452
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2452

Leu Arg Arg Phe Ser Thr Met Pro Phe Met Phe Xaa Asn Ile Asn Asn
1 5 10 15

Val Xaa Asn Phe
20

<210> SEQ ID NO 2453
<211> LENGTH: 9
<212> TYPE: PRT
<213> ORGANISM: Homo sapiens

<400> SEQUENCE: 2453

Leu Asn Arg Phe Ser Thr Met Pro Phe
1 5

<210> SEQ ID NO 2454
<211> LENGTH: 11
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (10)..(10)
<223> OTHER INFORMATION: Nle

<400> SEQUENCE: 2454

Leu Arg Arg Phe Ser Thr Leu Pro Phe Leu Phe
1 5 10

<210> SEQ ID NO 2455
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2455

Leu Arg Arg Phe Ser Thr Met Pro Ala Met Phe Xaa Asn Ile Asn Asn
1 5 10 15

Val Xaa Asn Phe
20

<210> SEQ ID NO 2456
<211> LENGTH: 20
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2456

Leu Arg Arg Phe Ser Thr Met Pro Phe Ala Phe Xaa Asn Ile Asn Asn
1 5 10 15

Val Xaa Asn Phe
20

<210> SEQ ID NO 2457
<211> LENGTH: 20
<212> TYPE: PRT

<213> ORGANISM: Homo sapiens
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2457

Leu Arg Arg Phe Ser Thr Met Pro Phe Met Ala Xaa Asn Ile Asn Asn
1 5 10 15

Val Xaa Asn Phe
20

<210> SEQ ID NO 2458
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Nle
<220> FEATURE:
<221> NAME/KEY: MOD_RES
<222> LOCATION: (12)..(12)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2458

Leu Arg Arg Phe Ser Thr Met Pro Phe Leu Phe Xaa Asn Ile Asn Asn
1 5 10 15

Val Xaa Asn Phe
20

<210> SEQ ID NO 2459
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Met(4-ClPhen)
<220> FEATURE:
<221> NAME/KEY: MOD_RES
<222> LOCATION: (11)..(11)
<223> OTHER INFORMATION: Abu
<220> FEATURE:
<221> NAME/KEY: MOD_RES
<222> LOCATION: (18)..(18)
<223> OTHER INFORMATION: Abu

<400> SEQUENCE: 2459

Leu Arg Arg Phe Ser Thr Met Pro Phe Met Xaa Cys Asn Ile Asn Asn
1 5 10 15

Val Xaa Asn Phe
20

<210> SEQ ID NO 2460
<211> LENGTH: 9
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Abu
<220> FEATURE:
<221> NAME/KEY: MOD_RES
<222> LOCATION: (8)..(8)
<223> OTHER INFORMATION: Abu

<400> SEQUENCE: 2460

Phe Xaa Asn Ile Asn Asn Val Xaa Asn
1               5

<210> SEQ ID NO 2461
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Abu

<400> SEQUENCE: 2461

Phe Xaa Asn Ile Asn
1               5

<210> SEQ ID NO 2462
<211> LENGTH: 20
<212> TYPE: PRT
<213> ORGANISM: Homo sapiens

<400> SEQUENCE: 2462

Leu Arg Arg Phe Ser Thr Met Pro Phe Met Phe Ser Asn Ile Asn Asn
1               5                   10                  15

Val Ser Asn Phe
            20

<210> SEQ ID NO 2463
<211> LENGTH: 20
<212> TYPE: PRT
<213> ORGANISM: Homo sapiens

<400> SEQUENCE: 2463

Leu Arg Arg Phe Ser Thr Met Pro Phe Met Phe Ala Asn Ile Asn Asn
1               5                   10                  15

Val Ala Asn Phe
            20

<210> SEQ ID NO 2464
<211> LENGTH: 20
<212> TYPE: PRT
<213> ORGANISM: Homo sapiens

<400> SEQUENCE: 2464

Leu Arg Arg Phe Ser Thr Met Pro Phe Met Phe Ile Asn Ile Asn Asn
1               5                   10                  15

Val Ile Asn Phe
            20

<210> SEQ ID NO 2465
<211> LENGTH: 20
<212> TYPE: PRT
<213> ORGANISM: Homo sapiens

<400> SEQUENCE: 2465

Leu Arg Arg Phe Ser Thr Met Pro Phe Met Phe Thr Asn Ile Asn Asn
1 5 10 15

Val Thr Asn Phe
20

<210> SEQ ID NO 2466
<211> LENGTH: 21
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: AllyGly
<220> FEATURE:
<221> NAME/KEY: MOD_RES
<222> LOCATION: (19)..(19)
<223> OTHER INFORMATION: AllyGly

<400> SEQUENCE: 2466

Leu Arg Arg Phe Ser Thr Met Pro Phe Met Phe Cys Gly Asn Ile Asn
1 5 10 15

Asn Val Gly Asn Phe
20

<210> SEQ ID NO 2467
<211> LENGTH: 20
<212> TYPE: PRT
<213> ORGANISM: Homo sapiens

<400> SEQUENCE: 2467

Leu Arg Arg Phe Ser Thr Met Pro Phe Met Phe Val Asn Ile Asn Asn
1 5 10 15

Val Val Asn Phe
20

<210> SEQ ID NO 2468
<211> LENGTH: 16
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: Abu

<400> SEQUENCE: 2468

Leu Arg Arg Phe Ser Thr Met Pro Phe Met Phe Xaa Asn Ile Asn Asn
1 5 10 15

<210> SEQ ID NO 2469
<211> LENGTH: 16
<212> TYPE: PRT
<213> ORGANISM: Homo sapiens

<400> SEQUENCE: 2469

Leu Arg Arg Phe Ser Thr Met Pro Phe Met Phe Thr Asn Ile Asn Val
1 5 10 15

<210> SEQ ID NO 2470
<211> LENGTH: 6
<212> TYPE: PRT
<213> ORGANISM: Homo sapiens
<220> FEATURE:
<221> NAME/KEY: MOD_RES
<222> LOCATION: (2)..(2)

<223> OTHER INFORMATION: Abu

<400> SEQUENCE: 2470

Phe Xaa Asn Ile Asn Val
1 5

<210> SEQ ID NO 2471
<211> LENGTH: 9
<212> TYPE: PRT
<213> ORGANISM: Homo sapiens

<400> SEQUENCE: 2471

Phe Thr Asn Ile Asn Asn Val Thr Asn
1 5

<210> SEQ ID NO 2472
<211> LENGTH: 16
<212> TYPE: PRT
<213> ORGANISM: Homo sapiens

<400> SEQUENCE: 2472

Leu Arg Arg Phe Ser Thr Met Pro Phe Met Phe Thr Asn Ile Asn Asn
1 5 10 15

<210> SEQ ID NO 2473
<211> LENGTH: 16
<212> TYPE: PRT
<213> ORGANISM: Homo sapiens

<400> SEQUENCE: 2473

Leu Arg Arg Phe Ser Thr Met Pro Phe Met Phe Ile Asn Ile Asn Asn
1 5 10 15

<210> SEQ ID NO 2474
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: D-Ala

<400> SEQUENCE: 2474

Leu Arg Arg Phe Ser Thr Met Pro Phe Ala Phe Ile Asn Ile Asn Asn
1 5 10 15

Val Ile Asn Phe
20

<210> SEQ ID NO 2475
<211> LENGTH: 20
<212> TYPE: PRT
<213> ORGANISM: Homo sapiens

<400> SEQUENCE: 2475

Leu Arg Arg Phe Ser Thr Ala Pro Phe Ala Phe Ile Asn Ile Asn Asn
1 5 10 15

Val Ile Asn Phe
20

<210> SEQ ID NO 2476
<211> LENGTH: 20
<212> TYPE: PRT
<213> ORGANISM: Homo sapiens

<400> SEQUENCE: 2476

Leu Arg Arg Phe Ser Thr Met Pro Phe Ala Phe Ile Asn Ile Asn Asn
1 5 10 15

Val Ile Asn Phe
20

<210> SEQ ID NO 2477
<211> LENGTH: 12
<212> TYPE: PRT
<213> ORGANISM: Homo sapiens

<400> SEQUENCE: 2477

Arg Leu Arg Leu Leu Thr Leu Gln Ser Trp Leu Leu
1 5 10

<210> SEQ ID NO 2478
<211> LENGTH: 13
<212> TYPE: PRT
<213> ORGANISM: Homo sapiens

<400> SEQUENCE: 2478

Leu Met Arg Lys Ser Gln Ile Leu Ile Ser Ser Trp Phe
1 5 10

<210> SEQ ID NO 2479
<211> LENGTH: 13
<212> TYPE: PRT
<213> ORGANISM: Homo sapiens

<400> SEQUENCE: 2479

Leu Leu Ile Val Ala Leu Leu Phe Ile Leu Ser Trp Leu
1 5 10

<210> SEQ ID NO 2480
<211> LENGTH: 13
<212> TYPE: PRT
<213> ORGANISM: Homo sapiens

<400> SEQUENCE: 2480

Leu Leu Arg Leu Leu Leu Leu Ile Glu Ser Trp Leu Glu
1 5 10

<210> SEQ ID NO 2481
<211> LENGTH: 14
<212> TYPE: PRT
<213> ORGANISM: Homo sapiens

<400> SEQUENCE: 2481

Leu Leu Arg Ser Ser Leu Ile Leu Leu Gln Gly Ser Trp Phe
1 5 10

<210> SEQ ID NO 2482
<211> LENGTH: 14
<212> TYPE: PRT
<213> ORGANISM: Homo sapiens

<400> SEQUENCE: 2482

Leu Leu His Ile Ser Leu Leu Leu Ile Glu Ser Arg Leu Glu
1 5 10

<210> SEQ ID NO 2483
<211> LENGTH: 14
<212> TYPE: PRT

<213> ORGANISM: Homo sapiens

<400> SEQUENCE: 2483

Leu Leu Arg Ile Ser Leu Leu Leu Ile Glu Ser Trp Leu Glu
1 5 10

<210> SEQ ID NO 2484
<211> LENGTH: 4
<212> TYPE: PRT
<213> ORGANISM: Homo sapiens

<400> SEQUENCE: 2484

Asp Glu Ala His
1

<210> SEQ ID NO 2485
<211> LENGTH: 11
<212> TYPE: PRT
<213> ORGANISM: Homo sapiens

<400> SEQUENCE: 2485

Glu Ile Glu Leu Val Glu Glu Glu Pro Pro Phe
1 5 10

<210> SEQ ID NO 2486
<211> LENGTH: 11
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(10)
<223> OTHER INFORMATION: Any amino acid

<400> SEQUENCE: 2486

Trp Xaa Xaa Cys Xaa Xaa Xaa Cys Xaa Xaa Gly
1 5 10

<210> SEQ ID NO 2487
<211> LENGTH: 7
<212> TYPE: PRT
<213> ORGANISM: Homo sapiens
<220> FEATURE:
<221> NAME/KEY: MOD_RES
<222> LOCATION: (3)..(5)
<223> OTHER INFORMATION: Any amino acid

<400> SEQUENCE: 2487

Cys Asn Xaa Xaa Xaa Val Cys
1 5

<210> SEQ ID NO 2488
<211> LENGTH: 12
<212> TYPE: PRT
<213> ORGANISM: Homo sapiens
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(9)

<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 2488

Leu Xaa Xaa Xaa Leu Leu Xaa Xaa Xaa Ser Xaa Leu
1 5 10

<210> SEQ ID NO 2489
<211> LENGTH: 7
<212> TYPE: PRT
<213> ORGANISM: Homo sapiens
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 2489

Leu Xaa Xaa Glu Glu Xaa Pro
1 5

<210> SEQ ID NO 2490
<211> LENGTH: 14
<212> TYPE: PRT
<213> ORGANISM: Homo sapiens

<400> SEQUENCE: 2490

Leu Leu Arg Ile Ser Leu Leu Leu Thr Gln Ser Trp Leu Glu
1 5 10

<210> SEQ ID NO 2491
<211> LENGTH: 14
<212> TYPE: PRT
<213> ORGANISM: Homo sapiens

<400> SEQUENCE: 2491

Leu Leu His Ile Ser Leu Leu Leu Ile Gln Ser Trp Leu Glu
1 5 10

<210> SEQ ID NO 2492
<211> LENGTH: 11
<212> TYPE: PRT
<213> ORGANISM: Homo sapiens

<400> SEQUENCE: 2492

Ala Glu Asp Leu Leu Ser Glu Glu Asp Pro Phe
1 5 10

<210> SEQ ID NO 2493
<211> LENGTH: 11
<212> TYPE: PRT
<213> ORGANISM: Homo sapiens

<400> SEQUENCE: 2493

Thr Leu Asp Leu Ile Gln Glu Glu Asp Pro Ser
1 5 10

<210> SEQ ID NO 2494
<211> LENGTH: 20
<212> TYPE: PRT
<213> ORGANISM: Homo sapiens

<400> SEQUENCE: 2494

Leu Pro Arg Phe Ser Thr Met Pro Phe Ile Tyr Cys Asn Ile Asn Glu
1               5                   10                  15

Val Cys His Tyr
            20

<210> SEQ ID NO 2495
<211> LENGTH: 20
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Ser, Thr, Gly, Gln, or Ala
<220> FEATURE:
<221> NAME/KEY: MOD_RES
<222> LOCATION: (2)..(2)
<223> OTHER INFORMATION: Pro, Glu, Ser, Ala, Gln, or Lys
<220> FEATURE:
<221> NAME/KEY: MOD_RES
<222> LOCATION: (4)..(4)
<223> OTHER INFORMATION: Ser, Thr, Gly, Glu, Asp, Arg, or Ala
<220> FEATURE:
<221> NAME/KEY: MOD_RES
<222> LOCATION: (5)..(5)
<223> OTHER INFORMATION: Pro, Ala, Gln, Asp, Glu, Lys, Arg, or Val
<220> FEATURE:
<221> NAME/KEY: MOD_RES
<222> LOCATION: (7)..(7)
<223> OTHER INFORMATION: Ser, Asn, or Thr
<220> FEATURE:
<221> NAME/KEY: MOD_RES
<222> LOCATION: (8)..(8)
<223> OTHER INFORMATION: Val, Ala, Arg, Lys, Gly, Ser, Thr, or Glu
<220> FEATURE:
<221> NAME/KEY: MOD_RES
<222> LOCATION: (9)..(9)
<223> OTHER INFORMATION: Thr, Ser, Arg, or Asn
<220> FEATURE:
<221> NAME/KEY: MOD_RES
<222> LOCATION: (11)..(11)
<223> OTHER INFORMATION: Gly, Ser, or Asn
<220> FEATURE:
<221> NAME/KEY: MOD_RES
<222> LOCATION: (12)..(12)
<223> OTHER INFORMATION: Gly, Lys, Arg, Met, Thr, Leu, Asp, Ser, or Pro
<220> FEATURE:
<221> NAME/KEY: MOD_RES
<222> LOCATION: (14)..(14)
<223> OTHER INFORMATION: Val, Ile, Met, Thr, His, Ala, Glu, Phe, Lys,
      Arg, Ser, Gln, Trp, or Tyr
<220> FEATURE:
<221> NAME/KEY: MOD_RES
<222> LOCATION: (15)..(15)
<223> OTHER INFORMATION: Gln, Ser, Arg, Lys, Tyr, or ala
<220> FEATURE:
<221> NAME/KEY: MOD_RES
<222> LOCATION: (16)..(16)
<223> OTHER INFORMATION: Thr, Phe, Lys, Gln, Ser, Leu, Glu, Met, Asn, or
      Val
<220> FEATURE:
<221> NAME/KEY: MOD_RES
<222> LOCATION: (17)..(17)
<223> OTHER INFORMATION: Arg, Ser, or Gln
<220> FEATURE:
<221> NAME/KEY: MOD_RES
<222> LOCATION: (18)..(18)
<223> OTHER INFORMATION: Ser, Thr, Val, Arg, His, Glu, Gln, Ala, or Ile
<220> FEATURE:
<221> NAME/KEY: MOD_RES
<222> LOCATION: (19)..(19)
<223> OTHER INFORMATION: Arg or Val

<400> SEQUENCE: 2495

Xaa Xaa Trp Xaa Xaa Cys Xaa Xaa Xaa Cys Xaa Xaa Gly Xaa Xaa Xaa
1 5 10 15

Xaa Xaa Xaa Arg
20

<210> SEQ ID NO 2496
<211> LENGTH: 22
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(4)
<223> OTHER INFORMATION: Lys, Glu, or Gln
<220> FEATURE:
<221> NAME/KEY: MOD_RES
<222> LOCATION: (5)..(5)
<223> OTHER INFORMATION: Ala, Ile, Leu, or Val
<220> FEATURE:
<221> NAME/KEY: MOD_RES
<222> LOCATION: (8)..(8)
<223> OTHER INFORMATION: Asp or Asn
<220> FEATURE:
<221> NAME/KEY: MOD_RES
<222> LOCATION: (10)..(10)
<223> OTHER INFORMATION: Ala, Glu, Asp, or Lys
<220> FEATURE:
<221> NAME/KEY: MOD_RES
<222> LOCATION: (11)..(11)
<223> OTHER INFORMATION: Ala, Ser, or Glu
<220> FEATURE:
<221> NAME/KEY: MOD_RES
<222> LOCATION: (13)..(13)
<223> OTHER INFORMATION: Phe, Ile, Met, Arg, or Trp
<220> FEATURE:
<221> NAME/KEY: MOD_RES
<222> LOCATION: (14)..(14)
<223> OTHER INFORMATION: Val, Leu, or Ile
<220> FEATURE:
<221> NAME/KEY: MOD_RES
<222> LOCATION: (15)..(15)
<223> OTHER INFORMATION: Lys or Gln
<220> FEATURE:
<221> NAME/KEY: MOD_RES
<222> LOCATION: (16)..(16)
<223> OTHER INFORMATION: Lys or Arg
<220> FEATURE:
<221> NAME/KEY: MOD_RES
<222> LOCATION: (17)..(18)
<223> OTHER INFORMATION: Ile or Val
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (21)..(21)
<223> OTHER INFORMATION: Ile, Phe, Lys, Met

<400> SEQUENCE: 2496

Xaa Gly Xaa Xaa Xaa Cys Leu Xaa Pro Xaa Xaa Pro Xaa Xaa Xaa Xaa
1 5 10 15

Xaa Xaa Xaa Lys Xaa Leu
20

-continued

<210> SEQ ID NO 2497
<211> LENGTH: 10
<212> TYPE: PRT
<213> ORGANISM: Homo sapiens

<400> SEQUENCE: 2497

```
Lys Cys His Gly His Gly Val Cys Asn Ser
1               5                   10
```

PEPTIDE/PARTICLE DELIVERY SYSTEMS

CROSS-REFERENCE TO RELATED APPLICATIONS

This application is a continuation of U.S. patent application Ser. No. 16/860,773, filed Apr. 28, 2020, which is a continuation of U.S. patent application Ser. No. 15/645,337, filed Jul. 10, 2017 and issued Sep. 29, 2020 as U.S. Pat. No. 10,786,463, which is a U.S. patent application Ser. No. 13/272,042, filed Oct. 12, 2011 and issued Aug. 1, 2017 as U.S. Pat. No. 9,717,694. U.S. Ser. No. 13/272,042 is a continuation-in-part of and claims priority to PCT Application No. PCT/US2010/035127, filed May 17, 2010. PCT/US2010/035127 claims the benefit of U.S. Provisional Application No. 61/178,611, filed May 15, 2009. U.S. Ser. No. 13/272,042 also claims the benefit of U.S. Provisional Application Nos. 61/392,224, filed Oct. 12, 2010; 61/542,995, filed Oct. 4, 2011; and 61/543,046, filed Oct. 4, 2011. The contents of each of the above-identified applications is incorporated herein by reference in its entirety.

FEDERALLY SPONSORED RESEARCH OR DEVELOPMENT

This invention was made with government support under CA131931 and CA152473 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created a Jan. 14, 2021, is 371,000 bytes in size and is named 39187-308_SEQUENCE_LISTING.

BACKGROUND

Biomaterials have the potential to significantly impact medicine as delivery systems for imaging agents, biosensors, drugs, and genes. Farokhzad O C. Nanotechnology for drug delivery: the perfect partnership. Expert Opin Drug Deliv 2008; 5(9):927-9; Putnam D. Polymers for gene delivery across length scales. Nat Mater 2006; 5(6):439-51; Brigger I, Dubernet C, Couvreur P. Nanoparticles in cancer therapy and diagnosis. Adv Drug Deliv Rev 2002; 54(5): 631-51. Challenges exist, however, in creating a delivery vehicle capable of effective, safe, and controlled release of sensitive biomolecules. Although rapid advances have been made for sustained delivery of small molecule drugs using biotechnology, similar advances have not been made for the delivery of peptides, siRNA, or combinations of biological agents.

SUMMARY

The presently disclosed subject matter provides polymeric nanoparticles, microparticles, and gels for delivering cargo, e.g., a therapeutic agent, such as a peptide, to a target, e.g., a cell, and their use for treating multiple diseases, including angiogenesis-dependent diseases, such as age-related macular degeneration and cancer. Methods for formulating, stabilizing, and administering single peptides or combinations of peptides via polymeric particle and gel delivery systems, for example, using a controlled release strategy, also are disclosed.

In some aspects, the presently disclosed subject matter provides a bioreducible, hydrolytically degradable polymer of formula (Ia):

(Ia)

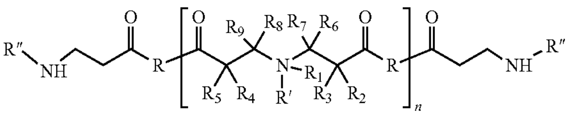

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and wherein at least one R comprises a backbone of a diacrylate having the following structure:

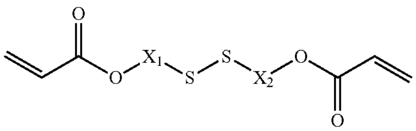

wherein $X_1$ and $X_2$ are each independently substituted or unsubstituted $C_2$-$C_{20}$ alkylene, and wherein each $X_1$ and $X_2$ can be the same or different.

In other aspects, the presently disclosed subject matter provides a nanoparticle, microparticle, or gel comprising a compound of formula (I):

(I)

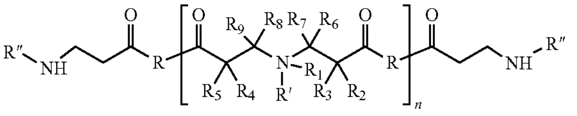

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and at least one of R, R', and R" comprise a reducible or degradable linkage, and wherein each R, R', or R" can independently be the same or different;

under the proviso that when at least one R group comprises an ester linkage of the formula —C(═O)—O— and the compound of formula (I) comprises a poly (beta-amino ester), then the compound of formula (I) must also comprise one or more of the following characteristics:

(a) each R group is different;

(b) each R" group is different;

(c) each R" group is not the same as any of R', $R_1$, $R_2$, $R_3$, $R_4$, $R_5$, $R_6$, $R_7$, $R_8$, and $R_9$;

(d) the R" groups degrade through a different mechanism than the ester-containing R groups, wherein the degradation of the R" group is selected from the group consisting of a bioreducible mechanism or an enzymatically degradable mechanism; and/or (e) the compound of formula (I) comprises a substructure of a larger cross-linked polymer, wherein the larger cross-linked polymer comprises different properties from compound of formula (I);

and one or more peptides selected from the group consisting of an anti-angiogenic peptide, an anti-lymphangiogenic peptide, an anti-tumorigenic peptide, and an anti-permeability peptide.

In other aspects, the presently disclosed subject matter provides a multilayer particle comprising a core and one or more layers, wherein the core comprises a material selected from the group consisting of a compound of formula (I), a gold nanoparticle, an inorganic nanoparticle, an organic polymer, and the one or more layers comprise a material selected from the group consisting of a compound of formula (I), an organic polymer, one or more peptides, and one or more additional biological agents. In yet other aspects, the presently disclosed subject matter provides a microparticle comprising a compound of formula (I), poly(lactide-co-glycolide) (PLGA), or combinations thereof.

In other aspects, the presently disclosed subject matter provides a method for stabilizing a suspension of nanoparticles and/or microparticles of formula (I), the method comprising: (a) providing a suspension of nanoparticles and/or microparticles of formula (I); (b) admixing a lyroprotectant with the suspension; (c) freezing the suspension for a period of time; and (d) lyophilizing the suspension for a period of time.

In further aspects, the presently disclosed subject matter provides a pellet or scaffold comprising one or more lyophilized particle, wherein the one or more lyophilized particle comprises a compound of formula (I).

In yet further aspects, the presently disclosed subject matter provides a method of treating a disease or condition, the method comprising administering to a subject in need of treatment thereof a therapeutically effective amount of a nanoparticle, microparticle, gel, or multilayer particle comprising a compound of formula (I), wherein the nanoparticle, microparticle, gel, or multilayer particle further comprises a therapeutic agent specific for the disease or condition to be treated. In some aspects, the disease or condition comprises an angiogenesis-dependent disease or condition, including, but not limited to, cancer and age-related macular degeneration. In other aspects, the disease or condition is a non-angiogenic disease or condition. In certain aspects, the therapeutic agent encapsulated with the presently disclosed particles can be selected from the group consisting of gene, DNA, RNA, siRNA, miRNA, isRNA, agRNA, smRNA, a nucleic acid, a peptide, a protein, a chemotherapeutic agent, a hydrophobic drug, a small molecule drug, and combinations thereof.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
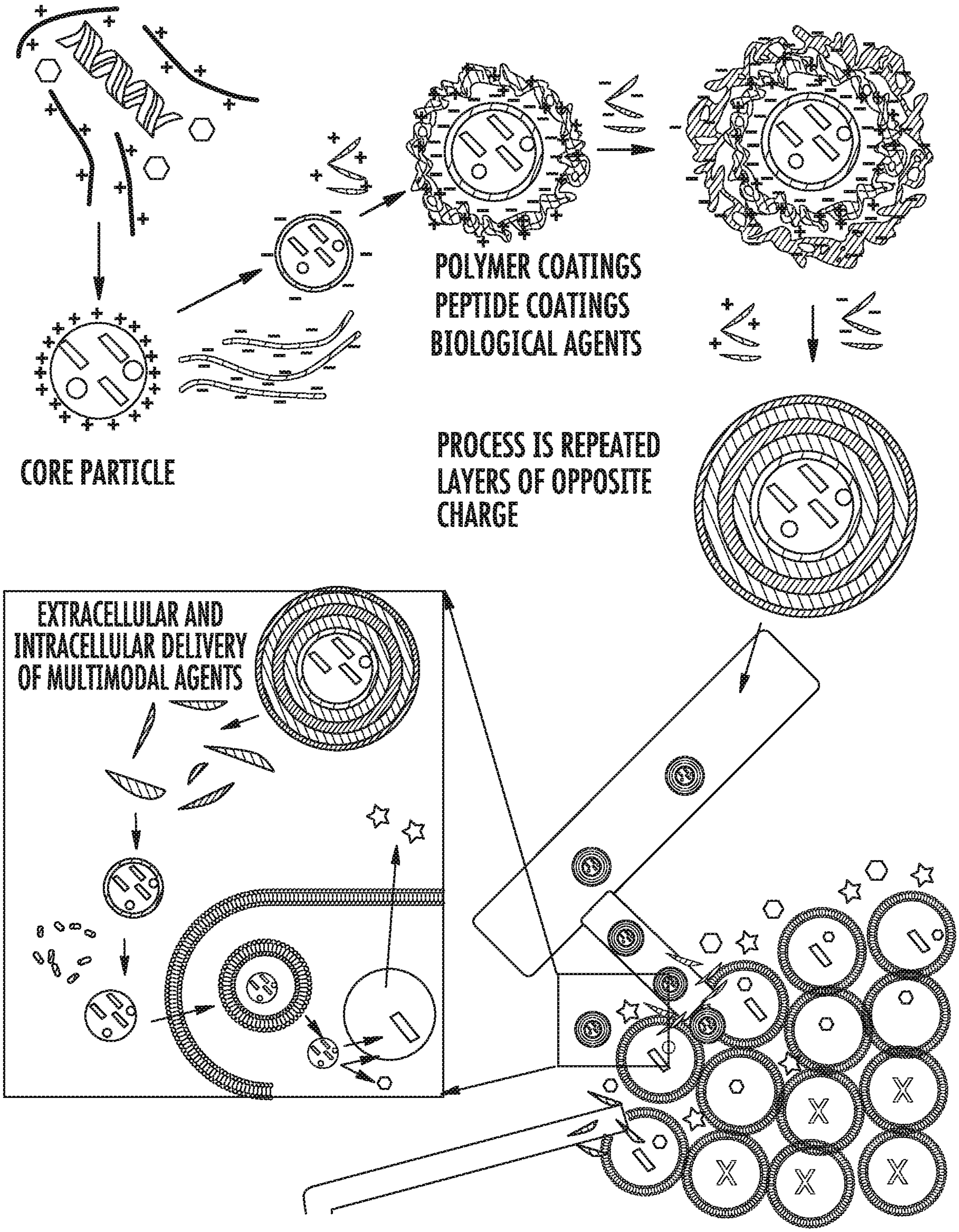
Figure 2:
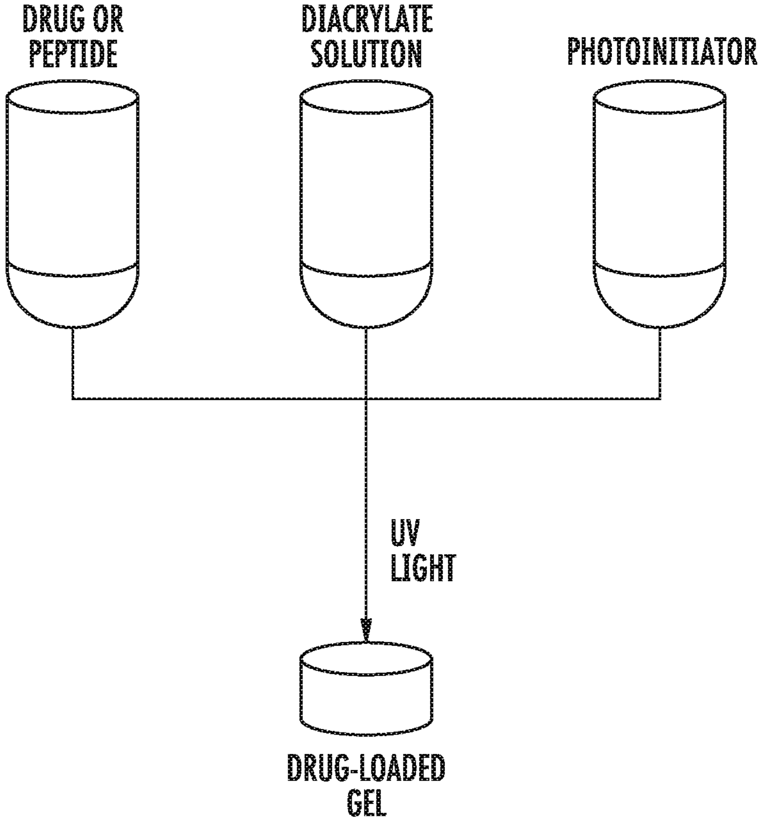

Having thus described the presently disclosed subject matter in general terms, reference will now be made to the accompanying Figures, which are not necessarily drawn to scale, and wherein:

FIG. 1 is an illustration of the presently disclosed multilayer particles;

FIG. 2 is a scheme for producing hydrogels comprising the presently disclosed materials.

Figure 3:
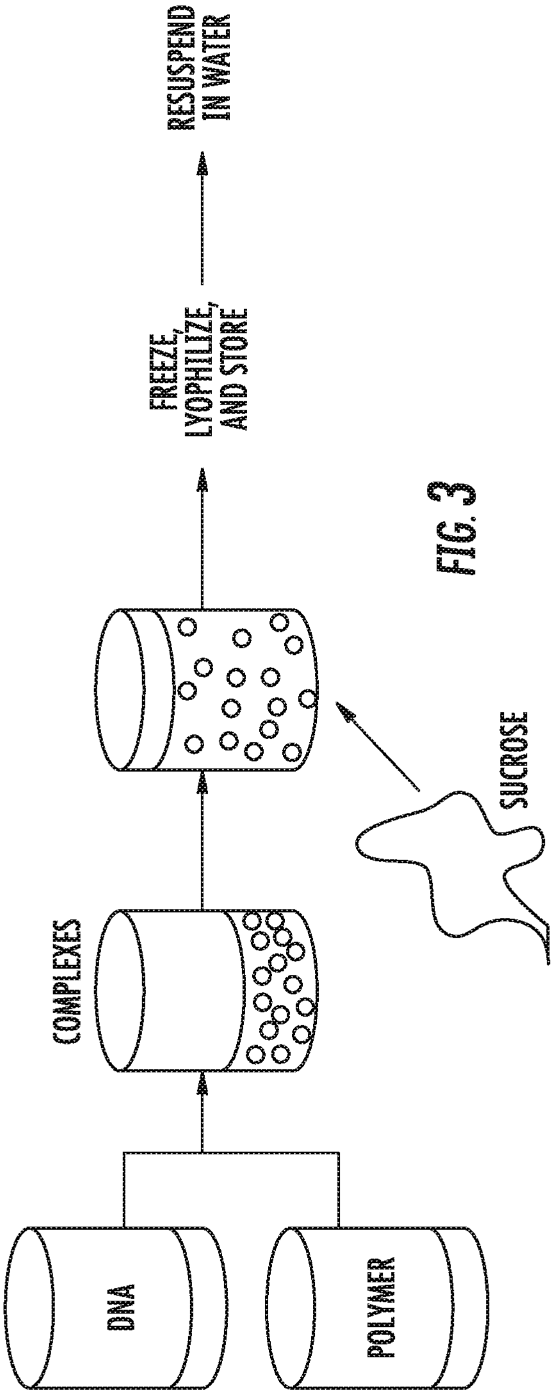
Figure 4B:
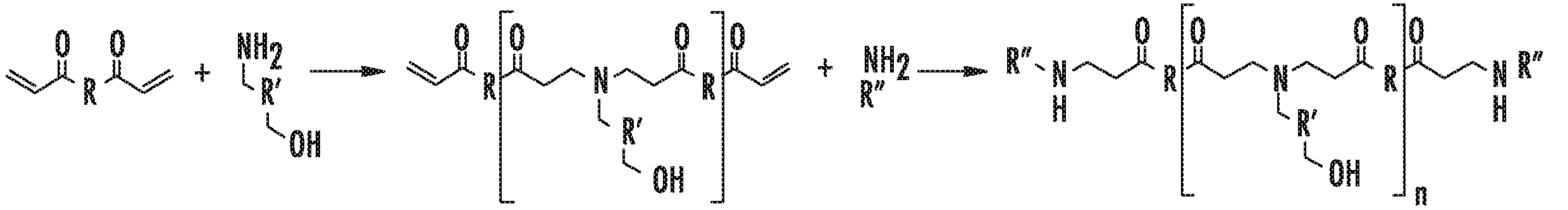
Figure 4B:
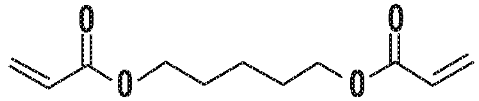
Figure 4B:
Figure 4B:
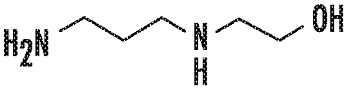
Figure 4B:
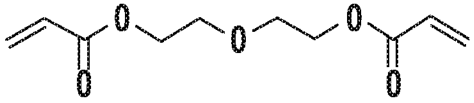
Figure 4B:
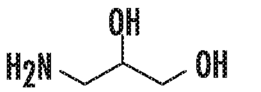
Figure 4B:
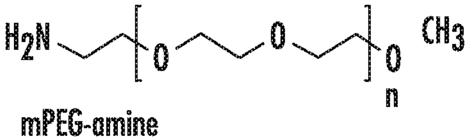
Figure 4B:
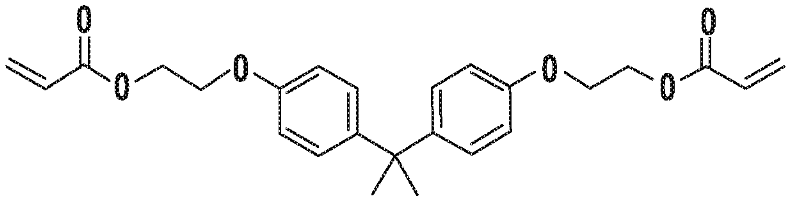
Figure 4B:
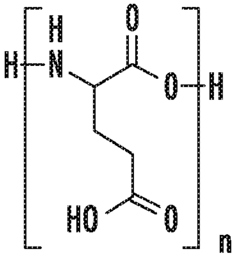
Figure 4C:
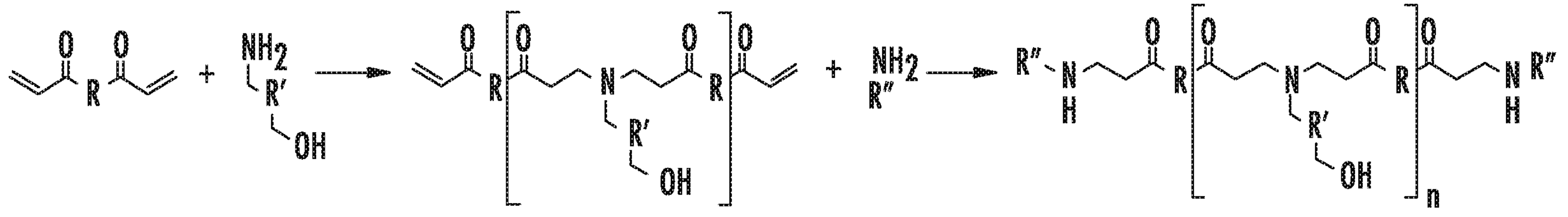
Figure 4C:
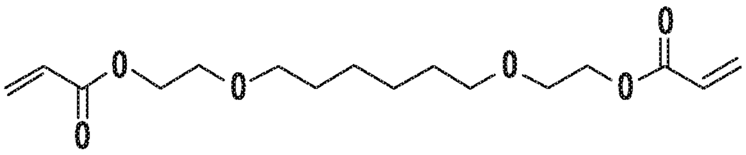
Figure 4C:
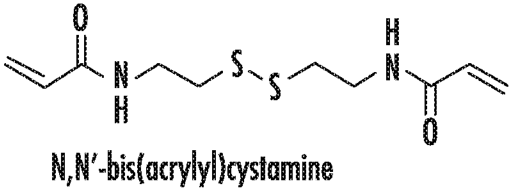
Figure 4C:
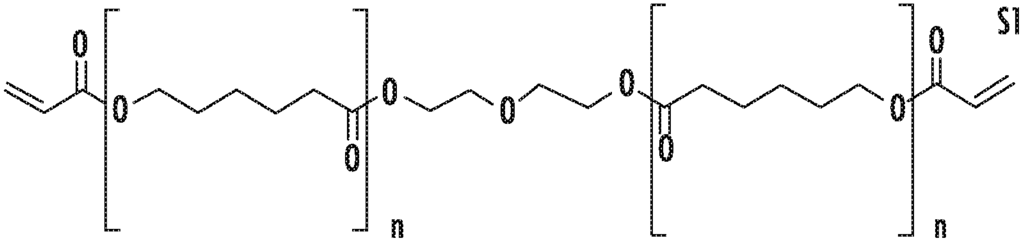
Figure 4C:
Figure 4C:
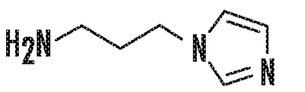
Figure 4C:
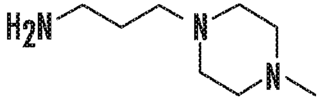
Figure 4C:
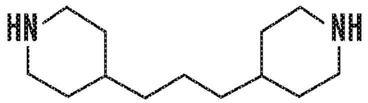
Figure 4C:
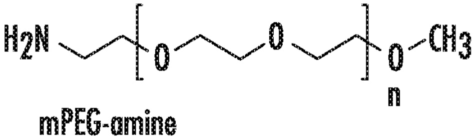
Figure 4D:
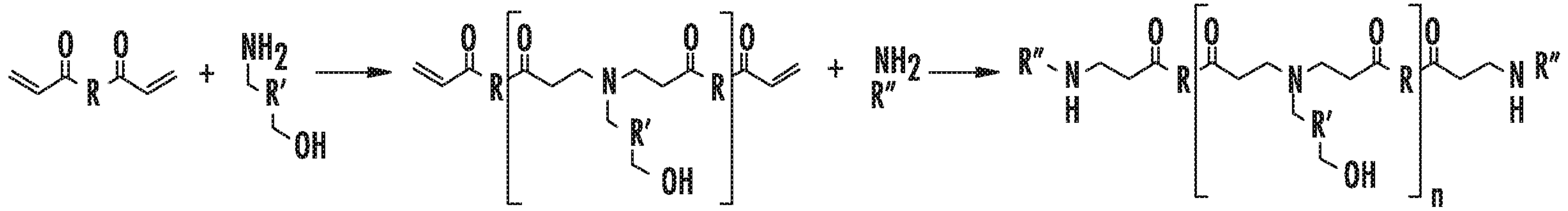
Figure 4D:
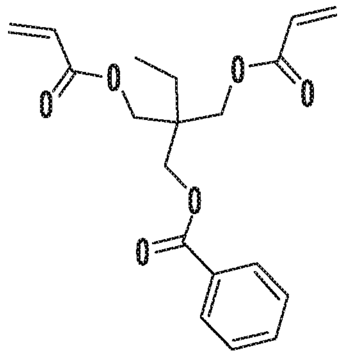
Figure 4D:
Figure 4D:
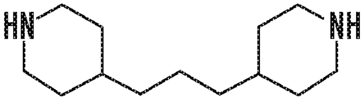
Figure 4D:
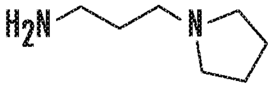
Figure 4D:
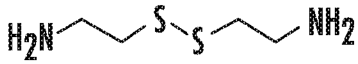
Figure 4D:
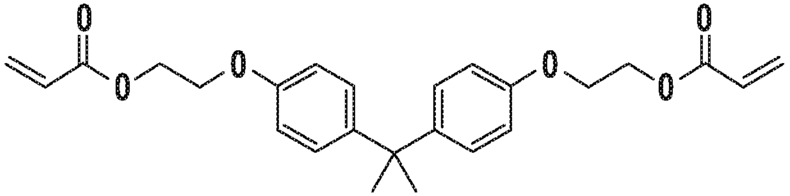
Figure 4D:
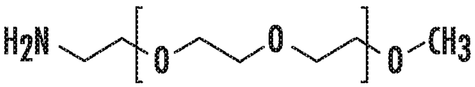
Figure 5A:
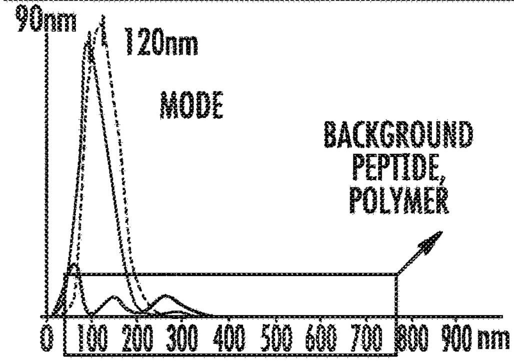
Figure 5A:
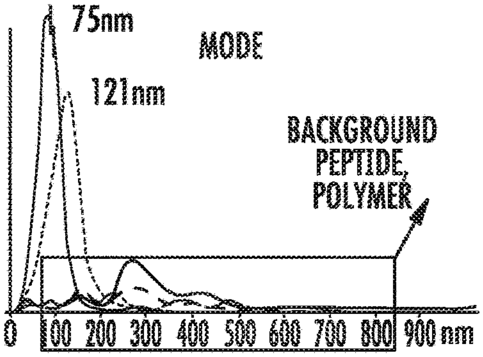
Figure 5B:
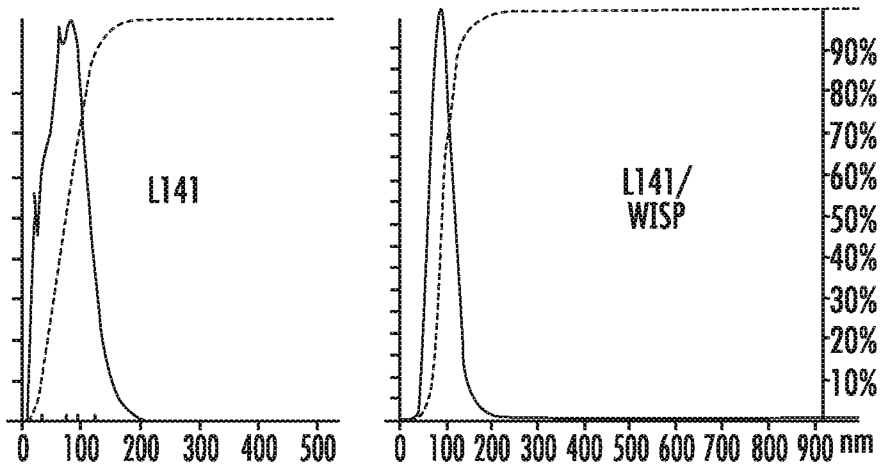
Figure 6:
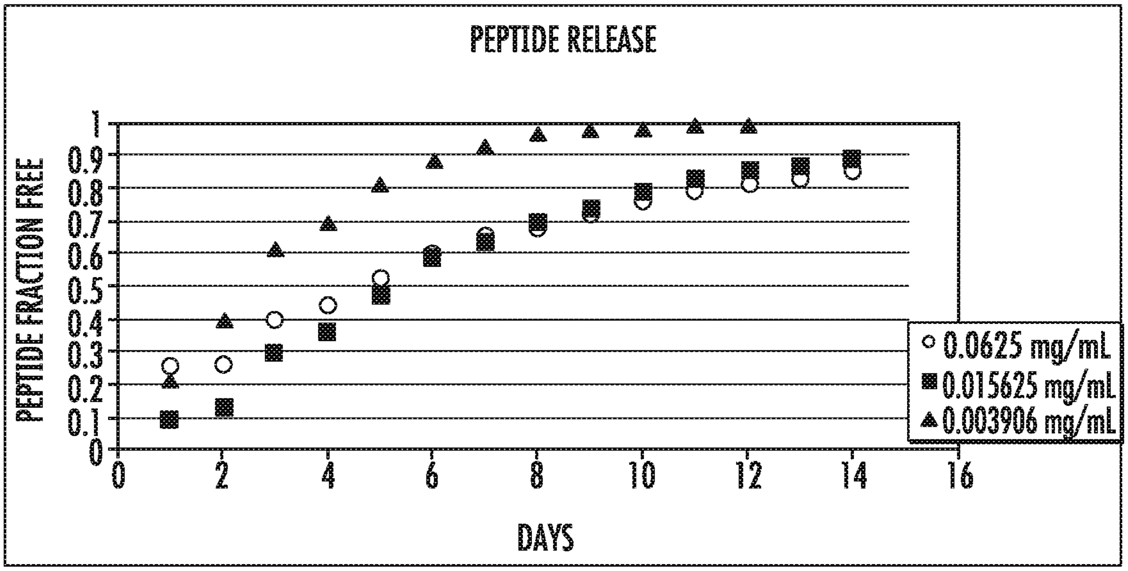
Figure 6:
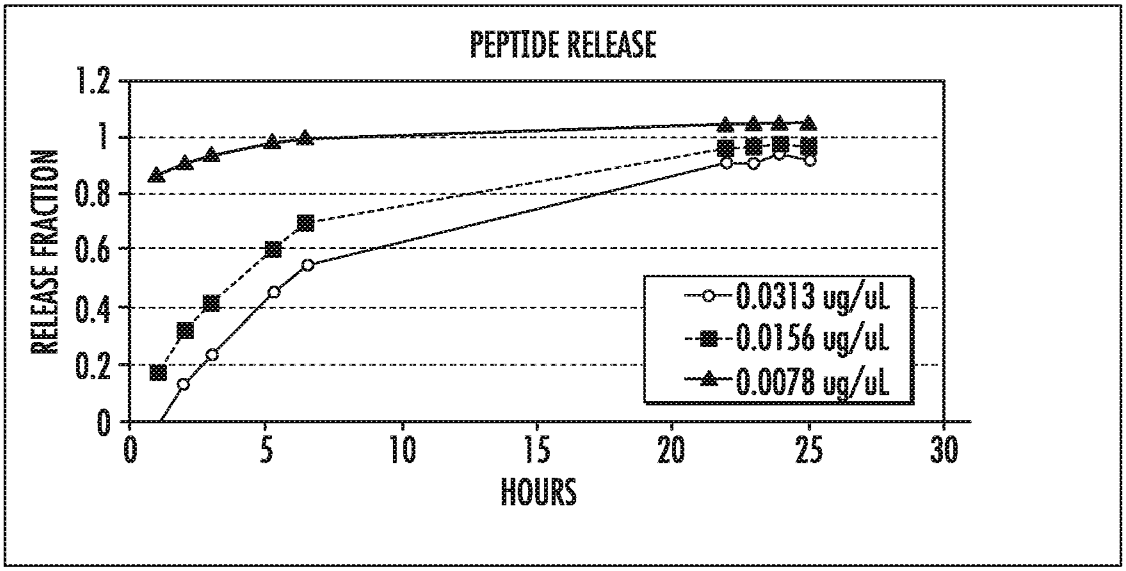
Figure 7:
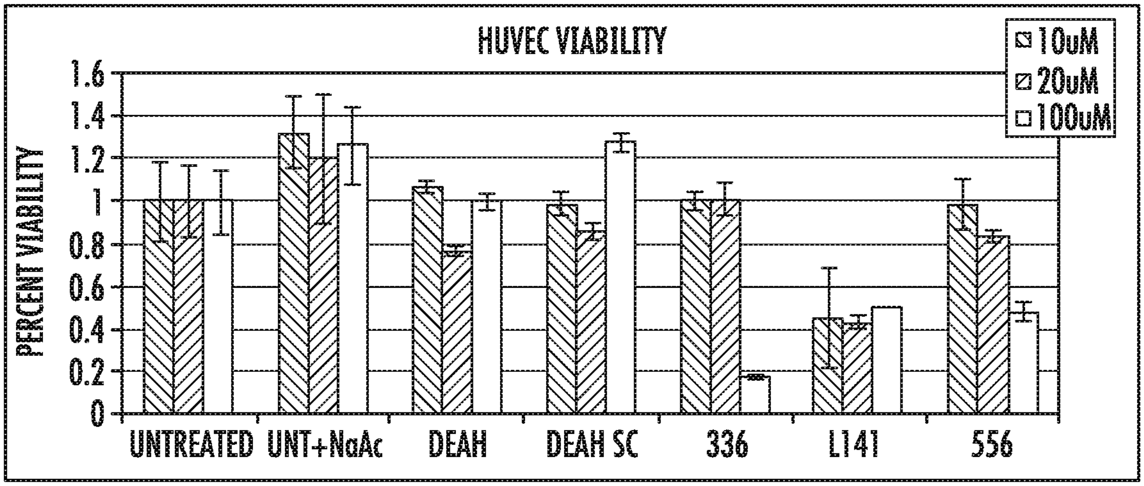
Figure 8:
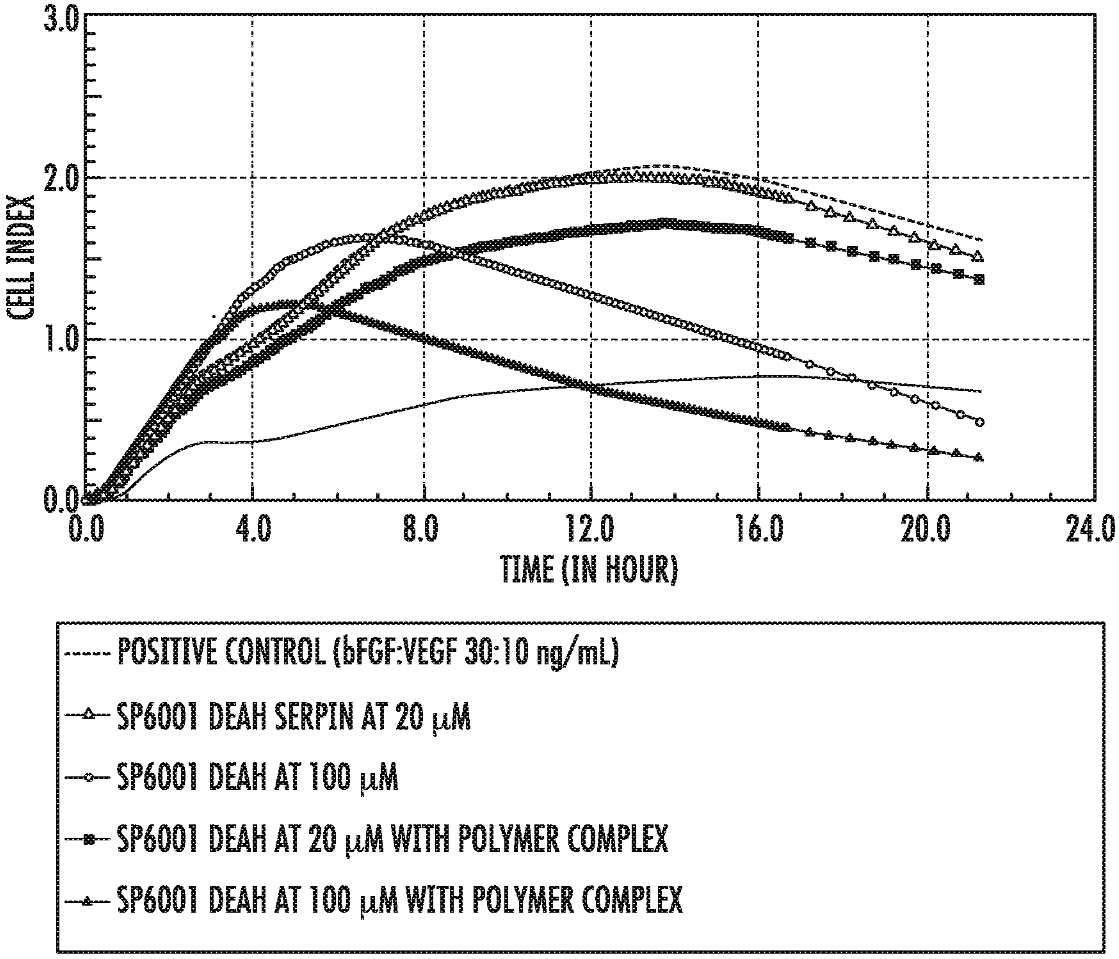
Figure 9:
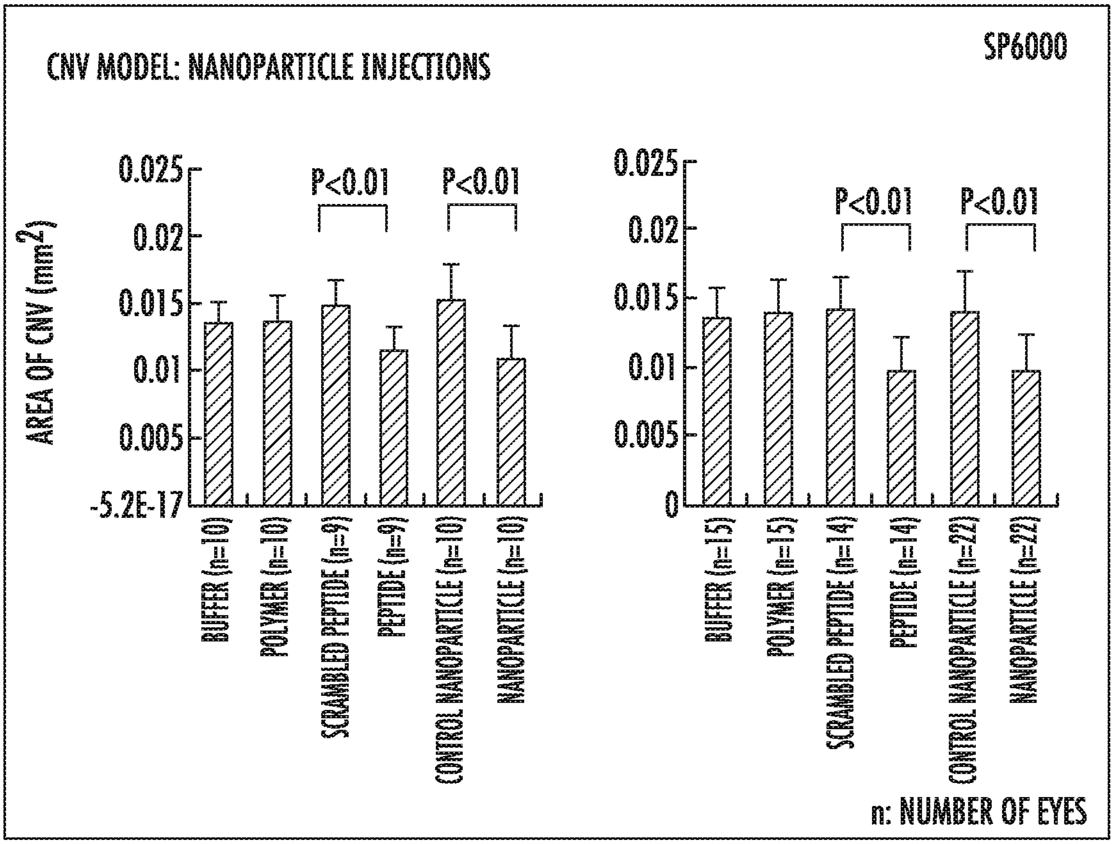
Figure 9:
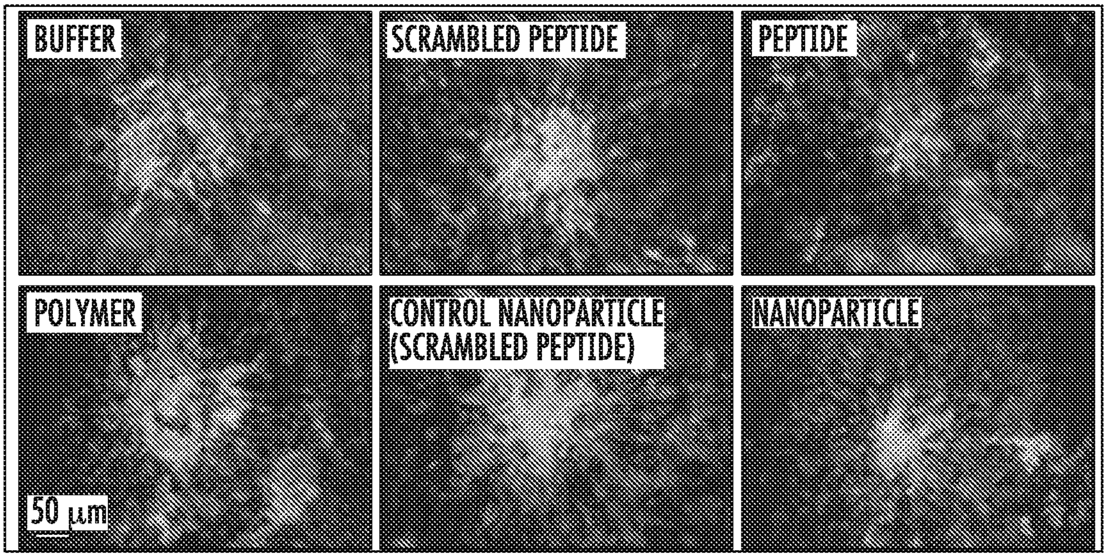
Figure 10:
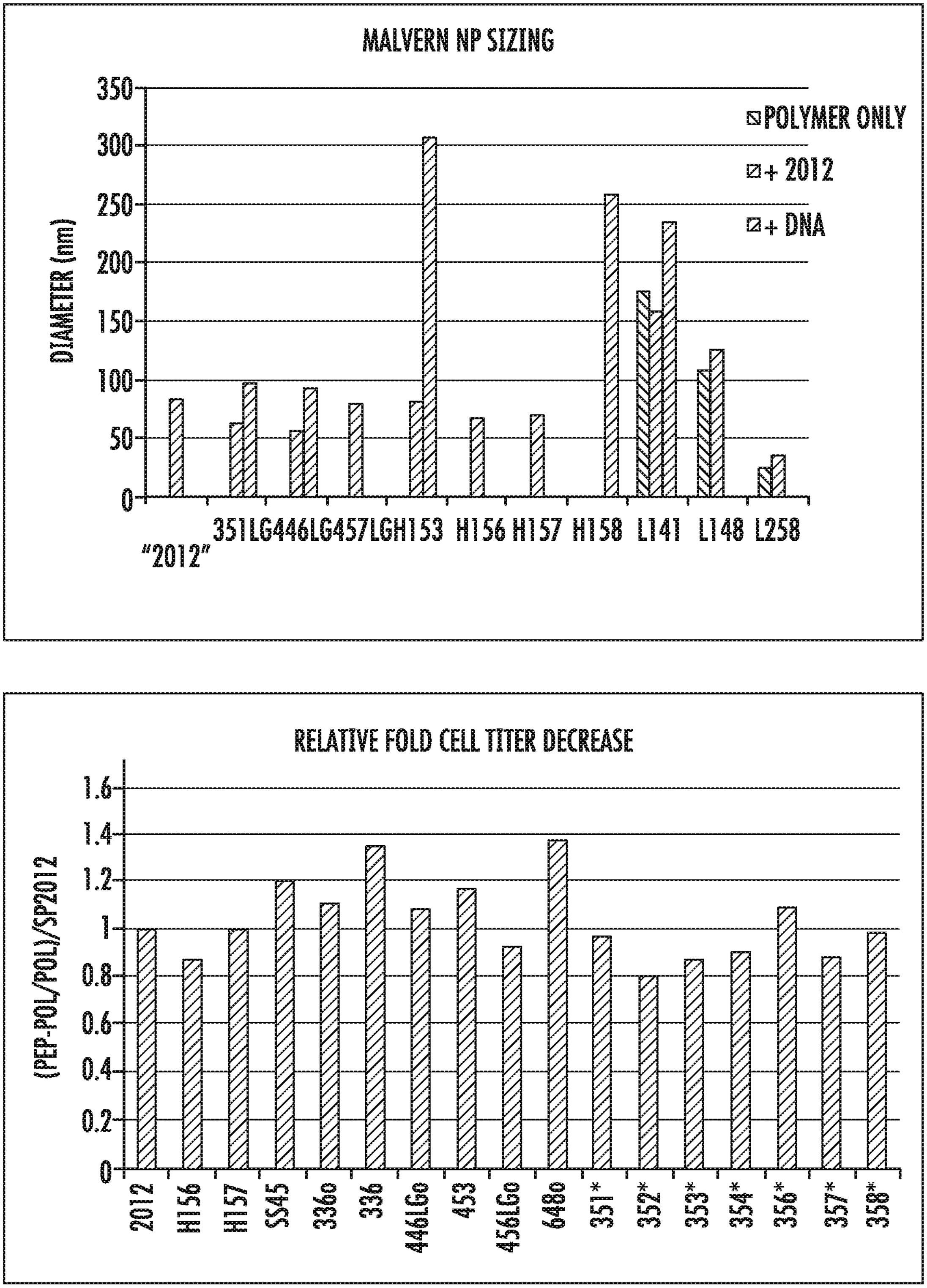
Figure 11:
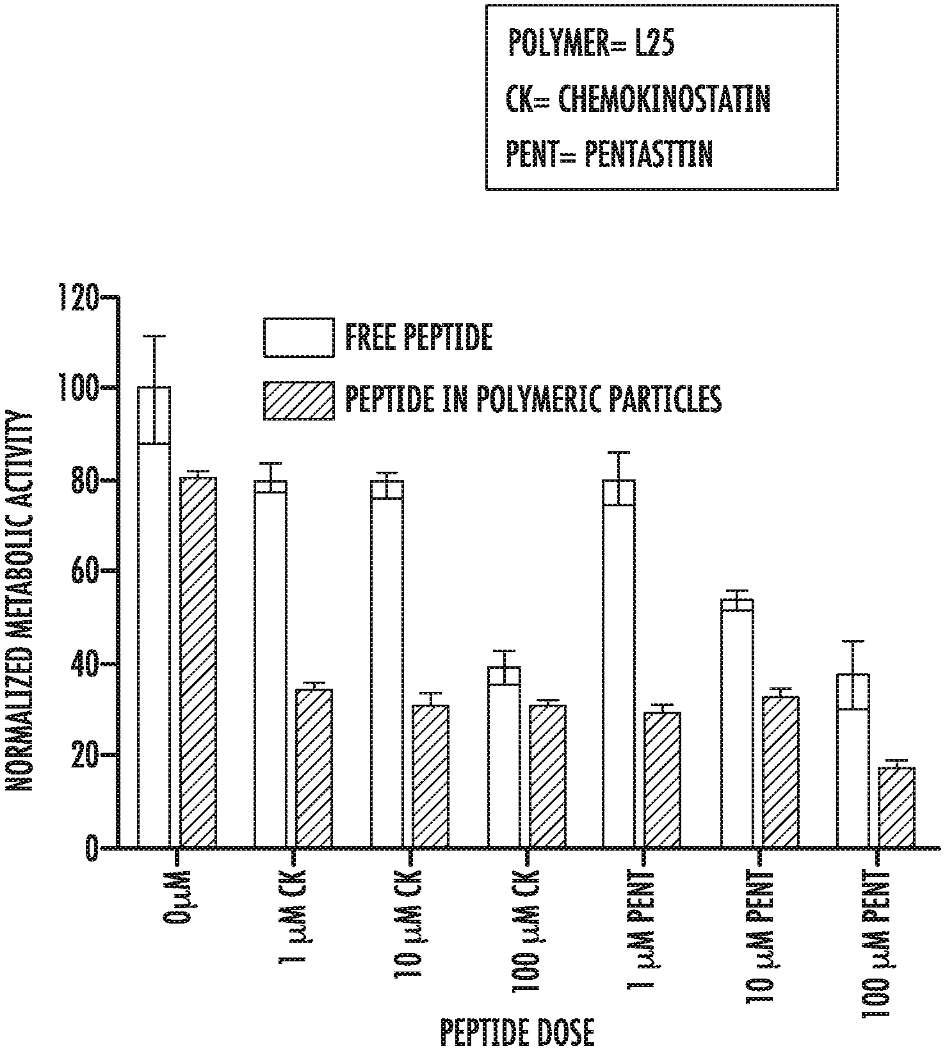
Figure 12:
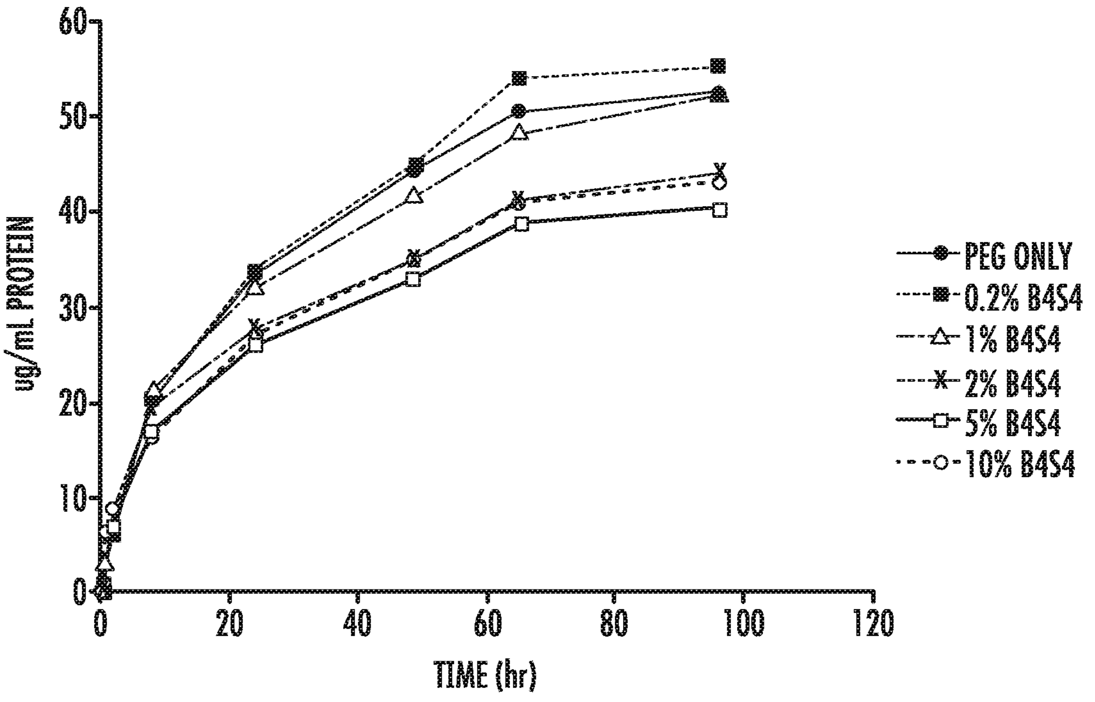
Figure 13:
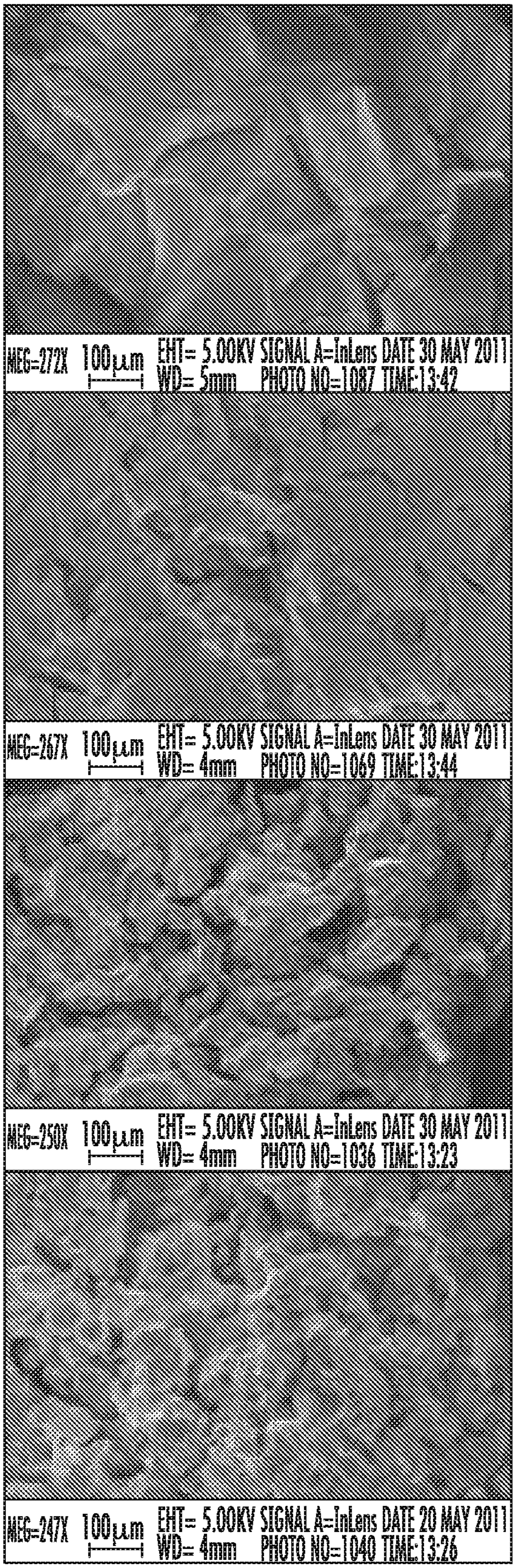
Figure 14:
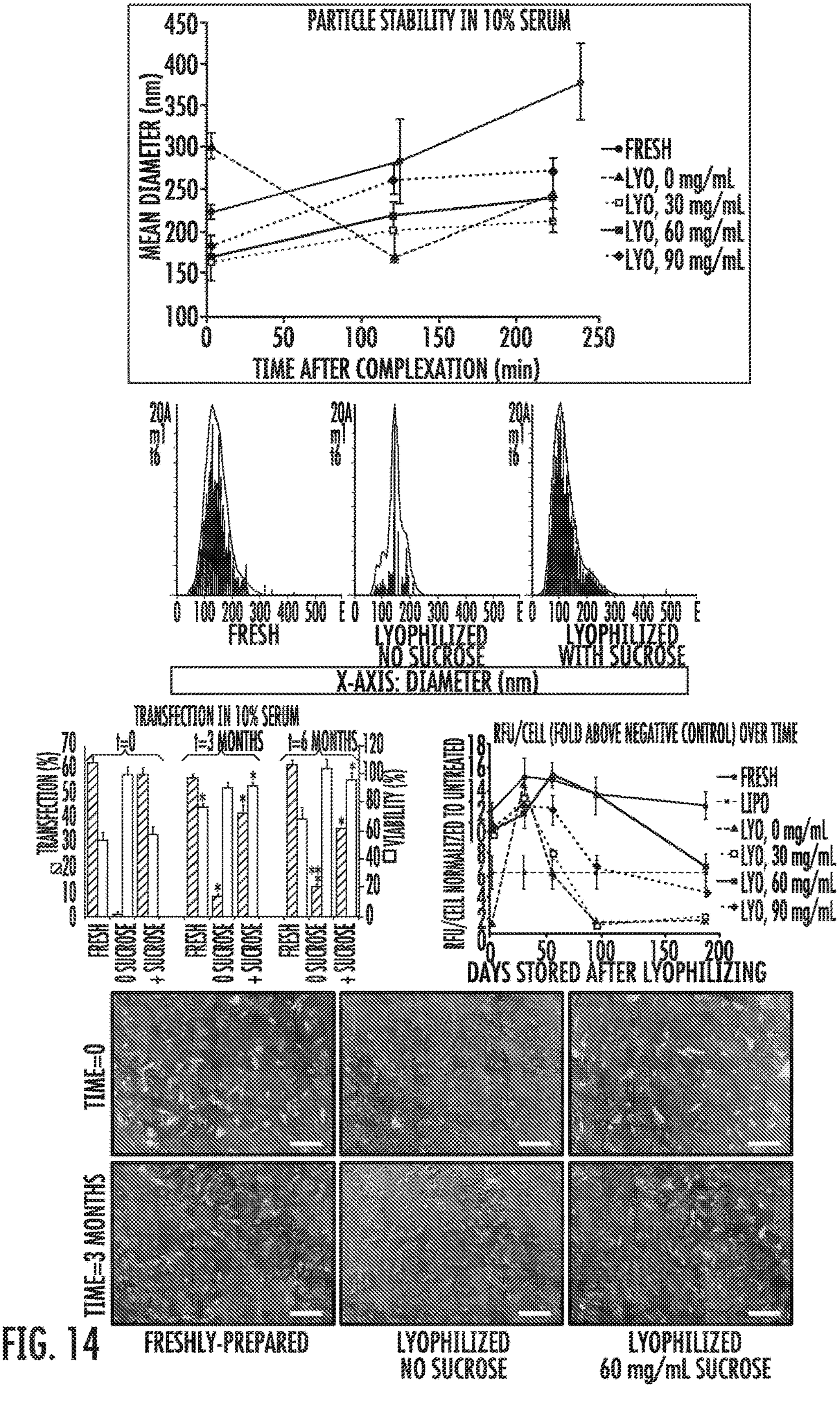
Figure 15:
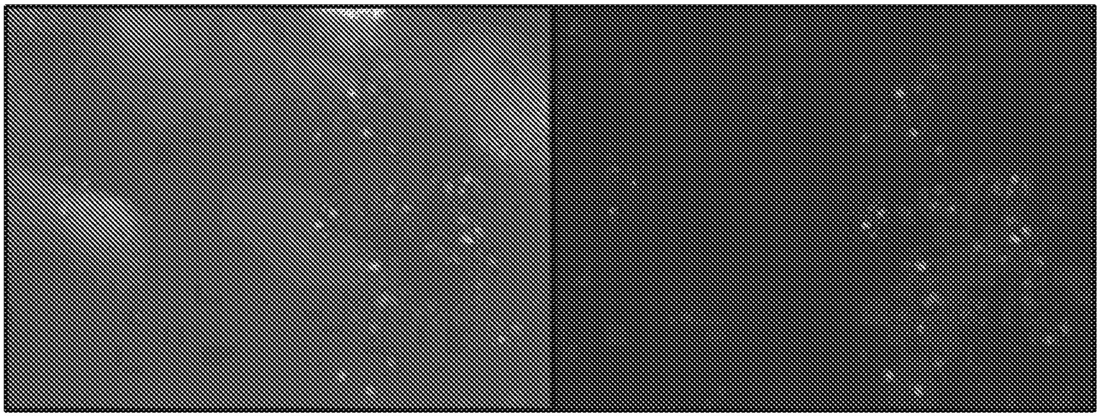
Figure 16:
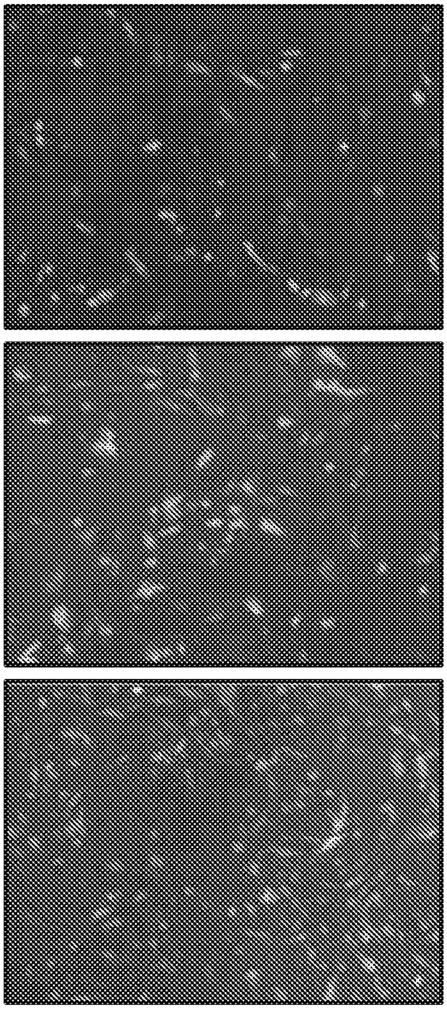
Figure 17:
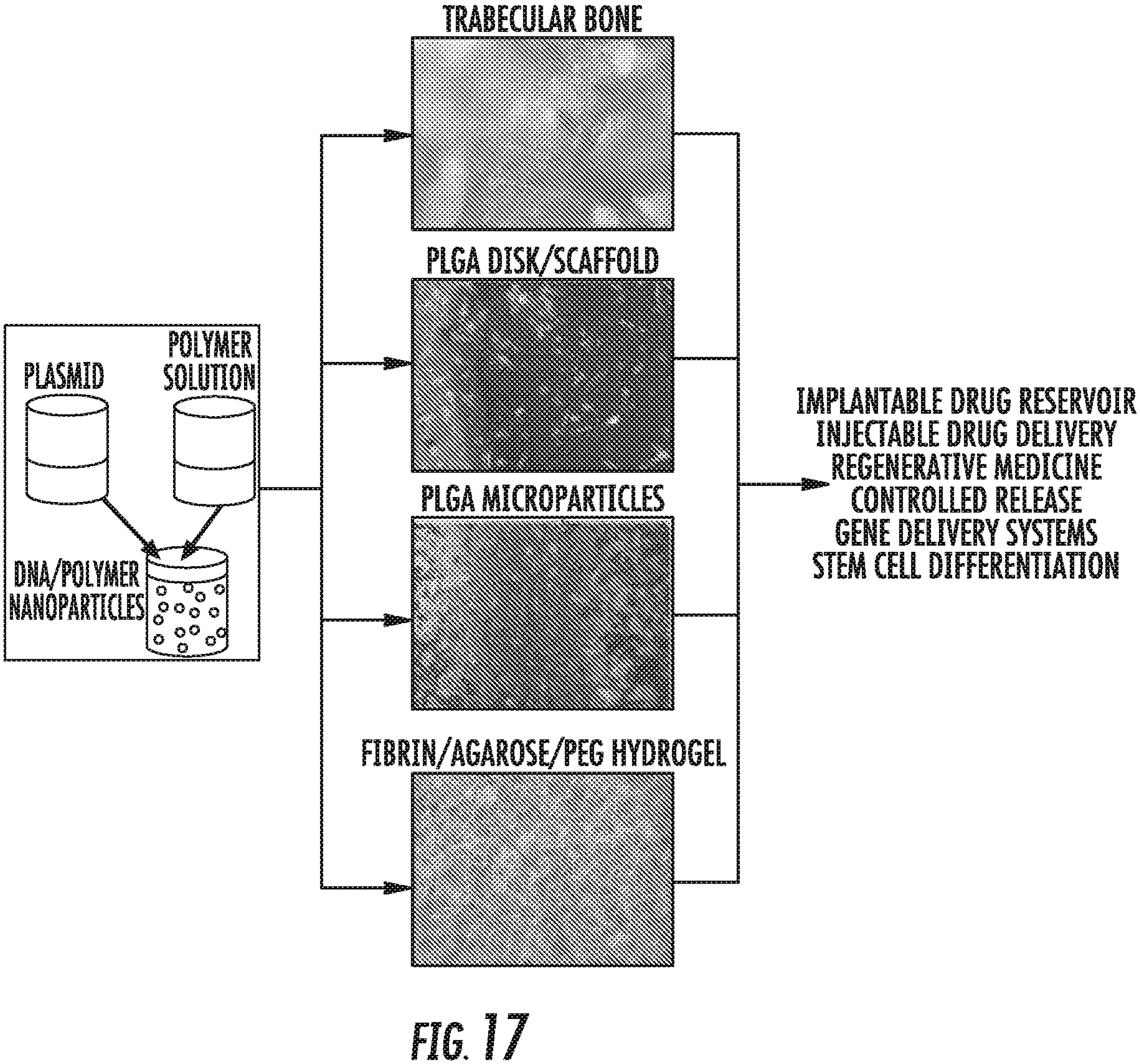
Figure 18:
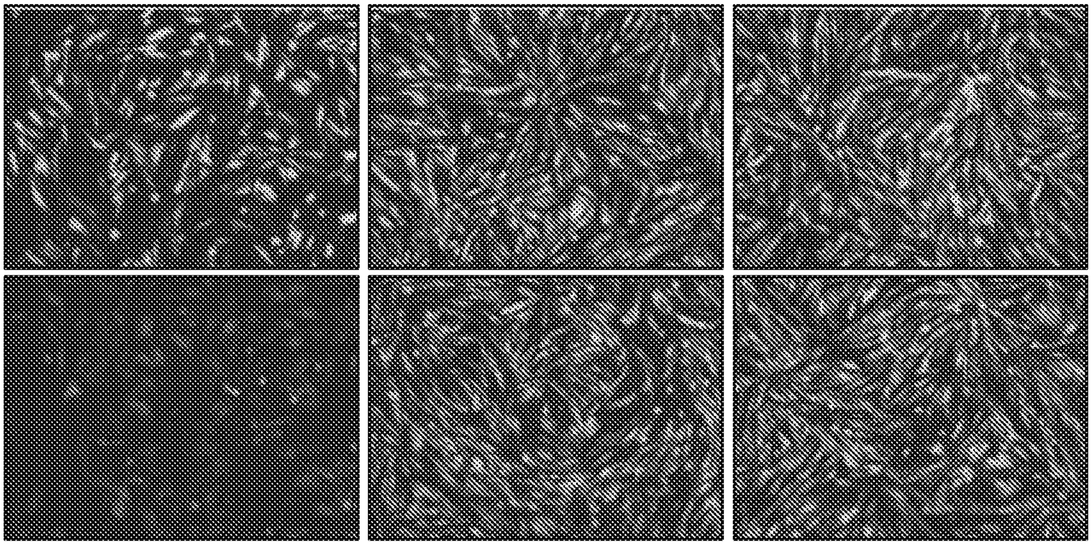
Figure 19A:
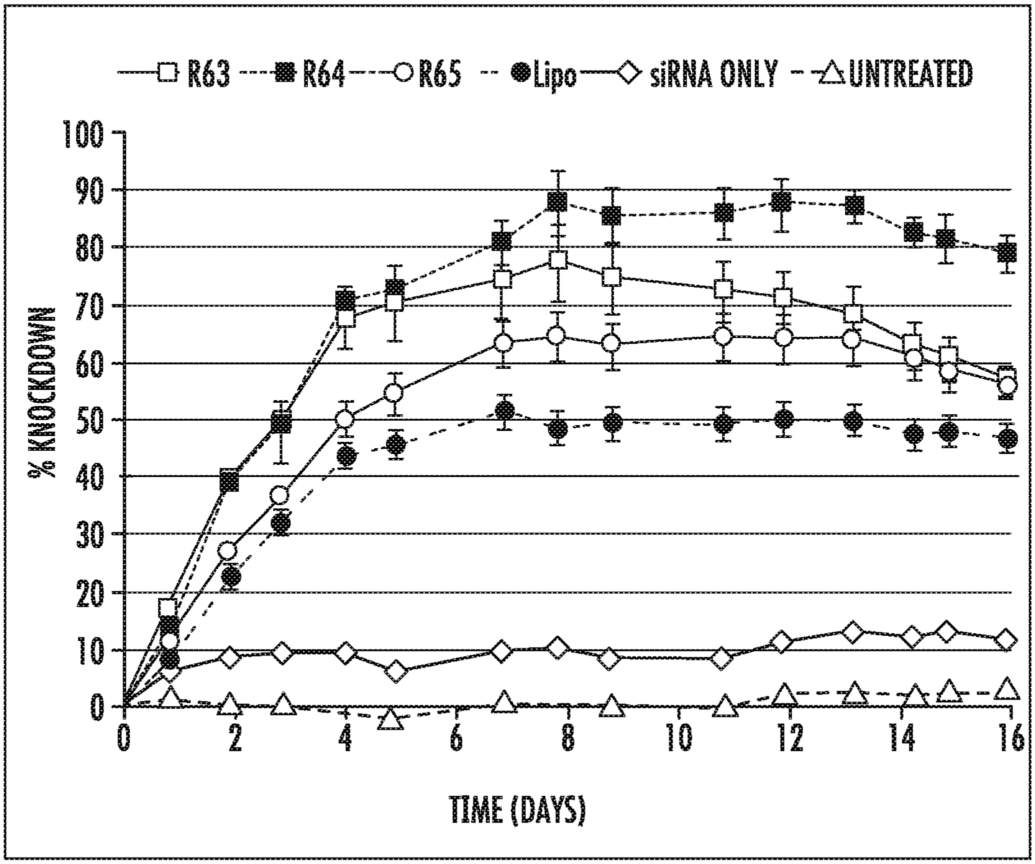
Figure 19B:
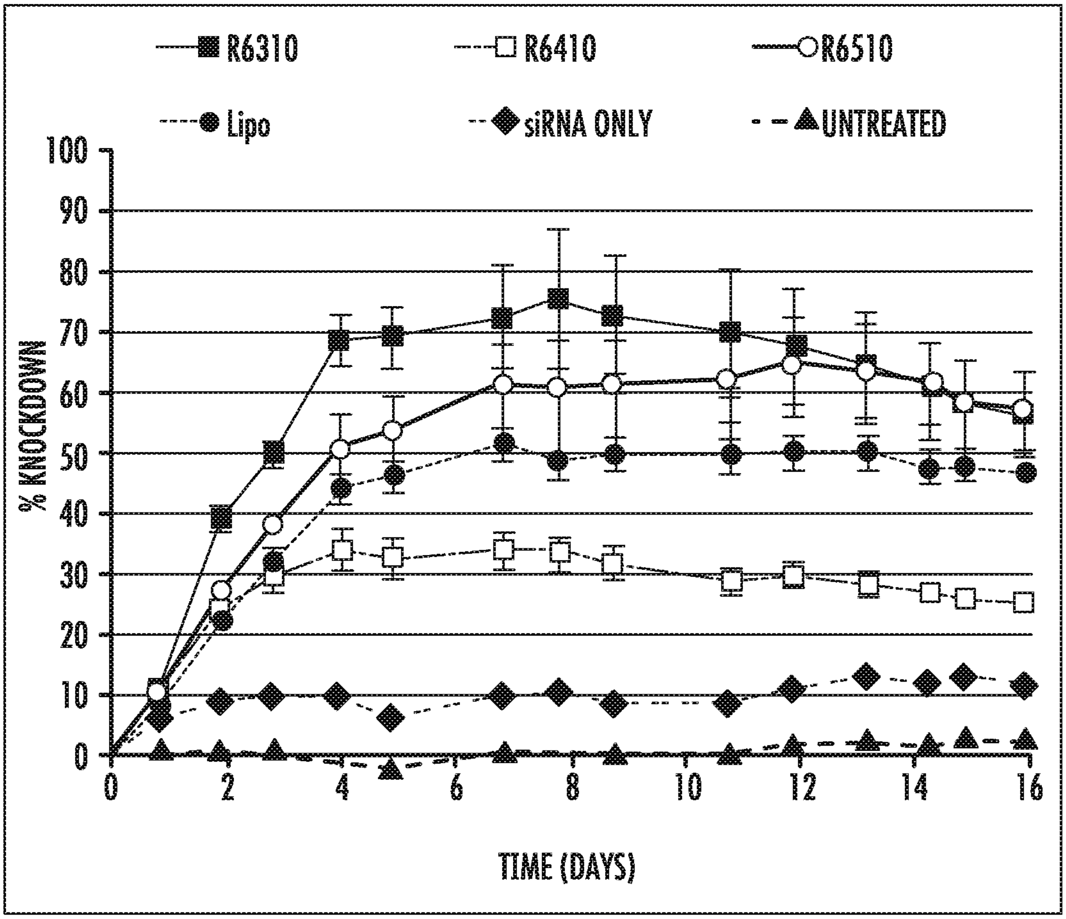
Figure 19C:
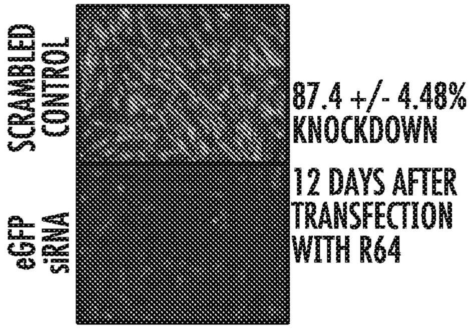
Figure 20:
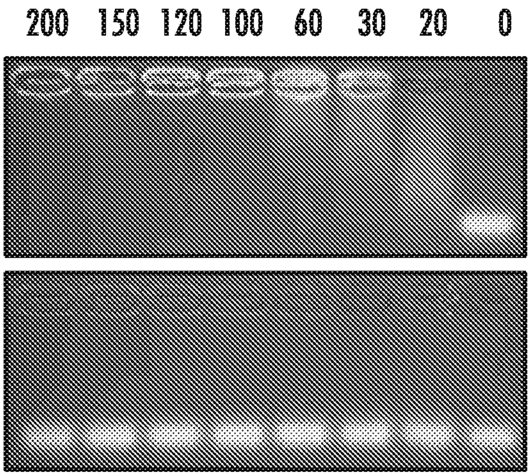
Figure 21:
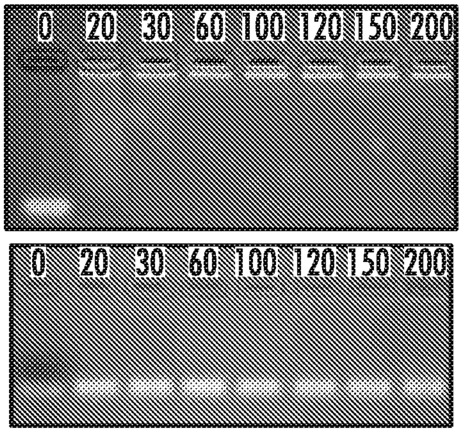
Figure 22:
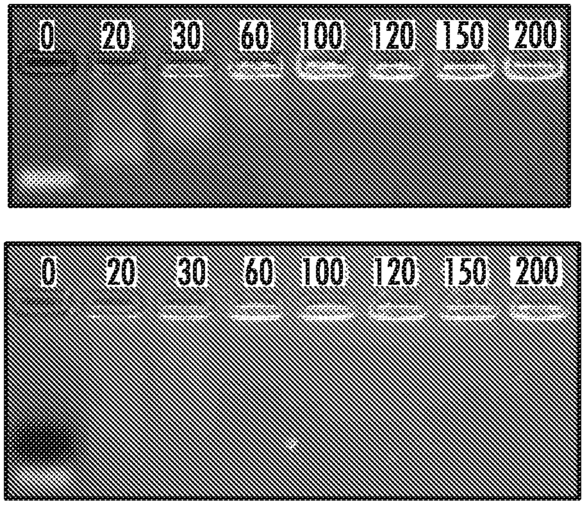
Figure 24:
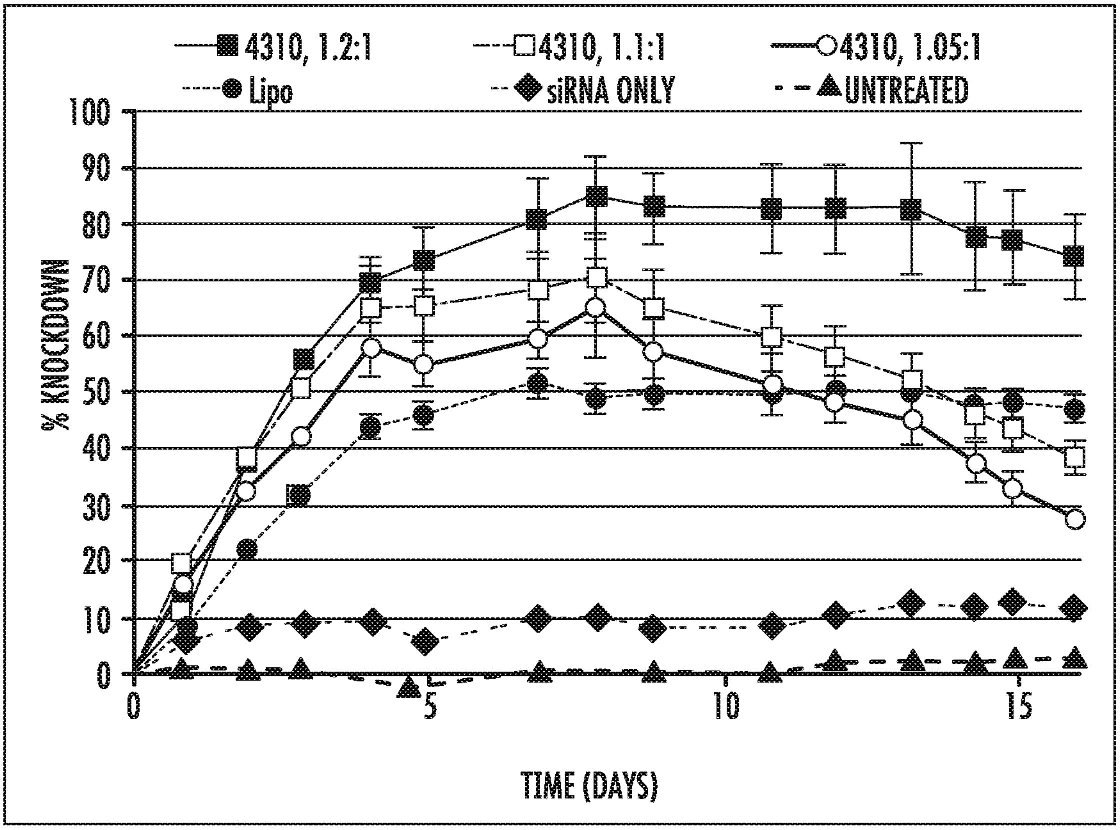
Figure 25:
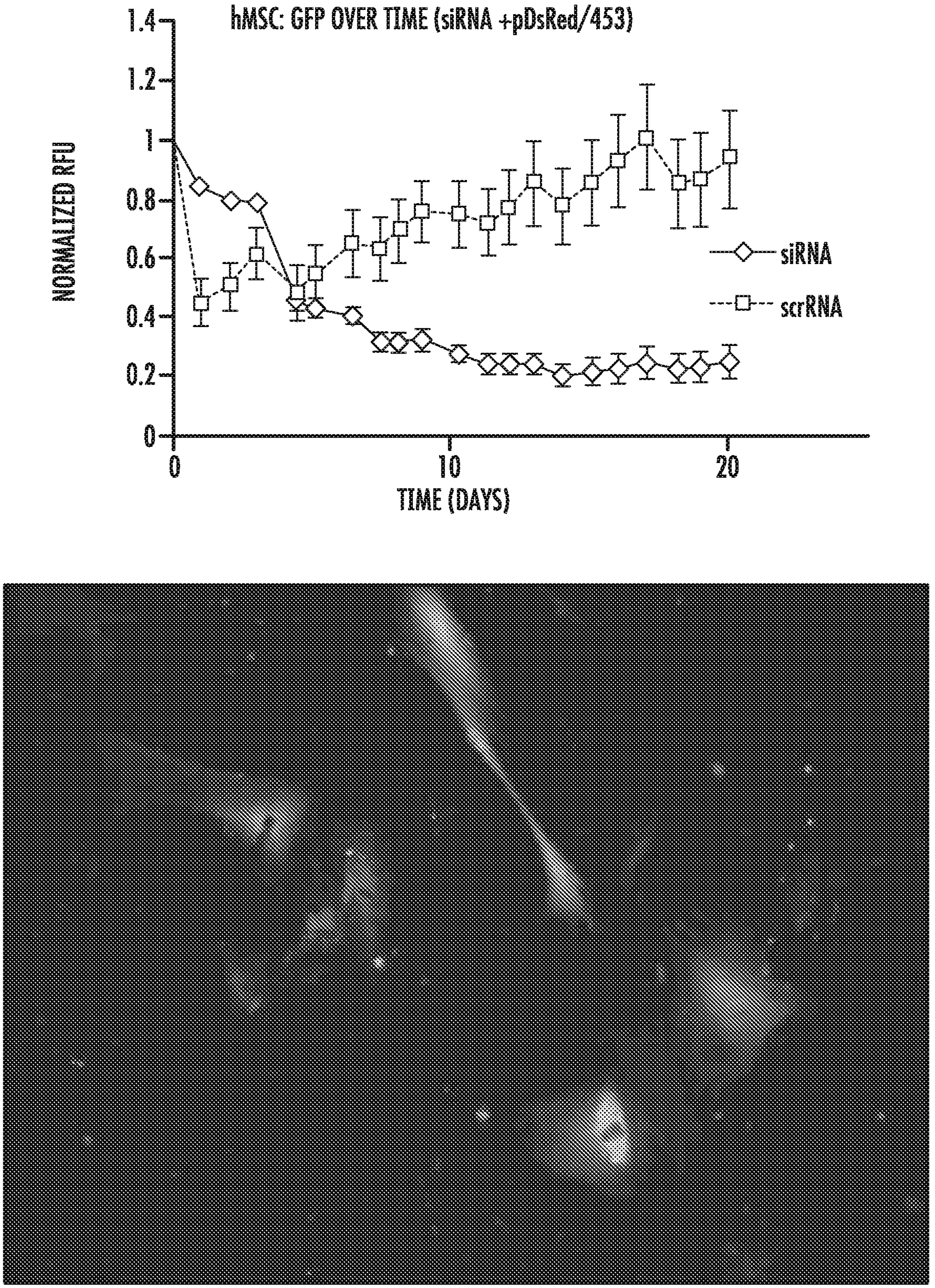
Figure 26:
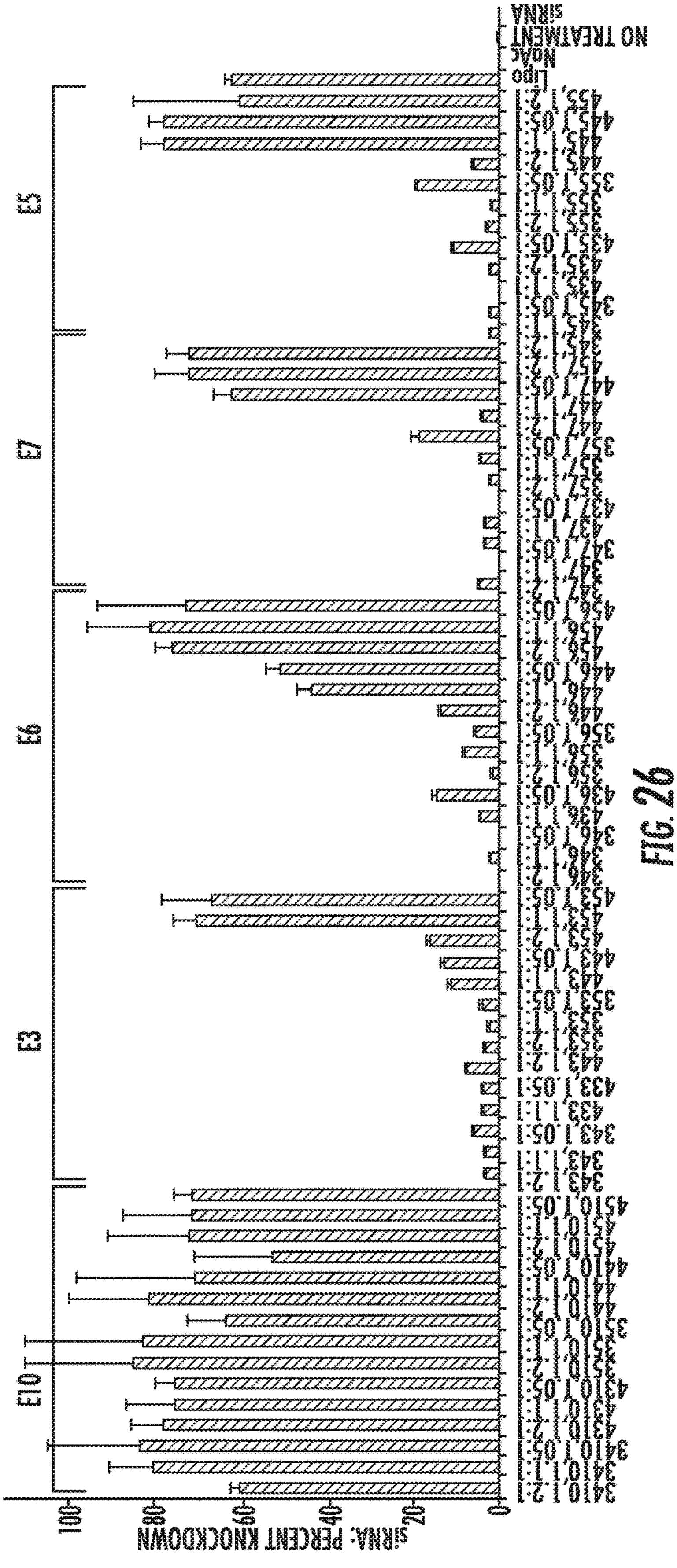
Figure 27:
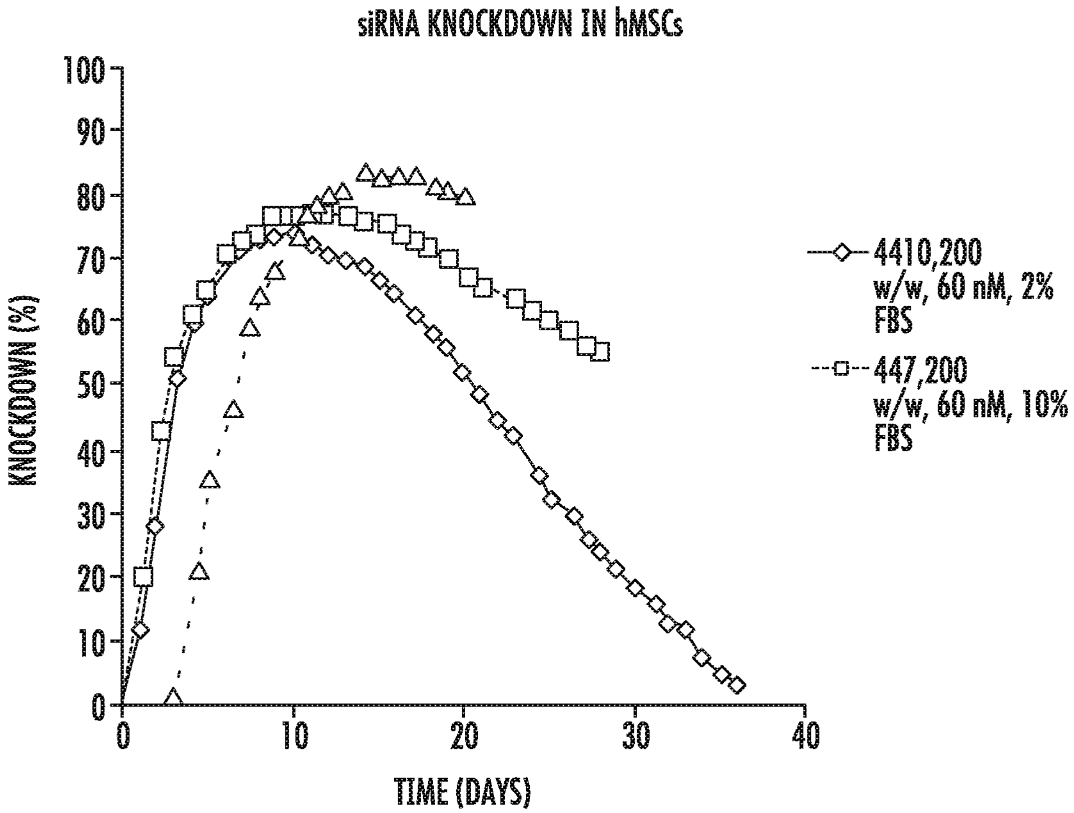
Figure 27:
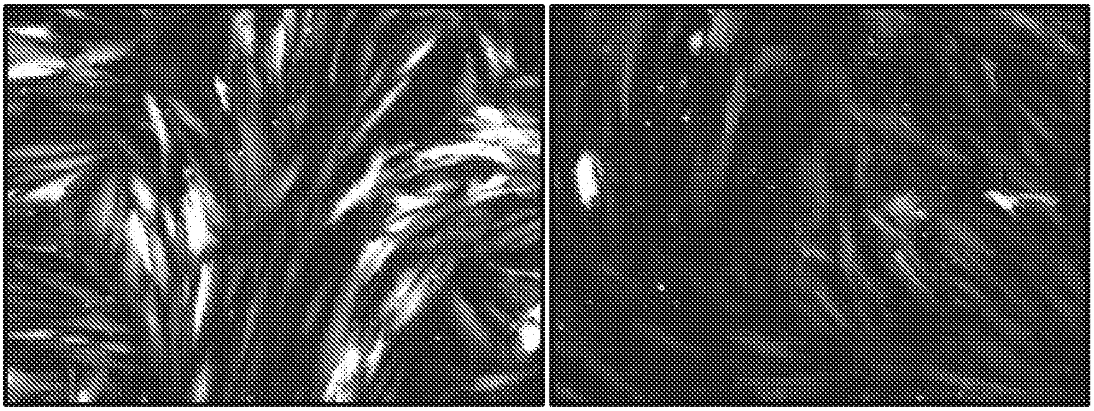
Figure 28:
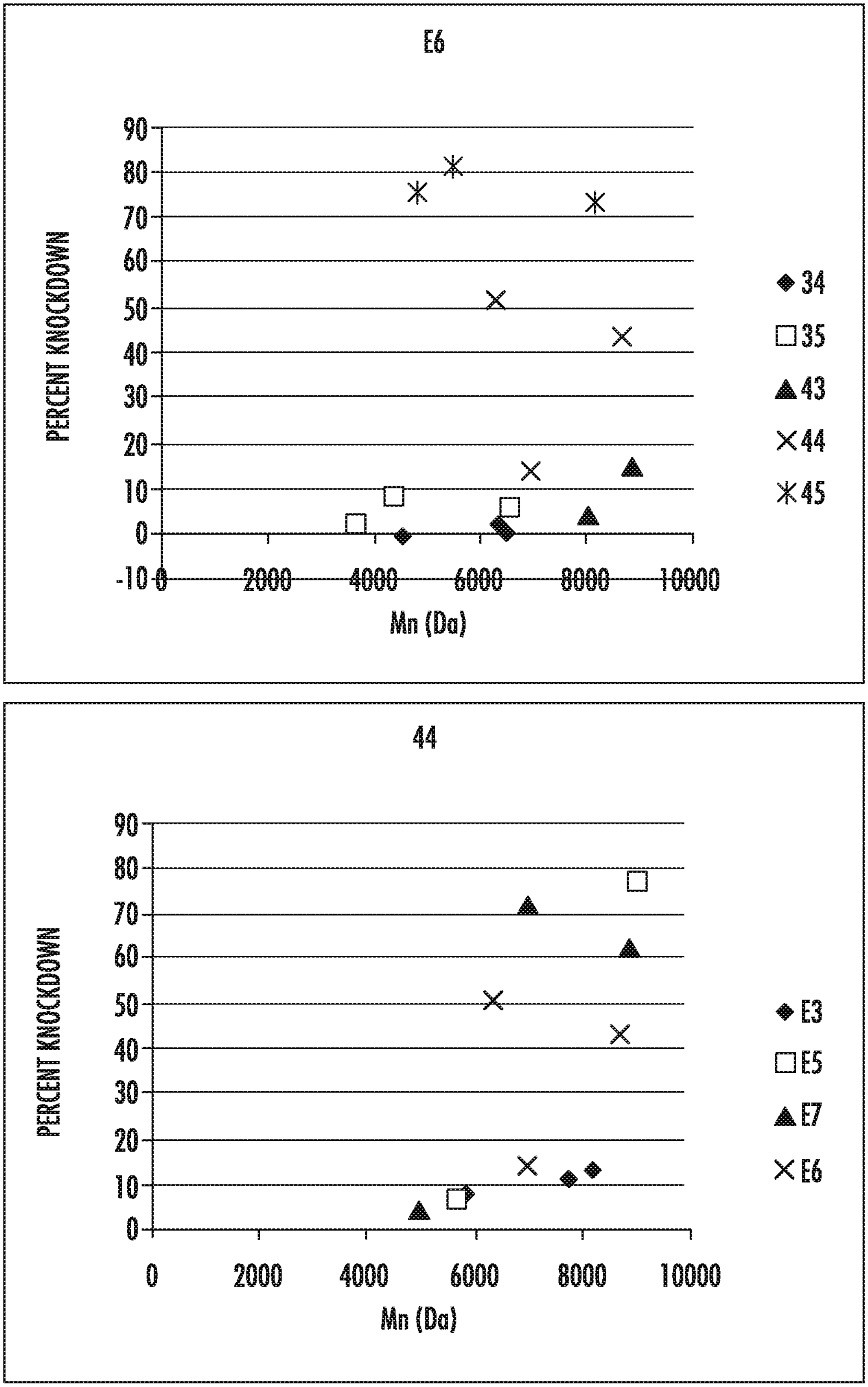
Figure 29:
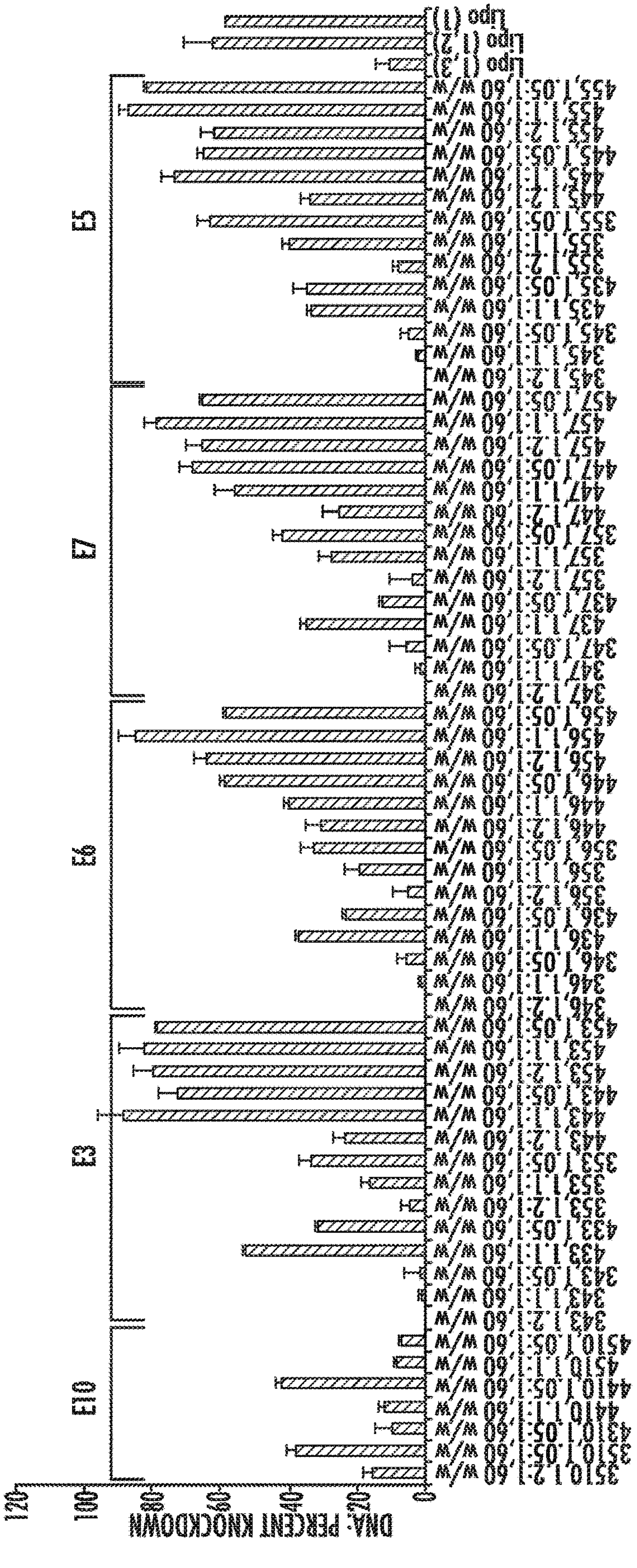
Figure 30:
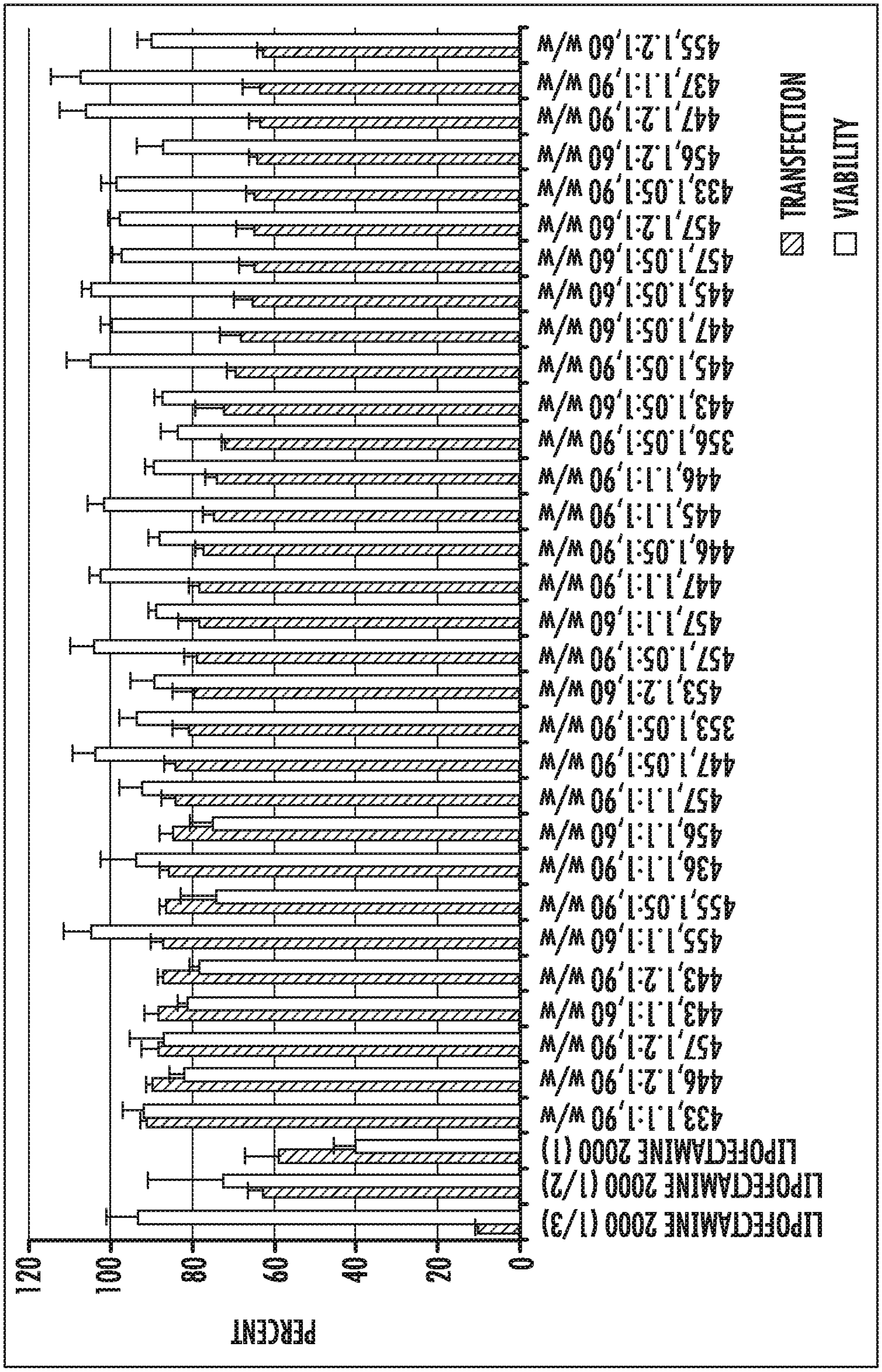
Figure 31:
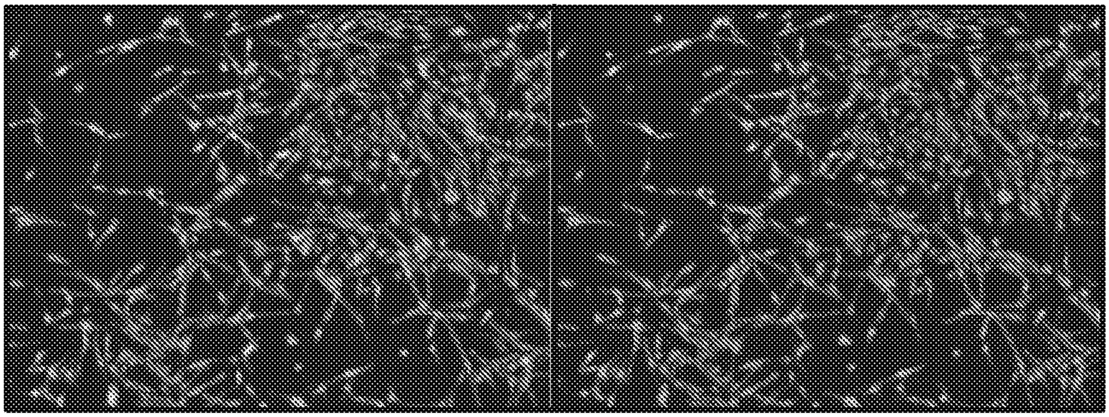
Figure 32:
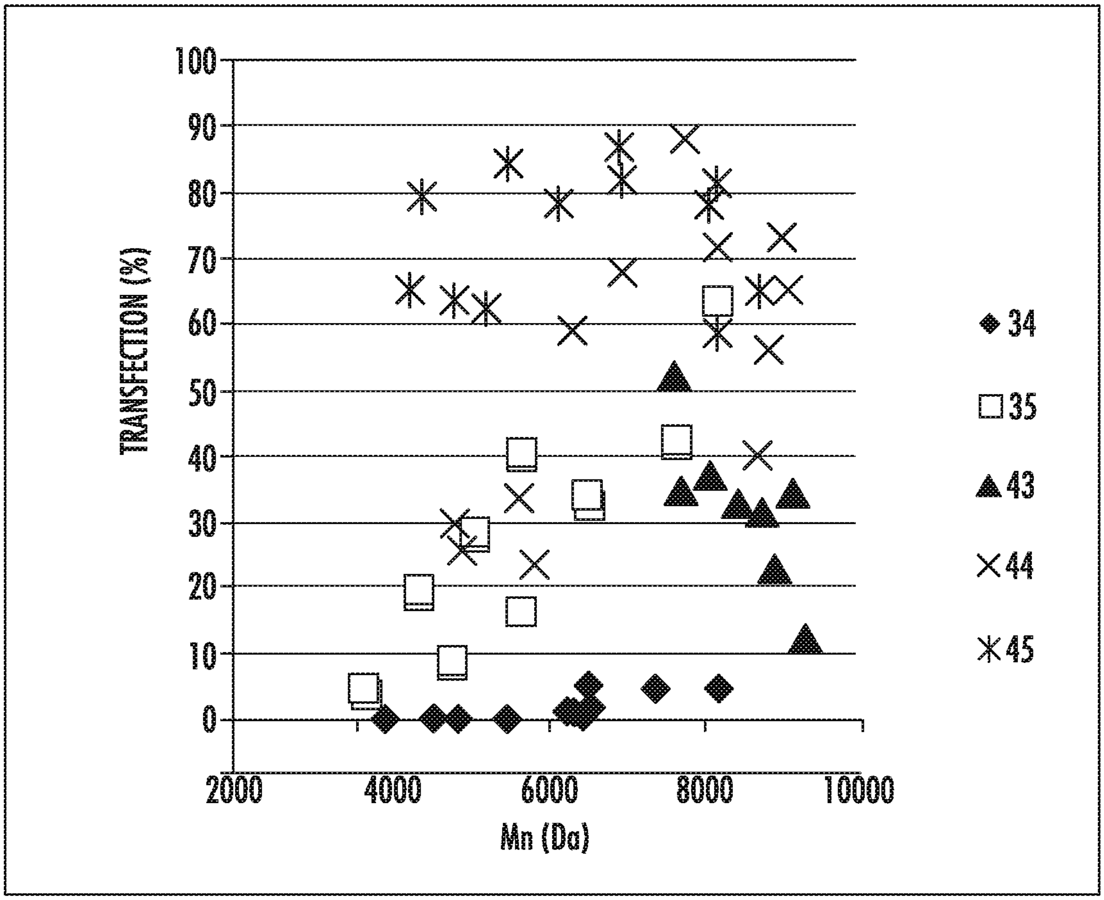
Figure 33:
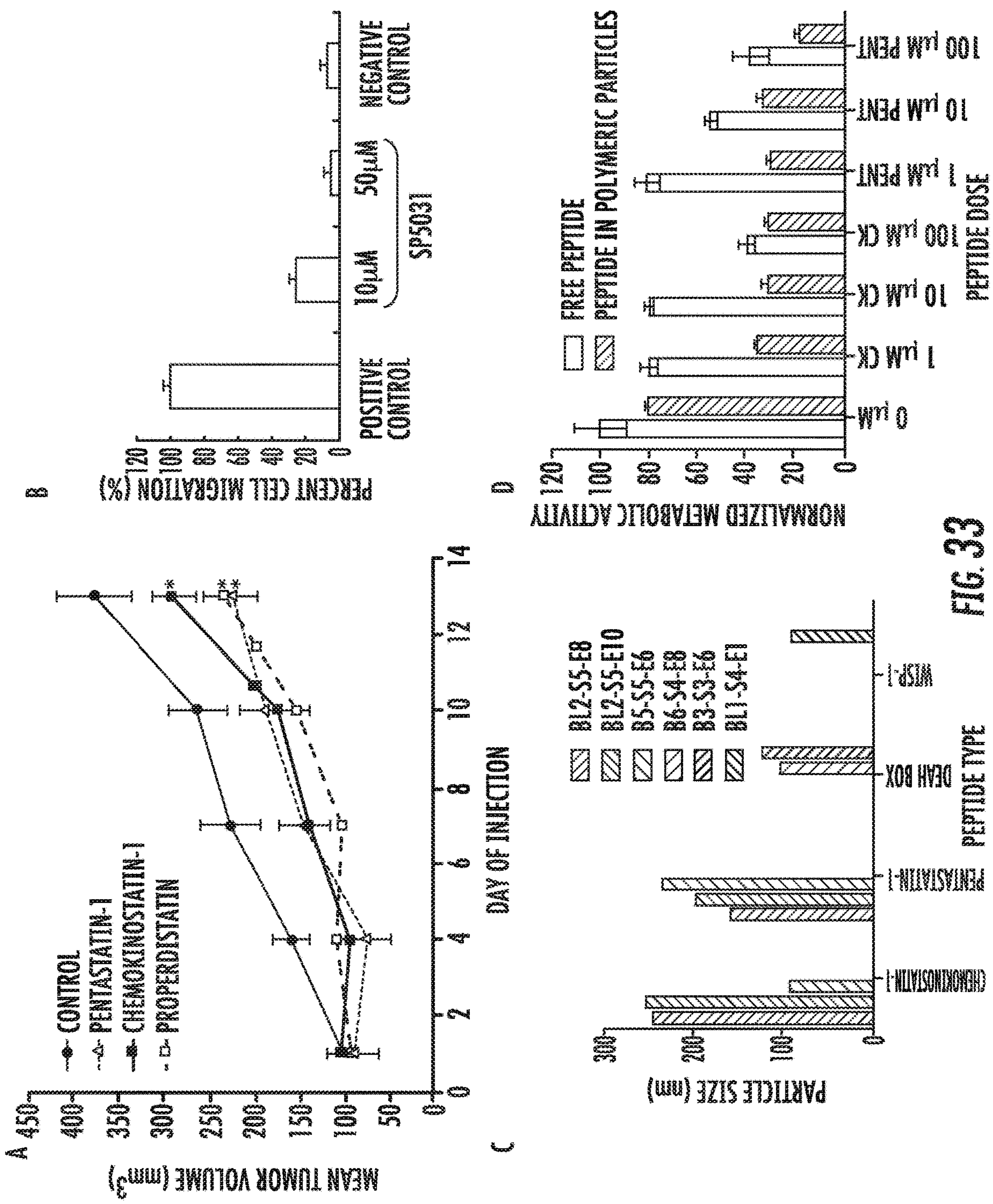
Figure 34:
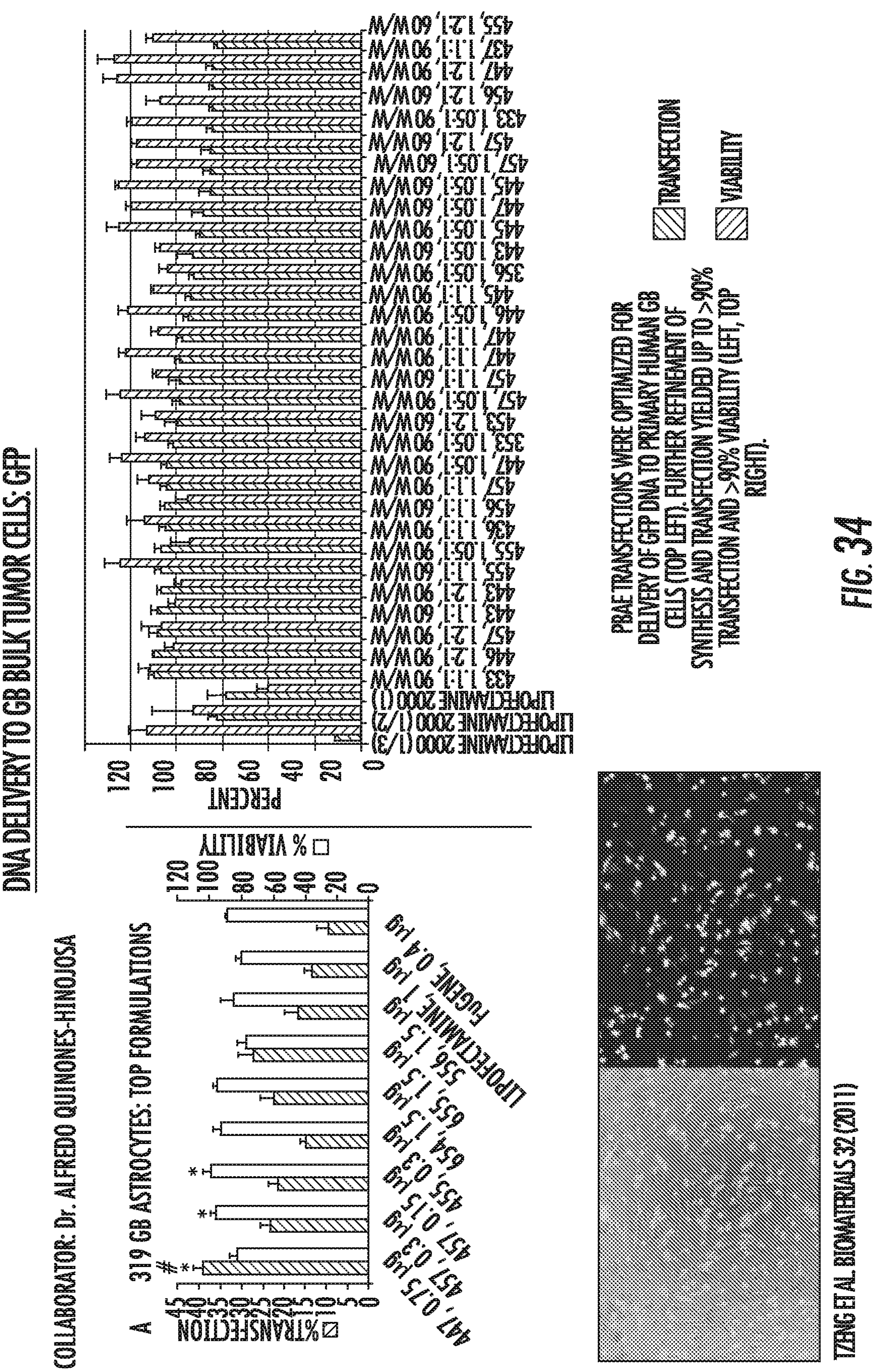
Figure 35:
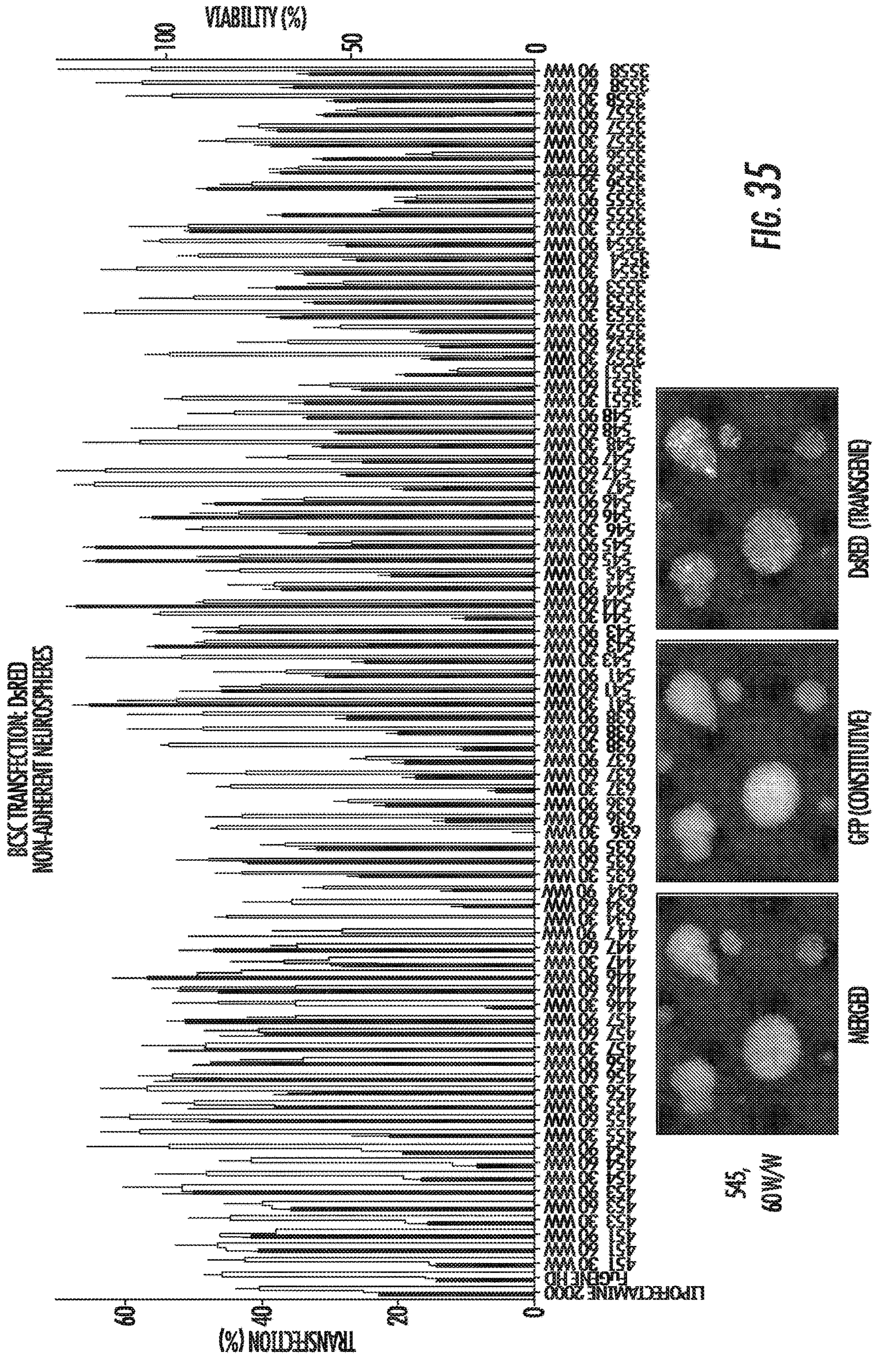
Figure 36:
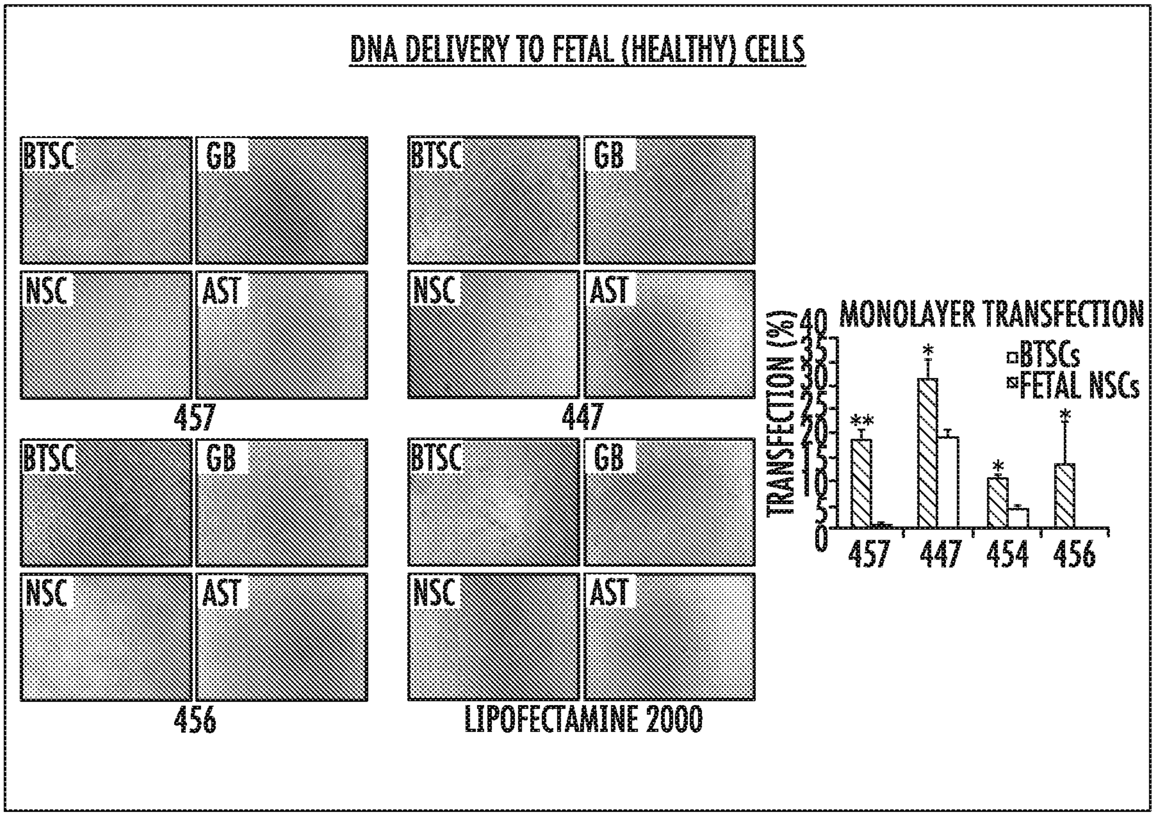
Figure 37:
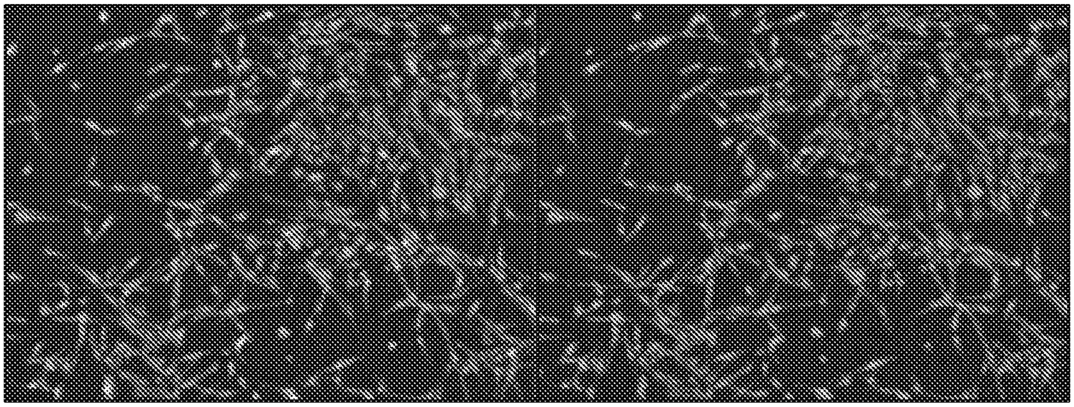
Figure 38:
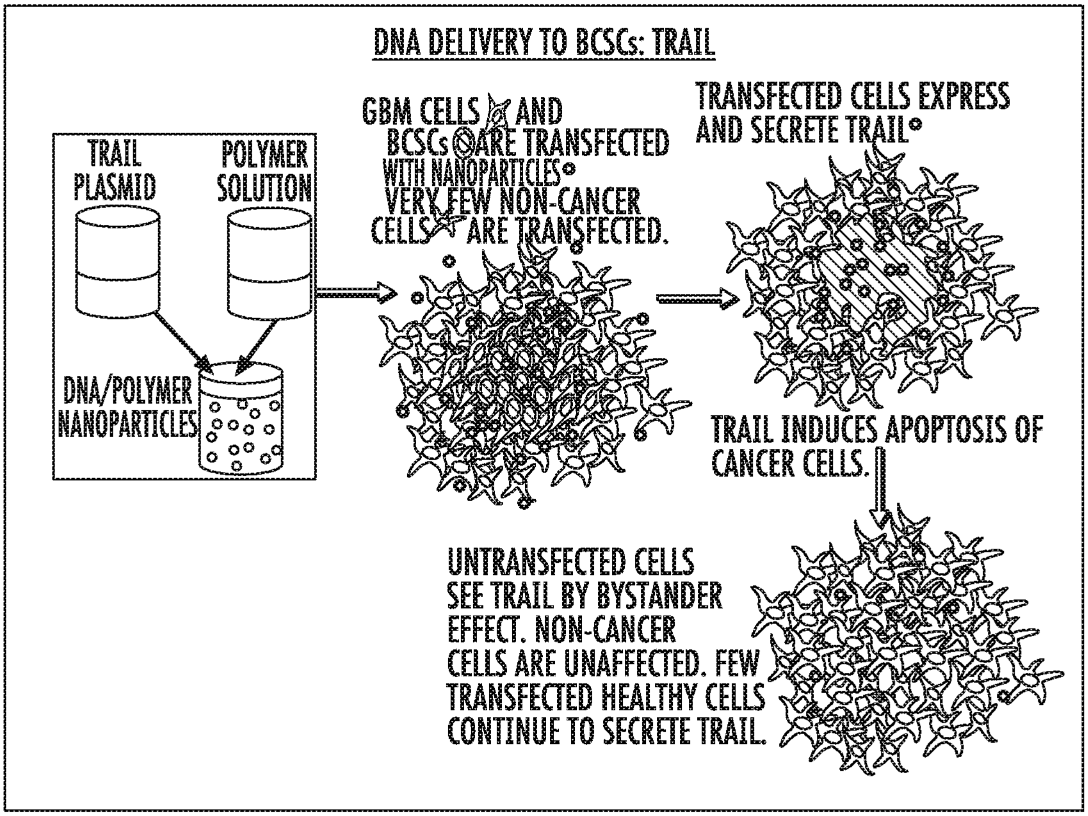
Figure 39:
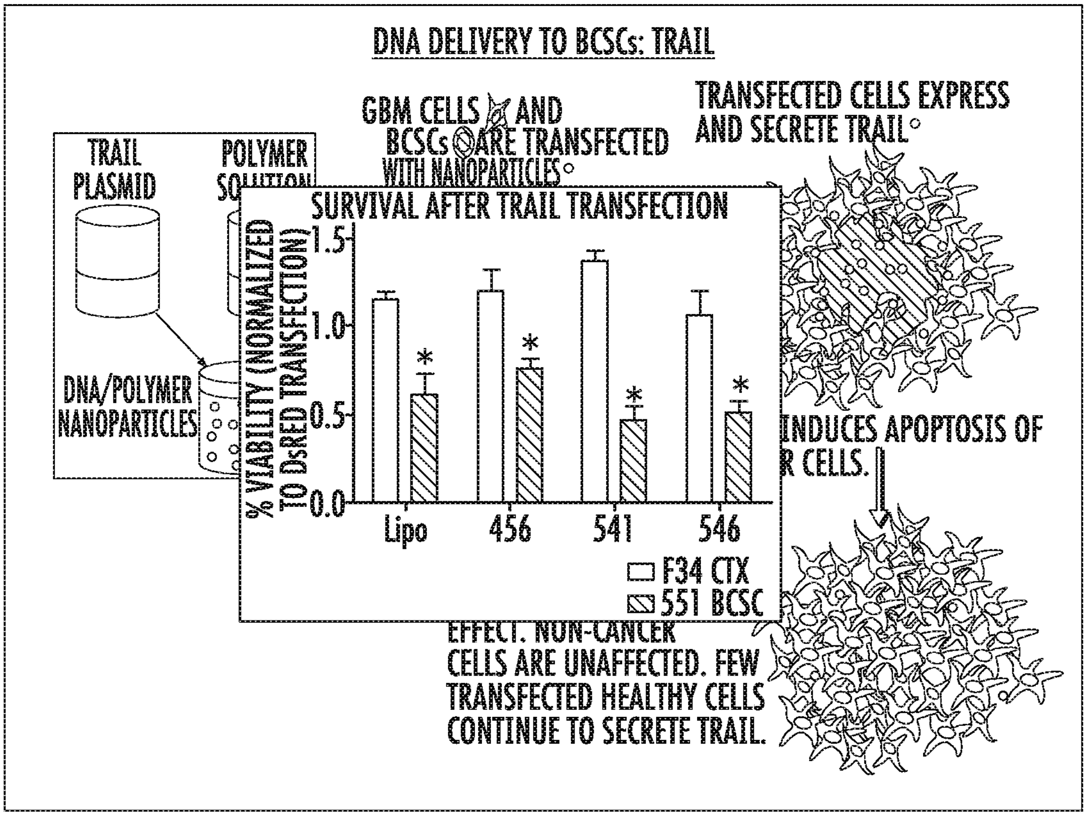
Figure 40:
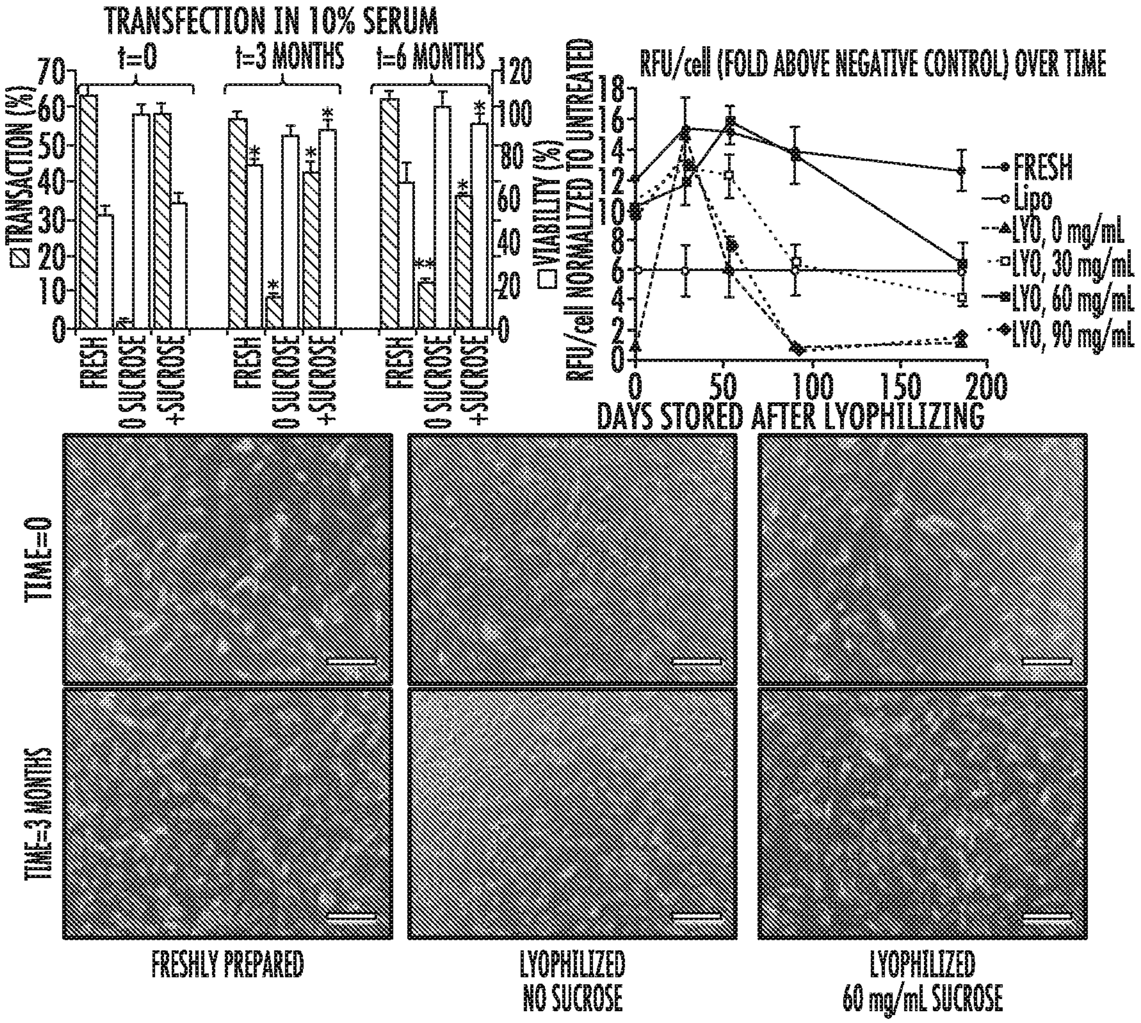
Figure 41:
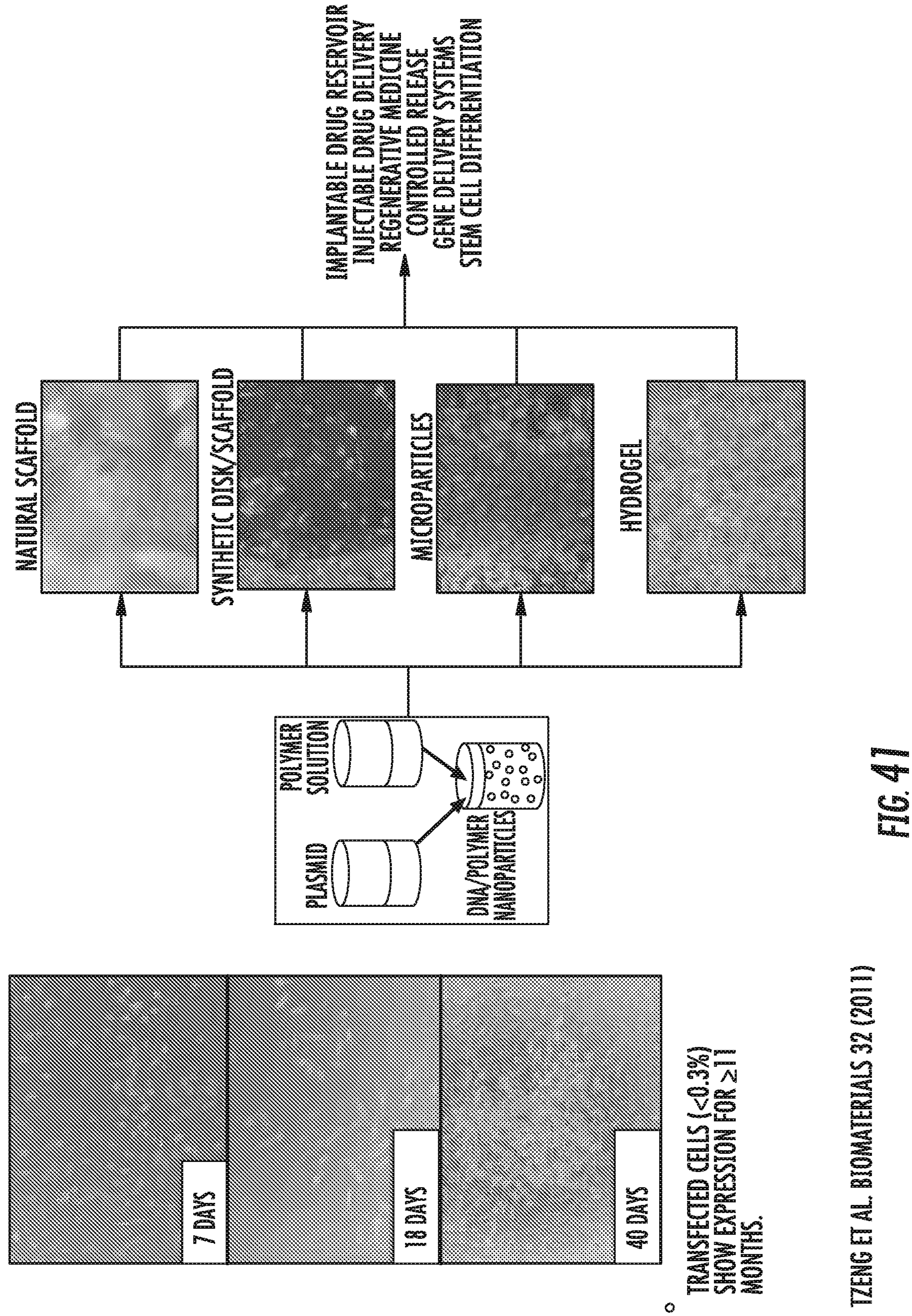
Figure 42:
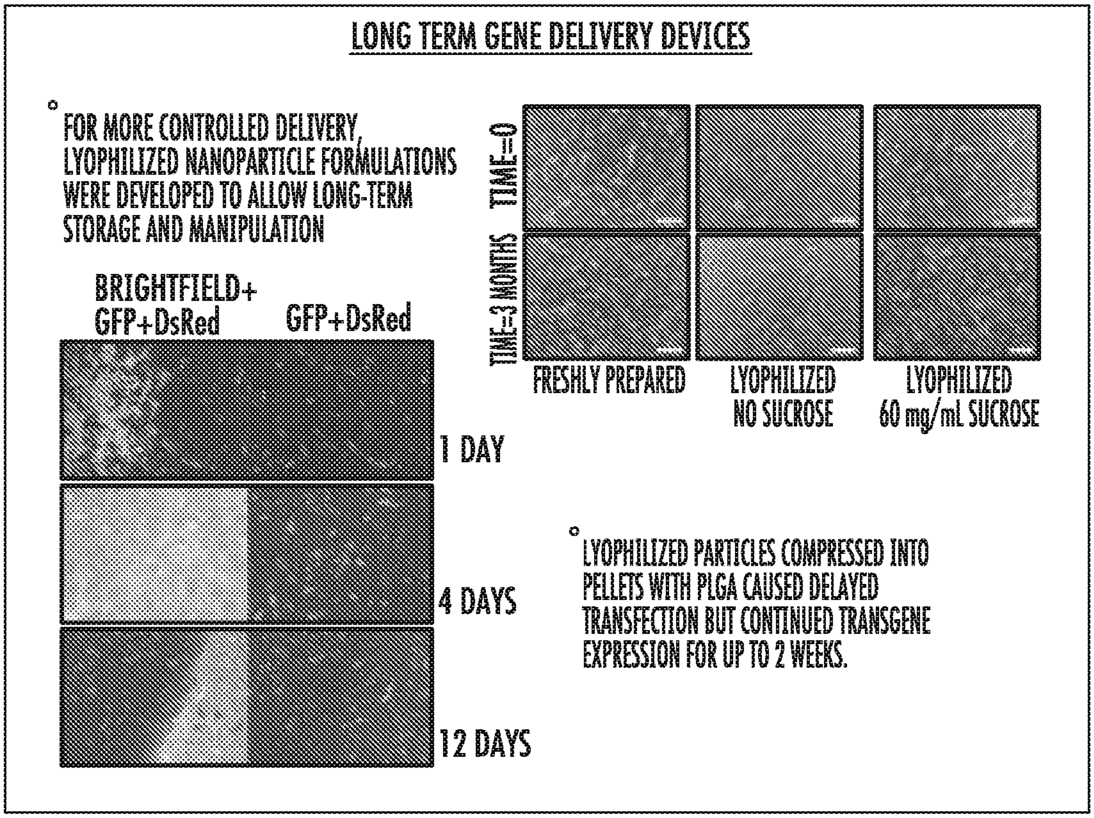
Figure 43:
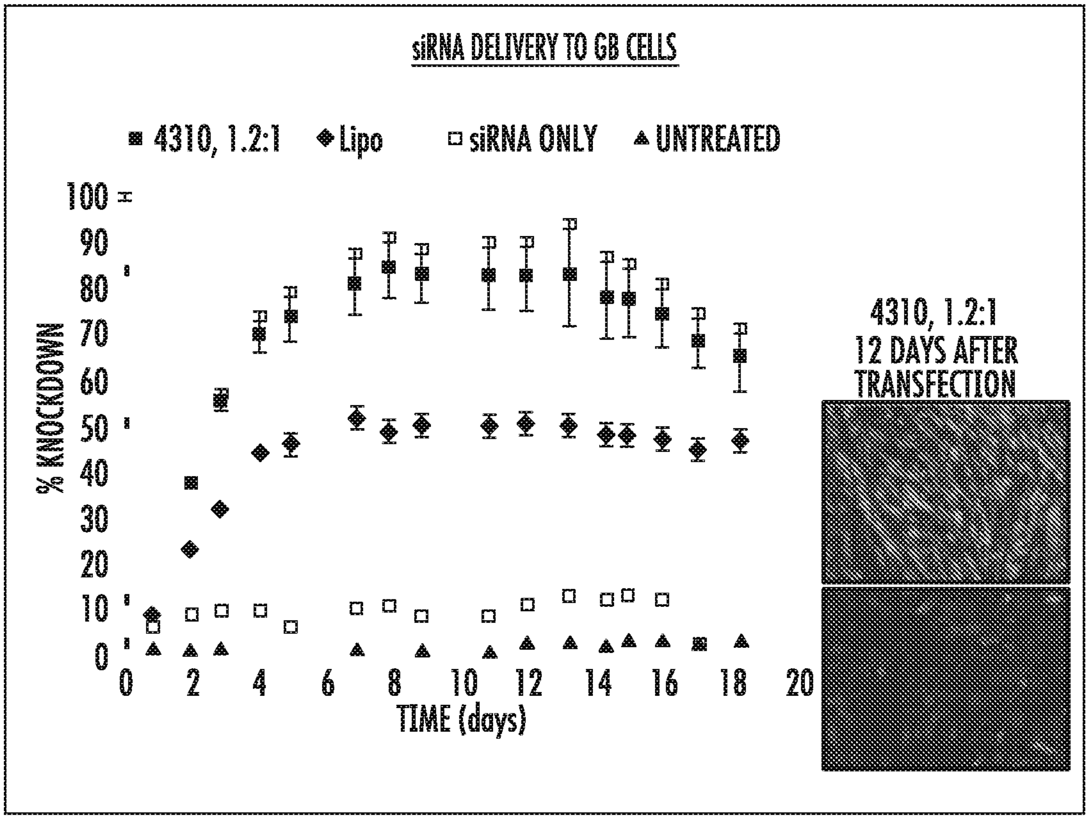
Figure 44:
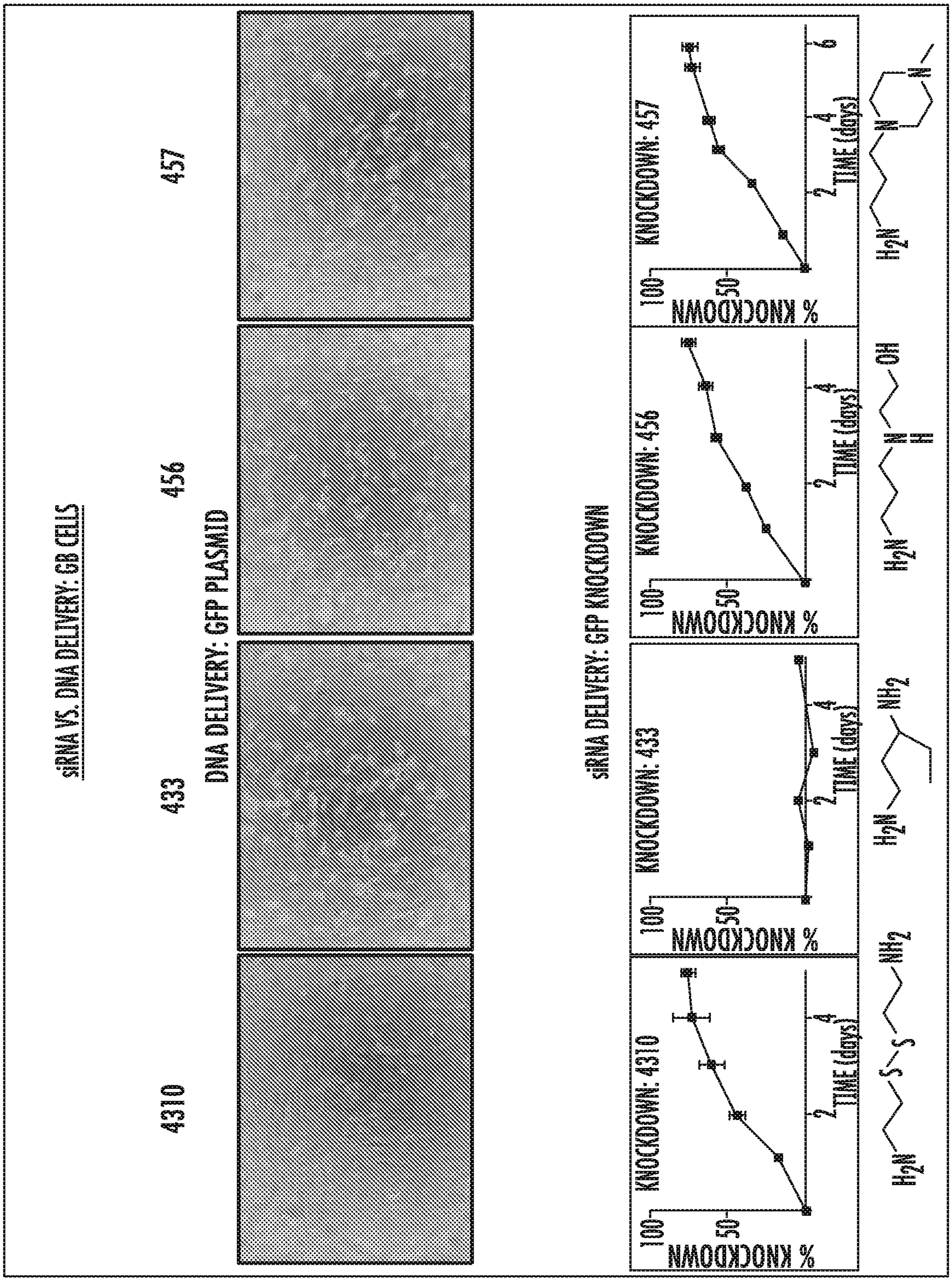
Figure 45:
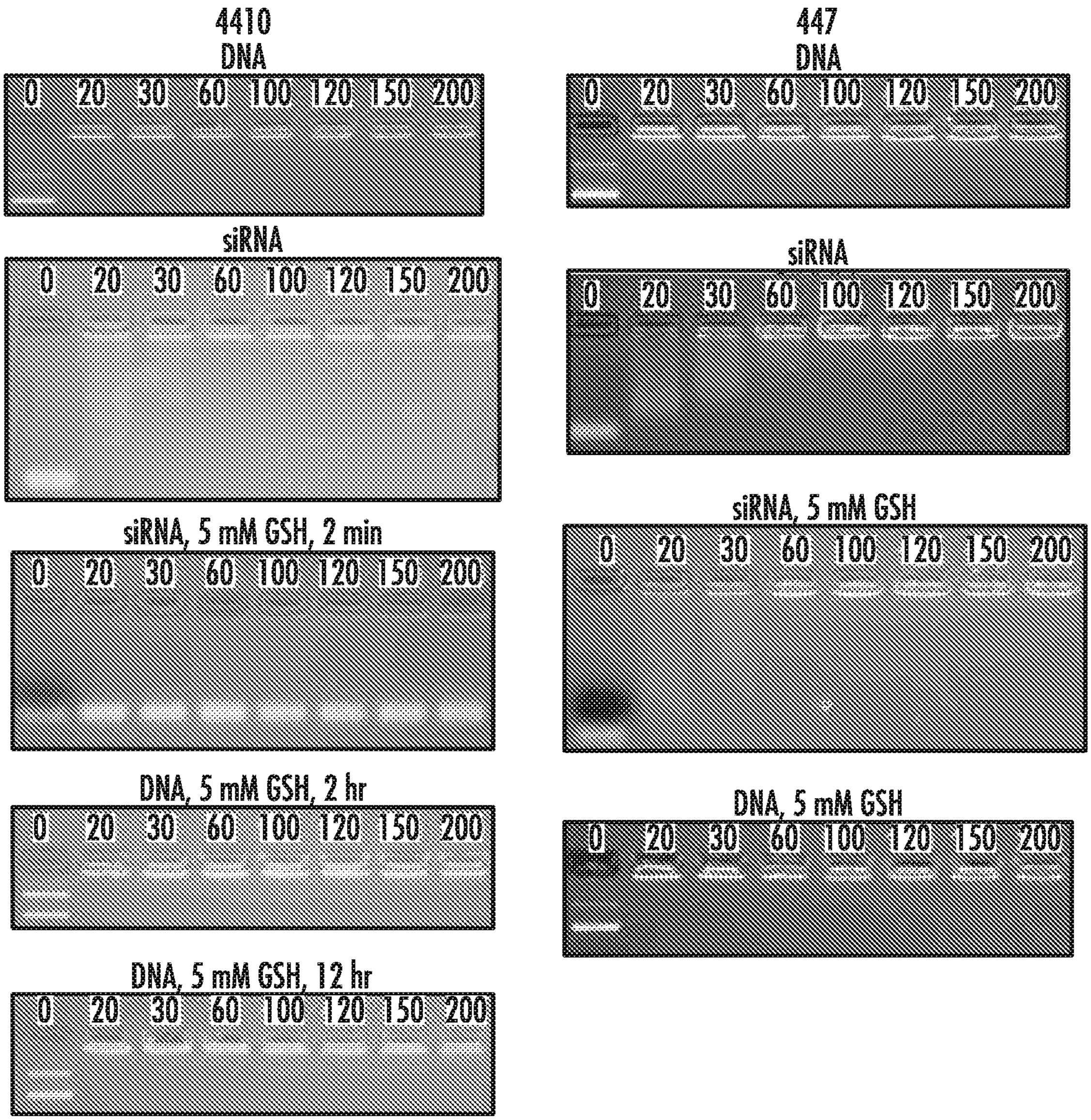
Figure 46:
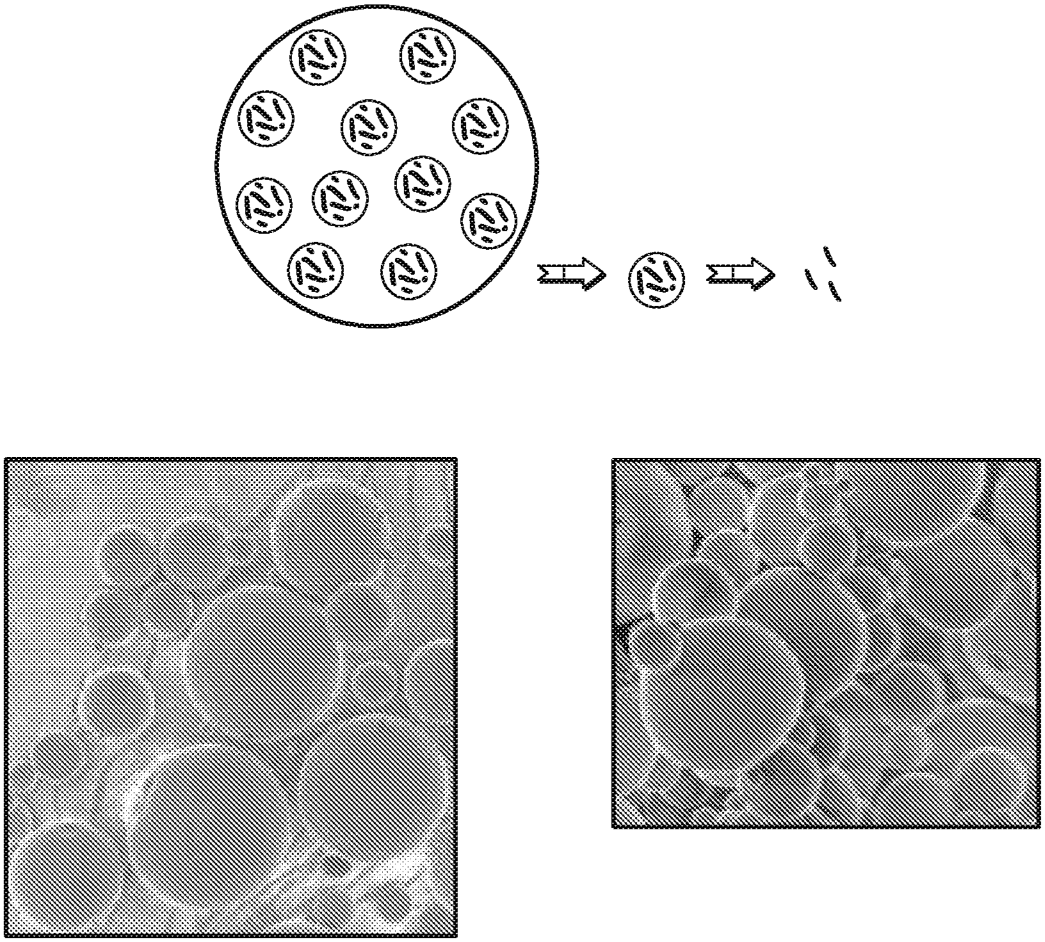
Figure 47:
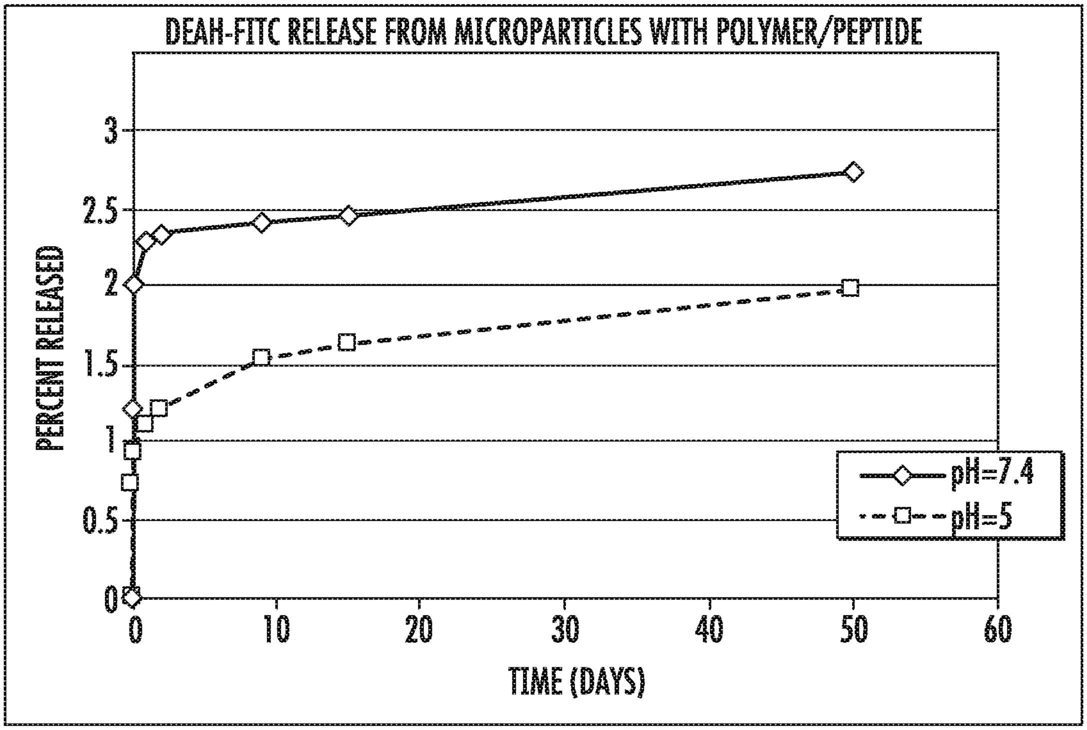
Figure 47:
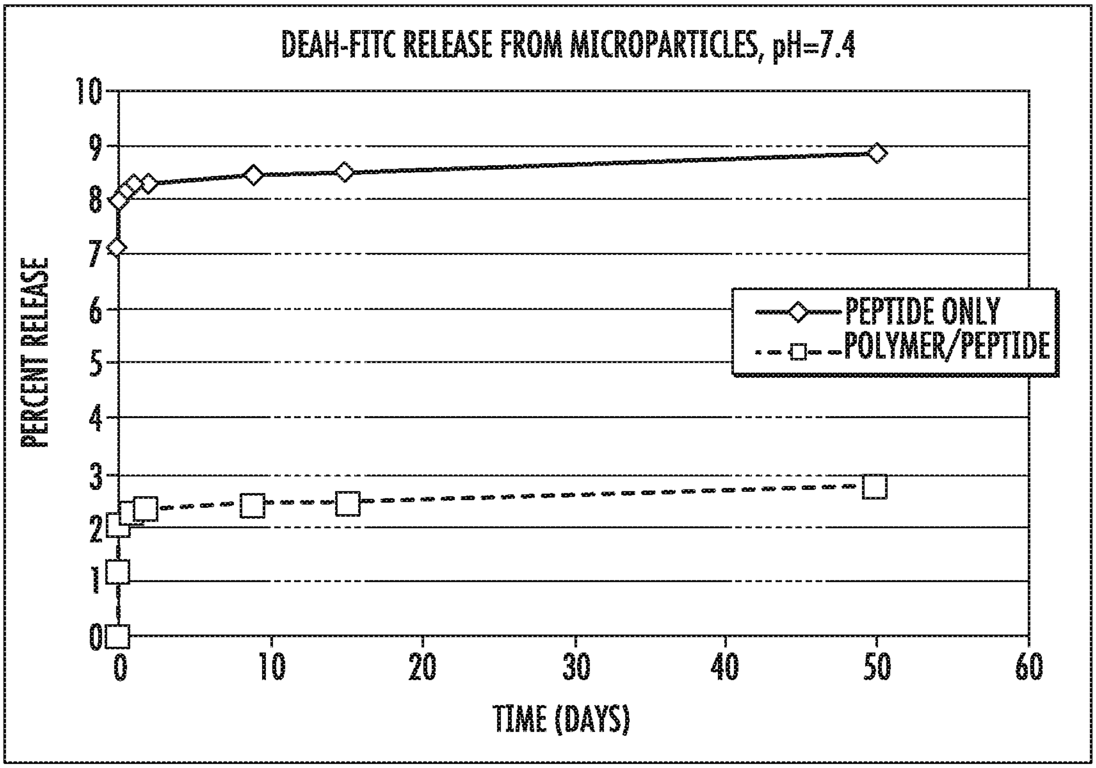
Figure 48:
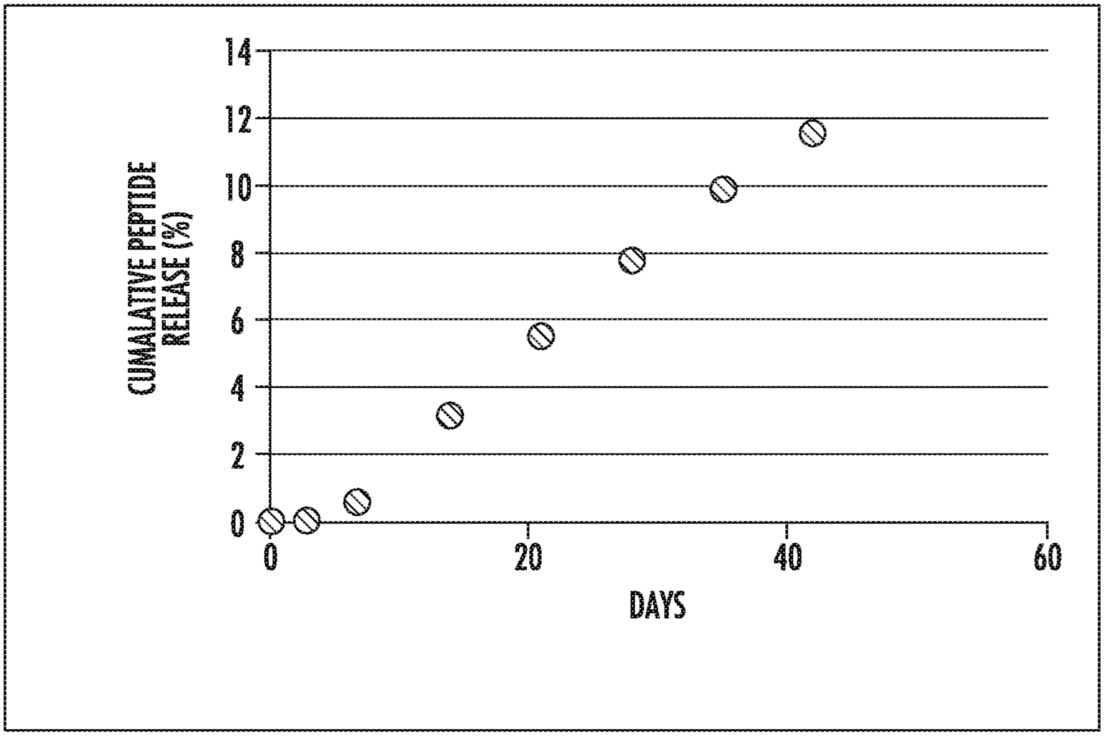
Figure 49A:
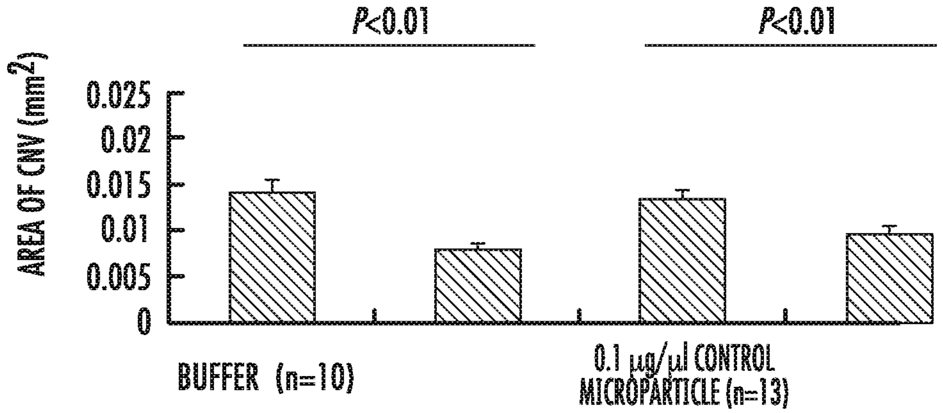
Figure 49B:
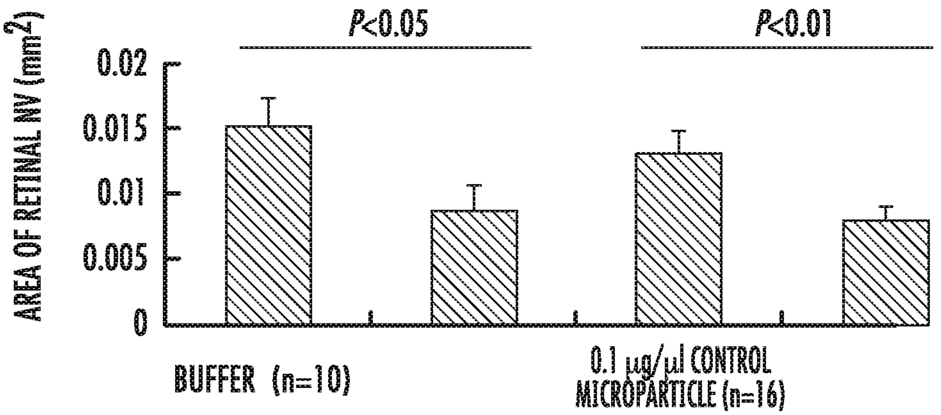
Figure 49C:
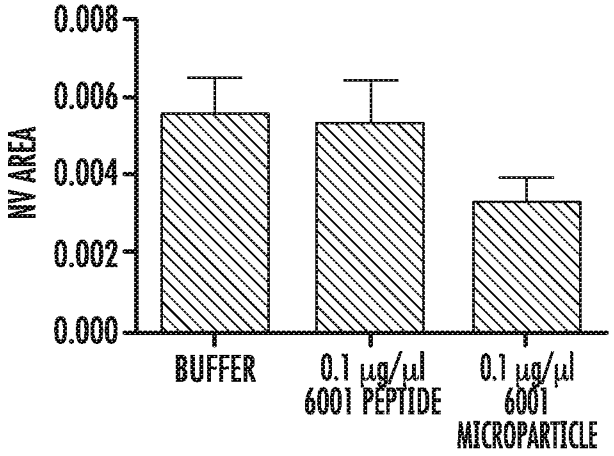

FIG. 3 shows a scheme for producing stable nanoparticle suspensions;

FIG. 4A-FIG. 4D show representative polymer structures tuned to peptide cargos (FIG. 4A discloses SEQ ID NOs: 2485 and 2484, respectively, in order of appearance. FIG. 4B discloses SEQ ID NO: 2388. FIG. 4C discloses SEQ ID NO: 2483. FIG. 4D discloses SEQ ID NO: 2452.);

FIG. 5A and FIG. 5B show representative formation and sizing of polymer/peptide nanoparticles (by nanoparticle tracking analysis on a Nanosight LM10) (FIG. 5A discloses "DEAH" as SEQ ID NO: 2484);

FIG. 6 shows DEAH peptide (SEQ ID NO: 2484) release by 336 nanoparticles at 4° C. (above) and 37° C. (below);

FIG. 7 shows HUVEC viability/proliferation assays with polymer/SP6001/DEAH peptide ("DEAH" disclosed as SEQ ID NO: 2484);

FIG. 8 shows HUVEC migration assays with 336 polymer/DEAH peptide ("DEAH" disclosed as SEQ ID NO: 2484);

FIG. 9 shows in vivo 336 polymer nanoparticle/SP6001 DEAH peptide ("DEAH" disclosed as SEQ ID NO: 2484)';

FIG. 10 shows (top) Particle size and (bottom) cell viability effects of various polymer/SP2012 nanoparticles as compared to peptide only of non-cytotoxic polymers;

FIG. 11 shows polymer/peptide formulations for alternative peptides;

FIG. 12 shows data for FITC-tagged bovine serum albumin (BSA) mixed with a macromer solution containing 10% (w/v) PEGDA (Mn-270 Da) with various amounts of B4S4, dissolved in a 1:1 (v/v) mixture of DMSO and PBS;

FIG. 13 shows an SEM of increasing B4S4 from top [0.2% w/w] to bottom [5% w/w]);

FIG. 14 shows the size distribution of appropriately freeze-dried particles (bottom left, right-most histogram) remains the same as freshly-prepared particles (bottom left, left-most histogram). Freeze-dried particles also remain more stable in serum-containing medium than freshly-prepared particles (upper left). Using DNA-loaded nanoparticles, transfection efficiency is comparable between fresh particles and particles lyophilized with sucrose (right) even after 3 months of storage;

FIG. 15 is Left: brightfield+GFP+DsRed, showing presence of cells (green) being transfected with DsRed (red) on a bone scaffold (brightfield). Right: GFP and DsRed shown only;

FIG. 16 demonstrates that DsRed expression was observed within 4 days and remained very robust even after 12 days: top=1 day, middle=4 days, bottom=12 days after transfection;

FIG. 17 demonstrates the incorporation of DNA-loaded nanoparticles into natural and synthetic scaffolds, disks, microparticles, and hydrogels;

FIG. 18 demonstrates transfection of $GFP^+$ glioblastoma cells with scrambled (control) siRNA (top panels) or siRNA against GFP (bottom);

FIG. 19A-FIG. 19C show activity of R6-series polymers at delivering siRNA to knockdown GFP signal in GB cells; % Knockdown of GFP expression in GFP+ glioblastoma cells transfected with siRNA against GFP, normalized to cells transfected with scrambled siRNA, using various BR6 polymers as a transfection agent: (FIG. 19A) transfection with acrylate-terminated BR6 polymers with either S3, S4 or S5 as the side chain; (FIG. 19B) transfection with E10 end-capped versions of the polymers in FIG. 19A; and (FIG. 19C) GFP fluorescence images of cells transfected with BR6-S4-Ac complexed scrambled RNA (top) vs. siRNA against GFP (bottom);

FIG. 20 shows gel retardation assay of siRNA with BR6-S5-E10 at varying ratios of polymer to RNA. The polymer effectively retards siRNA (top), but in the presence of 5 mM glutathione siRNA is released immediately (bottom). These data demonstrate the hypothesized intracellular release of siRNA and elucidates the mechanism by which nanoparticles formed using BR6 facilitate strong siRNA transfection and GFP knockdown;

FIG. 21 shows that an E10-endcapped polymer (top) retards siRNA efficiently, but upon addition of 5 mM glutathione, siRNA is immediately released (bottom). Numbers refer to the w/w ratio of polymer-to-siRNA in all cases;

FIG. 22 shows that the same base polymer as shown in FIG. 25 with a different endcap (E7, 1-(3-aminopropyl)-4-methylpiperazine) also retards siRNA (top) but is not affected by application of glutathione (bottom);

FIG. 23 provides gel permeation chromatography data of BR6 polymerized with S4 at a BR6:S4 ratio of 1.2:1 at 90° C. for 24 hours, before and after end-capping with E7;

FIG. 24 shows that knockdown efficiency also is affected by molecular weight of the polymer. 1.2:1, 1.1:1, and 1.05:1 refer to the ratio of reactants in the base polymer step growth reaction;

FIG. 25 demonstrates combined DNA (RFP) and siRNA delivery (against GFP) in GB;

FIG. 26 shows that siRNA knockdown is affected by the endcap (E), base polymer (increasing hydrophobicity from L to R within each E), and molecular weight (increasing L to R within each base polymer);

FIG. 27 shows 4410, 200 w/w (blue line on above graph), 8 days after transfection: Left: hMSCs treated with scrambled control; Right: hMSCs treated with siRNA;

FIG. 28 demonstrates that in variable molecular weight embodiments, polymer molecular weight is between 4.00-10.00 kDa for siRNA delivery;

FIG. 29 demonstrates the use of the presently disclosed materials for DNA delivery;

FIG. 30 shows GB Transfection;

FIG. 31 shows 551 GB cells cultured as neurospheres (undifferentiated);

FIG. 32 demonstrates that, for a DNA delivery application, in some embodiments, polymer molecular weight is between 3.00-10.0 kDa;

FIG. 33 provides representative characteristics exhibited by the presently disclosed biodegradable polymers;

FIG. 34 demonstrates the delivery of DNA to GB bulk tumor cells for representative biomaterials;

FIG. 35 demonstrates the transfection of genes to BCSC for representative presently disclosed biomaterials;

FIG. 36 demonstrates the delivery of DNA to fetal (healthy) cells;

FIG. 37 demonstrates the delivery of DNA to BCSCs;

FIG. 38 demonstrates the delivery of apoptosis-inducing genes in BCSCs;

FIG. 39 demonstrates the delivery of apoptosis-inducing genes in BCSCs;

FIG. 40 shows that particles lyophilized with sucrose and used immediately are as effective in transfection as freshly prepared particles;

FIG. 41 demonstrates the use of the presently disclosed materials and methods for long-term gene delivery;

FIG. 42 demonstrates the use of the presently disclosed materials and methods for long-term gene delivery;

FIG. 43 demonstrates siRNA delivery to GB cells;

FIG. 44 provides a comparison of siRNA vs. DNA delivery in GB cells;

FIG. 45 provides a comparison of siRNA vs. DNA delivery in GB cells;

FIG. 46 depicts a strategy of combining nanoparticles within microparticles to extend release further. PLGA or blends of PLGA with the presently disclosed polymers are used to form microparticles by single or double emulsion;

FIG. 47 shows DEAH-FITC release from microparticles comprising a presently disclosed polymer and a peptide ("DEAH" disclosed as SEQ ID NO: 2484);

FIG. 48 shows slow extended release from microparticles containing nanoparticles that contain peptides; and FIG. 49A-FIG. 49C show in vivo effects of microparticle formulations in both the CNV and rho/VEGF model over time.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Peptide/Particle Delivery Systems

The presently disclosed subject matter provides compositions of matter, methods of formulation, and methods of treatment utilizing drug delivery systems comprising one or more degradable polymers and one or more biological agents. The polymers described in these systems must be biodegradable. Mechanisms for this degradability include, but are not limited to, hydrolytic degradation, enzymatic degradation, and disulfide reduction. The biological agents described in these systems include, but are not limited to, therapeutic or diagnostic agents, such as small molecules, peptides, proteins, DNA, siRNA, miRNA, isRNA, contrast agents, and other agents one skilled in the field would wish to encapsulate. In particular embodiments, biological therapeutic agents that are sensitive to degradation and sized approximately 10,000-25,000 Da, including siRNA and peptides, are suitable for use with the presently disclosed materials.

Peptide drugs in polymeric delivery systems are useful for various therapeutic and diagnostic applications. Some embodiments of the presently disclosed subject matter are useful for treating angiogenesis-dependent diseases including, but not limited to, age-related macular degeneration (AMD) and cancer. One particular embodiment of the presently disclosed subject matter includes specific peptide sequences, as well as methods of formulating, stabilizing, and administering these peptides as single agents or as combinations of peptides via polymeric nanoparticle-based, microparticle-based, gel-based, or conjugate-based delivery systems.

The presently disclosed nanoparticles, microparticles, and gels can be used to deliver cargo, for example a therapeutic agent, such as a peptide or protein, to a target, for example, a cell. The cargo delivered by the presently disclosed nanoparticles, microparticles, and gels can act, in some embodiments, as a therapeutic agent or a biosensor agent. Combinations of polymeric materials and cargo, for example a single peptide or combination of peptides, can be formulated by the presently disclosed methods, which allows for the control, or tuning, of the time scale for delivery.

Further, the presently disclosed polymeric materials can be used to form self-assembled electrostatic complexes, micelles, polymersomes, emulsion-based particles, and other particle formulations known to one of ordinary skill in the art. Nanoparticles formed from the presently disclosed polymeric materials can be formulated into larger microparticles to further extend duration and timing of release. Lyophilized formulations that can maintain longer shelf life and stability also are described. The presently disclosed particles can be administered as a powder, cream, ointment, implant, or other reservoir device.

The presently disclosed nanoparticles, microparticles, and gels can be used to treat many diseases and conditions including, but not limited to, all types of cancers, ophthalmic diseases, cardiovascular diseases, and the like. In particular embodiments, the disease or condition treated by the presently disclosed nanoparticles, microparticles, and gels include breast cancer and age-related macular degeneration.

A. Bioreducible and Hydrolytically Degradable Two-Component Degradable Polymers The presently disclosed materials offer several advantages for use in delivering cargo, e.g., a therapeutic agent, such as a peptide or siRNA, to a target, e.g., a cell. Such advantages include a slower degradation in the extracellular environment and a quicker degradation in the intracellular environment. Further, the method of synthesis allows for diversity of monomer starting materials and corresponding facile permutations of polymer structure. The presently disclosed materials can be used to form self-assembled nanoparticles, blended microparticles, gels, and bioconjugates. The presently disclosed polymers also have the following advantages compared to other drug delivery polymers known in the art: a higher polymerization than with disulfide acrylamides, which is important for various applications because it can be used to tune both binding/encapsulation and release; two time scales for degradation (hydrolytic degradation in water and disulfide reduction due to glutathione inside the cell), which facilitates drug release and reduces potential cytotoxicity; tunable structural diversity, with hydrophobic, hydrophilic, and charged moieties to aid in encapsulation of a target biological agent; and, usefulness for drug delivery, including high siRNA delivery, even without end-modification of the polymer.

Certain polyesters have been shown previously to form nanoparticles in the presence of biological agents, such as nucleic acids, and facilitate their entry into a cell. In such materials, release of the nucleic acid is modulated by hydrolytic degradation of the polyester polymer. The addition of a bioreducible disulfide moiety into the backbone of these polymers, however, can specifically target release to the reducing intracellular environment.

Accordingly, a library of bioreducible polyesters can be synthesized by oxidizing and acrylating various mercaptoalcohols (representative diacrylates formed from the presently disclosed synthetic process are shown in Scheme 1 below), then reacting with amine side chains. The structure of a representative bioreducible polyester, e.g., 2,2'-disulfanediylbis(ethane-2,1-diyl) diacrylate (BR6) polymerized with S4, also is shown in Scheme 1.

Scheme 1. Representative diacrylate monomers comprising a disulfide linkage and a representative bioreducible polymer.

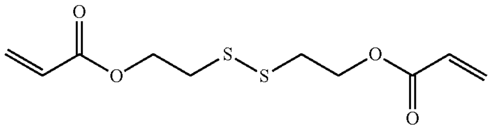

2, 2'-disulfanediylbis(ethane-2, 1-diyl) diacrylate

-continued

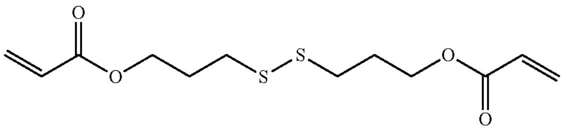

disulfanediylbis(propane-3, 1-diyl) diacrylate

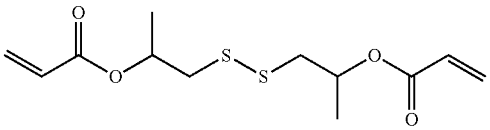

disulfanediylbis(propane-2, 1-diyl) diacrylate

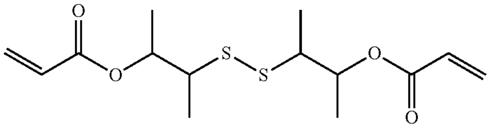

disulfanediylbis(butane-3, 2-diyl) diacrylate

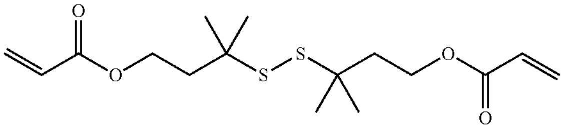

disulfanediylbis(3-methylbutane-3, 1-diyl) diacrylate

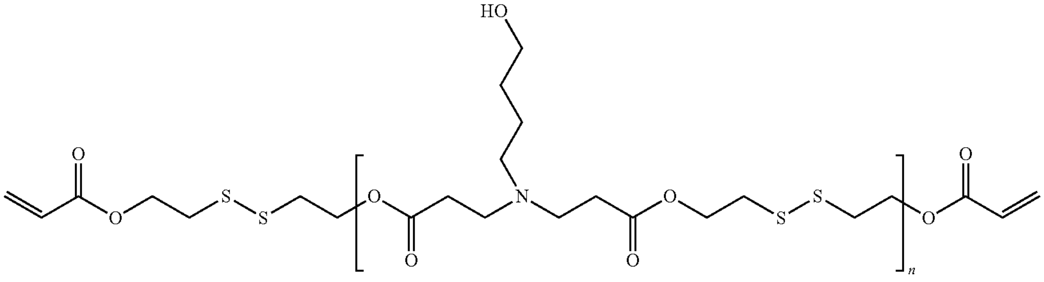

BR6-S4-Ac

In other embodiments, amine-containing molecules can be reacted to terminal groups of the polymer. In particular embodiments, this amine-containing molecule also contains poly(ethylene glycol) (PEG) or a targeting ligand. In other embodiments, the disulfide acrylates are not reacted with amines, but are instead polymerized through other mechanisms including, but not limited to, free radical polymerization to form network polymers and gels. In other embodiments, oligomers are first formed and then the oligomers are polymerized to form block co-polymers or gels.

More particularly, the presently disclosed subject matter provides a bioreducible, hydrolytically degradable polymer of formula (Ia):

(Ia)

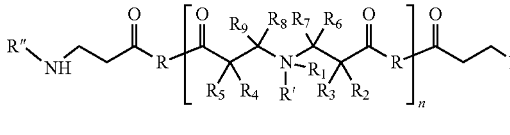

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and wherein at least one R comprises a backbone of a diacrylate having the following structure:

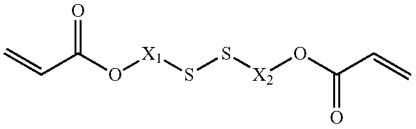

wherein $X_1$ and $X_2$ are each independently substituted or unsubstituted $C_2$-$C_{20}$ alkylene, and wherein each $X_1$ and $X_2$ can be the same or different.

In some embodiments, the bioreducible, hydrolytically degradable polymer of claim 1, wherein at least one R comprises a backbone of a diacrylate selected from the group consisting of:

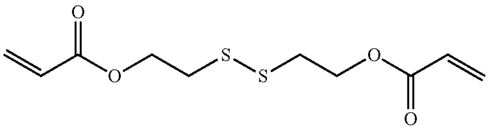
;

2, 2'-disulfanediylbis(ethane-2, 1-diyl) diacrylate

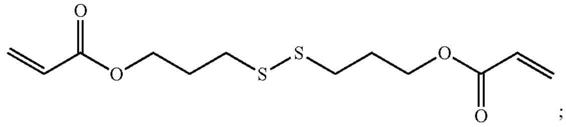
;

disulfanediylbis(propane-3, 1-diyl) diacrylate

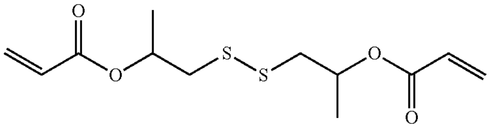
;

disulfanediylbis(propane-2, 1-diyl) diacrylate

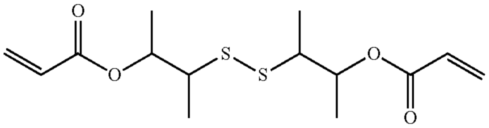
; and disulfanediylbis(butane-3, 2-diyl) diacrylate

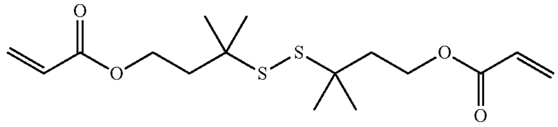
;

disulfanediylbis(3-methylbutane-3, 1-diyl) diacrylate or co-oligomers comprising combinations thereof, wherein the diacrylate can be the same or different.

Additional R, R', and R" groups are defined immediately herein below as for compounds disclosed in International PCT Patent Application Publication No. WO/2010/132879 for "Multicomponent Degradable Cationic Polymers," to Green et al., which is incorporated herein by reference in its entirety.

B. Hydrolytic and Bioreducible Polymeric Particle Formulations for Delivery of Peptides.

Multicomponent degradable cationic polymers suitable for the delivery of peptides to a target are disclosed in International PCT Patent Application Publication No. WO/2010/132879 for "Multicomponent Degradable Cationic Polymers," to Green et al., which is incorporated herein by reference in its entirety. Such polymers, in addition to the presently disclosed polymers can be used to deliver cargo, e.g., a therapeutic agent, to a target, e.g., a cell.

In some embodiments, the presently disclosed subject matter generally provides multicomponent degradable cationic polymers. In some embodiments, the presently disclosed polymers have the property of biphasic degradation. Modifications to the polymer structure can result in a change in the release of therapeutic agents, which can occur over multiple time scales. In some embodiments, the presently disclosed polymers include a minority structure, e.g., an endcapping group, which differs from the majority structure comprising most of the polymer backbone. In other embodiments, the bioreducible oligomers form block copolymers with hydrolytically degradable oligomers. In yet other embodiments, the end group/minority structure comprises an amino acid or chain of amino acids, while the backbone degrades hydrolytically and/or is bioreducible.

As described in more detail herein below, small changes in the monomer ratio used during polymerization, in combination with modifications to the chemical structure of the end-capping groups used post-polymerization, can affect the efficacy of delivery of a therapeutic agent to a target. Further, changes in the chemical structure of the polymer, either in the backbone of the polymer or end-capping groups, or both, can change the efficacy of target delivery to a cell. In some embodiments, small changes to the molecular weight of the polymer or changes to the endcapping groups of the polymer, while leaving the main chain, i.e., backbone, of the polymer the same, can enhance or decrease the overall delivery of the target to a cell. Further, the "R" groups that comprise the backbone or main chain of the polymer can be selected to degrade via different biodegradation mechanisms within the same polymer molecule. Such mechanisms include, but are not limited to, hydrolytic, bioreducible, enzymatic, and/or other modes of degradation.

In some embodiments, the presently disclosed compositions can be prepared according to Scheme 2:

Scheme 2. Representative synthesis scheme for preparing the presently disclosed polymers having biphasic biodegradation.

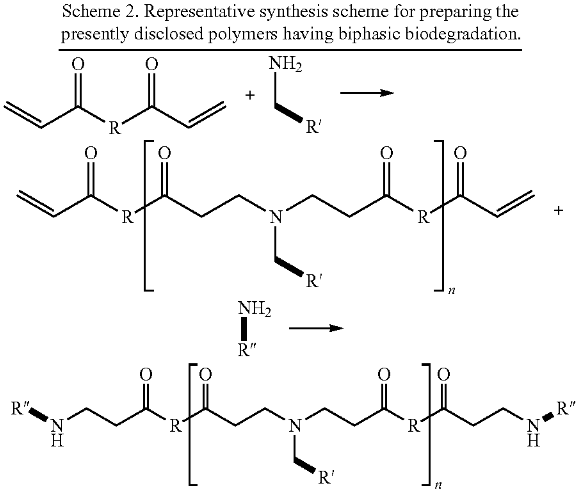

In some embodiments, at least one of the following groups R, R', and R" contain reducible linkages and, for many of the presently disclosed materials, additional modes of degradation also are present. More generally, R' can be any group that facilitates solubility in water and/or hydrogen bonding, for example, OH, $NH_2$ and SH. Representative degradable linkages include, but are not limited to:

Enzymatic Degradation ester

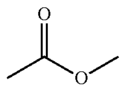

disulfide

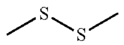

amide

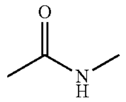

anhydride

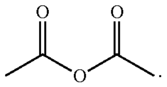

The end group structures, i.e., R" groups in Scheme 2, for the presently disclosed cationic polymers are distinct and separate from the backbone structures (R) structures, the side chain structures (R'), and end group structures of the intermediate precursor molecule for a given polymeric material.

More particularly, in some embodiments, the presently disclosed subject matter includes a nanoparticle, microparticle, or gel comprising a compound of formula (I):

(I)

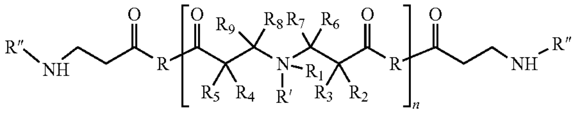

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and at least one of R, R', and R" comprise a reducible or degradable linkage, and wherein each R, R', or R" can independently be the same or different;

under the proviso that when at least one R group comprises an ester linkage of the formula —C(═O)—O— and the compound of formula (I) comprises a poly (beta-amino ester), then the compound of formula (I) must also comprise one or more of the following characteristics:

(a) each R group is different;

(b) each R" group is different;

(c) each R" group is not the same as any of R', $R_1$, $R_2$, $R_3$, $R_4$, $R_5$, $R_6$, $R_7$, $R_8$, and $R_9$;

(d) the R" groups degrade through a different mechanism than the ester-containing R groups, wherein the degradation of the R" group is selected from the group consisting of a bioreducible mechanism or an enzymatically degradable mechanism; and/or (e) the compound of formula (I) comprises a substructure of a larger cross-linked polymer, wherein the larger cross-linked polymer comprises different properties from compound of formula (I);

and one or more peptides selected from the group consisting of an anti-angiogenic peptide, an anti-lymphangiogenic peptide, an anti-tumorigenic peptide, and an anti-permeability peptide.

In some embodiments of the nanoparticle, microparticle, or gel n is an integer from 1 to 1,000; in some embodiments, n is an integer from 1 to 100; in some embodiments, n is an integer from 1 to 30; in some embodiments, n is an integer from 5 to 20; in some embodiments, n is an integer from 10 to 15; and in some embodiments, n is an integer from 1 to 10.

In particular embodiments, the reducible or degradable linkage comprising R, R', and R" is selected from the group consisting of an ester, a disulfide, an amide, an anhydride or a linkage susceptible to enzymatic degradation, subject to the proviso provided hereinabove.

In more particular embodiments, R comprises a backbone of a diacrylate selected from the group consisting of:

(B3)

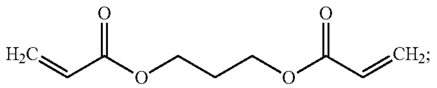

(B3b)

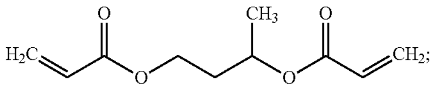

(B4)

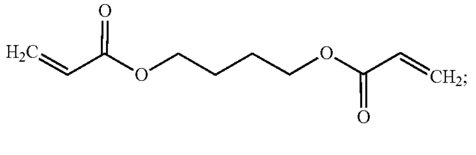

(B5)

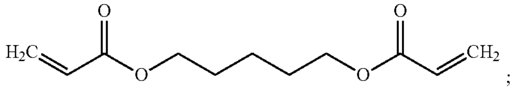

-continued
(B6)
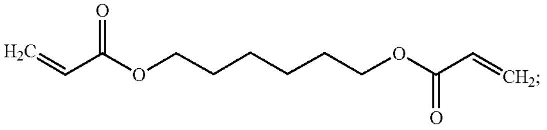
(B8)
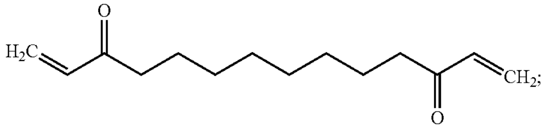
(BSS)
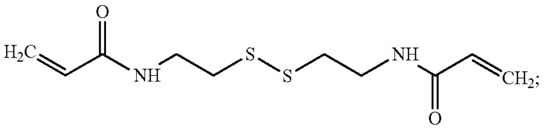
(BL1)
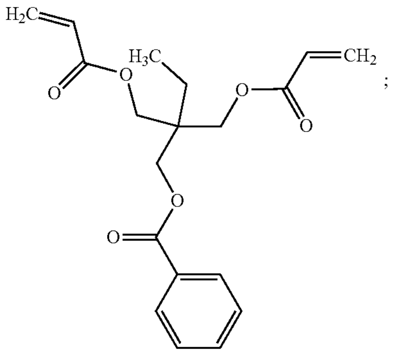
(BL2)
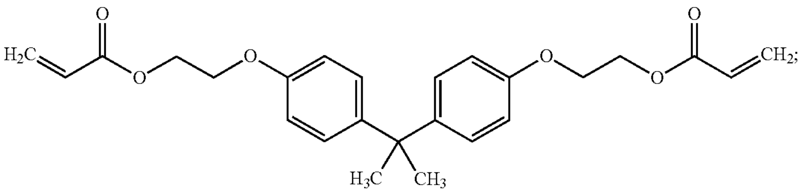
(BH1)
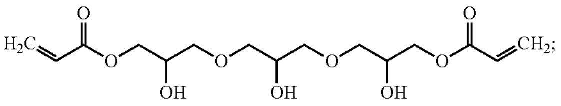
(BP1)
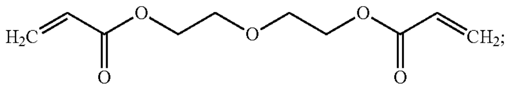
(BP2)
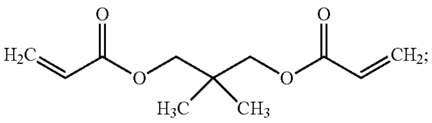
(BP3)
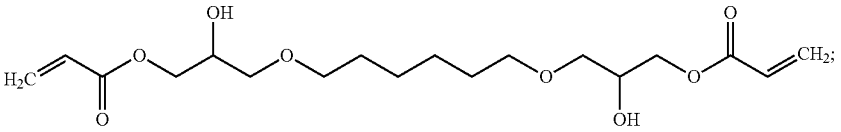
(BP4)
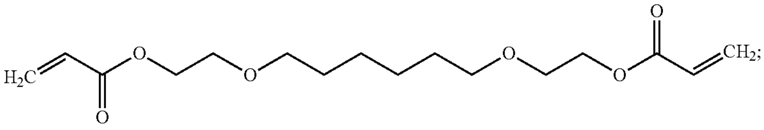
and
(BP5)
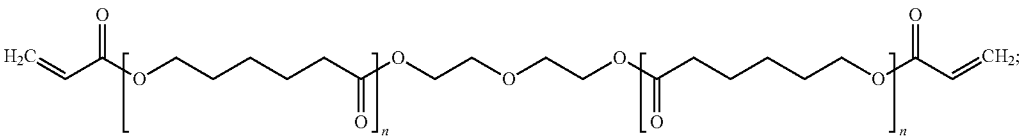
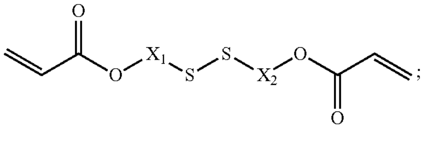
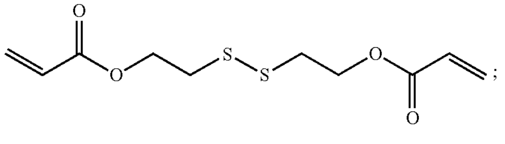
2,2′-disulfanediylbis(ethane-2,1-diyl) diacrylate -continued

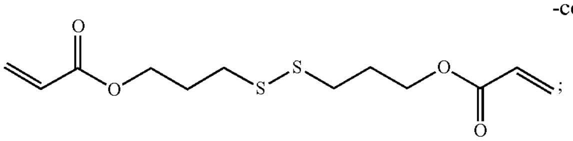

disulfanediylbis(propane-3,1-diyl) diacrylate

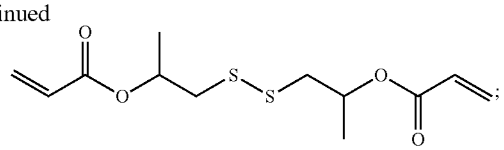

disulfanediylbis(propane-2,1-diyl) diacrylate

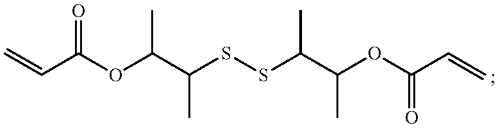

and disulfanediylbis(butane-3,2-diyl) diacrylate

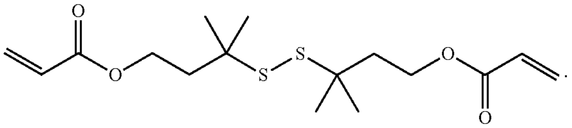

disulfanediylbis(3-methylbutane-3,1-diyl) diacrylate

In some embodiments, wherein R' comprises a side chain derived from compound selected from the group consisting of:

(S3)

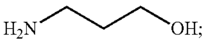

(S4)

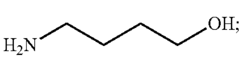

(S5)

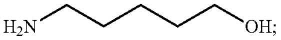

(S6)

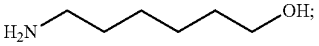

(S7)

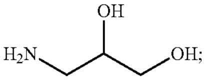

(S8)

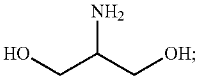

(S9)

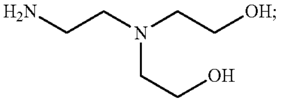

(S10)

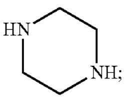

(S11)

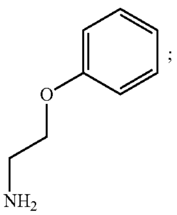

(S12)

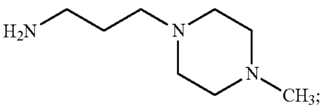

and

-continued (S13)

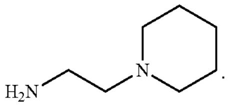

In some embodiments, R" comprises an end group derived from a compound selected from the group consisting of (E1)

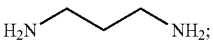

(E2)

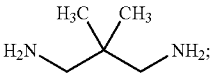

(E3)

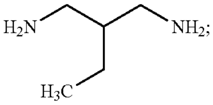

(E4)

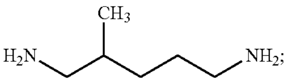

(E5)

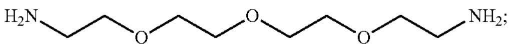

(E6)

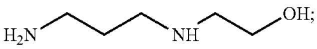

(E7)

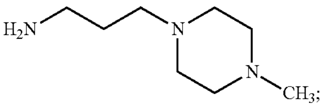

(E8)

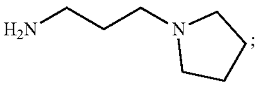

(E9)

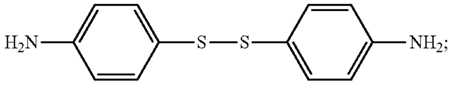

(E10)

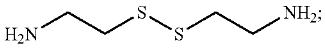

-continued (E11)

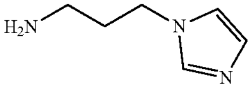

;

(E12)

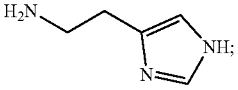

;

(E13)

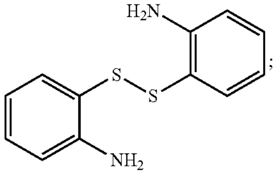

; and (E14)

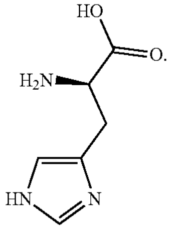

.

In other embodiments, the compound of formula (I) is subject to the further proviso that if at least one R group comprises an ester linkage, then the R" groups impart one or more of the following characteristics to the compound of formula (I): independent control of cell-specific uptake and/or intracellular delivery of a particle; independent control of endosomal buffering and endosomal escape; independent control of DNA release; triggered release of an active agent; modification of a particle surface charge; increased diffusion through a cytoplasm of a cell; increased active transport through a cytoplasm of a cell; increased nuclear import within a cell; increased transcription of an associated DNA within a cell; increased translation of an associated DNA within a cell; increased persistence of an associated therapeutic agent within a cell, wherein the therapeutic agent is selected from the group consisting of DNA, RNA, a peptide or a protein.

More particularly, any poly(beta-amino ester) specifically disclosed or claimed in U.S. Pat. Nos. 6,998,115; 7,427,394; U.S. patent application publication no. US2005/0265961; and U.S. patent publication no. US2010/0036084, each of which is incorporated herein by reference in its entirety, is explicitly excluded from the presently disclosed compounds of formula (I). In particular, the poly(beta-amino ester)s disclosed in U.S. Pat. Nos. 6,998,115; 7,427,394; U.S. patent application publication no. US2005/0265961; and U.S. patent publication no. US2010/0036084 are symmetrical, i.e., both R groups as defined in formula (I) herein are the same. In certain embodiments of the presently disclosed compounds of formula (I), when at least one R comprises an ester linkage, the two R groups of formula (I) are not the same, i.e., in such embodiments, the compounds of formula (I) are not symmetrical.

In particular embodiments, the reducible or degradable linkage comprising R, R', and R" is selected from the group consisting of an ester, a disulfide, an amide, an anhydride or a linkage susceptible to enzymatic degradation, subject to the above-mentioned provisos.

Further, in some embodiments of the compound of formula (I), n is an integer from 1 to 1,000; in other embodiments, n is an integer from 1 to 100; in other embodiments, n is an integer from 1 to 30; in other embodiments, n is an integer from 5 to 20; in other embodiments, n is an integer from 10 to 15; and in other embodiments, n is an integer from 1 to 10.

In some embodiments, R" can be an oligomer as described herein, e.g., one fully synthesized primary amine-terminated oligomer, and can be used as a reagent during the second reaction step of Scheme 2. This process can be repeated iteratively to synthesize increasingly complex molecules.

In other embodiments, R" can comprise a larger biomolecule including, but not limited to, poly(ethylenegly col) (PEG), a targeting ligand, including, but not limited to, a sugar, a small molecule, an antibody, an antibody fragment, a peptide sequence, or other targeting moiety known to one skilled in the art; a labeling molecule including, but not limited to, a small molecule, a quantum dot, a nanoparticle, a fluorescent molecule, a luminescent molecule, a contrast agent, and the like; and a branched or unbranched, substituted or unsubstituted alkyl chain.

In some embodiments, the branched or unbranched, substituted or unsubstituted alkyl chain is about 2 to about 5 carbons long; in some embodiments, the alkyl chain is about 6 to about 8 carbons long; in some embodiments, the alkyl chain is about 9 to about 12 carbons long; in some embodiments, the alkyl chain is about 13 to about 18 carbons long; in some embodiments, the alkyl chain is about 19 to about 30 carbons long; in some embodiments, the alkyl chain is greater than about 30 carbons long.

In certain embodiments, both R" groups, i.e., the end groups of the polymer, comprise alkyl chains. In other embodiments, only one R" group comprises an alkyl chain. In some embodiments, at least one alkyl chain is terminated with an amino ($NH_2$) group. In other embodiments, the at least one alkyl chain is terminated with a hydroxyl (OH) group.

In some embodiments, the PEG has a molecular weight of about 5 kDa or less; in some embodiments, the PEG has a molecular weight of about 5 kDa to about 10 kDa; in some embodiments, the PEG has a molecular weight of about 10 kDa to about 20 kDa; in some embodiments, the PEG has a molecular weight of about 20 kDa to about 30 kDa; in some embodiments, the PEG is greater than 30 kDa. In certain embodiments, both R" groups comprise PEG. In other embodiments, only one R" group comprises PEG.

Further, in some embodiments, one R" group is PEG and the other R" group is a targeting ligand and/or labeling molecule as defined herein above. In other embodiments, one R" group is an alkyl chain and the other R" group is a targeting ligand and/or labeling molecule.

Representative monomers used to synthesize the presently disclosed cationic polymers include, but are not limited to, those provided immediately herein below. The presently disclosed subject matter is not limited to the representative monomers disclosed herein, but also includes other structures that one skilled in the art could use to create similar biphasic degrading cationic polymers. For each type of cargo, a particular biodegradable polymer can be tuned through varying the constituent monomers used to form the backbone (designated as "B" groups), side-chains (designated as "S" groups), and end-groups (designated as "E" groups) of the polymer.

Scheme 3. Example structures of backbone ('B" or R), side chain ('S" or R'), and end groups. ("E" or R")

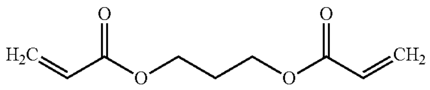
1-3-propanediol diacrylate
(B3)

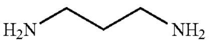
propane-1, 3-diamine
(E1)

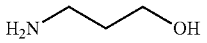
3-amino-1-propanol
(B3b)

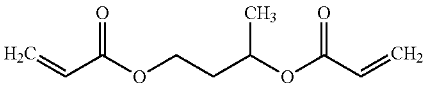
1-3-butanediol diacrylate
(S3)

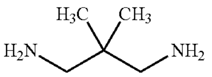
2,2-dimethylpropane-1, 3-diamine
(E2)

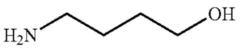
4-amino-1-butanol
(S4)

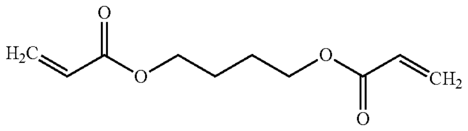
1, 4-butanediol diacrylate
(B4)

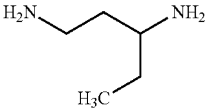
pentane-1, 3-diamine
(E3)

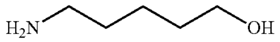
5-amino-1-pentanol
(B5)

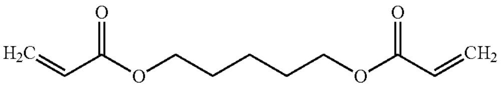
1, 5-pentanediol diacrylate
(S5)

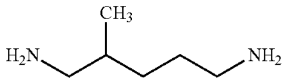
2-methylpentane-1, 5-diamine
(E4)

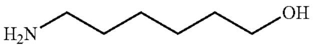
6-amino-1-hexanol
(S6)

Scheme 3 (continued). Example structures of backbone ("B" or R), side chain ("S" or R'), and end groups. ("E" or R")

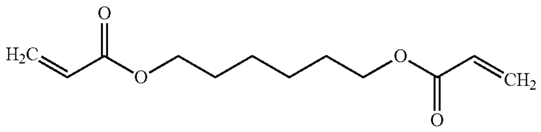
1, 6-hexanediol diacrylate
(B6)

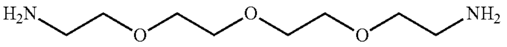
$(PEO)_4$-bis-amine
(E5)

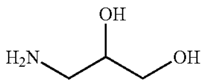
3-aminopropane-1, 2-diol
(S7)

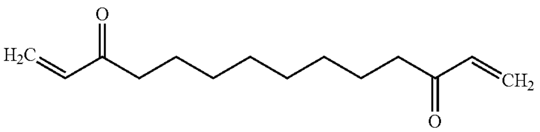
1, 8-octanediol diacrylate
(B8)

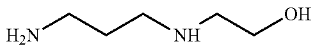
2-(3-aminopropylamino)etanol
(E6)

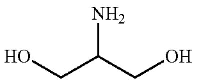
2-aminopropane-1, 3-diol
(S8)

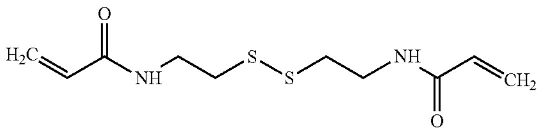
N, N'-bis(acrylyl)cystamine
(BSS)

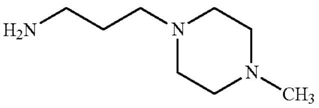
1-(3-aminopropyl)-4-methylpiperazine
(E7)

-continued (S9)

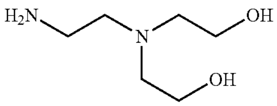

2, 2'-(2-aminoethylazanediyl)diethanol (BL1)

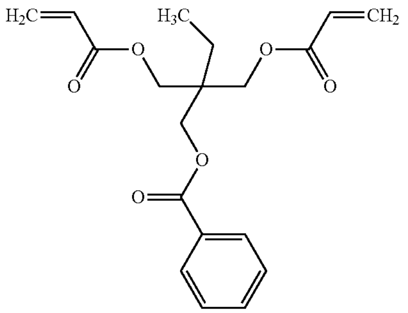

trimethylolpropane benzoate diacrylate (E8)

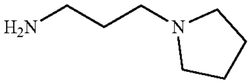

1-(3-aminopropyl)pyrrolidine (S10)

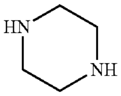

piperazine

Scheme 3 (continued). Example structures of backbone ("B" or R), side chain ("S" or R'), and end groups. ("E" or R")

(BL2)

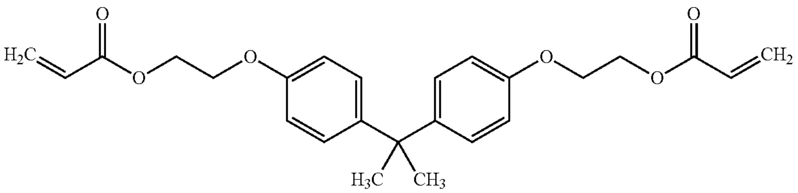

ethoxylated bisphenol A diacrylate (E9)

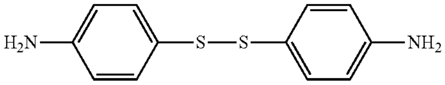

4-aminophenyl disulfide (S11)

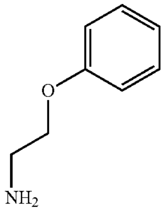

2-phenoxyethanamine (BH1)

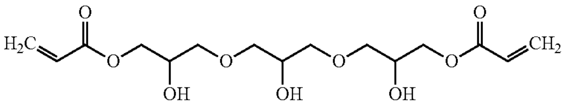

glycerol 1, 3-diglycerolate diacylate (E10)

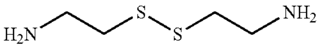

cystamine (BP1)

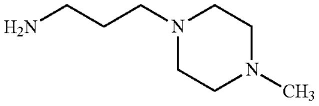

1-(3-aminopropyl)-4-methylpiperazine (S12)

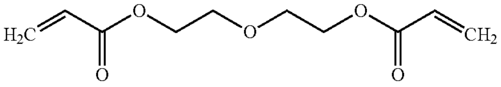

di(ethylene glycol) diacrylate (E11)

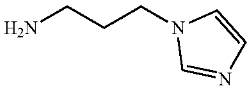

N-(3-aminopropyl)-imidazole (S13)

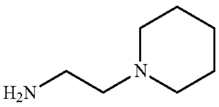

1-(2-Aminoethyl)piperidine

-continued (BP2)

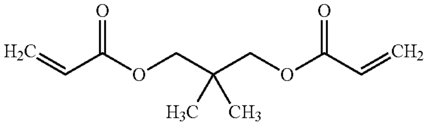

Neopentyl glycol diacrylate (E12)

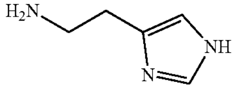

histamine

Scheme 3 (continued). Example structures of backbone ("B" or R), side chain ("S" or R'), and end groups. ("E" or R")

(BP3)

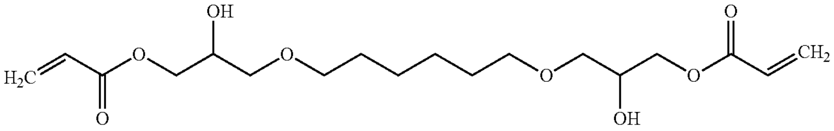

1, 6-Hexanediylbis[oxy(2-hydroxy-3, 1-propanediyl] bisacrylate (E13)

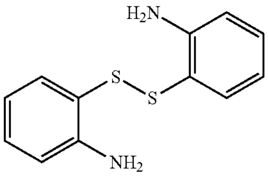

2, 2'-dithiobis-benzenamine (BP4)

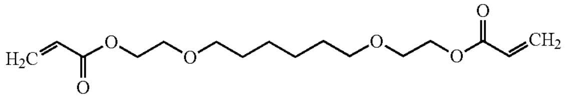

2, 2'-(hexane-1, 6-diylbis(oxy)bis(ethene-2, 1-diyl) diacrylate (E14)

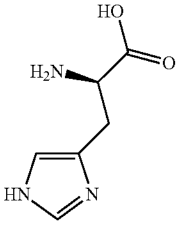

D-histidine (BP5)

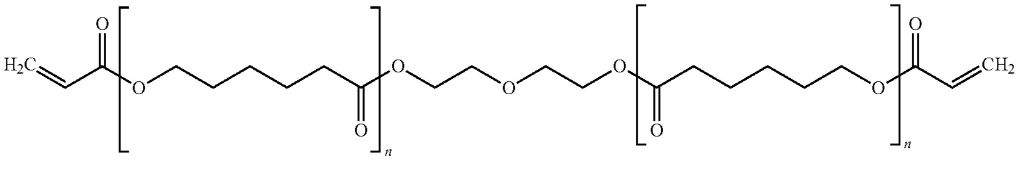

polycaprolactone diacrylate

In particular embodiments, as depicted in Scheme 4, the presently disclosed cationic polymers comprise a polyalcohol structure, i.e., the side chain represented by R' in Scheme 2 comprises an alcohol.

Scheme 4. Representative synthesis scheme for preparing the presently disclosed cationic polymers having an alcohol side chain.

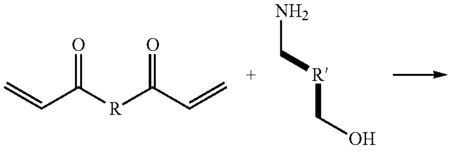

-continued

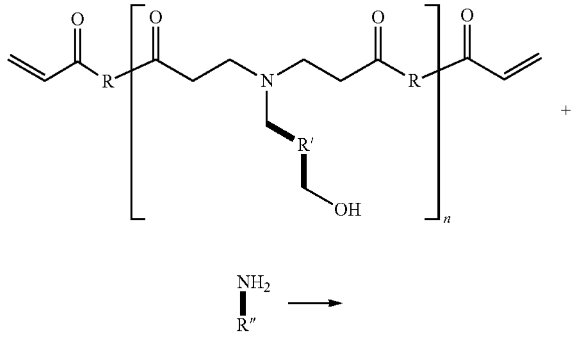

-continued

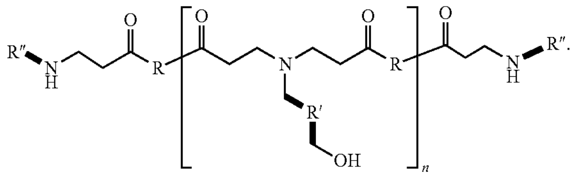

In such embodiments, the end group structures (R") and the backbone structures (R) are defined as above and the side chain must contain at least one hydroxyl (OH) group.

In yet other embodiments, the presently disclosed cationic polymer comprises a specific poly(ester amine) structure with secondary non-hydrolytic modes of degradation. In such embodiments, the cationic polymer comprises a polyester that degrades through ester linkages (hydrolytic degradation) that is further modified to comprise bioreducible groups as end (R") groups.

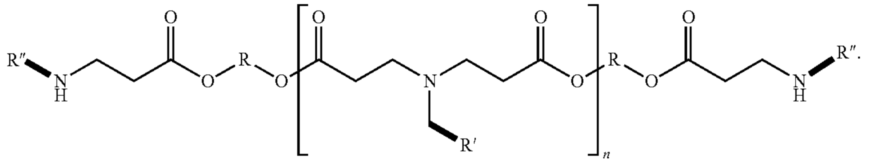

Representative bioreducible end groups in such embodiments include, but are not limited to:

E9

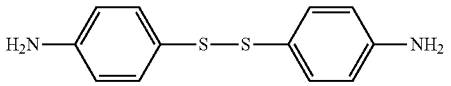

4-aminophenyl disulfide

E10

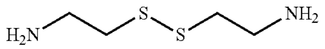

cystamine

E13

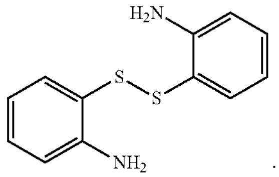

.

2-2′-dithiobis-benzenamine

In some embodiments, the presently disclosed cationic polymer comprises a specific poly(ester amine alcohol) structure with secondary non-hydrolytic modes of degradation. In such embodiments, the cationic polymer comprises a specific structure where a polyester that degrades through ester linkages (hydrolytic degradation) is modified to contain bioreducible groups as end groups.

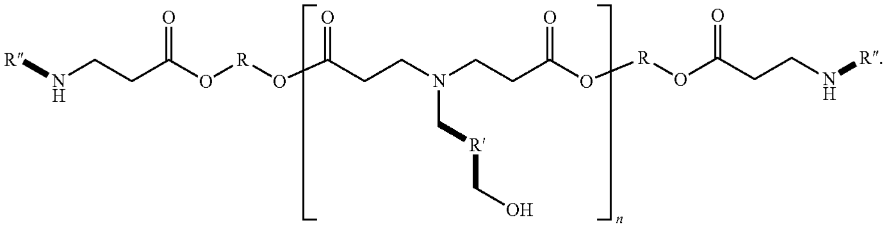

In yet other embodiments, the presently disclosed cationic polymer comprises a specific poly(amido amine) structure having disulfide linking groups in the polymer backbone and an independent, non-reducible amine contacting group at the terminal ends of the polymer.

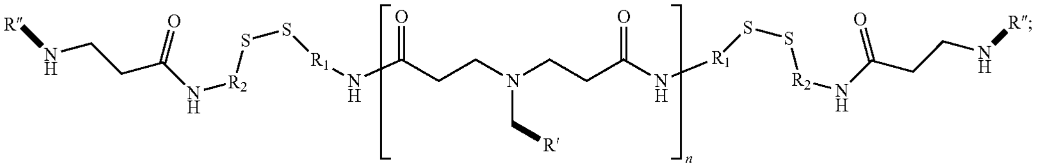

In such embodiments, $R_1$ and $R_2$ are alkyl chains. In some embodiments, the alkyl chain is 1-2 carbons long; in some embodiments, the alkyl chain is 3-5 carbons long; in some embodiments, the alkyl chain is 6-8 carbons long; in some embodiments, the alkyl chain is 9-12 carbons long; in some embodiments, the alkyl chain is 13-18 carbons long; in some embodiments, the alkyl chain is 19-30 carbons long; and in some embodiments, the alkyl chain is greater than 30 carbons long Suitable non-reducible amino R" groups for such embodiments include, but are not limited to:

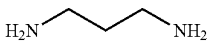

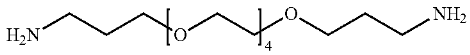

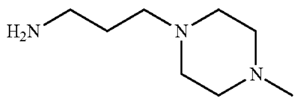

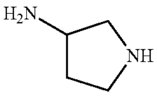

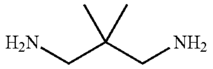

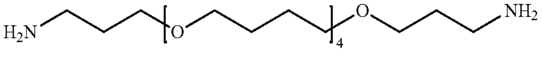

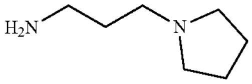

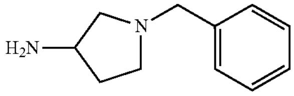

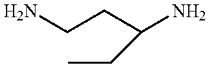

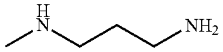

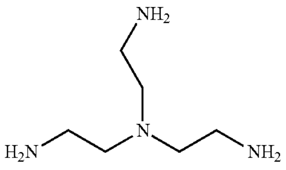

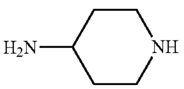

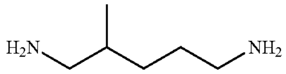

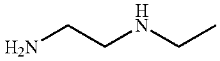

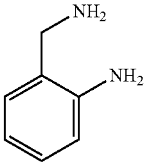

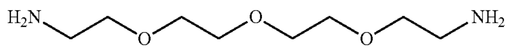

-continued

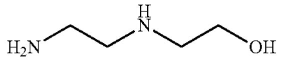

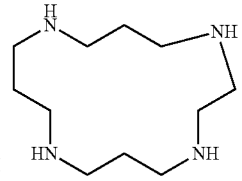

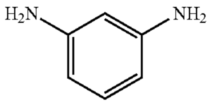

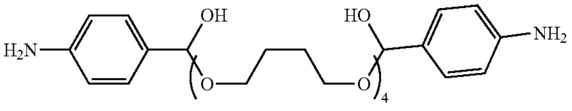

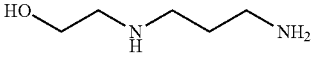

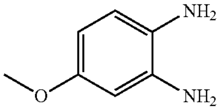

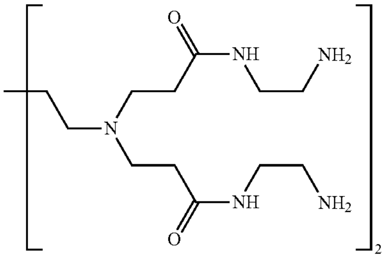

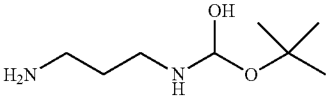

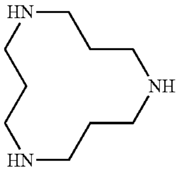

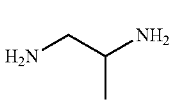

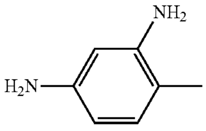

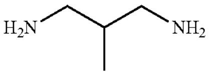

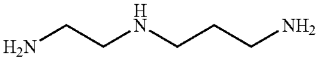

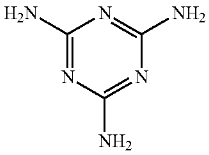

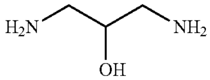

-continued
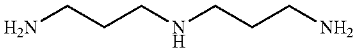
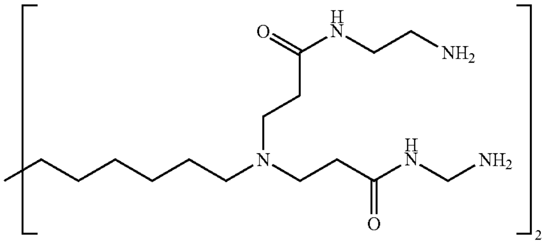
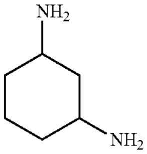
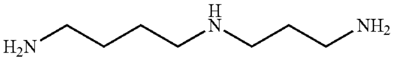
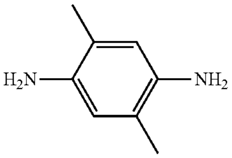
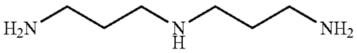
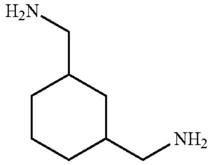
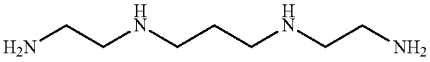
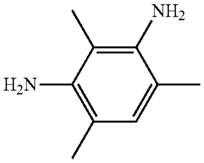
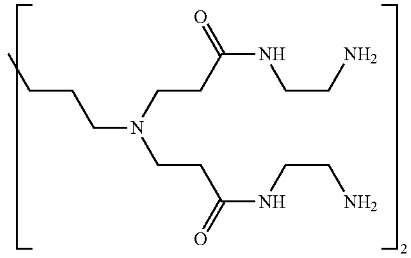
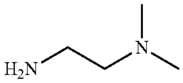
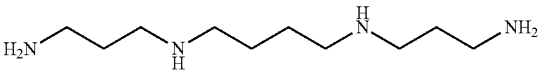
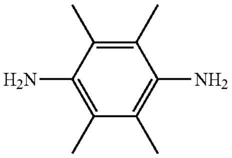
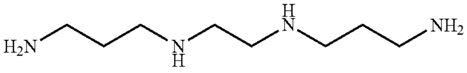
-continued
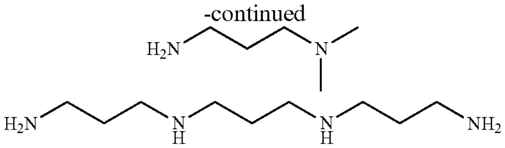
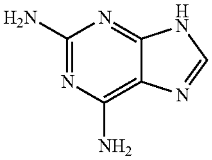
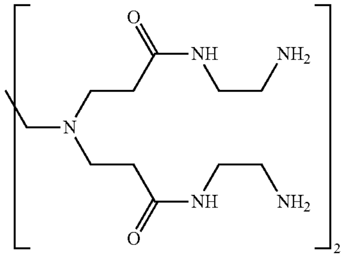
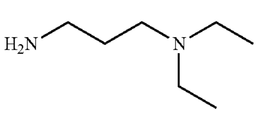
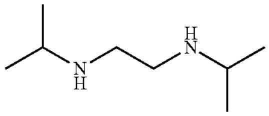
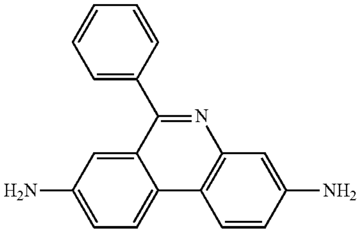
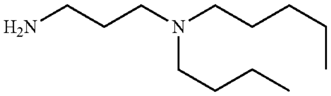
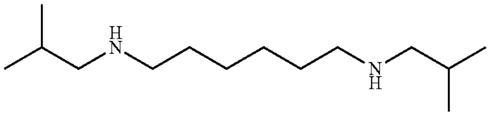
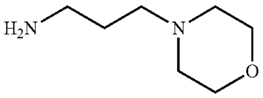
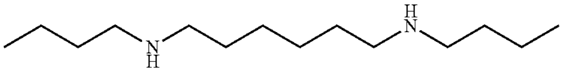
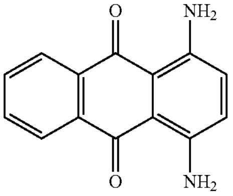
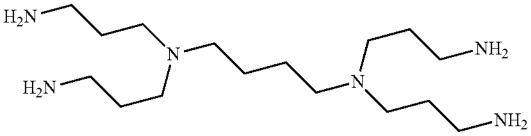
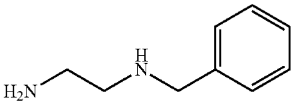

-continued

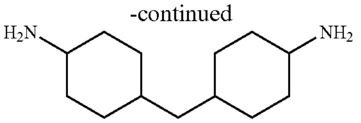

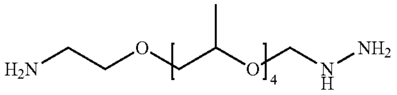

226 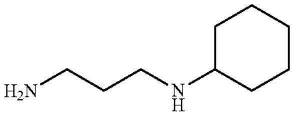

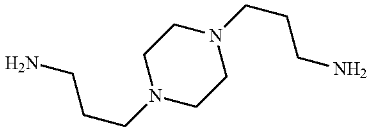

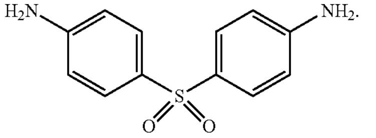

In other embodiments, the presently disclosed cationic polymers comprise a specific poly(amido amine alcohol) structure having disulfide linking groups in the polymer backbone and an independent non-reducible amine contacting group at the terminal ends of the polymer.

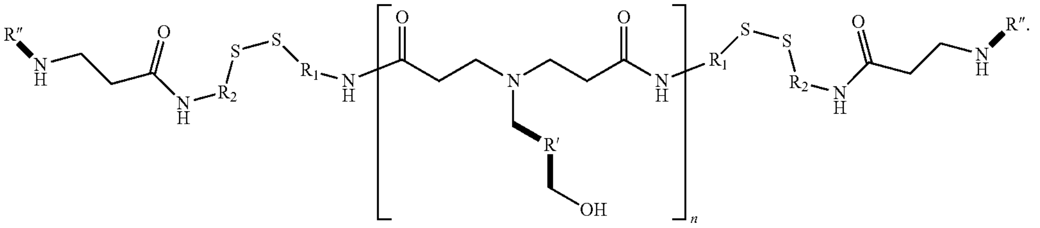

In yet other embodiments, the presently disclosed cationic polymer comprises a copolymer of representative oligomers as described hereinabove. Such embodiments include, but are not limited to, a poly(amido amine) structure having disulfides in the polymer backbone and an independently degradable (non-reducible) group at at least one end of the polymer. Such embodiments also include using a cross-linker to add bioreducible linkages to hydrolytically degradable materials and also provide for higher molecular weight materials. A representative example of this embodiment, along with suitable monomers is as follows:

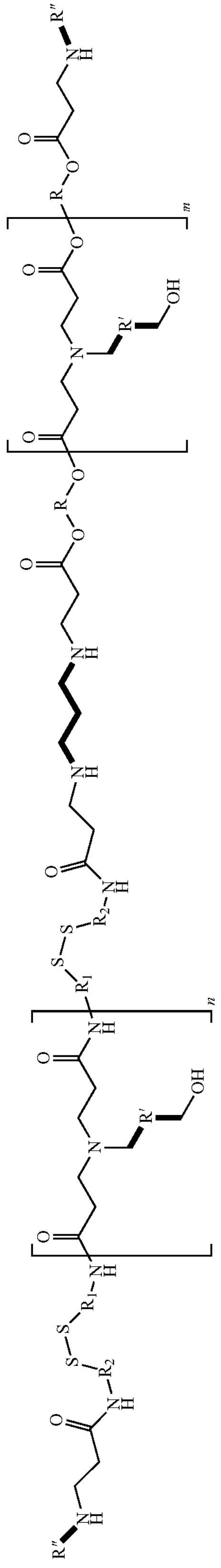
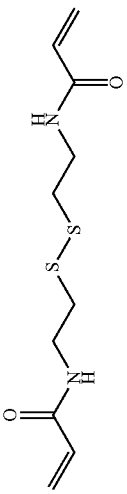
N,N'-bis(acrylyl)cystamine
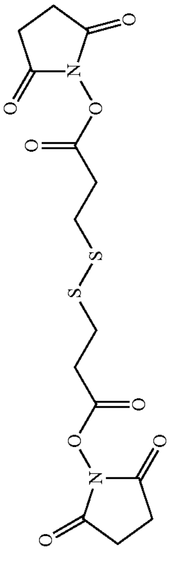
dithiobis(succinimidyl propionate)
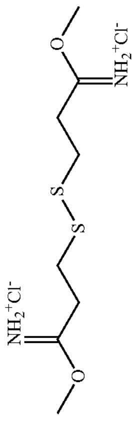
dimethyl-3,3'-dithiobispropionimidate
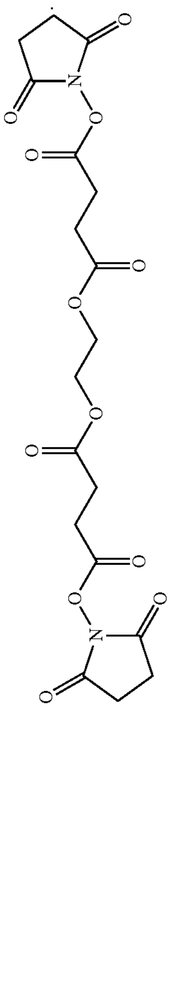
ethylene glycol bis(succinimidylsuccinate)

In particular embodiments, the presently disclosed polymer is selected from the group consisting of:
B4-S5-E9
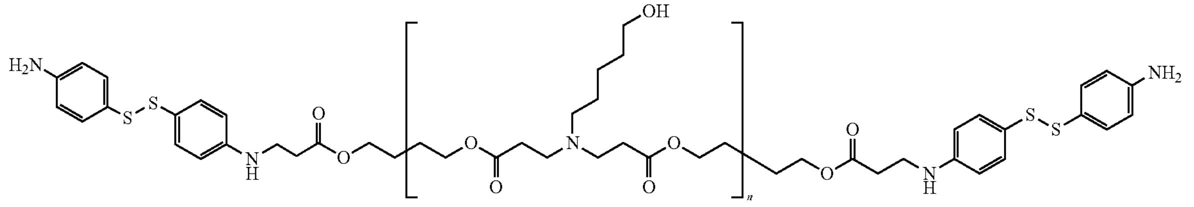
B3b-S4-E9
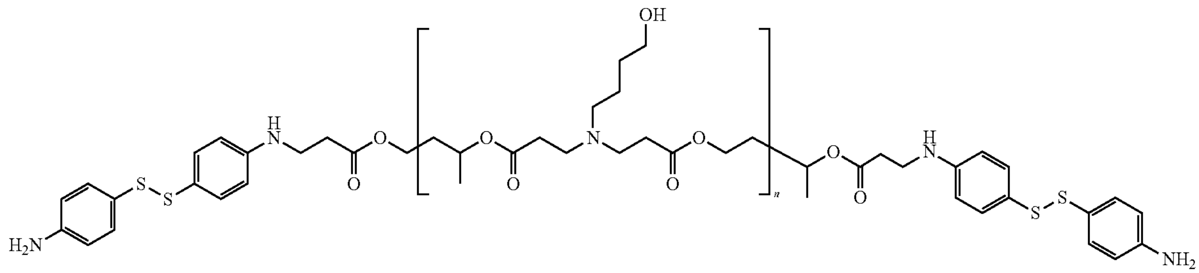
SL2-S5-E10
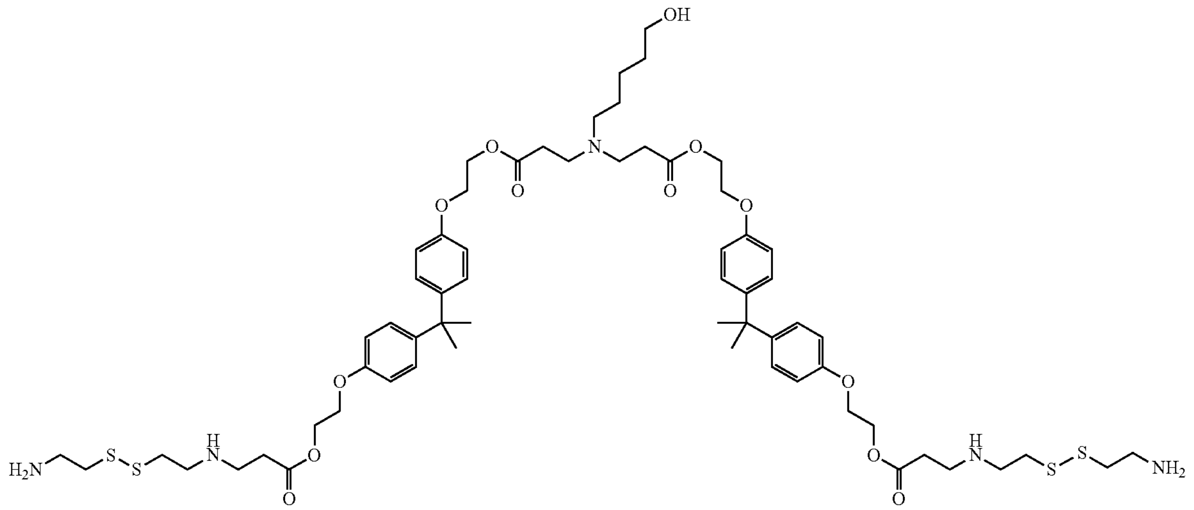
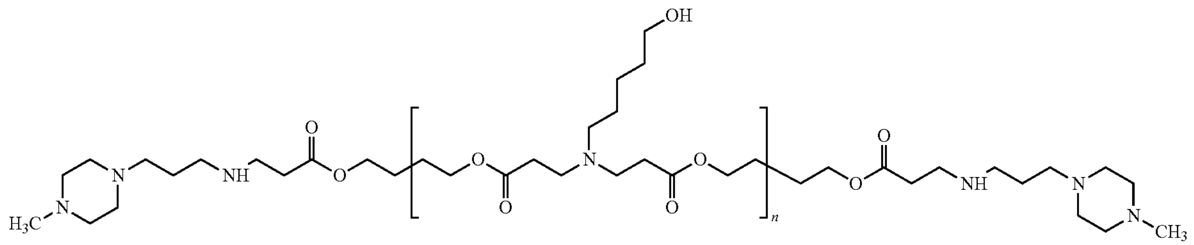
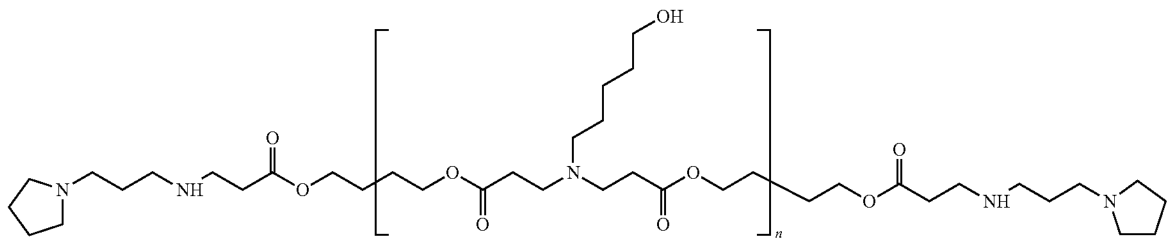

-continued

B3-S6-E7

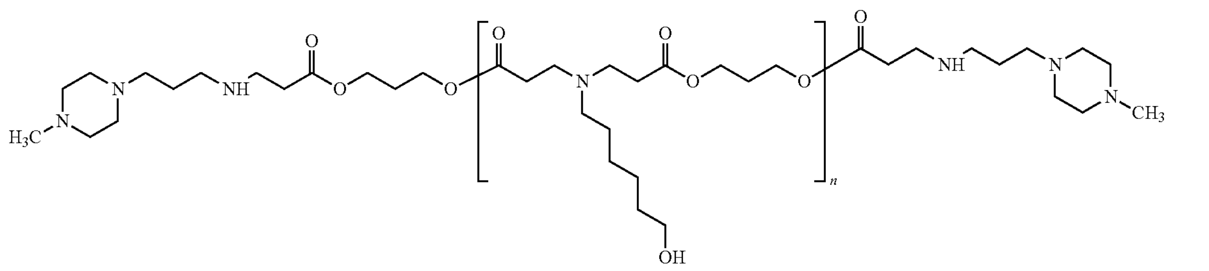

B5-S4-E10

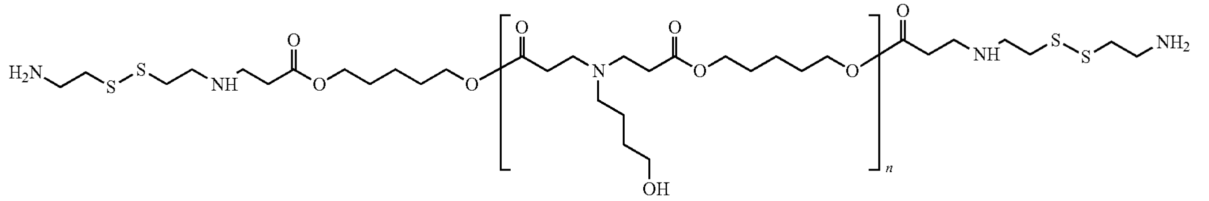

BSS-S3-E8

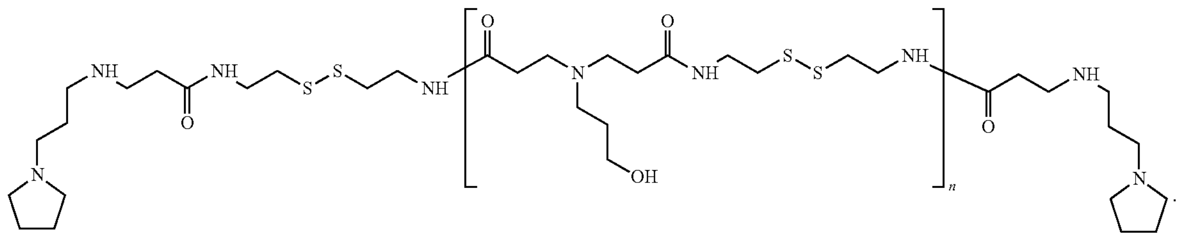

Further aspects of the presently disclosed subject matter include: (a) the R substituent groups that make up the presently disclosed polymers degrade via different biodegradation mechanisms within the same polymer. These biodegradation mechanisms can include hydrolytic, bioreducible, enzymatic, and/or other modes of degradation; (b) the ends of the polymer include a minority structure that differs from the majority structure that comprises most of the polymer backbone; (c) in several embodiments, the side chain molecules contain hydroxyl (OH)/alcohol groups.

In some embodiments: (a) the backbone is bioreducible and the end groups of the polymer degrade hydrolytically; (b) the backbone degrades hydrolytically and the end groups are bioreducible; and (c) hydrolytically degradable oligomers are cross-linked with a bioreducible cross-linker; (d) bioreducible oligomers form block copolymers with hydrolytically degradable oligomers; and (e) the end group/minority structure comprises an amino acid or chain of amino acids, whereas the backbone degrades hydrolytically and/or is bioreducible.

One way to synthesize the presently disclosed materials is by the conjugate addition of amine-containing molecules to acrylates or acrylamides. This reaction can be done neat or in a solvent, such as DMSO or THF. Reactions can take place at a temperature ranging from about room temperature up to about 90° C. and can have a duration from about a few hours to about a few weeks. The presently disclosed methods can be used to create linear or branched polymers. In some embodiments, the molecular weight (MW) has a range from about 1 kDa to about 5 kDa, in other embodiments, the MW has a range from about 5 kDa to about 10 kDa, in other embodiments the MW has a range from about 10 kDa to about 15 kDa, in other embodiments, the MW has a range from about 15 kDa to about 25 kDa, in other embodiments, the MW has a range from about 25 kDa to about 50 kDa, and in other embodiments, the MW has a range from about 50 kDa to about 100 kDa. In other embodiments, the polymer forms a network, gel, and/or scaffold of apparent molecular weight greater than 100 kDa.

In particular embodiments, the presently disclosed subject matter provides hydrolytic and bioreducible polymeric particle formulations for the delivery of one or more peptides to a target. In some embodiments of the presently disclosed formulations, the particles are nanoparticles and, in other embodiments, they are microparticles. Some applications are to cancer and others are to ophthalmic diseases.

Accordingly, in some embodiments, the presently disclosed approach includes degradable nanoparticles, microparticles, and gels that release a peptide, which is capable of therapeutic activity through multiple modes of action. The presently disclosed peptides can simultaneously inhibit: (1) endothelial cell proliferation; (2) endothelial cell adhesion, (3) endothelial cell migration, (4) tumor cell proliferation, (5) tumor cell adhesion, and (6) tumor cell migration.

When combined with such peptides, the presently disclosed nanoparticles, microparticles, and gels: (1) protect and increase the persistence of the peptides that would otherwise be rapidly cleared in vivo; (2) allow passive targeting of tumor vasculature via nanoparticle biophysical properties to enable enhanced efficacy at the target site of action; (3) enable extended peptide release and minimized dosing schedules for affected patients; and (4) facilitate a continuous peptide concentration rather than a pulsatile profile that would be caused by bolus injections and fast clearance.

The presently disclosed microparticles have similar benefits to the nanoparticles except that they also persist longer and have an easier route for clinical administration. On the other hand, another advantage of the presently disclosed nanoparticles is that they are better able to passively target the peptides to tumor vasculature than are the microparticles. Representative embodiments of the presently disclosed microparticles are provided in Example 10, herein below.

Further, in some embodiments, one or more peptides, which can be the same or different, can be combined, e.g., encapsulated, directly or individually into different nanoparticles that then can be combined into the same microparticles.

C. Biodegradable Nanoparticles for Sustained Peptide Delivery

Selected polymers are able to encapsulate selected peptides possessing varied chemical properties. Changes to polymer structure, including small changes to the ends of the polymer only, can vary biophysical properties of these particles. These properties can be important to tune for effective in vivo peptide delivery. A small subset of the potential polymer library was screened to measure the effect of encapsulating the antiangiogenic peptides chemokinostatin-1 and pentastatin-1 within polymeric particles compared to unencapsulated, free peptides. Polymeric encapsulation of peptides enhanced the ability of the peptides to inhibit the proliferation of endothelial cells. An example of representative polymers encapsulating peptides is provided in Scheme 5.

| Name | Sequence | Theor. Pl | MW |
|---|---|---|---|
| DEAH box poly8 ("DEAH" disclosed as SEQ ID NO: 2484) | EIELVEEEP PF (SEQ ID NO: 2485) | 3.51 | 1330.45 |
| Wispostatin-1 | SPWSPCSTS CGLGVSTRI (SEQ ID NO: 2360) | 7.80 | 1838.08 |
| Pentastatin | LRRFSTMPF MFCNINNVC NF (SEQ ID NO: 2375) | 9.02 | 2454.93 |
| Chemokinostatin | NGRKACLNP ASPIVKKII EKMLNS (SEQ ID NO: 2388) | 10.03 | 2625.19 |

In other embodiments, particles synthesized and composed as described above are then used as a "core" inner particle for future coatings to create multi-component (also referred to herein as multi-layer) particles. For other embodiments, other nanoparticles are used as cores, such as Scheme 5. Representative polymer B3-S3-E6 synthesized at a B:S molar ratio of a 1.05:1 at 90° C. and representative encapsulated peptides.

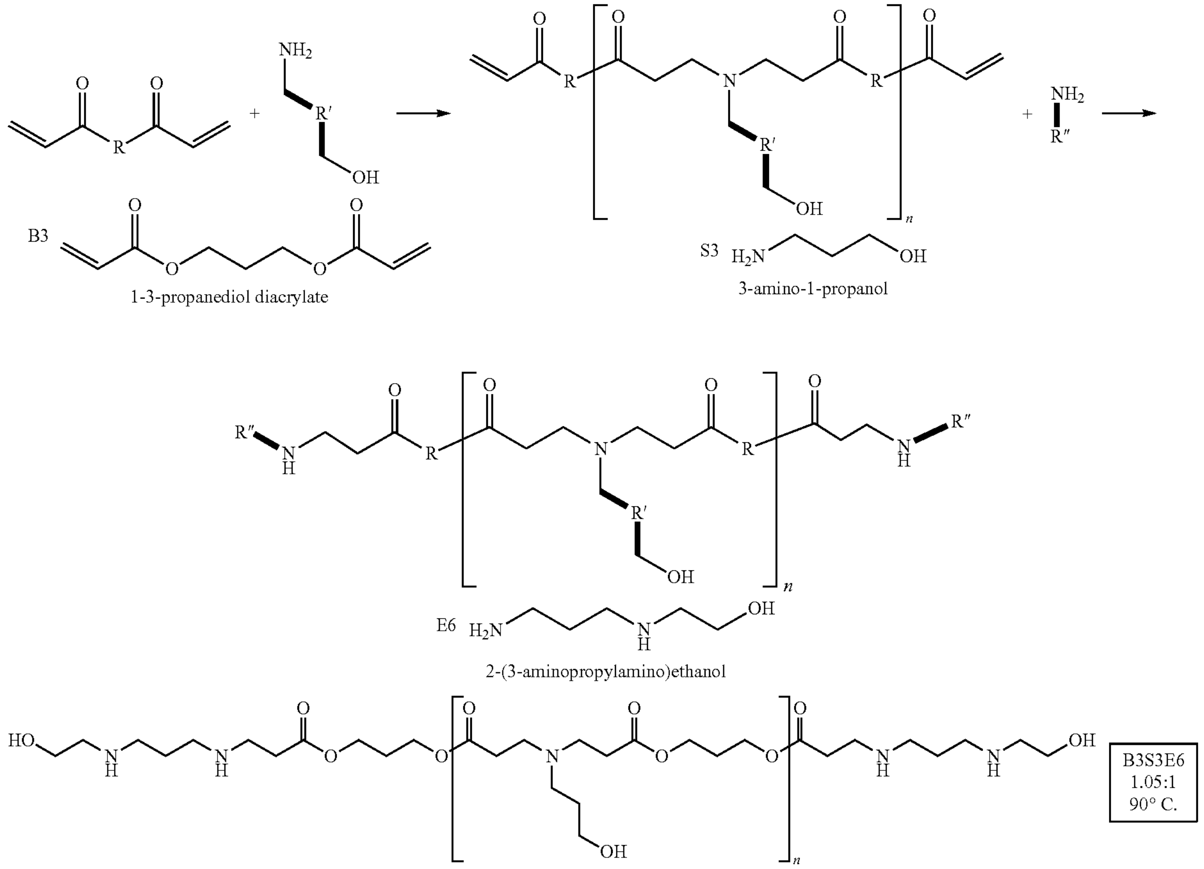

B3

1-3-propanediol diacrylate

S3

3-amino-1-propanol

E6

2-(3-aminopropylamino)ethanol

B3S3E6
1.05:1
90° C.

an inorganic nanoparticles (like gold) or soft polymeric nanoparticles, for example, as disclosed in International PCT Patent Application Publication No. WO/2010/132879 for "Multicomponent Degradable Cationic Polymers," to Green et al., which is incorporated herein by reference in its entirety. In each embodiment, the core particle is then coated with charged polymers as described above, peptides as described above, and other biological agents. Exemplary embodiments of multilayer particles are illustrated in FIG. 1.

Layering can be mediated by electrostatic forces and alternate cationic and anionic layers can be used to incorporate additional peptides and biological agents. Polyelectrolytes, including degradable polymers and peptides, also are used to provide structure to the multilayers. Multilayers can release drugs, peptides, and biological agents from the particle due to hydrolytic degradation, enzyme activity, disulfide reduction, and/or diffusion.

D. Polymeric Gels for Controlled Release of Biological Agents.

i. Hydrogels (or "Organogels") for Protein/Peptide Release

In some embodiments, the presently disclosed subject matter provides photocrosslinked gels for controlled release of cargo, including, but not limited to peptides and proteins. Such gels can be tuned for release of other drugs. In some embodiments, for example, as illustrated in FIG. 2, a solution of acrylate-terminated polymers is made using either acrylate-terminated polymers, such as poly(β-amino esters) (PBAEs), poly(ethylene glycol) diacrylate (PEGDA), small crosslinkers including, but not limited to, 1,4-butanediol diacrylate, or a mixture of the above. Because many of these materials are amphiphilic, a variety of solvents can be used, including water, PBS, and DMSO, to encapsulate drugs within them. Addition of a small amount (0.05% w/v) of photoinitiator and exposure to long-wave UV light for a period of time, e.g., 5-15 min at 1-3 mW, causes formation of a drug-loaded gel.

The gel swelling properties can vary with pH by taking advantage of the PBAE portions, which can be reversibly protonated. Changing ratios of PBAE to PEGDA and the addition of crosslinkers changes swelling properties by changing pore size or overall hydrophobicity. For example, doping in increasing amounts of a more hydrophobic PBAE (B4S4) into a network of hydrophilic PEGDA causes the release kinetics to slow when measuring protein release.

E. Stable Formulations

To increase stability of nanoparticles in suspension, especially with hydrolytically-degradable polymers, the presently disclosed subject matter provides a method of keeping DNA or other cargo stable and functional after storage. For example, freeze-drying often causes denaturation of biological molecules or irreversible aggregation and inactivation of nanoparticles. Referring now to FIG. 3, by adding sucrose as a lyoprotectant at a final concentration of, for example, 7.5-45 mg/mL, the presently disclosed subject matter demonstrates that particles can be freeze dried and stored, for example, at 4° C. or −20° C. for extended periods, e.g., months, without significant change in physicochemical or biological properties. Certain formulations, when stored dry, also might be stable at ambient temperatures up to 40° C. Furthermore, the presently disclosed process allows particles to be prepared in advance and used much more easily in a clinical setting. The presently disclosed subject matter also demonstrates that particles can be concentrated in this way much more highly than would be possible with free polymer, which may be advantageous for dose adjustment in clinical or pre-clinical models.

F. Inclusion of Lyophilized Nanoparticles into Pellets/Scaffolds for Long-Term Delivery The presently disclosed nanoparticles can be stored in a dry form and can be used in gene delivery via three-dimensional (3D) constructs. While DNA is used as a cargo in this example, other cargos of interest to one skilled in the art including, but not limited to, siRNA, peptides, protein, imaging agents, and the like, can be used, as well. In other embodiments, DNA-loaded nanoparticles were incorporated into natural and synthetic scaffolds, disks, microparticles, and hydrogels for various potential applications.

G. Methods of Treating Angiogenesis-Dependent Diseases

Although significant progress has been made in treating angiogenesis-dependent diseases, such as cancers, major challenges remain in terms of development of drug resistance, metastasis and overall survival rates. Studies designed to decipher the modes of drug resistance have revealed that tumors are very versatile and use multiple pathways to continue to survive and metastasize. See Chiang A C, Massague J. Molecular basis of metastasis. N Engl J Med 2008; 359(26):2814-23; Gupta G P, Massague J. Cancer metastasis: building a framework. Cell 2006; 127(4):679-95. Resistance has been observed for both cytotoxic and anti-angiogenic agents. Thus, multimodal therapeutic design emerges as a promising, and perhaps even a mandatory strategy for treatment of cancer. See Sawyers C L. Cancer: mixing cocktails. Nature 2007; 449(7165):993-6; Dorrell M I, Aguilar E, Scheppke L, Barnett F H, Friedlander M. Combination angiostatic therapy completely inhibits ocular and tumor angiogenesis. Proc Natl Acad Sci USA 2007; 104(3):967-72.

The key attributes of tumor growth and metastasis are: angiogenesis, which facilitates the supply of the growing tumor with oxygen and nutrients; lymphangiogenesis, which facilitates the spreading of cancer cells through the lymphatics; and cancer cell proliferation. Angiogenesis, in particular, plays a critical role in the growth of tumors and antiangiogenic therapies have the potential to treat cancer, either alone or in combination with conventional chemotherapies, by starving tumors of oxygen and nutrients. There is a need, however, to find more potent anti-cancer therapeutics, including antiangiogenic therapeutics, as well as delivery systems for these therapeutics. The presently disclosed subject matter can address all of these attributes in a combined system.

Many forms of cancer, including breast cancer, are dependent on angiogenesis, the growth of blood vessels. There is a great medical need for the development of a safe, effective, and inexpensive means of antiangiogenic therapy. One promising approach is the use of antiangiogenic peptides as the active agents. In some embodiments, the presently disclosed subject matter provides peptides derived from several classes of proteins that are effective at preventing angiogenesis. In other embodiments, the presently disclosed subject matter provides other peptides that are able to inhibit cancer through additional mechanisms including, but not limited to, antilymphangiogenesis and apoptosis. In their current form, however, all of these peptides have a short in vivo half-life and they are not suitable for systemic administration or for long-term action. Thus, there is a need to package, protect, and deliver these peptides in a more stable, sustained fashion.

Accordingly, the presently disclosed biomaterials facilitate delivery of combinations of these peptides in an engineered fashion to synergistically kill cancer or treat other diseases, in particular, other angiogenesis-dependent diseases. More particularly, the presently disclosed subject matter provides an effective array of safe, biodegradable polymers for use in forming peptide-containing nanoparticles, microparticles, gels, and conjugates. The presently disclosed biomaterials can be used to construct particles, gels, and conjugates that vary in their biophysical properties and in biological properties, such as tumor accumulation and peptide release.

The presently disclosed formulations work through one or more of the following mechanisms: antiangiogenesis; inhibition of human endothelial cell proliferation and migration; inhibition of lymphatic endothelial cell proliferation and migration; and promotion of cancer apoptosis, as well as other mechanisms. The presently disclosed materials and methods can safely, effectively, and relatively inexpensively treat age-related macular degeneration (AMD), cancer, and other diseases.

Further, siRNA is a promising technology to silence the activity of many biological targets in many diseases including cancer, cardiovascular diseases, infectious diseases, neurological diseases, ophthalmic diseases, and others. In some cases, siRNA can be used to reach previously undruggable targets. The method of delivery and examples described herein for siRNA delivery apply equally to other similar RNA molecules including, but not limited to, isRNA, agRNA, saRNA, and miRNA.

H. Nanoparticle-Mediated Multimodal Peptide Delivery

Conventional anti-angiogenesis treatments have proven to be very expensive with limited clinical success, particularly in breast cancer. The presently disclosed strategy combines more effective and multimodal therapeutic agents with nanomedicine to provide a delivery system to enhance their therapeutic effect. More particularly, the presently disclosed subject matter provides a single system that incorporates multimodal therapeutic activity, including, but not limited to, antiangiogenic activity, antilymphangiogenic activity, and apoptotic activity, and can be effective in limiting both tumor growth and metastasis.

Generally, small peptides possess many advantageous characteristics as therapeutic agents, including high specificity and low toxicity. Reichert J. Development trends for peptide therapeutics. Tufts Center for the Study of Drug Development 2008 [cited 2010]. [cited 2010; The main disadvantage of small peptides as therapeutic agents, however, is their short half-life. The presently disclosed subject matter capitalizes on the advantages of peptide agents by developing novel antiangiogenic, antilymphangiogenic, and apoptotic peptides targeting multiple pathways, and overcoming the disadvantages by designing a multi-agent nanocarrier system.

Approximately 25 peptides have been approved by the FDA, however, to date none of these approved peptides are antiangiogenic. Rosca E V, Koskimaki J E, Rivera C G, Pandey N B, Tamiz A P, Popel A S. Anti-angiogenic peptides for cancer therapeutics. Curr Pharm Biotechnol, 12(8):1101-1116 (2011). Several endogenous proteins/polypeptides, including angiostatin, endostatin, proteolytic fragments of collagen IV, pigment epithelium-derived factor, and thrombospondin, have antiangiogenic properties and can induce apoptosis in endothelial cells. Lucas R, Holmgren L, Garcia I, Jimenez B, Mandriota S J, Borlat F, et al. Multiple forms of angiostatin induce apoptosis in endothelial cells. Blood 1998; 92(12):4730-41. These proteins/polypeptides are large, however, and are not ideal for use as therapeutic agents. Further, full length human proteins, although theoretically not foreign to an individual's body, induce an immune response in some individuals.

More recently, a bioinformatics approach has allowed identification of candidate antiangiogenic regions of several proteins and synthetic peptides corresponding to those short sequences that possess the ability to suppress proliferation and migration of vascular endothelial cells in vitro and angiogenesis in vivo. Delivering such peptides to a cell and prolonging the duration of their activity, however, remains a challenge.

Although peptides are much easier to produce and are more scalable and less immunogenic than full-length proteins, they are eliminated from the body more quickly. The presently disclosed subject matter can increase and sustain residence time, increase accumulation in tumor vasculature, and maximize the therapeutic effects of such peptides. The presently disclosed subject matter combines biomaterial synthesis, sustained drug delivery, and anti-cancer peptide creation to provide nanoparticle-, microparticle-, and gel-based systems for sustained peptide delivery. The presently disclosed biodegradable biomaterials can be tuned for the encapsulation, protection, and sustained release of each type of peptide.

The use of the presently disclosed nanoparticles, microparticles, and gels limits toxicity because they can extravasate from the leaky neovasculature of the tumors and be trapped in the interstitium of the tumor once the anti-angiogenic compounds kill or normalize the vasculature. Further, the presently disclosed subject matter demonstrates that effective biomaterials for anti-cancer peptide nanoparticles, microparticles, and gels can be fabricated. Multiple anti-cancer peptides and other peptides can be combined within the same particle for multimodal peptide delivery, as well as multimodal therapy with other active agents including, but not limited to, other peptides, nucleic acids, proteins, small molecules, and the like.

More particularly, in some embodiments, the presently disclosed subject matter provides peptides that work through multiple biological mechanisms in combination with the presently disclosed biomaterials, including multilayer and multi-peptide nanoparticle formulations. An array of biodegradable polymers can be used to encapsulate peptides to create nanoparticles having varied biophysical properties and release kinetics. Each peptide can have a specialized subset of materials employed for its encapsulation. Referring now to FIG. 4, differing chemical structures can be synthesized by the conjugate addition of amines to acrylates or acrylamides of differing structure. The polymer structure can be tuned through variation to the backbone, side chain, end-group, hydrophobicity, and degradability. Unlike the polymeric materials disclosed in International PCT Patent Application Publication No. WO/2010/132879 for "Multi-component Degradable Cationic Polymers," to Green et al., which are cationic, i.e., positively charged, the presently disclosed polymers can be positively charged, whereas others can be negatively charged, others neutral and hydrophobic, and still others amphiphilic. The diversity of the presently disclosed biomaterials comes from the chemical diversity of the R groups (R, R', R") in the biomaterial array and from parameter tuning during particle fabrication.

For example, to create the presently disclosed multi-peptide particles, hydrophobic core particles first are constructed by self-assembly, for example between the somatotropin-derived peptide, the collagen IV-derived peptide, and a hydrophobic polymer. These nanoparticles are then coated by charged biodegradable polymers and peptides following a particle coating and layer-by-layer technique that modifies techniques previously described. Green J J, Chiu E, Leshchiner E S, Shi J, Langer R, Anderson D G.

Electrostatic ligand coatings of nanoparticles enable ligand-specific gene delivery to human primary cells. Nano Lett 2007; 7(4):874-9; Shmueli R B, Anderson D G, Green J J. Electrostatic surface modifications to improve gene delivery. Expert Opin Drug Deliv 7(4):535-50. Through this process, the charged peptides (serpin-derived and chemokine-derived) can be incorporated into these multilayers. Charged biological agents, such as peptides and nucleic acids, can serve as both the therapeutic agent and the support polyelectrolyte in the presently disclosed systems.

In one embodiment, peptides can self-assemble with the presently disclosed polymers in an aqueous buffer due to physical, hydrophobic, and electrostatic forces. Zhang S, Uludag H. Nanoparticulate systems for growth factor delivery. Pharm Res 2009; 26(7):1561-80. In other embodiments, peptide-containing micelles can be formed by synthetic polymer-mPEG (e.g., E15 from FIG. 4) block copolymers. Depending on formulation parameters, polymer/peptide particle sizes can be tuned from approximately 50 nm to approximately 500 nm.

As an alternative strategy for polymers in the library that are more hydrophobic or have higher glass transition temperatures, peptides can be encapsulated by a double emulsion procedure. In this method, droplets of aqueous buffer containing peptide are dispersed in the hydrophobic polymer phase and then the polymer phase is itself dispersed in another aqueous phase to form the polymeric particles. Jain R A. The manufacturing techniques of various drug loaded biodegradable poly(lactide-co-glycolide) (PLGA) devices. Biomaterials 2000; 21(23):2475-90. As an alternative technique, blends of novel hydrophobic polymers and poly (lactic-co-glycolic acid) also can be made to form particles with unique degradation properties. Little S R, Lynn D M, Ge Q, Anderson D G, Puram S V, Chen J Z, et al. Poly-beta amino ester-containing microparticles enhance the activity of nonviral genetic vaccines. Proc Natl Acad Sci USA 2004; 101(26):9534-9.

I. Peptides for Anti-Angiogenesis, Anti-Lymphangiogenesis, Anti-Tumor, and Anti-Permeability Activity.

Several classes of peptides have been developed that show either anti-proliferative or anti-migratory activity or both on endothelial cells. These peptides appear to function through distinct mechanisms of action and have been tested both in vitro and in vivo in tumor xenografts and in ocular mouse models. These peptides include a 24-mer peptide NGRKACLNPASPIVKKIIEKMLNS (SEQ ID NO: 2388) derived from the CXC chemokine protein GRO-α/CXCL1 and a collagen IV derived and modified 20-mer peptide LRRFSTMPFMF-Abu-NINNV-Abu-NF (SEQ ID NO: 2452) as a highly potent anti-proliferative and anti-migratory peptide targeting αvβ1 integrins on both endothelial and tumor cells; here Abu is the 2-Aminobutyric acid introduced in the sequence to facilitate translation to human.

An 11-mer anti-angiogenic peptide EIELVEEEPPF (SEQ ID NO: 2485) derived from the serpin domain of DEAH box polypeptide ("DEAH" disclosed as SEQ ID NO: 2484) also has been identified that shows significant inhibition of MDA-MB-231 tumor xenograft growth. A somatotropin family peptide LLRISLLLIESWLE (SEQ ID NO: 2483; SP5033) derived from transmembrane 45 protein that also has been identified and has anti-proliferative and anti-migratory activity on both endothelial cells and lymphatic endothelial cells. It is believed that this peptide is the first antilymphangiogenic peptide agent. Combining these peptides together can result in a peptide-based system that inhibits angiogenesis by several different mechanisms and also inhibits lymphangiogenesis that has been shown to promote tumor metastasis.

Representative peptides suitable for encapsulation with the presently disclosed biomaterials include those disclosed in International PCT Patent Application Publication Number WO2007/033215 A2 for "Compositions Having Antiangiogenic Activity and Uses Thereof," to Popel et al., published Mar. 22, 2007; International PCT Patent Application Publication Number WO2008/085828 A2 for "Peptide Modulators of Angiogenesis and Use Thereof," to Popel, published Jul. 17, 2008; U.S. Provisional Patent Application No. 61/421,706, filed Dec. 12, 2010, which is commonly owned; and U.S. Provisional Patent Application No. 61/489,500, filed May 24, 2011, which also is commonly owned, each of which is incorporated herein by reference in its entirety.

Accordingly, in some embodiments, peptide suitable for use in the presently disclosed subject matter are disclosed in Tables 1-10 of International PCT Patent Application Publication Number WO2008/085828 A2 for "Peptide Modulators of Angiogenesis and Use Thereof," to Popel, published Jul. 17, 2008, which is incorporated herein by reference in its entirety.

Accordingly, in some embodiments, the presently disclosed subject matter provides a nanoparticle, microparticle, or gel comprising one or more peptides, wherein the one or more peptide is selected from the group consisting of an isolated peptide or analog thereof comprising one of the following amino acid sequences:

```
TSP Motif:
                                   (SEQ ID NO: 2486)
W-X(2)-C-X(3)-C-X(2)-G,

CXC Motif:
G-X(3)-C-L

Collagen Motif:
                                   (SEQ ID NO: 2487)
C-N-X(3)-V-C

Collagen Motif:
P-F-X(2)-C

Somatotropin Motif:
                                   (SEQ ID NO: 2488)
L-X(3)-L-L-X(3)-S-X-L

Serpin Motif:
                                   (SEQ ID NO: 2489)
L-X(2)-E-E-X-P
```

wherein X denotes a variable amino acid and the number in parentheses denotes the number of variable amino acids; W denotes tryptophan; C denotes cysteine, G denotes glycine, V denotes valine; L denotes leucine, P is proline, and wherein the peptide reduces blood vessel formation in a cell, tissue or organ.

In other embodiments, the the one or more peptide comprises an amino acid sequence shown in Table 1-6, 8 and 9.

In other embodiments, the one or more peptide comprises an isolated peptide or analog thereof having at least 85% identity to an amino acid sequence shown in Table 1-10.

In other embodiments, the one or more peptide comprises an amino acid sequence shown in Table 1-10. In yet other embodiments, the one or more peptide consists essentially of an amino acid sequence shown in Table 1-10.

In particular embodiments, the one or more peptide comprises an isolated peptide or analog thereof comprising or consisting essentially of a sequence having at least 85% amino acid sequence identity to an amino acid sequence selected from the group consisting of:

Placental Lactogen
(SEQ ID NO: 2483)
LLRISLLLIESWLE hGH-V
(SEQ ID NO: 2490)
LLRISLLLTQSWLE

GH2
(SEQ ID NO: 2491)
LLHISLLLIQSWLE

Chorionic somatomammotropin
(SEQ ID NO: 2480)
LLRLLLLIESWLE

Chorionic somatomammotropin hormone-like 1
(SEQ ID NO: 2482)
LLHISLLLIESRLE

Transmembrane protein 45A
(SEQ ID NO: 2481)
LLRSSLILLQGSWF

IL-17 receptor C
(SEQ ID NO: 2477)
RLRLLTLQSWLL

Neuropeptide FF receptor 2
(SEQ ID NO: 2479)
LLIVALLFILSWL

Brush border myosin-I
(SEQ ID NO: 2478)
LMRKSQILISSWF wherein the peptide reduces blood vessel formation in a cell, tissue or organ.

In yet more particular embodiments, the one or more peptide comprises an isolated peptide or analog thereof comprising or consisting essentially of a sequence having at least 85% amino acid sequence identity to an amino acid sequence selected from the group consisting of:

DEAH box polypeptide 8
(SEQ ID NO: 2485)
EIELVEEEPPF
("DEAH" disclosed as SEQ ID NO: 2484)

Caspase 10
(SEQ ID NO: 2492)
AEDLLSEEDPF

CKIP-1
(SEQ ID NO: 2493)
TLDLIQEEDPS wherein the peptide reduces blood vessel formation in a cell, tissue or organ.

In further embodiments, the one or more peptide comprises an isolated peptide or analog thereof comprising or consisting essentially of a sequence having at least 85% amino acid sequence identity to an amino acid sequence selected from the group consisting of:

Collagen type IV, alpha6 fibril
(SEQ ID NO: 2494)
LPRFSTMPFIYCNINEVCHY wherein the peptide reduces blood vessel formation in a cell, tissue or organ.

TABLE 1

The TSP-1 containing 20-mer with all the possible amino acid substitutions (SEQ ID NO: 2495)

| AA#1 | AA#2 | AA#3 | AA#4 | AA#5 | AA#6 | AA#7 | AA#8 | AA#9 | AA#10 |
|---|---|---|---|---|---|---|---|---|---|
| S (9)<br>T (9)<br>G (6)<br>Q (2)<br>A (1) | P (13)<br>E (5)<br>S (3)<br>A (2)<br>Q (1)<br>K (1) | W (29) | S (14)<br>T (5)<br>G (5)<br>E (2)<br>D (1)<br>R (1)<br>A (1) | P (9)<br>A (5)<br>Q (4)<br>D (3)<br>E (3)<br>K (1)<br>R (1)<br>V (1) | C (29) | S (26)<br>N (2)<br>T (1) | V (7)<br>A (6)<br>R (5)<br>K (4)<br>G (2)<br>S (2)<br>T (2)<br>E (1) | T (15)<br>S (10)<br>R (3)<br>N (1) | C (29) |

| AA#11 | AA#12 | AA#13 | AA#14 | AA#15 | AA#16 | AA#17 | AA#18 | AA#19 | AA#20 |
|---|---|---|---|---|---|---|---|---|---|
| G (26)<br>S (2)<br>N (1) | G (10)<br>K (4)<br>R (4)<br>M (4)<br>T (2)<br>L (2)<br>D (1)<br>S (1)<br>P (1) | G (29) | V (8)<br>I (4)<br>M (3)<br>T (3)<br>H (2)<br>A (1)<br>E (1)<br>F (1)<br>K (1)<br>R (1)<br>S (1)<br>Q (1)<br>W (1)<br>Y (1) | Q (11)<br>S (7)<br>R (6)<br>K (2)<br>Y (2)<br>A (1) | T (10)<br>F (4)<br>K (3)<br>Q (3)<br>S (3)<br>L (2)<br>E (1)<br>M (1)<br>N (1)<br>V (1) | R (26)<br>S (2)<br>Q (1) | S (5)<br>T (5)<br>V (5)<br>R (3)<br>H (3)<br>E (2)<br>Q (2)<br>A (1)<br>I (1) | R (15)<br>V (1) | R (1) |

TABLE 2

TSPs
Motif: W-X(2)-C-X(3)-C-X(2)-G (SEQ ID NO: 2486)
Number of Locations: 166
Number of Different Proteins: 54

| SEQ ID NO: | Accession Number\|Protein Name | First Amino acid | Last Amino acid | Sequence |
|---|---|---|---|---|
| 1 | O00622\|CYR61_HUMAN | 236 | 246 | WsqCsktCgtG |
| 2 | O14514\|BAI1_HUMAN | 270 | 280 | WgeCtrdCggG |
| 3 | O14514\|BAI1_HUMAN | 363 | 373 | WsvCsstCgeG |
| 4 | O14514\|BAI1_HUMAN | 418 | 428 | WslCsstCgrG |
| 5 | O14514\|BAI1_HUMAN | 476 | 486 | WsaCsasCsqG |
| 6 | O14514\|BAI1_HUMAN | 531 | 541 | WgsCsvtCgaG |
| 7 | O15072\|ATS3_HUMAN | 975 | 985 | WseCsvtCgeG |
| 8 | O60241\|BAI2_HUMAN | 306 | 316 | WsvCsltCgqG |
| 9 | O60241\|BAI2_HUMAN | 361 | 371 | WslCsrsCgrG |
| 10 | O60241\|BAI2_HUMAN | 416 | 426 | WgpCstsCanG |
| 11 | O60241\|BAI2_HUMAN | 472 | 482 | WslCsktCdtG |
| 12 | O60242\|BAI3_HUMAN | 300 | 310 | WstCsvtCgqG |
| 13 | O60242\|BAI3_HUMAN | 354 | 364 | WslCsftCgrG |
| 14 | O60242\|BAI3_HUMAN | 409 | 419 | WsqCsvtCsnG |
| 15 | O60242\|BAI3_HUMAN | 464 | 474 | WsgCsksCdgG |
| 16 | O75173\|ATS4_HUMAN | 529 | 539 | WgdCsrtCggG |
| 17 | O76076\|WISP2_HUMAN | 201 | 211 | WgpCsttCglG |
| 18 | O95185\|UNC5C_HUMAN | 269 | 279 | WsvCnsrCgrG |
| 19 | O95388\|WISP1_HUMAN | 223 | 233 | WspCstsCglG |
| 20 | O95389\|WISP3_HUMAN | 216 | 226 | WtpCsrtCgmG |
| 21 | O95450\|ATS2_HUMAN | 863 | 873 | WspCskpCggG |
| 22 | O95450\|ATS2_HUMAN | 984 | 994 | WsqCsvtCgnG |
| 23 | P07996\|TSP1_HUMAN | 388 | 398 | WtsCstsCgnG |
| 24 | P07996\|TSP1_HUMAN | 444 | 454 | WssCsvtCgdG |
| 25 | P07996\|TSP1_HUMAN | 501 | 511 | WdiCsvtCggG |
| 26 | P13671\|CO6_HUMAN | 32 | 42 | WtsCsktCnsG |
| 27 | P13671\|CO6_HUMAN | 75 | 85 | WqrCpinCllG |
| 28 | P14222\|PERF_HUMAN | 374 | 384 | WrdCsrpCppG |
| 29 | P27918\|PROP_HUMAN | 86 | 96 | WapCsvtCseG |
| 30 | P27918\|PROP_HUMAN | 145 | 155 | WepCsvtCskG |
| 31 | P27918\|PROP_HUMAN | 202 | 212 | WtpCsasChgG |
| 32 | P29279\|CTGF_HUMAN | 206 | 216 | WsaCsktCgmG |
| 33 | P35442\|TSP2_HUMAN | 390 | 400 | WtqCsvtCgsG |

TABLE 2-continued

TSPs
Motif: W-X(2)-C-X(3)-C-X(2)-G (SEQ ID NO: 2486)
Number of Locations: 166
Number of Different Proteins: 54

| SEQ ID NO: | Accession Number\|Protein Name | First Amino acid | Last Amino acid | Sequence |
|---|---|---|---|---|
| 34 | P35442\|TSP2_HUMAN | 446 | 456 | WssCsvtCgvG |
| 35 | P35442\|TSP2_HUMAN | 503 | 513 | WsaCtvtCagG |
| 36 | P48745\|NOV_HUMAN | 213 | 223 | WtaCsksCgmG |
| 37 | P49327\|FAS_HUMAN | 627 | 637 | WeeCkqrCppG |
| 38 | P58397\|ATS12_HUMAN | 551 | 561 | WshCsrtCgaG |
| 39 | P58397\|ATS12_HUMAN | 832 | 842 | WteCsvtCgtG |
| 40 | P58397\|ATS12_HUMAN | 952 | 962 | WseCsysCggG |
| 41 | P58397\|ATS12_HUMAN | 1321 | 1331 | WseCsttCglG |
| 42 | P58397\|ATS12_HUMAN | 1372 | 1382 | WskCsrnCsgG |
| 43 | P58397\|ATS12_HUMAN | 1431 | 1441 | WsqCsrsCggG |
| 44 | P58397\|ATS12_HUMAN | 1479 | 1489 | WdlCstsCggG |
| 45 | P59510\|ATS20_HUMAN | 976 | 986 | WsqCsrsCggG |
| 46 | P59510\|ATS20_HUMAN | 1031 | 1041 | WseClvtCgkG |
| 47 | P59510\|ATS20_HUMAN | 1086 | 1096 | WgpCtttCghG |
| 48 | P59510\|ATS20_HUMAN | 1162 | 1172 | WtpCsysCgrG |
| 49 | P59510\|ATS20_HUMAN | 1217 | 1227 | WspCsasCghG |
| 50 | P59510\|ATS20_HUMAN | 1314 | 1324 | WgsCsssCsgG |
| 51 | P59510\|ATS20_HUMAN | 1368 | 1378 | WgeCsqtCggG |
| 52 | P59510\|ATS20_HUMAN | 1427 | 1437 | WtsCsasCgkG |
| 53 | P59510\|ATS20_HUMAN | 1483 | 1493 | WneCsvtCgsG |
| 54 | P59510\|ATS20_HUMAN | 1664 | 1674 | WskCsvtCgiG |
| 55 | P82987\|ATL3_HUMAN | 84 | 94 | WsdCsrtCggG |
| 56 | P82987\|ATL3_HUMAN | 427 | 437 | WtaCsysCggG |
| 57 | P82987\|ATL3_HUMAN | 487 | 497 | WsqCtvtCgrG |
| 58 | P82987\|ATL3_HUMAN | 573 | 583 | WsaCsttCgpG |
| 59 | P82987\|ATL3_HUMAN | 712 | 722 | WgpCsatCgvG |
| 60 | P82987\|ATL3_HUMAN | 768 | 778 | WqqCsrtCggG |
| 61 | P82987\|ATL3_HUMAN | 828 | 838 | WskCsysCgvG |
| 62 | P82987\|ATL3_HUMAN | 1492 | 1502 | WsqCsysCgeG |
| 63 | P82987\|ATL3_HUMAN | 1606 | 1616 | WkpCtaaCgrG |
| 64 | Q13591\|SEM5A_HUMAN | 604 | 614 | WspCsttCgiG |
| 65 | Q13591\|SEM5A_HUMAN | 662 | 672 | WerCtaqCggG |

TABLE 2-continued

TSPs
Motif: W-X(2)-C-X(3)-C-X(2)-G (SEQ ID NO: 2486)
Number of Locations: 166
Number of Different Proteins: 54

| SEQ ID NO: | Accession Number\| Protein Name | First Amino acid | Last Amino acid | Sequence |
|---|---|---|---|---|
| 66 | Q13591\|SEM5A_HUMAN | 793 | 803 | WsqCsrdCsrG |
| 67 | Q13591\|SEM5A_HUMAN | 850 | 860 | WtkCsatCggG |
| 68 | Q496M8\|CI094_HUMAN | 259 | 269 | WsaCtrsCggG |
| 69 | Q6S8J7\|POTE8_HUMAN | 27 | 37 | WccCcfpCcrG |
| 70 | Q6UXZ4\|UNC5D_HUMAN | 261 | 271 | WsaCnvrCgrG |
| 71 | Q6UY14\|ATL4_HUMAN | 53 | 63 | WasCsqpCgvG |
| 72 | Q6UY14\|ATL4_HUMAN | 732 | 742 | WtsCsrsCgpG |
| 73 | Q6UY14\|ATL4_HUMAN | 792 | 802 | WsqCsvrCgrG |
| 74 | Q6UY14\|ATL4_HUAN | 919 | 929 | WgeCsseCgsG |
| 75 | Q6UY14\|ATL4_HUMAN | 979 | 989 | WspCsrsCqgG |
| 76 | Q6ZMM2\|ATL5_HUMAN | 44 | 54 | WtrCsssCgrG |
| 77 | Q76LX8\|ATS13_HUMAN | 1081 | 1091 | WmeCsysCgdG |
| 78 | Q86TH1\|ATL2_HUMAN | 56 | 66 | WtaCsrsCggG |
| 79 | Q86TH1\|ATL2_HUMAN | 631 | 641 | WseCsrtCgeG |
| 80 | Q86TH1\|ATL2_HUMAN | 746 | 756 | WgpCsgsCgqG |
| 81 | Q86TH1\|ATL2_HUMAN | 803 | 813 | WerCnttCgrG |
| 82 | Q86TH1\|ATL2_HUMAN | 862 | 872 | WseCtktCgvG |
| 83 | Q8IUL8\|CILP2_HUMAN | 155 | 165 | WgpCsgsCgpG |
| 84 | Q8IZJ1\|UNC5B_HUMAN | 255 | 265 | WspCsnrCgrG |
| 85 | Q8N6G6\|ATL1_HUMAN | 42 | 52 | WseCsrtCggG |
| 86 | Q8N6G6\|ATL1_HUMAN | 385 | 395 | WtaCsssCggG |
| 87 | Q8N6G6\|ATL1_HUMAN | 445 | 455 | WspCtvtCgqG |
| 88 | Q8TE56\|ATS17_HUMAN | 552 | 562 | WsmCsrtCgtG |
| 89 | Q8TE56\|ATS17_HUMAN | 809 | 819 | WegCsvqCggG |
| 90 | Q8TE56\|ATS17_HUMAN | 870 | 880 | WspCsatCekG |
| 91 | Q8TE56\|ATS17_HUMAN | 930 | 940 | WsqCsasCgkG |
| 92 | Q8TE56\|ATS17_HUMAN | 981 | 991 | WstCsstCgkG |
| 93 | Q8TE57\|ATS16_HUMAN | 595 | 605 | WspCsrtCggG |
| 94 | Q8TE57\|ATS16_HUMAN | 936 | 946 | WsaCsrtCggG |
| 95 | Q8TE57\|ATS16_HUMAN | 995 | 1005 | WaeCshtCgkG |
| 96 | Q8TE57\|ATS16_HUMAN | 1060 | 1070 | WsqCsvtCerG |
| 97 | Q8TE57\|ATS16_HUMAN | 1135 | 1145 | WsqCtasCggG |
| 98 | Q8TE58\|ATS15_HUMAN | 848 | 858 | WgpCsasCgsG |
| 99 | Q8TE58\|ATS15_HUMAN | 902 | 912 | WspCsksCgrG |
| 100 | Q8TE59\|ATS19_HUMAN | 642 | 652 | WspCsrtCsaG |
| 101 | Q8TE59\|ATS19_HUMAN | 924 | 934 | WedCdatCggG |
| 102 | Q8TE59\|ATS19_HUMAN | 985 | 995 | WtpCsrtCgkG |
| 103 | Q8TE59\|ATS19_HUMAN | 1096 | 1106 | WskCsitCgkG |
| 104 | Q8TE60\|ATS18_HUMAN | 598 | 608 | WseCsrtCggG |
| 105 | Q8TE60\|ATS18_HUMAN | 940 | 950 | WstCskaCagG |
| 106 | Q8TE60\|ATS18_HUMAN | 1000 | 1010 | WsqCsktCgrG |
| 107 | Q8TE60\|ATS18_HUMAN | 1061 | 1071 | WseCsatCgIG |
| 108 | Q8TE60\|ATS18_HUMAN | 1132 | 1142 | WqqCtvtCggG |
| 109 | Q8WXS8\|ATS14_HUMAN | 856 | 866 | WapCskaCggG |
| 110 | Q8WXS8\|ATS14_HUMAN | 977 | 987 | WsqCsatCgeG |
| 111 | Q92947\|GCDH_HUMAN | 225 | 235 | WarCedgCirG |
| 112 | Q96RW7\|HMCN1_HUMAN | 4538 | 4548 | WraCsvtCgkG |
| 113 | Q96RW7\|HMCN1_HUMAN | 4595 | 4605 | WeeCtrsCgrG |
| 114 | Q96RW7\|HMCN1_HUMAN | 4652 | 4662 | WgtCsesCgkG |
| 115 | Q96RW7\|HMCN1_HUMAN | 4709 | 4719 | WsaCsysCggG |
| 116 | Q96RW7\|HMCN1_HUMAN | 4766 | 4776 | WgtCsrtCngG |
| 117 | Q96RW7\|HMCN1_HUMAN | 4823 | 4833 | WsqCsasCggG |
| 118 | Q99732\|LITAF_HUMAN | 116 | 126 | WIsCgslCllG |
| 119 | Q9C0I4\|THS7B_HUMAN | 49 | 59 | WgrCtgdCgpG |
| 120 | Q9C0I4\|THS7B_HUMAN | 345 | 355 | WspCsktCrsG |
| 121 | Q9C0I4\|THS7B_HUMAN | 746 | 756 | WtpCprmCgaG |
| 122 | Q9C0I4\|THS7B_HUMAN | 1009 | 1019 | WgsCsssCgiG |
| 123 | Q9C0I4\|THS7B_HUMAN | 1258 | 1268 | WteCsqtCghG |
| 124 | Q9C0I4\|THS7B_HUMAN | 1381 | 1391 | WstCeltCidG |
| 125 | Q9H324\|ATS10_HUMAN | 530 | 540 | WgdCsrtCggG |
| 126 | Q9H324\|ATS10_HUMAN | 808 | 818 | WtkCsaqCagG |

TABLE 2-continued

TSPs
Motif: W-X(2)-C-X(3)-C-X(2)-G (SEQ ID NO: 2486)
Number of Locations: 166
Number of Different Proteins: 54

| SEQ ID NO: | Accession Number\|Protein Name | First Amino acid | Last Amino acid | Sequence |
|---|---|---|---|---|
| 127 | Q9H324\|ATS10_HUMAN | 867 | 877 | WslCsrsCdaG |
| 128 | Q9H324\|ATS10_HUMAN | 927 | 937 | WseCtpsCgpG |
| 129 | Q9H324\|ATS10_HUMAN | 986 | 996 | WgeCsaqCgvG |
| 130 | Q9HCB6\|SPON1_HUMAN | 510 | 520 | WspCsisCgmG |
| 131 | Q9HCB6\|SPON1_HUMAN | 567 | 577 | WdeCsatCgmG |
| 132 | Q9HCB6\|SPON1_HUMAN | 623 | 633 | WsdCsvtCgkG |
| 133 | Q9HCB6\|SPON1_HUMAN | 677 | 687 | WseCnksCgkG |
| 134 | Q9HCB6\|SPON1_HUMAN | 763 | 773 | WseCtklCggG |
| 135 | Q9NS62\|THSD1_HUMAN | 349 | 359 | WsqCsatCgdG |
| 136 | Q9P283\|SEM5B_HUMAN | 615 | 625 | WalCstsCgiG |
| 137 | Q9P283\|SEM5B_HUMAN | 673 | 683 | WskCssnCggG |
| 138 | Q9P283\|SEM5B_HUMAN | 804 | 814 | WssCsrdCeIG |
| 139 | Q9P283\|SEM5B_HUMAN | 861 | 871 | WspCsasCggG |
| 140 | Q9P2N4\|ATS9_HUMAN | 1006 | 1016 | WteCsksCdgG |
| 141 | Q9P2N4\|ATS9_HUMAN | 1061 | 1071 | WseClvtCgkG |
| 142 | Q9P2N4\|ATS9_HUMAN | 1116 | 1126 | WvqCsvtCgqG |
| 143 | Q9P2N4\|ATS9_HUMAN | 1191 | 1201 | WtpCsatCgkG |
| 144 | Q9P2N4\|ATS9_HUMAN | 1247 | 1257 | WssCsvtCgqG |
| 145 | Q9P2N4\|ATS9_HUMAN | 1337 | 1347 | WgaCsstCagG |
| 146 | Q9P2N4\|ATS9_HUMAN | 1391 | 1401 | WgeCtklCggG |
| 147 | Q9P2N4\|ATS9_HUMAN | 1450 | 1460 | WssCsysCgrG |
| 148 | Q9P2N4\|ATS9_HUMAN | 1506 | 1516 | WsqCsysCgrG |
| 149 | Q9P2N4\|ATS9_HUMAN | 1564 | 1574 | WqeCtktCgeG |
| 150 | Q9P2N4\|ATS9_HUMAN | 1621 | 1631 | WseCsvtCgkG |
| 151 | Q9P2N4\|ATS9_HUMAN | 1686 | 1696 | WgsCsysCgvG |
| 152 | Q9UH18\|ATS1_HUMAN | 568 | 578 | WgdCsrtCggG |
| 153 | Q9UH18\|ATS1_HUMAN | 863 | 873 | WgeCsksCeIG |
| 154 | Q9UH18\|ATS1_HUMAN | 917 | 927 | WssCsktCgkG |
| 155 | Q9UKP4\|ATS7_HUMAN | 547 | 557 | WsiCsrsCgmG |
| 156 | Q9UKP4\|ATS7_HUMAN | 924 | 934 | WtkCtvtCgrG |
| 157 | Q9UKP5\|ATS6_HUMAN | 519 | 529 | WgeCsrtCggG |
| 158 | Q9UKP5\|ATS6_HUMAN | 801 | 811 | WseCsatCagG |
| 159 | Q9UNA0\|ATS5_HUMAN | 576 | 586 | WgqCsrsCggG |
| 160 | Q9UNA0\|ATS5_HUMAN | 884 | 894 | WlaCsrtCdtG |
| 161 | Q9UP79\|ATS8_HUMAN | 536 | 546 | WgeCsrtCggG |
| 162 | Q9UP79\|ATS8_HUMAN | 842 | 852 | WseCsstCgaG |
| 163 | Q9UPZ6\|THS7A_HUMAN | 203 | 213 | WseCsktCgsG |
| 164 | Q9UPZ6\|THS7A_HUMAN | 780 | 790 | WtsCpssCkeG |
| 165 | Q9UPZ6\|THS7A_HUMAN | 1044 | 1054 | WsrCsksCgsG |
| 166 | Q9UPZ6\|THS7A_HUMAN | 1423 | 1433 | WslCqltCvnG |

TABLE 3

The C-X-C chemokine 22-mer with all the possible amino acid substitutions (SEQ ID NO: 2496)

| AA#1 | AA#2 | AA#3 | AA#4 | AA#5 | AA#6 | AA#7 | AA#8 | AA#9 | AA#10 | AA#11 |
|---|---|---|---|---|---|---|---|---|---|---|
| N (4)<br>D (2) | G (6) | R (3)<br>K (3) | K (3)<br>E (2)<br>Q (1) | A (2)<br>I (2)<br>L (1)<br>V (1) | C (6) | L (6) | D (4)<br>N (2) | P (6) | A (2)<br>E (2)<br>D (1)<br>K (1) | A (3)<br>S (2)<br>E (1) |

| AA#12 | AA#13 | AA#14 | AA#15 | AA#16 | AA#17 | AA#18 | AA#19 | AA#20 | AA#21 | AA#22 |
|---|---|---|---|---|---|---|---|---|---|---|
| P (6) | F (2)<br>I (1)<br>M (1)<br>R (1)<br>W (1) | V (3)<br>L (2)<br>I (1) | K (4)<br>Q (2) | K (5)<br>R (1) | I (3)<br>V (3) | I (4)<br>V (2) | E (3)<br>Q (3) | K (6) | I (3)<br>F (1)<br>K (1)<br>M (1) | L (6) |

TABLE 4

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 167 | O00142\|KITM_HUMAN | 62 | 67 | GkttCL |
| 168 | O00167\|EYA2_HUMAN | 361 | 366 | GanlCL |
| 169 | O00220\|TR10A_HUMAN | 332 | 337 | GeaqCL |
| 170 | O00291\|HIP1_HUMAN | 699 | 704 | GattCL |
| 171 | O00409\|FOXN3_HUMAN | 465 | 470 | GirsCL |
| 172 | O00444\|PLK4_HUMAN | 775 | 780 | GhriCL |
| 173 | O00462\|MANBA_HUMAN | 744 | 749 | GeavCL |
| 174 | O00468\|AGRIN_HUMAN | 1549 | 1554 | GdhpCL |
| 175 | O00468\|AGRIN_HUMAN | 2012 | 2017 | GfvgCL |
| 176 | O00476\|NPT4_HUMAN | 144 | 149 | GcvcCL |
| 177 | O00488\|ZN593_HUMAN | 41 | 46 | GlhrCL |
| 178 | O00501\|CLD5_HUMAN | 10 | 15 | GlvlCL |
| 179 | O00624\|NPT3_HUMAN | 220 | 225 | GcvcCL |
| 180 | O14514\|BAI1_HUMAN | 243 | 248 | GpenCL |
| 181 | O14522\|PTPRT_HUMAN | 736 | 741 | GtplCL |
| 182 | O14548\|COX7R_HUMAN | 97 | 102 | GtiyCL |
| 183 | O14617\|AP3D1_HUMAN | 1113 | 1118 | GhhvCL |
| 184 | O14628\|ZN195_HUMAN | 51 | 56 | GlitCL |
| 185 | O14772\|FPGT_HUMAN | 515 | 520 | GnktCL |
| 186 | O14773\|TPP1_HUMAN | 2 | 7 | GlqaCL |
| 187 | O14792\|OST1_HUMAN | 261 | 266 | GrdrCL |
| 188 | O14817\|TSN4_HUMAN | 68 | 73 | GfvgCL |
| 189 | O14841\|OPLA_HUMAN | 1240 | 1245 | GdvfCL |
| 190 | O14842\|FFAR1_HUMAN | 166 | 171 | GspvCL |
| 191 | O14894\|T4S5_HUMAN | 100 | 105 | GaiyCL |
| 192 | O14981\|BTAF1_HUMAN | 608 | 613 | GawlCL |
| 193 | O15021\|MAST4_HUMAN | 1534 | 1539 | GsheCL |
| 194 | O15031\|PLXB2_HUMAN | 308 | 313 | GaglCL |
| 195 | O15056\|SYNJ2_HUMAN | 27 | 32 | GrddCL |
| 196 | O15060\|ZBT39_HUMAN | 272 | 277 | GtnsCL |
| 197 | O15063\|K0355_HUMAN | 244 | 249 | GcdgCL |
| 198 | O15067\|PUR4_HUMAN | 914 | 919 | GlvtCL |
| 199 | O15067\|PUR4_HUMAN | 1040 | 1045 | GpsyCL |
| 200 | O15084\|ANR28_HUMAN | 449 | 454 | GnleCL |
| 201 | O15084\|ANR28_HUMAN | 549 | 554 | GhrlCL |
| 202 | O15084\|ANR28_HUMAN | 661 | 666 | GhseCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 203 | O15105\|SMAD7_HUMAN | 293 | 298 | GngfCL |
| 204 | O15146\|MUSK_HUMAN | 648 | 653 | GkpmCL |
| 205 | O15229\|KMO_HUMAN | 320 | 325 | GfedCL |
| 206 | O15230\|LAMA5_HUMAN | 1933 | 1938 | GrtqCL |
| 207 | O15296\|LX15B_HUMAN | 157 | 162 | GwphCL |
| 208 | O15305\|PMM2_HUMAN | 5 | 10 | GpalCL |
| 209 | O15354\|GPR37_HUMAN | 448 | 453 | GcyfCL |
| 210 | O15379\|HDAC3_HUMAN | 214 | 219 | GryyCL |
| 211 | O15397\|IPO8_HUMAN | 148 | 153 | GsllCL |
| 212 | O15554\|KCNN4_HUMAN | 263 | 268 | GkivCL |
| 213 | O43156\|K0406_HUMAN | 642 | 647 | GkdfCL |
| 214 | O43175\|SERA_HUMAN | 111 | 116 | GmimCL |
| 215 | O43175\|SERA_HUMAN | 416 | 421 | GfgeCL |
| 216 | O43184\|ADA12_HUMAN | 407 | 412 | GmgvCL |
| 217 | O43283\|M3K13_HUMAN | 133 | 138 | GlfgCL |
| 218 | O43396\|TXNL1_HUMAN | 32 | 37 | GcgpCL |
| 219 | O43396\|TXNL1_HUMAN | 144 | 149 | GfdnCL |
| 220 | O43405\|COCH_HUMAN | 10 | 15 | GlgvCL |
| 221 | O43541\|SMAD6_HUMAN | 363 | 368 | GsgfCL |
| 222 | O43609\|SPY1_HUMAN | 219 | 224 | GtcmCL |
| 223 | O43638\|FREA_HUMAN | 315 | 320 | GltpCL |
| 224 | O43747\|AP1G1_HUMAN | 65 | 70 | GqleCL |
| 225 | O43820\|HYAL3_HUMAN | 12 | 17 | GvalCL |
| 226 | O43837\|IDH3B_HUMAN | 181 | 186 | GvieCL |
| 227 | O43889\|CREB3_HUMAN | 330 | 335 | GntsCL |
| 228 | O60244\|CRSP2_HUMAN | 447 | 452 | GnseCL |
| 229 | O60266\|ADCY3_HUMAN | 44 | 49 | GsclCL |
| 230 | O60266\|ADCY3_HUMAN | 944 | 949 | GgieCL |
| 231 | O60292\|SI1L3_HUMAN | 658 | 663 | GekvCL |
| 232 | O60423\|AT8B3_HUMAN | 238 | 243 | GdvvCL |
| 233 | O60504\|VINEX_HUMAN | 478 | 483 | GehiCL |
| 234 | O60508\|PRP17_HUMAN | 320 | 325 | GerrCL |
| 235 | O60613\|SEP15_HUMAN | 4 | 9 | GpsgCL |
| 236 | O60656\|UD19_HUMAN | 510 | 515 | GyrkCL |
| 237 | O60662\|KBTBA_HUMAN | 447 | 452 | GmiyCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 238 | O60669\|MOT2_HUMAN | 93 | 98 | GllcCL |
| 239 | O60673\|DPOLZ_HUMAN | 47 | 52 | GqktCL |
| 240 | O60704\|TPST2_HUMAN | 229 | 234 | GkekCL |
| 241 | O60706\|ABCC9_HUMAN | 1046 | 1051 | GiflCL |
| 242 | O60883\|ETBR2_HUMAN | 315 | 320 | GcyfCL |
| 243 | O75037\|KI21B_HUMAN | 1454 | 1459 | GpvmCL |
| 244 | O75037\|KI21B_HUMAN | 1617 | 1622 | GltpCL |
| 245 | O75052\|CAPON_HUMAN | 420 | 425 | GrrdCL |
| 246 | O75077\|ADA23_HUMAN | 487 | 492 | GggaCL |
| 247 | O75078\|ADA11_HUMAN | 429 | 434 | GggsCL |
| 248 | O75094\|SLIT3_HUMAN | 1428 | 1433 | GepyCL |
| 249 | O75095\|MEGF6_HUMAN | 695 | 700 | GaclCL |
| 250 | O75173\|ATS4_HUMAN | 19 | 24 | GaqpCL |
| 251 | O75173\|ATS4_HUMAN | 419 | 424 | GyghCL |
| 252 | O75311\|GLRA3_HUMAN | 387 | 392 | GmgpCL |
| 253 | O75326\|SEM7A_HUMAN | 499 | 504 | GchgCL |
| 254 | O75342\|LX12B_HUMAN | 299 | 304 | GegtCL |
| 255 | O75342\|LX12B_HUMAN | 552 | 557 | GfprCL |
| 256 | O75346\|ZN253_HUMAN | 131 | 136 | GlnqCL |
| 257 | O75426\|FBX24_HUMAN | 119 | 124 | GrrrCL |
| 258 | O75436\|VP26A_HUMAN | 169 | 174 | GiedCL |
| 259 | O75443\|TECTA_HUMAN | 1687 | 1692 | GdgyCL |
| 260 | O75445\|USH2A_HUMAN | 1668 | 1673 | GfvgCL |
| 261 | O75445\|USH2A_HUMAN | 4401 | 4406 | GqglCL |
| 262 | O75446\|SAP30_HUMAN | 64 | 69 | GqlcCL |
| 263 | O75508\|CLD11_HUMAN | 164 | 169 | GavlCL |
| 264 | O75569\|PRKRA_HUMAN | 268 | 273 | GqyqCL |
| 265 | O75592\|MYCB2_HUMAN | 1087 | 1092 | GfgvCL |
| 266 | O75636\|FCN3_HUMAN | 16 | 21 | GgpaCL |
| 267 | O75678\|RFPL2_HUMAN | 117 | 122 | GcavCL |
| 268 | O75679\|RFPL3_HUMAN | 56 | 61 | GctvCL |
| 269 | O75689\|CENA1_HUMAN | 37 | 42 | GvfiCL |
| 270 | O75691\|UTP20_HUMAN | 2132 | 2137 | GalqCL |
| 271 | O75694\|NU155_HUMAN | 230 | 235 | GkdgCL |
| 272 | O75843\|AP1G2_HUMAN | 67 | 72 | GqmeCL |
| 273 | O75886\|STAM2_HUMAN | 42 | 47 | GakdCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 274 | O75911\|DHRS3_HUMAN | 168 | 173 | GhivCL |
| 275 | O75916\|RGS9_HUMAN | 642 | 647 | GsgtCL |
| 276 | O75923\|DYSF_HUMAN | 378 | 383 | GahfCL |
| 277 | O75923\|DYSF_HUMAN | 1574 | 1579 | GpqeCL |
| 278 | O75925\|PIAS1_HUMAN | 431 | 436 | GvdgCL |
| 279 | O75954\|TSN9_HUMAN | 4 | 9 | GcicCL |
| 280 | O75954\|TSN9_HUMAN | 68 | 73 | GflgCL |
| 281 | O76000\|OR2B3_HUMAN | 108 | 113 | GateCL |
| 282 | O76013\|K1H6_HUMAN | 58 | 63 | GlgsCL |
| 283 | O76064\|RNF8_HUMAN | 15 | 20 | GrswCL |
| 284 | O76075\|DFFB_HUMAN | 43 | 48 | GsrlCL |
| 285 | O94759\|TRPM2_HUMAN | 272 | 277 | GnltCL |
| 286 | O94759\|TRPM2_HUMAN | 713 | 718 | GkttCL |
| 287 | O94761\|RECQ4_HUMAN | 543 | 548 | GlppCL |
| 288 | O94779\|CNTN5_HUMAN | 169 | 174 | GhyqCL |
| 289 | O94779\|CNTN5_HUMAN | 265 | 270 | GsyiCL |
| 290 | O94779\|CNTN5_HUMAN | 454 | 459 | GmyqCL |
| 291 | O94829\|IPO13_HUMAN | 159 | 164 | GqgrCL |
| 292 | O94856\|NFASC_HUMAN | 312 | 317 | GeyfCL |
| 293 | O94887\|FARP2_HUMAN | 192 | 197 | GqqhCL |
| 294 | O94900\|TOX_HUMAN | 22 | 27 | GpspCL |
| 295 | O94907\|DKK1_HUMAN | 107 | 112 | GvqiCL |
| 296 | O94919\|ENDD1_HUMAN | 371 | 376 | GiesCL |
| 297 | O94933\|SLIK3_HUMAN | 898 | 903 | GfvdCL |
| 298 | O94955\|RHBT3_HUMAN | 386 | 391 | GkinCL |
| 299 | O94956\|SO2B1_HUMAN | 449 | 454 | GmllCL |
| 300 | O95071\|EDD1_HUMAN | 531 | 536 | GtqvCL |
| 301 | O95153\|RIMB1_HUMAN | 79 | 84 | GaeaCL |
| 302 | O95153\|RIMB1_HUMAN | 1485 | 1490 | GlasCL |
| 303 | O95163\|IKAP_HUMAN | 472 | 477 | GfkyCL |
| 304 | O95202\|LETM1_HUMAN | 43 | 48 | GlrnCL |
| 305 | O95210\|GET1_HUMAN | 285 | 290 | GdheCL |
| 306 | O95239\|KIF4A_HUMAN | 27 | 32 | GcqmCL |
| 307 | O95248\|MTMR5_HUMAN | 159 | 164 | GlnyCL |
| 308 | O95248\|MTMR5_HUMAN | 381 | 386 | GyrwCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 309 | O95255\|MRP6_HUMAN | 845 | 850 | GalvCL |
| 310 | O95255\|MRP6_HUMAN | 943 | 948 | GtplCL |
| 311 | O95255\|MRP6_HUMAN | 992 | 997 | GllgCL |
| 312 | O95256\|I18RA_HUMAN | 447 | 452 | GyslCL |
| 313 | O95279\|KCNK5_HUMAN | 122 | 127 | GvplCL |
| 314 | O95294\|RASL1_HUMAN | 130 | 135 | GqgrCL |
| 315 | O95342\|ABCBB_HUMAN | 327 | 332 | GfvwCL |
| 316 | O95373\|IPO7_HUMAN | 147 | 152 | GillCL |
| 317 | O95396\|MOCS3_HUMAN | 250 | 255 | GvlgCL |
| 318 | O95405\|ZFYV9_HUMAN | 137 | 142 | GnlaCL |
| 319 | O95477\|ABCA1_HUMAN | 2120 | 2125 | GrfrCL |
| 320 | O95500\|CLD14_HUMAN | 178 | 183 | GtllCL |
| 321 | O95551\|TTRAP_HUMAN | 217 | 222 | GnelCL |
| 322 | O95602\|RPA1_HUMAN | 1556 | 1561 | GitrCL |
| 323 | O95620\|DUS4L_HUMAN | 125 | 130 | GygaCL |
| 324 | O95633\|FSTL3_HUMAN | 88 | 93 | GlvhCL |
| 325 | O95671\|ASML_HUMAN | 588 | 593 | GeyqCL |
| 326 | O95714\|HERC2_HUMAN | 717 | 722 | GsthCL |
| 327 | O95714\|HERC2_HUMAN | 3265 | 3270 | GalhCL |
| 328 | O95714\|HERC2_HUMAN | 4047 | 4052 | GgkhCL |
| 329 | O95715\|SCYBE_HUMAN | 68 | 73 | GqehCL |
| 330 | O95780\|ZN682_HUMAN | 132 | 137 | GlnqCL |
| 331 | O95803\|NDST3_HUMAN | 815 | 820 | GktkCL |
| 332 | O95858\|TSN15_HUMAN | 285 | 290 | GtgcCL |
| 333 | O95873\|CF047_HUMAN | 171 | 176 | GpeeCL |
| 334 | O95886\|DLGP3_HUMAN | 284 | 289 | GgpfCL |
| 335 | O95967\|FBLN4_HUMAN | 76 | 81 | GgylCL |
| 336 | O95977\|EDG6_HUMAN | 333 | 338 | GpgdCL |
| 337 | O96006\|ZBED1_HUMAN | 221 | 226 | GapnCL |
| 338 | O96008\|TOM40_HUMAN | 72 | 77 | GacgCL |
| 339 | O96009\|NAPSA_HUMAN | 350 | 355 | GvrlCL |
| 340 | P00505\|AATM_HUMAN | 268 | 273 | GinvCL |
| 341 | P00750\|TPA_HUMAN | 515 | 520 | GplyCL |
| 342 | P00751\|CFAB_HUMAN | 288 | 293 | GakkCL |
| 343 | P01130\|LDLR_HUMAN | 314 | 319 | GtneCL |
| 344 | P01133\|EGF_HUMAN | 741 | 746 | GadpCL |
| 345 | P01266\|THYG_HUMAN | 2020 | 2025 | GevtCL |
| 346 | P01375\|TNFA_HUMAN | 26 | 31 | GsrrCL |
| 347 | P01730\|CD4_HUMAN | 366 | 371 | GmwqCL |
| 348 | P01833\|PIGR_HUMAN | 437 | 442 | GfywCL |
| 349 | P02775\|SCYB7_HUMAN | 101 | 106 | GrkiCL |
| 350 | P02776\|PLF4_HUMAN | 37 | 42 | GdlqCL |
| 351 | P02776\|PLF4_HUMAN | 79 | 84 | GrkiCL |
| 352 | P02778\|SCYBA_HUMAN | 70 | 75 | GekrCL |
| 353 | P02787\|TRFE_HUMAN | 209 | 214 | GafkCL |
| 354 | P02787\|TRFE_HUMAN | 538 | 543 | GafrCL |
| 355 | P02788\|TRFL_HUMAN | 213 | 218 | GafkCL |
| 356 | P02788\|TRFL_HUMAN | 549 | 554 | GafrCL |
| 357 | P03986\|TCC_HUMAN | 28 | 33 | GtylCL |
| 358 | P04350\|TBB4_HUMAN | 235 | 240 | GyttCL |
| 359 | P04920\|B3A2_HUMAN | 751 | 756 | GvvfCL |
| 360 | P05108\|CP11A_HUMAN | 458 | 463 | GvrqCL |
| 361 | P05141\|ADT2_HUMAN | 155 | 160 | GlgdCL |
| 362 | P05549\|AP2A_HUMAN | 371 | 376 | GiqsCL |
| 363 | P06401\|PRGR_HUMAN | 484 | 489 | GasgCL |
| 364 | P06756\|ITAV_HUMAN | 905 | 910 | GvaqCL |
| 365 | P07202\|PERT_HUMAN | 819 | 824 | GgfqCL |
| 366 | P07339\|CATD_HUMAN | 362 | 367 | GktlCL |
| 367 | P07357\|CO8A_HUMAN | 117 | 122 | GdqdCL |
| 368 | P07437\|TBB5_HUMAN | 235 | 240 | GyttCL |
| 369 | P07686\|HEXB_HUMAN | 483 | 488 | GgeaCL |
| 370 | P07814\|SYEP_HUMAN | 261 | 266 | GhscCL |
| 371 | P07942\|LAMB1_HUMAN | 1052 | 1057 | GqclCL |
| 372 | P07988\|PSPB_HUMAN | 244 | 249 | GicqCL |
| 373 | P08151\|GLI1_HUMAN | 14 | 19 | GepcCL |
| 374 | P08151\|GLI1_HUMAN | 828 | 833 | GlapCL |
| 375 | P08243\|ASNS_HUMAN | 8 | 13 | GsddCL |
| 376 | P08319\|ADH4_HUMAN | 241 | 246 | GatdCL |
| 377 | P08582\|TRFM_HUMAN | 212 | 217 | GafrCL |
| 378 | P08582\|TRFM_HUMAN | 558 | 563 | GafrCL |
| 379 | P08686\|CP21A_HUMAN | 424 | 429 | GaryCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 380 | P08697\|A2AP_HUMAN | 139 | 144 | GsgpCL |
| 381 | P08709\|FA7_HUMAN | 14 | 19 | GlqgCL |
| 382 | P08922\|ROS_HUMAN | 2248 | 2253 | GdviCL |
| 383 | P09001\|RM03_HUMAN | 291 | 296 | GhknCL |
| 384 | P09326\|CD48_HUMAN | 5 | 10 | GwdsCL |
| 385 | P09341\|GROA_HUMAN | 81 | 86 | GrkaCL |
| 386 | P09848\|LPH_HUMAN | 1846 | 1851 | GphaCL |
| 387 | P10071\|GLI3_HUMAN | 1359 | 1364 | GpesCL |
| 388 | P10109\|ADX_HUMAN | 151 | 156 | GcqiCL |
| 389 | P10145\|IL8_HUMAN | 73 | 78 | GrelCL |
| 390 | P10635\|CP2D6_HUMAN | 439 | 444 | GrraCL |
| 391 | P10646\|TFPI1_HUMAN | 213 | 218 | GpswCL |
| 392 | P10720\|PF4V_HUMAN | 40 | 45 | GdlqCL |
| 393 | P10720\|PF4V_HUMAN | 82 | 87 | GrkiCL |
| 394 | P10745\|IRBP_HUMAN | 328 | 333 | GyvhCL |
| 395 | P11047\|LAMC1_HUMAN | 903 | 908 | GqceCL |
| 396 | P11362\|FGFR1_HUMAN | 337 | 342 | GeytCL |
| 397 | P11717\|MPRI_HUMAN | 231 | 236 | GtaaCL |
| 398 | P12236\|ADT3_HUMAN | 155 | 160 | GlgdCL |
| 399 | P13473\|LAMP2_HUMAN | 228 | 233 | GndtCL |
| 400 | P13498\|CY24A_HUMAN | 45 | 50 | GvfvCL |
| 401 | P13569\|CFTR_HUMAN | 124 | 129 | GiglCL |
| 402 | P13686\|PPA5_HUMAN | 215 | 220 | GpthCL |
| 403 | P13804\|ETFA_HUMAN | 49 | 54 | GevsCL |
| 404 | P13807\|GYS1_HUMAN | 185 | 190 | GvglCL |
| 405 | P13861\|KAP2_HUMAN | 354 | 359 | GdvkCL |
| 406 | P14222\|PERF_HUMAN | 530 | 535 | GggtCL |
| 407 | P14543\|NID1_HUMAN | 24 | 29 | GpvgCL |
| 408 | P14867\|GBRA1_HUMAN | 6 | 11 | GlsdCL |
| 409 | P15151\|PVR_HUMAN | 119 | 124 | GnytCL |
| 410 | P15538\|C11B1_HUMAN | 446 | 451 | GmrqCL |
| 411 | P15692\|VEGFA_HUMAN | 168 | 173 | GarcCL |
| 412 | P16109\|LYAM3_HUMAN | 271 | 276 | GnmiCL |
| 413 | P16112\|PGCA_HUMAN | 2183 | 2188 | GhviCL |
| 414 | P16581\|LYAM2_HUMAN | 376 | 381 | GymnCL |
| 415 | P17038\|ZNF43_HUMAN | 127 | 132 | GfnqCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 416 | P17040\|ZNF31_HUMAN | 184 | 189 | GnsvCL |
| 417 | P17936\|IBP3_HUMAN | 66 | 71 | GcgcCL |
| 418 | P18510\|IL1RA_HUMAN | 87 | 92 | GgkmCL |
| 419 | P18564\|ITB6_HUMAN | 674 | 679 | GeneCL |
| 420 | P18577\|RHCE_HUMAN | 306 | 311 | GgakCL |
| 421 | P19099\|C11B2_HUMAN | 446 | 451 | GmrqCL |
| 422 | P19224\|UD16_HUMAN | 512 | 517 | GyrkCL |
| 423 | P19367\|HXK1_HUMAN | 713 | 718 | GdngCL |
| 424 | P19835\|CEL_HUMAN | 96 | 101 | GdedCL |
| 425 | P19875\|MIP2A_HUMAN | 81 | 86 | GqkaCL |
| 426 | P19876\|MIP2B_HUMAN | 81 | 86 | GkkaCL |
| 427 | P19883\|FST_HUMAN | 252 | 257 | GgkkCL |
| 428 | P20062\|TCO2_HUMAN | 79 | 84 | GyqqCL |
| 429 | P20273\|CD22_HUMAN | 691 | 696 | GlgsCL |
| 430 | P20648\|ATP4A_HUMAN | 108 | 113 | GglqCL |
| 431 | P20701\|ITAL_HUMAN | 76 | 81 | GtghCL |
| 432 | P20701\|ITAL_HUMAN | 1150 | 1155 | GdpgCL |
| 433 | P20813\|CP2B6_HUMAN | 432 | 437 | GkriCL |
| 434 | P20916\|MAG_HUMAN | 301 | 306 | GvyaCL |
| 435 | P20929\|NEBU_HUMAN | 4517 | 4522 | GyvhCL |
| 436 | P21554\|CNR1_HUMAN | 427 | 432 | GdsdCL |
| 437 | P21580\|TNAP3_HUMAN | 99 | 104 | GdgnCL |
| 438 | P21802\|FGFR2_HUMAN | 5 | 10 | GrfiCL |
| 439 | P21802\|FGFR2_HUMAN | 338 | 343 | GeytCL |
| 440 | P21817\|RYR1_HUMAN | 840 | 845 | GpsrCL |
| 441 | P21860\|ERBB3_HUMAN | 513 | 518 | GpgqCL |
| 442 | P21964\|COMT_HUMAN | 30 | 35 | GwglCL |
| 443 | P22064\|LTB1S_HUMAN | 938 | 943 | GsfrCL |
| 444 | P22064\|LTB1S_HUMAN | 1359 | 1364 | GsykCL |
| 445 | P22105\|TENX_HUMAN | 565 | 570 | GrgqCL |
| 446 | P22309\|UD11_HUMAN | 276 | 281 | GginCL |
| 447 | P22309\|UD11_HUMAN | 513 | 518 | GyrkCL |
| 448 | P22310\|UD14_HUMAN | 514 | 519 | GyrkCL |
| 449 | P22314\|UBE1_HUMAN | 230 | 235 | GyvtCL |
| 450 | P22455\|FGFR4_HUMAN | 97 | 102 | GrylCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 451 | P22455\|FGFR4_HUMAN | 220 | 225 | GtytCL |
| 452 | P22455\|FGFR4_HUMAN | 329 | 334 | GeytCL |
| 453 | P22607\|FGFR3_HUMAN | 335 | 340 | GeytCL |
| 454 | P22680\|CP7A1_HUMAN | 330 | 335 | GnpiCL |
| 455 | P22732\|GTR5_HUMAN | 348 | 353 | GfsiCL |
| 456 | P23142\|FBLN1_HUMAN | 269 | 274 | GihnCL |
| 457 | P23142\|FBLN1_HUMAN | 547 | 552 | GgfrCL |
| 458 | P23416\|GLRA2_HUMAN | 376 | 381 | GmghCL |
| 459 | P23759\|PAX7_HUMAN | 466 | 471 | GqseCL |
| 460 | P24386\|RAE1_HUMAN | 395 | 400 | GgiyCL |
| 461 | P24557\|THAS_HUMAN | 475 | 480 | GprsCL |
| 462 | P24592\|IBP6_HUMAN | 100 | 105 | GrgrCL |
| 463 | P24593\|IBP5_HUMAN | 96 | 101 | GrgyCL |
| 464 | P24821\|TENA_HUMAN | 143 | 148 | GagcCL |
| 465 | P24903\|CP2F1_HUMAN | 432 | 437 | GrrlCL |
| 466 | P25205\|MCM3_HUMAN | 239 | 244 | GtyrCL |
| 467 | P25874\|UCP1_HUMAN | 21 | 26 | GiaaCL |
| 468 | P25940\|CO5A3_HUMAN | 1581 | 1586 | GgetCL |
| 469 | P26374\|RAE2_HUMAN | 397 | 402 | GgiyCL |
| 470 | P26951\|IL3RA_HUMAN | 363 | 368 | GleeCL |
| 471 | P27487\|DPP4_HUMAN | 335 | 340 | GrwnCL |
| 472 | P27540\|ARNT_HUMAN | 332 | 337 | GskfCL |
| 473 | P27987\|IP3KB_HUMAN | 284 | 289 | GtrsCL |
| 474 | P28332\|ADH6_HUMAN | 237 | 242 | GateCL |
| 475 | P28340\|DP0D1_HUMAN | 709 | 714 | GklpCL |
| 476 | P29274\|AA2AR_HUMAN | 162 | 167 | GqvaCL |
| 477 | P29353\|SHC1_HUMAN | 570 | 575 | GselCL |
| 478 | P29459\|IL12A_HUMAN | 33 | 38 | GmfpCL |
| 479 | P30040\|ERP29_HUMAN | 153 | 158 | GmpgCL |
| 480 | P30530\|UFO_HUMAN | 106 | 111 | GqyqCL |
| 481 | P30532\|ACHA5_HUMAN | 279 | 284 | GekiCL |
| 482 | P30566\|PUR8_HUMAN | 169 | 174 | GkrcCL |
| 483 | P31323\|KAP3_HUMAN | 368 | 373 | GtvkCL |
| 484 | P32004\|L1CAM_HUMAN | 308 | 313 | GeyrCL |
| 485 | P32004\|L1CAM_HUMAN | 493 | 498 | GryfCL |
| 486 | P32314\|FOXN2_HUMAN | 319 | 324 | GirtCL |
| 487 | P32418\|NAC1_HUMAN | 414 | 419 | GtyqCL |
| 488 | P32929\|CGL_HUMAN | 80 | 85 | GakyCL |
| 489 | P32970\|TNFL7_HUMAN | 29 | 34 | GlviCL |
| 490 | P33402\|GCYA2_HUMAN | 284 | 289 | GncsCL |
| 491 | P34913\|HYES_HUMAN | 258 | 263 | GpavCL |
| 492 | P34981\|TRFR_HUMAN | 94 | 99 | GyvgCL |
| 493 | P34998\|CRFR1_HUMAN | 83 | 88 | GyreCL |
| 494 | P35227\|PCGF2_HUMAN | 316 | 321 | GslnCL |
| 495 | P35251\|RFC1_HUMAN | 402 | 407 | GaenCL |
| 496 | P35270\|SPRE_HUMAN | 6 | 11 | GravCL |
| 497 | P35367\|HRH1_HUMAN | 96 | 101 | GrplCL |
| 498 | P35452\|HXD12_HUMAN | 176 | 181 | GvasCL |
| 499 | P35498\|SCN1A_HUMAN | 964 | 969 | GqamCL |
| 500 | P35499\|SCN4A_HUMAN | 774 | 779 | GqamCL |
| 501 | P35503\|UD13_HUMAN | 514 | 519 | GyrkCL |
| 502 | P35504\|UD15_HUMAN | 514 | 519 | GyrkCL |
| 503 | P35555\|FBN1_HUMAN | 1259 | 1264 | GeyrCL |
| 504 | P35555\|FBN1_HUMAN | 1385 | 1390 | GsyrCL |
| 505 | P35555\|FBN1_HUMAN | 1416 | 1421 | GnggCL |
| 506 | P35555\|FBN1_HUMAN | 1870 | 1875 | GsfyCL |
| 507 | P35555\|FBN1_HUMAN | 2034 | 2039 | GsfkCL |
| 508 | P35556\|FBN2_HUMAN | 1303 | 1308 | GeyrCL |
| 509 | P35556\|FBN2_HUMAN | 1952 | 1957 | GsynCL |
| 510 | P35556\|FBN2_HUMAN | 1994 | 1999 | GsfkCL |
| 511 | P35556\|FBN2_HUMAN | 2076 | 2081 | GgfqCL |
| 512 | P35590\|TIE1_HUMAN | 280 | 285 | GltfCL |
| 513 | P35916\|VGFR3_HUMAN | 4 | 9 | GaalCL |
| 514 | P35968\|VGFR2_HUMAN | 638 | 643 | GdyvCL |
| 515 | P36509\|UD12_HUMAN | 510 | 515 | GyrkCL |
| 516 | P36888\|FLT3_HUMAN | 99 | 104 | GnisCL |
| 517 | P37058\|DHB3_HUMAN | 13 | 18 | GllvCL |
| 518 | P38398\|BRCA1_HUMAN | 949 | 954 | GsrfCL |
| 519 | P38571\|LICH_HUMAN | 7 | 12 | GlvvCL |
| 520 | P38571\|LICH_HUMAN | 58 | 63 | GyilCL |
| 521 | P38606\|VATA1_HUMAN | 390 | 395 | GrvkCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 522 | P38607\|VATA2_HUMAN | 388 | 393 | GrvkCL |
| 523 | P39059\|COFA1_HUMAN | 8 | 13 | GqcwCL |
| 524 | P40205\|NCYM_HUMAN | 100 | 105 | GrppCL |
| 525 | P40939\|ECHA_HUMAN | 709 | 714 | GfppCL |
| 526 | P41217\|OX2G_HUMAN | 117 | 122 | GcymCL |
| 527 | P42331\|RHG25_HUMAN | 4 | 9 | GqsaCL |
| 528 | P42345\|FRAP_HUMAN | 1479 | 1484 | GrmrCL |
| 529 | P42785\|PCP_HUMAN | 339 | 344 | GqvkCL |
| 530 | P42830\|SCYB5_HUMAN | 87 | 92 | GkeiCL |
| 531 | P42892\|ECE1_HUMAN | 79 | 84 | GlvaCL |
| 532 | P43378\|PTN9_HUMAN | 334 | 339 | GdvpCL |
| 533 | P43403\|ZAP70_HUMAN | 113 | 118 | GvfdCL |
| 534 | P43403\|ZAP70_HUMAN | 245 | 250 | GliyCL |
| 535 | P46379\|BAT3_HUMAN | 872 | 877 | GlfeCL |
| 536 | P46531\|NOTC1_HUMAN | 1354 | 1359 | GslrCL |
| 537 | P47775\|GPR12_HUMAN | 166 | 171 | GtsiCL |
| 538 | P47804\|RGR_HUMAN | 275 | 280 | GiwqCL |
| 539 | P48048\|IRK1_HUMAN | 204 | 209 | GgklCL |
| 540 | P48052\|CBPA2_HUMAN | 12 | 17 | GhiyCL |
| 541 | P48059\|PINC_HUMAN | 176 | 181 | GelyCL |
| 542 | P48067\|SC6A9_HUMAN | 457 | 462 | GtqfCL |
| 543 | P48230\|T4S4_HUMAN | 5 | 10 | GcarCL |
| 544 | P48745\|NOV_HUMAN | 60 | 65 | GcscCL |
| 545 | P49247\|RPIA_HUMAN | 100 | 105 | GgggCL |
| 546 | P49327\|FAS_HUMAN | 1455 | 1460 | GlynCL |
| 547 | P49588\|SYAC_HUMAN | 897 | 902 | GkitCL |
| 548 | P49640\|EVX1_HUMAN | 345 | 350 | GpcsCL |
| 549 | P49641\|MA2A2_HUMAN | 862 | 867 | GwrgCL |
| 550 | P49646\|YYY1_HUMAN | 393 | 398 | GetpCL |
| 551 | P49753\|ACOT2_HUMAN | 296 | 301 | GgelCL |
| 552 | P49903\|SPS1_HUMAN | 323 | 328 | GlliCL |
| 553 | P49910\|ZN165_HUMAN | 32 | 37 | GqdtCL |
| 554 | P50851\|LRBA_HUMAN | 2736 | 2741 | GpenCL |
| 555 | P51151\|RAB9A_HUMAN | 79 | 84 | GsdcCL |
| 556 | P51168\|SCNNB_HUMAN | 532 | 537 | GsvlCL |
| 557 | P51589\|CP2J2_HUMAN | 444 | 449 | GkraCL |
| 558 | P51606\|RENBP_HUMAN | 37 | 42 | GfftCL |
| 559 | P51674\|GPM6A_HUMAN | 170 | 175 | GanlCL |
| 560 | P51685\|CCR8_HUMAN | 150 | 155 | GttlCL |
| 561 | P51790\|CLCN3_HUMAN | 520 | 525 | GaaaCL |
| 562 | P51790\|CLCN3_HUMAN | 723 | 728 | GlrqCL |
| 563 | P51793\|CLCN4_HUMAN | 520 | 525 | GaaaCL |
| 564 | P51793\|CLCN4_HUMAN | 721 | 726 | GlrqCL |
| 565 | P51795\|CLCN5_HUMAN | 506 | 511 | GaaaCL |
| 566 | P51795\|CLCN5_HUMAN | 707 | 712 | GlrqCL |
| 567 | P51800\|CLCKA_HUMAN | 613 | 618 | GhqqCL |
| 568 | P51801\|CLCKB_HUMAN | 613 | 618 | GhqqCL |
| 569 | P51957\|NEK4_HUMAN | 322 | 327 | GegkCL |
| 570 | P52306\|GDS1_HUMAN | 25 | 30 | GcldCL |
| 571 | P52306\|GDS1_HUMAN | 265 | 270 | GlveCL |
| 572 | P52429\|DGKE_HUMAN | 411 | 416 | GtkdCL |
| 573 | P52744\|ZN138_HUMAN | 48 | 53 | GlnqCL |
| 574 | P52789\|HXK2_HUMAN | 713 | 718 | GdngCL |
| 575 | P52803\|EFNA5_HUMAN | 147 | 152 | GrrsCL |
| 576 | P52823\|STC1_HUMAN | 55 | 60 | GafaCL |
| 577 | P52848\|NDST1_HUMAN | 824 | 829 | GktkCL |
| 578 | P52849\|NDST2_HUMAN | 302 | 307 | GkrlCL |
| 579 | P52849\|NDST2_HUMAN | 823 | 828 | GktrCL |
| 580 | P52961\|NAR1_HUMAN | 220 | 225 | GiwtCL |
| 581 | P53355\|DAPK1_HUMAN | 1326 | 1331 | GkdwCL |
| 582 | P54132\|BLM_HUMAN | 891 | 896 | GiiyCL |
| 583 | P54277\|PMS1_HUMAN | 837 | 842 | GmanCL |
| 584 | P54750\|PDE1A_HUMAN | 32 | 37 | GilrCL |
| 585 | P54753\|EPHB3_HUMAN | 297 | 302 | GegpCL |
| 586 | P54826\|GAS1_HUMAN | 19 | 24 | GawlCL |
| 587 | P55160\|NCKPL_HUMAN | 938 | 943 | GpieCL |
| 588 | P55268\|LAMB2_HUMAN | 501 | 506 | GcdrCL |
| 589 | P55268\|LAMB2_HUMAN | 1063 | 1068 | GqcpCL |
| 590 | P56192\|SYMC_HUMAN | 8 | 13 | GvpgCL |
| 591 | P56749\|CLD12_HUMAN | 63 | 68 | GssdCL |
| 592 | P57077\|TAK1L_HUMAN | 68 | 73 | GflkCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 593 | P57679\|EVC_HUMAN | 683 | 688 | GssqCL |
| 594 | P58215\|LOXL3_HUMAN | 13 | 18 | GlllCL |
| 595 | P58397\|ATS12_HUMAN | 447 | 452 | GwgfCL |
| 596 | P58418\|USH3A_HUMAN | 69 | 74 | GscgCL |
| 597 | P58512\|CU067_HUMAN | 166 | 171 | GfpaCL |
| 598 | P59047\|NALP5_HUMAN | 64 | 69 | GlqwCL |
| 599 | P59510\|ATS20_HUMAN | 458 | 463 | GygeCL |
| 600 | P60370\|KR105_HUMAN | 32 | 37 | GtapCL |
| 601 | P60371\|KR106_HUMAN | 16 | 21 | GsrvCL |
| 602 | P60409\|KR107_HUMAN | 16 | 21 | GsrvCL |
| 603 | P60413\|KR10C_HUMAN | 11 | 16 | GsrvCL |
| 604 | P60602\|CT052_HUMAN | 38 | 43 | GtfsCL |
| 605 | P61011\|SRP54_HUMAN | 129 | 134 | GwktCL |
| 606 | P61550\|ENT1_HUMAN | 343 | 348 | GnasCL |
| 607 | P61619\|S61A1_HUMAN | 143 | 148 | GagiCL |
| 608 | P62072\|TIM10_HUMAN | 46 | 51 | GesvCL |
| 609 | P62312\|LSM6_HUMAN | 32 | 37 | GvlaCL |
| 610 | P62714\|PP2AB_HUMAN | 161 | 166 | GqifCL |
| 611 | P67775\|PP2AA_HUMAN | 161 | 166 | GqifCL |
| 612 | P68371\|TBB2C_HUMAN | 235 | 240 | GyttCL |
| 613 | P69849\|NOMO3_HUMAN | 507 | 512 | GkvsCL |
| 614 | P78310\|CXAR_HUMAN | 219 | 224 | GsdqCL |
| 615 | P78324\|SHPS1_HUMAN | 12 | 17 | GpllCL |
| 616 | P78325\|ADAM8_HUMAN | 101 | 106 | GqdhCL |
| 617 | P78346\|RPP30_HUMAN | 253 | 258 | GdedCL |
| 618 | P78357\|CNTP1_HUMAN | 1205 | 1210 | GfsgCL |
| 619 | P78423\|X3CL1_HUMAN | 350 | 355 | GllfCL |
| 620 | P78504\|JAG1_HUMAN | 898 | 903 | GprpCL |
| 621 | P78509\|RELN_HUMAN | 2862 | 2867 | GhgdCL |
| 622 | P78524\|ST5_HUMAN | 127 | 132 | GvaaCL |
| 623 | P78549\|NTHL1_HUMAN | 286 | 291 | GqqtCL |
| 624 | P78559\|MAP1A_HUMAN | 2433 | 2438 | GpqgCX |
| 625 | P80162\|SCYB6_HUMAN | 87 | 92 | GkqvCL |
| 626 | P82279\|CRUM1_HUMAN | 1092 | 1097 | GlqgCL |
| 627 | P83105\|HTRA4_HUMAN | 10 | 15 | GlgrCL |
| 628 | P98088\|MUC5A_HUMAN | 853 | 858 | GcprCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 629 | P98095\|FBLN2_HUMAN | 1047 | 1052 | GsfrCL |
| 630 | P98153\|IDD_HUMAN | 289 | 294 | GddpCL |
| 631 | P98160\|PGBM_HUMAN | 3181 | 3186 | GtyvCL |
| 632 | P98161\|PKD1_HUMAN | 649 | 654 | GaniCL |
| 633 | P98164\|LRP2_HUMAN | 1252 | 1257 | GhpdCL |
| 634 | P98164\|LRP2_HUMAN | 3819 | 3824 | GsadCL |
| 635 | P98173\|FAM3A_HUMAN | 83 | 88 | GpkiCL |
| 636 | P98194\|AT2C1_HUMAN | 158 | 163 | GdtvCL |
| 637 | Q00872\|MYPC1_HUMAN | 447 | 452 | GkeiCL |
| 638 | Q00973\|B4GN1_HUMAN | 408 | 413 | GlgnCL |
| 639 | Q01064\|PDE1B_HUMAN | 243 | 248 | GmvhCL |
| 640 | Q01433\|AMPD2_HUMAN | 103 | 108 | GpapCL |
| 641 | Q02246\|CNTN2_HUMAN | 107 | 112 | GvyqCL |
| 642 | Q02246\|CNTN2_HUMAN | 203 | 208 | GnysCL |
| 643 | Q02318\|CP27A_HUMAN | 472 | 477 | GvraCL |
| 644 | Q02985\|FHR3_HUMAN | 188 | 193 | GsitCL |
| 645 | Q03923\|ZNF85_HUMAN | 133 | 138 | GlnqCL |
| 646 | Q03923\|ZNF85_HUMAN | 184 | 189 | GmisCL |
| 647 | Q03924\|ZN117_HUMAN | 103 | 108 | GlnqCL |
| 648 | Q03936\|ZNF92_HUMAN | 132 | 137 | GlnqCL |
| 649 | Q03938\|ZNF90_HUMAN | 132 | 137 | GlnqCL |
| 650 | Q04721\|NOTC2_HUMAN | 476 | 481 | GgftCL |
| 651 | Q05469\|LIPS_HUMAN | 716 | 721 | GeriCL |
| 652 | Q06730\|ZN33A_HUMAN | 530 | 535 | GktfCL |
| 653 | Q06732\|ZN11B_HUMAN | 531 | 536 | GktfCL |
| 654 | Q07325\|SCYB9_HUMAN | 70 | 75 | GvqtCL |
| 655 | Q07617\|SPAG1_HUMAN | 133 | 138 | GsnsCL |
| 656 | Q07954\|LRP1_HUMAN | 875 | 880 | GdndCL |
| 657 | Q07954\|LRP1_HUMAN | 3001 | 3006 | GsykCL |
| 658 | Q08629\|TICN1_HUMAN | 178 | 183 | GpcpCL |
| 659 | Q09428\|ABCC8_HUMAN | 1073 | 1078 | GivlCL |
| 660 | Q10471\|GALT2_HUMAN | 535 | 540 | GsnlCL |
| 661 | Q12796\|PNRC1_HUMAN | 63 | 68 | GdgpCL |
| 662 | Q12805\|FBLN3_HUMAN | 66 | 71 | GgylCL |
| 663 | Q12809\|KCNH2_HUMAN | 719 | 724 | GfpeCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 664 | Q12841\|FSTL1_HUMAN | 48 | 53 | GeptCL |
| 665 | Q12852\|M3K12_HUMAN | 90 | 95 | GlfgCL |
| 666 | Q12860\|CNTN1_HUMAN | 110 | 115 | GiyyCL |
| 667 | Q12882\|DPYD_HUMAN | 988 | 993 | GctlCL |
| 668 | Q12933\|TRAF2_HUMAN | 387 | 392 | GykmCL |
| 669 | Q12986\|NFX1_HUMAN | 537 | 542 | GdfsCL |
| 670 | Q13077\|TRAF1_HUMAN | 302 | 307 | GyklCL |
| 671 | Q13129\|RLF_HUMAN | 48 | 53 | GlrpCL |
| 672 | Q13200\|PSMD2_HUMAN | 135 | 140 | GereCL |
| 673 | Q13224\|NMDE2_HUMAN | 584 | 589 | GynrCL |
| 674 | Q13224\|NMDE2_HUMAN | 1392 | 1397 | GddqCL |
| 675 | Q13255\|MGR1_HUMAN | 136 | 141 | GinrCL |
| 676 | Q13275\|SEM3F_HUMAN | 305 | 310 | GghcCL |
| 677 | Q13308\|PTK7_HUMAN | 429 | 434 | GyldCL |
| 678 | Q13309\|SKP2_HUMAN | 107 | 112 | GifsCL |
| 679 | Q13322\|GRB10_HUMAN | 219 | 224 | GlerCL |
| 680 | Q13370\|PDE3B_HUMAN | 253 | 258 | GgagCL |
| 681 | Q13371\|PHLP_HUMAN | 200 | 205 | GcmiCL |
| 682 | Q13387\|JIP2_HUMAN | 594 | 599 | GlfsCL |
| 683 | Q13410\|BT1A1_HUMAN | 8 | 13 | GlprCL |
| 684 | Q13444\|ADA15_HUMAN | 405 | 410 | GmgsCL |
| 685 | Q13470\|TNK1_HUMAN | 105 | 110 | GglkCL |
| 686 | Q13485\|SMAD4_HUMAN | 359 | 364 | GdrfCL |
| 687 | Q13554\|KCC2B_HUMAN | 472 | 477 | GpppCL |
| 688 | Q13591\|SEM5A_HUMAN | 819 | 824 | GgmpCL |
| 689 | Q13591\|SEM5A_HUMAN | 876 | 881 | GgdiCL |
| 690 | Q13639\|5HT4R_HUMAN | 89 | 94 | GevfCL |
| 691 | Q13642\|FHL1_HUMAN | 23 | 28 | GhhcCL |
| 692 | Q13686\|ALKB1_HUMAN | 300 | 305 | GlphCL |
| 693 | Q13698\|CAC1S_HUMAN | 1210 | 1215 | GglyCL |
| 694 | Q13751\|LAMB3_HUMAN | 449 | 454 | GrclCL |
| 695 | Q13772\|NCOA4_HUMAN | 97 | 102 | GqfnCL |
| 696 | Q13772\|NCOA4_HUMAN | 364 | 369 | GnlkCL |
| 697 | Q13795\|ARFRP_HUMAN | 159 | 164 | GrrdCL |
| 698 | Q13822\|ENPP2_HUMAN | 21 | 26 | GvniCL |
| 699 | Q13885\|TBB2A_HUMAN | 235 | 240 | GyttCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 700 | Q14008\|CKAP5_HUMAN | 109 | 114 | GieiCL |
| 701 | Q14008\|CKAP5_HUMAN | 1237 | 1242 | GvigCL |
| 702 | Q14114\|LRP8_HUMAN | 175 | 180 | GnrsCL |
| 703 | Q14114\|LRP8_HUMAN | 336 | 341 | GlneCL |
| 704 | Q14159\|K0146_HUMAN | 513 | 518 | GtraCL |
| 705 | Q14264\|ENR1_HUMAN | 358 | 363 | GeltCL |
| 706 | Q14315\|FLNC_HUMAN | 1649 | 1654 | GlgaCL |
| 707 | Q14344\|GNA13_HUMAN | 314 | 319 | GdphCL |
| 708 | Q14392\|LRC32_HUMAN | 360 | 365 | GslpCL |
| 709 | Q14393\|GAS6_HUMAN | 138 | 143 | GnffCL |
| 710 | Q14393\|GAS6_HUMAN | 217 | 222 | GsysCL |
| 711 | Q14435\|GALT3_HUMAN | 93 | 98 | GerpCL |
| 712 | Q14435\|GALT3_HUMAN | 513 | 518 | GqplCL |
| 713 | Q14451\|GRB7_HUMAN | 517 | 522 | GilpCL |
| 714 | Q14520\|HABP2_HUMAN | 121 | 126 | GrgqCL |
| 715 | Q14524\|SCN5A_HUMAN | 911 | 916 | GqslCL |
| 716 | Q14566\|MCM6_HUMAN | 154 | 159 | GtflCL |
| 717 | Q14593\|ZN273_HUMAN | 100 | 105 | GlnqCL |
| 718 | Q14656\|ITBA1_HUMAN | 197 | 202 | GvlsCL |
| 719 | Q14669\|TRIPC_HUMAN | 562 | 567 | GladCL |
| 720 | Q14669\|TRIPC_HUMAN | 1136 | 1141 | GgaeCL |
| 721 | Q14703\|MBTP1_HUMAN | 845 | 850 | GdsnCL |
| 722 | Q14714\|SSPN_HUMAN | 91 | 96 | GiivCL |
| 723 | Q14766\|LTB1L_HUMAN | 1139 | 1144 | GsfrCL |
| 724 | Q14766\|LTB1L_HUMAN | 1560 | 1565 | GsykCL |
| 725 | Q14767\|LTBP2_HUMAN | 990 | 995 | GsytCL |
| 726 | Q14767\|LTBP2_HUMAN | 1156 | 1161 | GsyqCL |
| 727 | Q14767\|LTBP2_HUMAN | 1197 | 1202 | GsffCL |
| 728 | Q14767\|LTBP2_HUMAN | 1238 | 1243 | GsfnCL |
| 729 | Q14767\|LTBP2_HUMAN | 1324 | 1329 | GsfrCL |
| 730 | Q14767\|LTBP2_HUMAN | 1366 | 1371 | GsflCL |
| 731 | Q14774\|HLX1_HUMAN | 483 | 488 | GalgCL |
| 732 | Q14916\|NPT1_HUMAN | 110 | 115 | GfalCL |
| 733 | Q14916\|NPT1_HUMAN | 207 | 212 | GcavCL |
| 734 | Q14940\|SL9A5_HUMAN | 576 | 581 | GsgaCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 735 | Q14957\|NMDE3_HUMAN | 941 | 946 | GpspCL |
| 736 | Q15021\|CND1_HUMAN | 730 | 735 | GtiqCL |
| 737 | Q15034\|HERC3_HUMAN | 145 | 150 | GnwhCL |
| 738 | Q15048\|LRC14_HUMAN | 281 | 286 | GrftCL |
| 739 | Q15058\|KIF14_HUMAN | 438 | 443 | GfntCL |
| 740 | Q15061\|WDR43_HUMAN | 103 | 108 | GtctCL |
| 741 | Q15147\|PLCB4_HUMAN | 987 | 992 | GgsnCL |
| 742 | Q15155\|NOMO1_HUMAN | 507 | 512 | GkvsCL |
| 743 | Q15274\|NADC_HUMAN | 92 | 97 | GpahCL |
| 744 | Q15303\|ERBB4_HUMAN | 516 | 521 | GpdqCL |
| 745 | Q15334\|L2GL1_HUMAN | 722 | 727 | GvvrCL |
| 746 | Q15399\|TLR1_HUMAN | 663 | 668 | GmqiCL |
| 747 | Q15413\|RYR3_HUMAN | 229 | 234 | GhdeCL |
| 748 | Q15413\|RYR3_HUMAN | 1656 | 1661 | GlrtCL |
| 749 | Q15418\|KS6A1_HUMAN | 548 | 553 | GnpeCL |
| 750 | Q15546\|PAQRB_HUMAN | 185 | 190 | GliyCL |
| 751 | Q15633\|TRBP2_HUMAN | 321 | 326 | GlcqCL |
| 752 | Q15650\|TRIP4_HUMAN | 196 | 201 | GsgpCL |
| 753 | Q15652\|JHD2C_HUMAN | 1864 | 1869 | GfvvCL |
| 754 | Q15735\|PI5PA_HUMAN | 379 | 384 | GpgrCL |
| 755 | Q15746\|MYLK_HUMAN | 229 | 234 | GvytCL |
| 756 | Q15746\|MYLK_HUMAN | 579 | 584 | GtytCL |
| 757 | Q15858\|SCN9A_HUMAN | 940 | 945 | GqamCL |
| 758 | Q15911\|ATBF1_HUMAN | 3527 | 3532 | GsyhCL |
| 759 | Q16342\|PDCD2_HUMAN | 121 | 126 | GesvCL |
| 760 | Q16363\|LAMA4_HUMAN | 1001 | 1006 | GfvgCL |
| 761 | Q16549\|PCSK7_HUMAN | 16 | 21 | GlptCL |
| 762 | Q16617\|NKG7_HUMAN | 15 | 20 | GlmfCL |
| 763 | Q16647\|PTGIS_HUMAN | 437 | 442 | GhnhCL |
| 764 | Q16787\|LAMA3_HUMAN | 1526 | 1531 | GvssCL |
| 765 | Q30KQ9\|DB111_HUMAN | 60 | 65 | GthcCL |
| 766 | Q32MQ0\|ZN750_HUMAN | 121 | 126 | GthrCL |
| 767 | Q3KNT7\|NSN5B_HUMAN | 134 | 139 | GaehCL |
| 768 | Q3L183\|KR241_HUMAN | 153 | 158 | GqlnCL |
| 769 | Q3SYG4\|PTHB1_HUMAN | 822 | 827 | GgrlCL |
| 770 | Q3T8J9\|GON4L_HUMAN | 1740 | 1745 | GcadCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 771 | Q495M9\|USH1G_HUMAN | 76 | 81 | GhlhCL |
| 772 | Q496M8\|CI094_HUMAN | 170 | 175 | GefsCL |
| 773 | Q499Z4\|ZN672_HUMAN | 40 | 45 | GrfrCL |
| 774 | Q4G0F5\|VP26B_HUMAN | 167 | 172 | GiedCL |
| 775 | Q4KMG0\|CDON_HUMAN | 93 | 98 | GyyqCL |
| 776 | Q53G59\|KLH12_HUMAN | 426 | 431 | GviyCL |
| 777 | Q53H47\|SETMR_HUMAN | 72 | 77 | GtcsCL |
| 778 | Q53R12\|T4S20_HUMAN | 213 | 218 | GflgCL |
| 779 | Q58EX2\|SDK2_HUMAN | 469 | 474 | GtytCL |
| 780 | Q5HYK3\|COQ5_HUMAN | 240 | 245 | GrflCL |
| 781 | Q5IJ48\|CRUM2_HUMAN | 243 | 248 | GsfrCL |
| 782 | Q5JPE7\|NOMO2_HUMAN | 507 | 512 | GkvsCL |
| 783 | Q5JQC9\|AKAP4_HUMAN | 242 | 247 | GkskCL |
| 784 | Q5JVG8\|ZN506_HUMAN | 132 | 137 | GlkqCL |
| 785 | Q5JWF2\|GNAS1_HUMAN | 2 | 7 | GyrnCL |
| 786 | Q5JWF2\|GNAS1_HUMAN | 584 | 589 | GtsgCL |
| 787 | Q5JWF8\|CT134_HUMAN | 111 | 116 | GccyCL |
| 788 | Q5MJ68\|SPDYC_HUMAN | 138 | 143 | GkdwCL |
| 789 | Q5NUL3\|GP120_HUMAN | 72 | 77 | GataCL |
| 790 | Q5SRN2\|CF010_HUMAN | 117 | 122 | GsikCL |
| 791 | Q5T2D3\|OTUD3_HUMAN | 72 | 77 | GdgnCL |
| 792 | Q5T5C0\|STXB5_HUMAN | 322 | 327 | GrrpCL |
| 793 | Q5T751\|LCE1C_HUMAN | 72 | 77 | GggcCL |
| 794 | Q5T752\|LCE1D_HUMAN | 68 | 73 | GggcCL |
| 795 | Q5T753\|LCE1E_HUMAN | 72 | 77 | GggcCL |
| 796 | Q5T754\|LCE1F_HUMAN | 72 | 77 | GggcCL |
| 797 | Q5T7P2\|LCE1A_HUMAN | 64 | 69 | GggcCL |
| 798 | Q5T7P3\|LCE1B_HUMAN | 72 | 77 | GggcCL |
| 799 | Q5TA78\|LCE4A_HUMAN | 55 | 60 | GggcCL |
| 800 | Q5TA79\|LCE2A_HUMAN | 64 | 69 | GggcCL |
| 801 | Q5TA82\|LCE2D_HUMAN | 68 | 73 | GggcCL |
| 802 | Q5TCM9\|LCE5A_HUMAN | 64 | 69 | GggcCL |
| 803 | Q5TEA3\|CT194_HUMAN | 465 | 470 | GgngCL |
| 804 | Q5TEJ8\|ICB1_HUMAN | 39 | 44 | GnecCL |
| 805 | Q5THJ4\|VP13D_HUMAN | 1215 | 1220 | GslgCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 806 | Q5VST9\|OBSCN_HUMAN | 3315 | 3320 | GdryCL |
| 807 | Q5VST9\|OBSCN_HUMAN | 4189 | 4194 | GvqwCL |
| 808 | Q5VST9\|OBSCN_HUMAN | 5195 | 5200 | GvyrCL |
| 809 | Q5VST9\|OBSCN_HUMAN | 6425 | 6430 | GvytCL |
| 810 | Q5VT25\|MRCKA_HUMAN | 1325 | 1330 | GaltCL |
| 811 | Q5VUA4\|ZN318_HUMAN | 1984 | 1989 | GpspCL |
| 812 | Q5VZ18\|SHE_HUMAN | 8 | 13 | GasaCL |
| 813 | Q5VZM2\|RRAGB_HUMAN | 366 | 371 | GpkqCL |
| 814 | Q5W111\|CLLD6_HUMAN | 50 | 55 | GtggCL |
| 815 | Q5XUX1\|FBXW9_HUMAN | 184 | 189 | GgslCL |
| 816 | Q5ZPR3\|CD276_HUMAN | 216 | 221 | GtysCL |
| 817 | Q5ZPR3\|CD276_HUMAN | 434 | 439 | GtysCL |
| 818 | Q5ZPR3\|CD276_HUMAN | 472 | 477 | GlsvCL |
| 819 | Q63ZY6\|NSN5C_HUMAN | 216 | 221 | GaehCL |
| 820 | Q63ZY6\|NSN5C_HUMAN | 293 | 298 | GkgrCL |
| 821 | Q68CP9\|ARID2_HUMAN | 566 | 571 | GfykCL |
| 822 | Q6BDS2\|URFB1_HUMAN | 549 | 554 | GnlfCL |
| 823 | Q6GQQ9\|OTU7B_HUMAN | 190 | 195 | GdgnCL |
| 824 | Q6GTX8\|LAIR1_HUMAN | 10 | 15 | GlvlCL |
| 825 | Q6IS24\|GLTL3_HUMAN | 564 | 569 | GtgrCL |
| 826 | Q6ISS4\|LAIR2_HUMAN | 10 | 15 | GlvlCL |
| 827 | Q6ISS4\|LAIR2_HUMAN | 97 | 102 | GlyrCL |
| 828 | Q6N022\|TEN4_HUMAN | 139 | 144 | GrssCL |
| 829 | Q6NUM9\|RETST_HUMAN | 366 | 371 | GnarCL |
| 830 | Q6P1M0\|S27A4_HUMAN | 297 | 302 | GigqCL |
| 831 | Q6P1R4\|DUS1L_HUMAN | 209 | 214 | GniqCL |
| 832 | Q6P587\|FAHD1_HUMAN | 96 | 101 | GyalCL |
| 833 | Q6P656\|CO026_HUMAN | 144 | 149 | GqdfCL |
| 834 | Q6PCB7\|S27A1_HUMAN | 300 | 305 | GvgqCL |
| 835 | Q6PCT2\|FXL19_HUMAN | 222 | 227 | GgdaCL |
| 836 | Q6Q0C0\|TRAF7_HUMAN | 397 | 402 | GpvwCL |
| 837 | Q6Q4G3\|LAEVR_HUMAN | 794 | 799 | GledCL |
| 838 | Q6TGC4\|PADI6_HUMAN | 22 | 27 | GteiCL |
| 839 | Q6UB99\|ANR11_HUMAN | 498 | 503 | GssgCL |
| 840 | Q6UWJ8\|C16L2_HUMAN | 15 | 20 | GgccCL |
| 841 | Q6UWN5\|LYPD5_HUMAN | 15 | 20 | GaalCL |
| 842 | Q6UX01\|LMBRL_HUMAN | 394 | 399 | GncyCL |
| 843 | Q6UX53\|MET7B_HUMAN | 199 | 204 | GdgcCL |
| 844 | Q6UX65\|TMM77_HUMAN | 99 | 104 | GilsCL |
| 845 | Q6UXV0\|GFRAL_HUMAN | 127 | 132 | GmwsCL |
| 846 | Q6UY09\|CEA20_HUMAN | 226 | 231 | GlyrCL |
| 847 | Q6V0L0\|CP26C_HUMAN | 455 | 460 | GarsCL |
| 848 | Q6V0L0\|CP26C_HUMAN | 517 | 522 | GnglCL |
| 849 | Q6VVB1\|NHLC1_HUMAN | 47 | 52 | GhvyCL |
| 850 | Q6VVX0\|CP2R1_HUMAN | 444 | 449 | GrrhCL |
| 851 | Q6W4X9\|MUC6_HUMAN | 1095 | 1100 | GdceCL |
| 852 | Q6WN34\|CRDL2_HUMAN | 54 | 59 | GlmyCL |
| 853 | Q6ZN16\|M3K15_HUMAN | 82 | 87 | GarqCL |
| 854 | Q6ZN17\|LN28B_HUMAN | 103 | 108 | GgspCL |
| 855 | Q6ZRI6\|CO039_HUMAN | 141 | 146 | GlstCL |
| 856 | Q6ZRQ5\|CF167_HUMAN | 1116 | 1121 | GilkCL |
| 857 | Q6ZSY5\|PPR3F_HUMAN | 647 | 652 | GaevCL |
| 858 | Q6ZV89\|SH2D5_HUMAN | 195 | 200 | GghsCL |
| 859 | Q6ZVD8\|PHLPL_HUMAN | 5 | 10 | GsrnCL |
| 860 | Q6ZW76\|ANKS3_HUMAN | 632 | 637 | GqalCL |
| 861 | Q75N90\|FBN3_HUMAN | 551 | 556 | GsfsCL |
| 862 | Q75N90\|FBN3_HUMAN | 1217 | 1222 | GghrCL |
| 863 | Q75N90\|FBN3_HUMAN | 1826 | 1831 | GsymCL |
| 864 | Q75N90\|FBN3_HUMAN | 1866 | 1871 | GsynCL |
| 865 | Q75N90\|FBN3_HUMAN | 1908 | 1913 | GsfhCL |
| 866 | Q75N90\|FBN3_HUMAN | 1990 | 1995 | GsfqCL |
| 867 | Q7L099\|RUFY3_HUMAN | 37 | 42 | GewlCL |
| 868 | Q7L0J3\|SV2A_HUMAN | 230 | 235 | GrrqCL |
| 869 | Q7L3T8\|SYPM_HUMAN | 149 | 154 | GkeyCL |
| 870 | Q7L622\|K1333_HUMAN | 310 | 315 | GitdCL |
| 871 | Q7LBC6\|JHD2B_HUMAN | 1049 | 1054 | GfgvCL |
| 872 | Q7LBC6\|JHD2B_HUMAN | 1388 | 1393 | GrllCL |
| 873 | Q7RTN6\|STRAD_HUMAN | 294 | 299 | GtvpCL |
| 874 | Q7RTP0\|NIPA1_HUMAN | 122 | 127 | GklgCL |
| 875 | Q7RTU9\|STRC_HUMAN | 1077 | 1082 | GacsCL |
| 876 | Q7RTX0\|TS1R3_HUMAN | 20 | 25 | GaplCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 877 | Q7Z2W7\|TRPM8_HUMAN | 652 | 657 | GgsnCL |
| 878 | Q7Z333\|SETX_HUMAN | 1106 | 1111 | GekkCL |
| 879 | Q7Z3K3\|POGZ_HUMAN | 749 | 754 | GrqtCL |
| 880 | Q7Z3T1\|OR2W3_HUMAN | 108 | 113 | GgveCL |
| 881 | Q7Z401\|MYCPP_HUMAN | 948 | 953 | GsadCL |
| 882 | Q7Z460\|CLAP1_HUMAN | 146 | 151 | GiclCL |
| 883 | Q7Z4S6\|KI21A_HUMAN | 1493 | 1498 | GpvmCL |
| 884 | Q7Z5G4\|GOGA7_HUMAN | 68 | 73 | GclaCL |
| 885 | Q7Z5K2\|WAPL_HUMAN | 850 | 855 | GaerCL |
| 886 | Q7Z713\|ANR37_HUMAN | 75 | 80 | GsleCL |
| 887 | Q7Z7E8\|UB2Q1_HUMAN | 36 | 41 | GpgpCL |
| 888 | Q7Z7M0\|MEGF8_HUMAN | 403 | 408 | GcgwCL |
| 889 | Q7Z7M1\|GP144_HUMAN | 343 | 348 | GselCL |
| 890 | Q86SG6\|NEK8_HUMAN | 418 | 423 | GsngCL |
| 891 | Q86SQ6\|GP123_HUMAN | 1058 | 1063 | GraaCL |
| 892 | Q86SQ6\|GP123_HUMAN | 1091 | 1096 | GhasCL |
| 893 | Q86T20\|CF001_HUMAN | 75 | 80 | GvldCL |
| 894 | Q86T65\|DAAM2_HUMAN | 570 | 575 | GappCL |
| 895 | Q86TX2\|ACOT1_HUMAN | 234 | 239 | GgelCL |
| 896 | Q86U44\|MTA70_HUMAN | 479 | 484 | GkehCL |
| 897 | Q86UE6\|LRTM1_HUMAN | 19 | 24 | GvvlCL |
| 898 | Q86UK0\|ABCAC_HUMAN | 1251 | 1256 | GwlcCL |
| 899 | Q86UK5\|LBN_HUMAN | 26 | 31 | GgrgCL |
| 900 | Q86UQ4\|ABCAD_HUMAN | 4056 | 4061 | GppfCL |
| 901 | Q86UQ4\|ABCAD_HUMAN | 4932 | 4937 | GsfkCL |
| 902 | Q86UU1\|PHLB1_HUMAN | 119 | 124 | GcmlCL |
| 903 | Q86UU1\|PHLB1_HUMAN | 1245 | 1250 | GvdtCL |
| 904 | Q86UV5\|UBP48_HUMAN | 50 | 55 | GnpnCL |
| 905 | Q86UW9\|DTX2_HUMAN | 347 | 352 | GlpvCL |
| 906 | Q86V24\|ADR2_HUMAN | 190 | 195 | GailCL |
| 907 | Q86V71\|ZN429_HUMAN | 132 | 137 | GlnqCL |
| 908 | Q86VH4\|LRTM4_HUMAN | 271 | 276 | GtfkCL |
| 909 | Q86WB7\|UN93A_HUMAN | 178 | 183 | GasdCL |
| 910 | Q86WG5\|MTMRD_HUMAN | 369 | 374 | GyrsCL |
| 911 | Q86WK7\|AMGO3_HUMAN | 348 | 353 | GlfvCL |
| 912 | Q86WR7\|CJ047_HUMAN | 84 | 89 | GgvcCL |
| 913 | Q86X76\|NIT1_HUMAN | 288 | 293 | GpglCL |
| 914 | Q86XN8\|RKHD1_HUMAN | 192 | 197 | GtdvCL |
| 915 | Q86Y01\|DTX1_HUMAN | 345 | 350 | GlpvCL |
| 916 | Q86Y56\|HEAT2_HUMAN | 271 | 276 | GwllCL |
| 917 | Q86YC3\|LRC33_HUMAN | 396 | 401 | GlasCL |
| 918 | Q8IU80\|TMPS6_HUMAN | 503 | 508 | GqpdCL |
| 919 | Q8IUK8\|CBLN2_HUMAN | 27 | 32 | GcgsCL |
| 920 | Q8IUL8\|CILP2_HUMAN | 464 | 469 | GcqkCL |
| 921 | Q8IVF6\|ANR18_HUMAN | 706 | 711 | GykkCL |
| 922 | Q8IVH4\|MMAA_HUMAN | 96 | 101 | GqraCL |
| 923 | Q8IWB7\|WDFY1_HUMAN | 200 | 205 | GsvaCL |
| 924 | Q8IWN6\|CX052_HUMAN | 89 | 94 | GskrCL |
| 925 | Q8IWV2\|CNTN4_HUMAN | 380 | 385 | GmyqCL |
| 926 | Q8IWY4\|SCUB1_HUMAN | 342 | 347 | GsfqCL |
| 927 | Q8IX30\|SCUB3_HUMAN | 337 | 342 | GsfqCL |
| 928 | Q8IXI1\|MIRO2_HUMAN | 515 | 520 | GqtpCL |
| 929 | Q8IXW0\|CK035_HUMAN | 268 | 273 | GslpCL |
| 930 | Q8IY26\|PPAC2_HUMAN | 149 | 154 | GtlyCL |
| 931 | Q8IY49\|PAQRA_HUMAN | 216 | 221 | GvfyCL |
| 932 | Q8IYB9\|ZN595_HUMAN | 132 | 137 | GvyqCL |
| 933 | Q8IYG6\|LRC56_HUMAN | 194 | 199 | GnlvCL |
| 934 | Q8IZ96\|CKLF1_HUMAN | 112 | 117 | GgslCL |
| 935 | Q8IZD0\|SAM14_HUMAN | 95 | 100 | GgsfCL |
| 936 | Q8IZE3\|PACE1_HUMAN | 322 | 327 | GetpCL |
| 937 | Q8IZF4\|GP114_HUMAN | 521 | 526 | GkllCL |
| 938 | Q8IZJ1\|UNC5B_HUMAN | 547 | 552 | GtfgCL |
| 939 | Q8IZL8\|PELP1_HUMAN | 317 | 322 | GlarCL |
| 940 | Q8IZY2\|ABCA7_HUMAN | 2001 | 2006 | GrfrCL |
| 941 | Q8N122\|RPTOR_HUMAN | 549 | 554 | GqeaCL |
| 942 | Q8N122\|RPTOR_HUMAN | 1302 | 1307 | GaisCL |
| 943 | Q8N1F7\|NUP93_HUMAN | 518 | 523 | GdppCL |
| 944 | Q8N1G0\|ZN687_HUMAN | 1133 | 1138 | GaqqCL |
| 945 | Q8N283\|ANR35_HUMAN | 65 | 70 | GlteCL |
| 946 | Q8N283\|ANR35_HUMAN | 703 | 708 | GlwdCL |
| 947 | Q8N357\|CB018_HUMAN | 57 | 62 | GefsCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 948 | Q8N3C7\|RSNL2_HUMAN | 201 | 206 | GavkCL |
| 949 | Q8N3V7\|SYNPO_HUMAN | 28 | 33 | GsyrCL |
| 950 | Q8N441\|FGRL1_HUMAN | 334 | 339 | GmyiCL |
| 951 | Q8N442\|GUF1_HUMAN | 334 | 339 | GdtlCL |
| 952 | Q8N4B4\|FBX39_HUMAN | 114 | 119 | GllsCL |
| 953 | Q8N5D0\|WDTC1_HUMAN | 48 | 53 | GcvnCL |
| 954 | Q8N5D6\|GBGT1_HUMAN | 9 | 14 | GlgfCL |
| 955 | Q8N655\|CJ012_HUMAN | 468 | 473 | GdvkCL |
| 956 | Q8N6F8\|WBS27_HUMAN | 160 | 165 | GglvCL |
| 957 | Q8N6T3\|ARFG1_HUMAN | 38 | 43 | GiwiCL |
| 958 | Q8N6V9\|TEX9_HUMAN | 3 | 8 | GrslCL |
| 959 | Q8N6Y1\|PCD20_HUMAN | 27 | 32 | GpfsCL |
| 960 | Q8N6Y1\|PCD20_HUMAN | 881 | 886 | GiyiCL |
| 961 | Q8N726\|CD2A2_HUMAN | 160 | 165 | GrarCL |
| 962 | Q8N813\|CC056_HUMAN | 42 | 47 | GsctCL |
| 963 | Q8N895\|ZN366_HUMAN | 695 | 700 | GrdeCL |
| 964 | Q8N8A2\|ANR44_HUMAN | 543 | 548 | GhrqCL |
| 965 | Q8N8A2\|ANR44_HUMAN | 645 | 650 | GhtlCL |
| 966 | Q8N8Q9\|NIPA2_HUMAN | 112 | 117 | GkigCL |
| 967 | Q8N8R3\|MCATL_HUMAN | 133 | 138 | GsldCL |
| 968 | Q8N9B4\|ANR42_HUMAN | 142 | 147 | GrlgCL |
| 969 | Q8N9B4\|ANR42_HUMAN | 281 | 286 | GhieCL |
| 970 | Q8N9L9\|ACOT4_HUMAN | 234 | 239 | GadiCL |
| 971 | Q8NB46\|ANR52_HUMAN | 434 | 439 | GnveCL |
| 972 | Q8NB46\|ANR52_HUMAN | 732 | 737 | GcedCL |
| 973 | Q8NB46\|ANR52_HUMAN | 802 | 807 | GhedCL |
| 974 | Q8NB49\|AT11C_HUMAN | 110 | 115 | GyedCL |
| 975 | Q8NBJ9\|SIDT2_HUMAN | 296 | 301 | GmlfCL |
| 976 | Q8NBV4\|PPAC3_HUMAN | 128 | 133 | GtilCL |
| 977 | Q8NCL4\|GALT6_HUMAN | 505 | 510 | GtnqCL |
| 978 | Q8NCL4\|GALT6_HUMAN | 593 | 598 | GsgtCL |
| 979 | Q8NCN4\|RN169_HUMAN | 67 | 72 | GcagCL |
| 980 | Q8NDX1\|PSD4_HUMAN | 183 | 188 | GlkcCL |
| 981 | Q8NDX1\|PSD4_HUMAN | 821 | 826 | GedhCL |
| 982 | Q8NEN9\|PDZD8_HUMAN | 724 | 729 | GgliCL |
| 983 | Q8NFP4\|MDGA1_HUMAN | 622 | 627 | GsaaCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 984 | Q8NFP9\|NBEA_HUMAN | 2819 | 2824 | GpenCL |
| 985 | Q8NFU7\|CXXC6_HUMAN | 1660 | 1665 | GvtaCL |
| 986 | Q8NG94\|O11H1_HUMAN | 112 | 117 | GtseCL |
| 987 | Q8NG99\|OR7G2_HUMAN | 109 | 114 | GlenCL |
| 988 | Q8NGC9\|O11H4_HUMAN | 118 | 123 | GtteCL |
| 989 | Q8NGH6\|O52L2_HUMAN | 96 | 101 | GytyCL |
| 990 | Q8NGH7\|O52L1_HUMAN | 96 | 101 | GyivCL |
| 991 | Q8NGI2\|O52N4_HUMAN | 95 | 100 | GfdeCL |
| 992 | Q8NGJ0\|OR5A1_HUMAN | 111 | 116 | GlseCL |
| 993 | Q8NGK5\|O52M1_HUMAN | 95 | 100 | GldaCL |
| 994 | Q8NGR9\|OR1N2_HUMAN | 112 | 117 | GldnCL |
| 995 | Q8NGS6\|O13C3_HUMAN | 108 | 113 | GsteCL |
| 996 | Q8NGT2\|O13J1_HUMAN | 108 | 113 | GsteCL |
| 997 | Q8NGT5\|OR9A2_HUMAN | 247 | 252 | GygsCL |
| 998 | Q8NGT9\|O2A42_HUMAN | 107 | 112 | GhseCL |
| 999 | Q8NGU2\|OR9A4_HUMAN | 251 | 256 | GygsCL |
| 1000 | Q8NGZ9\|O2T10_HUMAN | 109 | 114 | GaecCL |
| 1001 | Q8NH09\|OR8S1_HUMAN | 109 | 114 | GteaCL |
| 1002 | Q8NH19\|O10AG_HUMAN | 99 | 104 | GgteCL |
| 1003 | Q8NH40\|OR6S1_HUMAN | 66 | 71 | GnlsCL |
| 1004 | Q8NHA8\|OR1FC_HUMAN | 50 | 55 | GsdhCL |
| 1005 | Q8NHU2\|CT026_HUMAN | 158 | 163 | GnipCL |
| 1006 | Q8NHU2\|CT026_HUMAN | 582 | 587 | GfksCL |
| 1007 | Q8NHW6\|OTOSP_HUMAN | 8 | 13 | GlalCL |
| 1008 | Q8NHX4\|SPTA3_HUMAN | 175 | 180 | GsrsCL |
| 1009 | Q8NHY2\|RFWD2_HUMAN | 628 | 633 | GkpyCL |
| 1010 | Q8NHY3\|GA2L2_HUMAN | 463 | 468 | GpaeCL |
| 1011 | Q8TB24\|RIN3_HUMAN | 31 | 36 | GmrlCL |
| 1012 | Q8TB24\|RIN3_HUMAN | 971 | 976 | GsppCL |
| 1013 | Q8TCB7\|METL6_HUMAN | 89 | 94 | GvgnCL |
| 1014 | Q8TCN5\|ZN507_HUMAN | 142 | 147 | GmyrCL |
| 1015 | Q8TCT7\|PSL1_HUMAN | 262 | 267 | GlysCL |
| 1016 | Q8TCT7\|PSL1_HUMAN | 329 | 334 | GiafCL |
| 1017 | Q8TCT8\|PSL2_HUMAN | 321 | 326 | GiafCL |
| 1018 | Q8TD26\|CHD6_HUMAN | 1627 | 1632 | GnlcCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1019 | Q8TD43\|TRPM4_HUMAN | 238 | 243 | GthgCL |
| 1020 | Q8TD43\|TRPM4_HUMAN | 306 | 311 | GaadCL |
| 1021 | Q8TD43\|TRPM4_HUMAN | 650 | 655 | GdatCL |
| 1022 | Q8TD43\|TRPM4_HUMAN | 764 | 769 | GgrrCL |
| 1023 | Q8TDJ6\|DMXL2_HUMAN | 188 | 193 | GkddCL |
| 1024 | Q8TDM6\|DLG5_HUMAN | 1672 | 1677 | GykdCL |
| 1025 | Q8TDN4\|CABL1_HUMAN | 135 | 140 | GsgpCL |
| 1026 | Q8TDU6\|GPBAR_HUMAN | 81 | 86 | GywsCL |
| 1027 | Q8TDU9\|RL3R2_HUMAN | 187 | 192 | GvrlCL |
| 1028 | Q8TDV0\|GP151_HUMAN | 183 | 188 | GvemCL |
| 1029 | Q8TDX9\|PK1L1_HUMAN | 317 | 322 | GealCL |
| 1030 | Q8TDY2\|RBCC1_HUMAN | 897 | 902 | GelyCL |
| 1031 | Q8TDZ2\|MICA1_HUMAN | 743 | 748 | GhfyCL |
| 1032 | Q8TE49\|OTU7A_HUMAN | 206 | 211 | GdgnCL |
| 1033 | Q8TE58\|ATS15_HUMAN | 418 | 423 | GhgdCL |
| 1034 | Q8TE85\|GRHL3_HUMAN | 429 | 434 | GvkgCL |
| 1035 | Q8TEM1\|PO210_HUMAN | 1489 | 1494 | GdvlCL |
| 1036 | Q8TF62\|AT8B4_HUMAN | 282 | 287 | GfliCL |
| 1037 | Q8TF76\|HASP_HUMAN | 190 | 195 | GtsaCL |
| 1038 | Q8WTV0\|SCRB1_HUMAN | 319 | 324 | GfcpCL |
| 1039 | Q8WUB8\|PHF10_HUMAN | 320 | 325 | GhpsCL |
| 1040 | Q8WUM0\|NU133_HUMAN | 112 | 117 | GgwaCL |
| 1041 | Q8WWQ8\|STAB2_HUMAN | 1358 | 1363 | GngiCL |
| 1042 | Q8WWQ8\|STAB2_HUMAN | 2026 | 2031 | GsgqCL |
| 1043 | Q8WWX0\|ASB5_HUMAN | 179 | 184 | GhheCL |
| 1044 | Q8WWZ1\|IL1FA_HUMAN | 63 | 68 | GgsrCL |
| 1045 | Q8WXI2\|CNKR2_HUMAN | 22 | 27 | GlddCL |
| 1046 | Q8WXI7\|MUC16_HUMAN | 22110 | 22115 | GlitCL |
| 1047 | Q8WXK4\|ASB12_HUMAN | 75 | 80 | GhlsCL |
| 1048 | Q8WXS8\|ATS14_HUMAN | 489 | 494 | GyqtCL |
| 1049 | Q8WXS8\|ATS14_HUMAN | 587 | 592 | GgrpCL |
| 1050 | Q8WYB5\|MYST4_HUMAN | 244 | 249 | GhpsCL |
| 1051 | Q8WYP5\|AHTF1_HUMAN | 112 | 117 | GsvlCL |
| 1052 | Q8WYP5\|AHTF1_HUMAN | 318 | 323 | GnrkCL |
| 1053 | Q8WYP5\|AHTF1_HUMAN | 526 | 531 | GynrCL |
| 1054 | Q8WZ42\|TITIN_HUMAN | 4919 | 4924 | GkytCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1055 | Q8WZ42\|TITIN_HUMAN | 5147 | 5152 | GsavCL |
| 1056 | Q8WZ42\|TITIN_HUMAN | 7829 | 7834 | GdysCL |
| 1057 | Q8WZ42\|TITIN_HUMAN | 16742 | 16747 | GaqdCL |
| 1058 | Q8WZ42\|TITIN_HUMAN | 20237 | 20242 | GtnyCL |
| 1059 | Q8WZ73\|RFFL_HUMAN | 81 | 86 | GprlCL |
| 1060 | Q8WZ74\|CTTB2_HUMAN | 924 | 929 | GfknCL |
| 1061 | Q92481\|AP2B_HUMAN | 379 | 384 | GiqsCL |
| 1062 | Q92496\|FHR4_HUMAN | 130 | 135 | GsitCL |
| 1063 | Q92520\|FAM3C_HUMAN | 82 | 87 | GpkiCL |
| 1064 | Q92527\|ANKR7_HUMAN | 148 | 153 | GeppCL |
| 1065 | Q92529\|SHC3_HUMAN | 581 | 586 | GselCL |
| 1066 | Q92546\|K0258_HUMAN | 248 | 253 | GtvaCL |
| 1067 | Q92583\|CCL17_HUMAN | 30 | 35 | GrecCL |
| 1068 | Q92621\|NU205_HUMAN | 950 | 955 | GfveCL |
| 1069 | Q92636\|FAN_HUMAN | 824 | 829 | GtdgCL |
| 1070 | Q92673\|SORL_HUMAN | 1415 | 1420 | GpstCL |
| 1071 | Q92750\|TAF4B_HUMAN | 410 | 415 | GaaiCL |
| 1072 | Q92752\|TENR_HUMAN | 293 | 298 | GqrqCL |
| 1073 | Q92782\|DPF1_HUMAN | 256 | 261 | GhpsCL |
| 1074 | Q92783\|STAM1_HUMAN | 41 | 46 | GpkdCL |
| 1075 | Q92785\|REQU_HUMAN | 302 | 307 | GhpsCL |
| 1076 | Q92794\|MYST3_HUMAN | 237 | 242 | GhpsCL |
| 1077 | Q92832\|NELL1_HUMAN | 618 | 623 | GgfdCL |
| 1078 | Q92854\|SEM4D_HUMAN | 620 | 625 | GvyqCL |
| 1079 | Q92900\|RENT1_HUMAN | 370 | 375 | GdeiCL |
| 1080 | Q92932\|PTPR2_HUMAN | 35 | 40 | GrlgCL |
| 1081 | Q92932\|PTPR2_HUMAN | 634 | 639 | GliyCL |
| 1082 | Q92947\|GCDH_HUMAN | 285 | 290 | GpfgCL |
| 1083 | Q92947\|GCDH_HUMAN | 346 | 351 | GlhaCL |
| 1084 | Q92952\|KCNN1_HUMAN | 361 | 366 | GkgvCL |
| 1085 | Q92956\|TNR14_HUMAN | 89 | 94 | GlskCL |
| 1086 | Q92968\|PEX13_HUMAN | 216 | 221 | GtvaCL |
| 1087 | Q93038\|TNR25_HUMAN | 66 | 71 | GnstCL |
| 1088 | Q969L2\|MAL2_HUMAN | 37 | 42 | GafvCL |
| 1089 | Q969P0\|IGSF8_HUMAN | 402 | 407 | GtyrCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1090 | Q96A54\|ADR1_HUMAN | 179 | 184 | GavlCL |
| 1091 | Q96AP0\|ACD_HUMAN | 269 | 274 | GalvCL |
| 1092 | Q96AQ2\|TM125_HUMAN | 71 | 76 | GtvlCL |
| 1093 | Q96B26\|EXOS8_HUMAN | 230 | 235 | GklcCL |
| 1094 | Q96B86\|RGMA_HUMAN | 311 | 316 | GlylCL |
| 1095 | Q96BD0\|SO4A1_HUMAN | 698 | 703 | GletCL |
| 1096 | Q96CE8\|T4S18_HUMAN | 8 | 13 | GclsCL |
| 1097 | Q96CW5\|GCP3_HUMAN | 190 | 195 | GvgdCL |
| 1098 | Q96D59\|RN183_HUMAN | 95 | 100 | GhqlCL |
| 1099 | Q96DN5\|WDR67_HUMAN | 52 | 57 | GtgdCL |
| 1100 | Q96DZ5\|CLR59_HUMAN | 212 | 217 | GaakCL |
| 1101 | Q96EP1\|CHFR_HUMAN | 528 | 533 | GcygCL |
| 1102 | Q96EY5\|F125A_HUMAN | 51 | 56 | GyflCL |
| 1103 | Q96EZ4\|MYEOV_HUMAN | 232 | 237 | GrraCL |
| 1104 | Q96F46\|I17RA_HUMAN | 628 | 633 | GsqaCL |
| 1105 | Q96GC6\|ZN274_HUMAN | 256 | 261 | GttcCL |
| 1106 | Q96H40\|ZN486_HUMAN | 132 | 137 | GlnqCL |
| 1107 | Q96H96\|COQ2_HUMAN | 172 | 177 | GvllCL |
| 1108 | Q96I82\|KAZD1_HUMAN | 249 | 254 | GtyrCL |
| 1109 | Q96IV0\|NGLY1_HUMAN | 70 | 75 | GaveCL |
| 1110 | Q96IW7\|SC22A_HUMAN | 234 | 239 | GtaaCL |
| 1111 | Q96J02\|ITCH_HUMAN | 160 | 165 | GvslCL |
| 1112 | Q96J94\|PIWL1_HUMAN | 674 | 679 | GlkyCL |
| 1113 | Q96JH7\|VCIP1_HUMAN | 215 | 220 | GdghCL |
| 1114 | Q96JK2\|WDR22_HUMAN | 178 | 183 | GepfCL |
| 1115 | Q96JT2\|S45A3_HUMAN | 27 | 32 | GlevCL |
| 1116 | Q96JT2\|S45A3_HUMAN | 485 | 490 | GrgiCL |
| 1117 | Q96K31\|CH076_HUMAN | 98 | 103 | GqarCL |
| 1118 | Q96KC8\|DNJC1_HUMAN | 228 | 233 | GiwfCL |
| 1119 | Q96KM6\|K1196_HUMAN | 782 | 787 | GkyrCL |
| 1120 | Q96LC7\|SIG10_HUMAN | 373 | 378 | GqslCL |
| 1121 | Q96LD4\|TRI47_HUMAN | 25 | 30 | GhnfCL |
| 1122 | Q96LQ0\|CN050_HUMAN | 366 | 371 | GeprCL |
| 1123 | Q96ME1\|FXL18_HUMAN | 352 | 357 | GcvhCL |
| 1124 | Q96ME7\|ZN512_HUMAN | 320 | 325 | GqpeCL |
| 1125 | Q96ME7\|ZN512_HUMAN | 438 | 443 | GkykCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1126 | Q96MU7\|YTDC1_HUMAN | 485 | 490 | GtqlCL |
| 1127 | Q96MU8\|KREM1_HUMAN | 53 | 58 | GgkpCL |
| 1128 | Q96NL3\|ZN599_HUMAN | 373 | 378 | GktfCL |
| 1129 | Q96NX9\|DACH2_HUMAN | 585 | 590 | GnyyCL |
| 1130 | Q96P11\|NSUN5_HUMAN | 400 | 405 | GaehCL |
| 1131 | Q96PH1\|NOX5_HUMAN | 272 | 277 | GcgqCL |
| 1132 | Q96PL5\|ERMAP_HUMAN | 122 | 127 | GsyrCL |
| 1133 | Q96PP9\|GBP4_HUMAN | 321 | 326 | GavpCL |
| 1134 | Q96Q04\|LMTK3_HUMAN | 676 | 681 | GacsCL |
| 1135 | Q96Q15\|SMG1_HUMAN | 2809 | 2814 | GnvtCL |
| 1136 | Q96Q27\|ASB2_HUMAN | 101 | 106 | GqvgCL |
| 1137 | Q96Q27\|ASB2_HUMAN | 135 | 140 | GhldCL |
| 1138 | Q96Q91\|B3A4_HUMAN | 455 | 460 | GaafCL |
| 1139 | Q96QG7\|MTMR9_HUMAN | 85 | 90 | GmeeCL |
| 1140 | Q96QS1\|TSN32_HUMAN | 258 | 263 | GpthCL |
| 1141 | Q96QU8\|XPO6_HUMAN | 413 | 418 | GyfsCL |
| 1142 | Q96R30\|OR2V2_HUMAN | 103 | 108 | GlfvCL |
| 1143 | Q96RV3\|PCX1_HUMAN | 696 | 701 | GtvaCL |
| 1144 | Q96RW7\|HMCN1_HUMAN | 677 | 682 | GiygCL |
| 1145 | Q96RW7\|HMCN1_HUMAN | 2546 | 2551 | GrytCL |
| 1146 | Q96RW7\|HMCN1_HUMAN | 3595 | 3600 | GrytCL |
| 1147 | Q96SM3\|CPXM1_HUMAN | 262 | 267 | GgapCL |
| 1148 | Q96SQ9\|CP2S1_HUMAN | 436 | 441 | GkryCL |
| 1149 | Q96SU4\|OSBL9_HUMAN | 542 | 547 | GcvsCL |
| 1150 | Q99250\|SCN2A_HUMAN | 955 | 960 | GqtmCL |
| 1151 | Q99466\|NOTC4_HUMAN | 216 | 221 | GsfqCL |
| 1152 | Q99466\|NOTC4_HUMAN | 375 | 380 | GsfsCL |
| 1153 | Q99466\|NOTC4_HUMAN | 414 | 419 | GstlCL |
| 1154 | Q99466\|NOTC4_HUMAN | 457 | 462 | GsfnCL |
| 1155 | Q99466\|NOTC4_HUMAN | 609 | 614 | GaffCL |
| 1156 | Q99466\|NOTC4_HUMAN | 787 | 792 | GffsCL |
| 1157 | Q99466\|NOTC4_HUMAN | 1121 | 1126 | GgpdCL |
| 1158 | Q99466\|NOTC4_HUMAN | 1872 | 1877 | GggaCL |
| 1159 | Q99558\|M3K14_HUMAN | 536 | 541 | GhavCL |
| 1160 | Q99611\|SPS2_HUMAN | 373 | 378 | GlliCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1161 | Q99678\|GPR20_HUMAN | 115 | 120 | GargCL |
| 1162 | Q99741\|CDC6_HUMAN | 207 | 212 | GktaCL |
| 1163 | Q99758\|ABCA3_HUMAN | 1590 | 1595 | GqfkCL |
| 1164 | Q99797\|PMIP_HUMAN | 277 | 282 | GqlkCL |
| 1165 | Q99848\|EBP2_HUMAN | 52 | 57 | GlkqCL |
| 1166 | Q99867\|TBB4Q_HUMAN | 235 | 240 | GyttCL |
| 1167 | Q99884\|SC6A7_HUMAN | 543 | 548 | GllsCL |
| 1168 | Q99973\|TEP1_HUMAN | 1464 | 1469 | GpfaCL |
| 1169 | Q99973\|TEP1_HUMAN | 1486 | 1491 | GarlCL |
| 1170 | Q99973\|TEP1_HUMAN | 1720 | 1725 | GisaCL |
| 1171 | Q99973\|TEP1_HUMAN | 2595 | 2600 | GsysCL |
| 1172 | Q99996\|AKAP9_HUMAN | 3063 | 3068 | GllnCL |
| 1173 | Q9BQ08\|RSNB_HUMAN | 2 | 7 | GpssCL |
| 1174 | Q9BQG2\|NUD12_HUMAN | 348 | 353 | GmftCL |
| 1175 | Q9BQR3\|PRS27_HUMAN | 231 | 236 | GplyCL |
| 1176 | Q9BQS2\|SYT15_HUMAN | 23 | 28 | GascCL |
| 1177 | Q9BRB3\|PIGQ_HUMAN | 373 | 378 | GlsaCL |
| 1178 | Q9BRP4\|WDR71_HUMAN | 206 | 211 | GrsaCL |
| 1179 | Q9BRZ2\|TRI56_HUMAN | 343 | 348 | GpapCL |
| 1180 | Q9BS86\|ZPBP1_HUMAN | 346 | 351 | GaktCL |
| 1181 | Q9BT40\|SKIP_HUMAN | 131 | 136 | GvniCL |
| 1182 | Q9BT51\|CU122_HUMAN | 6 | 11 | GfshCL |
| 1183 | Q9BTF0\|THUM2_HUMAN | 407 | 412 | GikkCL |
| 1184 | Q9BTX1\|NDC1_HUMAN | 310 | 315 | GsdeCL |
| 1185 | Q9BUY5\|ZN426_HUMAN | 14 | 19 | GdpvCL |
| 1186 | Q9BUY5\|ZN426_HUMAN | 430 | 435 | GypsCL |
| 1187 | Q9BV38\|WDR18_HUMAN | 81 | 86 | GpvtCL |
| 1188 | Q9BV38\|WDR18_HUMAN | 139 | 144 | GgkdCL |
| 1189 | Q9BV73\|CP250_HUMAN | 806 | 811 | GevrCL |
| 1190 | Q9BV99\|LRC61_HUMAN | 113 | 118 | GqlqCL |
| 1191 | Q9BVA1\|TBB2B_HUMAN | 235 | 240 | GyttCL |
| 1192 | Q9BVH7\|SIA7E_HUMAN | 8 | 13 | GlavCL |
| 1193 | Q9BVK2\|ALG8_HUMAN | 361 | 366 | GflrCL |
| 1194 | Q9BWT7\|CAR10_HUMAN | 916 | 921 | GkkhCL |
| 1195 | Q9BWU0\|NADAP_HUMAN | 185 | 190 | GtsyCL |
| 1196 | Q9BWU0\|NADAP_HUMAN | 196 | 201 | GcdvCL |
| 1197 | Q9BWV1\|BOC_HUMAN | 1053 | 1058 | GppcCL |
| 1198 | Q9BXC9\|BBS2_HUMAN | 26 | 31 | GthpCL |
| 1199 | Q9BXL6\|CAR14_HUMAN | 850 | 855 | GfkkCL |
| 1200 | Q9BXM7\|PINK1_HUMAN | 408 | 413 | GgngCL |
| 1201 | Q9BXR0\|TGT_HUMAN | 50 | 55 | GcriCL |
| 1202 | Q9BXS4\|TMM59_HUMAN | 229 | 234 | GflrCL |
| 1203 | Q9BXT5\|TEX15_HUMAN | 1099 | 1104 | GekkCL |
| 1204 | Q9BXU8\|FHL17_HUMAN | 78 | 83 | GghiCL |
| 1205 | Q9BY15\|EMR3_HUMAN | 562 | 567 | GctwCL |
| 1206 | Q9BY41\|HDAC8_HUMAN | 283 | 288 | GigkCL |
| 1207 | Q9BYB4\|GNB1L_HUMAN | 163 | 168 | GmpmCL |
| 1208 | Q9BYE0\|HES7_HUMAN | 95 | 100 | GfreCL |
| 1209 | Q9BYJ1\|LOXE3_HUMAN | 309 | 314 | GqdtCL |
| 1210 | Q9BYK8\|PR285_HUMAN | 1908 | 1913 | GfslCL |
| 1211 | Q9BYT1\|CT059_HUMAN | 398 | 403 | GswtCL |
| 1212 | Q9BYX4\|IFIH1_HUMAN | 265 | 270 | GsysCL |
| 1213 | Q9BZ11\|ADA33_HUMAN | 400 | 405 | GggaCL |
| 1214 | Q9BZ76\|CNTP3_HUMAN | 509 | 514 | GfqgCL |
| 1215 | Q9BZ76\|CNTP3_HUMAN | 1163 | 1168 | GftgCL |
| 1216 | Q9BZC7\|ABCA2_HUMAN | 2262 | 2267 | GrlrCL |
| 1217 | Q9BZF3\|OSBL6_HUMAN | 554 | 559 | GrraCL |
| 1218 | Q9BZF9\|UACA_HUMAN | 79 | 84 | GnleCL |
| 1219 | Q9BZF9\|UACA_HUMAN | 112 | 117 | GhalCL |
| 1220 | Q9BZH6\|BRWD2_HUMAN | 79 | 84 | GspyCL |
| 1221 | Q9BZS1\|FOXP3_HUMAN | 228 | 233 | GraqCL |
| 1222 | Q9BZY9\|TRI31_HUMAN | 32 | 37 | GhnfCL |
| 1223 | Q9BZZ2\|SN_HUMAN | 1507 | 1512 | GmyhCL |
| 1224 | Q9C004\|SPY4_HUMAN | 197 | 202 | GtcmCL |
| 1225 | Q9C0A0\|CNTP4_HUMAN | 1163 | 1168 | GftgCL |
| 1226 | Q9C0C6\|K1737_HUMAN | 47 | 52 | GsseCL |
| 1227 | Q9GZK3\|OR2B2_HUMAN | 108 | 113 | GsteCL |
| 1228 | Q9GZR3\|CFC1_HUMAN | 144 | 149 | GalhCL |
| 1229 | Q9GZY1\|PBOV1_HUMAN | 118 | 123 | GlecCL |
| 1230 | Q9H013\|ADA19_HUMAN | 400 | 405 | GggmCL |
| 1231 | Q9H093\|NUAK2_HUMAN | 587 | 592 | GpgsCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1232 | Q9H0A0\|NAT10_HUMAN | 654 | 659 | GrfpCL |
| 1233 | Q9H0B3\|K1683_HUMAN | 578 | 583 | GkirCL |
| 1234 | Q9H0J9\|PAR12_HUMAN | 272 | 277 | GdqiCL |
| 1235 | Q9H0M4\|ZCPW1_HUMAN | 249 | 254 | GfgqCL |
| 1236 | Q9H172\|ABCG4_HUMAN | 588 | 593 | GdltCL |
| 1237 | Q9H195\|MUC3B_HUMAN | 545 | 550 | GqcaCL |
| 1238 | Q9H1B7\|CN004_HUMAN | 294 | 299 | GgpaCL |
| 1239 | Q9H1D0\|TRPV6_HUMAN | 10 | 15 | GlilCL |
| 1240 | Q9H1K4\|GHC2_HUMAN | 47 | 52 | GmidCL |
| 1241 | Q9H1M3\|DB129_HUMAN | 23 | 28 | GlrrCL |
| 1242 | Q9H1M4\|DB127_HUMAN | 50 | 55 | GrycCL |
| 1243 | Q9H1P6\|CT085_HUMAN | 107 | 112 | GlnkCL |
| 1244 | Q9H1R3\|MYLK2_HUMAN | 240 | 245 | GqalCL |
| 1245 | Q9H1V8\|S6A17_HUMAN | 421 | 426 | GldpCL |
| 1246 | Q9H221\|ABCG8_HUMAN | 421 | 426 | GaeaCL |
| 1247 | Q9H228\|EDG8_HUMAN | 347 | 352 | GlrrCL |
| 1248 | Q9H252\|KCNH6_HUMAN | 571 | 576 | GfpeCL |
| 1249 | Q9H2D1\|MFTC_HUMAN | 64 | 69 | GilhCL |
| 1250 | Q9H2G2\|SLK_HUMAN | 1208 | 1213 | GeseCL |
| 1251 | Q9H2M9\|RBGPR_HUMAN | 387 | 392 | GesiCL |
| 1252 | Q9H2S1\|KCNN2_HUMAN | 371 | 376 | GkgyCL |
| 1253 | Q9H2X9\|S12A5_HUMAN | 602 | 607 | GmslCL |
| 1254 | Q9H2Y7\|ZF106_HUMAN | 975 | 980 | GegnCL |
| 1255 | Q9H324\|ATS10_HUMAN | 422 | 427 | GlglCL |
| 1256 | Q9H324\|ATS10_HUMAN | 556 | 561 | GgkyCL |
| 1257 | Q9H3D4\|P73L_HUMAN | 557 | 562 | GcssCL |
| 1258 | Q9H3R1\|NDST4_HUMAN | 814 | 819 | GktkCL |
| 1259 | Q9H4F1\|SIA7D_HUMAN | 29 | 34 | GlplCL |
| 1260 | Q9H5U8\|CX045_HUMAN | 403 | 408 | GfdsCL |
| 1261 | Q9H5V8\|CDCP1_HUMAN | 373 | 378 | GcfvCL |
| 1262 | Q9H6E5\|TUT1_HUMAN | 15 | 20 | GfrcCL |
| 1263 | Q9H6R4\|NOL6_HUMAN | 391 | 396 | GislCL |
| 1264 | Q9H792\|SG269_HUMAN | 1661 | 1666 | GilqCL |
| 1265 | Q9H7F0\|AT133_HUMAN | 109 | 114 | GhavCL |
| 1266 | Q9H7M9\|GI24_HUMAN | 142 | 147 | GlycCL |
| 1267 | Q9H808\|TLE6_HUMAN | 315 | 320 | GpdaCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1268 | Q9H8X2\|IPPK_HUMAN | 110 | 115 | GyamCL |
| 1269 | Q9H9S3\|S61A2_HUMAN | 143 | 148 | GagiCL |
| 1270 | Q9HAF5\|CO028_HUMAN | 120 | 125 | GvrmCL |
| 1271 | Q9HAS0\|NJMU_HUMAN | 123 | 128 | GcyyCL |
| 1272 | Q9HAT1\|LMA1L_HUMAN | 8 | 13 | GplfCL |
| 1273 | Q9HAV4\|XPO5_HUMAN | 266 | 271 | GaaeCL |
| 1274 | Q9HAW7\|UD17_HUMAN | 510 | 515 | GyrkCL |
| 1275 | Q9HAW8\|UD110_HUMAN | 510 | 515 | GyrkCL |
| 1276 | Q9HAW9\|UD18_HUMAN | 510 | 515 | GyrkCL |
| 1277 | Q9HBX8\|LGR6_HUMAN | 550 | 555 | GvlgCL |
| 1278 | Q9HBZ2\|ARNT2_HUMAN | 295 | 300 | GskyCL |
| 1279 | Q9HC07\|TM165_HUMAN | 138 | 143 | GlmtCL |
| 1280 | Q9HC84\|MUC5B_HUMAN | 780 | 785 | GklsCL |
| 1281 | Q9HC84\|MUC5B_HUMAN | 1281 | 1286 | GlgaCL |
| 1282 | Q9HCC6\|HES4_HUMAN | 113 | 118 | GfheCL |
| 1283 | Q9HCC9\|ZFY28_HUMAN | 555 | 560 | GatnCL |
| 1284 | Q9HCE9\|TM16H_HUMAN | 541 | 546 | GgrrCL |
| 1285 | Q9HCM2\|PLXA4_HUMAN | 990 | 995 | GkqpCL |
| 1286 | Q9HCM4\|E41L5_HUMAN | 111 | 116 | GspyCL |
| 1287 | Q9HCU4\|CELR2_HUMAN | 1308 | 1313 | GgytCL |
| 1288 | Q9HCU4\|CELR2_HUMAN | 1757 | 1762 | GfrgCL |
| 1289 | Q9HCU4\|CELR2_HUMAN | 1917 | 1922 | GsptCL |
| 1290 | Q9NNW5\|WDR6_HUMAN | 460 | 465 | GvvaCL |
| 1291 | Q9NP73\|GT281_HUMAN | 82 | 87 | GagsCL |
| 1292 | Q9NP90\|RAB9B_HUMAN | 79 | 84 | GadcCL |
| 1293 | Q9NPA1\|KCMB3_HUMAN | 121 | 126 | GkypCL |
| 1294 | Q9NPA3\|M1IP1_HUMAN | 58 | 63 | GsggCL |
| 1295 | Q9NPD7\|NRN1_HUMAN | 37 | 42 | GfsdCL |
| 1296 | Q9NPF8\|CENA2_HUMAN | 41 | 46 | GifiCL |
| 1297 | Q9NPG4\|PCD12_HUMAN | 807 | 812 | GwdpCL |
| 1298 | Q9NPH5\|NOX4_HUMAN | 51 | 56 | GlglCL |
| 1299 | Q9NQ25\|SLAF7_HUMAN | 3 | 8 | GsptCL |
| 1300 | Q9NQ30\|ESM1_HUMAN | 125 | 130 | GtgkCL |
| 1301 | Q9NQ75\|CT032_HUMAN | 50 | 55 | GwwkCL |
| 1302 | Q9NQB0\|TF7L2_HUMAN | 492 | 497 | GegsCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1303 | Q9NQQ7\|S35C2_HUMAN | 302 | 307 | GfalCL |
| 1304 | Q9NQS5\|GPR84_HUMAN | 195 | 200 | GifyCL |
| 1305 | Q9NQU5\|PAK6_HUMAN | 662 | 667 | GlpeCL |
| 1306 | Q9NR09\|BIRC6_HUMAN | 511 | 516 | GanpCL |
| 1307 | Q9NR61\|DLL4_HUMAN | 204 | 209 | GnlsCL |
| 1308 | Q9NR63\|CP26B_HUMAN | 437 | 442 | GvrtCL |
| 1309 | Q9NR81\|ARHG3_HUMAN | 203 | 208 | GwlpCL |
| 1310 | Q9NR99\|MXRA5_HUMAN | 2414 | 2419 | GnytCL |
| 1311 | Q9NR15\|DISC1_HUMAN | 23 | 28 | GsrdCL |
| 1312 | Q9NRX5\|SERC1_HUMAN | 19 | 24 | GsapCL |
| 1313 | Q9NS15\|LTBP3_HUMAN | 846 | 851 | GsyrCL |
| 1314 | Q9NS40\|KCNH7_HUMAN | 722 | 727 | GfpeCL |
| 1315 | Q9NS62\|THSD1_HUMAN | 419 | 424 | GislCL |
| 1316 | Q9NSD7\|RL3R1_HUMAN | 243 | 248 | GeelCL |
| 1317 | Q9NS16\|BRWD1_HUMAN | 204 | 209 | GsddCL |
| 1318 | Q9NSN8\|SNTG1_HUMAN | 242 | 247 | GiiqCL |
| 1319 | Q9NST1\|ADPN_HUMAN | 24 | 29 | GatrCL |
| 1320 | Q9NST1\|ADPN_HUMAN | 97 | 102 | GlckCL |
| 1321 | Q9NT68\|TEN2_HUMAN | 858 | 863 | GlvdCL |
| 1322 | Q9NU22\|MDN1_HUMAN | 427 | 432 | GrgdCL |
| 1323 | Q9NUB4\|CT141_HUMAN | 156 | 161 | GlafCL |
| 1324 | Q9NUP1\|CNO_HUMAN | 67 | 72 | GyaaCL |
| 1325 | Q9NVE7\|PANK4_HUMAN | 304 | 309 | GqlaCL |
| 1326 | Q9NVG8\|TBC13_HUMAN | 38 | 43 | GglrCL |
| 1327 | Q9NVX2\|NLE1_HUMAN | 474 | 479 | GkdkCL |
| 1328 | Q9NW08\|RPC2_HUMAN | 765 | 770 | GfgrCL |
| 1329 | Q9NWT1\|PK1IP_HUMAN | 83 | 88 | GtitCL |
| 1330 | Q9NWU5\|RM22_HUMAN | 142 | 147 | GrgqCL |
| 1331 | Q9NWZ3\|IRAK4_HUMAN | 255 | 260 | GddlCL |
| 1332 | Q9NX02\|NALP2_HUMAN | 139 | 144 | GnviCL |
| 1333 | Q9NXJ0\|M4A12_HUMAN | 106 | 111 | GivlCL |
| 1334 | Q9NXR5\|ANR10_HUMAN | 69 | 74 | GkleCL |
| 1335 | Q9NXR5\|ANR10_HUMAN | 103 | 108 | GhpqCL |
| 1336 | Q9NXS3\|BTBD5_HUMAN | 293 | 298 | GlfaCL |
| 1337 | Q9NXW9\|ALKB4_HUMAN | 19 | 24 | GirtCL |
| 1338 | Q9NY15\|STAB1_HUMAN | 122 | 127 | GhgtCL |
| 1339 | Q9NY15\|STAB1_HUMAN | 177 | 182 | GdgsCL |
| 1340 | Q9NY15\|STAB1_HUMAN | 752 | 757 | GngaCL |
| 1341 | Q9NY15\|STAB1_HUMAN | 1256 | 1261 | GssrCL |
| 1342 | Q9NY15\|STAB1_HUMAN | 1991 | 1996 | GsgqCL |
| 1343 | Q9NY15\|STAB1_HUMAN | 2250 | 2255 | GfhlCL |
| 1344 | Q9NY33\|DPP3_HUMAN | 515 | 520 | GlylCL |
| 1345 | Q9NY35\|CLDND_HUMAN | 213 | 218 | GwsfCL |
| 1346 | Q9NY46\|SCN3A_HUMAN | 956 | 961 | GqtmCL |
| 1347 | Q9NY91\|SC5A4_HUMAN | 507 | 512 | GtgsCL |
| 1348 | Q9NY99\|SNTG2_HUMAN | 14 | 19 | GrqgCL |
| 1349 | Q9NYJ7\|DLL3_HUMAN | 235 | 240 | GecrCL |
| 1350 | Q9NYQ6\|CELR1_HUMAN | 168 | 173 | GrpiCL |
| 1351 | Q9NYQ7\|CELR3_HUMAN | 2070 | 2075 | GsdsCL |
| 1352 | Q9NYQ8\|FAT2_HUMAN | 3908 | 3913 | GfegCL |
| 1353 | Q9NYQ8\|FAT2_HUMAN | 4285 | 4290 | GggpCL |
| 1354 | Q9NYW6\|TA2R3_HUMAN | 104 | 109 | GvlyCL |
| 1355 | Q9NZ56\|FMN2_HUMAN | 1694 | 1699 | GkeqCL |
| 1356 | Q9NZ71\|RTEL1_HUMAN | 47 | 52 | GktlCL |
| 1357 | Q9NZ94\|NLGN3_HUMAN | 19 | 24 | GrslCL |
| 1358 | Q9NZH0\|GPC5B_HUMAN | 164 | 169 | GlalCL |
| 1359 | Q9NZH7\|IL1F8_HUMAN | 68 | 73 | GkdlCL |
| 1360 | Q9NZL3\|ZN224_HUMAN | 550 | 555 | GwasCL |
| 1361 | Q9NZR2\|LRP1B_HUMAN | 866 | 871 | GdddCL |
| 1362 | Q9NZR2\|LRP1B_HUMAN | 2987 | 2992 | GtykCL |
| 1363 | Q9NZV5\|SEPN1_HUMAN | 273 | 278 | GavaCL |
| 1364 | Q9P0K1\|ADA22_HUMAN | 429 | 434 | GggaCL |
| 1365 | Q9P0K7\|RAI14_HUMAN | 64 | 69 | GhveCL |
| 1366 | Q9P0L1\|ZN167_HUMAN | 617 | 622 | GlskCL |
| 1367 | Q9P0M9\|RM27_HUMAN | 84 | 89 | GknkCL |
| 1368 | Q9P0U3\|SENP1_HUMAN | 531 | 536 | GvhwCL |
| 1369 | Q9P0X4\|CAC1I_HUMAN | 290 | 295 | GrecCL |
| 1370 | Q9P203\|BTBD7_HUMAN | 265 | 270 | GnqnCL |
| 1371 | Q9P255\|ZN492_HUMAN | 143 | 148 | GlnqCL |
| 1372 | Q9P273\|TEN3_HUMAN | 142 | 147 | GrssCL |
| 1373 | Q9P273\|TEN3_HUMAN | 1590 | 1595 | GtngCL |

TABLE 4-continued

CXCs
Motif: G-X(3)-C-L
Number of Locations: 1337
Number of Different Proteins: 1170

| SEQ ID NO: | Accession Number\| Protein Name | First Amino acid | Last Amino acid | Sequence |
|---|---|---|---|---|
| 1374 | Q9P275\|UBP36_HUMAN | 824 | 829 | GsetCL |
| 1375 | Q9P283\|SEM5B_HUMAN | 589 | 594 | GgldCL |
| 1376 | Q9P283\|SEM5B_HUMAN | 887 | 892 | GediCL |
| 1377 | Q9P298\|HIG1B_HUMAN | 34 | 39 | GlggCL |
| 1378 | Q9P2B2\|FPRP_HUMAN | 844 | 849 | GllsCL |
| 1379 | Q9P2C4\|TM181_HUMAN | 406 | 411 | GerkCL |
| 1380 | Q9P2E3\|ZNFX1_HUMAN | 1162 | 1167 | GqlfCL |
| 1381 | Q9P2I0\|CPSF2_HUMAN | 759 | 764 | GlegCL |
| 1382 | Q9P2J9\|PDP2_HUMAN | 125 | 130 | GvasCL |
| 1383 | Q9P2J9\|PDP2_HUMAN | 298 | 303 | GmwsCL |
| 1384 | Q9P2N4\|ATS9_HUMAN | 490 | 495 | GygeCL |
| 1385 | Q9P2P6\|STAR9_HUMAN | 715 | 720 | GeadCL |
| 1386 | Q9P2R3\|ANFY1_HUMAN | 720 | 725 | GpggCL |
| 1387 | Q9P2R7\|SUCB1_HUMAN | 316 | 321 | GnigCL |
| 1388 | Q9P2S2\|NRX2A_HUMAN | 1061 | 1066 | GfqgCL |
| 1389 | Q9UBD9\|CLCF1_HUMAN | 10 | 15 | GmlaCL |
| 1390 | Q9UBE0\|ULE1A_HUMAN | 338 | 343 | GiveCL |
| 1391 | Q9UBG0\|MRC2_HUMAN | 50 | 55 | GlqgCL |
| 1392 | Q9UBG0\|MRC2_HUMAN | 89 | 94 | GtmqCL |
| 1393 | Q9UBG0\|MRC2_HUMAN | 938 | 943 | GdqrCL |
| 1394 | Q9UBG7\|RBPSL_HUMAN | 56 | 61 | GvrrCL |
| 1395 | Q9UBG7\|RBPSL_HUMAN | 326 | 331 | GtylCL |
| 1396 | Q9UBH0\|IL1F5_HUMAN | 63 | 68 | GgsqCL |
| 1397 | Q9UBM4\|OPT_HUMAN | 124 | 129 | GlptCL |
| 1398 | Q9UBP5\|HEY2_HUMAN | 125 | 130 | GfreCL |
| 1399 | Q9UBS8\|RNF14_HUMAN | 258 | 263 | GqvqCL |
| 1400 | Q9UBY5\|EDG7_HUMAN | 37 | 42 | GtffCL |
| 1401 | Q9UBY8\|CLN8_HUMAN | 145 | 150 | GflgCL |
| 1402 | Q9UDX3\|S14L4_HUMAN | 250 | 255 | GnpkCL |
| 1403 | Q9UDX3\|S14L4_HUMAN | 351 | 356 | GsltCL |
| 1404 | Q9UDX4\|S14L3_HUMAN | 250 | 255 | GnpkCL |
| 1405 | Q9UGF7\|O12D3_HUMAN | 62 | 67 | GnlsCL |
| 1406 | Q9UG16\|KCNN3_HUMAN | 525 | 530 | GkgvCL |
| 1407 | Q9UGU5\|HM2L1_HUMAN | 567 | 572 | GplaCL |
| 1408 | Q9UHA7\|IL1F6_HUMAN | 69 | 74 | GlnlCL |
| 1409 | Q9UHC6\|CNTP2_HUMAN | 1174 | 1179 | GftgCL |
| 1410 | Q9UHD0\|IL19_HUMAN | 24 | 29 | GlrrCL |
| 1411 | Q9UH18\|ATS1_HUMAN | 458 | 463 | GhgeCL |
| 1412 | Q9UHW9\|S12A6_HUMAN | 687 | 692 | GmsiCL |
| 1413 | Q9UHX3\|EMR2_HUMAN | 742 | 747 | GctwCL |
| 1414 | Q9UIA9\|XPO7_HUMAN | 933 | 938 | GccsCL |
| 1415 | Q9UIE0\|ZN230_HUMAN | 286 | 291 | GksfCL |
| 1416 | Q9UIF8\|BAZ2B_HUMAN | 627 | 632 | GmqwCL |
| 1417 | Q9UIF9\|BAZ2A_HUMAN | 1006 | 1011 | GpeeCL |
| 1418 | Q9UIH9\|KLF15_HUMAN | 117 | 122 | GehfCL |
| 1419 | Q9UIR0\|BTNL2_HUMAN | 337 | 342 | GqyrCL |
| 1420 | Q9UK10\|ZN225_HUMAN | 466 | 471 | GwasCL |
| 1421 | Q9UK11\|ZN223_HUMAN | 294 | 299 | GksfCL |
| 1422 | Q9UK12\|ZN222_HUMAN | 263 | 268 | GksfCL |
| 1423 | Q9UK13\|ZN221_HUMAN | 488 | 493 | GwasCL |
| 1424 | Q9UK13\|ZN221_HUMAN | 572 | 577 | GwasCL |
| 1425 | Q9UK99\|FBX3_HUMAN | 189 | 194 | GlkyCL |
| 1426 | Q9UKB1\|FBW1B_HUMAN | 281 | 286 | GsvlCL |
| 1427 | Q9UKP4\|ATS7_HUMAN | 443 | 448 | GwglCL |
| 1428 | Q9UKP5\|ATS6_HUMAN | 545 | 550 | GgkyCL |
| 1429 | Q9UKQ2\|ADA28_HUMAN | 500 | 505 | GkghCL |
| 1430 | Q9UKU0\|ACSL6_HUMAN | 104 | 109 | GngpCL |
| 1431 | Q9UL25\|RAB21_HUMAN | 121 | 126 | GneiCL |
| 1432 | Q9ULB1\|NRX1A_HUMAN | 1048 | 1053 | GfqgCL |
| 1433 | Q9ULL4\|PLXB3_HUMAN | 1191 | 1196 | GrgeCL |
| 1434 | Q9ULV0\|MYO5B_HUMAN | 1496 | 1501 | GtvpCL |
| 1435 | Q9UM47\|NOTC3_HUMAN | 1228 | 1233 | GgfrCL |
| 1436 | Q9UM82\|SPAT2_HUMAN | 37 | 42 | GsdeCL |
| 1437 | Q9UMF0\|ICAM5_HUMAN | 879 | 884 | GeavCL |
| 1438 | Q9UMW8\|UBP18_HUMAN | 61 | 66 | GqtcCL |
| 1439 | Q9UNA0\|ATS5_HUMAN | 467 | 472 | GhgnCL |
| 1440 | Q9UNA0\|ATS5_HUMAN | 525 | 530 | GqmvCL |
| 1441 | Q9UNI1\|ELA1_HUMAN | 208 | 213 | GplhCL |
| 1442 | Q9UP79\|ATS8_HUMAN | 421 | 426 | GhgdCL |
| 1443 | Q9UP79\|ATS8_HUMAN | 562 | 567 | GgryCL |
| 1444 | Q9UP95\|S12A4_HUMAN | 622 | 627 | GmslCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1445 | Q9UPA5\|BSN_HUMAN | 1765 | 1770 | GspvCL |
| 1446 | Q9UPZ6\|THS7A_HUMAN | 881 | 886 | GiheCL |
| 1447 | Q9UQ05\|KCNH4_HUMAN | 213 | 218 | GgsrCL |
| 1448 | Q9UQ49\|NEUR3_HUMAN | 380 | 385 | GlfgCL |
| 1449 | Q9UQ52\|CNTN6_HUMAN | 96 | 101 | GmyqCL |
| 1450 | Q9UQD0\|SCN8A_HUMAN | 949 | 954 | GqamCL |
| 1451 | Q9Y219\|JAG2_HUMAN | 907 | 912 | GwkpCL |
| 1452 | Q9Y236\|OSGI2_HUMAN | 480 | 485 | GvtrCL |
| 1453 | Q9Y263\|PLAP_HUMAN | 721 | 726 | GkaqCL |
| 1454 | Q9Y278\|OST2_HUMAN | 51 | 56 | GaprCL |
| 1455 | Q9Y297\|FBW1A_HUMAN | 344 | 349 | GsvlCL |
| 1456 | Q9Y2H6\|FNDC3_HUMAN | 790 | 795 | GivtCL |
| 1457 | Q9Y2L6\|FRM4B_HUMAN | 871 | 876 | GsqrCL |
| 1458 | Q9Y2P5\|S27A5_HUMAN | 345 | 350 | GilgCL |
| 1459 | Q9Y2P5\|S27A5_HUMAN | 452 | 457 | GkmsCL |
| 1460 | Q9Y2Q1\|ZN257_HUMAN | 132 | 137 | GlnqCL |
| 1461 | Q9Y2T5\|GPR52_HUMAN | 205 | 210 | GfivCL |
| 1462 | Q9Y385\|UB2J1_HUMAN | 87 | 92 | GkkiCL |
| 1463 | Q9Y3B6\|CN122_HUMAN | 38 | 43 | GeclCL |
| 1464 | Q9Y3C8\|UFC1_HUMAN | 112 | 117 | GgkiCL |
| 1465 | Q9Y311\|FBX7_HUMAN | 71 | 76 | GdliCL |
| 1466 | Q9Y3N9\|OR2W1_HUMAN | 108 | 113 | GsveCL |
| 1467 | Q9Y3R4\|NEUR2_HUMAN | 160 | 165 | GpghCL |
| 1468 | Q9Y3S2\|ZN330_HUMAN | 182 | 187 | GqhsCL |
| 1469 | Q9Y485\|DMXL1_HUMAN | 187 | 192 | GkddCL |
| 1470 | Q9Y485\|DMXL1_HUMAN | 2862 | 2867 | XrnyCL |
| 1471 | Q9Y493\|ZAN_HUMAN | 1152 | 1157 | GtatCL |
| 1472 | Q9Y4C0\|NRX3A_HUMAN | 1014 | 1019 | GfqgCL |
| 1473 | Q9Y4F1\|FARP1_HUMAN | 820 | 825 | GvphCL |
| 1474 | Q9Y4K1\|AIM1_HUMAN | 1473 | 1478 | GhypCL |
| 1475 | Q9Y4W6\|AFG32_HUMAN | 31 | 36 | GeqpCL |
| 1476 | Q9Y535\|RPC8_HUMAN | 43 | 48 | GlciCL |
| 1477 | Q9Y561\|LRP12_HUMAN | 241 | 246 | GnidCL |
| 1478 | Q9Y574\|ASB4_HUMAN | 86 | 91 | GhveCL |
| 1479 | Q9Y575\|ASB3_HUMAN | 291 | 296 | GhedCL |
| 1480 | Q9Y5F7\|PCDGL_HUMAN | 729 | 734 | GtcaCL |

TABLE 4-continued

CXCs
Motif: G-X(3)-C-L
Number of Locations: 1337
Number of Different Proteins: 1170

| SEQ ID NO: | Accession Number\|Protein Name | First Amino acid | Last Amino acid | Sequence |
|---|---|---|---|---|
| 1481 | Q9Y5J3\|HEY1_HUMAN | 126 | 131 | GfreCL |
| 1482 | Q9Y5N5\|HEMK2_HUMAN | 45 | 50 | GveiCL |
| 1483 | Q9Y5Q5\|CORIN_HUMAN | 424 | 429 | GdqrCL |
| 1484 | Q9Y5R5\|DMRT2_HUMAN | 130 | 135 | GvvsCL |
| 1485 | Q9Y5R6\|DMRT1_HUMAN | 153 | 158 | GsnpCL |
| 1486 | Q9Y5S2\|MRCKB_HUMAN | 1374 | 1379 | GsvqCL |
| 1487 | Q9Y5W8\|SNX13_HUMAN | 73 | 78 | GvpkCL |
| 1488 | Q9Y616\|IRAK3_HUMAN | 395 | 400 | GldsCL |
| 1489 | Q9Y644\|RFNG_HUMAN | 203 | 208 | GagfCL |
| 1490 | Q9Y662\|OST3B_HUMAN | 7 | 12 | GgrsCL |
| 1491 | Q9Y666\|S12A7_HUMAN | 622 | 627 | GmslCL |
| 1492 | Q9Y6H5\|SNCAP_HUMAN | 361 | 366 | GhaeCL |
| 1493 | Q9Y614\|UBP3_HUMAN | 449 | 454 | GpesCL |
| 1494 | Q9Y6N6\|LAMC3_HUMAN | 885 | 890 | GqcsCL |
| 1495 | Q9Y6R1\|S4A4_HUMAN | 512 | 517 | GaifCL |
| 1496 | Q9Y6R7\|FCGBP_HUMAN | 1661 | 1666 | GqgvCL |
| 1497 | Q9Y6R7\|FCGBP_HUMAN | 2388 | 2393 | GqcgCL |
| 1498 | Q9Y6R7\|FCGBP_HUMAN | 2862 | 2867 | GqgvCL |
| 1499 | Q9Y6R7\|FCGBP_HUMAN | 3589 | 3594 | GqcgCL |
| 1500 | Q9Y6R7\|FCGBP_HUMAN | 4063 | 4068 | GqgvCL |
| 1501 | Q9Y6R7\|FCGBP_HUMAN | 4790 | 4795 | GqcgCL |
| 1502 | Q9Y6R7\|FCGBP_HUMAN | 4852 | 4857 | GcgrCL |
| 1503 | Q9Y6R7\|FCGBP_HUMAN | 5032 | 5037 | GcpvCL |

TABLE 5

Collagens
Motif: C-N-X(3)-V-C (SEQ ID NO: 2487)
Number of Locations: 24
Number of Different Proteins: 24

| SEQ ID NO: | Accession Number\|Protein Name | First Amino acid | Last Amino acid | Sequence |
|---|---|---|---|---|
| 1504 | O14514\|BAI1_HUMAN | 400 | 406 | CNnsaVC |
| 1505 | O75093\|SLIT1_HUMAN | 507 | 513 | CNsdvVC |
| 1506 | O75534\|CSDE1_HUMAN | 733 | 739 | CNvwrVC |
| 1507 | P02462\|CO4A1_HUMAN | 1505 | 1511 | CNinnVC |
| 1508 | P08572\|CO4A2_HUMAN | 1549 | 1555 | CNpgdVC |

TABLE 5-continued

Collagens
Motif: C-N-X(3)-V-C (SEQ ID NO: 2487)
Number of Locations: 24
Number of Different Proteins: 24

| SEQ ID NO: | Accession Number\| Protein Name | First Amino acid | Last Amino acid | Sequence |
|---|---|---|---|---|
| 1509 | P09758\|TACD2_HUMAN | 119 | 125 | CNqtsVC |
| 1510 | P25391\|LAMA1_HUMAN | 751 | 757 | CNvhgVC |
| 1511 | P29400\|CO4A5_HUMAN | 1521 | 1527 | CNinnVC |
| 1512 | P53420\|CO4A4_HUMAN | 1525 | 1531 | CNihqVC |
| 1513 | P83110\|HTRA3_HUMAN | 48 | 54 | CNcclVC |
| 1514 | Q01955\|CO4A3_HUMAN | 1505 | 1511 | CNvndVC |
| 1515 | Q13625\|ASPP2_HUMAN | 1002 | 1008 | CNnvqVC |
| 1516 | Q13751\|LAMB3_HUMAN | 572 | 578 | CNrypVC |
| 1517 | Q14031\|CO4A6_HUMAN | 1527 | 1533 | CNineVC |
| 1518 | Q8WWQ8\|STAB2_HUMAN | 1970 | 1976 | CNnrgVC |
| 1519 | Q96GX1\|TECT2_HUMAN | 642 | 648 | CNrneVC |
| 1520 | Q99965\|ADAM2_HUMAN | 621 | 627 | CNdrgVC |
| 1521 | Q9BX93\|PG12B_HUMAN | 112 | 118 | CNqldVC |
| 1522 | Q9BYD5\|CNFN_HUMAN | 32 | 38 | CNdmpVC |
| 1523 | Q9H013\|ADA19_HUMAN | 659 | 665 | CNghgVC |
| 1524 | Q9HBG6\|IF122_HUMAN | 436 | 442 | CNllvVC |
| 1525 | Q9P2R7\|SUCB1_HUMAN | 152 | 158 | CNqvlVC |
| 1526 | Q9UBX1\|CATF_HUMAN | 89 | 95 | CNdpmVC |
| 1527 | Q9UKF2\|ADA30_HUMAN | 638 | 644 | CNtrgVC |

TABLE 6

Collagens
Motif: P-F-X2-C
Number of Locations: 306
Number of Different Proteins: 288

| SEQ ID NO: | Accession Number\| Protein Name | First Amino acid | Last Amino acid | Sequence |
|---|---|---|---|---|
| 1528 | O00116\|ADAS_HUMAN | 561 | 565 | PFstC |
| 1529 | O00182\|LEG9_HUMAN | 98 | 102 | PFdlC |
| 1530 | O00206\|TLR4_HUMAN | 702 | 706 | PFqlC |
| 1531 | O00270\|GPR31_HUMAN | 2 | 6 | PFpnC |
| 1532 | O00398\|P2Y10_HUMAN | 288 | 292 | PFclC |
| 1533 | O00507\|USP9Y_HUMAN | 259 | 263 | PFgqC |
| 1534 | O14646\|CHD1_HUMAN | 450 | 454 | PFkdC |
| 1535 | O14843\|FFAR3_HUMAN | 84 | 88 | PFilC |
| 1536 | O14978\|ZN263_HUMAN | 547 | 551 | PFseC |
| 1537 | O15015\|ZN646_HUMAN | 880 | 884 | PFlcC |

TABLE 6-continued

Collagens
Motif: P-F-X2-C
Number of Locations: 306
Number of Different Proteins: 288

| SEQ ID NO: | Accession Number\| Protein Name | First Amino acid | Last Amino acid | Sequence |
|---|---|---|---|---|
| 1538 | O15031\|PLXB2_HUMAN | 611 | 615 | PFydC |
| 1539 | O15037\|K0323_HUMAN | 423 | 427 | PFtlC |
| 1540 | O15453\|NBR2_HUMAN | 9 | 13 | PFlpC |
| 1541 | O15529\|GPR42_HUMAN | 84 | 88 | PFilC |
| 1542 | O43556\|SGCE_HUMAN | 207 | 211 | PFssC |
| 1543 | O60299\|K0552_HUMAN | 308 | 312 | PFaaC |
| 1544 | O60343\|TBCD4_HUMAN | 89 | 93 | PFlrC |
| 1545 | O60431\|OR1I1_HUMAN | 93 | 97 | PFvgC |
| 1546 | O60449\|LY75_HUMAN | 1250 | 1254 | PFqnC |
| 1547 | O60481\|ZIC3_HUMAN | 331 | 335 | PFpgC |
| 1548 | O60486\|PLXC1_HUMAN | 618 | 622 | PFtaC |
| 1549 | O60494\|CUBN_HUMAN | 3302 | 3306 | PFsiC |
| 1550 | O60603\|TLR2_HUMAN | 669 | 673 | PFklC |
| 1551 | O60656\|UD19_HUMAN | 149 | 153 | PFdnC |
| 1552 | O60706\|ABCC9_HUMAN | 627 | 631 | PFesC |
| 1553 | O75152\|ZC11A_HUMAN | 23 | 27 | PFrhC |
| 1554 | O75197\|LRP5_HUMAN | 317 | 321 | PFytC |
| 1555 | O75419\|CC45L_HUMAN | 444 | 448 | PFlyC |
| 1556 | O75473\|LGR5_HUMAN | 547 | 551 | PFkpC |
| 1557 | O75478\|TAD2L_HUMAN | 38 | 42 | PFflC |
| 1558 | O75581\|LRP6_HUMAN | 304 | 308 | PFyqC |
| 1559 | O75794\|CD123_HUMAN | 147 | 151 | PFihC |
| 1560 | O75882\|ATRN_HUMAN | 969 | 973 | PFgqC |
| 1561 | O76031\|CLPX_HUMAN | 313 | 317 | PFaiC |
| 1562 | O95006\|OR2F2_HUMAN | 93 | 97 | PFqsC |
| 1563 | O95007\|OR6B1_HUMAN | 285 | 289 | PFiyC |
| 1564 | O95149\|SPN1_HUMAN | 195 | 199 | PFydC |
| 1565 | O95202\|LETM1_HUMAN | 51 | 55 | PFgcC |
| 1566 | O95409\|ZIC2_HUMAN | 336 | 340 | PFpgC |
| 1567 | O95450\|ATS2_HUMAN | 569 | 573 | PFgsC |
| 1568 | O95759\|TBCD8_HUMAN | 67 | 71 | PFsrC |
| 1569 | O95841\|ANGL1_HUMAN | 276 | 280 | PFkdC |
| 1570 | O95886\|DLGP3_HUMAN | 98 | 102 | PFdtC |
| 1571 | P02461\|CO3A1_HUMAN | 80 | 84 | PFgeC |
| 1572 | P02462\|CO4A1_HUMAN | 1501 | 1505 | PFlfC |

TABLE 6-continued

Collagens
Motif: P-F-X2-C
Number of Locations: 306
Number of Different Proteins: 288

| SEQ ID NO: | Accession Number\| Protein Name | First Amino acid | Last Amino acid | Sequence |
|---|---|---|---|---|
| 1573 | P02462\|CO4A1_HUMAN | 1612 | 1616 | PFieC |
| 1574 | P08151\|GLI1_HUMAN | 173 | 177 | PFptC |
| 1575 | P08572\|CO4A2_HUMAN | 1545 | 1549 | PFlyC |
| 1576 | P08572\|CO4A2_HUMAN | 1654 | 1658 | PFieC |
| 1577 | P08581\|MET_HUMAN | 534 | 538 | PFvqC |
| 1578 | P09172\|DOPO_HUMAN | 136 | 140 | PFgtC |
| 1579 | P0C0L4\|CO4A_HUMAN | 731 | 735 | PFlsC |
| 1580 | P0C0L5\|CO4B_HUMAN | 731 | 735 | PFlsC |
| 1581 | P15309\|PPAP_HUMAN | 157 | 161 | PFrnC |
| 1582 | P17021\|ZNF17_HUMAN | 350 | 354 | PFycC |
| 1583 | P18084\|ITB5_HUMAN | 546 | 550 | PFceC |
| 1584 | P20645\|MPRD_HUMAN | 3 | 7 | PFysC |
| 1585 | P20851\|C4BB_HUMAN | 130 | 134 | PFpiC |
| 1586 | P20933\|ASPG_HUMAN | 13 | 17 | PFllC |
| 1587 | P21673\|SAT1_HUMAN | 50 | 54 | PFyhC |
| 1588 | P21854\|CD72_HUMAN | 222 | 226 | PFftC |
| 1589 | P22309\|UD11_HUMAN | 152 | 156 | PFlpC |
| 1590 | P22362\|CCL1_HUMAN | 29 | 33 | PFsrC |
| 1591 | P22681\|CBL_HUMAN | 417 | 421 | PFcrC |
| 1592 | P23942\|RDS_HUMAN | 210 | 214 | PFscC |
| 1593 | P24043\|LAMA2_HUMAN | 2679 | 2683 | PFegC |
| 1594 | P24043\|LAMA2_HUMAN | 3083 | 3087 | PFrgC |
| 1595 | P24903\|CP2F1_HUMAN | 483 | 487 | PFqlC |
| 1596 | P25098\|ARBK1_HUMAN | 252 | 256 | PFivC |
| 1597 | P25490\|TYY1_HUMAN | 386 | 390 | PFdgC |
| 1598 | P25929\|NPY1R_HUMAN | 117 | 121 | PFvqC |
| 1599 | P26718\|NKG2D_HUMAN | 52 | 56 | PFffC |
| 1600 | P26927\|HGFL_HUMAN | 439 | 443 | PFdyC |
| 1601 | P27987\|IP3KB_HUMAN | 869 | 873 | PFfkC |
| 1602 | P29400\|CO4A5_HUMAN | 1517 | 1521 | PFmfC |
| 1603 | P29400\|CO4A5_HUMAN | 1628 | 1632 | PFieC |
| 1604 | P34896\|GLYC_HUMAN | 244 | 248 | PFehC |
| 1605 | P35504\|UD15_HUMAN | 153 | 157 | PFhlC |
| 1606 | P35523\|CLCN1_HUMAN | 26 | 30 | PFehC |
| 1607 | P35626\|ARBK2_HUMAN | 252 | 256 | PFivC |
| 1608 | P36383\|CXA7_HUMAN | 205 | 209 | PFyvC |
| 1609 | P36508\|ZNF76_HUMAN | 258 | 262 | PFegC |
| 1610 | P36509\|UD12_HUMAN | 149 | 153 | PFdnC |
| 1611 | P36894\|BMR1A_HUMAN | 57 | 61 | PFlkC |
| 1612 | P41180\|CASR_HUMAN | 538 | 542 | PFsnC |
| 1613 | P42338\|PK3CB_HUMAN | 650 | 654 | PFldC |
| 1614 | P42575\|CASP2_HUMAN | 141 | 145 | PFpvC |
| 1615 | P45974\|UBP5_HUMAN | 528 | 532 | PFssC |
| 1616 | P46531\|NOTC1_HUMAN | 1411 | 1415 | PFyrC |
| 1617 | P48637\|GSHB_HUMAN | 405 | 409 | PFenC |
| 1618 | P49257\|LMAN1_HUMAN | 471 | 475 | PFpsC |
| 1619 | P49888\|ST1E1_HUMAN | 79 | 83 | PFleC |
| 1620 | P50052\|AGTR2_HUMAN | 315 | 319 | PFlyC |
| 1621 | P50876\|UB7I4_HUMAN | 273 | 277 | PFvlC |
| 1622 | P51606\|RENBP_HUMAN | 376 | 380 | PFkgC |
| 1623 | P51617\|IRAK1_HUMAN | 195 | 199 | PFpfC |
| 1624 | P51689\|ARSD_HUMAN | 581 | 585 | PFcsC |
| 1625 | P51690\|ARSE_HUMAN | 576 | 580 | PFplC |
| 1626 | P52740\|ZN132_HUMAN | 369 | 373 | PFecC |
| 1627 | P52747\|ZN143_HUMAN | 318 | 322 | PFegC |
| 1628 | P53420\|CO4A4_HUMAN | 1521 | 1525 | PFayC |
| 1629 | P53420\|CO4A4_HUMAN | 1630 | 1634 | PFleC |
| 1630 | P53621\|COPA_HUMAN | 1165 | 1169 | PFdiC |
| 1631 | P54198\|HIRA_HUMAN | 215 | 219 | PFdeC |
| 1632 | P54793\|ARSF_HUMAN | 570 | 574 | PFclC |
| 1633 | P54802\|ANAG_HUMAN | 401 | 405 | PFiwC |
| 1634 | P55157\|MTP_HUMAN | 823 | 827 | PFlvC |
| 1635 | P62079\|TSN5_HUMAN | 183 | 187 | PFscC |
| 1636 | P78357\|CNTP1_HUMAN | 926 | 930 | PFvgC |
| 1637 | P78527\|PRKDC_HUMAN | 2853 | 2857 | PFvsC |
| 1638 | P81133\|SIM1_HUMAN | 200 | 204 | PFdgC |
| 1639 | P98088\|MUC5A_HUMAN | 290 | 294 | PFkmC |
| 1640 | Q01955\|CO4A3_HUMAN | 1501 | 1505 | PFlfC |
| 1641 | Q01955\|CO4A3_HUMAN | 1612 | 1616 | PFleC |
| 1642 | Q02817\|MUC2_HUMAN | 597 | 601 | PFgrC |
| 1643 | Q02817\|MUC2_HUMAN | 1375 | 1379 | PFglC |

TABLE 6-continued

Collagens
Motif: P-F-X2-C
Number of Locations: 306
Number of Different Proteins: 288

| SEQ ID NO: | Accession Number\| Protein Name | First Amino acid | Last Amino acid | Sequence |
|---|---|---|---|---|
| 1644 | Q02817\|MUC2_HUMAN | 4916 | 4920 | PFywC |
| 1645 | Q03395\|ROM1_HUMAN | 213 | 217 | PFscC |
| 1646 | Q07912\|ACK1_HUMAN | 293 | 297 | PFawC |
| 1647 | Q12830\|BPTF_HUMAN | 2873 | 2877 | PFyqC |
| 1648 | Q12836\|ZP4_HUMAN | 238 | 242 | PFtsC |
| 1649 | Q12866\|MERTK_HUMAN | 313 | 317 | PFrnC |
| 1650 | Q12950\|FOXD4_HUMAN | 291 | 295 | PFpcC |
| 1651 | Q12968\|NFAC3_HUMAN | 327 | 331 | PFqyC |
| 1652 | Q13191\|CBLB_HUMAN | 409 | 413 | PFcrC |
| 1653 | Q13258\|PD2R_HU MAN | 4 | 8 | PFyrC |
| 1654 | Q13356\|PPIL2_HUMAN | 38 | 42 | PFdhC |
| 1655 | Q13607\|OR2F1_HUMAN | 93 | 97 | PFqsC |
| 1656 | Q13753\|LAMC2_HUMAN | 409 | 413 | PFgtC |
| 1657 | Q13936\|CAC1C_HUMAN | 2179 | 2183 | PFvnC |
| 1658 | Q14031\|CO4A6_HUMAN | 1523 | 1527 | PFiyC |
| 1659 | Q14031\|CO4A6_HUMAN | 1632 | 1636 | PFieC |
| 1660 | Q14137\|BOP1_HUMAN | 400 | 404 | PFptC |
| 1661 | Q14330\|GPR18_HUMAN | 247 | 251 | PFhiC |
| 1662 | Q14643\|ITPR1_HUMAN | 526 | 530 | PFtdC |
| 1663 | Q15042\|RB3GP_HUMAN | 267 | 271 | PFgaC |
| 1664 | Q15389\|ANGP1_HUMAN | 282 | 286 | PFrdC |
| 1665 | Q15583\|TGIF_HUMAN | 269 | 273 | PFhsC |
| 1666 | Q15583\|TGIF_HUMAN | 314 | 318 | PFslC |
| 1667 | Q15761\|NPY5R_HUMAN | 128 | 132 | PFlqC |
| 1668 | Q15915\|ZIC1_HUMAN | 305 | 309 | PFpgC |
| 1669 | Q16363\|LAMA4_HUMAN | 1788 | 1792 | PFtgC |
| 1670 | Q16572\|VACHT_HUMAN | 517 | 521 | PFdeC |
| 1671 | Q16586\|SGCA_HUMAN | 205 | 209 | PFstC |
| 1672 | Q16773\|KAT1_HUMAN | 123 | 127 | PFfdC |
| 1673 | Q16878\|CDO1_HUMAN | 160 | 164 | PFdtC |
| 1674 | Q2TBC4\|CF049_HUMAN | 298 | 302 | PFstC |
| 1675 | Q49AM1\|MTER3_HUMAN | 28 | 32 | PFlaC |
| 1676 | Q53FE4\|CD017_HUMAN | 77 | 81 | PFanC |
| 1677 | Q53G59\|KLH12_HUMAN | 240 | 244 | PFirC |
| 1678 | Q53T03\|RBP22_HUMAN | 517 | 521 | PFpvC |
| 1679 | Q5IJ48\|CRUM2_HUMAN | 762 | 766 | PFrgC |
| 1680 | Q5T442\|CXA12_HUMAN | 241 | 245 | PFfpC |
| 1681 | Q5VYX0\|RENAL_HUMAN | 310 | 314 | PFlaC |
| 1682 | Q5W0N0\|CI057_HUMAN | 89 | 93 | PFhgC |
| 1683 | Q6NSW7\|NANP8_HUMAN | 239 | 243 | PFynC |
| 1684 | Q6P2Q9\|PRP8_HUMAN | 1892 | 1896 | PFqaC |
| 1685 | Q6PRD1\|GP179_HUMAN | 232 | 236 | PFleC |
| 1686 | Q6TCH4\|PAQR6_HUMAN | 95 | 99 | PFasC |
| 1687 | Q6UB98\|ANR12_HUMAN | 1949 | 1953 | PFsaC |
| 1688 | Q6UB99\|ANR11_HUMAN | 2552 | 2556 | PFsaC |
| 1689 | Q6UXZ4\|UNC5D_HUMAN | 766 | 770 | PFtaC |
| 1690 | Q7Z434\|MAVS_HUMAN | 431 | 435 | PFsgC |
| 1691 | Q7Z6J6\|FRMD5_HUMAN | 87 | 91 | PFtmC |
| 1692 | Q7Z7G8\|VP13B_HUMAN | 441 | 445 | PFfdC |
| 1693 | Q7Z7G8\|VP13B_HUMAN | 1423 | 1427 | PFrnC |
| 1694 | Q7Z7M1\|GP144_HUMAN | 352 | 356 | PFlcC |
| 1695 | Q86SJ6\|DSG4_HUMAN | 523 | 527 | PFtfC |
| 1696 | Q86SQ6\|GP123_HUMAN | 863 | 867 | PFiiC |
| 1697 | Q86T65\|DAAM2_HUMAN | 548 | 552 | PFacC |
| 1698 | Q86V97\|KBTB6_HUMAN | 355 | 359 | PFlcC |
| 1699 | Q86X12\|CNDG2_HUMAN | 1043 | 1047 | PFsrC |
| 1700 | Q86YT6\|MIB1_HUMAN | 909 | 913 | PFimC |
| 1701 | Q81UH2\|CREG2_HUMAN | 152 | 156 | PFgnC |
| 1702 | Q81WU5\|SULF2_HUMAN | 745 | 749 | PFcaC |
| 1703 | Q81WV8\|UBR2_HUMAN | 1514 | 1518 | PFlkC |
| 1704 | Q81WX5\|SGPP2_HUMAN | 257 | 261 | PFflC |
| 1705 | Q81X07\|FOG1_HUMAN | 293 | 297 | PFpqC |
| 1706 | Q81X29\|FBX16_HUMAN | 287 | 291 | PFplC |
| 1707 | Q8IXT2\|DMRTD_HUMAN | 224 | 228 | PFttC |
| 1708 | Q81ZF5\|GP113_HUMAN | 62 | 66 | PFpaC |
| 1709 | Q8IZQ8\|MYCD_HUMAN | 403 | 407 | PFqdC |
| 1710 | Q81ZW8\|TENS4_HUMAN | 423 | 427 | PFttC |
| 1711 | Q8NOW3\|FUK_HUMAN | 100 | 104 | PFddC |
| 1712 | Q8N122\|RPTOR_HUMAN | 1033 | 1037 | PFtpC |
| 1713 | Q8N1G1\|REXO1_HUMAN | 278 | 282 | PFgsC |
| 1714 | Q8N1G2\|K0082_HUMAN | 790 | 794 | PFhiC |

TABLE 6-continued

Collagens
Motif: P-F-X2-C
Number of Locations: 306
Number of Different Proteins: 288

| SEQ ID NO: | Accession Number\|Protein Name | First Amino acid | Last Amino acid | Sequence |
|---|---|---|---|---|
| 1715 | Q8N201\|INT1_HUMAN | 1573 | 1577 | PFpaC |
| 1716 | Q8N475\|FSTL5_HUMAN | 61 | 65 | PFgsC |
| 1717 | Q8N567\|ZCHC9_HUMAN | 182 | 186 | PFakC |
| 1718 | Q8N7R0\|NANG2_HUMAN | 166 | 170 | PFynC |
| 1719 | Q8N8U9\|BMPER_HUMAN | 234 | 238 | PFgsC |
| 1720 | Q8N9L1\|ZIC4_HUMAN | 207 | 211 | PFpgC |
| 1721 | Q8NB16\|MLKL_HUMAN | 411 | 415 | PFqgC |
| 1722 | Q8NG11\|TSN14_HUMAN | 183 | 187 | PFscC |
| 1723 | Q8NGC3\|O10G2_HUMAN | 98 | 102 | PFggC |
| 1724 | Q8NGC4\|O10G3_HUMAN | 94 | 98 | PFggC |
| 1725 | Q8NGJ1\|OR4D6_HUMAN | 165 | 169 | PFpfC |
| 1726 | Q8NH69\|OR5W2_HUMAN | 93 | 97 | PFygC |
| 1727 | Q8NH85\|OR5R1_HUMAN | 93 | 97 | PFhaC |
| 1728 | Q8NHU2\|CT026_HUMAN | 442 | 446 | PFntC |
| 1729 | Q8NHY3\|GA2L2_HUMAN | 359 | 363 | PFlrC |
| 1730 | Q8N151\|BORIS_HUMAN | 369 | 373 | PFqcC |
| 1731 | Q8TCB0\|IFI44_HUMAN | 246 | 250 | PFilC |
| 1732 | Q8TCE9\|PPL13_HUMAN | 88 | 92 | PFelC |
| 1733 | Q8TCT7\|PSL1_HUMAN | 275 | 279 | PFgkC |
| 1734 | Q8TD94\|KLF14_HUMAN | 198 | 202 | PFpgC |
| 1735 | Q8TF76\|HASP_HUMAN | 474 | 478 | PFshC |
| 1736 | Q8WW14\|CJ082_HUMAN | 22 | 26 | PFlsC |
| 1737 | Q8WW38\|FOG2_HUMAN | 299 | 303 | PFpqC |
| 1738 | Q8WWG1\|NRG4_HUMAN | 32 | 36 | PFcrC |
| 1739 | Q8WWZ7\|ABCA5_HUMAN | 361 | 365 | PFchC |
| 1740 | Q8WXT5\|FX4L4_HUMAN | 295 | 299 | PFpcC |
| 1741 | Q8WYR1\|PI3R5_HUMAN | 814 | 818 | PFavC |
| 1742 | Q8WZ42\|TITIN_HUMAN | 31091 | 31095 | PFpiC |
| 1743 | Q8WZ60\|KLHL6_HUMAN | 432 | 436 | PFhnC |
| 1744 | Q92485\|ASM3B_HUMAN | 41 | 45 | PFqvC |
| 1745 | Q92793\|CBP_HUMAN | 1279 | 1283 | PFvdC |
| 1746 | Q92838\|EDA_HUMAN | 328 | 332 | PFlqC |
| 1747 | Q92995\|UBP13_HUMAN | 540 | 544 | PFsaC |
| 1748 | Q93008\|USP9X_HUMAN | 251 | 255 | PFgqC |
| 1749 | Q96F10\|SAT2_HUMAN | 50 | 54 | PFyhC |
| 1750 | Q96FV3\|TSN17_HUMAN | 185 | 189 | PFscC |

TABLE 6-continued

Collagens
Motif: P-F-X2-C
Number of Locations: 306
Number of Different Proteins: 288

| SEQ ID NO: | Accession Number\|Protein Name | First Amino acid | Last Amino acid | Sequence |
|---|---|---|---|---|
| 1751 | Q96IK0\|TM101_HUMAN | 27 | 31 | PFwgC |
| 1752 | Q96L50\|LLR1_HUMAN | 344 | 348 | PFhlC |
| 1753 | Q96L73\|NSD1_HUMAN | 456 | 460 | PFedC |
| 1754 | Q96P88\|GNRR2_HUMAN | 184 | 188 | PFtqC |
| 1755 | Q96PZ7\|CSMD1_HUMAN | 2139 | 2143 | PFprC |
| 1756 | Q96R06\|SPAG5_HUMAN | 378 | 382 | PFstC |
| 1757 | Q96RG2\|PASK_HUMAN | 542 | 546 | PFasC |
| 1758 | Q96RJ0\|TAAR1_HUMAN | 266 | 270 | PFfiC |
| 1759 | Q96RQ9\|OXLA_HUMAN | 32 | 36 | PFekC |
| 1760 | Q96SE7\|ZN347_HUMAN | 798 | 802 | PFsiC |
| 1761 | Q96T25\|ZIC5_HUMAN | 470 | 474 | PFpgC |
| 1762 | Q99666\|RGPD8_HUMAN | 517 | 521 | PFpvC |
| 1763 | Q99698\|LYST_HUMAN | 254 | 258 | PFdlC |
| 1764 | Q99726\|ZNT3_HUMAN | 51 | 55 | PFhhC |
| 1765 | Q9BSE5\|SPEB_HUMAN | 204 | 208 | PFrrC |
| 1766 | Q9BWQ6\|YIPF2_HUMAN | 124 | 128 | PFwiC |
| 1767 | Q9BXC9\|BBS2_HUMAN | 530 | 534 | PFqvC |
| 1768 | Q9BXJ4\|C1QT3_HUMAN | 18 | 22 | PFclC |
| 1769 | Q9BXK1\|KLF16_HUMAN | 130 | 134 | PFpdC |
| 1770 | Q9BZE2\|PUS3_HUMAN | 261 | 265 | PFqlC |
| 1771 | Q9C0C4\|SEM4C_HUMAN | 719 | 723 | PFrpC |
| 1772 | Q9C0E2\|XPO4_HUMAN | 50 | 54 | PFavC |
| 1773 | Q9C014\|THS7B_HUMAN | 1482 | 1486 | PFsyC |
| 1774 | Q9GZN6\|S6A16_HUMAN | 271 | 275 | PFflC |
| 1775 | Q9GZU2\|PEG3_HUMAN | 1330 | 1334 | PFyeC |
| 1776 | Q9GZZ0\|HXD1_HUMAN | 162 | 166 | PFpaC |
| 1777 | Q9H0A6\|RNF32_HUMAN | 344 | 348 | PFhaC |
| 1778 | Q9H0B3\|K1683_HUMAN | 326 | 330 | PFqiC |
| 1779 | Q9H267\|VP33B_HUMAN | 189 | 193 | PFpnC |
| 1780 | Q9H2J1\|CI037_HUMAN | 102 | 106 | PFekC |
| 1781 | Q9H3H5\|GPT_HUMAN | 77 | 81 | PFlnC |
| 1782 | Q9H8V3\|ECT2_HUMAN | 239 | 243 | PFqdC |
| 1783 | Q9H9S0\|NANOG_HUMAN | 239 | 243 | PFynC |
| 1784 | Q9H9V4\|RN122_HUMAN | 3 | 7 | PFqwC |
| 1785 | Q9HAQ2\|KIF9_HUMAN | 291 | 295 | PFrqC |

TABLE 6-continued

| Collagens<br>Motif: P-F-X2-C<br>Number of Locations: 306<br>Number of Different Proteins: 288 | | | | |
|---|---|---|---|---|
| SEQ ID NO: | Accession Number\|Protein Name | First Amino acid | Last Amino acid | Sequence |
| 1786 | Q9HAW7\|UD17_HUMAN | 149 | 153 | PFdaC |
| 1787 | Q9HAW8\|UD110_HUMAN | 149 | 153 | PFdtC |
| 1788 | Q9HAW9\|UD18_HUMAN | 149 | 153 | PFdaC |
| 1789 | Q9HBX8\|LGR6_HUMAN | 412 | 416 | PFkpC |
| 1790 | Q9NQW8\|CNGB3_HUMAN | 309 | 313 | PFdiC |
| 1791 | Q9NRZ9\|HELLS_HUMAN | 273 | 277 | PFlvC |
| 1792 | Q9NTG7\|SIRT3_HUMAN | 30 | 34 | PFgaC |
| 1793 | Q9NWZ5\|UCKL1_HUMAN | 370 | 374 | PFqdC |
| 1794 | Q9NY30\|BTG4_HUMAN | 98 | 102 | PFevC |
| 1795 | Q9NYM4\|GPR83_HUMAN | 342 | 346 | PFiyC |
| 1796 | Q9NYV6\|RRN3_HUMAN | 561 | 565 | PFdpC |
| 1797 | Q9NYW1\|TA2R9_HUMAN | 190 | 194 | PFilC |
| 1798 | Q9NYW3\|TA2R7_HUMAN | 193 | 197 | PFcvC |
| 1799 | Q9NZ56\|FMN2_HUMAN | 716 | 720 | PFsdC |
| 1800 | Q9NZ71\|RTEL1_HUMAN | 495 | 499 | PFpvC |
| 1801 | Q9NZD2\|GLTP_HUMAN | 31 | 35 | PFfdC |
| 1802 | Q9P2N4\|ATS9_HUMAN | 596 | 600 | PFgtC |
| 1803 | Q9UBR1\|BUP1_HUMAN | 124 | 128 | PFafC |
| 1804 | Q9UBS0\|KS6B2_HUMAN | 344 | 348 | PFrpC |
| 1805 | Q9UET6\|RRMJ1_HUMAN | 234 | 238 | PFvtC |
| 1806 | Q9UHD4\|CIDEB_HUMAN | 37 | 41 | PFrvC |
| 1807 | Q9UKA4\|AKA11_HUMAN | 917 | 921 | PFshC |
| 1808 | Q9ULC3\|RAB23_HUMAN | 230 | 234 | PFssC |
| 1809 | Q9ULJ3\|ZN295_HUMAN | 125 | 129 | PFptC |
| 1810 | Q9ULK4\|CRSP3_HUMAN | 1086 | 1090 | PFpnC |
| 1811 | Q9ULL4\|PLXB3_HUMAN | 24 | 28 | PFglC |
| 1812 | Q9ULV8\|CBLC_HUMAN | 387 | 391 | PFcrC |
| 1813 | Q9UM47\|NOTC3_HUMAN | 1357 | 1361 | PFfrC |
| 1814 | Q9UNQ2\|DIMT1_HUMAN | 146 | 150 | PFfrC |
| 1815 | Q9Y3D5\|RT18C_HUMAN | 86 | 90 | PFtgC |
| 1816 | Q9Y3F1\|TA6P_HUMAN | 25 | 29 | PFpsC |
| 1817 | Q9Y3R5\|CU005_HUMAN | 255 | 259 | PFytC |
| 1818 | Q9Y450\|HBS1L_HUMAN | 487 | 491 | PFrlC |
| 1819 | Q9Y493\|ZAN_HUMAN | 1364 | 1368 | PFetC |
| 1820 | Q9Y493\|ZAN_HUMAN | 1751 | 1755 | PFsqC |
| 1821 | Q9Y493\|ZAN_HUMAN | 2556 | 2560 | PFaaC |

TABLE 6-continued

| Collagens<br>Motif: P-F-X2-C<br>Number of Locations: 306<br>Number of Different Proteins: 288 | | | | |
|---|---|---|---|---|
| SEQ ID NO: | Accession Number\|Protein Name | First Amino acid | Last Amino acid | Sequence |
| 1822 | Q9Y548\|YIPF1_HUMAN | 123 | 127 | PFwiC |
| 1823 | Q9Y5L3\|ENP2_HUMAN | 324 | 328 | PFsrC |
| 1824 | Q9Y5P8\|2ACC_HUMAN | 272 | 276 | PFqdC |
| 1825 | Q9Y664\|KPTN_HUMAN | 143 | 147 | PFqlC |
| 1826 | Q9Y678\|COPG_HUMAN | 226 | 230 | PFayC |
| 1827 | Q9Y6E0\|STK24_HUMAN | 371 | 375 | PFsqC |
| 1828 | Q9Y6R7\|FCGBP_HUMAN | 683 | 687 | PFavC |
| 1829 | Q9Y6R7\|FCGBP_HUMAN | 1074 | 1078 | PFreC |
| 1830 | Q9Y6R7\|FCGBP_HUMAN | 1888 | 1892 | PFttC |
| 1831 | Q9Y6R7\|FCGBP_HUMAN | 3089 | 3093 | PFttC |
| 1832 | Q9Y6R7\|FCGBP_HUMAN | 4290 | 4294 | PFttC |
| 1833 | Q9Y6R7\|FCGBP_HUMAN | 5059 | 5063 | PFatC |

TABLE 7A

| Table of the amino acid sequences of the peptides predicted similar to Growth Hormone | | | |
|---|---|---|---|
| Protein Name | Peptide Location | Peptide sequence | SEQ ID NO: |
| Placental Lactogen | AAA98621 (101-114) | LLRISLLL IESWLE | 2483 |
| hGH-V | AAB59548 (101-114) | LLRISLLL TQSWLE | 2490 |
| GH2 | CAG46722 (101-114) | LLHISLLL IQSWLE | 2491 |
| Chorionic somatomammotropin | AAA52116 (101-113) | LLRLLLLI ESWLE | 2480 |
| Chorionic somatomammotropin hormone-like 1 | AAI19748 (12-25) | LLHISLLL IESRLE | 2482 |
| Transmembrane protein 45A | NP_060474 (181-194) | LLRSSLIL LQGSWF | 2481 |
| IL-17 receptor C | Q8NAC3 (376-387) | RLRLLTLQ SWLL | 2477 |
| Neuropeptide FF receptor 2 | Q9Y5X5 (378-390) | LLIVALLF ILSWL | 2479 |
| Brush border myosin-I | AAC27437 (719-731) | LMRKSQIL ISSWF | 2478 |

TABLE 7B

Table of the amino acid sequences of the peptides predicted similar to PEDF.

| Protein Name | Peptide Location | Peptide sequence | SEQ ID NO: |
|---|---|---|---|
| DEAH box polypeptide 8 ("DEAH" disclosed as SEQ ID NO: 2484) | AAH47327 (438-448) | EIELVEEE PPF | 2485 |
| Caspase 10 | CAD32371 (67-77) | AEDLLSEE DPF | 2492 |
| CKIP-1 | CAI14263 (66-76) | TLDLIQEE DPS | 2493 |

TABLE 8

Amino acid sequences of peptides that contain the somatotropin motif.
Somatotropins
Motif: L-X(3)-L-L-X(3)-S-X-L (SEQ ID NO: 2488)
Number of Locations: 139
Number of Different Proteins: 139

| SEQ ID NO: | Accession Number\|Protein Name | First Amino acid | Last Amino acid | Sequence |
|---|---|---|---|---|
| 1834 | O14569\|C56D2_HUMAN | 164 | 175 | LvgyLLgsaSlL |
| 1835 | O15287\|FANCG_HUMAN | 416 | 427 | LceeLLsrtSsL |
| 1836 | O15482\|TEX28_HUMAN | 338 | 349 | LatvLLvfvStL |
| 1837 | O43914\|TYOBP_HUMAN | 11 | 22 | LllpLLlavSgL |
| 1838 | O60609\|GFRA3_HUMAN | 15 | 26 | LmllLLlppSpL |
| 1839 | O75844\|FACE1_HUMAN | 279 | 290 | LfdtLLeeySvL |
| 1840 | O95747\|OXSR1_HUMAN | 90 | 101 | LvmkLLsggSvL |
| 1841 | P01241\|SOMA_HUMAN | 102 | 113 | LrisLLliqSwL |
| 1842 | P01242\|SOM2_HUMAN | 102 | 113 | LrisLLliqSwL |
| 1843 | P01243\|CSH_HUMAN | 102 | 113 | LrisLLlieSwL |
| 1844 | P02750\|A2GL_HUMAN | 83 | 94 | LpanLLqgaSkL |
| 1845 | P03891\|NU2M_HUMAN | 149 | 160 | LnvsLLltlSiL |
| 1846 | P04201\|MAS_HUMAN | 151 | 162 | LvcaLLwalScL |
| 1847 | P05783\|K1C18_HUMAN | 338 | 349 | LngiLLhleSeL |
| 1848 | P07359\|GP1BA_HUMAN | 3 | 14 | LlllLLllpSpL |
| 1849 | P09848\|LPH_HUMAN | 35 | 46 | LtndLLhnlSgL |
| 1850 | P11168\|GTR2_HUMAN | 136 | 147 | LvgaLLmgfSkL |
| 1851 | P12034\|FGF5_HUMAN | 3 | 14 | LsflLLlffShL |
| 1852 | P13489\|RINI_HUMAN | 247 | 258 | LcpgLLhpsSrL |
| 1853 | P14902\|I23O_HUMAN | 196 | 207 | LlkaLLeiaScL |
| 1854 | P16278\|BGAL_HUMAN | 135 | 146 | LpawLLekeSiL |
| 1855 | P19838\|NFKB1_HUMAN | 558 | 569 | LvrdLLevtSgL |
| 1856 | P22079\|PERL_HUMAN | 512 | 523 | LvrgLLakkSkL |
| 1857 | P23276\|KELL_HUMAN | 53 | 64 | LilgLLlcfSvL |

TABLE 8-continued

Amino acid sequences of peptides that contain the somatotropin motif.
Somatotropins
Motif: L-X(3)-L-L-X(3)-S-X-L (SEQ ID NO: 2488)
Number of Locations: 139
Number of Different Proteins: 139

| SEQ ID NO: | Accession Number\|Protein Name | First Amino acid | Last Amino acid | Sequence |
|---|---|---|---|---|
| 1858 | P24394\|IL4RA_HUMAN | 4 | 15 | LcsgLLfpvScL |
| 1859 | P29320\|EPHA3_HUMAN | 5 | 16 | LsilLLlscSvL |
| 1860 | P31512\|FMO4_HUMAN | 524 | 535 | LaslLLickSsL |
| 1861 | P35270\|SPRE_HUMAN | 26 | 37 | LlasLLspgSvL |
| 1862 | P41250\|SYG_HUMAN | 20 | 31 | LpprLLarpSlL |
| 1863 | P42575\|CASP2_HUMAN | 114 | 125 | LedmLLttlSgL |
| 1864 | P46721\|SO1A2_HUMAN | 396 | 407 | LleyLLyflSfL |
| 1865 | P51665\|PSD7_HUMAN | 201 | 212 | LnskLLdirSyL |
| 1866 | P59531\|T2R12_HUMAN | 188 | 199 | LisfLLsliSlL |
| 1867 | P69849\|NOMO3_HUMAN | 1180 | 1191 | LiplLLqltSrL |
| 1868 | P98161\|PKD1_HUMAN | 82 | 93 | LdvgLLanlSaL |
| 1869 | P98171\|RHG04_HUMAN | 153 | 164 | LqdeLLevvSeL |
| 1870 | P98196\|AT11A_HUMAN | 1077 | 1088 | LaivLLvtiSlL |
| 1871 | Q08431\|MFGM_HUMAN | 10 | 21 | LcgaLLcapSlL |
| 1872 | Q08AF3\|SLFN5_HUMAN | 533 | 544 | LvivLLgfkSfL |
| 1873 | Q12952\|FOXL1_HUMAN | 293 | 304 | LgasLLaasSsL |
| 1874 | Q13275\|SEM3F_HUMAN | 2 | 13 | LvagLLlwaSlL |
| 1875 | Q13394\|MB211_HUMAN | 300 | 311 | LngiLLqliScL |
| 1876 | Q13609\|DNSL3_HUMAN | 8 | 19 | LlllLLsihSaL |
| 1877 | Q13619\|CUL4A_HUMAN | 213 | 224 | LlrsLLgmlSdL |
| 1878 | Q13620\|CUL4B_HUMAN | 349 | 360 | LlrsLLsmlSdL |
| 1879 | Q14406\|CSHL_HUMAN | 84 | 95 | LhisLLlieSrL |
| 1880 | Q14667\|K0100_HUMAN | 8 | 19 | LlvlLLvalSaL |
| 1881 | Q15155\|NOMO1_HUMAN | 1180 | 1191 | LiplLLqltSrL |
| 1882 | Q15760\|GPR19_HUMAN | 279 | 290 | LilnLLfllSwL |
| 1883 | Q53RE8\|ANR39_HUMAN | 166 | 177 | LacdLLpcnSdL |
| 1884 | Q5FWE3\|PRRT3_HUMAN | 586 | 597 | LatdLLstwSvL |
| 1885 | Q5GH73\|XKR6_HUMAN | 630 | 641 | LlyeLLqyeSsL |
| 1886 | Q5GH77\|XKR3_HUMAN | 194 | 205 | LnraLLmtfSlL |
| 1887 | Q5JPE7\|NOMO2_HUMAN | 1180 | 1191 | LiplLLqltSrL |
| 1888 | Q5JWR5\|DOP1_HUMAN | 506 | 517 | LpqlLLrmiSaL |
| 1889 | Q5UIP0\|RIF1_HUMAN | 2413 | 2424 | LsknLLaqiSaL |
| 1890 | Q5VTE6\|ANGE2_HUMAN | 175 | 186 | LsqdLLednShL |
| 1891 | Q5VU43\|MYOME_HUMAN | 1932 | 1943 | LreaLLssrShL |

TABLE 8-continued

Amino acid sequences of peptides that contain the somatotropin motif.
Somatotropins
Motif: L-X(3)-L-L-X(3)-S-X-L (SEQ ID NO: 2488)
Number of Locations: 139
Number of Different Proteins: 139

| SEQ ID NO: | Accession Number\| Protein Name | First Amino acid | Last Amino acid | Sequence |
|---|---|---|---|---|
| 1892 | Q5VYK3\|ECM29_HUMAN | 1296 | 1307 | LipaLLeslSvL |
| 1893 | Q68D06\|SLN13_HUMAN | 554 | 565 | LvivLLgfrSlL |
| 1894 | Q6GYQ0\|GRIPE_HUMAN | 641 | 652 | LwddLLsvlSsL |
| 1895 | Q6NTF9\|RHBD2_HUMAN | 166 | 177 | LvpwLLlgaSwL |
| 1896 | Q6ZMH5\|S39A5_HUMAN | 217 | 228 | LavlLLslpSpL |
| 1897 | Q6ZMZ3\|SYNE3_HUMAN | 532 | 543 | LhnsLLqrkSkL |
| 1898 | Q6ZVD8\|PHLPL_HUMAN | 313 | 324 | LfpiLLceiStL |
| 1899 | Q6ZVE7\|GOT1A_HUMAN | 23 | 34 | LfgtLLyfdSvL |
| 1900 | Q70J99\|UN13D_HUMAN | 927 | 938 | LrveLLsasSlL |
| 1901 | Q7Z3Z4\|PIWL4_HUMAN | 139 | 150 | LriaLLyshSeL |
| 1902 | Q7Z6Z7\|HUWE1_HUMAN | 841 | 852 | LqegLLqldSiL |
| 1903 | Q7Z7L1\|SLN11_HUMAN | 554 | 565 | LvivLLgfrSlL |
| 1904 | Q86SM5\|MRGRG_HUMAN | 223 | 234 | LlnfLLpvfSpL |
| 1905 | Q86U44\|MTA70_HUMAN | 78 | 89 | LekkLLhhlSdL |
| 1906 | Q86UQ4\|ABCAD_HUMAN | 3182 | 3193 | LlnsLLdivSsL |
| 1907 | Q86WI3\|NLRC5_HUMAN | 1485 | 1496 | LlqsLLlslSeL |
| 1908 | Q86YC3\|LRC33_HUMAN | 263 | 274 | LffpLLpqySkL |
| 1909 | Q8IYK4\|GT252_HUMAN | 9 | 20 | LawsLLllsSaL |
| 1910 | Q8IYS0\|GRM1C_HUMAN | 485 | 496 | LesdLLieeSvL |
| 1911 | Q8IZL8\|PELP1_HUMAN | 33 | 44 | LrllLLesvSgL |
| 1912 | Q8IZY2\|ABCA7_HUMAN | 1746 | 1757 | LftlLLqhrSqL |
| 1913 | Q8N0X7\|SPG20_HUMAN | 322 | 333 | LfedLLrqmSdL |
| 1914 | Q8N6M3\|CT142_HUMAN | 33 | 44 | LagsLLkelSpL |
| 1915 | Q8N816\|TMM99_HUMAN | 96 | 107 | LlpcLLgvgSwL |
| 1916 | Q8NBM4\|PDHL1_HUMAN | 15 | 26 | LsksLLlvpSaL |
| 1917 | Q8NCG7\|DGLB_HUMAN | 555 | 566 | LtqpLLgeqSlL |
| 1918 | Q8NFR9\|I17RE_HUMAN | 80 | 91 | LcqhLLsggSgL |
| 1919 | Q8NGE3\|O10P1_HUMAN | 9 | 20 | LpefLLlgfSdL |
| 1920 | Q8TCV5\|WFDC5_HUMAN | 8 | 19 | LlgaLLavgSqL |
| 1921 | Q8TDL5\|LPLC1_HUMAN | 165 | 176 | LriqLLhklSfL |
| 1922 | Q8TE82\|S3TC1_HUMAN | 1025 | 1036 | LeggLLetiSqL |
| 1923 | Q8TEQ8\|PIGO_HUMAN | 857 | 868 | LvflLLflqSfL |
| 1924 | Q8TEZ7\|MPRB_HUMAN | 127 | 138 | LlahLLqskSeL |
| 1925 | Q8WWN8\|CEND3_HUMAN | 1481 | 1492 | LeeqLLqelSsL |
| 1926 | Q8WZ84\|OR8D1_HUMAN | 43 | 54 | LgmiLLiavSpL |

TABLE 8-continued

Amino acid sequences of peptides that contain the somatotropin motif.
Somatotropins
Motif: L-X(3)-L-L-X(3)-S-X-L (SEQ ID NO: 2488)
Number of Locations: 139
Number of Different Proteins: 139

| SEQ ID NO: | Accession Number\| Protein Name | First Amino acid | Last Amino acid | Sequence |
|---|---|---|---|---|
| 1927 | Q92535\|PIGC_HUMAN | 253 | 264 | LfalLLmsiScL |
| 1928 | Q92538\|GBF1_HUMAN | 1224 | 1235 | LrilLLmkpSvL |
| 1929 | Q92743\|HTRA1_HUMAN | 262 | 273 | LpvlLLgrsSeL |
| 1930 | Q92935\|EXTL1_HUMAN | 19 | 30 | LllvLLggfSlL |
| 1931 | Q93074\|MED12_HUMAN | 401 | 412 | LqtiLLccpSaL |
| 1932 | Q96DN6\|MBD6_HUMAN | 740 | 751 | LgasLLgdlSsL |
| 1933 | Q96GR4\|ZDH12_HUMAN | 48 | 59 | LtflLLvlgSlL |
| 1934 | Q96HP8\|T176A_HUMAN | 29 | 40 | LaklLLtccSaL |
| 1935 | Q96K12\|FACR2_HUMAN | 380 | 391 | LmnrLLrtvSmL |
| 1936 | Q96KP1\|EXOC2_HUMAN | 339 | 350 | LldkLLetpStL |
| 1937 | Q96MX0\|CKLF3_HUMAN | 40 | 51 | LkgrLLlaeSgL |
| 1938 | Q96Q45\|AL2S4_HUMAN | 387 | 398 | LvvaLLvglSwL |
| 1939 | Q96QZ0\|PANX3_HUMAN | 136 | 147 | LssdLLfiiSeL |
| 1940 | Q96RQ9\|OXLA_HUMAN | 269 | 280 | LpraLLsslSgL |
| 1941 | Q9BY08\|EBPL_HUMAN | 178 | 189 | LipgLLlwqSwL |
| 1942 | Q9BZ97\|TTY13_HUMAN | 30 | 41 | LclmLLlagScL |
| 1943 | Q9H1Y0\|ATG5_HUMAN | 85 | 96 | LlfdLLassSaL |
| 1944 | Q9H254\|SPTN4_HUMAN | 1422 | 1433 | LdkkLLhmeSqL |
| 1945 | Q9H330\|CI005_HUMAN | 430 | 441 | LgkfLLkvdSkL |
| 1946 | Q9H418\|SEHL2_HUMAN | 175 | 186 | LlqrLLksnShL |
| 1947 | Q9HCN3\|TMEM8_HUMAN | 200 | 211 | LpqtLLshpSyL |
| 1948 | Q9NQ34\|TMM9B_HUMAN | 4 | 15 | LwggLLrlgSlL |
| 1949 | Q9NR09\|BIRC6_HUMAN | 1400 | 1411 | LlkaLLdnmSfL |
| 1950 | Q9NRA0\|SPHK2_HUMAN | 296 | 307 | LgldLLlncSlL |
| 1951 | Q9NRU3\|CNNM1_HUMAN | 156 | 167 | LgalLLlalSaL |
| 1952 | Q9NTT1\|U2D3L_HUMAN | 99 | 110 | LskyLLsicSlL |
| 1953 | Q9NVH2\|INT7_HUMAN | 623 | 634 | LridLLqafSqL |
| 1954 | Q9NVM9\|CL011_HUMAN | 350 | 361 | LtnfLLngrSvL |
| 1955 | Q9NZD1\|GPC5D_HUMAN | 60 | 71 | LptqLLfllSvL |
| 1956 | Q9P2E9\|RRBP1_HUMAN | 1226 | 1237 | LrqlLLesqSqL |
| 1957 | Q9P2G4\|K1383_HUMAN | 397 | 408 | LlnaLLvelSlL |
| 1958 | Q9P2V4\|LRIT1_HUMAN | 541 | 552 | LpltLLvccSaL |
| 1959 | Q9UDY8\|MALT1_HUMAN | 33 | 44 | LrepLLrrlSeL |
| 1960 | Q9UEW8\|STK39_HUMAN | 138 | 149 | LvmkLLsggSmL |

TABLE 8-continued

Amino acid sequences of peptides that contain the somatotropin motif.
Somatotropins
Motif: L-X(3)-L-L-X(3)-S-X-L (SEQ ID NO: 2488)
Number of Locations: 139
Number of Different Proteins: 139

| SEQ ID NO: | Accession Number\| Protein Name | First Amino acid | Last Amino acid | Sequence |
|---|---|---|---|---|
| 1961 | Q9UGN4\|CM35H_HUMAN | 188 | 199 | LlllLLvgaSlL |
| 1962 | Q9UHD4\|CIDEB_HUMAN | 189 | 200 | LghmLLgisStL |
| 1963 | Q9U1G8\|SO3A1_HUMAN | 270 | 281 | LcgaLLffsSlL |
| 1964 | Q9UPA5\|BSN_HUMAN | 353 | 364 | LgasLLtqaStL |
| 1965 | Q9UPX8\|SHAN2_HUMAN | 609 | 620 | LtgrLLdpsSpL |
| 1966 | Q9Y239\|NOD1_HUMAN | 318 | 329 | LsgkLLkgaSkL |
| 1967 | Q9Y212\|NTNG1_HUMAN | 526 | 537 | LlttLLgtaSpL |
| 1968 | Q9Y2U2\|KCNK7_HUMAN | 92 | 103 | LpsaLLfaaSiL |
| 1969 | Q9Y2Y8\|PRG3_HUMAN | 7 | 18 | LpflLLgtvSaL |
| 1970 | Q9Y586\|MB212_HUMAN | 300 | 311 | LngiLLqliScL |
| 1971 | Q9Y5X0\|SNX10_HUMAN | 106 | 117 | LqnaLLlsdSsL |
| 1972 | Q9Y5X5\|NPFF2_HUMAN | 379 | 390 | LivaLLfilSwL |

TABLE 9

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\| Protein Name | First Amino acid | Last Amino acid | Sequence |
|---|---|---|---|---|
| 1973 | O00160\|MYO1F_HUMAN | 744 | 751 | LglEErPe |
| 1974 | O00507\|USP9Y_HUMAN | 2474 | 2481 | LcpEEePd |
| 1975 | O00625\|PIR_HUMAN | 134 | 141 | LksEEiPk |
| 1976 | O14641\|DVL2_HUMAN | 20 | 27 | LdeEEtPy |
| 1977 | O14686\|MLL2_HUMAN | 2819 | 2826 | LgpEErPp |
| 1978 | O14709\|ZN197_HUMAN | 193 | 200 | LsqEEnPr |
| 1979 | O14795\|UN13B_HUMAN | 1499 | 1506 | LgnEEgPe |
| 1980 | O15013\|ARHGA_HUMAN | 199 | 206 | LssEEpPt |
| 1981 | O15055\|PER2_HUMAN | 994 | 1001 | LqlEEaPe |
| 1982 | O15528\|CP27B_HUMAN | 297 | 304 | LfrEElPa |
| 1983 | O15534\|PER1_HUMAN | 987 | 994 | LqlEElPr |
| 1984 | O43390\|HNRPR_HUMAN | 12 | 19 | LkeEEePm |
| 1985 | O60216\|RAD21_HUMAN | 504 | 511 | LppEEpPn |
| 1986 | O60237\|MYPT2_HUMAN | 339 | 346 | LyeEEtPk |
| 1987 | O60346\|PHLPP_HUMAN | 483 | 490 | LeaEEkPl |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\| Protein Name | First Amino acid | Last Amino acid | Sequence |
|---|---|---|---|---|
| 1988 | O60779\|S19A2_HUMAN | 259 | 266 | LnmEEpPv |
| 1989 | O60885\|BRD4_HUMAN | 913 | 920 | LedEEpPa |
| 1990 | O75128\|COBL_HUMAN | 1064 | 1071 | LerEEkPs |
| 1991 | O75420\|PERQ1_HUMAN | 334 | 341 | LeeEEePs |
| 1992 | O75787\|RENR_HUMAN | 116 | 123 | LfsEEtPv |
| 1993 | O75914\|PAK3_HUMAN | 5 | 12 | LdnEEkPp |
| 1994 | O94933\|SLIK3_HUMAN | 227 | 234 | LqlEEnPw |
| 1995 | O94966\|UBP19_HUMAN | 1251 | 1258 | LeaEEePv |
| 1996 | O94986\|CE152_HUMAN | 847 | 854 | LknEEvPv |
| 1997 | O94991\|SLIK5_HUMAN | 230 | 237 | LqlEEnPw |
| 1998 | O95153\|RIMB1_HUMAN | 915 | 922 | LngEEcPp |
| 1999 | O95279\|KCNK5_HUMAN | 443 | 450 | LagEEsPq |
| 2000 | O95712\|PA24B_HUMAN | 772 | 779 | LkiEEpPs |
| 2001 | O95881\|TXD12_HUMAN | 94 | 101 | LedEEePk |
| 2002 | O96018\|APBA3_HUMAN | 116 | 123 | LhcEEcPp |
| 2003 | O96024\|B3GT4_HUMAN | 217 | 224 | LhsEEvPl |
| 2004 | P04275\|VWF_HUMAN | 1012 | 1019 | LqvEEdPv |
| 2005 | P05160\|F13B_HUMAN | 18 | 25 | LyaEEkPc |
| 2006 | P06858\|LIPL_HUMAN | 279 | 286 | LinEEnPs |
| 2007 | P07237\|PDIA1_HUMAN | 307 | 314 | LkkEEcPa |
| 2008 | P07949\|RET_HUMAN | 1033 | 1040 | LseEEtPl |
| 2009 | P08519\|APOA_HUMAN | 3880 | 3887 | LpsEEaPt |
| 2010 | P09769\|FGR_HUMAN | 497 | 504 | LdpEErPt |
| 2011 | P10745\|IRBP_HUMAN | 708 | 715 | LvvEEaPp |
| 2012 | P11532\|DMD_HUMAN | 2255 | 2262 | LlvEElPl |
| 2013 | P14317\|HCLS1_HUMAN | 352 | 359 | LqvEEePv |
| 2014 | P16150\|LEUK_HUMAN | 369 | 376 | LkgEEePl |
| 2015 | P17025\|ZN182_HUMAN | 79 | 86 | LevEEcPa |
| 2016 | P17600\|SYN1_HUMAN | 239 | 246 | LgtEEfPl |
| 2017 | P18583\|SON_HUMAN | 1149 | 1156 | LppEEpPt |
| 2018 | P18583\|SON_HUMAN | 1160 | 1167 | LppEEpPm |
| 2019 | P18583\|SON_HUMAN | 1171 | 1178 | LppEEpPe |
| 2020 | P19484\|TFEB_HUMAN | 350 | 357 | LpsEEgPg |
| 2021 | P21333\|FLNA_HUMAN | 1034 | 1041 | LprEEgPy |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\|Protein Name | First Amino acid | Last Amino acid | Sequence |
|---|---|---|---|---|
| 2022 | P21802\|FGFR2_HUMAN | 33 | 40 | LepEEpPt |
| 2023 | P22001\|KCNA3_HUMAN | 152 | 159 | LreEErPl |
| 2024 | P31629\|ZEP2_HUMAN | 772 | 779 | LvsEEsPs |
| 2025 | P34925\|RYK_HUMAN | 578 | 585 | LdpEErPk |
| 2026 | P36955\|PEDF_HUMAN | 39 | 46 | LveEEdPf |
| 2027 | P40189\|IL6RB_HUMAN | 787 | 794 | LdsEErPe |
| 2028 | P42898\|MTHR_HUMAN | 598 | 605 | LyeEEsPs |
| 2029 | P48729\|KC1A_HUMAN | 266 | 273 | LrfEEaPd |
| 2030 | P51512\|MMP16_HUMAN | 165 | 172 | LtfEEvPy |
| 2031 | P52746\|ZN142_HUMAN | 750 | 757 | LgaEEnPl |
| 2032 | P53370\|NUDT6_HUMAN | 284 | 291 | LtvEElPa |
| 2033 | P53801\|PTTG_HUMAN | 167 | 174 | LfkEEnPy |
| 2034 | P53804\|TTC3_HUMAN | 2001 | 2008 | LltEEsPs |
| 2035 | P55285\|CADH6_HUMAN | 116 | 123 | LdrEEkPv |
| 2036 | P55289\|CAD12_HUMAN | 117 | 124 | LdrEEkPf |
| 2037 | P56645\|PER3_HUMAN | 929 | 936 | LlqEEmPr |
| 2038 | P59797\|SELV_HUMAN | 163 | 170 | LlpEEdPe |
| 2039 | Q01826\|SATB1_HUMAN | 409 | 416 | LrkEEdPk |
| 2040 | Q04725\|TLE2_HUMAN | 200 | 207 | LveEErPs |
| 2041 | Q06330\|SUH_HUMAN | 7 | 14 | LpaEEpPa |
| 2042 | Q06889\|EGR3_HUMAN | 24 | 31 | LypEEiPs |
| 2043 | Q07157\|ZO1_HUMAN | 1155 | 1162 | LrhEEqPa |
| 2044 | Q13072\|BAGE1_HUMAN | 19 | 26 | LmkEEsPv |
| 2045 | Q13087\|PDIA2_HUMAN | 497 | 504 | LptEEpPe |
| 2046 | Q13255\|GRM1_HUMAN | 995 | 1002 | LtaEEtPl |
| 2047 | Q13315\|ATM_HUMAN | 954 | 961 | LpgEEyPl |
| 2048 | Q13439\|GOGA4_HUMAN | 2092 | 2099 | LeqEEnPg |
| 2049 | Q13596\|SNX1_HUMAN | 265 | 272 | LekEElPr |
| 2050 | Q13634\|CAD18_HUMAN | 446 | 453 | LdrEEtPw |
| 2051 | Q14028\|CNGB1_HUMAN | 137 | 144 | LmaEEnPp |
| 2052 | Q14126\|DSG2_HUMAN | 117 | 124 | LdrEEtPf |
| 2053 | Q14204\|DYHC_HUMAN | 3973 | 3980 | LwsEEtPa |
| 2054 | Q14315\|FLNC_HUMAN | 1738 | 1745 | LphEEePs |
| 2055 | Q14524\|SCN5A_HUMAN | 46 | 53 | LpeEEaPr |
| 2056 | Q14554\|PDIA5_HUMAN | 166 | 173 | LkkEEkPl |
| 2057 | Q14562\|DHX8_HUMAN | 411 | 418 | LskEEfPd |
| 2058 | Q14562\|DHX8_HUMAN | 441 | 448 | LveEEpPf |
| 2059 | Q14573\|ITPR3_HUMAN | 315 | 322 | LaaEEnPs |
| 2060 | Q14674\|ESPL1_HUMAN | 613 | 620 | LspEEtPa |
| 2061 | Q14676\|MDC1_HUMAN | 145 | 152 | LtvEEtPr |
| 2062 | Q14684\|RRP1B_HUMAN | 244 | 251 | LsaEEiPe |
| 2063 | Q15021\|CND1_HUMAN | 1179 | 1186 | LgvEEePf |
| 2064 | Q15735\|PI5PA_HUMAN | 189 | 196 | LasEEqPp |
| 2065 | Q15788\|NCOA1_HUMAN | 982 | 989 | LimEErPn |
| 2066 | Q15878\|CAC1E_HUMAN | 797 | 804 | LnrEEaPt |
| 2067 | Q2TAL6\|VWC2_HUMAN | 179 | 186 | LctEEgPl |
| 2068 | Q32MZ4\|LRRF1_HUMAN | 82 | 89 | LrvEErPe |
| 2069 | Q32P28\|P3H1_HUMAN | 215 | 222 | LysEEqPq |
| 2070 | Q3KNS1\|PTHD3_HUMAN | 96 | 103 | LpeEEtPe |
| 2071 | Q3ZCX4\|ZN568_HUMAN | 100 | 107 | LeqEEePw |
| 2072 | Q495W5\|FUT11_HUMAN | 144 | 151 | LlhEEsPl |
| 2073 | Q52LD8\|RFTN2_HUMAN | 123 | 130 | LviEEcPl |
| 2074 | Q53GL0\|PKHO1_HUMAN | 189 | 196 | LiqEEdPs |
| 2075 | Q53GL0\|PKHO1_HUMAN | 289 | 296 | LraEEpPt |
| 2076 | Q53GL7\|PAR10_HUMAN | 693 | 700 | LeaEEpPd |
| 2077 | Q53H47\|SETMR_HUMAN | 499 | 506 | LdqEEaPk |
| 2078 | Q567U6\|CCD93_HUMAN | 300 | 307 | LsaEEsPe |
| 2079 | Q580R0\|CB027_HUMAN | 41 | 48 | LelEEaPe |
| 2080 | Q58719\|SFT2C_HUMAN | 136 | 143 | LrcEEaPs |
| 2081 | Q5H9T9\|CN155_HUMAN | 427 | 434 | LlpEEaPr |
| 2082 | Q5H9T9\|CN155_HUMAN | 697 | 704 | LpaEEtPi |
| 2083 | Q5H9T9\|CN155_HUMAN | 736 | 743 | LltEEfPi |
| 2084 | Q5JUK9\|GGED1_HUMAN | 38 | 45 | LqqEEpPi |
| 2085 | Q5JXB2\|UE2NL_HUMAN | 58 | 65 | LlaEEyPm |
| 2086 | Q5MCW4\|ZN569_HUMAN | 60 | 67 | LeqEEePw |
| 2087 | Q5SYB0\|FRPD1_HUMAN | 553 | 560 | LikEEqPp |
| 2088 | Q5THJ4\|VP13D_HUMAN | 2943 | 2950 | LtgEEiPf |
| 2089 | Q5VYS4\|CM033_HUMAN | 293 | 300 | LesEEtPn |
| 2090 | Q5VZP5\|DUS27_HUMAN | 942 | 949 | LrtEEkPp |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\| Protein Name | First Amino acid | Last Amino acid | Sequence |
|---|---|---|---|---|
| 2091 | Q5VZY2\|PPC1A_HUMAN | 247 | 254 | LkkEErPt |
| 2092 | Q63HR2\|TENC1_HUMAN | 564 | 571 | LddEEqPt |
| 2093 | Q66K74\|MAP1S_HUMAN | 777 | 784 | LgaEEtPp |
| 2094 | Q68CZ1\|FTM_HUMAN | 1181 | 1188 | LpaEEtPv |
| 2095 | Q68DD2\|PA24F_HUMAN | 470 | 477 | LyqEEnPa |
| 2096 | Q6BDS2\|URFB1_HUMAN | 1304 | 1311 | LedEEiPv |
| 2097 | Q6DCA0\|AMERL_HUMAN | 183 | 190 | LtrEElPk |
| 2098 | Q6DN90\|IQEC1_HUMAN | 263 | 270 | LhtEEaPa |
| 2099 | Q6DT37\|MRCKG_HUMAN | 1264 | 1271 | LypEElPp |
| 2100 | Q6HA08\|ASTL_HUMAN | 62 | 69 | LilEEtPe |
| 2101 | Q6IFS5\|HSN2_HUMAN | 298 | 305 | LnqEElPp |
| 2102 | Q6NUN7\|CK063_HUMAN | 74 | 81 | LdeEEsPr |
| 2103 | Q6P2Q9\|PRP8_HUMAN | 1852 | 1859 | LpvEEqPk |
| 2104 | Q6P5W5\|S39A4_HUMAN | 473 | 480 | LvaEEsPe |
| 2105 | Q6P6B1\|CH047_HUMAN | 249 | 256 | LgkEEqPq |
| 2106 | Q6PD74\|P34_HUMAN | 141 | 148 | LspEElPe |
| 2107 | Q6P148\|SYDM_HUMAN | 488 | 495 | LpkEEnPr |
| 2108 | Q6PJ61\|FBX46_HUMAN | 246 | 253 | LrkEErPg |
| 2109 | Q6S8J7\|POTE8_HUMAN | 307 | 314 | LtsEEePq |
| 2110 | Q6SZW1\|SARM1_HUMAN | 396 | 403 | LlgEEvPr |
| 2111 | Q6UX39\|AMTN_HUMAN | 114 | 121 | LssEElPq |
| 2112 | Q6ZMY3\|SPOC1_HUMAN | 184 | 191 | LskEEpPg |
| 2113 | Q6ZN11\|ZN793_HUMAN | 60 | 67 | LeqEEaPw |
| 2114 | Q6ZNL6\|FGD5_HUMAN | 382 | 389 | LraEEnPm |
| 2115 | Q6ZV29\|PLPL7_HUMAN | 854 | 861 | LhrEEgPa |
| 2116 | Q7OCQ4\|UBP31_HUMAN | 527 | 534 | LpqEEqPl |
| 2117 | Q70SY1\|CR3L2_HUMAN | 153 | 160 | LekEEpPl |
| 2118 | Q7L8C5\|SYT13_HUMAN | 229 | 236 | LaeEElPt |
| 2119 | Q7Z3E5\|ARMC9_HUMAN | 570 | 577 | LnsEElPd |
| 2120 | Q7Z410\|TMPS9_HUMAN | 691 | 698 | LacEEaPg |
| 2121 | Q86SP6\|GP149_HUMAN | 217 | 224 | LcsEEpPr |
| 2122 | Q86V87\|RAI16_HUMAN | 496 | 503 | LdlEEdPy |
| 2123 | Q86VQ0\|CF152_HUMAN | 428 | 435 | LerEEkPe |
| 2124 | Q86W50\|MET10_HUMAN | 454 | 461 | LsqEEnPe |
| 2125 | Q86Y13\|DZIP3_HUMAN | 1192 | 1199 | LlpEEfPg |
| 2126 | Q86Y27\|BAGE5_HUMAN | 19 | 26 | LmkEEsPv |
| 2127 | Q86Y28\|BAGE4_HUMAN | 19 | 26 | LmkEEsPv |
| 2128 | Q86Y29\|BAGE3_HUMAN | 19 | 26 | LmkEEsPv |
| 2129 | Q86Y30\|BAGE2_HUMAN | 19 | 26 | LmkEEsPv |
| 2130 | Q8IU99\|FA26C_HUMAN | 315 | 322 | LgqEEpPl |
| 2131 | Q8IUA0\|WFDC8_HUMAN | 217 | 224 | LqdEEcPl |
| 2132 | Q8IV63\|VRK3_HUMAN | 438 | 445 | LtyEEkPp |
| 2133 | Q8IWY9\|CDAN1_HUMAN | 948 | 955 | LlpEEtPa |
| 2134 | Q8IXI1\|MIRO2_HUMAN | 24 | 31 | LvgEEfPe |
| 2135 | Q8IXI2\|MIRO1_HUMAN | 24 | 31 | LvsEEfPe |
| 2136 | Q8IYS5\|OSCAR_HUMAN | 122 | 129 | LvtEElPr |
| 2137 | Q8IZ26\|ZNF34_HUMAN | 251 | 258 | LhtEEkPy |
| 2138 | Q8IZH2\|XRN1_HUMAN | 1143 | 1150 | LfdEEfPg |
| 2139 | Q8IZP0\|ABI1_HUMAN | 7 | 14 | LleEEiPs |
| 2140 | Q8N201\|INT1_HUMAN | 1587 | 1594 | LlqEEePl |
| 2141 | Q8N309\|LRC43_HUMAN | 373 | 380 | LlvEEsPe |
| 2142 | Q8N3C0\|HELC1_HUMAN | 451 | 458 | LsfEEkPv |
| 2143 | Q8N3C0\|HELC1_HUMAN | 1579 | 1586 | LatEEdPk |
| 2144 | Q8N475\|FSTL5_HUMAN | 786 | 793 | LkaEEwPw |
| 2145 | Q8N4L2\|TM55A_HUMAN | 132 | 139 | LisEEqPa |
| 2146 | Q8N752\|KC1AL_HUMAN | 266 | 273 | LrfEEvPd |
| 2147 | Q8NC74\|CT151_HUMAN | 178 | 185 | LrgEEkPa |
| 2148 | Q8NE71\|ABCF1_HUMAN | 701 | 708 | LrmEEtPt |
| 2149 | Q8NEG5\|ZSWM2_HUMAN | 43 | 50 | LlrEEePe |
| 2150 | Q8NEM7\|FA48A_HUMAN | 115 | 122 | LdaEElPp |
| 2151 | Q8NEZ4\|MLL3_HUMAN | 3046 | 3053 | LllEEqPl |
| 2152 | Q8NEZ4\|MLL3_HUMAN | 4023 | 4030 | LvkEEpPe |
| 2153 | Q8NFM7\|I17RD_HUMAN | 702 | 709 | LgeEEpPa |
| 2154 | Q8NFP4\|MDGA1_HUMAN | 489 | 496 | LplEEtPd |
| 2155 | Q8NHJ6\|LIRB4_HUMAN | 60 | 67 | LdkEEsPa |
| 2156 | Q8N151\|BORIS_HUMAN | 120 | 127 | LwlEEgPr |
| 2157 | Q8TBH0\|ARRD2_HUMAN | 387 | 394 | LysEEdPn |
| 2158 | Q8TDX9\|PK1L1_HUMAN | 1101 | 1108 | LsaEEsPg |
| 2159 | Q8TE68\|ES8L1_HUMAN | 408 | 415 | LspEEgPp |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\| Protein Name | First Amino acid | Last Amino acid | Sequence |
|---|---|---|---|---|
| 2160 | Q8TER0\|SNED1_HUMAN | 1083 | 1090 | LrgEEhPt |
| 2161 | Q8WU49\|CG033_HUMAN | 8 | 15 | LslEEcPw |
| 2162 | Q8WUA2\|PPIL4_HUMAN | 16 | 23 | LytEErPr |
| 2163 | Q8WU14\|HDAC7_HUMAN | 943 | 950 | LveEEePm |
| 2164 | Q8WWN8\|CEND3_HUMAN | 1456 | 1463 | LgqEErPp |
| 2165 | Q8WZ42\|TITIN_HUMAN | 12132 | 12139 | LvvEElPv |
| 2166 | Q8WZ42\|TITIN_HUMAN | 13832 | 13839 | LfvEEiPv |
| 2167 | Q92538\|GBF1_HUMAN | 1062 | 1069 | LqrEEtPs |
| 2168 | Q92738\|US6NL_HUMAN | 51 | 58 | LheEElPd |
| 2169 | Q92765\|SFRP3_HUMAN | 134 | 141 | LacEElPv |
| 2170 | Q92851\|CASPA_HUMAN | 70 | 77 | LlsEEdPf |
| 2171 | Q92888\|ARHG1_HUMAN | 390 | 397 | LepEEpPg |
| 2172 | Q93008\|USP9X_HUMAN | 2466 | 2473 | LcpEEePd |
| 2173 | Q969V6\|MKL1_HUMAN | 497 | 504 | LvkEEgPr |
| 2174 | Q96B01\|R51A1_HUMAN | 55 | 62 | LrkEEiPv |
| 2175 | Q96D15\|RCN3_HUMAN | 192 | 199 | LhpEEfPh |
| 2176 | Q96DC7\|TMCO6_HUMAN | 219 | 226 | LqaEEaPe |
| 2177 | Q96FT7\|ACCN4_HUMAN | 90 | 97 | LslEEqPl |
| 2178 | Q96G97\|BSCL2_HUMAN | 326 | 333 | LseEEkPd |
| 2179 | Q96GW7\|PGCB_HUMAN | 880 | 887 | LhpEEdPe |
| 2180 | Q96H72\|S39AD_HUMAN | 340 | 347 | LleEEdPw |
| 2181 | Q96H78\|S2544_HUMAN | 265 | 272 | LmaEEgPw |
| 2182 | Q96J42\|TXD15_HUMAN | 42 | 49 | LwsEEqPa |
| 2183 | Q96J17\|SPTCS_HUMAN | 1940 | 1947 | LleEEaPd |
| 2184 | Q96JL9\|ZN333_HUMAN | 80 | 87 | LkpEElPs |
| 2185 | Q96JQ0\|PCD16_HUMAN | 3106 | 3113 | LyrEEgPp |
| 2186 | Q96MZ0\|GD1L1_HUMAN | 195 | 202 | LdhEEePq |
| 2187 | Q96NZ9\|PRAP1_HUMAN | 71 | 78 | LttEEkPr |
| 2188 | Q96PQ6\|ZN317_HUMAN | 109 | 116 | LeqEEePr |
| 2189 | Q96RE7\|BTB14_HUMAN | 133 | 140 | LhaEEaPs |
| 2190 | Q96RG2\|PASK_HUMAN | 1196 | 1203 | LvfEEnPf |
| 2191 | Q96RL1\|UIMC1_HUMAN | 388 | 395 | LllEEePt |
| 2192 | Q96SB3\|NEB2_HUMAN | 435 | 442 | LseEEdPa |
| 2193 | Q96SJ8\|TSN18_HUMAN | 167 | 174 | LdsEEvPe |
| 2194 | Q99102\|MUC4_HUMAN | 1306 | 1313 | LhrEErPn |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\| Protein Name | First Amino acid | Last Amino acid | Sequence |
|---|---|---|---|---|
| 2195 | Q99543\|DNJC2_HUMAN | 68 | 75 | LqlEEfPm |
| 2196 | Q9BQS2\|SYT15_HUMAN | 36 | 43 | LtyEElPg |
| 2197 | Q9BVI0\|PHF20_HUMAN | 483 | 490 | LepEEsPg |
| 2198 | Q9BY44\|EIF2A_HUMAN | 461 | 468 | LheEEpPq |
| 2199 | Q9BY78\|RNF26_HUMAN | 356 | 363 | LneEEpPg |
| 2200 | Q9BYD3\|RM04_HUMAN | 221 | 228 | LthEEmPq |
| 2201 | Q9BZA7\|PC11X_HUMAN | 315 | 322 | LdrEEtPn |
| 2202 | Q9BZA8\|PC11Y_HUMAN | 347 | 354 | LdrEEtPn |
| 2203 | Q9C009\|FOXQ1_HUMAN | 227 | 234 | LrpEEaPg |
| 2204 | Q9H095\|IQCG_HUMAN | 122 | 129 | LitEEgPn |
| 2205 | Q9HOD2\|ZN541_HUMAN | 149 | 156 | LggEEpPg |
| 2206 | Q9H2C0\|GAN_HUMAN | 36 | 43 | LdgEEiPv |
| 2207 | Q9H2X9\|S12A5_HUMAN | 681 | 688 | LrlEEgPp |
| 2208 | Q9H334\|FOXP1_HUMAN | 291 | 298 | LshEEhPh |
| 2209 | Q9H3T3\|SEM6B_HUMAN | 26 | 33 | LfpEEpPp |
| 2210 | Q9H579\|CT132_HUMAN | 138 | 145 | LvqEErPh |
| 2211 | Q9H5V8\|CDCP1_HUMAN | 788 | 795 | LatEEpPp |
| 2212 | Q9H6F5\|CCD86_HUMAN | 227 | 234 | LnkEElPv |
| 2213 | Q9H6Z4\|RANB3_HUMAN | 4 | 11 | LanEEkPa |
| 2214 | Q9H7E9\|CH033_HUMAN | 94 | 101 | LapEEvPl |
| 2215 | Q9H8Y1\|CN115_HUMAN | 137 | 144 | LcsEEsPe |
| 2216 | Q9H9E1\|ANRA2_HUMAN | 13 | 20 | LivEEcPs |
| 2217 | Q9H9F9\|ARP5_HUMAN | 415 | 422 | LfsEEtPg |
| 2218 | Q9HAV4\|XPO5_HUMAN | 521 | 528 | LnrEEiPv |
| 2219 | Q9HCE7\|SMUF1_HUMAN | 364 | 371 | LedEElPa |
| 2220 | Q9NPR2\|SEM4B_HUMAN | 47 | 54 | LgsEErPf |
| 2221 | Q9NR50\|EI2BG_HUMAN | 333 | 340 | LcpEEpPv |
| 2222 | Q9NRJ7\|PCDBG_HUMAN | 200 | 207 | LdrEEePq |
| 2223 | Q9NTN9\|SEM4G_HUMAN | 203 | 210 | LrtEEtPm |
| 2224 | Q9NUR3\|CT046_HUMAN | 104 | 111 | LhsEEgPa |
| 2225 | Q9NVR7\|TBCC1_HUMAN | 138 | 145 | LigEEwPs |
| 2226 | Q9NX46\|ARHL2_HUMAN | 235 | 242 | LgmEErPy |
| 2227 | Q9NYB9\|ABI2_HUMAN | 7 | 14 | LleEEiPg |
| 2228 | Q9P1Y5\|K1543_HUMAN | 827 | 834 | LlaEEtPp |

TABLE 9-continued

Table of the amino acid sequences of the peptides identified to contain the serpin motif.
Serpins
Motif: L-X(2)-E-E-X-P (SEQ ID NO: 2489)
Number of Locations: 314
Number of Different Proteins: 302

| SEQ ID NO: | Accession Number\|Protein Name | First Amino acid | Last Amino acid | Sequence |
|---|---|---|---|---|
| 2229 | Q9P1Y5\|K1543_HUMAN | 938 | 945 | LaqEEaPg |
| 2230 | Q9P2E7\|PCD10_HUMAN | 316 | 323 | LdyEEsPv |
| 2231 | Q9P2K9\|PTHD2_HUMAN | 673 | 680 | LevEEePv |
| 2232 | Q9UBB4\|ATX10_HUMAN | 289 | 296 | LasEEpPd |
| 2233 | Q9UBN6\|TR10D_HUMAN | 78 | 85 | LkeEEcPa |
| 2234 | Q9UBT6\|POLK_HUMAN | 251 | 258 | LlfEEsPs |
| 2235 | Q9UGF5\|OR5U1_HUMAN | 303 | 310 | LskEElPq |
| 2236 | Q9UGL1\|JAD1B_HUMAN | 879 | 886 | LlsEEtPs |
| 2237 | Q9UHW9\|S12A6_HUMAN | 743 | 750 | LrlEEgPp |
| 2238 | Q9U1F9\|BAZ2A_HUMAN | 609 | 616 | LsaEEiPs |
| 2239 | Q9UIG0\|BAZ1B_HUMAN | 75 | 82 | LlkEEfPa |
| 2240 | Q9ULD6\|PDZD6_HUMAN | 390 | 397 | LpaEEvPl |
| 2241 | Q9ULG1\|INOC1_HUMAN | 235 | 242 | LssEEsPr |
| 2242 | Q9ULI4\|KI26A_HUMAN | 1396 | 1403 | LrgEEePr |
| 2243 | Q9ULQ1\|TPC1_HUMAN | 29 | 36 | LgqEElPs |
| 2244 | Q9UMS0\|NFU1_HUMAN | 93 | 100 | LvtEEtPs |
| 2245 | Q9UN72\|PCDA7_HUMAN | 200 | 207 | LdrEEtPe |
| 2246 | Q9UN73\|PCDA6_HUMAN | 200 | 207 | LdrEEaPa |
| 2247 | Q9UN74\|PCDA4_HUMAN | 200 | 207 | LdrEEaPe |
| 2248 | Q9UNA0\|ATS5_HUMAN | 481 | 488 | LgpEElPg |
| 2249 | Q9UP95\|S12A4_HUMAN | 678 | 685 | LrlEEgPp |
| 2250 | Q9UPQ7\|PZRN3_HUMAN | 385 | 392 | LlpEEhPs |
| 2251 | Q9UPV0\|CE164_HUMAN | 488 | 495 | LatEEePp |
| 2252 | Q9UPW6\|SATB2_HUMAN | 398 | 405 | LrkEEdPr |
| 2253 | Q9UPW8\|UN13A_HUMAN | 332 | 339 | LeeEElPe |
| 2254 | Q9UPX6\|K1024_HUMAN | 371 | 378 | LntEEvPd |
| 2255 | Q9UQ05\|KCNH4_HUMAN | 761 | 768 | LlgEElPp |
| 2256 | Q9UQ26\|RIMS2_HUMAN | 201 | 208 | LrnEEaPq |
| 2257 | Q9UQ26\|RIMS2_HUMAN | 1327 | 1334 | LsfEEsPq |
| 2258 | Q9Y250\|LZTS1_HUMAN | 293 | 300 | LayEErPr |
| 2259 | Q9Y216\|NLP_HUMAN | 759 | 766 | LelEEpPq |
| 2260 | Q9Y2K7\|JHD1A_HUMAN | 661 | 668 | LinEElPn |
| 2261 | Q9Y2L6\|FRM4B_HUMAN | 438 | 445 | LpsEEdPa |
| 2262 | Q9Y2V3\|RX_HUMAN | 126 | 133 | LseEEqPk |
| 2263 | Q9Y343\|SNX24_HUMAN | 87 | 94 | LenEElPk |
| 2264 | Q9Y310\|CV028_HUMAN | 466 | 473 | LvmEEaPe |
| 2265 | Q9Y3L3\|3BP1_HUMAN | 130 | 137 | LseEElPa |
| 2266 | Q9Y3L3\|3BP1_HUMAN | 494 | 501 | LasEElPs |
| 2267 | Q9Y3R5\|DOP2_HUMAN | 1084 | 1091 | LseEElPy |
| 2268 | Q9Y426\|CU025_HUMAN | 98 | 105 | LsfEEdPr |
| 2269 | Q9Y566\|SHAN1_HUMAN | 1838 | 1845 | LpwEEgPg |
| 2270 | Q9Y572\|RIPK3_HUMAN | 352 | 359 | LnlEEpPs |
| 2271 | Q9Y5E2\|PCDB7_HUMAN | 200 | 207 | LdrEEiPe |
| 2272 | Q9Y5E3\|PCDB6_HUMAN | 199 | 206 | LdrEEqPq |
| 2273 | Q9Y5E4\|PCDB5_HUMAN | 200 | 207 | LdrEErPe |
| 2274 | Q9Y5E5\|PCDB4_HUMAN | 199 | 206 | LdrEEqPe |
| 2275 | Q9Y5E6\|PCDB3_HUMAN | 200 | 207 | LdrEEqPe |
| 2276 | Q9Y5E7\|PCDB2_HUMAN | 202 | 209 | LdrEEqPe |
| 2277 | Q9Y5F1\|PCDBC_HUMAN | 200 | 207 | LdyEErPe |
| 2278 | Q9Y5F2\|PCDBB_HUMAN | 200 | 207 | LdyEElPe |
| 2279 | Q9Y5F3\|PCDB1_HUMAN | 200 | 207 | LdrEEqPe |
| 2280 | Q9Y5G1\|PCDGF_HUMAN | 200 | 207 | LdrEEqPh |
| 2281 | Q9Y5G2\|PCDGE_HUMAN | 410 | 417 | LdrEEiPe |
| 2282 | Q9Y5H5\|PCDA9_HUMAN | 200 | 207 | LdrEEtPe |
| 2283 | Q9Y512\|PCDAA_HUMAN | 199 | 206 | LdrEEnPq |
| 2284 | Q9Y513\|PCDA1_HUMAN | 200 | 207 | LdrEEtPe |
| 2285 | Q9Y5Q9\|TF3C3_HUMAN | 42 | 49 | LsaEEnPd |
| 2286 | Q9Y5R2\|MMP24_HUMAN | 201 | 208 | LtfEEvPy |

TABLE 10

Table containing the amino acid sequence of the peptide predicted similar to Tumstatin/Tum4

| Protein Name | Peptide Location | Peptide sequence |
|---|---|---|
| Collagen type IV, alpha6 fibril | CAI40758.1: 1630-1648 | LPRFSTMPFIYCNINEVCHY (SEQ ID NO: 2494) |

In other embodiments, the following peptides suitable for use with the presently disclosed subject matter are disclosed in Table 1 of International PCT Patent Application Publication Number WO2007/033215 A2 for "Compositions Having Antiangiogenic Activity and Uses Thereof," to Popel et al., published Mar. 22, 2007, which is incorporated herein by reference in its entirety.

TABLE 11

Anti-Angiogenic Peptide sequences

| SEQ ID NO. | | | |
|---|---|---|---|
| | Thrombospondin Containing Proteins | | |
| 2287 | ADAM-9 | Q13443: 649-661 | KCHGHGVCNSNKN |
| 2288 | ADAM-12 | O43184: 662-675 | MQCHGRGVCNNRKN |
| 2289 | ADAMTS-1 | Q9UHI8: 566-584 | GPWGDCSRTCGGGVQYTMR |
| 2290 | ADAMTS-2 | CAA05880.1: 982-998 | GPWSQCSVTCGNGTQER |
| 2291 | ADAMTS-3 | NP_055058.1: 973-989 | GPWSECSVTCGEGTEVR |
| 2292 | ADAMTS-4 | CAH72146.1: 527-540 | GPWGDCSRTCGGGV |
| 2293 | ADAMTS-4 | CAH72146.1: 527-545 | GPWGDCSRTCGGGVQFSSR |
| 2294 | ADAMTS-5 | NP_008969.1: 882-898 | GPWLACSRTCDTGWHTR |
| 2295 | ADAMTS-6 | NP_922932.2: 847-860 | QPWSECSATCAGGV |
| 2296 | ADAMTS-6 | NP_922932.2: 847-863 | QPWSECSATCAGGVQRQ |
| 2297 | ADAMTS-7 | AAH61631.1: 1576-1592 | GPWGQCSGPCGGGVQRR |
| 2298 | ADAMTS-7 | AAH61631.1: 828-841 | GPWTKCTVTCGRGV |
| 2299 | ADAMTS-8 | Q9UP79: 534-547 | GPWGECSRTCGGGV |
| 2300 | ADAMTS-8 | Q9UP79: 534-552 | GPWGECSRTCGGGVQFSHR |
| 2301 | ADAMTS-9 | Q9P2N4: 1247-1261 | WSSCSVTCGQGRATR |
| 2302 | ADAMTS-9 | Q9P2N4: 1335-1351 | GPWGACSSTCAGGSQRR |
| 2303 | ADAMTS-9 | Q9P2N4: 595-613 | SPFGTCSRTCGGGIKTAIR |
| 2304 | ADAMTS-10 | Q9H324: 528-546 | TPWGDCSRTCGGGVSSSSR |
| 2305 | ADAMTS-12 | P58397: 1479-1493 | WDLCSTSCGGGFQKR |
| 2306 | ADAMTS-12 | P58397: 549-562 | SPWSHCSRTCGAGV |
| 2307 | ADAMTS-13 | AAQ88485.1: 751-765 | WMECSVSCGDGIQRR |
| 2308 | ADAMTS-14 | CAI13857.1: 980-994 | WSQCSATCGEGIQQR |
| 2309 | ADAMTS-15 | CAC86014.1: 900-916 | SAWSPCSKSCGRGFQRR |
| 2310 | ADAMTS-16 | Q8TE57: 1133-1149 | SPWSQCTASCGGGVQTR |
| 2311 | ADAMTS-16 | Q8TE57: 1133-1150 | SPWSQCTASCGGGVQTRS |
| 2312 | ADAMTS-18 | Q8TE60: 1131-1146 | PWQQCTVTCGGGVQTR |
| 2313 | ADAMTS-18 | Q8TE60: 1131-1147 | PWQQCTVTCGGGVQTRS |
| 2314 | ADAMTS-18 | Q8TE60: 998-1014 | GPWSQCSKTCGRGVRKR |
| 2315 | ADAMTS-18 | Q8TE60: 596-614 | SKWSECSRTCGGGVKFQER |
| 2316 | ADAMTS-19 | CAC84565.1: 1096-1111 | WSKCSITCGKGMQSRV |
| 2317 | ADAMTS-20 | CAD56159.3: 1478-1494 | NSWNECSVTCGSGVQQR |
| 2318 | ADAMTS-20 | CAD56159.3: 1309-1326 | GPWGQCSSSCSGGLQHRA |
| 2319 | ADAMTS-20 | CAD56159.3: 1661-1675 | WSKCSVTCGIGIMKR |
| 2320 | ADAMTS-20 | CAD56160.2: 564-581 | PYSSCSRTCGGGIESATR |
| 2321 | BAI-1 | O14514: 361-379 | SPWSVCSSTCGEGWQTRTR |
| 2322 | BAI-2 | O60241: 304-322 | SPWSVCSLTCGQGLQVRTR |
| 2323 | BAI-3 | CAI21673.1: 352-370 | SPWSLCSFTCGRGQRTRTR |

TABLE 11-continued

| Anti-Angiogenic Peptide sequences | | | |
|---|---|---|---|
| SEQ ID NO. | | | |
| 2324 | C6 | AAB59433.1: 30-48 | TQWTSCSKTCNSGTQSRHR |
| 2325 | CILP | AAQ89263.1: 156-175 | SPWSKCSAACGQTGVQTRTR |
| 2326 | CILP-2 | AAN17826.1: 153-171 | GPWGPCSGSCGPGRRLRRR |
| 2327 | CTGF | CAC44023.1: 204-221 | TEWSACSKTCGMGISTRV |
| 2328 | CYR61 | AAR05446.1: 234-251 | TSWSQCSKTCGTGISTRV |
| 2329 | Fibulin-6 | CAC37630.1: 1574-1592 | SAWRACSVTCGKGIQKRSR |
| 2330 | Fibulin-6 | CAC37630.1: 1688-1706 | QPWGTCSESCGKGTQTRAR |
| 2331 | Fibulin-6 | CAC37630.1: 1745-1763 | ASWSACSVSCGGGARQRTR |
| 2332 | NOVH | AAL92490.1: 211-228 | TEWTACSKSCGMGFSTRV |
| 2333 | Papilin | NP_775733.2: 33-51 | SQWSPCSRTCGGGVSFRER |
| 2334 | Papilin | NP_775733.2: 342-359 | GPWAPCSASCGGGSQSRS |
| 2335 | Properdin | AAP43692.1: 143-161 | GPWEPCSVTCSKGTRTRRR |
| 2336 | ROR-1 | CAH71706.1: 313-391 | CYNSTGVDYRGTVSVTKSGRQCQPWNSQYPHTHTFTALRFPEL NGGHSYCRNPGNQKEAPWCFTLDENFKSDLCDIPAC |
| 2337 | ROR-1 | CAH71706.1: 310-391 | NHKCYNSTGVDYRGTVSVTKSGRQCQPWNSQYPHTHTFTALRF PELNGGHSYCRNPGNQKEAPWCFTLDENFKSDLCDIPAC |
| 2338 | ROR-1 | CAH71706.1: 311-388 | HKCYNSTGVDYRGTVSVTKSGRQCQPWNSQYPHTHTFTALRFP ELNGGHSYCRNPGNQKEAPWCFTLDENFKSDLCDI |
| 2339 | ROR-1 | CAH71706.1: 311-391 | HKCYNSTGVDYRGTVSVTKSGRQCQPWNSQYPHTHTFTALRFP ELNGGHSYCRNPGNQKEAPWCFTLDENFKSDLCDIPAC |
| 2340 | ROR-1 | CAH71706.1: 312-392 | KCYNSTGVDYRGTVSVTKSGRQCQPWNSQYPHTHTFTALRFPE LNGGHSYCRNPGNQKEAPWCFTLDENFKSDLCDIPACD |
| 2341 | ROR-2 | Q01974: 315-395 | QCYNGSGMDYRGTASTTKSGHQCQPWALQHPHSHHLSSTDFPE LGGGHAYCRNPGGQMEGPWCFTQNKNVRMELCDVPSCS |
| 2342 | ROR-2 | Q01974: 314-391 | HQCYNGSGMDYRGTASTTKSGHQCQPWALQHPHSHHLSSTDFP ELGGGHAYCRNPGGQMEGPWCFTQNKNVRMELCDV |
| 2343 | ROR-2 | Q01974: 314-394 | HQCYNGSGMDYRGTASTTKSGHQCQPWALQHPHSHHLSSTDFP ELGGGHAYCRNPGGQMEGPWCFTQNKNVRMELCDVPSC |
| 2344 | ROR-2 | Q01974: 314-395 | HQCYNGSGMDYRGTASTTKSGHQCQPWALQHPHSHHLSSTDFP ELGGGHAYCRNPGGQMEGPWCFTQNKNVRMELCDVPSCS |
| 2345 | ROR-2 | Q01974: 315-394 | QCYNGSGMDYRGTASTTKSGHQCQPWALQHPHSHHLSSTDFPE LGGGHAYCRNPGGQMEGPWCFTQNKNVRMELCDVPSC |
| 2346 | Semaphorin 5A | NP_003957.1: 660-678 | GPWERCTAQCGGGIQARRR |
| 2347 | Semaphorin 5A | NP_003957.1: 848-866 | SPWTKCSATCGGGHYMRTR |
| 2348 | Semaphorin 5B | AAQ88491.1: 916-934 | TSWSPCSASCGGGHYQRTR |
| 2349 | SCO-spondin | XP_379967.2: 3781-3799 | GPWEDCSVSCGGGEQLRSR |
| 2350 | THSD1 | AAQ88516.1: 347-365 | QPWSQCSATCGDGVRERRR |
| 2351 | THSD3 | AAH33140.1: 280-298 | SPWSPCSGNCSTGKQQRTR |
| 2352 | THSD6 | AAH40620.1: 44-60 | WTRCSSSCGRGVSVRSR |
| 2353 | TSP-2 | CAI23645.1: 444-462 | SPWSSCSVTCGVGNITRIR |
| 2354 | TSP-2 | CAI23645.1: 501-519 | SPWSACTVTCAGGIRERTR |
| 2355 | TSRC1 | AAH27478.1: 140-159 | SPWSQCSVRCGRGQRSRQVR |

TABLE 11-continued

| SEQ ID NO. | | | |
|---|---|---|---|
| | Anti-Angiogenic Peptide sequences | | |
| 2356 | UNC5C | AAH41156.1: 267-285 | TEWSVCNSRCGRGYQKRTR |
| 2357 | UNC5D | AAQ88514.1: 259-277 | TEWSACNVRCGRGWQKRSR |
| 2358 | VSGP/F-spondin | BAB18461.1: 567-583 | WDECSATCGMGMKKRHR |
| 2359 | VSGP/F-spondin | BAB18461.1: 621-639 | SEWSDCSVTCGKGMRTRQR |
| 2360 | WISP-1 | AAH74841.1: 221-238 | SPWSPCSTSCGLGVSTRI |
| 2361 | WISP-2 | AAQ89274.1: 199-216 | TAWGPCSTTCGLGMATRV |
| 2362 | WISP-3 | CAB16556.1: 191-208 | TKWTPCSRTCGMGISNRV |
| | Collagens | | |
| 2363 | α1CIV | CAH74130.1: 1479-1556 | NERAHGQDLGTAGSCLRKFSTMPFLFCNINNVCNFASRNDYSY WLSTPEPMPMSMAPITGENIRPFISRCAVCEAPAM |
| 2364 | α1CIV | CAH74130.1: 1494-1513 | LRKFSTMPFLFCNINNVCNF |
| 2365 | α1CIV | CAH74130.1: 1504-1523 | FCNINNVCNFASRNDYSYWL |
| 2366 | α1CIV | CAH74130.1: 1610-1628 | SAPFIECHGRGTCNYYANA |
| 2367 | α2CIV | CAH71366.1: 1517-1593 | QEKAHNQDLGLAGSCLARFSTMPFLYCNPGDVCYYASRNDKSY WLSTTAPLPMMPVAEDEIKPYISRCSVCEAPAIA |
| 2368 | α2CIV | CAH71366.1: 1542-1561 | YCNPGDVCYYASRNDKSYWL |
| 2369 | α2CIV | CAH71366.1: 1646-1664 | ATPFIECNGGRGTCHYYAN |
| 2370 | α4CIV | CAA56943.1: 1499-1575 | QEKAHNQDLGLAGSCLPVFSTLPFAYCNIHQVCHYAQRNDRSY WLASAAPLPMMPLSEEAIRPYVSRCAVCEAPAQA |
| 2371 | α4CIV | CAA56943.1: 1514-1533 | LPVFSTLPFAYCNIHQVCHY |
| 2372 | α4CIV | CAA56943.1: 1524-1543 | YCNIHQVCHYAQRNDRSYWL |
| 2373 | α4CIV | CAA56943.1: 1628-1646 | AAPFLECQGRQGTCHFFAN |
| 2374 | α5CIV | AAC27816.1: 1495-1572 | NKRAHGQDLGTAGSCLRRFSTMPFMFCNINNVCNFASRNDYSY WLSTPEPMPMSMQPLKGQSIQPFISRCAVCEAPAV |
| 2375 | α5CIV | AAC27816.1: 1510-1529 | LRRFSTMPFMFCNINNVCNF |
| 2376 | α5CIV | AAC27816.1: 1520-1539 | FCNINNVCNFASRNDYSYWL |
| 2377 | α5CIV | AAC27816.1: 1626-1644 | SAPFIECHGRGTCNYYANS |
| 2378 | α6CIV | CAI40758.1: 1501-1577 | QEKAHNQDLGFAGSCLPRFSTMPFIYCNINEVCHYARRNDKSY WLSTTAPIPMMPVSQTQIPQYISRCSVCEAPSQA |
| 2379 | α6CIV | CAI40758.1: 1526-1545 | YCNINEVCHYARRNDKSYWL |
| 2380 | α6CIV | CAI40758.1: 1630-1648 | ATPFIECSGARGTCHYFAN |
| | CXC Chemokines | | |
| 2381 | ENA-78/CXCL5 | AAP35453.1: 86-108 | NGKEICLDPEAPFLKKVIQKILD |
| 2382 | ENA-78/CXCL5 | AAP35453.1: 48-103 | RCVCLQTTQGVHPKMISNLQVFAIGPQCSKVEVVASLKNGKEIC LDPEAPFLKKVI |
| 2383 | ENA-78/CXCL5 | AAP35453.1: 51-107 | CLQTTQGVHPKMISNLQVFAIGPQCSKVEVVASLKNGKEICLDP EAPFLKKVIQKIL |
| 2384 | GCP-2/CXCL6 | AAH13744.1: 86-109 | NGKQVCLDPEAPFLKKVIQKILDS |
| 2385 | GCP-2/CXCL6 | AAH13744.1: 47-106 | LRCTCLRVTLRVNPKTIGKLQVFPAGPQCSKVEVVASLKNGKQV CLDPEAPFLKKVIQKI |
| 2386 | GCP-2/CXCL6 | AAH13744.1: 48-103 | RCTCLRVTLRVNPKTIGKLQVFPAGPQCSKVEVVASLKNGKQV CLDPEAPFLKKVI |

TABLE 11-continued

| SEQ ID NO. | | | |
|---|---|---|---|
| | | **Anti-Angiogenic Peptide sequences** | |
| 2387 | GCP-2/CXCL6 | AAH13744.1: 51-107 | CLRVTLRVNPKTIGKLQVFPAGPQCSKVEVVASLKNGKQVCLDP EAPFLKKVIQKIL |
| 2388 | GRO-α/CXCL1 | AAP35526.1: 80-103 | NGRKACLNPASPIVKKIIEKMLNS |
| 2389 | GRO-α/CXCL1 | AAP35526.1: 42-97 | RCQCLQTLQGIHPKNIQSVNVKSPGPHCAQTEVIATLKNGRKAC LNPASPIVKKII |
| 2390 | GRO-α/CXCL1 | AAP35526.1: 44-101 | QCLQTLQGIHPKNIQSVNVKSPGPHCAQTEVIATLKNGRKACLN PASPIVKKIIEKML |
| 2391 | Gro-β/CXCL2 | AAH15753.1: 42-97 | RCQCLQTLQGIHLKNIQSVKVKSPGPHCAQTEVIATLKNGQKAC LNPASPMVKKII |
| 2392 | GRO-γ/MIP-2β/CXCL3 | AAA63184.1: 79-100 | NGKKACLNPASPMVQKIIEKIL |
| 2393 | GRO-γ/MIP-2β/CXCL3 | AAA63184.1: 43-100 | QCLQTLQGIHLKNIQSVNVRSPGPHCAQTEVIATLKNGKKACLN PASPMVQKIIEKIL |
| 2394 | GRO-γ/MIP-2β/CXCL3 | AAA63184.1: 41-96 | RCQCLQTLQGIHLKNIQSVNVRSPGPHCAQTEVIATLKNGKKAC LNPASPMVQKII |
| 2395 | IL-8/CXCL8 | AAP35730.1: 35-94 | QCIKTYSKPFHPKFIKELRVIESGPHCANTEIIVKLSDGRELCLDP KENWVQRVVEKFLK |
| 2396 | IL-8/CXCL8 | AAP35730.1: 72-94 | DGRELCLDPKENWVQRVVEKFLK |
| 2397 | IP-10/CXCL10 | AAH10954.1: 29-86 | RCTCISISNQPVNPRSLEKLEIIPASQFCPRVEIIATMKKKGEKRCL NPESKAIKNLL |
| 2398 | MIG/CXCL9 | Q07325: 32-91 | SCISTNQGTIHLQSLKDLKQFAPSPSCEKIEIIATLKNGVQTCLNP DSADVKELIKKWEK |
| 2399 | PF-4/CXCL4 | AAK29643.1: 43-100 | CVKTTSQVRPRHITSLEVIKAGPHCPTAQLIATLKNGRKICLDLQ APLYKKIIKKLLE |
| 2400 | THBG-β/CXCL7 | AAB46877.1: 100-121 | DGRKICLDPDAPRIKKIVQKKL |
| 2401 | THBG-β/CXCL7 | AAB46877.1: 62-117 | RCMCIKTTSGIHPKNIQSLEVIGKGTHCNQVEVIATLKDGRKICL DPDAPRIKKIV |
| 2402 | THBG-β/CXCL7 | AAB46877.1: 64-121 | MCIKTTSGIHPKNIQSLEVIGKGTHCNQVEVIATLKDGRKICLDP DAPRIKKIVQKKL |
| | | **Kringle Containing Proteins** | |
| 2403 | AK-38 protein | AAK74187.1: 14-93 | DCMFGNGKGYRGKKATTVTGTPCQEWAAQEPHRHSTFIPGTNK WAGLEKNYCRNPDGDINGPWCYTMNPRKLFDYCDIPLCA |
| 2404 | AK-38 protein | AAK74187.1: 12-94 | QDCMFGNGKGYRGKKATTVTGTPCQEWAAQEPHRHSTFIPGTN KWAGLEKNYCRNPDGDINGPWCYTMNPRKLFDYCDIPLCA |
| 2405 | AK-38 protein | AAK74187.1: 13-90 | DCMFGNGKGYRGKKATTVTGTPCQEWAAQEPHRHSTFIPGTNK WAGLEKNYCRNPDGDINGPWCYTMNPRKLFDYCDI |
| 2406 | AK-38 protein | AAK74187.1: 14-93 | CMFGNGKGYRGKKATTVTGTPCQEWAAQEPHRHSTFIPGTNK WAGLEKNYCRNPDGDINGPWCYTMNPRKLFDYCDIPLC |
| 2407 | Hageman fct/cf XII | AAM97932.1: 216-292 | SCYDGRGLSYRGLARTTLSGAPCQPWASEATYRNVTAEQARN WGLGGHAFCRNPDNDIRPWCFVLNRDRLSWEYCDL |
| 2408 | Hageman fct/cf XII | AAM97932.1: 214-295 | KASCYDGRGLSYRGLARTTLSGAPCQPWASEATYRNVTAEQAR NWGLGGHAFCRNPDNDIRPWCFVLNRDRLSWEYCDLAQC |
| 2409 | Hageman fct/cf XII | AAM97932.1: 215-296 | ASCYDGRGLSYRGLARTTLSGAPCQPWASEATYRNVTAEQARN WGLGGHAFCRNPDNDIRPWCFVLNRDRLSWEYCDLAQCQ |
| 2410 | HGF | P14210: 127-206 | NCIIGKGRSYKGTVSITKSGIKCQPWSSMIPHEHSFLPSSYRGKDL QENYCRNPRGEEGGPWCFTSNPEVRYEVCDIPQC |
| 2411 | HGF | P14210: 127-207 | NCIIGKGRSYKGTVSITKSGIKCQPWSSMIPHEHSFLPSSYRGKDL QENYCRNPRGEEGGPWCFTSNPEVRYEVCDIPQCS |
| 2412 | HGF | P14210: 304-377 | ECIQGQGEGYRGTVNTIWNGIPCQRWDSQYPHEHDMTPENFKC KDLRENYCRNPDGSESPWCFTTDPNIRVGYC |

TABLE 11-continued

| Anti-Angiogenic Peptide sequences | | | |
|---|---|---|---|
| SEQ ID NO. | | | |
| 2413 | HGF | P14210: 210-289 | ECMTCNGESYRGLMDHTESGKICQRWDHQTPHRHKFLPERYPD KGFDDNYCRNPDGQPRPWCYTLDPHTRWEYCAIKTCA |
| 2414 | HGF | P14210: 304-383 | ECIQGQGEGYRGTVNTIWNGIPCQRWDSQYPHEHDMTPENFKC KDLRENYCRNPDGSESPWCFTTDPNIRVGYCSQIPNC |
| 2415 | Hyaluronan binding | NP_004123.1: 192-277 | DDCYVGDGYSYRGKMNRTVNQHACLYWNSHLLLQENYNMFM EDAETHGIGEHNFCRNPDADEKPWCFIKVTNDKVKWEYCDVSA CS |
| 2416 | Hyaluronan binding | NP_004123.1: 192-276 | DDCYVGDGYSYRGKMNRTVNQHACLYWNSHLLLQENYNMFM EDAETHGIGEHNFCRNPDADEKPWCFIKVTNDKVKWEYCDVSAC |
| 2417 | KREMEN-1 | BAB40969.1: 31-114 | ECFTANGADYRGTQNWTALQGGKPCLFWNETFQHPYNTLKYP NGEGGLGEHNYCRNPDGDVS-PWCYVAEHEDGVYWKYCEIPAC |
| 2418 | KREMEN-1 | BAB40969.1: 31-115 | ECFTANGADYRGTQNWTALQGGKPCLFWNETFQHPYNTLKYP NGEGGLGEHNYCRNPDGDVSPWCYVAEHEDGVYWKYCEIPACQ |
| 2419 | KREMEN-2 | BAD97142.1: 35-119 | ECFQVNGADYRGHQNRTGPRGAGRPCLFWDQTQQHSYSSASDP HGRWGLGAHNFCRNPDGDVQ-PWCYVAETEEGIYWRYCDIPSC |
| 2420 | KREMEN-2 | BAD97142.1: 34-119 | SECFQVNGADYRGHQNRTGPRGAGRPCLFWDQTQQHSYSSASD PHGRWGLGAHNFCRNPDGDVQPWCYVAETEEGIYWRYCDIPSC |
| 2421 | Lp(a) | NP_005568.1: 1615-1690 | TEQRPGVQECYHGNGQSYRGTYSTTVTGRTCQAWSSMTPHSHS RTPEYYPNAGLIMNYCRNPDAVAAPYCYTRDPG |
| 2422 | Lp(a) | NP_005568.1: 3560-3639 | QDCYYHYGQSYRGTYSTTVTGRTCQAWSSMTPHQHSRTPENYP NAGLTRNYCRNPDAEIRPWCYTMDPSVRWEYCNLTQC |
| 2423 | Lp(a) | NP_005568.1: 4123-4201 | QCYHGNGQSYRGTFSTTVTGRTCQSWSSMTPHRHQRTPENYPN DGLTMNYCRNPDADTGPWCFTMDPSIRWEYCNLTRC |
| 2424 | Lp(a) | NP_005568.1: 4225-4308 | EQDCMFGNGKGYRGKKATTVTGTPCQEWAAQEPHRHSTFIPGT NKWAGLEKNYCRNPDGDINGPWCYTMNPRKLFDYCDIPLCA |
| 2425 | Macrophage stim. 1 | AAH48330.1: 188-268 | EAACVWCNGEEYRGAVDRTESGRECQRWDLQHPHQHPFEPGK FLDQGLDDNYCRNPDGSERPWCYTTDPQIEREFCDLPRC |
| 2426 | Macrophage stim. 1 | AAH48330.1: 368-448 | QDCYHGAGEQYRGTVSKTRKGVQCQRWSAETPHKPQFTFTSEP HAQLEENFCRNPDGDSHGPWCYTMDPRTPFDYCALRRC |
| 2427 | Macrophage stim. 1 | AAH48330.1: 368-449 | QDCYHGAGEQYRGTVSKTRKGVQCQRWSAETPHKPQFTFTSEP HAQLEENFCRNPDGDSHGPWCYTMDPRTPFDYCALRRCA |
| 2428 | Macrophage stim. 1 | AAH48330.1: 370-448 | CYHGAGEQYRGTVSKTRKGVQCQRWSAETPHKPQFTFTSEPHA QLEENFCRNPDGDSHGPWCYTMDPRTPFDYCALRRC |
| 2429 | Thrombin/cf II | AAL77436.1: 105-186 | EGNCAEGLGTNYRGHVNITRSGIECQLWRSRYPHKPEINSTTHP GADLQENFCRNPDSSTTGPWCYTTDPTVRRQECSIPVC |
| 2430 | Thrombin/cf II | AAL77436.1: 106-186 | GNCAEGLGTNYRGHVNITRSGIECQLWRSRYPHKPEINSTTHPG ADLQENFCRNPDSSTTGPWCYTTDPTVRRQECSIPVC |
| 2431 | Thrombin/cf II | AAL77436.1: 107-183 | NCAEGLGTNYRGHVNITRSGIECQLWRSRYPHKPEINSTTHPGA DLQENFCRNPDSSTTGPWCYTTDPTVRRQECSI |
| 2432 | Thrombin/cf II | AAL77436.1: 107-186 | NCAEGLGTNYRGHVNITRSGIECQLWRSRYPHKPEINSTTHPGA DLQENFCRNPDSSTTGPWCYTTDPTVRRQECSIPVC |
| 2433 | tPA | AAH95403.1: 214-293 | DCYFGNGSAYRGTHSLTESGASCLPWNSMILIGKVYTAQNPSAQ ALGLGKHNYCRNPDGDAKPWCHVLKSRRLTWEYCDV |
| 2434 | tPA | AAH95403.1: 213-296 | SDCYFGNGSAYRGTHSLTESGASCLPWNSMILIGKVYTAQNPSA QALGLGKHNYCRNPDGDAKPWCHVLKSRRLTWEYCDVPSC |
| 2435 | tPA | AAH95403.1: 213-297 | SDCYFGNGSAYRGTHSLTESGASCLPWNSMILIGKVYTAQNPSA QALGLGKHNYCRNPDGDAKPWCHVLKSRRLTWEYCDVPSCS |
| 2436 | tPA | AAH95403.1: 214-296 | DCYFGNGSAYRGTHSLTESGASCLPWNSMILIGKVYTAQNPSAQ ALGLGKHNYCRNPDGDAKPWCHVLKSRRLTWEYCDVPSC |

TABLE 11-continued

| Anti-Angiogenic Peptide sequences | | | |
|---|---|---|---|
| SEQ ID NO. | | | |
| Somatotropins | | | |
| 2437 | GH-1 | NP_000506.2: 26-160 | AFPTIPLSRLFDNAMLRAHRLHQLAFDTYQEFEEAYIPKEQKYSF LQNPQTSLCFSESIPTPSNREETQQKSNLELLRISLLLIQSWLEPVQ FLRSVFANSLVYGASDSNVYDLLKDLEEGIQTLMGRLEDGSPR |
| 2438 | GH-2 | CAG46700.1: 26-160 | AFPTIPLSRLFDNAMLRARRLYQLAYDTYQEFEEAYILKEQKYSF LQNPQTSLCFSESIPTPSNRAKTQQKSNLELLRISLLLIQSWLEPV QLLRSVFANSLVYGASDSNVYRHLKDLEEGIQTLMWRLEDGSPR |
| 2439 | Placental lactogen | AAP35572.1: 26-160 | AVQTVPLSRLFDHAMLQAHRAHQLAIDTYQEFEETYIPKDQKYS FLHDSQTSFCFSDSIPTPSNMEETQQKSNLELLRISLLLIESWLEPV RFLRSMFANNLVYDTSDSDDYHLLKDLEEGIQTLMGRLEDGSRR |
| 2440 | Somatoliberin | AAH62475.1: 26-145 | AFPTIPLSRLFDNASLRAHRLHQLAFDTYQEFNPQTSLCFSESIPT PSMREETQQKSNLELLRISLLLIQSWLEPVQFLRSVFANSLVYGA SDSNVYDLLKDLEEGIQTLMGRLEDGSPR |
| TIMPs | | | |
| 2441 | TIMP 3 | AAA21815.1: 148-171 | ECLWTDMLSNFGYPGYQSKHYACI |
| 2442 | TIMP 4 | AAV38433.1: 175-198 | ECLWTDWLLERKLYGYQAQHYVCM |

In particular embodiments, the presently disclosed subject matter provides a nanoparticle, microparticle, or gel comprising a compound of Formula (I), wherein the one or more peptide is selected from the group consisting of an isolated peptide or analog thereof comprising the amino acid sequence W-$X_2$-C-$X_3$-C-$X_2$-G, wherein X denotes a variable amino acid; W is tryptophan; C is cysteine, G is glycine; and wherein the peptide reduces blood vessel formation in a cell, tissue or organ.

In some embodiments, the one or more peptide is selected from the group consisting of an isolated peptide or analog thereof comprising or consisting essentially of a sequence having at least 85% amino acid sequence identity to an amino acid sequence selected from the group consisting of:

THSD-1: (SEQ ID NO: 2350)
QPWSQCSATCGDGVRERRR;

THSD-3: (SEQ ID NO: 2351)
SPWSPCSGNCSTGKQQRTR;

THSD-6: (SEQ ID NO: 2352)
WTRCSSSCGRGVSVRSR;

CILP: (SEQ ID NO: 2325)
SPWSKCSAACGQTGVQTRTR;

WISP-1: (SEQ ID NO: 2360)
SPWSPCSTSCGLGVSTRI;

WISP-2: (SEQ ID NO: 2361)
TAWGPCSTTCGLGMATRV;

WISP-3: (SEQ ID NO: 2362)
TKWTPCSRTCGMGISNRV;

-continued

F-spondin: (SEQ ID NO: 2359)
SEWSDCSVTCGKGMRTRQR;

F-spondin: (SEQ ID NO: 2358)
WDECSATCGMGMKKRHR;

CTGF: (SEQ ID NO: 2327)
TEWSACSKTCGMGISTRV;

fibulin-6: (SEQ ID NO: 2331)
ASWSACSVSCGGGARQRTR;

fibulin-6: (SEQ ID NO: 2330)
QPWGTCSESCGKGTQTRAR;

fibulin-6: (SEQ ID NO: 2329)
SAWRACSVTCGKGIQKRSR;

CYR61: (SEQ ID NO: 2328)
TSWSQCSKTCGTGISTRV;

NOVH: (SEQ ID NO: 2332)
TEWTACSKSCGMGFSTRV;

UNC5-C: (SEQ ID NO: 2356)
TEWSVCNSRCGRGYQKRTR;

UNC5-D: (SEQ ID NO: 2357)
TEWSACNVRCGRGWQKRSR;

SCO-spondin: (SEQ ID NO: 2349)
GPWEDCSVSCGGGEQLRSR;

-continued

Properdin:
(SEQ ID NO: 2335)
GPWEPCSVTCSKGTRTRRR;

C6:
(SEQ ID NO: 2324)
TQWTSCSKTCNSGTQSRHR;

ADAMTS-like-4:
(SEQ ID NO: 2355)
SPWSQCSVRCGRGQRSRQVR;

ADAMTS-4:
(SEQ ID NO: 2293)
GPWGDCSRTCGGGVQFSSR;

ADAMTS-8:
(SEQ ID NO: 2300)
GPWGECSRTCGGGVQFSHR;

ADAMTS-16:
(SEQ ID NO: 2310)
SPWSQCTASCGGGVQTR;

ADAMTS-18:
(SEQ ID NO: 2315)
SKWSECSRTCGGGVKFQER;

semaphorin 5A:
(SEQ ID NO: 2346)
GPWERCTAQCGGGIQARRR;

semaphorin 5A:
(SEQ ID NO: 2347)
SPWTKCSATCGGGHYMRTR;

semaphoring 5B:
(SEQ ID NO: 2348)
TSWSPCSASCGGGHYQRTR;

papilin:
(SEQ ID NO: 2334)
GPWAPCSASCGGGSQSRS;

papilin:
(SEQ ID NO: 2333)
SQWSPCSRTCGGGVSFRER;

ADAM-9: K
(SEQ ID NO: 2497)
CHGHGVCNS
and;

ADAM-12:
(SEQ ID NO. 7788)
MQCHGRGVCNNRKN, wherein A is alanine; I is isoleucine; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine wherein the peptide reduces blood vessel formation in a cell, tissue or organ.

In other embodiments, the one or more peptide is selected from the group consisting of an isolated peptide or analog thereof having at least 85% identity to an amino acid sequence selected from the group consisting of:

ENA-78:
(SEQ ID NO: 2381)
NGKEICLDPEAPFLKKVIQKILD;

CXCL6:
(SEQ ID NO: 2384)
NGKQVCLDPEAPFLKKVIQKILDS;

-continued

CXCL1:
(SEQ ID NO: 2388)
NGRKACLNPASPIVKKIIEKMLNS;

Gro-γ:
(SEQ ID NO: 2392)
NGKKACLNPASPMVQKIIEKIL;

Beta thromboglobulin/CXCL7:
(SEQ ID NO: 2400)
DGRKICLDPDAPRIKKIVQKKL,

Interleukin 8 (IL-8)/CXCL8:
(SEQ ID NO: 2396)
DGRELCLDPKENWVQRVVEKFLK,

GCP-2:
(SEQ ID NO: 2384)
NGKQVCLDPEAPFLKKVIQKILDS, wherein A is alanine; I is isoleucine; F is phenylalanine; D is aspartic acid; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine; and wherein the peptide reduces blood vessel formation in a cell, tissue or organ.

In yet other embodiments, the one or more peptide is selected from the group consisting of an isolated peptide or analog thereof having at least 85% amino acid sequence identity to an amino acid sequence selected from the group consisting of Alpha 6 fibril of type 4 collagen:
(SEQ ID NO: 2379)
YCNINEVCHYARRNDKSYWL;

Alpha 5 fibril of type 4 collagen:
(SEQ ID NO: 2443)
LRRFSTMPFMFCNINNVCNF;

Alpha 4 fibril of type 4 collagen:
(SEQ ID NO: 2373)
AAPFLECQGRQGTCHFFAN;

Alpha 4 fibril of type 4 collagen:
(SEQ ID NO: 2371)
LPVFSTLPFAYCNIHQVCHY;

Alpha 4 fibril of type 4 collagen:
(SEQ ID NO: 2372)
YCNIHQVCHYAQRNDRSYWL,
and

Collagen type IV, alpha6 fibril
(SEQ ID NO: 2494)
LPRFSTMPFIYCNINEVCHY;

wherein A is alanine; I is isoleucine; F is phenylalanine; D is aspartic acid; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine wherein the peptide reduces blood vessel formation in a cell, tissue or organ.

In other embodiments, peptides suitable for use in the presently disclosed subject matter are disclosed in U.S. Provisional Patent Application No. 61/421,706, filed Dec. 12, 2010, which is commonly owned, and is incorporated herein by reference in its entirety.

| SEQ ID NO: | ID | Sequence |
|---|---|---|
| 2443 | SP2000 | LRRFSTMPFMFCNINNVCNF |
| 2444 | SP2002 | LRRFSTMPFMFGNINNVGNF |
| 2445 | SP2004 | LRRFSTMPFMF |
| 2446 | SP2006 | LRRFSTMPFMF-Abu-NINV |
| 2447 | SP2007 | LRRFSTMPFMF-Abu |
| 2448 | SP2008 | LRRFSTMP |
| 2449 | SP2009 | NINNV-Abu-NF |
| 2450 | SP2010 | FMF-Abu-NINNV-Abu-NF |
| 2451 | SP2011 | STMPFMF-Abu-NINNV-Abu-NF |
| 2452 | SP2012 | LRRFSTMPFMF-Abu-NINNV-Abu-NF |
| 2453 | SP2013 | LNRFSTMPF |
| 2454 | SP2014 | LRRFST-Nle-PF-Nle-F |
| 2455 | SP2015 | LRRFSTMPAMF-Abu-NINNV-Abu-NF |
| 2456 | SP2016 | LRRFSTMPFAF-Abu-NINNV-Abu-NF |
| 2457 | SP2017 | LRRFSTMPFMA-Abu-NINNV-Abu-NF |
| 2458 | SP2018 | LRRFSTMPF-Nle-F-Abu-NINNV-Abu-NF |
| 2459 | SP2019 | LRRFSTMPFM(4-ClPhen)-Abu-CNINNV-Abu-NF |
| 2460 | SP2020 | F-Abu-NINNV-Abu-N |
| 2461 | SP2021 | F-Abu-NIN |
| 2462 | SP2022 | LRRFSTMPFMFSNINNVSNF |
| 2463 | SP2023 | LRRFSTMPFMFANINNVANF |
| 2464 | SP2024 | LRRFSTMPFMFININNVINF |
| 2465 | SP2025 | LRRFSTMPFMFTNINNVTNF |
| 2466 | SP2026 | LRRFSTMPFMFC(AllyGly)NINNV(AllyGly)NF |
| 2467 | SP2027 | LRRFSTMPFMFVNINNVVNF |
| 2468 | SP2028 | LRRFSTMPFMF-Abu-NINN |
| 2469 | SP2029 | LRRFSTMPFMFTNINV |
| 2470 | SP2030 | F-Abu-NINV |
| 2471 | SP2031 | FTNINNVTN |
| 2472 | SP2032 | LRRFSTMPFMFTNINN |
| 2473 | SP2033 | LRRFSTMPFMFININN |
| 2474 | SP2034 | LRRFSTMPF-Da-FININNVINF |
| 2475 | SP2035 | LRRFSTAPFAFININNVINF |
| 2476 | SP2036 | LRRFSTMPFAFININNVINF; |

wherein Abu is 2-aminobutyric acid; Nle is Norleucine; and AllyGly is allyglycine.

In other embodiments, peptides suitable for use in the presently disclosed subject matter are disclosed in U.S. Provisional Patent Application No. 61/489,500, filed May 24, 2011, which also is commonly owned, and is incorporated herein by reference in its entirety.

| SEQ ID NO: | ID | Sequence |
|---|---|---|
| 2477 | SP5001 | RLRLLTLQSWLL |
| 2478 | SP5028 | LMRKSQILISSWF |
| 2479 | SP5029 | LLIVALLFILSWL |
| 2480 | SP5030 | LLRLLLLIESWLE |
| 2481 | SP5031 | LLRSSLILLQGSWF |
| 2482 | SP5032 | LLHISLLLIESRLE |
| 2483 | SP5033 | LLRISLLLIESWLE |

III. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae I-X are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

A named "R" or group will generally have the structure that is recognized in the art as corresponding to a group having that name, unless specified otherwise herein. For the purposes of illustration, certain representative "R" groups as set forth above are defined below.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, iso-propyl, cyclopropyl, allyl, vinyl, n-butyl, tert-butyl, ethynyl, cyclohexyl, methoxy, diethylamino, and the like.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom. Representative alkyl groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, and the like, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of N, O, and S, and optionally can include one or more double bonds. The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, and the like.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propyne, 3-hexyne, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene ($—CH_2—$); ethylene ($—CH_2—CH_2—$); propylene ($—(CH_2)_3—$); cyclohexylene ($—C_6H_{10}—$); $—CH{=}CH—CH{=}CH—$; $—CH{=}CH—CH_2—$; $—(CH_2)_q—N(R)—(CH_2)_r—$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($—O—CH_2—O—$); and ethylenedioxyl ($—O—(CH_2)_2—O—$). An alkylene group can have about 2 to about 3 carbon atoms and can further have 6-20 carbons.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, alkenyl, alkynyl, aryl, substituted aryl, aralkyl, hydroxyl, alkoxyl, aryloxyl, aralkyloxyl, carboxyl, acyl, halo, haloalkyl, nitro, alkoxycarbonyl, aryloxycarbonyl, aralkoxycarbonyl, acyloxyl, amino, alkylamino, dialkylamino, trialkylamino, acylamino, aroylamino, carbamoyl, cyano, alkylcarbamoyl, dialkylcarbamoyl, carboxyaldehyde, carboxyl, alkoxycarbonyl, carboxamide, arylthio, alkylthio, alkylene, thioalkoxyl, and mercapto.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The terms "heteroaryl" and "aromatic heterocycle" and "aromatic heterocyclic" are used interchangeably herein and refer to a cyclic aromatic radical having from five to ten ring atoms of which one ring atom is selected from sulfur, oxygen, and nitrogen; zero, one, or two ring atoms are additional heteroatoms independently selected from sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide. Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl) piperazine, 4(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl) piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole. The heteroaryl ring can be fused or otherwise attached to one or more heteroaryl rings, aromatic or non-aromatic hydrocarbon rings, or heterocycloalkyl rings. A structure represented generally by the formula:

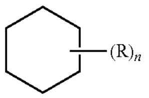

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

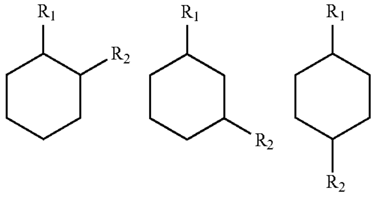

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

When a named atom of an aromatic ring or a heterocyclic aromatic ring is defined as being "absent," the named atom is replaced by a direct bond.

As used herein, the term "acyl" refers to an organic acid group wherein the —OH of the carboxyl group has been replaced with another substituent and has the general formula RC(═O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —$CONH_2$.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

The terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C═O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

Further, as used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle. Thus, the term "microparticle" includes particles having at least one dimension in the range of about one micrometer (μm), i.e., $1\times10^{-6}$ meters, to about 1000 μm. The term "particle" as used herein is meant to include nanoparticles and microparticles.

It will be appreciated by one of ordinary skill in the art that nanoparticles suitable for use with the presently disclosed methods can exist in a variety of shapes, including, but not limited to, spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes. In particular embodiments, the presently disclosed nanoparticles have a spherical shape.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Associated with": When two entities are "associated with" one another as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, etc.

"Biocompatible": The term "biocompatible", as used herein is intended to describe compounds that are not toxic to cells. Compounds are "biocompatible" if their addition to cells in vitro results in less than or equal to 20% cell death, and their administration in vivo does not induce inflammation or other such adverse effects.

"Biodegradable": As used herein, "biodegradable" compounds are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compounds are uncatalyzed.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

"Peptide" or "protein": A "peptide" or "protein" comprises a string of at least three amino acids linked together by peptide bonds. The terms "protein" and "peptide" may be used interchangeably. Peptide may refer to an individual peptide or a collection of peptides. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc. In a preferred embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

"Polynucleotide" or "oligonucleotide": Polynucleotide or oligonucleotide refers to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, 0(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

"Small molecule": As used herein, the term "small molecule" refers to organic compounds, whether naturally-occurring or artificially created (e.g., via chemical synthesis) that have relatively low molecular weight and that are not proteins, polypeptides, or nucleic acids. Typically, small molecules have a molecular weight of less than about 1500 g/mol. Also, small molecules typically have multiple carbon-carbon bonds. Known naturally-occurring small molecules include, but are not limited to, penicillin, erythromycin, taxol, cyclosporin, and rapamycin. Known synthetic small molecules include, but are not limited to, ampicillin, methicillin, sulfamethoxazole, and sulfonamides.

By "analog" is meant a chemical compounds having a structure that is different from the general structure of a reference agent, but that functions in a manner similar to the reference agent. For example, a peptide analog having a variation in sequence or having a modified amino acid.

By "thrombospondin (TSP) derived peptide" is meant a peptide comprising a TSP motif: W-X(2)-C-X(3)-C-X(2)-G (SEQ ID NO: 2486). Exemplary TSP derived peptides are shown in Tables 1 and 2. If desired, the peptide includes at least about 5, 10, 20, 30, 40, 50 or more amino acids that flank the carboxy or amino terminus of the motif in the naturally occurring amino acid sequence of the peptide. TSP1 derived peptides include, for example, those derived from proteins WISP-1 (SPWSPCSTSCGLGVSTRI; SEQ ID NO: 2360), NOVH (TEWTACSKSCGMGFSTRV; SEQ ID NO: 2332) and UNC5C (TEWSVCNSRCGRGYQKRTR; SEQ ID NO: 2456).

By "CXC derived peptide" is meant a peptide comprising a CXC Motif: G-X(3)-C-L. Exemplary CXC derived peptides are shown in Table 3. If desired, the peptide includes at least about 5, 10, 20, 30, 40, 50 or more amino acids that flank the carboxy or amino terminus of the motif in the naturally occurring amino acid sequence. CXC derived peptides include, for example, those derived from proteins GRO-α/CXCL1 (NGRKACLNPASPIVKKIIEKMLNS (SEQ ID NO: 2388)), GRO-γ/MIP-20/CXCL3 (NGKKACLNPASPMVQKIIEKIL (SEQ ID NO: 2392)), and ENA-78/CXCL5 (NGKEICLDPEAPFLKKVIQKILD (SEQ ID NO: 2381)).

By "Collagen IV derived peptide" is meant a peptide comprising a C-N-X(3)-V-C (SEQ ID NO: 2487) or P-F-X(2)-C collagen motif Exemplary collagen IV derived peptides are shown in Table 5. If desired, the peptide includes at least about 5, 10, 20, 30, 40, 50 or more amino acids that flank the carboxy or amino terminus of the motif in the naturally occurring amino acid sequence. Type IV collagen derived peptides include, for example, LRRFSTMPFMFCNINNVCNF (SEQ ID NO: 2375) and FCNINNVCNFASRNDYSYWL (SEQ ID NO: 2365), and LPRFSTMPFIYCNINEVCHY (SEQ ID NO: 2494).

By "Somatotropin derived peptide" is meant a peptide comprising a Somatotropin Motif: L-X(3)-L-L-X(3)-S-X-L (SEQ ID NO: 2488). Exemplary somatotropin derived peptides are shown in Table 8. If desired, the peptide includes at least about 5, 10, 20, 30, 40, 50 or more amino acids that flank the carboxy or amino terminus of the motif in the naturally occurring amino acid sequence.

By "Serpin derived peptide" is meant a peptide comprising a Serpin Motif: L-X(2)-E-E-X-P (SEQ ID NO: 2489). Exemplary serpin derived peptides are shown in Table 9. If desired, the peptide includes at least about 5, 10, 20, 30, 40, 50 or more amino acids that flank the carboxy or amino terminus of the motif in the naturally occurring amino acid sequence.

By "Beta 1 integrin" is meant a polypeptide that binds a collagen IV derived peptide or that has at least about 85% identity to NP_596867 or a fragment thereof.

By "Beta 3 integrin" is meant a polypeptide that binds a collagen IV derived peptide or that has at least about 85% identity to P05106 or a fragment thereof.

By "CD36" is meant a CD36 glycoprotein that binds to a thrombospondin-derived peptide or that has at least about 85% identity to NP_001001548 or a fragment thereof. CD36 is described, for example, by Oquendo et al., "CD36 directly mediates cytoadherence of *Plasmodium falciparum* parasitized erythrocytes," Cell 58: 95-101, 1989.

By "CD47" is meant a CD47 glycoprotein that binds to a thrombospondin-derived peptides or that has at least about 85% identity to NP_000315 or a fragment thereof. CD47 is described, for example, by Han et al., "CD47, a ligand for the macrophage fusion receptor, participates in macrophage multinucleation." J. Biol. Chem. 275: 37984-37992, 2000.

By "CXCR3" is meant a G protein coupled receptor or fragment thereof having at least about 85% identity to NP_001495. CXCR3 is described, for example, by Trentin et al., "The chemokine receptor CXCR3 is expressed on malignant B cells and mediates chemotaxis." J. Clin. Invest. 104: 115-121, 1999.

By "blood vessel formation" is meant the dynamic process that includes one or more steps of blood vessel development and/or maturation, such as angiogenesis, vasculogenesis, formation of an immature blood vessel network, blood vessel remodeling, blood vessel stabilization, blood vessel maturation, blood vessel differentiation, or establishment of a functional blood vessel network.

By "angiogenesis" is meant the growth of new blood vessels originating from existing blood vessels. Angiogenesis can be assayed by measuring the total length of blood vessel segments per unit area, the functional vascular density (total length of perfused blood vessel per unit area), or the vessel volume density (total of blood vessel volume per unit volume of tissue).

By "vasculogenesis" is meant the development of new blood vessels originating from stem cells, angioblasts, or other precursor cells.

By "blood vessel stability" is meant the maintenance of a blood vessel network.

By "alteration" is meant a change in the sequence or in a modification (e.g., a post-translational modification) of a gene or polypeptide relative to an endogeneous wild-type reference sequence.

By "ameliorate" is meant decrease, suppress, attenuate, diminish, arrest, or stabilize the development or progression of a disease.

By "antibody" is meant any immunoglobulin polypeptide, or fragment thereof, having immunogen binding ability.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

By "disease" is meant any condition or disorder that damages or interferes with the normal function of a cell, tissue, or organ.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "isolated nucleic acid molecule" is meant a nucleic acid (e.g., a DNA) that is free of the genes, which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weiaght, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

"By "neoplasia" is meant a disease that is caused by or results in inappropriately high levels of cell division, inappropriately low levels of apoptosis, or both. Solid tumors, hematological disorders, and cancers are examples of neoplasias.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "peptide" is meant any fragment of a polypeptide. Typically peptide lengths vary between 5 and 1000 amino acids (e.g., 5, 10, 15, 20, 25, 50, 100, 200, 250, 500, 750, and 1000).

By "polypeptide" is meant any chain of amino acids, regardless of length or post-translational modification.

By "promoter" is meant a polynucleotide sufficient to direct transcription.

By "reduce" is meant a decrease in a parameter (e.g., blood vessel formation) as detected by standard art known methods, such as those described herein. As used herein, reduce includes a 10% change, preferably a 25% change, more preferably a 40% change, and even more preferably a 50% or greater change.

By "reference" is meant a standard or control condition.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and even more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.,* 4: 11-17, 1988, for example, as implemented in the program PC/GENE (Intelligenetics, Mountain View, Calif, USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 85%, 90%, and even more preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

The term "operably linked" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 5, 10, or 15 amino acids, preferably at least about 20 amino acids, more preferably at least about 25 amino acids, and even more preferably about 35 amino acids, about 50 amino acids, about 100 amino acids, or about 150 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides about 300 nucleotides or about 450 nucleotides or any integer thereabout or therebetween.

Methods of alignment of sequences for comparison are well-known in the art. Optimal alignment of sequences for comparison may be conducted by the local homology algorithm of Smith and Waterman, *Adv. Appl. Math.,* 2: 482, 1981; by the homology alignment algorithm of Needleman and Wunsch, *J. Mol. Biol.,* 48: 443, 1970; by the search for similarity method of Pearson and Lipman, *Proc. Natl. Acad. Sci. USA,* 8: 2444, 1988; by computerized implementations of these algorithms, including, but not limited to: CLUSTAL in the PC/Gene program by Intelligenetics, Mountain View, Calif, GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, *Gene,* 73: 237-244, 1988; Corpet, et al., *Nucleic Acids Research,* 16:10881-10890, 1988; Huang, et al., *Computer Applications in the Biosciences,* 8:1-6, 1992; and Pearson, et al., *Methods in Molecular Biology,* 24:7-331, 1994. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters (Altschul et al., *Nucleic Acids Res,* 2:3389-3402, 1997). It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149-163, 1993) and XNU (Clayerie and States, *Comput. Chem.,* 17:191-1, 1993) low-complexity filters can be employed alone or in combination.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

A "tumor," as used herein, refers to all neoplastic cell growth and proliferation, whether malignant or benign, and all precancerous and cancerous cells and tissues.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Methods

Synthesis of BR6

All chemicals were purchased from Sigma-Aldrich Chemical Co. (St. Louis, MO, USA) and used without further purification. Bis(2-hydroxyethyl) disulfide (15.4 g, 10 mmol) and triethylamine (TEA, 37.5 mL, 300 mmol) were dissolved in 450 mL of tetrahydrofuran previously dried with $NaSO_4$ in a 1000 ml round bottom flask. The flask was flushed with $N_2$ for 10 min and then maintained under a $N_2$ environment. Acryloyl chloride (24.4 mL, 300 mmol) was dissolved in 50 mL tetrahydrofuran then added to the flask dropwise over 2 hrs while stirring. The reaction was carried out for 24 hrs, then the TEA HCl precipitate was removed by filtration, and the solvent was removed by rotary evaporation. The product was dissolved in 100 mL dichloromethane and washed five times with 200 mL of an aqueous solution of 0.2 M $Na_2CO_3$ and three times with distilled water. The solution was dried with $NaSO_4$ and the solvent was removed by rotary evaporation.

Polymer Synthesis

Base monomer BR6 was polymerized with side chain monomers S3, S4, and S5 at a base:side chain ratio of 1.2:1 by weight without solvent at 90° C. for 24 hrs while stirring. For end-capping with E10, base polymer was dissolved in anhydrous dimethyl sulfoxide at 100 mg/mL with 0.2 mM end-cap. The reaction was allowed to proceed for 1 hr at room temperature while shaking.

Example 2

Characteristics of Representative Polymer/Peptide Nanoparticles

Referring now to FIG. 5 are shown representative formation and sizing of polymer/peptide nanoparticles (by nanoparticle tracking analysis on a Nanosight LM10). Selected peptides and PBAEs were diluted in 25 mM sodium acetate buffer and then together in different weight-to-weight ratios. In some embodiments w/w is unity, 1:1, in other embodiments there is an excess of polymer to peptide. In some embodiments this ratio is 5:1, in other embodiments between 1:1-10:1, in other embodiments it is 10:1 to 20:1. In FIG. 6, both a 5:1 and 1:1 ratio is shown. The mixtures were incubated at room temperature for up to 10 minutes to allow for self-assembly and then loaded into the NanoSight laser cell. Using NanoSight nanoparticle tracking software and analysis, individual particles were tracked in order to determine the average size distribution of the particles. In the case of more hydrophilic peptides (DEAH Box poly8; "DEAH" disclosed as SEQ ID NO: 2484) and PBAEs (336), there were very few background particles, that is very few particles of peptide or PBAE only. However, when self-assembled, a noticeable nanoparticle distribution was observed, with an average size ranging from 100-150 nm. In the case of hydrophobic peptides and PBAEs, they have the possibility of aggregating with themselves. In the case of the peptide-PBAE mixture, a shift in the mean can be observed as a way to detect difference in nanoparticle formation.

Referring now to FIG. 6, is shown DEAH peptide (SEQ ID NO: 2484) release by 336 nanoparticles at 4° C. (above) and 37° C. (below). Changing polymer to peptide formulation ratios and concentrations are key to tune release. Slowing the reaction rate of degradation of the liable polymer bonds extends release from nanoparticles. This is shown by change in temperature, but could also be accomplished by increasing hydrophobicity of the polymer, increasing the molecular weight between liable ester groups, or other modifications known by someone in the art; FITC labeled DEAH peptide (SEQ ID NO: 2484) and 336 polymer were mixed and incubated for up to 10 minutes in sodium acetate buffer. Mixtures at different peptide concentrations, but constant polymer to peptide ratios, as well as peptide only were added to a 96-well plate. Fluorescence measurements were obtained using a plate reader and measured over time. The plates were kept either at 4° C. or 37° C.

Referring now to FIG. 7, is shown HUVEC viability/proliferation assays with polymer/SP6001/DEAH peptide ("DEAH" disclosed as SEQ ID NO: 2484); the CellTiter 96® $AQ_{ueous}$ One Solution Cell Proliferation assay was used to see the effect of both peptide and polymer on cell proliferation and viability. Polymers at the right concentrations have minimal cytotoxic effect on the cells, such as 336 below 100 uM. The individual peptides and Polymers were diluted in sodium acetate buffer and added to HUVECs in a 96-well plate. After incubating for a few days, the assay substrate was added and then incubated for a few hours at 37° C. Absorbance measurements were performed using a plate reader.

Referring now to FIG. 8 is shown HUVEC migration assays with 336 polymer/DEAH peptide ("DEAH" disclosed as SEQ ID NO: 2484). These nanoparticles inhibit endothelial migration in addition to proliferation and viability. Peptide-polymer nanoparticles were made as described previously. Samples were added to HUVEC cells and migration was measured using the ACEA time course cell migration system. Nanoparticle formulations at a total peptide concentration of 20 uM were able to inhibit migration more than any peptide only at 20 μM.

Referring now to FIG. 9 is shown in vivo 336 polymer nanoparticle/SP6001 DEAH peptide ("DEAH" disclosed as SEQ ID NO: 2484); Peptide-336 polymer nanoparticles were formulated as previously described and intravitreously injected to test in vivo efficacy. ACNV laser mouse model was used on C57 BL/6 female mice. The mice receive laser eye treatments on day zero, followed by the intravitreous injections. Mice are then perfused with fluorescein labeled dextran on day 14 and choroidal flat mounts (bottom) were analyzed via fluorescence microscopy. On day 14, both the peptide only and nanoparticles formulations significantly reduced angiogenesis in the eye (top) and did so to a similar extent. This suggests that all peptide was released from nanoparticles by day 14.

Referring now to FIG. 10 is shown (top) Particle size and (bottom) cell viability effects of various polymer/SP2012 nanoparticles as compared to peptide only of non-cytotoxic polymers; a range of polymer structures were mixed with SP2000 series peptides, in a similar manner as described above. Similar sizing is found with peptides from the same class with similar structural properties. For example, SP2000, SP2012, SP2024, SP2034, and SP2036 can be encapsulated similarly to each other with the same polymers, but different from peptides from other classes such as SP6001. Sizing was performed using the Malzern Zetasizer. Size strongly depends on polymer choice. Using the same cell viability assay as described previously, effects of nanoparticle vs. peptide only on HUVECs in a 96-well plate. Non-cytotoxic polymers are shown here. Referring once again to FIG. 10, the (top) panel suggests that some of these peptide-polymer formulations have an increased effect on HUVEC cell proliferation and viability (y-axis ratio less than one) as compared to peptide only. (Data also are normalized to any polymer-only effects. Pep-pol/pol/SP2012 refers to the change in cell proliferation/viability due to the peptide/polymer nanoparticle formulation divided by any change in cell proliferation/viability from the same dose of polymer by itself and this quantity divided by the change in cell proliferation/viability by delivering the same amount of peptide SP2012 as a bolus);

FIG. 11 shows polymer/peptide formulations for alternative peptides. Peptide-polymer formulations made as described previously. Here two different classes of peptides are used. Experiments performed in a 96-well plate, with final results obtained using the same cell viability/proliferation assay as described previously. An increased effect (decreased metabolic activity) is observed for the nanoparticle formulations over the free peptide.

Example 3

Hydrogels for Protein/Peptide Release

As shown in FIG. 12, FITC-tagged bovine serum albumin (BSA) was mixed with a macromer solution containing 10% (w/v) PEGDA (Mn-270 Da) with various amounts of B4S4, dissolved in a 1:1 (v/v) mixture of DMSO and PBS. Irgacure 2959 was added at 0.05% (w/v), and the solution was briefly vortexed and immediately polymerized to form gels. The gels were incubated at 37° C. in 1×PBS with shaking. PBS was removed at each time point to measure fluorescence.

The observed slowed release is due to two factors: first, increased overall hydrophobicity can decrease the movement of water in and out of the gel, reducing degradation rate and protein release. Furthermore, this method of mixing relatively hydrophobic diacrylates with hydrophilic diacrylates in a co-solvent (mixture of water and DMSO) that can dissolve both types of polymer causes the spontaneous formation of micro-emulsions within the gel (see SEM in FIG. 13; increasing B4S4 from top [0.2% w/w] to bottom [5% w/w]). Similar to traditionally studied controlled-release microparticles, these microparticles within photopolymerized gels could serve as another way to tune the release of an encapsulated peptide, protein, or drug.

Example 4

Stable Formulations

In this formulation nanoparticles were formed by mixing PBAE and DNA in 25 mM sodium acetate buffer (pH 5) at a 30:1 polymer:DNA ratio (w/w). After 10 min of incubation, sucrose solution was added at various concentrations. The particles were mixed, then frozen at −80° C. for 1 hr and lyophilized for 48 hr. They then were used for transfection or sizing or were stored at either room temperature, 4° C. or −20° C. and tested at various timepoints.

Referring now to FIG. 14, the size distribution of appropriately freeze-dried particles (bottom left, right-most histogram) remains the same as freshly-prepared particles (bottom left, left-most histogram). Freeze-dried particles also remain more stable in serum-containing medium than freshly-prepared particles (upper left). Using DNA-loaded nanoparticles, transfection efficiency is comparable between fresh particles and particles lyophilized with sucrose (right) even after 3 months of storage. Modifying type of sugar and concentration of sugar modulates the stability of the degradable nanoparticles.

Example 5

Inclusion of Lyophilized Nanoparticles into Pellets/Scaffolds

For coating of natural or pre-made synthetic scaffolds, DNA nanoparticles were prepared by mixing DNA and polymer in a sodium acetate buffer. Sucrose was added for a final concentration of 15 mg/mL, and the solution was used to coat the surface of a trabecular bone construct. This construct was then lyophilized for 2 days before being seeded with primary human cells (~50% $GFP^+$ for ease of visualization). Referring now to FIG. 15, DsRed expression was observed within 24 hr, indicating that the nanoparticles remained functional and able to transfect cells in this new system.

Lyophilized nanoparticles also can be mixed with PLGA microparticles to form a larger construct that can be more easily manipulated and also can tune controlled release properties. In this embodiment, DsRed DNA-containing nanoparticles were compressed into a pellet with PLGA microparticles. This pellet was then placed within a well containing primary human glioblastoma cells (~20% $GFP^+$ for ease of visualization through the opaque pellet). Referring now to FIG. 16, DsRed expression was observed within 4 days and remained very robust even after 12 days. Referring once again to FIG. 16, top=1 day, middle=4 days, bottom=12 days after transfection.

Further, as demonstrated in FIG. 17, DNA-loaded nanoparticles have been incorporated into natural and synthetic scaffolds, disks, microparticles, and hydrogels.

Example 6

Bioreducible Polymeric Particle Formulations for Delivery of siRNA.

Reducible functional groups mediate successful siRNA-delivery, including transfection. In this example, $GFP^+$ primary human glioblastoma cells were seeded in 96-well plates at a density of $10^4$ cells/well in complete culture medium (DMEM/F-12 with 10% FBS and 1% antibiotic-antimycotic) and allowed to adhere overnight. Just before transfection, the culture medium was changed to serum-free medium. Particles were prepared by diluting polymer and siRNA both in 25 mM sodium acetate buffer (pH 5), then mixing them at a 100:1 polymer:siRNA ratio (w/w). Nanoparticles formed spontaneously after 10 min of incubation and were added to the cells in medium at a 1:5 ratio (v/v) and a final concentration of 60 nM. Each polymer/siRNA treatment group was paired with a control group using a scrambled siRNA sequence (scrRNA). Cells were incubated with the particles for 4 hr. The medium and particles were then aspirated and replaced with complete medium. On each of the following days, GFP expression was measured using a Synergy 2 multiplate fluorescence reader (Biotek). Background fluorescence was measured from GFP-cells in medium and was subtracted from all other readings. Knockdown was calculated by normalizing GFP fluorescence (excitation 485 nm, emission 528 nm) from the siRNA-treated cells to the scrRNA-treated cells. Medium was changed every 3 days.

The reducible disulfide bond in the endgroup E10 (cystamine dihydrochloride) drastically improves siRNA delivery and gene knockdown. Referring now to FIG. 18, $GFP^+$ glioblastoma cells were transfected with scrambled (control) siRNA (top panels) or siRNA against GFP (bottom). The polymers used as transfection agents consisted of B3-S5 at a 1.1:1 molar ratio, endcapped with (from left to right) E10, E3 (1,3=diaminopentane), or E6 (2-(3-aminopropylamino) ethanol). With the endgroups tested, the base polymer B3-S5 was able to achieve up to 8% knockdown; with E10 as the endgroup, over 80% knockdown was observed.

Referring now to FIG. 19A-FIG. 19C, the activity of R6-series polymers at delivering siRNA to knockdown GFP signal is GB cells is further demonstrated. % Knockdown of GFP expression in GFP+ glioblastoma cells transfected with siRNA against GFP, normalized to cells transfected with scrambled siRNA, using various BR6 polymers as a transfection agent. (A) Transfection with acrylate-terminated BR6 polymers with either S3, S4 or S5 as the side chain; (B) Transfection with E10 end-capped versions of the polymers in Figure A; and (C) GFP fluorescence images of cells transfected with BR6-S4-Ac complexed scrambled RNA (top) vs. siRNA against GFP (bottom);

Without wishing to be bound to any one particular theory, it is likely that E10 facilitates siRNA delivery by augmenting intracellular release because it degrades in the reducing intracellular environment. Results from gel retardation assay supports this hypothesis. Gel retardation assays were carried out by adding polymer of varying concentrations in sodium acetate buffer to a constant concentration of siRNA in sodium acetate. After 10 min of incubation, a solution of 30% glycerol in water was added at a 1:5 volumetric ratio as a loading buffer. Bromophenol blue or other dyes were not added, as they were found to interfere with binding. Samples were loaded into a 1% agarose gel with 1 g/mL ethidium bromide at 125 ng siRNA per well. Samples were run for 15 min under 100 V, then visualized using UV exposure.

Referring now to FIG. 20, a gel retardation assay of siRNA with BR6-S5-E10 at varying ratios of polymer to RNA is shown. The polymer effectively retards siRNA (top), but in the presence of 5 mM glutathione siRNA is released immediately (bottom). These data demonstrate the hypothesized intracellular release of siRNA and elucidates the mechanism by which nanoparticles formed using BR6 facilitate strong siRNA transfection and GFP knockdown.

Referring also to FIG. 21, an E10-endcapped polymer (top) retards siRNA efficiently, but upon addition of 5 mM glutathione, siRNA is immediately released (bottom). Numbers refer to the w/w ratio of polymer-to-siRNA in all cases.

Referring now to FIG. 22, the same polymer as in FIG. 21, but with a different endcap (E7, 1-(3-aminopropyl)-4-methylpiperazine) also retards siRNA (top), but is not affected by application of glutathione (bottom).

Referring now to FIG. 23, gel permeation chromatography data of BR6 polymerized with S4 at a BR6:S4 ratio of 1.2:1 at 90° C. for 24 hours, before and after end-capping with E7, are provided.

Referring now to FIG. 24, knockdown efficiency also is affected by molecular weight of the polymer. In FIG. 24, 1.2:1, 1.1:1, and 1.05:1 refer to the ratio of reactants in the base polymer step growth reaction, which affects the ultimate molecular weight. Top 4310 formulations were able to achieve greater knockdown over time compared to commercially available reagents like Lipofectamine 2000 (Lipo).

Referring now to FIG. 25, combined DNA (RFP) and siRNA delivery (against GFP) in GB; GFP+ GB cells were treated with scrambled siRNA (top) or siRNA against GFP (bottom), causing visible knockdown. Interestingly, different polymer structures seem ideal for siRNA versus DNA delivery or for both. One polymer effective in both was used to deliver both siRNA against GFP and plasmid DsRed DNA to GFP+ hMSCs, resulting in the ability to turn green cells red.

Referring now to FIG. 26, siRNA knockdown is affected by the endcap (E), base polymer (increasing hydrophobicity from L to R within each E), and molecular weight (increasing L to R within each base polymer). One endcap that shows high knockdown even at lower molecular weights is E10, which is strikingly more effective than the other endcaps tested for the same base polymers. Other PBAEs were also highly effective when synthesized at high molecular weight.

Referring now to FIG. 27, is shown 4410, 200 w/w (blue line on above graph), 8 days after transfection: Left: hMSCs treated with scrambled control; Right: hMSCs treated with siRNA.

Referring now to FIG. 28, in some embodiments, polymer molecular weight is between 4.00-10.00 kDa for siRNA delivery.

Example 7

DNA Delivery

Referring now to FIG. 29, the presently disclosed biomaterial can be used for other forms of delivery, for example DNA delivery. DNA transfection shows some similar trends compared with siRNA, but with different optimal endcaps. Specific polymer structure is critical to determine which polymers are effective for DNA delivery or siRNA delivery or both. Both DNA and siRNA transfection depend less on MW with high polymer hydrophobicity. High GFP DNA delivery was achieved using PBAEs, with transfection in 10% serum and at 5 g DNA/mL. Referring now to FIG. 30, several formulations with up to 90% transfection and high (>90%) viability are shown.

Referring now to FIG. 31, GB transfection is demonstrated. More particularly, 551 GB cells cultured as neurospheres (undifferentiated). They were plated in monolayer on laminin 24 hr before transfection with DsRed DNA using 447 LG (red). 48 hr after transfection, they were stained for nestin (blue). Red and blue overlaid (left) show that transfection occurred in nestin+ cells (nestin only: right).

Referring now to FIG. 32, for a DNA delivery application, in some embodiments, polymer molecular weight is between 3.00-10.0 kDa.

Example 8

In Vivo Activity for Selected Peptides

In some embodiments, the presently disclosed subject matter demonstrates in vivo activity for selected peptides in DIVAA angioreactors and a lung cancer xenograft model, Koskimaki J E, Karagiannis E D, Tang B C, Hammers H, Watkins D N, Pili R, et al. Pentastatin-1, a collagen IV derived 20-mer peptide, suppresses tumor growth in a small cell lung cancer xenograft model. BMC Cancer 2010; 10:29, and in a breast cancer xenograft model using MDA-MB-231 cells. Koskimaki J E, Karagiannis E D, Rosca E V, Vesuna F, Winnard P T, Jr., Raman V, et al. Peptides derived from type IV collagen, CXC chemokines, and thrombospondin-1 domain-containing proteins inhibit neovascularization and suppress tumor growth in MDA-MB-231 breast cancer xenografts. Neoplasia 2009; 11(12):1285-91.

Following orthotopic inoculation of SCID mice in the mammary fat pad area using $2\times10^6$ cells, tumors grew to approximately 100 $mm^3$ in 2 weeks; at that time 100 μL of peptide solution was injected i.p. once a day at peptide doses 10-20 mg/kg. PBS solution was injected as control. Several peptides have been found to inhibit tumor growth. See FIG. 33A. The microvessel density was determined by screening the immunohistologically stained CD31 sections. Inhibition of LEC migration in the ACEA migration assay also was determined (see FIG. 33B).

Representative data showing the activity of free peptide and peptide encapsulated in the presently disclosed polymeric particles are shown in FIG. 33D, which shows the metabolic activity of free peptides and peptides in polymeric particles.

Example 9

Non-Viral Gene Delivery for Treatment of Glioblastoma and Brain Cancer Stem Cells Glioblastoma (GB) is a grade IV brain cancer as defined by the WHO and is the most common primary CNS tumor in the United States. Current treatment includes surgical resection, radiotherapy, and chemotherapy. The median survival with treatment is approximately 14 months.

Brain cancer stem cells (BCSCs) possess genetic and morphological features similar to neural stem cells. Small numbers of BCSCs can initiate gliomas. BCSCs are refactory to conventional anti-cancer treatments.

Gene delivery typically is accomplished by either vaccine-mediated or polymer mediates techniques. Virus-mediated gene delivery is highly efficient, insertional mutagenesis, and toxicity/immunogenicity. Polymer-mediated gene delivery is chemically versatile, potentially safer than vaccine-mediated gene delivery, but typically is less efficient. See Green et al., 2008. Acc. Chem. Res. 41(6):749-59; Putnam 2006. Nat. Mater. 5(6):439-51.

Non-viral, e.g., polymer-mediated gene delivery, can be accomplished, in some embodiments, by using poly(beta-amino esters) (PBAEs). In particular embodiments, PBAEs suitable for use in target delivery can be synthesized in a two-step reaction provided herein below in Scheme 6 and can form nanocomplexes with negatively-charged cargo (e.g., DNA, siRNA) via electrostatic interactions as disclosed, for example, in some embodiments described in International PCT Patent Application Publication No. WO/2010/132879 for "Multicomponent Degradable Cationic Polymers," to Green et al., which is incorporated herein by reference in its entirety.

Scheme 6: Reaction sequence for preparing representative poly(beta-amino esters).

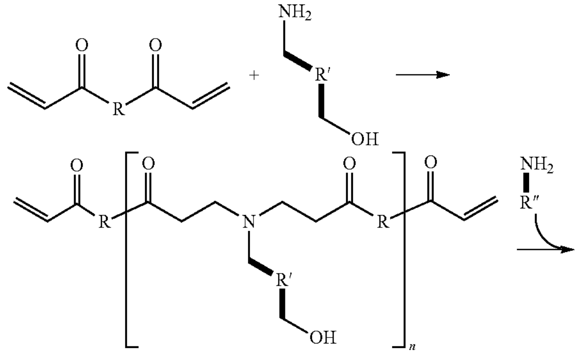

-continued

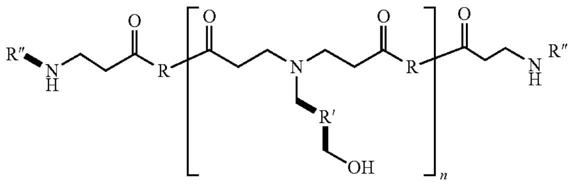

B3b

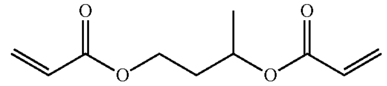

1-3-butanediol diacrylate

B4

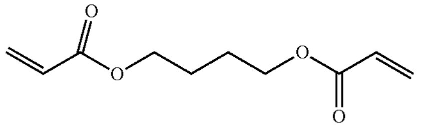

butane-1,4-diyl diacrylate

B5

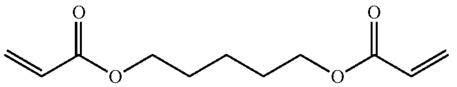

pentane-1,5-diyl diacrylate

B6

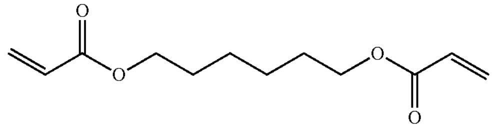

hexane-1,6-diyl diacrylate

S3

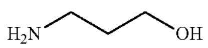

3-amino-1-propanol

S4

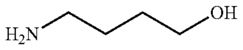

4-amino-1-butanol

S5

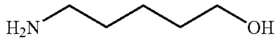

5-amino-1-pentanol

E1

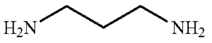

propane-1,3-diamine

E3

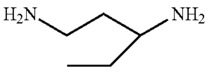

pentane-1,3-diamine

E4

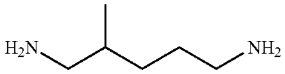

2-methylpentane-1,5-diamine

E5

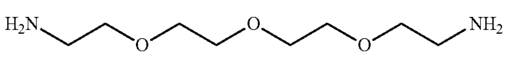

$(PEO)_4$-bis-amine

E6

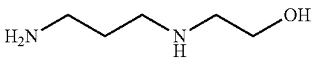

2-((3-aminopropyl)amino)ethanol

-continued

E7

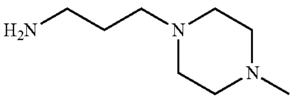

1-(3-aminopropyl)-4-methylpiperazine

E8

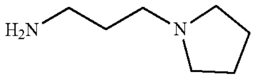

1-(3-aminopropyl)pyrrolidine

In some embodiments, the presently disclosed subject matter demonstrates the delivery of DNA to GB cells, i.e., bulk tumor (non-stem cells; verifies the efficacy of the presently disclosed methods in BCSCs; demonstrates the delivery of apoptosis-inducing genes in BCSCs; provides practical considerations for translation of the presently disclosed methods; and discusses how the presently disclosed methods can be used in conjunction with other methods for treating GB.

The delivery of DNA to GB cells, bulk tumor (non-stem cells) and the efficacy of the presently disclosed methods to deliver DNA to BCSCs is demonstrated in FIG. 36-FIG. 39.

Referring now to FIG. 34, the delivery of DNA to GB bulk tumor cells is demonstrated for representative biomaterials. Referring now to FIG. 35, the transfection of genes to BCSC is demonstrated for representative presently disclosed biomaterials. FIG. 36 demonstrates the delivery of DNA to fetal (healthy) cells. FIG. 37 also demonstrates the delivery of DNA to BCSCs. The delivery of apoptosis-inducing genes in BCSCs is demonstrated in FIG. 38 to FIG. 39.

These data demonstrate that PBAEs can be used for highly effective DNA delivery to GB cells, including tumor-initiating stem cells; transfection occurs even in 3D neurospheres in suspension; transfection is much less efficient in non-cancer cells (F34 fetal cells) as compared to GB cells; and transfection with secreted TRAIL causes more death in BCSCs with not significant effect on healthy cells.

In practical considerations for translation, for lyophilized nanoparticles, the presently disclosed methods provide an ease of preparation, e.g., only water needs to be added to the lyophilized nanoparticles, long-term storage, large, consistent batches, manipulation for uses in other devices, and stability in suspension. See scheme in FIG. 3.

As shown in FIG. 40, particles lyophilized with sucrose and used immediately are as effective in transfection as freshly prepared particles. Further, no loss in efficiency is observed within three months; and approximately 50% efficiency is retained after six months. The use of the presently disclosed materials and methods for long-term gene delivery is demonstrated in FIG. 41 and FIG. 42. Other methods for treatment of GB include siRNA delivery to GB cells (FIG. 43).

A comparison of siRNA vs. DNA delivery in GB cells is shown in FIG. 44 and FIG. 45. More particularly, as shown in FIG. 45, both 4410 and 447 can form complexes with DNA and siRNA; a higher weight ratio of polymer-to-nucleic acid is needed for siRNA than for DNA; E10 polymers release siRNA immediately, but not DNA, upon addition of glutathione (GSH).

In summary, PBAE/nucleic acid nanoparticles can be fabricated in a form that remains stable over time and allow flexibility for clinical use; PBAEs can be used for effective DNA or siRNA delivery to GB-derived BCSCs; and efficient release of cargo is necessary for effective nucleic acid delivery, especially with siRNA.

Example 10

Microparticles for Peptide Delivery

In some embodiments, microparticles for controlled release of nanoparticles, which themselves encapsulate biological agents, are illustrated in FIG. 14-FIG. 17.

More particularly, FIG. 46 depicts a strategy of combining nanoparticles within microparticles to extend release further. PLGA or blends of PLGA can be combined with the presently disclosed polymers to form microparticles by double emulsion. FIG. 47 shows release of a representative peptide, DEAH-FITC ("DEAH" disclosed as SEQ ID NO: 2484), from a presently disclosed microparticle. FIG. 48 shows slow extended release from microparticles containing nanoparticles that contain peptides; FITC-DEAH ("DEAH" disclosed as SEQ ID NO: 2484) peptide was first mixed with the 336 PBAE to allow for self-assembly into nanoparticles and was then mixed with BSA (middle) or not (bottom) to form an aqueous mixture. This mixture was added to a DCM-PLGA phase and sonicated to form a w/o suspension. This suspension was then added to a PVA solution and homogenized to form the final w/o/w suspension. This mixture was finally added to another PVA solution to allow for the DCM to evaporate and harden the formed microparticle. Different release profiles can potentially be obtained as seen above for the different microparticle formulations. In all cases, there is a long-term release of the peptide. Forming nanoparticles that encapsulate the peptide within the microparticles, extends the release compared to encapsulating peptide directly into microparticles (middle figure). The particles can be designed to have different release depending on the local environment (top figure). In some embodiments, release is constant over time and zero-order with respect to time (bottom figure).

Referring now to FIG. 49 in shown the in vivo effects of microparticle formulations in both the CNV and rho/VEGF model over time. DEAH (SP6001)-336 PBAE nanoparticle formulation made as described previously ("DEAH" disclosed as SEQ ID NO: 2484). (Top) Intravitreal injections into CNV model mice as described previously show comparable effects after 14 days, even though only small fraction of peptide is released over that time from microparticles. (Middle) and (Bottom) A genetic model of wet form of age-related macular degeneration in mice used to test long-term effect of microparticles. After 1 week (middle) comparable effects seen in reduction of angiogenesis. After 8 weeks (bottom), however, while peptide only no longer inhibits angiogenesis, the microparticle still does, as it is still releasing peptide over this time. While PLGA is used to form the microparticles used above, other polymers may be used including the synthetic polyesters and polyamides described above. In certain embodiments, blends of these polymer are combined with PLGA to form microparticles with differing environmental sensitivity and release properties; (a) the effect of microparticle (SP-6001) in CNV model mouse; (b) the effect of microparticle (SP-6001) in rho/VEGF (V6) mouse, 1 week after injection; and (c) the effect of microparticle (SP-6001) in rho/VEGF (V6) mouse, 8 weeks after injection.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Chiang A C, Massague J. Molecular basis of metastasis. N Engl J Med 2008; 359(26):2814-23.

Gupta G P, Massague J. Cancer metastasis: building a framework. Cell 2006; 127(4):679-95.

Sawyers C L. Cancer: mixing cocktails. Nature 2007; 449 (7165):993-6.

Dorrell M I, Aguilar E, Scheppke L, Barnett F H, Friedlander M. Combination angiostatic therapy completely inhibits ocular and tumor angiogenesis. Proc Natl Acad Sci USA 2007; 104(3):967-72.

Farokhzad O C. Nanotechnology for drug delivery: the perfect partnership. Expert Opin Drug Deliv 2008; 5(9): 927-9.

Putnam D. Polymers for gene delivery across length scales. Nat Mater 2006; 5(6):439-51.

Brigger I, Dubernet C, Couvreur P. Nanoparticles in cancer therapy and diagnosis. Adv Drug Deliv Rev 2002; 54(5): 631-51.

Green J J, Shi J, Chiu E, Leshchiner E S, Langer R, Anderson D G. Biodegradable polymeric vectors for gene delivery to human endothelial cells. Bioconjug Chem 2006; 17:1162-9.

Green J J, Chiu E, Leshchiner E S, Shi J, Langer R, Anderson D G. Electrostatic ligand coatings of nanoparticles enable ligand-specific gene delivery to human primary cells. Nano Lett 2007; 7(4):874-9.

Harris T J, Green J J, Fung P W, Langer R, Anderson D G, Bhatia S N. Tissue-specific gene delivery via nanoparticle coating. Biomaterials 2010; 31(5):998-1006.

Green J J, Zugates G T, Tedford N C, Huang Y, Griffith L G, Lauffenburger D A, et al. Combinatorial modification of degradable polymers enables transfection of human cells comparable to adenovirus. Adv Mater 2007; 19(19):2836-42.

Lee J S, Green J J, Love K T, Sunshine J, Langer R, Anderson D G. Gold, poly(beta-amino ester) nanoparticles for small interfering RNA delivery. Nano Lett 2009; 9(6):2402-6.

Reichert J. Development trends for peptide therapeutics. Tufts Center for the Study of Drug Development 2008 [cited 2010; Available from: http://www.peptidetherapeutics.org/PTF_Summary_2008.pdf Rosca E V, Koskimaki J E, Rivera C G, Pandey N B, Tamiz A P, Popel A S. Anti-angiogenic peptides for cancer therapeutics. Curr Pharm Biotechnol 12(8):1101-1116 (2011).

Lucas R, Holmgren L, Garcia I, Jimenez B, Mandriota S J, Borlat F, et al. Multiple forms of angiostatin induce apoptosis in endothelial cells. Blood 1998; 92(12):4730-41.

Green J J, Langer R, Anderson D G. A combinatorial polymer library approach yields insight into nonviral gene delivery. Acc Chem Res 2008; 41(6):749-59.

Shmueli R B, Anderson D G, Green J J. Electrostatic surface modifications to improve gene delivery. Expert Opin Drug Deliv 7(4):535-50.

Zhang S, Uludag H. Nanoparticulate systems for growth factor delivery. Pharm Res 2009; 26(7):1561-80.
Jain R A. The manufacturing techniques of various drug loaded biodegradable poly(lactide-co-glycolide) (PLGA) devices. Biomaterials 2000; 21(23):2475-90.
Little S R, Lynn D M, Ge Q, Anderson D G, Puram S V, Chen J Z, et al. Poly-beta amino ester-containing microparticles enhance the activity of nonviral genetic vaccines. Proc Natl Acad Sci USA 2004; 101(26):9534-9.
Koskimaki J E, Karagiannis E D, Tang B C, Hammers H, Watkins D N, Pili R, et al. Pentastatin-1, a collagen IV derived 20-mer peptide, suppresses tumor growth in a small cell lung cancer xenograft model. BMC Cancer 2010; 10:29.
Koskimaki J E, Karagiannis E D, Rosca E V, Vesuna F, Winnard P T, Jr., Raman V, et al. Peptides derived from type IV collagen, CXC chemokines, and thrombospondin-1 domain-containing proteins inhibit neovascularization and suppress tumor growth in MDA-MB-231 breast cancer xenografts. Neoplasia 2009; 11(12):1285-91.

Although the foregoing subject matter has been described in some detail by way of illustration and example for purposes of clarity of understanding, it will be understood by those skilled in the art that certain changes and modifications can be practiced within the scope of the appended claims.

We claim:

1. A nanoparticle, microparticle, or gel comprising a compound of formula (I):

(I)

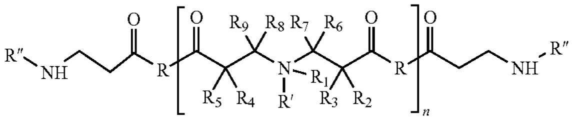

wherein:

n is an integer from 1 to 10,000;

$R_2$, $R_3$, $R_4$, $R_5$, $R_6$, $R_7$, $R_8$, and $R_9$ are each hydrogen wherein $R_1$ is absent; and wherein R' comprises a side chain selected from the group consisting of:

(S3)

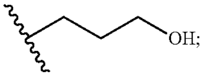

(S4)

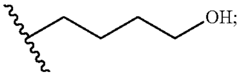

(S5)

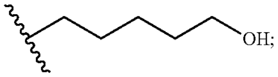

(S6)

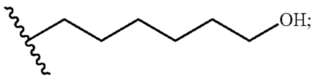

(S7)

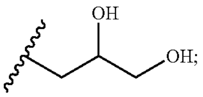

(S8)

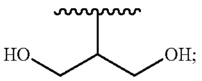

(S9)

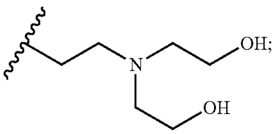

-continued (S10)

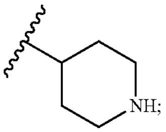

(S11)

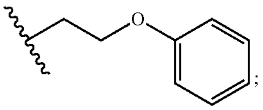

(S12)

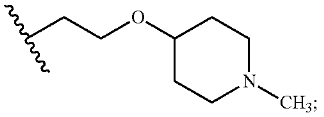

and (S13)

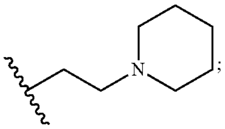

wherein R" comprises an end group selected from the group consisting of (E1)

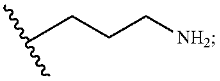

(E2)

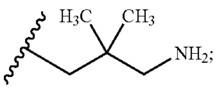

(E3)

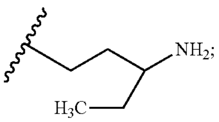

(E4)

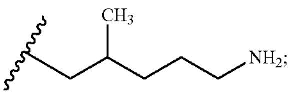

(E5)

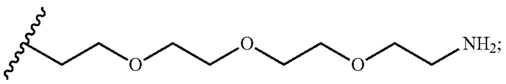

-continued (E6)

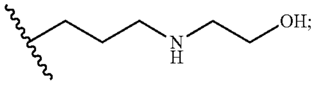

(E7)

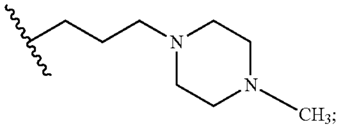

(E8)

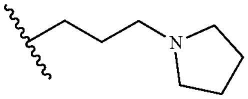

(E9)

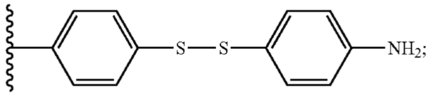

(E10)

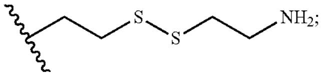

(E11)

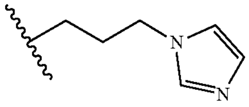

(E12)

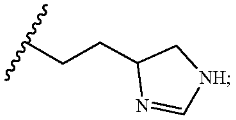

(E13)

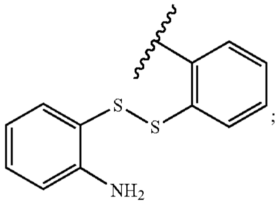

; and (E14)

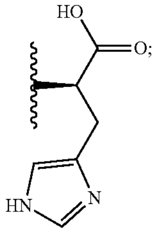

wherein R comprises (BSS)

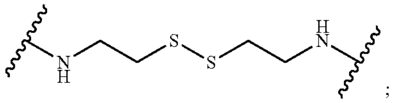

and one or more nucleic acids.

2. The nanoparticle, microparticle, or gel of claim 1, wherein n is an integer selected from the group consisting of from 1 to 1,000, from 1 to 100, from 1 to 30, from 5 to 20, from 10 to 15, and from 1 to 10.

3. The nanoparticle, microparticle, or gel of claim 1, wherein the nucleic acid is selected from the group consisting of a gene, DNA, RNA, siRNA, miRNA, isRNA, agRNA, smRNA, and combinations thereof.

4. The nanoparticle, microparticle, or gel of claim 3, wherein the nucleic acid is an siRNA or a combination of siRNA.

5. The nanoparticle, microparticle, or gel of claim 1, wherein:

R comprises:

(BSS)

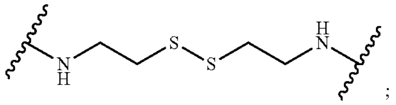

R' comprises:

(S4)

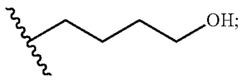

and

R" comprises:

(E6)

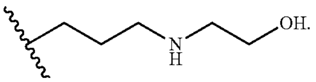

6. The nanoparticle, microparticle, or gel of claim 1, wherein the nucleic acid comprises siRNA.

* * * * *